(12) United States Patent
Kurek et al.

(10) Patent No.: US 9,957,534 B2
(45) Date of Patent: May 1, 2018

(54) ENGINEERED CO2-FIXING CHEMOTROPHIC MICROORGANISMS PRODUCING CARBON-BASED PRODUCTS AND METHODS OF USING THE SAME

(71) Applicant: Kiverdi, Inc., Hayward, CA (US)

(72) Inventors: Itzhak Kurek, San Francisco, CA (US); John S. Reed, Berkeley, CA (US); Lisa Dyson, Berkeley, CA (US); Henrik Fyrst, Oakland, CA (US); Christer Jansson, Berkeley, CA (US); David Galgoczy, San Francisco, CA (US)

(73) Assignee: Kiverdi, Inc., Hayward, CA (US)

( * ) Notice: Subject to any disclaimer, the term of this patent is extended or adjusted under 35 U.S.C. 154(b) by 0 days. days.

(21) Appl. No.: 15/233,512

(22) Filed: Aug. 10, 2016

(65) Prior Publication Data
US 2017/0152533 A1    Jun. 1, 2017

Related U.S. Application Data

(63) Continuation of application No. 14/388,756, filed as application No. PCT/US2013/032362 on Mar. 15, 2013, now abandoned, which is a continuation-in-part of application No. 13/623,089, filed on Sep. 19, 2012, which is a continuation-in-part of application No. PCT/US2011/034218, filed on Apr. 27, 2011, which is a continuation-in-part of application No. PCT/US2010/001402, filed on May 12, 2010, which is a continuation-in-part of application No. 12/613,550, filed on Nov. 6, 2009, now abandoned.

(60) Provisional application No. 61/616,560, filed on Mar. 28, 2012, provisional application No. 61/635,238, filed on Apr. 18, 2012, provisional application No. 61/708,057, filed on Oct. 1, 2012, provisional application No. 61/536,056, filed on Sep. 19, 2011, provisional application No. 61/111,794, filed on Nov. 6, 2008, provisional application No. 61/542,823, filed on Oct. 4, 2011.

(51) Int. Cl.
| | |
|---|---|
| *C12N 1/20* | (2006.01) |
| *C12P 7/64* | (2006.01) |
| *C07H 21/04* | (2006.01) |
| *C12N 9/16* | (2006.01) |
| *C12N 9/02* | (2006.01) |

(52) U.S. Cl.
CPC ............ *C12P 7/649* (2013.01); *C12N 9/0083* (2013.01); *C12N 9/16* (2013.01); *C12Y 114/99033* (2013.01); *C12Y 301/02014* (2013.01)

(58) Field of Classification Search
None
See application file for complete search history.

(56) References Cited

U.S. PATENT DOCUMENTS

| | | | |
|---|---|---|---|
| 7,883,882 | B2 | 2/2011 | Franklin |
| 7,923,598 | B2 | 4/2011 | Meesapyodsuk et al. |
| 8,003,853 | B2 | 8/2011 | Meesapyodsuk et al. |
| 2010/0249470 | A1 | 9/2010 | Schirmer et al. |
| 2010/0304453 | A1 | 12/2010 | Trawick et al. |
| 2012/0070868 | A1 | 3/2012 | Lee et al. |
| 2012/0151833 | A1 | 6/2012 | Myllyntausta et al. |
| 2013/0078690 | A1 | 3/2013 | Reed |
| 2013/0089899 | A1 | 4/2013 | Kurek et al. |
| 2013/0149755 | A1 | 6/2013 | Reed et al. |

(Continued)

FOREIGN PATENT DOCUMENTS

| | | |
|---|---|---|
| WO | WO00070052 A1 | 11/2000 |
| WO | WO2009140695 A1 | 11/2009 |

(Continued)

OTHER PUBLICATIONS

U.S. Appl. No. 14/214,784, Office Action dated Feb. 5, 2016.
U.S. Appl. No. 14/214,784, Office Action dated Jul. 14, 2015.
Le Bouquin, R., et al., Cloning and Functional Characterization of CYP94A2, a Medium Chain Fatty Acid Hydroxylase from Vicia sativa, Biochemical and Biophysical Research Communications, 1999; 261:156-162.
Benveniste, I., et al., CYP86A1 from *Arabidopsis thaliana* Encodes a Cytochrome P450-Dependent Fatty Acid Omega-Hydroxylase Biochem. Biophys. Res. Commun., 1998; 243:688-693.
Koiwai, A., et al., Hydroxy and Normal Fatty Acid Distribution in Stigmas of Nicotiana and Other Plants, Phytochemistry,1988; 27(9): 2827-2830.

(Continued)

*Primary Examiner* — Iqbal H Chowdhury
(74) *Attorney, Agent, or Firm* — Jill A. Jacobson

(57) ABSTRACT

Disclosed herein are microorganisms containing exogenous or heterologous nucleic acid sequences, wherein the microorganisms are capable of growing on gaseous carbon dioxide, gaseous hydrogen, syngas, or combinations thereof. In some embodiments the microorganisms are chemotrophic bacteria that produce or secrete at least 10% of lipid by weight. Also disclosed are methods of fixing gaseous carbon into organic carbon molecules useful for industrial processes. Also disclosed are methods of manufacturing chemicals or producing precursors to chemicals useful in jet fuel, diesel fuel, and biodiesel fuel. Exemplary chemicals or precursors to chemicals useful in fuel production are alkanes, alkenes, alkynes, fatty acid alcohols, fatty acid aldehydes, desaturated hydrocarbons, unsaturated fatty acids, hydroxyl acids, or diacids with carbon chains between six and thirty carbon atoms long. Also disclosed are microorganisms and methods using disclosed microorganisms for the production of butanediol and its chemical precursors in low-oxygen or anaerobic fermentation. Also disclosed are microorganisms and methods using disclosed microorganisms for generating hydroxylated fatty acids in microbes through the transfer of enzymes that are known to hydroxylate fatty acids in plants or microbes. Also disclosed are microorganisms and methods using disclosed microorganisms for the production of shorter-chain fatty acids in microbes through the introduction of exogenous fatty acyl-CoA binding proteins.

17 Claims, 55 Drawing Sheets

(56) References Cited

U.S. PATENT DOCUMENTS

| | | | |
|---|---|---|---|
| 2013/0189763 | A1 | 7/2013 | Dalla-Betta et al. |
| 2014/0024091 | A1 | 1/2014 | Reed et al. |
| 2014/0273112 | A1 | 9/2014 | Reed et al. |

FOREIGN PATENT DOCUMENTS

| | | | |
|---|---|---|---|
| WO | WO2011006137 | A2 | 1/2011 |
| WO | WO2011056183 | A1 | 5/2011 |
| WO | WO2011139804 | A2 | 11/2011 |
| WO | WO2013082309 | A1 | 6/2013 |
| WO | WO2013090769 | A2 | 6/2013 |
| WO | WO2013148348 | A1 | 10/2013 |
| WO | WO2014145194 | A2 | 9/2014 |
| WO | WO2015027209 | A2 | 2/2015 |

OTHER PUBLICATIONS

Benveniste, I., et al., Cytochrome P-450-Dependent w-Hydroxylation of Lauric Acid by Microsomes from Pea Seedlings, Plant Phisiology, 1982; 70:122-126.

Pinot, F., et al., w-hydroxylation of 9-octadecenoic, Z9,10-epoxystearic and 9,10-dihydroxystearic acids by microsomal cytochrome P450 systems from Vicia sativa, Biochemical and Biophysical Research Communications, 1992; 184(1):183-193.

Tijet, N., et al., Functional expression in yeast and characterization of a clofibrate-inducible plant cytochrome P-450 (CYP94A1) involved in cutin monomers synthesis, Biochem. J., 1998; 332:583-589.

Le Bouquin, R., et al., CYP94A5, a new cytochrome P450 from Nicotiana tabacum is able to catalyze the oxidation of fatty acids to the w-alcohol and to the corresponding diacid, Eur. J. Biochem, 2001; 268:3083-3090.

Imaishi H., et al., CYP78A1 Perferentially Expressed in Developing Inflorescence of *Zea mays* Encoded a Cytochrome P450-Dependent Lauric Acid 12-Monooxygenase, Biosci. Biotechnol. Biochem., 2000; 64(8):1696-1701.

Petkova-Andonova, M., et al., CYP92B1, A Cytochrome P450, Expressedin Petunia Flower Buds, That Catalyzes Monooxidation of Long-Chain Fatty Acids, Biosci. Biotechnol. Biochem., 2002; 66(9):1819-1828.

Pompon, D., et al., Yeast Expression of Animal and Plant P450s in Optimized Redox Environments, Methods in Enzymology, 1996; 272:51-64.

Kandel, S., et al., Cloning, Functional Expression, and Characterization of CYP709C1, the First Sub-terminal Hydroxylase of Long Chain Fatty Acid in Plants: Induction by Chemicals and Methyl Jasmonate, J. Bio. Chem., 2005; 280:35881-35889.

Kroha, K., Industrial Biotechnology Provides Opportunities for Commercial Production of New Long-Chain Dibasic Acids, Inform, 2004; 15:568-571.

English, J., et al., The Wound Hormones of Plants. IV. Structure and Synthesis of a Traumatin, Science, 1939; 51:3434-3436.

Carballeira, N., et al., Unusual Fatty Acid Compositions of the Hyperthermophilic Archaean Pyrococcus furiosus and the Bacterium Thermotoga maritima., J. Bacterial., 1997; 179(8):2766-2768.

Altschul, S., et al., Gapped BLAST and PSI-BLAST: a new generation of protein database search programs, Nuc. Acids Res., 1997; 25(17):3389-3402.

Altschul, S., et al., Basic Local Alignment Search Tool, J. Mol. Biol., 1990; 215:403-410.

Henikoff, S., et al., Amino Acid Substitution Matrices From Protein Blocks, Proc. Natl. Acad. Sci. USA, 1992; 89, 10915-10919.

Karlin, S., et al., Applications and Sequences for Multiple High-scoring Segments in Molecular Sequences, Proc. Natl. Acad. Sci. USA, 1993; 90:5873-5787.

Shively, J., et al., Something From Almost Nothing: Carbon Dioxide Fixation in Chemoautotrophs, Annu. Rev. Microbiol., 1998;52:191-230.

Smith, A., et al., Biochemical Basis of Obligate Autotrophy in Blue-Green Algae and Thiobacilli, J. Bacteriol., 1967; 94: 972-983.

Hugler, M., et al., Evidence for Autotrophic CO2 Fixation via the Reductive Tricarboxylic Acid Cycle by Members of the Epsilon Subdivision of Proteobacteria, J. Bacteriol., 2005; 187(9):3020-3027.

Kovach, M., et al., Four new derivatives of the broad-host-range cloning vector pBBR1MCS, carrying different antibiotic-resistance cassettes, Gene, 1995; 166:175-176.

Scott, K., et al., CO2 Uptake and Fixation by Endosymbiotic Chemoautotrophs from the Bivalve Solemya velum, Appl. Environ. Microbiol., Feb. 2007; 73(4)1174-1179.

Ljungdahl, L., The Autotrophic Pathway of Acetate Synthesis in Acetogenic Bacteria, Annual Review of Microbiology, 1986; 40: 415-450.

Dauk, M., et al., A FAD2 Homologue From Lewquerella lindheimeri has Predominantly Fatty Acid Hydroxylase Activity, Plant Sci., 2007, 173(1):43-49.

Lee, S., et al., Fermentative Butanol Production by Clostridia, Biotechnology & Bioengineering, 2008; 101(2)209-228.

Fischer, C., et al., Selection and optimization of microbial hosts for biofuels production, Metab Eng., Nov. 2008;10(6):295-304.

Thauer, R. K., et al., Methanogenic archaea: ecologically relevant differences in energy conservation, Nat Rev Microbiol, Aug. 2008; 6(8):579-91.

Papoutsakis, E., Equations and Calculations for Fermentations of Butyric Acid Bacteria, Biotechnol Bioeng., Feb. 1984; 26(2):174-87.

Heise, R., et al., Sodium Dependence of Acetate Formation by the Acetogenic Bacterium Acetobacterium woodii, Journal of Bacteriology, Oct. 1989; 171(10):5473-5478.

Bongers, L., Energy Generation and Utilization in Hydrogen Bacteria, J. Bacteriology, Oct. 1970; 145-151.

McKeon, T. A., The Enzymology of Castor Oil Biosynthesis, Eds. Janick J., Whipkey A., "Issues in new crops and new uses", ASHS Press, 2007; 101-104.

Meesapyodsuk, D., et al., An Oleate Hydroxylase From the Fungus Claviceps purpurea: Cloning, Functional Analysis, and Expression in Arabidopsis., Plant Physiol., Jul. 2008; 147:1325-1333.

Nishida, M., et al., Molecular Cloning and Site-directed Mutagenesis of Glutathione S-Transferase from *Escherichia coli*, J. Biol Chem., 1994; 269(51):32536-32541.

Piccolomini, R., et al., Glutathione Transferase in Bacteria: Subunit Composition and Antigenic Characterization, J. Gen. Microbiol., 1989; 135:3119-3125.

Paterson, E.S., et al., Genetic Analysis of the Mobilization and Leading Regions of the IncN plasmids pKM101 and pCU1, J. Bacteriol, 1999; 181(8):2572-2583.

Fukuda, H., Roles of Tral Protein With Activities of Cleaving and Rejoining the Single-stranded DNA in Both Initiation and Termination of Conjugal DNA Transfer, Genes to Cells, 1997; 2:735-751.

Mogensen, I., et al., A novel acyl-CoA-binding protein from bovine liver, Biochem. J., 1987; 241:189-192.

Mikkelsen, J., et al., Acyl-CoA-binding protein from cow, Biochem. J., 1987; 248:709-714.

Doan, T., et al., Functional expression of five Arabidopsis fatty acyl-CoA reductase genes in *Escherichia coli*, J Plant Physiol., 2008; 166(8):787-96.

Kavangh, K. L., et al., The SDR superfamily: functional and structural diversity within a family of metabolic and regulatory enzymes, Cell Mol Life Sci, 2008; 65:3895-3906.

Labesse, G., et al., Structural comparisons lead to the definition of a new superfamily of NAD(P)(H)-accepting oxidoreductases: the single-domain reductases/epimerases/dehydrogenases (the 'RED' family), Biochem J, 1994; 304:95-99.

Na, K-S., et al., Development of a Genetic Transformation System for Benzene-Tolerant Rhodococcus opacus Strains, J Biosci Bioeng, 2005; 99:408-414.

Alton, N.K., et al., Nucleotide Sequence Analysis of The Chloramphenicol Resistance Transposon Tn9, Nature, 1979; 282:864-869.

Shumunogo, V.K., et al., Obschaya biologiya pod red, Moskava "Prosvechinie", 2004; pp. 64-65.

(56) References Cited

OTHER PUBLICATIONS

Lysak, V.V., Mikrobiologiya. Uchebnoe posobie dlya studentov mikrobiologi-cheskikh spetsialnostey, Minsk, BGU, 2005; p. 29.

Craft, D., et al., Identification and Characterization of the CYP52 Family of *Candida tropicalis* ATCC 20336, Important for the Conversion of Fatty Acids and Alkanes to a,w-Dicarboxylic Acids, Applied and Environmental Microbiology, Oct. 2003; 69(10):5983-5991.

Yano, S., et al., Carbon Monoxide Utilization of an Extremely Oligotrophic Bacaterium, Rhodococcus Erythropolis N9T-4, Journal of Bioscience and Bioengineering, 2012, 114(1):53-55.

Sharma, S., et al., Biodegradation and Conversion of Alkanes and Crude Oil by a Marine *Rhodococcus* sp., 2000, 11:289-294.

Alvaraz, H., et al., Accumulation of Storage Lipids in Species of Rhodococcus and Nocardia and Effect of Inhibitors and Polyethylene Glycol, 1997, Fett/Lipid 99:2239-246.

FIG. 1

| DSM # | Name | Synonyms | Reference |
|---|---|---|---|
| 44193 | Rhodococcus opacus | Rhodococcus opacus PD 630 | 1 |
| 43205 | Rhodococcus opacus | Rhodococcus opacus ISO-5 | 2 |
| 3346 | Rhodococcus sp. | Nocardia opaca MR 22 | 3 |
| 531 | Cupriavidus necator | Ralstonia eutropha | 4 |

Fig. 3

| Definition | GenBank # | Length (bases) | Identity to NR_026186.1 (%) |
|---|---|---|---|
| Rhodococcus opacus strain DSM 43205 | NR_026188.1 | 1291 | 100 |
| Rhodococcus opacus GM14 | X89710.1 | 1271 | 98.4 |
| Rhodococcus opacus strain DSM43206T | X89710.1 | 1283 | 99.2 |
| Cupriavidus necator strain DSM 2839 | NR_043444.1 | 1291 | 73.7 |
| Ralstonia sp. HB1 | JN196539.1 | 1316 | 73.6 |
| Gordonia alkanivorans strain DSM 44187 | AY995556.1 | 1291 | 93.3 |
| Gordonia sp. CC-MJ-39a 16S ribosomal RNA gene, partial sequence | EU288488.1 | 1296 | 93.8 |
| Mycobacterium fortuitum subsp. Acetamidolyticum strain DSM44220T | FR733720.1 | 1297 | 92.7 |
| Mycobacterium parafortuitum strain DSM 43528 | NR_026285.1 | 1280 | 93.3 |
| Mycobacterium sphagni strain S32418 | AB649002.1 | 1301 | 93.5 |
| Nocardia farcinica strain DSM 43665 | AF430033.1 | 1281 | 94.3 |
| Nocardia sp. I7 | AY524801.1 | 1300 | 94.3 |
| Rhodococcus rhodochrous strain CG30 | AB562467.1 | 1303 | 95.0 |
| Rhodococcus coprophilus strain DSM43347T | X80626.1 | 1295 | 95.9 |
| Rhodococcus triatomae strain IMMIB RIV-085 | AJ854055.1 | 1272 | 94.8 |
| Nocardia coeliaca strain DSM44595T | FR733721.1 | 1296 | 95.6 |
| Nocardia globerula strain DSM 44596T | FR749915.1 | 1297 | 95.7 |
| Rhodococcus equi strain S32003 | AB649016.1 | 1300 | 95.9 |
| Rhodococcus sp. A2Y26 | AY512637.1 | 1288 | 96.4 |
| Rhodococcus sp. 871-AN040 | AF420421.1 | 1300 | 97.1 |
| Rhodococcus jostii | AB458522.1 | 1282 | 95.9 |
| Rhodococcus opacus strain 1CP | Y11893.1 | 1294 | 99.1 |
| Rhodococcus imtechensis strain RKJ300 | AY525785.2 | 1296 | 97.0 |
| Rhodococcus koreensis strain DNP505 | NR_024973.1 | 1280 | 97.8 |
| Rhodococcus opacus strainB-4 | AB192962.1 | 1308 | 96.4 |
| Rhodococcus sp. TCH14 | AB183440.1 | 292 | 97.0 |
| Rhodococcus opacus strain DNP14-6 | AY027585.1 | 1281 | 98.7 |
| Rhodococcus sp. pnp-5 | EF017807.1 | 1300 | 98.3 |
| Rhodococcus sp. Sutt-822 | AM922188.1 | 1270 | 97.0 |
| Rhodococcus wratislaviensis strain J7 | AY940038.1 | 1291 | 98.5 |

FIG 4

R.opacus DSM 43205

(1) ————————CCTGGCTCAGGACGAACGCTGGCGGCGTGCTTAACACATGCAAGTCGAGCGGTAAGGCC
C—TTCGG—GGTACACGAGCGGCGAACGGGTGAGTAACACGTGGGTGATCTGCCCTGCACTTCGGGATA
AGCCTGGGAAACTGGGTCTAATACCGGATATGACCTTCGGCTGCATGG-CTGAGGGTGGAAAGGTTTACTG
GTGCAGGATGGGCCCGCGGCCTATCAGCTTGTTGGTGGGGTAATGGCCTACCAAGGCGACGACGGGTAG
CCGACCTGAGAGGGTGACCGGCCACACTGGGACTGAGACACGGCCCAGACTCCTACGGGAGGCAGCAG
TGGGGAATATTGCACAATGGGCGAAAGCCTGATGCAGCGACGCCGCGTGAGGGATGACGGCCTTCGGGT
TGTAAACCTCTTTCAGCAGGGACGAA——————————GCGAAAGTGACGGTACCTGCAGAAGAAGCACCGG
CCAACTACGTGCCAGCAGCCGCGGTAATACGTAGGGTGCAAGCGTTGTCCGGAATTACTGGGCGTAAAGA
GCTCGTAGGCGGTTTGTCGCGTCGTCTGTGAAAACTCANAGCTCAACCTCGAGCTTGCAGGCGATACGGG
CAGACTTGAGTACTGCAGGGGAGACTGGAATTCCTGGTGTAGCGGTGAAATGCGCAGATATCAGGAGGAA
CACCGGTGGCGAAGGCG-GGTCTCTGGGCAGTAACTGACGCTGAGGAGCGAAAGCGTGGGTAGCAAACA
GGATTAGATACCCTGGTAGTCCACGCCGTAAACGGTGGGCGCTAGGTGTGGGTTTCCTTCCACGGGATCC
GTGCCGTAGTTAACGCATTAAGCGCCCCGCCTGGGGAGTACGGCCGCAAGGTTAAAACTCAAAGGAATTG
ACGGGGGCCCGCACAAGCGGCGGAGCATGTGGATTAATTCGATGCAACGCGAAGAACCTTACCTGGGTTT
GACATATACCGGAAAGCCGTAGAGATACC—GC—CCCCCTTGTGGTCG—GTATACAGGTGGTGCATGGCT
GTCGTCAGCTCGTGTCGTGAGATGTTGGGTTAAGTCCCGCAACGAGCGCAACCCTTGTCTTATGTTGCCA
GCA-CGTAATGGTGGGGACTCGTAAGAGACTGCCGGGGTCAACTCGGAGGAAGGTGGGGACGACGTCAA
GTCATCATGCCCCTTATGTCCAGGGCTTCACACATGCTACAATGGCCGGTACAGAGGGCTGCGATACCGT
GAGGTGGAGCGAATCCCTT-AAAGCCGGTCTCAGTTCGGATCGGGGTCTGCAACTCGACCCCGTGAAGTC
GGAGTCGCTAGTAATCGCAGATCAGCAACGCTGCGGTGAATACGTTCCCGGGCCTTGTACACACCGCCCG
TCACGTCATGAAAGTCGGTAACACCCGAAGCCGGTGGCCTAACCCCTTGTGGGAGGGAGCCGTCGAAGG
TGGGATCGGCGATTGGGACGAAGTCGTAACAAGGTAGCCGTACCGGAAGG—————————

R. opacus GM14

(1) ————————————————GGCGGCGTGCTTAACACATGCAAGTCGAGCGGTAAGGCCC—TTCGG—G
GTACACGAGCGGCGAACGGGTGAGTAACACGTGGGTGATCTGCCCTGCACTTCGGGATAAGCCTGGGAA
ACTGGGTCTAATACCGGATATGACCTTCGGCTGCATGG-CTGAGGGTGGAAAGGTTTACTGGTGCAGGATG
GGCCCGCGGCCTATCAGCTTGTTGGTGGGGTAATGGCCTACCAAGGCGACGACGGGTAGCCGACCTGAG
AGGGTGACCGGCCACACTGGGACTGAGACACGGCCCAGACTCCTACGGGAGGCAGCAGTGGGGAATATT
GCACAATGGGCGAAAGCCTGATGCAGCGACGCCGCGTGAGGGATGACGGCCTTCGGGTTGTAAACCTCT
TTCAGCAGGGACGAA——————————GCGAAAGTGACGGTACCTGCAGAAGAAGCACCGGCCAACTACGTG
CCAGCAGCCGCGGTAATACGTAGGGTGCAAGCGTTGTCCGGAATTACTGGGCGTAAAGAGCTCGTAGGC
GGTTTGTCGCGTCGTCTGTGAAAACTCACAGCTCAACCTCGAGCTTGCAGGCGATACGGGCAGACTTGAG
TACTGCAGGGGAGACTGGAATTCCTGGTGTAGCGGTGAAATGCGCAGATATCAGGAGGAACACCGGTGG
CGAAGGCG-GGTCTCTGGGCAGTAACTGACGCTGAGGAGCGAAAGCGTGGGTAGCAAACAGGATTAGATA
CCCTGGTAGTCCACGCCGTAAACGGTGGGCGCTAGGTGTGGGTTTCCTTCCACGGGATCCGTGCCGTAG
NTAACGCATTAAGCGCCCCGCCTGGGGAGTACGGCCGCAAGGTTAAAACTCAAAGGAATTGACGGGGGC
CCGCACAAGCGGCGGAGCATGTGGATTAATTCGATGCAACGCGAAGAACCTTACCTGGGTTTGACATATA
CCGGAAAGCCGTAGAGATACC—GC—CCCCCTTGTGGTCG-GTATACAGGTGGTGCATGGCTGTCGTCAG
CTCGTGTCGTGAGATGTTGGGTTAAGTCCCGCAACGAGCGCAACCCTTGTCTTATGTTGCCAGCA-
CGTAATGGTGGGGACTCGTAAGAGACTGCCGGGGTCAACTCGGAGGAAGGTGGGGACGACGTCAAGTCA
TCATGCCCCTTATGTCCAGGGCTTCACACATGCTACAATGGCCGGTACAGAGGGCTGCGATACCGTGAGG
TGGAGCGAATCCCTT-AAAGCCGGTCTCAGTTCGGATCGGGGTCTGCAACTCGACCCCGTGAAGTCGGAG
TCGCTAGTAATCGCAGATCAGCAACGCTGCGGTGAATACGTTCCCGGGCCTTGTACACACCGCCCGTCAC
GTCATGAAAGTCGGTAACACCCGAAGCCGGTGGCCTAACCCCTTGTGGGAGGGAGCCGTCGAAGGTGGG
ATCGGCGATTGGGACGAAGTCGTAACAAGGTAGCCGTACCGGAAG——————————

FIG. 4 (continued)

R. opacus DSM 43206T (1) ————————AGGACGAACGCTGGCGGCGTGCTTAACACATGCAAGTCGAGCGGTAAGGCCC—TT
CGG—GGTACACGAGCGGCGAACGGGTGAGTAACACGTGGGTGATCTGCCCTGCACTTCGGGATAAGCCT
GGGAAACTGGGTCTAATACCGGATATGACCTTCGGCTGCATGG-CTGAGGGTGGAAAGGTTTACTGGTGC
AGGATGGGCCCGCGGCCTATCAGCTTGTTGGTGGGGTAATGGCCTACCAAGCCGACGACGGGTAGCCGA
CCTGAGAGGGTGACCGGCCACACTGGGACTGAGACACGGCCCAGACTCCTACGGGAGGCAGCAGTGGG
GAATATTGCACAATGGGCGAAAGCCTGATGCAGCGACGCCGCGTGAGGGATGACGGCCTTCGGGTTGTA
AACCTCTTTCAGCAGGGACGAA——————GCGAAAGTGACGGTACCTGCAGAAGAAGCACCGGCCAA
CTACGTGCCAGCAGCCGCGGTAATACGTAGGGTGCAAGCGTTGTCCGGAATTACTGGGCGTAAAGAGCTC
GTAGGCGGTTTGTCGCGTCGTCTGTGAAAACTCANAGCTCAACCTCGAGCTTGCAGGCGATACGGGCAGA
CTTGAGTACTGCAGGGGAGACTGGAATTCCTGGTGTAGCGGTGAAATGCGCAGATATCAGGAGGAACACC
GGTGGCGAAGGCG-GGTCTCTGGGCAGTAACTGACGCTGAGGAGCGAAAGCGTGGGTAGCAAACAGGAT
TAGATACCCTGGTAGTCCACGCCGTAAACGGTGGGCGCTAGGTGTGGGTTTCCTTCCACGGGATCCGTGC
CGTAGCTAACGCATTAAGCGCCCCGCCTGGGGAGTACGGCCGCAAGGCTAAAACTCAAAGGAATTGACG
GGGGCCCGCACAAGCGGCGGAGCATGTGGATTAATTCGATGCAACGCGAAGAACCTTACCTGGGTTTGAC
ATATACCGGAAAGCCGTAGAGATACG—GC—CCCCCTTGTGGTCG—GTATACAGGTGGTGCATGGCTGTC
GTCAGCTCGTGTCGTGAGATGTTGGGTTAAGTCCCGCAACGAGCGCAACCCTTGTCTTATGTTGCCAGCA-
CGTAATGGTGGGGACTCGTAAGAGACTGCCGGGGTCAACTCGGAGGAAGGTGGGGACGACGTCAAGTCA
TCATGCCCCTTATGTCCAGGGCTTCACACATGCTACAATGGCCGGTACAGAGGGCTGCGATACCGTGAGG
TGGAGCGAATCCCTT-AAAGCCGGTCTCAGTTCGGATCGGGGTCTGCAACTCGACCCCGTGAAGTCGGAG
TCGCTAGTAATCGCAGATCAGCAACGCTGCGGTGAATACGTTCCCGGGCCTTGTACACACCGCCCGTCAC
GTCATGAAAGTCGGTAACACCCGAAGCCGGTGGCCTAACCCCTTGTGGGAGGGAGCCGTCGAAGGTGGG
ATCGGCGATTGGGACGAAGTCGTAACAAGGTAGCCGTACCGGAAGG———————

Cupriavidus necator (1) ——————————ACG-TGGCGGCATGCCTTACACATGCAAGTCGAACGGCA—GCGCGGACTTCG
GTCTGGCGG-CGAGTGGCGAACGGGTGAGTAATACATCGG-AACGTACCCTGTTGTGGGGGATAACTAGTC
GAAAGATTAGCTAATACCGCATACGACCTGAGGGTGAAAGT—GGGGGACCGCAAGGCCTCACGCAGCAG
GAGCGGCCGATGTCTGATTAGCTAGTTGGTGGGGTAAAGGCCCACCAAGGCGACGATCAGTAGCTGGTCT
GAGAGGACGATCAGCCACACTGGGACTGAGACACGGCCCAGACTCCTACGGGAGGCAGCAGTGGGGAAT
TTTGGACAATGGGGGCAACCCTGATCCAGCAATGCCGCGTGTGTGAAGAAGGCCTTCGGGTTGTAAAGCA
CTTTTGTCCGGAAAGAAATCGCGCTGGTTAATACCT-GCGTGA-TGACGGTACCGGAAGAATAAGCACCGG
CTAACTACGTGCCAGCAGCCGCGGTAATACGTAGGGTGCGAGCGTTAATCGGAATTACTGGGCGTAAAGC
GTGCGCAGGCGGTTTTGTAAGACAGGCGTGAAATCCCCGGGCTTAACCTGGGAATTGCGCTTGTGACTGC
AAGGCTAGAGTGCGTCAGAGGGGGTAGAATTCCACGTGTAGCAGTGAAATGCGTAGAGATGTGGAGGA
ATACCGATGGCGAAGGCGAGCCCCCTGGACCTTGACTGACGCTCATGCACGAAAGCGTGGGGAGCAAAC
AGGATTAGATACCCTGGTAGTCCACGCCCTAAACGATGTCAACTAGTTGTTGGGA—TTCATTTTCTCAGTA
ACGTAGCTAACGCGTGAAGTTGACCGCCTGGGGAGTACGGCTGCAAGATTAAAACTCAAAGGAATTGACG
GGGACCCGCACAAGCGGTGGATGATGTGGATTAATTCGATGCAACGCGAAAAACCTTACCTACCCTTGAC
ATGC—CCTAACGAAGCAGAGATGCATTAGTGCCCGCAAAGGGAAAGTGGGACACAGGTGCTGCATGGCT
GTCGTCAGCTCGTGTCGTGAGATGTTGGGTTAAGTCCCGCAACGAGCGCAACCCTTGTCTCTAGTTGCCTA
CGC—AA—GAGCACTCTAGAGAGACTGCCGGTGACAAACGGAGGAAGGTGGGGATGACGTCAAGTCCT
CATGGCCCTTATGGGTAGGGCTTCACACGTCATACAATGGTGCGTACAGAGGGTTGCCAACCCGCGAGGG
GGAGCTAATCCCAG-AAAACGCATCGTAGTCGGATCGTAGTCTGCAACTCGACTACGTGAAGCTGGAATC
GCTAGTAATCGCGGATCAGCAT-GCCGCGGTGAATACGTTCCCGGGTCTTGTACACACCGCCCGTCACAC
CATGGGAGTGGGTTTTGCCAGAAGTAGTTAGCCTAACCGC—AAGGAGGGCGATTACCACGGCAGGGTTC
ATGACTGGGGTGAAGTCGTAACAAGGT——————————

Ralstonia sp. HB1

(1) ——AGTTTGATCCTGGCTCAGATTGAACGCTGGCGGCATGCCTTACACATGCAAGTCGAACGGCA-G
CGCGGACTTCGGTCTGGCGG-CGAGTGGCGAACGGGTGAGTAATACATCGG-AACGTACCCTGTTGTGGG
GGATAACTAGTCGAAAGATTAGCTAATACCGCATACGACCTGAGGGTGAAAGC—GGGGGACCGTAAGGCC
TCGCGCAGCAGGAGCGGCCGATGTCTGATTAGCTAGTTGGTGGGGTAAAGGCCCACCAAGGCGACGATC
AGTAGCTGGTCTGAGAGGACGATCAGCCACACTGGGACTGAGACACGGCCCAGACTCCTACGGGAGGCA
GCAGTGGGGAATTTTGGACAATGGGGGCAACCCTGATCCAGCAATGCCGCGTGTGTGAAGAAGGCCTTC
GGGTTGTAAAGCACTTTTGTCCGGAAAGAAAACGCTCTGGTTAATACCTGGAGTGGATGACGGTACCGGA

FIG. 4 (continued)

AGAATAAGCACCGGCTAACTACGTGCCAGCAGCCGCGGTAATACGTAGGGTGCGAGCGTTAATCGGAATT
ACTGGGCGTAAAGCGTGCGCAGGCGGTTTTGTAAGACAGGCGTGAAATCCCCGAGCTCAACTTGGGAATT
GCGCTTGTGACTGCAAGGCTAGAGTATGTCAGAGGGGGGTAGAATTCCACGTGTAGCAGTGAAATGCGTA
GAGATGTGGAGGAATACCGATGGCGAAGGCA-GCCCCCTGGGACGTCACTGACGCTCATGCACGAAAGC
GTGGGGAGCAAACAGGATTAGATACCCTGGTAGTCCACGCCCTAAACGATGTCAACTAGTTGTTGGGG---A
TTCATTTCTTCAGTAACGTAGCTAACGCGTGAAGTTGACCGCCTGGGGAGTACGGTCGCAAGATTAAAACT
CAAAGGAATTGACGGGGACCCGCACAAGCGGTGGATGATGTGGATTAATTCGATGCAACGCGAAAAACCT
TACCTACCCTTGACATGC-CACTAACGAAGCAGAGATGCATCAGGTGCCCGAAAGGGAAAGT-GGACACAG
GTGCTGCATGGCTGTCGTCAGCTCGTGTCGTGAGATGTTGGGTTAAGTCCCGCAACGAGCGCAACCCTTA
TCTTTAGTTGCTACGC-----AA---GGGCACTCTAGAGAGACTGCCGGTGACAAACCGGAGGAAGGTGGGGAT
GACGTCAAGTCCTCATGGCCCTTATGGGTAGGGCTTCACACGTCATACAATGGTGCGTACAGAGGGTTGC
CAACCCGCGAGGGGGAGCTAATCCCAG-AAAACGCATCGTAGTCCGGATCGCAGTCTGCAACTCGACTGC
GTGAAGCTGGAATCGCTAGTAATCGCGGATCAGCAT-GCCGCGGTGAATACGTTCCCGGGTCTTGTACACA
CCGCCCGTCACACCATGGGAGTGGGTTTTGCCAGAAGTAGTTAGCCTAACCGC--AAGGAGGGCGATTACC
ACGGCAGGGTTCATGACTGGGGTGAAGTCGT-------------------------

G.alkanivorans (1) -------------GCTCAGGACGAACGCTGGCGGCGTGCTTAACACATGCAAGTCGAACGGAAAGGCCCA
GCTTGCTG---GGTACTCGAGTGGCGAACGGGTGAGTAACACGTGGGTGATCTGCCCTGAACTTTGGGATA
AGCCTGGGAAACTGGGTCTAATACCGGATATGACCTTGGAGTGCATGCTCTG-GGGTGGAAAGCTTTTGCG
GTTCAGGATGGGCCCGCGGCCTATCAGCTTGTTGGTGGGGTAATGGCCTACCAAGGCGACGACGGGTAG
CCGACCTGAGAGGGTGATCGGCCACACTGGGACTGAGACACGGCCCAGACTCCTACGGGAGGCAGCAGT
GGGGAATATTGCACAATGGGCGCAAGCCTGATGCAGCGACGCCGCGTGAGGGATGACGGCCTTCGGGTT
GTAAACCTCTTTCACCAGGGACGAA---------------GCGCAAGTGACGGTACCTGGAGAAGAAGCACCGGC
CAACTACGTGCCAGCAGCCGCGGTAATACGTAGGGTGCGAGCGTTGTCCGGAATTACTGGGCGTAAAGA
GCTCGTAGGCGGTTTGTCGCGTCGTCTGTGAAATTCTGCAACTCAATTGTAGGCGTGCAGGCGATACGGG
CAGACTTGAGTACTACAGGGGAGACTGGAATTCCTGGTGTAGCGGTGAAATGCGCAGATATCAGGAGGAA
CACCGGTGGCGAAGGCG-GGTCTCTGGGTAGTAACTGACGCTGAGGAGCGAAAGCGTGGGTAGCGAACA
GGATTAGATACCCTGGTAGTCCACGCCGTAAACGGTGGGTACTAGGTGTGGGGCTCATTTCACGAGTTCC
GTGCCGTAGCTAACGCATTAAGTACCCCGCCTGGGGAGTACGGCCGCAAGGCTAAAACTCAAAGGAATTG
ACGGGGGCCCGCACAAGCGGCGGAGCATGTGGATTAATTCGATGCAACGCGAAGAACCTTACCTGGGTTT
GACATACACCAGACGCATGTAGAGATACA---TG--TTCCCTTGTGGTTG--GTGTACAGGTGGTGCATGGCTG
TCGTCAGCTCGTGTCGTGAGATGTTGGGTTAAGTCCCGCAACGAGCGCAACCCTTGTCCTGTATTGCCAG
CG-GGTTATGCCGGGGACTTGCAGGAGACTGCCGGGGTCAACTCGGAGGAAGGTGGGGATGACGTCAAG
TCATCATGCCCCTTATGTCCAGGGCTTCACACATGCTACAATGGCTGGTACAGAGGGCTGCGATACCGTG
AGGTGGAGCGAATCCCTT-AAAGCCAGTCTCAGTTCGGATTGGGGTCTGCAACTCGACCCCATGAAGTCG
GAGTCGCTAGTAATCGCAGATCAGCAACGCTGCGGTGAATACGTTCCCGGGCCTTGTACACACCGCCCGT
CACGTCATGAAAGTCGGTAACACCCGAAGCCGGTGGCCTAACCCCTTGTGGGAGGGAGCTGTCGAAGGT
GGGATCGGCGATTGGGACGAAGTCGTAACAAGGTAGCCGTACCGGAAGGTGCGG----------------

G. CC-MJ-39a (1) ----------GATCATGGCTCAGGACGAACGCTGGCGGCGTGCTTAACACATGCAAGTCGAACGGAAAGGC
CCG--CTTGCG---GGTACTCGAGTGGCGAACGGGTGAGTAACACGTGGGTGATCTGCCCTGGACTCTGGGA
TAAGCCTGGGAAACTGGGTCTAATACCGGATATGACCTTACATCGCATGG-TGTTTGGTGGAAAGCTTTTGC
GGTTCAGGATGGGCCCGCGGCCTATCAGCTTGTTGGTGGGGTAATGGCCTACCAAGGCGACGACGGGTA
GCCGACCTGAGAGGGTGATCGGCCACACTGGGACTGAGACACGGCCCAGACTCCTACGGGAGGCAGCA
GTGGGGAATATTGCACAATGGGCGCAAGCCTGATGCAGCGACGCCGCGTGAGGGATGACGGCCTTCGGG
TTGTAAACCTCTTTCACCAGGGACGAA---------------GCGCAAGTGACGGTACCTGGAGAAGAAGCACCG
GCCAACTACGTGCCAGCAGCCGCGGTAATACGTAGGGTGCGAGCGTTGTCCGGAATTACTGGGCGTAAA
GAGCTCGTAGGCGGTTTGTCGCGTCGTCTGTGAAATTCTGCAACTCAATTGTAGGCGTGCAGGCGATACG
GGCAGACTTGAGTACTACAGGGGAGACTGGAATTCCTGGTGTAGCGGTGAAATGCGCAGATATCAGGAGG
AACACCGGTGGCGAAGGCG-GGTCTCTGGGTAGTAACTGACGCTGAGGAGCGAAAGCGTGGGTAGCGAA
CAGGATTAGATACCCTGGTAGTCCACGCCGTAAACGGTGGGTACTAGGTGTGGGGCTCATTTCACGAGTT
CCGTGCCGTAGCTAACGCATTAAGTACCCCGCCTGGGGAGTACGGCCGCAAGGCTAAAACTCAAAGGAAT
TGACGGGGGCCCGCACAAGCGGCGGAGCATGTGGATTAATTCGATGCAACGCGAAGAACCTTACCTGGG

FIG. 4 (continued)

TTTGACATACACCAGAAAGCTATAGAGATATA---GC--CCCCCTTGTGGTTG--GTGTACAGGTGGTGCATGG
CTGTCGTCAGCTCGTGTCGTGAGATGTTGGGTTAAGTCCCGCAACGAGCGCAACCCTTGTCCTGTATTGC
CAGCG-GGTTATGCCGGGGACTTGCAGGAGACTGCCGGGGTCAACTCGGAGGAAGGTGGGGATGACGTC
AAGTCATCATGCCCCTTATGTCCAGGGCTTCACACATGCTACAATGGCTGGTACAGAGGGCTGCGATACC
GTGAGGTGGAGCGAATCCCTT-AAAGCCAGTCTCAGTTCGGATTGGGGTCTGCAACTCGACCCCATGAAGT
CGGAGTCGCTAGTAATCGCAGATCAGCAACGCTGCGGTGAATACGTTCCCGGGCCTTGTACACACCGCCC
GTCACGTCATGAAAGTCGGTAACACCCGAAGCCGGTGGCCTAACCCCTTGTGGGAGGGAGCTGTCGAAG
GTGGGATCGGCGATTGGGACGAAGTCGTAACAAGGTAGCCGTACCGGAAGGTGCGG-----------

M. fortuitum (1) ----------TTGATCCTGGCTCAGGACGAACGCTGGCGGCGTGCTTAACACATGCAAGTCGAACGGAAAGG
CCC----TTCGG---GGTACTCGAGTGGCGAACGGGTGAGTAACACGTGGGTGATCTGCCCTGCACTTTGGGA
TAAGCCTGGGAAACTGGGTCTAATACCGAATATGACCACGCGCTTCATGG-TGTGTGGTGGAAAGCTTTTG
CGGTGTGGGATGGGCCCGCGGCCTATCAGCTTGTTGGTGGGGTAATGGCCTACCAAGGCGACGACGGGT
AGCCGGCCTGAGAGCCTGGGAAACTGGGTCTAATACCGAATATGACCACGCGCTTCATGG-TGTGTGGTG
GAAAGCTTTTGCGGTGTGGGATGGGCCCGCGGCCTATCAGCTTGTTGGTGGGTAATGGCCTACCAAGG
CGACGACGGGTAGCCGGCCTGAGAGGGTGACCGGCCACACTGGGACTGAGATACGGCCCAGACTCCTAC
GGGAGGCAGCAGTGGGGAATATTGCACAATGGGCGCAAGCCTGATGCAGCGACGCCGCGTGAGGGATG
ACGGCCTTCGGGTTGTAAACCTCTTTCAATAGGGACGAA-----------------GCGCAAGTGACGGTACCTATAG
AAGAAGGACCGGCCAACTACGTGCCAGCAGCCGCGGTAATACGTAGGGTCCGAGCGTTGTCCGGAATTA
CTGGGCGTAAAGAGCTCGTAGGTGGTTTGTCGCGTTGTTCGTGAAAACTCACAGCTTAACTGTGGGCGTG
CGGGCGATACGGGCAGACTAGAGTACTGCAGGGGAGACTGGAATTCCTGGTGTAGCGGTGGAATGCGCA
GATATCAGGAGGAACACCGGTGGCGAAGGCG-GGTCTCTGGGCAGTAACTGACGCTGAGGAGCGAAAGC
GTGGGGAGCGAACAGGATTAGATACCCTGGTAGTCCACGCCGTAAACGGTGGGTACTAGGTGTGGGTTTC
CTTCCTTGGGATCCGTGCCGTAGCTAACGCATTAAGTACCCCGCCTGGGGAGTACGGCCGCAAGGCTAAA
ACTCAAAGGAATTGACGGGGGCCCGCACAAGCGGCGGAGCATGTGGATTAATTCGATGCAACGCGAAGA
ACCTTACCTGGGTTTGACATGCACAGGACGACTGCAGAGATGTG---GT--TTCCCTTGTGGCCT--GTGTGCA
GGTGGTGCATGGCTGTCGTCAGCTCGTGTCGTGAGATGTTGGGTTAAGTCCCGCAACGAGCGCAACCCTT
GTCTCATGTTGCCAGCA-CGTTATGGTGGGGACTCGTGAGAGACTGCCGGGGTCAACTCGGAGGAAGGTG
GGGATGACGTCAAGTCATCATGCCCCTTATGTCCAGGGCTTCACACATGCTACAATGGCCGGTACAAAGG
GCTGCGATGCCGTGAGGTGGAGCGAATCCTTTCAAAGCCGGTCTCAGTTCGGATCGGGGTCTGCAACTCG
ACCCCGTGAAGTCGGAGTCGCTAGTAATCGCAGATCAGCAACGCTGCGGTGAATACGTTCCCGGGCCTTG
TACACACCGCCCGTCACGTCATGAAAGTCGGTAACACCCGAAGCCGGTGGCCTAACCC-TTGTGG-AGGGA
GCCGTCGAAGGTGGGATCGGCGATTGGGACGAAGTCGTAACAAGGTAGCCGTACCGGAAGGTGCGGCTG
GATCACCTCCTT---

M. parafortuitum (1) --------------------CGAACGCTGGCGGCGTGCTTAACACATGCAAGTCGAACGGAAAGGCCC---TTCG
G---GGTACTCGAGTGGCGAACGGGTGAGTAACACGTGGGTGATCTGCCCTGCACTTTGGGATAAGCCTGG
GAAACTGGGTCTAATACCGAATATGATCATTGGCTTCCTGG-CTGGTGGTGGAAAGCTTTTGCGGTGTGGG
ATGGGCCCGCGGCCTATCAGCTTGTTGGTGGGGTAATGGCCTACCAAGGCGACGACGGGTAGCCGGCCT
GAGAGGGTGACCGGCCACACTGGGACTGAGATACGGCCCAGACTCCTACGGGAGGCAGCAGTGGGGAA
TATTGCACAATGGGCGCAAGCCTGATGCAGCGACGCCGCGTGAGGGATGACGGCCTTCGGGTTGTAAAC
CTCTTTCGCCAGGGACGAA----------------GCGCAAGTGACGGTACCTGGAGAAGAAGGACCGGCCAACTA
CGTGCCAGCAGCCGCGGTAATACGTAGGGTCCGAGCGTTGTCCGGAATTACTGGGCGTAAAGAGCTCGT
AGGTGGTTTGTCGCGTTGTTCGTGAAAACTCACAGCTTAACTGTGGGCGTGCGGGCGATACGGGCAGACT
AGAGTACTGCAGGGGAGACTGGAATTCCTGGTGTAGCGGTGGAATGCGCAGATATCAGGAGGAACACCG
GTGGCGAAGGCG-GGTCTCTGGGCAGTAACTGACGCTGAGGAGCGAAAGCGTGGGGAGCGAACAGGATT
AGATACCCTGGTAGTCCACGCCGTAAACGGTGGGTACTAGGTGTGGGTTCCTTCCTTGGGATCCGTGCC
GTAGCTAACGCATTAAGTACCCCGCCTGGGGAGTACGGCCGCAAGGCTAAAACTCAAAGAAATTGACGGG
GGCCCGCACAAGCGGCGGAGCATGTGGATTAATTCGATGCAACGCGAAGAACCTTACCTGGGTTTGACAT
GCACAGGACGCCGGCAGAGATGTC---GG--TTCCCTTGTGCCCT--GTGTGCAGGTGGTGCATGGCTGTCGT
CAGCTCGTGTCGTGAGATGTTGGGTTAAGTCCCGCAACGAGCGCAACCCTTGTCTCATGTTGCCAGCA-CG
TAATGGTGGGGACTCGTGAGAGACTGCCGGGGTCAACTCGGAGGAAGGTGGGGATGACGTCAAGTCATC
ATGCCCCTTATGTCCAGGGCTTCACACATGCTACAATGGCCGGTACAAAGGGCTGCGATGCCGTGAGGTG
GAGCGAATCCTTTCAAAGCCGGTCTCAGTTCGGATCGGGGTCTGCAACTCGACCCCGTGAAGTCGGAGTC
GCTAGTAATCGCAGATCAGCAACGCTGCGGTGAATACGTTCCCGGGCCTTGTACACACCGCCCGTCACGT

FIG. 4 (continued)

CATGAAAGTCGGTAACACCCGAAGCCGGTGGCCTAACCCCTTGTGGGAGGGAGCCGTCGAAGGTGGGAT
CGGCGATTGGGACGAAGTCGTAACAAGGTAGCCG————————————

M. sphagni (1) ——GAGTTTGATCCTGGCTCAGGACGAACGCTGGCGGCGTGCTTAACACATGCAAGTCGAACGGAAA
GGCCC—TTCGG—GGTACTCGAGTGGCGAACGGGTGAGTAACACGTGGGTGATCTGCCCTGCACTTTGG
GATAAGCCTGGGAAACTGGGTCTAATACCGAATAGGACCGCATGCTTCATGG-TGTGTGGTGGAAAGCTTT
TGCGGTGTGGGATGGGCCCGCGGCCTATCAGCTTGTTGGTGGGGTAATGGCCTACCAAGGCGACGACGG
GTAGCCGGCCTGAGAGGGTGTCCGGCCACACTGGGACTGAGATACGGCCCAGACTCCTACGGGAGGCA
GCAGTGGGGAATATTGCACAATGGGCGCAAGCCTGATGCAGCGACGCCGCGTGAGGGATGACGGCCTTC
GGGTTGTAAACCTCTTTCAGCAGGGACGAA———————————GCGCAAGTGACGGTACCTGTAGAAGAAGCA
CCGGCCAACTACGTGCCAGCAGCCGCGGTAATACGTAGGGTGCGAGCGTTGTCCGGAATTACTGGGCGT
AAAGAGCTCGTAGGTGGTTTGTCGCGTTGTTCGTGAAAACTCACAGCTCAACTGTGGGCGTGCGGGCGAT
ACGGGCAGACTTGAGTACTGCAGGGGAGACTGGAATTCCTGGTGTAGCGGTGGAATGCGCAGATATCAG
GAGGAACACCGGTGGCGAAGGCG-GGTCTCTGGGCAGTAACTGACGCTGAGGAGCGAAAGCGTGGGGAG
CGAACAGGATTAGATACCCTGGTAGTCCACGCCGTAAACGGTGGGTACTAGGTGTGGGTTTCCTTCCTTG
GGATCCGTGCCGTAGCTAACGCATTAAGTACCCCGCCTGGGGAGTACGGCCGCAAGGCTAAAACTCAAAG
AAATTGACGGGGGCCCGCACAAGCGGCGGAGCATGTGGATTAATTCGATGCAACGCGAAGAACCTTACCT
GGGTTTGACATGCACAGGACGCCGGCAGAGATGTC—GG—TTCCCTTGTGGCCT—GTGTGCAGGTGGTGC
ATGGCTGTCGTCAGCTCGTGTCGTGAGATGTTGGGTTAAGTCCCGCAACGAGCGCAACCCTTGTCTCATG
TTGCCAGCA-CGTAATGGTGGGGACTCGTGAGAGACTGCCGGGGTCAACTCGGAGGAAGGTGGGGATGA
CGTCAAGTCATCATGCCCCTTATGTCCAGGGCTTCACACATGCTACAATGGCCGGTACAAAGGGCTGCGA
TGCCGTGAGGTGGAGCGAATCCTTTCAAAGCCGGTCTCAGTTCGGATCGGGGTCTGCAACTCGACCCCGT
GAAGTCGGAGTCGCTAGTAATCGCAGATCAGCAACGCTGCGGTGAATACGTTCCCGGGCCTTGTACACAC
CGCCCGTCACGTCATGAAAGTCGGTAACACCCGAAGCCGGTGGCCTAACCCCTTGTGGGAGGGAGCCGT
CGAAGGTGGGATCGGCGATTGGGACGAAGTCGTAACAAGGTAGCC———————————

N. farcinica (1) ———————————GACGAACGCTGGCGGCGTGCTTAACACATGCAAGTCGAGCGGTAAGGCCC—TTC
GG—GGTACACGAGCGGCGAACGGGTGAGTAACACGTGGGTGATCTGCCCTGTACTTCGGGATAAGCCTG
GGAAACTGGGTCTAATACCGGATATGACCTTACATCGCATGG-TGTTTGGTGGAAAGATTTATCGGTACAG
GATGGGCCCGCGGCCTATCAGCTTGTTGGTGGGGTAATGGCCTACCAAGGCGACGACGGGTAGCCGGCC
TGAGAGGGCGACCGGCCACACTGGGACTGAGACACGGCCCAGACTCCTACGGGAGGCAGCAGTGGGGA
ATATTGCACAATGGGCGAAAGCCTGATGCAGCGACGCCGCGTGAGGGATGACGGCCTTCGGGTTGTAAA
CCTCTTTCGACAGGGACGAA———————————GCGCAAGTGACGGTACCTGTAGAAGAAGCACCGGCCAACT
ACGTGCCAGCAGCCGCGGTAATACGTAGGGTGCGAGCGTTGTCCGGAATTACTGGGCGTAAAGAGCTTGT
AGGCGGTTTGTCGCGTCGTCCGTGAAAACTTGGGGCTCAACCCCAAGCTTGCGGGCGATACGGGCAGAC
TTGAGTACTGCAGGGGAGACTGGAATTCCTGGTGTAGCGGTGAAATGCGCAGATATCAGGAGGAACACCG
GTGGCGAAGGCG-GGTCTCTGGGCAGTAACTGACGCTGAGGAGCGAAAGCGTGGGTAGCGAACAGGATT
AGATACCCTGGTAGTCCACGCCGTAAACGGTGGGCGCTAGGTGTGGGTTTCCTTCCACGGGATCCGTGCC
GTAGCTAACGCATTAAGCGCCCCGCCTGGGGAGTACGGCCGCAAGGCTAAAACTCAAAGGAATTGACGG
GGGCCCGCACAAGCGGCGGAGCATGTGGATTAATTCGATGCAACGCGAAGAACCTTACCTGGGTTTGACA
TACACCGGAAACCTGCAGAGATGTA—GG—CCCCCTTGTGGTCG—GTGTACAGGTGGTGCATGGCTGTCG
TCAGCTCGTGTCGTGAGATGTTGGGTTAAGTCCCGCAACGAGCGCAACCCTTGTCCTGTGTTGCCAGCG-C
GTTATGGCGGGGACTCGCAGGAGACTGCCGGGGTCAACTCGGAGGAAGGTGGGGACGACGTCAAGTCAT
CATGCCCCTTATGTCCAGGGCTTCACACATGCTACAATGGCCGGTACAGAGGGCTGCGATACCGTGAGGT
GGAGCGAATCCCTT-AAAGCCGGTCTCAGTTCGGATCGGGGTCTGCAACTCGACCCCGTGAAGTTGGAGT
CGCTAGTAATCGCAGATCAGCAACGCTGCGGTGAATACGTTCCCGGGCCTTGTACACACCGCCCGTCACG
TCATGAAAGTCGGTAACACCCGAAGCCGGTGGCCTAACCCCTTGTGGGAGGGAGCCGTCGAAGGTGGGA
TCGGCGATTGGGACGAAGTCGTAACAAGGTAGCCGTACCGGAAGGTGCGGCTGGATCACCTCCTTTCT- N. sp (1) ——GAGTTTGATCCTGGCTCAGGACGAACGCTGGCGGCGTGCTTAACACATGCAAGTCGAGCGGTAA
GGCCC—TTCGG—GGTACACGAGCGGCGAACGGGTGAGTAACACGTGGGTGATCTGCCCTGTACTTCGG
GATAAGCCTGGGAAACTGGGTCTAATACCGGATATGACCTTACATCGCATGG-TGTTTGGTGGAAAGATTTA

FIG. 4 (continued)

TCGGTACAGGATGGGCCCGCGGCCTATCAGCTTGTTGGTGGGGTAATGGCCTACCAAGGCGACGACGGG
TAGCCGGCCTGAGAGGGCGACCGGCCACACTGGGACTGAGACACGGCCCAGACTCCTACGGGAGGCAG
CAGTGGGGAATATTGCACAATGGGCGAAAGCCTGATGCAGCGACGCCGCGTGAGGGATGACGGCCTTCG
GGTTGTAAACCTCTTTCGACAGGGACGAA—————————GCGCAAGTGACGGTACCTGTAGAAGAAGCACC
GGCCAACTACGTGCCAGCAGCCGCGGTAATACGTAGGGTGCGAGCGTTGTCCGGAATTACTGGGCGTAA
AGAGCTTGTAGGCGGTTTGTCGCGTCGTCCGTGAAAACTTGGGGCTCAACCCCAAGCTTGCGGGCGATAC
GGGCAGACTTGAGTACTGCAGGGGAGACTGGAATTCCTGGTGTAGCGGTGAAATGCGCAGATATCAGGA
GGAACACCGGTGGCGAAGGCG-GGTCTCTGGGCAGTAACCGACGCTGAGAAGCGAAAGCGTGGGTAGCG
AACAGGATTAGATACCCTGGTAGTCCACGCCGTAAACGGTGGGCGCTAGGTGTGGGTTTCCTTCCACGGG
ATCCGTGCCGTAGCTAACGCATTAAGCGCCCCGCCTGGGGAGTACGGCCGCAAGGCTAAAACTCAAAGG
AATTGACGGGGGCCCGCACAAGCGGCGGAGCATGTGGATTAATTCGATGCAACGCGAAGAACCTTACCTG
GGTTTGACATACACCGGAAACCTGCAGAGATGTA---GG--CCCCCTTGTGGTCG--GTGTACAGGTGGTGCAT
GGCCGTCGTCAGCTCGTGTCGTGAGATGTTGGGTTAAGTCCCGCAACGAGCGCAACCCTTGTCCTGTGTT
GCCAGCG-CGTTATGGCGGGGACTCGCAGGAGACTGCCGGGGTCAACTCGGAGGAAGGTGGGGACGAC
GTCAAGTCATCATGCCCCTTATGTCCAGGGCTTCACACATGCTACAATGGCCGGTACAGAGGGCTGCGAT
ACCGTGAGGTGGAGCGAATCCCTT-AAAGCCGGTCTCAGTTCGGATCGGGGTCTGCAACTCGACCCCGTG
AAGTTGGAGTCGCTAGTAATCGCAGATCAGCAACGCTGCGGTGAATACGTTCCCGGGCCTTGTACACACC
GCCCGTCACGTCATGAAAGTCGGTAACACCCGAAGCCGGTGGCCTAACCCCTTGTGGGAGGGAGCCGTC
GAAGGTGGGATCGGCGATTGGGACGAAGTCGTAACAAGGTAGCCGTACCGGAAGGTGCGGCTGGATCAC
CTCCTTTCT-

R.rhodochrous CG30

(1) —————GAGTTTGAATCTGGCTCAGGACGAACGCTGGCGGCGTGCTTAACACATGCAAGTCGAACGATGA
AGCCCAGCTTGCTG---GGTGGATTAGTGGCGAACGGGTGAGTAACACGTGGGTGATCTGCCCTGCACTCT
GGGATAAGCCTGGGAAACTGGGTCTAATACCGGATATGACCTCTTGCTGCATGG-CGAGGGGTGGAAAGT
TTTTC-GGTGCAGGATGAGCCCGCGGCCTATCAGCTTGTTGGTGGGGTAATGGCCTACCAAGGCGACGAC
GGGTAGCCGGCCTGAGAGGGCGACCGGCCACACTGGGACTGAGACACGGCCCAGACTCCTACGGGAGG
CAGCAGTGGGGAATATTGCACAATGGGCGAAAGCCTGATGCAGCGACGCCGCGTGAGGGATGACGGCCT
TCGGGTTGTAAACCTCTTTCAGCAGGGACGAA—————————GCGAAAGTGACGGTACCTGCAGAAGAAG
CACCGGCCAACTACGTGCCAGCAGCCGCGGTAATACGTAGGGTGCGAGCGTTGTCCGGAATTACTGGGC
GTAAAGAGCTCGTAGGCGGTTTGTCGCGTCGTCTGTGAAATCCCGCAGCTCAACTGCGGGCTTGCAGGCG
ATACGGGCAGACTCGAGTACTGCAGGGGAGACTGGAATTCCTGGTGTAGCGGTGAAATGCGCAGATATCA
GGAGGAACACCGGTGGCGAAGGCG-GGTCTCTGGGCAGTAACTGACGCTGAGGAGCGAAAGCGTGGGTA
GCGAACAGGATTAGATACCCTGGTAGTCCACGCCGTAAACGGTGGGCGCTAGGTGTGGGTTTCCTTCCAC
GGGATCCGTGCCGTAGCCAACGCATTAAGCGCCCCGCCTGGGGAGTACGGCCGCAAGGCTAAAACTCAA
AGGAATTGACGGGGGCCCGCACAAGCGGCGGAGCATGTGGATTAATTCGATGCAACGCGAAGAACCTTA
CCTGGGTTTGACATGTACCGGACGACTGCAGAGATGTG---GT--TTCCCTTGTGGCCG--GTAGACAGGTGGT
GCATGGCTGTCGTCAGCTCGTGTCGTGAGATGTTGGGTTAAGTCCCGCAACGAGCGCAACCCTTGTCCTG
TGTTGCCAGCA-CGTAATGGTGGGGACTCGCAGGAGACTGCCGGGGTCAACTCGGAGGAAGGTGGGGAC
GACGTCAAGTCATCATGCCCCTTATGTCCAGGGCTTCACACATGCTACAATGGTCGGTACAGAGGGCTGC
GATACCGTGAGGTGGAGCGAATCCCTT-AAAGCCGGTCTCAGTTCGGATCGGGGTCTGCAACTCGACCCC
GTGAAGTCGGTCGCTAGTAATCGCAGATCAGCAACGCTGCGGTGAATACGTTCCCGGGCCTTGTACAC
ACCGCCCGTCACGTCATGAAAGTCGGTAACACCCGAAGCCGGTGGCCTAACCCCTTGTGGGAGGGAGCC
GTCGAAGGTGGGATCGGCGATTGGGACGAAGTCGTAACAAGGTAGCCGTACCGGA—————————

R.coprophilus (1) ——————————CCTGGCTCAGGACGAACGCTGGCGGCGTGCTTAACACATGCAAGTCGAACGATGATGCC
CAGCTTGCTG—GGCGGATTAGTGGCGAACGGGTGAGTAACACGTGGGTGATCTGCCCTGCACTTCGGGA
TAAGCCTGGGAAACTGGGTCTAATACCGGATATGACCATGGGATGCATGT-CCTGTGGTGGAAAGGTTTAC
TGGTGCAGGATGAGCCCGCGGCCTATCAGCTTGTTGGTGGGGTAATGGCCTACCAAGGCGACGACGGGT
AGCCGGCCTGAGAGGGCGACCGGCCACACTGGGACTGAGACACGCCCAGACTCCTACGGGAGGCAGC
AGTGGGGAATATTGCACAATGGGCGAAAGCCTGATGCAGCGACGCCGCGTGAGGGATGACGGCCTTCGG
GTTGTAAACCTCTTTCAGCAGGGACGAA—————————GCGCAAGTGACTGTACCTGCAGAAGAAGCACCG

FIG. 4 (continued)

GCTAACTACGTGCCAGCAGCCGCGGTAATACGTAGGGTGCGAGCGTTGTCCGGAATTACTGGGCGTAAAG
AGTTCGTAGGCGGTTTGTCGCGTCGTGTGTGAAATCCCGCAGCTCAACTGCGGGCTTGCAGGCGATACGG
GCAGACTTGAGTACTGCAGGGGAGACTGGAATTCCTGGTGTAGCGGTGAAATGCGCAGATATCAGGAGGA
ACACCGGTGGCGAAGGCG-GGTCTCTGGGCAGTAACTGACGCTGAGGAACGAAAGCGTGGGTAGCGAAC
AGGATTAGATACCCTGGTAGTCCACGCCGTAAACGGTGGGCGCTAGGTGTGGGTTTCCTTCCACGGGATC
CGTGCCGTAGCTAACGCATTAAGCGCCCCGCCTGGGGAGTACGGCCGCAAGGCTAAAACTCAAAGGAATT
GACGGGGGCCCGCACAAGCGGCGGAGCATGTGGATTAATTCGATGCAACGCGAAGAACCTTACCTGGGT
TTGACATATACCGGACGACTGCAGAGATGTG---GT--TTCCCTTGTGGTCG-GTATACAGGTGGTGCATGGC
TGTCGTCAGCTCGTGTCGTGAGATGTTGGGTTAAGTCCCGCAACGAGCGCAACCCTTGTCTTATGTTGCCA
GCA-CGTAATGGGGGGACTCGTAAGAGACTGCCGGGGTCAACTCGGAGGAAGGTGGGGACGACGTCAA
GTCATCATGCCCCTTATGTCCAGGGCTTCACACATGCTACAATGGTCGGTACAGAGGGCTGCGATACCGT
GAGGTGGAGCGAATCCCTT-AAAGCCGGTCTCAGTTCGGATCGGGGTCTGCAACTCGACCCCGTGAAGTC
GGAGTCGCTAGTAATCGCAGATCAGCAACGCTGCGGTGAATACGTTCCCGGGCCTTGTACACACCGCCCG
TCACGTCATGAAAGTCGGTAACACCCGAAGCCGGTGGCCTAACCCCTTGTGGGAGGGAGCCGTCGAAGG
TGGGATCGGCGATTGGGACGAAGTCGTAACAAGGTAGCCGTACCGG----------

R. triatomae (1) --------------------------GGCGGCGTGCTTAACACATGCAAGTCGAGCGGTAAGGCCT----TTCGG---G
GTACACGAGCGGCGAACGGGTGAGTAACACGTGGGTGATCTGCCCTGCACTCTGGGATAAGCCTGGGAA
ACTGGGTCTAATACCGGATATGACTACCGGCTGCATGGTCTGGTGGTGGAAAGATTTATCGGTGCAGGAT
GGGCCCGCGGCCTATCAGCTTGTTGGTGGGGTAATGGCCTACCAAGGCGACGACGGGTAGCCGACCTGA
GAGGGTGACCGGCCACACTGGGACTGAGACACGGCCCAGACTCCTACGGGAGGCAGCAGTGGGGAATAT
TGCACAATGGGCGAAAGCCTGATGCAGCGACGCCGCGTGAGGGATGACGGCCTTCGGGTTGTAAACCTC
TTTCAACAGGGACGAA------------GCGCAAGTGACGGTACCTGTAGAAGAAGCACCGGCCAACTACGT
GCCAGCAGCCGCGGTAATACGTAGGGTGCGAGCGTTGTCCGGAATTACTGGGCGTAAAGAGCTCGTAGG
CGGTTTGTCGCGTCGTCTGTGAAAACCAGCAGCTCAACTGCTGGCTTGCAGGCGATACGGGCAGACTTGA
GTACTGCAGGGGAGACTGGAATTCCTGGTGTAGCGGTGAAATGCGCAGATATCAGGAGGAACACCGGTG
GCGAAGGCG-GGTCTCTGGGCAGTAACTGACGCTGAGGAGCGAAAGCGTGGGTAGCGAACAGGATTAGA
TACCCTGGTAGTCCACGCCGTAAACGGTGGGCGCTAGGTGTGGGTTTCCTTCCACGGATCCGTGCCGTA
GCTAACGCATTAAGCGCCCCGCCTGGGGAGTACGGCCGCAAGGCTAAAACTCAAAGGAATTGACGGGGG
CCCGCACAAGCGGCGGAGCATGTGGATTAATTCGATGCAACGCGAAGAACCTTACCTGGGTTTGACATAC
ACCGGAAAGCCGTAGAGATACG---GC--CCCCCTTGTGGTCG--GTGTACAGGTGGTGCATGGCTGTCGTCA
GCTCGTGTCGTGAGATGTTGGGTTAAGTCCCGCAACGAGCGCAACCCTTGTCCTGTGTTGCCAGCA-CGTA
ATGGTGGGGACTCGCAGGAGACTGCCGGGGTCAACTCGGAGGAAGGTGGGGACGACGTCAAGTCATCAT
GCCCCTTATGTCCAGGGCTTCACACATGCTACAATGGCCGGTACAGAGGGCTGCGATACCGTGAGGTGGA
GCGAATCCCTT-AAAGCCGGTCTCAGTTCGGATCGGGGTCTGCAACTCGACCCCGTGAAGTCGGAGTCGC
TAGTAATCGCAGATCAGCAACGCTGCGGTGAATACGTTCCCGGGCCTTGTACACACCGCCCGTCACGTCA
TGAAAGTCGGTAACACCCGAAGCCGGTGGCCTAACCCCTTGTGGGAGGGAGCCGTCGAAGGTGGGATCG
GCGATTGGGACGAAGTCGTAACAAGGTAGCCGTACCGGAAGGTGCGGCTGGATCACTTCCTTTCTA N. coeliaca (1) ---------TTTGATCCTGGCTCAGGACGAACGCTGGCGGCGTGCTTAACACATGCAAGTCGAGCGGTAAG
GCCT----TTCGG---GGTACACGAGCGGCGAACGGGTGAGTAACACGTGGGTGATCTGCCCTGCACTTCGGG
ATAAGCCTGGGAAACTGGGTCTAATACCGGATATGACCTCAGGTTGCATGA-CTTGGGGTGGAAAGATTTA
TCGGTGCAGGATGGGCCCGCGGCCTATCAGCTTGTTGGTGGGGTAATGGCCTACCAAGGCGACGACGGG
TAGCCGACCTGAGAGGGTGACCGGCCACACTGGGACTGAGACACGGCCCAGACTCCTACGGGAGGCAG
CAGTGGGGAATATTGCACAATGGGCGAAAGCCTGATGCAGCGACGCCGCGTGAGGGATGACGGCCTTCG
GGTTGTAAACCTCTTTCAGCAGGGACGAA------------GCGCAAGTGACGGTACCTGCAGAAGAAGCAC
CGGCTAACTACGTGCCAGCAGCCGCGGTAATACGTAGGGTGCAAGCGTTGTCCGGAATTACTGGGCGTAA
AGAGTTCGTAGGCGGTTTGTCGCGTCGTTTGTGAAAACCAGCAGCTCAACTGCTGGCTTGCAGGCGATAC
GGGCAGACTTGAGTACTGCAGGGGAGACTGGAATTCCTGGTGTAGCGGTGAAATGCGCAGATATCAGGA
GGAACACCGGTGGCGAAGGCG-GGTCTCTGGGCAGTAACTGACGCTGAGGAACGAAAGCGTGGGTAGCG
AACAGGATTAGATACCCTGGTAGTCCACGCCGTAAACGGTGGGCGCTAGGTGTGGGTT-CCTTCCACGGA

FIG. 4 (continued)

ATCCGTGCCGTAGCTAACGCATTAAGCGCCCCGCCTGGGGAGTACGGCCGCAAGGCTAAAACTCAAAGG
AATTGACGGGGGCCCGCACAAGCGGCGGAGCATGTGGATTAATTCGATGCAACGCGAAGAACCTTACCTG
GGTTTGACATATACCGGAAAGCTGCAGAGATGTG---GC-CCCCCTTGTGGTCG-GTATACAGGTGGTGCAT
GGCTGTCGTCAGCTCGTGTCGTGAGATGTTGGGTTAAGTCCCGCAACGAGCGCAACCCCTATCTTATGTT
GCCAGCA-CGTTATGGTGGGGACTCGTAAGAGACTGCCGGGGTCAACTCGGAGGAAGGTGGGGACGACG
TCAAGTCATCATGCCCCTTATGTCCAGGGCTTCACACATGCTACAATGGCCAGTACAGAGGGCTGCGAGA
CCGTGAGGTGGAGCGAATCCCTT-AAAGCTGGTCTCAGTTCGGATCGGGGTCTGCAACTCGACCCCGTGA
AGTCGGAGTCGCTAGTAATCGCAGATCAGCAACGCTGCGGTGAATACGTTCCCGGGCCTTGTACACACCG
CCCGTCACGTCATGAAAGTCGGTAACACCCGAAGCCGGTGGCTTAACCCCTTGTGGGAGGGAGCCGTCG
AAGGTGGGATCGGCGATTGGGACGAAGTCGTAACAAGGTAGCCGTACCGGAAGGTGCGGCTGGATCACC
TCCTTT---

N. globerula (1) ------GTTTGATCCTGGCTCAGGACGAACGCTGGCGGCGTGCTTAACACATGCAAGTCGAGCGGTAAG
GCCT---TTCGG--GGTACACGAGCGGCGAACGGGTGAGTAACACGTGGGTGATCTGCCCTGCACTTCGGG
ATAAGCCTGGGAAACTGGGTCTAATACCGGATATGACCTCCTATCGCATGG-TGGGTGGTGGAAAGATTTA
TCGGTGCAGGATGGGCCCGCGGCCTATCAGCTTGTTGGTGGGGTAATGGCCTACCAAGGCGACGACGGG
TAGCCGACCTGAGAGGGTGACCGGCCACACTGGGACTGAGACACGGCCCAGACTCCTACGGGAGGCAG
CAGTGGGGAATATTGCACAATGGGCGAAAGCCTGATGCAGCGACGCCGCGTGAGGGACGACGGCCTTCG
GGTTGTAAACCTCTTTCAGCAGGGACGAA---------------GCGCAAGTGACGGTACCTGCAGAAGAAGCAC
CGGCTAACTACGTGCCAGCAGCCGCGGTAATACGTAGGGTGCAAGCGTTGTCCGGAATTACTGGGCGTAA
AGAGTTCGTAGGCGGTTTGTCACGTCGTTTGTGAAAACTCACAGCTCAACTGTGAGCCTGCAGGCGATAC
GGGCAGACTTGAGTACTGCAGGGGAGACTGGAATTCCTGGTGTAGCGGTGAAATGCGCAGATATCAGGA
GGAACACCGGTGGCGAAGGCG-GGTCTCTGGGCAGTAACTGACGCTGAGGAACGAAAGCGTGGGTAGCG
AACAGGATTAGATACCCTGGTAGTCCACGCCGTAAACGGTGGGCGCTAGGTGTGGGTT-CCTTCCACGGA
ATCCGTGCCGTAGCTAACGCATTAAGCGCCCCGCCTGGGGAGTACGGCCGCAAGGCTAAAACTCAAAGG
AATTGACGGGGGCCCGCACAAGCGGCGGAGCATGTGGATTAATTCGATGCAACGCGAAGAACCTTACCTG
GGTTTGACATATACCGGAAAGCCGTAGAGATACG--GC-CCCCCTTGTGGTCG-GTATACAGGTGGTGCAT
GGCTGTCGTCAGCTCGTGTCGTGAGATGTTGGGTTAAGTCCCGCAACGAGCGCAACCCCTATCTTATGTT
GCCAGCA-CGTTATGGTGGGGACTCGTAAGAGACTGCCGGGGTCAACTCGGAGGAAGGTGGGGACGACG
TCAAGTCATCATGCCCCTTATGTCCAGGGCTTCACACATGCTACAATGGCCAGTACAGAGGGCTGCGAGA
CCGTGAGGTGGAGCGAATCCCTT-AAAGCTGGTCTCAGTTCGGATCGGGGTCTGCAACTCGACCCCGTGA
AGTCGGAGTCGCTAGTAATCGCAGATCAGCAACGCTGCGGTGAATACGTTCCCGGGCCTTGTACACACCG
CCCGTCACGTCATGAAAGTCGGTAACACCCGAAGCCGGTGGCTTAACCCCTTGTGGGAGGGAGCCGTCG
AAGGTGGGATCGGCGATTGGGACGAAGTCGTAACAAGGTAGCCGTACCGGAAGGTGCGGCTGGATCACC
TCCTT---

R. equi (1) ------GAGTTTGATCCTGGCTCAGGACGAACGCTGGCGGCGTGCTTAACACATGCAAGTCGAGCGGTAG
GGCCC---TTCGG--GGTACACGAGCGGCGAACGGGTGAGTAACACGTGGGTGATCTGCCCTGCACTTCGG
GATAAGCTTGGGAAACTGGGTCTAATACCGGATATGAGCCTCTACTGCATGG-TGGAGGTTGGAAAGGTTT
ACTGGTGCAGGATGGGCCCGCGGCCTATCAGCTTGTTGGTGGGGTAATGGCCTACCAAGGCGACGACGG
GTAGCCGGCCTGAGAGGGCGACCGGCCACACTGGGACTGAGACACGGCCCAGACTCCTACGGGAGGCA
GCAGTGGGGAATATTGCACAATGGGCGAAAGCCTGATGCAGCGACGCCGCGTGAGGGATGACGGCCTTC
GGGTTGTAAACCTCTTTCAGCAGGGACGAA---------------GCGAGAGTGACGGTACCTGCAGAAGAAGCA
CCGGCCAACTACGTGCCAGCAGCCGCGGTAATACGTAGGGTGCGAGCGTTGTCCGGAATTACTGGGCGT
AAAGAGCTCGTAGGCGGTTTGTCGCGTCGTCGGTGAAAACCAGCAGCTCAACTGCTGGCTTGCAGGCGAT
ACGGGCAGACTTGAGTACTGCAGGGGAGACTGGAATTCCTGGTGTAGCGGTGAAATGCGCAGATATCAGG
AGGAACACCGGTGGCGAAGGCG-GGTCTCTGGGCAGTAACTGACGCTGAGGAGCGAAAGCGTGGGTAGC
GAACAGGATTAGATACCCTGGTAGTCCACGCCGTAAACGGTGGGCGCTAGGTGTGGGTTTCCTTCCACGG
GATCCGTGCCGTAGCTAACGCATTAAGCGCCCCGCCTGGGGAGTACGGCCGCAAGGCTAAAACTCAAAG
GAATTGACGGGGGCCCGCACAAGCGGCGGAGCATGTGGATTAATTCGATGCAACGCGAAGAACCTTACCT
GGGTTTGACATATACCGGAAAGCCGTAGAGATACG---GC--CCCCCTTGTGGTCG-GTATACAGGTGGTGCA

FIG. 4 (continued)

TGGCTGTCGTCAGCTCGTGTCGTGAGATGTTGGGTTAAGTCCCGCAACGAGCGCAACCCTTGTCCTGTGT
TGCCAGCA-CGTAATGGTGGGGACTCGCAGGAGACCGCCGGGGTCAACTCGGAGGAAGGTGGGGACGAC
GTCAAGTCATCATGCCCCTTATGTCCAGGGCTTCACACATGCTACAATGGCCGGTACAGAGGGCTGCGAT
ACCGTGAGGTGGAGCGAATCCCTT-AAAGCCGGTCTCAGTTCGGATCGGGGTCTGCAACTCGACCCCGTG
AAGTCGGAGTCGCTAGTAATCGCAGATCAGCAACGCTGCGGTGAATACGTTCCCGGGCCTTGTACACACC
GCCCGTCACGTCATGAAAGTCGGTAACACCCGAAGCCGGTGGCCTAACCC-TTGTGG-AGGGAGCCGTCG
AAGGTGGGATCGGCGATTGGGACGAAGTCGTAACAAGGTAGCCGTACCGGAAGGTGCGGCTGGATCACC
TCCTT---

R. A2Y26

(1) ---------------CTGGCTCAGGACGAACGCTGGCGGCGTGCTTAACACATGCAAGTCGAGCGGTAAGGCCC
----TTCGG---GGTACACGAGCGGCGAACGGGTGAGTAACACGTGGGTGATCTGCCCTGCACTTCGGGATAA
GCCTGGGAAACTGGGTCTAATACCGGATATGACCTTCGGCTGCATGG-CTGAGGGTGGAAAGGTTTACTG
GTGCAGGATGAGCCCGCGGCCTATCAGCTTGTTGGTGGGGTAATGGCCTACCAAGGCGACGACGGGTAG
CCGACCTGAGAGGGTGACCGGCCACACTGGGACTGAGACACGGCCCAGACTCCTACGGGAGGCAGCAG
TGGGGAATATTGCACAATGGGCGAAAGCCTGATGCAGCGACGCCGCGTGAGGGATGACGGCCTCGGGT
TGTAAACCTCTTTCAGCAGGGACGAA----------------GCGAAAGTGACGGTACCTGCAGAAGAAGCACCGG
CTAACTACGTGCCAGCAGCCGCGGTAATACGTAGGGTGCAAGCGTTGTCCGGAATTACTGGGCGTAAAGA
GTTCGTAGGCGGTTTGTCGCGTCGTCTGTGAAAACTCACAGCTCAACTGTGAGCTTGCAGGCGATACGGG
CAGACTTGAGTACTGCAGGGGAGACTGGAATTCCTGGTGTAGCGGTGAAATGCGCAGATATCAGGAGGAA
CACCGGTGGCGAAGGCG-GGTCTCTGGGCAGTAACTGACGCTGAGGAACGAAAGCGTGGGTAGCAAACA
GGATTAGATACCCTGGTAGTCCACGCCGTAAACGGTGGGCGCTAGGTGTGGGTT-CCTTCCACGGGATCT
GTGCCGTAGCTAACGCATTAAGCGCCCCGCCTGGGGAGTACGGCCGCAAGGCTAAAACTCAAAGGAATTG
ACGGGGGCCCGCACAAGCGGCGGAGCATGTGGATTAATTCGATGCAACGCGAAGAACCTTACCTGGGTTT
GACATATACCGGAAAGCCGTAGAGATACG---GC--CCCCCTTGTGGTCG--GTATACAGGTGGTGCATGGCT
GTCGTCAGCTCGTGTCGTGAGATGTTGGGTTAAGTCCCGCAACGAGCGCAACCCTTGTCTTATGTTGCCA
GCA-CGTAATGGTGGGGACTCGTAAGAGACTGCCGGGGTCAACTCGGAGGAAGGTGGGGACGACGTCAA
GTCATCATGCCCCTTATGTCCAGGGCTTCACACATGCTACAATGGCCAGTACAGAGGGCTGCGA-ACCGTG
AGGTGGAGCGAATCCCTT-AAAGCYGGTCTCAGTTCGGATCGGGGTCTGCAACTCGACCCCGTGAAGTCG
GAGTCGCTAGTAATCGCAGATCAGCAACGCTGCGGTGAATACGTTCCCGGGCCTTGTACACACCGCCCGT
CACGTCATGAAAGTCGGTAACACCCGAAGCCGGTGGCCTAACCCCTTGTGGGAGGGAGCCGTCGAAGGT
GGGATCGGCGATT--------------------------------

R. 871-AN040

(1) -----AGAGTTTGATCCTGGCTCAGGACGAACGCTGGCGGCGTGCTTAACACATGCAAGTCGAGCGGTA
AGGCCC----TTCGG---GGTACACGAGCGGCGAACGGGTGAGTAACACGTGGGTGATCTGCCCTGCACTTCG
GATAAGCCTGGGAAACTGGGTCTAATACCGGATATGACCTTCGGCTGCATGG-CTGAGGGTGGAAAGGT
TTACTGGTGCAGGATGAGCCCGCGGCCTATCAGCTTGTTGGTGGGGTAATGGCCTACCAAGGCGACGAC
GGGTAGCCGACCTGAGAGGGTGACCGGCCACACTGGGACTGAGACACGGCCCAGACTCCTACGGGAGG
CAGCAGTGGGGAATATTGCACAATGGGCGAAAGCCTGATGCAGCGACGCCGCGTGAGGGATGACGGCCT
TCGGGTTGTAAACCTCTTTCAGCAGGGACGAA-----------------GCGAAAGTGACGGTACCTGCAGAAGAAG
CACCGGCTAACTACGTGCCAGCAGCCGCGGTAATACGTAGGGTGCAAGCGTTGTCCGGAATTACTGGGC
GTAAAGAGTTCGTAGGCGGTTTGTCGCGTCGTTTGTGAAAACTCAMRGCTCAACTGTGAGCTTGCAGGCG
ATACGGGCAGACTTGAGTACTGCAGGGGAGACTGGAATTCCTGGTGTAGCGGTGAAATGCGCAGATATCA
GGAGGAACACCGGTGGCGAAGGCG-GGTCTCTGGGCAGTAACTGACGCTGAGGAACGAAAGCGTGGGTA
GCAAACAGGATTAGATACCCTGGTAGTCCACGCCGTAAACGGTGGGCGCTAGGTGTGGGTT-CCTTCCAC
GGGATCTGTGCCGTAGCTAACGCATTAAGCGCCCCGCCTGGGGAGTACGGCCGCAAGGCTAAAACTCAA
AGGAATTGACGGGGGCCCGCACAAGCGGCGGAGCATGTGGATTAATTCGATGCAACGCGAAGAACCTTA
CCTGGGTTTGACATATACCGGAAAGCCGTAGAGATACG---GC--CCCCCTTGTGGTCG--GTATACAGGTGGT
GCATGGCTGTCGTCAGCTCGTGTCGTGAGATGTTGGGTTAAGTCCCGCAACGAGCGCAACCCTTGTCTTA
TGTTGCCAGCA-CGTAATGGTGGGGACTCGTAAGAGACTGCCGGGGTCAACTCGGAGGAAGGTGGGGAC

FIG. 4 (continued)

GACGTCAAGTCATCATGCCCCTTATGTCCAGGGCTTCACACATGCTACAATGGCCAGTACAGAGGGCTGC
GAGACCGTGAGGTGGAGCGAATCCCTT-AAAGCTGGTCTCAGTTCGGATCGGGGTCTGCAACTCGACCCC
GTGAAGTCGGAGTCGCTAGTAATCGCAGATCAGCAACGCTGCGGTGAATACGTTCCCGGGCCTTGTACAC
ACCGCCCGTCACGTCATGAAAGTCGGTAACACCCGAAGCCGGTGGCCTAACCCCTTGTGGGAGGGAGCC
GTCGAAGGTGGGATCGGCGATTGGGACGAAGTCGTAACAAGG————————————————

R. jostii (1) ———————————AGGACGAACGCTGGCGGCGTGCTTAACACATGCAAGTCGAGCGGTAAGGCCC—TT
CGG—GGTACACGAGCGGCGAACGGGTGAGTAACACGTGGGTGATCTGCCCTGCACTTCGGGATAAGCCT
GGGAAACTGGGTCTAATACCGGATATGACCTTCGGCTGCATGG-CTGAGGGTGGAAAGGTTTACTGGTGC
AGGATGGGCCCGCGGCCTATCAGCTTGTTGGTGGGGTAATGGCCTACCAAGGCGACGACGGGTAGCCGA
CCTGAGAGGGTGACCGGCCACACTGGGACTGAGACACGGCCCAGACTCCTACGGGAGGCAGCAGTGGG
GAATATTGCACAATGGGCGAAAGCCTGATGCAGCGACGCCGCGTGAGGGATGACGGCCTTCGGGTTGTA
AACCTCTTTCAGCAGGGACGAA————————GCGAAAGTGACGGTACCTGCAGAAGAAGCACCGGCTAA
CTACGTGCCAGCAGCCGCGGTAATACGTAGGGTGCAAGCGTTGTCCGGAATTACTGGGCGTAAAGAGTTC
GTAGGCGGTTTGTCGCGTCGTTTGTGAAAACTCACAGCTCAACTGTGAGCCTGCAGGCGATACGGGCAGA
CTTGAGTACTGCAGGGGAGACTGGAATTCCTGGTGTAGCGGTGAAATGCGCAGATATCAGGAGGAACACC
GGTGGCGAAGGCG-GGTCTCTGGGCAGTAACTGACGCTGAGGAACGAAAGCGTGGGTAGCAAACAGGAT
TAGATACCCTGGTAGTCCACGCCGTAAACGGTGGGCGCTAGGTGTGGGTT-CCTTCCACGGGATCTGTGC
CGTAGCTAACGCATTAAGCGCCCCGCCTGGGGAGTACGGCCGCAAGGCTAAAACTCAAAGGAATTGACG
GGGGCCCGCACAAGCGGCGGAGCATGTGGATTAATTCGATGCAACGCGAAGAACCTTACCTGGGTTTGAC
ATATACCGGAAAGCCGTAGAGATACG—GC--CCCCCTTGTGGTCG--GTATACAGGTGGTGCATGGCTGTCG
TCAGCTCGTGTCGTGAGATGTTGGGTTAAGTCCCGCAACGAGCGCAACCCTTGTCTTATGTTGCCAGCA-C
GTAATGGTGGGGACTCGTAAGAGACTGCCGGGGTCAACTCGGAGGAAGGTGGGGACGACGTCAAGTCAT
CATGCCCCTTATGTCCAGGGCTTCACACATGCTACAATGGCCAGTACAGAGGCTGCGAGACCGTGAGGT
GGAGCGAATCCCTT-AAAGCTGGTCTCAGTTCGGATCGGGGTCTGCAACTCGACCCCGTGAAGTCGGAGT
CGCTAGTAATCGCAGATCAGCAACGCTGCGGTGAATACGTTCCCGGGCCTTGTACACACCGCCCGTCACG
TCATGAAAGTCGGTAACACCCGAAGCCGGTGGCCTAACCCCTTGTGGGAGGGAGCCGTCGAAGGTGGGA
TCGGCGATTG——————————————————————

R. opacus 1CP (1) ————————GATCCTGGCTCAGGACGAACGCTGGCGGCGTGCTTAACACATGCAAGTCGAGCGGTAAGGC
CC—-TTCGG—GGTACACGAGCGGCGAACGGGTGAGTAACACGTGGGTGATCTGCCCTGCACTTCGGGAT
AAGCCTGGGAAACTGGGTCTAATACCGGATATGACCTTCGGCTGCATGG-CTGAGGGTGGAAAGGTTTACT
GGTGCAGGATGGGCCCGCGGCCTATCAGCTTGTTGGTGGGGTAATGGCCTACCAAGGCGACGACGGGTA
GCCGACCTGAGAGGGTGACCGGCCACACTGGGACTGAGACACGGCCCAGACTCCTACGGGAGGCAGCA
GTGGGGAATATTGCACAATGGGCGAAAGCCTGATGCAGCGACGCCGCGTGAGGGATGACGGCCTTCGGG
TTGTAAACCTCTTTCAGCAGGGACGAA.————————GCGAAAGTGACGGTACCTGCAGAAGAAGCACCG
GCCAACTACGTGCCAGCAGCCGCGGTAATACGTAGGGTGCAAGCGTTGTCCGGAATTACTGGGCGTAAAG
AGTTCGTAGGCGGTTTGTCGCGTCGTCTGTGAAAACTCAAAGCTCAACCTCGAGCCTGCAGGCGATACGG
GCAGACTTGAGTACTGCAGGGGAGACTGGAATTCCTGGTGTAGCGGTGAAATGCGCAGATATCAGGAGGA
ACACCGGTGGCGAAGGCG-GGTCTCTGGGCAGTAACTGACGCTGAGGAACGAAAGCGTGGGTAGCGAAC
AGGATTAGATACCCTGGTAGTCCACGCCGTAAACGGTGGGCGCTAGGTGTGGGTTTCCTTCCACGGGATC
NGTGCCGTAGCTAACGCATTAAGCGCCCCGCCTGGGGAGTACGGCCGCAAGGCTAAAACTCAAAGGAATT
GACGGGGGCCCGCACAAGCGGCGGAGCATGTGGATTAATTCGATGCAACGCGAAGAACCTTACCTGGGT
TTGACATATACCGGAAAGCCGTAGAGATACG—-GC--CCCCCTTGTGGTCG–GTATACAGGTGGTGCATGGC
TGTCGTCAGCTCGTGTCGTGAGATGTTGGGTTAAGTCCCGCAACGAGCGCAACCCTTGTCTTATGTTGCCA
GCA-CGTAATGGTGGGGACTCGTAAGAGACTGCCGGGGTCAACTCGGAGGAAGGTGGGGACGACGTCAA
GTCATCATGCCCCTTATGTCCAGGGCTTCACACATGCTACAATGGCCGGTACAGAGGGCTGCGATACCGT
GAGGTGGAGCGAATCCCTT-AAAGCTGGTCTCAGTTCGGATCGGGGTCTGCAACTCGACCCCGTGAAGTC
GGAGTCGCTAGTAATCGCAGATCAGCAACGCTGCGGTGAATACGTTCCCGGGCCTTGTACACACCGCCCG
TCACGTCATGAAAGTCGGTAACACCCGAAGCCGGTGGCCTAACCCCTTGTGGGAGGGAGCCGTCGAAGG
TGGGATCGGCGATTGGGACGAAGTCGTAACAAGGTAGCCGTACCGGAAGGT——————————

FIG. 4 (continued)

R. imtechensis RKJ300

(1) ---------TTGATCCTGGCTCAGGACGAACGCTGGCGGCGTGCTTAACACATGCAAGTCGAGCGGTAAGG
CCC----TTCGG---GGTACACGAGCGGCGAACGGGTGAGTAACACGTGGGTGATCTGCCCTGCACTTCGGGA
TAAGCCTGGGAAACTGGGTCTAATACCGGATATGACCTTCGGCTGCATGG-CTGAGGGTGGAAAGGTTTAC
TGGTGCAGGATGGGCCCGCGGCCTATCAGCTTGTTGGTGGGGTAATGGCCTACCAAGGCGACGACGGGT
AGCCGACCTGAGAGGGTGACCGGCCACACTGGGACTGAGACACGGCCCAGACTCCTACGGGAGGCAGC
AGTGGGGAATATTGCACAATGGGCGAAAGCCTGATGCAGCGACGCCGCGTGAGGGATGACGGCCTTCGG
GTTGTAAACCTCTTTCAGCAGGGACGAA---------------GCGAAAGTGACGGTACCTGCAGAAGAAGCACC
GGCCAACTACGTGCCATCAGCCGCGGTAATACGTAGGGTGCAAGCGTTGTCCGGAATTACTGGGCGTAAA
GAGCTCGTAGGCGGTTTGTCGTGTCGTCTGTGAAAACTCGAGGCTCAACCTCGAGCTTGCAGGCGATACG
GGCAGACTTGAGTACTGCAGGGGAGACTGGAATTCCTGGTGTAGCGGTGAAATGCGCAGATATCAGGAG
GAACACCGGTGGCGAAGGCG-GGTCTCTGGGCAGTAACTGACGCTGAGGAGCGAAAGCGTGGAAACCGA
ACAGGATTAGATACCCTGGTAGTCCACGCCGTAAACGGTGGGCGCTAGGTGTGGGTTTCCTTCCACGGGA
TCCGTGCCGTAGCTAACGCATTAAGCGCCCCGCCTGGGGAGTACGGCCGCAAGGCTAAAACTCAAAGGA
ATTGACGGGGGCCCGCACAAGCGGCGGAGCATGTGGATTAATTCGATGCAACGCGAAGAACCTTACCTG
GGTTTGACATATACCGGAAAGCCGTAGAGATACG---GC-CCCCCTTGTGGTCG-GTATACAGGTGGTGCAT
GGCTGTCGTCAGCTCGTGTCGTAAGATGTTGGGTTAAGTCCCGCAACGAGCGCAACCCTTGTCTTATGTTG
CCAGCA-CGTAATGGTGGGGACTCGTAAGAGACTGCCGGGGTCAACTCGGAGGAAGGTGGGGACGACGT
CAAGTCATCATGCCCCTTATGTCCAGGGCTTCACACATGCTACAATGGCCAGTACAGAGGGCTGCGAGAC
CGTGAGGTGGAGCGAATCCCTT-AAAGCTGGTCTCAGTTCGGATCGGGGTCTGCAACTCGACCCCGTGAA
GTCGGAGTCGCTAGTAATCGCAGATCAGCAACGCTGCGGTGAATACGTTCCCAGGCCTTGTACACACCGC
CCGTCACGTCATGAAAGTCGGTAACACCCGAAGCCGGTGGCCTAACCCCTTGTGGGAGGGAGCCGTCGA
AGGTGGGATCGGCGATTGGGACGAAGTCGTAACAAGGTAGCCGTACCGGAAGGTGCGGCTGGAAACTGC
CGAGGGGG

R. koreensis DNP505

(1) ----------------GACGAACGCTGGCGGCGTGCTTAACACATGCAAGTCGAGCGGTAAGGCCC----TTC
GG---GGTACACGAGCGGCGAACGGGTGAGTAACACGTGGGTGATCTGCCCTGCACTTCGGGATAAGCCTG
GGAAACTGGGTCTAATACCGGATATGACCAAGGACTGCATGG-TTTTTGGTGGAAAGGTTTACTGGTGCAG
GATGGGCCCGCGGCCTATCAGCTTGTTGGTGGGGTAATGGCCTACCAAGGCGACGACGGGTAGCCGACC
TGAGAGGGTGACCGGCCACACTGGGACTGAGACACGGCCCAGACTCCTACGGGAGGCAGCAGTGGGGA
ATATTGCACAATGGGCGAAAGCCTGATGCAGCGACGCCGCGTGAGGGATGACGGCCTTCGGGTTGTAAA
CCTCTTTCAGCAGGGACGAA--------------GCGAGAGTGACGGTACCTGCAGAAGAAGCACCGGCCAACT
ACGTGCCAGCAGCCGCGGTAATACGTAGGGTGCAAGCGTTGTCCGGAATTACTGGGCGTAAAGAGCTCGT
AGGCGGTTTGTCGCGTCGTCTGTGAAAACTCGAGGCTCAACCTCGAGCTTGCAGGCGATACGGGCAGACT
TGAGTACTGCAGGGGAGACTGGAATTCCTGGTGTAGCGGTGAAATGCGCAGATATCAGGAGGAACACCG
GTGGCGAAGGCG-GGTCTCTGGGCAGTAACTGACGCTGAGGAGCGAAAGCGTGGGTAGCGAACAGGATT
AGATACCCTGGTAGTCCACGCCGTAAACGGTGGGCGCTAGGTGTGGGTT-CCTTCCACGGGATCCGTGCC
GTAGCTAACGCATTAAGCGCCCCGCCTGGGGAGTACGGCCGCAAGGCTAAAACTCAAAGGAATTGACGG
GGGCCCGCACAAGCGGCGGAGCATGTGGATTAATTCGATGCAACGCGAAGAACCTTACCTGGGTTTGACA
TATACCGGAAAGCCGTAGAGATACG---GC-CCCCCTTGTGGTCG-GTATACAGGTGGTGCATGGCTGTCGT
CAGCTCGTGTCGTGAGATGTTGGGTTAAGTCCCGCAACGAGCGCAACCCTTGTCTTATGTTGCCAGCA-CG
TAATGGTGGGGACTCGTAAGAGACTGCCGGGGTCAACTCGGAGGAAGGTGGGGACGACGTCAAGTCATC
ATGCCCCTTATGTCCAGGGCTTCACACATGCTACAATGGCCAGTACAGAGGGCTGCGAGACCGTGAGGTG
GAGCGAATCCCTT-AAAGCTGGTCTCAGTTCGGATCGGGGTCTGCAACTCGACCCCGTGAAGTCGGAGTC
GCTAGTAATCGCAGATCAGCAACGCTGCGGTGAATACGTTCCCGGGCCTTGTACACACCGCCCGTCACGT
CATGAAAGTCGGTAACACCCGAAGCCGGTGGCCTAACCCCTTGTGGGAGGGAGCCGTCGAAGGTGGGAT
CGGCGATTGGGACGAAGTCGTAACAAGGTAGCCGTACCGGAAGGTGC--------------------

R. opacus B-4

(1)TCAACGGAGAGTTTGATCCTGGCTCAGGACGAACGCTGGCGGCGTGCTTAACACATGCAAGTCGAGCG
GTAAGGCCC----TTCGG---GGTACACGAGCGGCGAACGGGTGAGTAACACGTGGGTGATCTGCCCTGCACT

FIG. 4 (continued)

TCGGGATAAGCCTGGGAAACTGGGTCTAATACCGGATATGACCTTCGGCTGCATGG-CCGTTGGTGGAAA
GGTTTACTGGTGCAGGATGGGCCCGCGGCCTATCAGCTTGTTGGTGGGGTAATGGCCTACCAAGGCGAC
GACGGGTAGCCGACCTGAGAGGGTGACCGGCCACACTGGGACTGAGACACGGCCCAGACTCCTACGGG
AGGCAGCAGTGGGGAATATTGCACAATGGGCGAAAGCCTGATGCAGCGACGCCGCGTGAGGGATGACGG
CCTTCGGGTTGTAAACCTCTTTCAGCAGGGACGAA————————GCGAAAGTGACGGTACCTGCAGAAGA
AGCACCGGCCAACTACGTGCCAGCAGCCGCGGTAATACGTAGGGTGCAAGCGTTGTCCGGAATTACTGG
GCGTAAAGAGCTCGTAGGCGGTTTGTCGCGTCGTCTGTGAAAACTCGAGGCTCAACCTCGAGCTTGCAGG
CGATACGGGCAGACTTGAGTACTGCAGGGGAGACTGGAATTCCTGGTGTAGCGGTGAAATGCGCAGATAT
CAGGAGGAACACCGGTGGCGAAGGCG-GGTCTCTGGGCAGTAACTGACGCTGAGGAGCGAAAGCGTGGG
TAGCGAACAGGATTAGATACCCTGGTAGTCCACGCCGTAAACGGTGGGCGCTAGGTGTGGGTTTCCTTCC
ACGGGATCCGTGCCGTAGCTAACGCATTAAGCGCCCCGCCTGGGGAGTACGGCCGCAAGGCTAAAACTC
AAAGGAATTGACGGGGGCCCGCACAAGCGGCGGAGCATGTGGATTAATTCGATGCAACGCGAAGAACCTT
ACCTGGGTTTGACATATACCGGAAAGCTGCAGAGATGTG—GC--CCCCCTTGTGGTCG--GTATACAGGTGG
TGCATGGCTGTCGTCAGCTCGTGTCGTGAGATGTTGGGTTAAGTCCCGCAACGAGCGCAACCCTTGTCTT
ATGTTGCCAGCA-CGTAATGGTGGGGACTCGTAAGAGACTGCCGGGGTCAACTCGGAGGAAGGTGGGGA
CGACGTCAAGTCATCATGCCCCTTATGTCCAGGGCTTCACACATGCTACAATGGCCGGTACAGAGGGCTG
CGATACCGTGAGGTGGAGCGAATCCCTT-AAAGCCGGTCTCAGTTCGGATCGGGGTCTGCAACTCGACCC
CGTGAAGTCGGAGTCGCTAGTAATCGCAGATCAGCAACGCTGCGGTGAATACGTTCCCGGGCCTTGTACA
CACCGCCCGTCACGTCATGAAAGTCGGTAACACCCGAAGCCGGTGGCCTAACCCCTCGTGGGAGGGAGC
CGTCGAAGGTGGGATCGGCGATTGGGACGAAGTCGTAACAAGGTAGCCGTACCGGAAGGTGCGGCTGGA
TCACCTCCTTTCT-

R. TCH14
(1) ————————TCCTGGCTCAGGACGAACGCTGGCGGCGTGCTTAACACATGCAAGTCGAGCGGTAAGGCC
C—-TTCGG—GGTACACGAGCGGCGAACGGGTGAGTAACACGTGGGTGATCTGCCCTGCACTTCGGGATA
AGCCTGGGAAACTGGGTCTAATACCGGATATGACCTTCGGCTGCATGG-CTGTTGGTGGAAAGGTTTACTG
GTGCAGGATGGGCCCGCGGCCTATCAGCTTGTTGGTGGGGTAATGGCCTACCAAGGCGACGACGGGTAG
CCGACCTGAGAGGGTGACCGGCCACACTGGGACTGAGACACGGCCCAGACTCCTACGGGAGGCAGCAG
TGGGGAATATTGCACAATGGGCGAAAGCCTGATGCAGCGACGCCGCGTGAGGGATGACGGCCTTCGGGT
TGTAAACCTCTTTCAGCAGGGACGAA————————GCGAGAGTGACGGTACCTGCAGAAGAAGCACCGG
CCAACTACGTGCCAGCAGCCGCGGTAATACGTAGGGTGCAAGCGTTGTCCGGAATTACTGGGCGTAAAGA
GCTCGTAGGCGGTTTGTCGCGTCGTCTGTGAAAACTCGAGGCTCAACCTCGAGCTTGCAGGCGATACGGG
CAGACTTGAGTACTGCAGGGGAGACTGGAATTCCTGGTGTAGCGGTGAAATGCGCAGATATCAGGAGGAA
CACCGGTGGCGAAGGCG-GGTCTCTGGGCAGTAACTGACGCTGAGGAGCGAAAGCGTGGGTAGCGAACA
GGATTAGATACCCTGGTAGTCCACGCCGTAAACGGTGGGCGCTAGGTGTGGGTTTCCTTCCACGGGATCC
GTGCCGTAGCTAACGCATTAAGCGCCCCGCCTGGGGAGTACGGCCGCAAGGCTAAAACTCAAAGGAATTG
ACGGGGGCCCGCACAAGCGGCGGAGCATGTGGATTAATTCGATGCAACGCGAAGAACCTTACCTGGGTTT
GACATATACCGGAAAGCCGTAGAGATACG—GC--CCCCCTTGTGGTCG--GTATACAGGTGGTGCATGGCT
GTCGTCAGCTCGTGTCGTGAGATGTTGGGTTAAGTCCCGCAACGAGCGCAACCCTTGTCTTATGTTGCCA
GCA-CGTAATGGTGGGGACTCGTAAGAGACTGCCGGGGTCAACTCGGAGGAAGGTGGGGACGACGTCAA
GTCATCATGCCCCTTATGTCCAGGGCTTCACACATGCTACAATGGCCGGTACAGAGGGCTGCGATACCGT
GAGGTGGAGCGAATCCCTT-AAAGCCGGTCTCAGTTCGGATCGGGGTCTGCAACTCGACCCCGTGAAGTC
GGAGTCGCTAGTAATCGCAGATCAGCAACGCTGCGGTGAATACGTTCCCGGGCCTTGTACACACCGCCCG
TCACGTCATGAAAGTCGGTAACACCCGAAGCCGGTGGCCTAACCCCTCGTGGGAGGGAGCCGTCGAAGG
TGGGATCGGCGATTGGGA————————————————

R. opacus DNP14-5
(1) ————————————GACGAACGCTGGCGGCGTGCTTAACACATGCAAGTCGAGCGGTAAGGCCC----TTC
GG—GGTACACGAGCGGCGAACGGGTGAGTAACACGTGGGTGATCTGCCCTGCACTTCGGGATAAGCCTG
GGAAACTGGGTCTAATACCGGATATGACCTTCGGCTGCATGG-CTGAGGGTGGAAAGGTTTACTGGTGCA
GGATGGGCCCGCGGCCTATCAGCTTGTTGGTGGGGTAATGGCCTACCAAGGCGACGACGGGTAGCCGAC
CTGAGAGGGTGACCGGCCACACTGGGACTGAGACACGGCCCAGACTCCTACGGGAGGCAGCAGTGGGG
AATATTGCACAATGGGCGAAAGCCTGATGCAGCGACGCCGCGTGAGGGATGACGGCCTTCGGGTTGTAAA
CCTCTTTCAGCAGGGACGAA————————GCGAGAGTGACGGTACCTGCAGAAGAAGCACCGGCCAACT

FIG. 4 (continued)

ACGTGCCAGCAGCCGCGGTAATACGTAGGGTGCAAGCGTTGTCCGGAATTACTGGGCGTAAAGAGCTCGT
AGGCGGTTTGTCGCGTCGTCTGTGAAAACTCGAGGCTCAACCTCGAGCTTGCAGGCGATACGGGCAGACT
TGAGTACTGCAGGGGAGACTGGAATTCCTGGTGTAGCGGTGAAATGCGCAGATATCAGGAGGAACACCG
GTGGCGAAGGCG-GGTCTCTGGGCAGTAACTGACGCTGAGGAGCGAAAGCGTGGGTAGCGAACAGGATT
AGATACCCTGGTAGTCCACGCCGTAAACGGTGGGCGCTAGGTGTGGGTTTCCTTCCACGGGATCCGTGCC
GTAGCTAACGCATTAAGCGCCCCGCCTGGGGAGTACGGCCGCAAGGCTAAAACTCAAAGGAATTGACGG
GGGCCCGCACAAGCGGCGGAGCATGTGGATTAATTCGATGCAACGCGAAGAACCTTACCTGGGTTTGACA
TATACCGGAAAGCCGTAGAGATACG---GC--CCCCCTTGTGGTCG--GTATACAGGTGGTGCATGGCTGTCGT
CAGCTCGTGTCGTGAGATGTTGGGTTAAGTCCCGCAACGAGCGCAACCCTTGTCTTATGTTGCCAGCA-CG
TAATGGTGGGGACTCGTAAGAGACTGCCGGGGTCAACTCGGAGGAAGGTGGGGACGACGTCAAGTCATC
ATGCCCCTTATGTCCAGGGCTTCACACATGCTACAATGGCCGGTACAGAGGGCTGCGATACCGTGAGGTG
GAGCGAATCCCTT-AAAGCCGGTCTCAGTTCGGATCGGGGTCTGCAACTCGACCCCGTGAAGTCGGAGTC
GCTAGTAATCGCAGATCAGCAACGCTGCGGTGAATACGTTCCCGGGCCTTGTACACACCGCCCGTCACGT
CATGAAAGTCGGTAACACCCGAAGCCGGTGGCCTAACCCCTCGTGGGAGGGAGCCGTCGAAGGTGGGAT
CGGCGATTGGGACGAAGTCGTAACAAGGTAGCCGTACCGGAAGG-----------------

R. pnp-5
(1) -----GAGTTTGATCCTGGCTCAGGACGAACGCTGGCGGCGTGCTTAACACATGCAAGTCGAGCGGTAA
GGCCC---TTCGG---GGTACACGAGCGGCGAACGGGTGAGTAACACGTGGGTGATCTGCCCTGCACTTCGG
GATAAGCCTGGGAAACTGGGTCTAATACCGGATATGACCTTCGGCTGCATGG-CTGAGGGTGGAAAGGTTT
ACTGGTGCAGGATGGGCCCGCGGCCTATCAGCTTGTTGGTGGGGTAATGGCCTACCAAGGCGACGACGG
GTAGCCGACCTGAGAGGGTGACCGGCCACACTGGGACTGAGACACGGCCCAGACTCCTACGGGAGGCA
GCAGTGGGGAATATTGCACAATGGGCGAAAGCCTGATGCAGCGACGCCGCGTGAGGGATGACGACCTTC
GGGTTGTAAACCTCTTTCAGCAGGGACGAA-------------GCGAAAGTGACGGTACCTGCAGAAGAAGCA
CCGGCCAACTACGTGCCAGCAGCCGCGGTAATACGTAGGGTGCAAGCGTTGTCCGGAATTACTGGGCGT
AAAGAGCTCGTAGGCGGTTTGTCGCGTCGTCTGTGAAAACTCGAGGCTCAACCTCGAGCTTGCAGGCGAT
ACGGGCAGACTTGAGTACTGCAGGGGAGACTGGAATTCCTGGTGTAGCGGTGAAATGCGCAGATATCAGG
AGGAACACCGGTGGCGAAGGCG-GGTCTCTGGGCAGTAACTGACGCTGAGGAGCGAAAGCGTGGGTAGC
GAACAGGATTAGATACCCTGGTAGTCCACGCCGTAAACGGTGGGCGCTAGGTGTGGGTTCCTTCCACGG
GATCCGTGCCGTAGCTAACGCATTAAGCGCCCCGCCTGGGGAGTACGGCCGCAAGGCTAAAACTCAAAG
GAATTGACGGGGGCCCGCACAAGCGGCGGAGCATGTGGATTAATTCGATGCAACGCGAAGAACCTTACCT
GGGTTTGACATATACCGGAAAGCCGTAGAGATACG---GC--CCCCCTTGTGGTCG--GTATACAGGTGGTGCA
TGGCTGTCGTCAGCTCGTGTCGTGAGATGTTGGGTTAAGTCCCGCAACGAGCGCAACCCTTGTCTTATGTT
GCCAGCA-CGTAATGGTGGGGACTCGTAAGAGACTGCCGGGGTCAACTCGGAGGAAGGTGGGGACGACG
TCAAGTCATCATGCCCCTTATGTCCAGGGCTTCACACATGCTACAATGGCCGGTACAGAGGGCTGCGATA
CCGTGAGGTGGAGCGAATCCCTT-AAAGCCGGTCTCAGTTCGGATCGGGGTCTGCAACTCGACCCCGTGA
AGTCGGAGTCGCTAGTAATCGCAGATCAGCAACGCTGCGGTGAATACGTTCCCGGGCCTTGTACACACCG
CCCGTCACGTCATGAAAGTCGGTAACACCCGAAGCCGGTGGCCTAACCCCTTGTGGGAGGGAGCCGTCG
AAGGTGGGATCGGCGATTGGGACGAAGTCGTAACAAGGTAGCCGTA-------------

R. Sulf-822
(1) ---------------------GCGGCGTGCTTAACACATGCAAGTCGAGCGGTAAGGCCC---TTCGG--GG
TACACGAGCGGCGAACGGGTGAGTAACACGTGGGTGATCTGCCCTGCACTTCGGGATAAGCCTGGGAAA
CTGGGTCTAATACCGGATATGACCTTCGGCTGCATGG-CTGAGGGTGGAAAGGTTTACTGGTGCAGGATG
GGCCCGCGGCCTATCAGCTTGTTGGTGGGGTAATGGCCTACCAAGGCGACGACGGGTAGCCGACCTGAG
AGGGTGACCGGCCACACTGGGACTGAGACACGGCCCAGACTCCTACGGGAGGCAGCAGTGGGGAATATT
GCACAATGGGCGAAAGCCTGATGCAGCGACGCCGCGTGAGGGATGACGGCCTTCGGGTTGTAAACCTCT

FIG. 4 (continued)

CCCGCACAAGCGGCGGAGCATGTGGATTAATTCGATGCAACGCGAAGAACCTTACCTGGGTTTGACATAT
ACCGGAAAGCCGTAGAGATACG—GC--CCCCCTTGTGGTCG--GTATACAGGTGGTGCATGGCTGTCGTCA
GCTCGTGTCGTGAGATGTTGGGTTAAGTCCCGCAACGAGCGCAACCCTTGTCTTATGTTGCCAGCA-CGTA
ATGGTGGGGACTCGTAAGAGACTGCCGGGGTCAACTCGGAGGAAGGTGGGGACGACGTCAAGTCATCAT
GCCCCTTATGTCCAGGGCTTCACACATGCTACAATGGCCGGTACAGAGGGCTGCGATACCGTGAGGTGGA
GCGAATCCCTT-AAAGCCGGTCTCAGTTCGGATCGGGGTCTGCAACTCGACCCCGTGAAGTCGGAGTCGC
TAGTAATCGCAGATCAGCAACGCTGCGGTGAATACGTTCCCGGGCCTTGTACACACCGCCCGTCACGTCA
TGAAAGTCGGTAACACCCGAAGCCAGTGGCCTAACCCCTTGTGGGAGGGAGCCGTCGAAGGTGGGATCG
GCGATTGGGACGAAGTCGTAACAAGGTA————————————————

R. wratislaviensis (1)—————————CCTGGCTCAGGACGAACGCTGGCGGCGTGCTTAACACATGCAAGTCGAGCGGTAAGGCC
C—-TTCGG—GGTACACGAGCGGCGAACGGGTGAGTAACACGTGGGTGATCTGCCCTGCACTTCGGGATA
AGCCTGGGAAACTGGGTCTAATACCGGATATGACCTTCGGCTGCATGG-CTGAGGGTGGAAAGGTTTACTG
GTGCAGGATGGGCCCGCGGCCTATCAGCTTGTTGGTGGGGTAATGGCCTACCAAGGCGACGACGGGTAG
CCGACCTGAGAGGGTGACCGGCCACACTGGGACTGAGACACGGCCCAGACTCCTACGGGAGGCAGCAG
TGGGGAATATTGCACAATGGGCGAAAGCCTGATGCAGCGACGCCGCGTGAGGGATGACGGCCTTCGGGT
TGTAAACCTCTTTCAGCAGGGACGAA——————————GCGAAAGTGACGGTACCTGCAGAAGAAGCACCGG
CCAACTACGTGCCAGCAGCCGCGGTAATACGTAGGGTGCAAGCGTTGTCCGGAATTACTGGGCGTAAAGA
GCTCGTAGGCGGTTTGTCGCGTCGTCTGTGAAAACTCGAGGCTCAACCTCGAGCTTGCAGGCGATACGGG
CAGACTTGAGTACTGCAGGGGAGACTGGAATTCCTGGTGTAGCGGTGAAATGCGCAGATATCAGGAGGAA
CACCGGTGGCGAAGGCG-GGTCTCTGGGCAGTAACTGACGCTGAGGAGCGAAAGCGTGGGTAGCGAACA
GGATTAGATACCCTGGTAGTCCACGCCGTAAACGGTGGGCGCTAGGTGTGGGTTTCCTTCCACGGGATCC
GTGCCGTAGCTAACGCATTAAGCGCCCCGCCTGGGGAGTACGGCCGCAAGGCTAAAACTCAAAGGAATTG
ACGGGGGCCCGCACAAGCGGCGGAGCATGTGGATTAATTCGATGCAACGCGAAGAACCTTACCTGGGTTT
GACATATACCGGAAAGCCGTAGAGATACG—GC--CCCCCTTGTGGTCG--GTATACAGGTGGTGCATGGCT
GTCGTCAGCTCGTGTCGTGAGATGTTGGGTTAAGTCCCGCAACGAGCGCAACCCTTGTCTTATGTTGCCA
GCA-CGTAATGGTGGGGACTCGTAAGAGACTGCCGGGGTCAACTCGGAGGAAGGTGGGGACGACGTCAA
GTCATCATGCCCCTTATGTCCAGGGCTTCACACATGCTACAATGGCCGGTACAGAGGGCTGCGATACCGT
GAGGTGGAGCGAATCCCTT-AAAGCCGGTCTCAGTTCGGATCGGGGTCTGCAACTCGACCCCGTGAAGTC
GGAGTCGCTAGTAATCGCAGATCAGCAACGCTGCGGTGAATACGTTCCCGGGCCTTGTACACACCGCCCG
TCACGTCATGAAAGTCGGTAACACCCGAAGCCGGTGGCCTAACCCCTTGTGGGAGGGAGCCGTCGAAGG
TGGGATCGGCGATTGGGACGAAGTCGTAACAAGGTAGCCGTACCGGAAGGTGCGGCTGGATCACCT——

Fig. 5

| Organism | Growth conditions | | |
|---|---|---|---|
| | Heterotrophic | Chemoautotrophic | Single carbon compound |
| R. opacus (DSM 44193) | 9.00 (6d) | 0.00 | ND |
| R. opacus (DSM 43205) | 9.00 (6d) | 1.00 (5d) | 2.70 (20d) |
| Rhodococcus sp. (DSM 3346) | 2.40 (3d) | 0.51 (9d) | ND |
| Cupriavidus necator (DSM 531) | 2.20 (3d) | 0.23 (3d) | ND |

| Organism | Lipid content (% of CDM) | |
|---|---|---|
| | Heterotrophic | Chemoautotrophic |
| R. opacus (DSM 44193) | 49.3% | No growth |
| R. opacus (DSM 43205) | 61.2% | 10.3% |
| Rhodococcus sp. (DSM 3346) | 19% | 3.7% |
| Cupriavidus necator (DSM 531) | 0.5% | ND |

Fig. 6

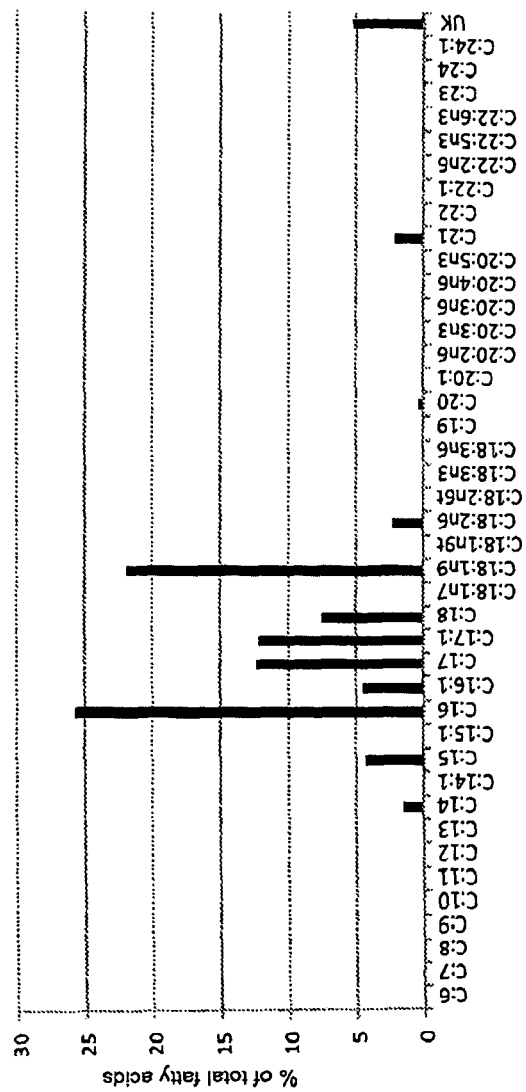

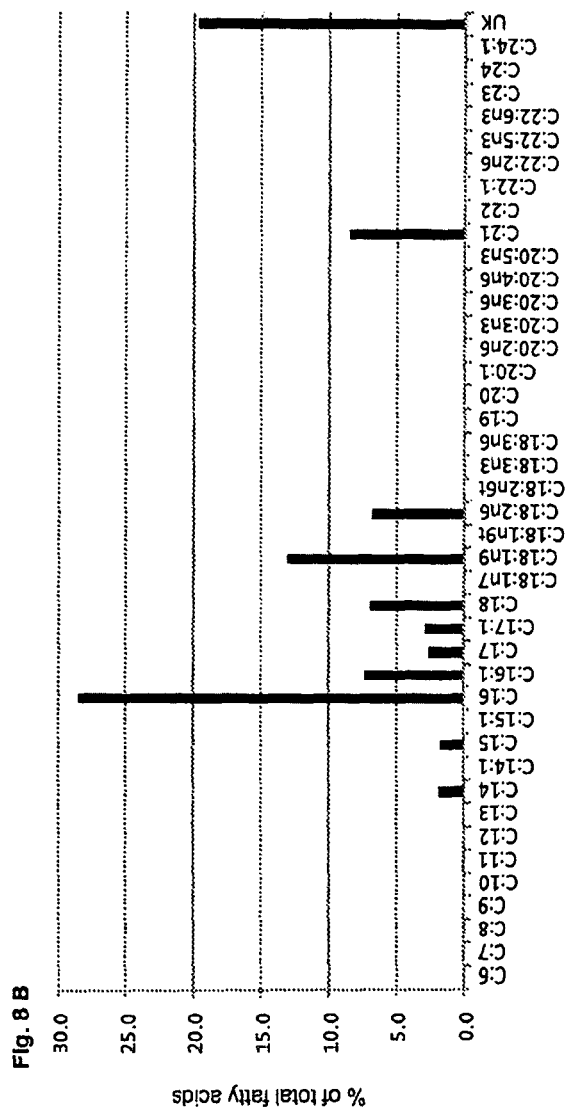

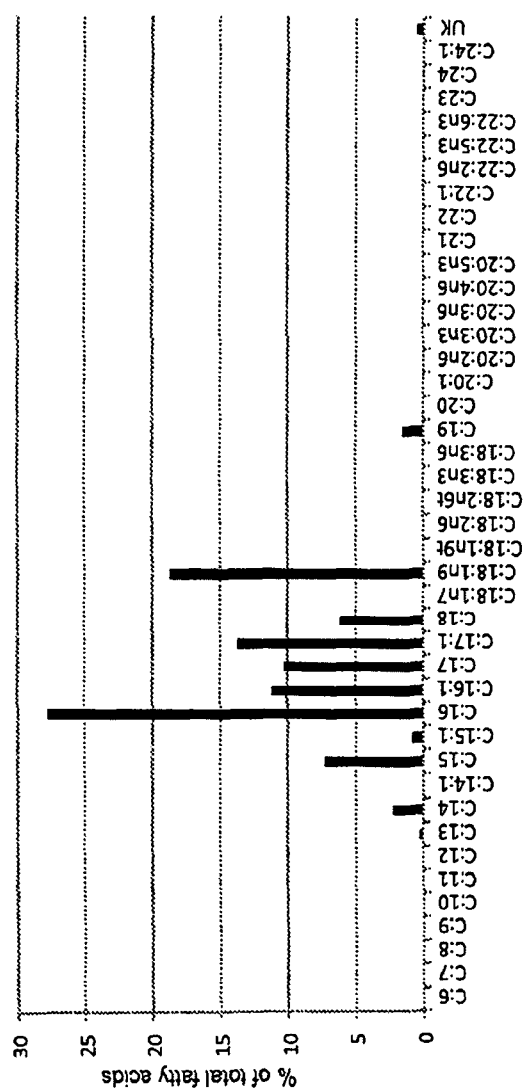

Fig. 10A

| Plasmid | Organisms | Backbone | Transformation method | Sequence ID |
|---|---|---|---|---|
| pSeqCo1 | E. coli Rhodococci | PUC18 | Electroporation | SEQ ID NO: 01 |
| pSeqCO2 | E. Coli Cupriavidus | pBBR1 | Bacterial conjugation Electroporation | SEQ ID NO: 02 |
| pVer1 | E. coli Rhodococci Cupriavidus | pBBR1MCS-2 | Bacterial conjugation Electroporation | SEQ ID NO: 03 |
| pVer2 | E. coli Rhodococci Cupriavidus | pBBR1MCS-2 | Bacterial conjugation Electroporation | SEQ ID NO: 04 |

Fig. 10B

| Plasmid | Replication gene | Mobilization gene | Antibiotic resistance | Direct selection gene | Cloning site |
|---|---|---|---|---|---|
| pSeqCo1 | Rep (pMB1)[1] RepAB (pKNR01)[2] | | Ampicillin Kanamycin | LacZ operon | MCS |
| pSeqCO2 | Rep (pBBR1)[3] | Mob[4] | Kanamycin | LacZ operon | MCS |
| pVer1 | Rep (pBBR1) RepAB (pKNR01) | Mob[4] | Kanamycin | LacZ operon | MCS |
| pVer2 | Rep (pBBR1) RepAB (pKNR01) | Mob[4] | Kanamycin Chloramphenicol | LacZ operon | MCS |

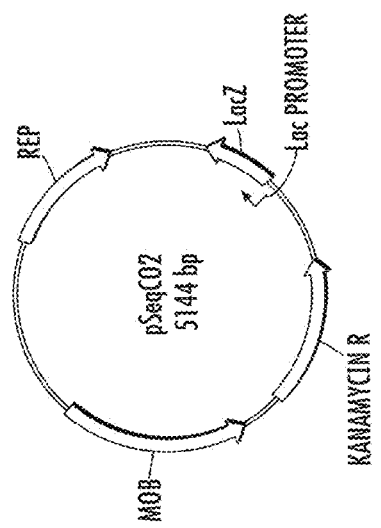
FIG. 11A
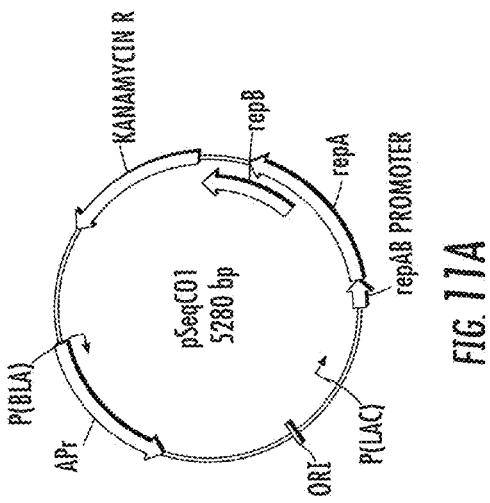
FIG. 11B
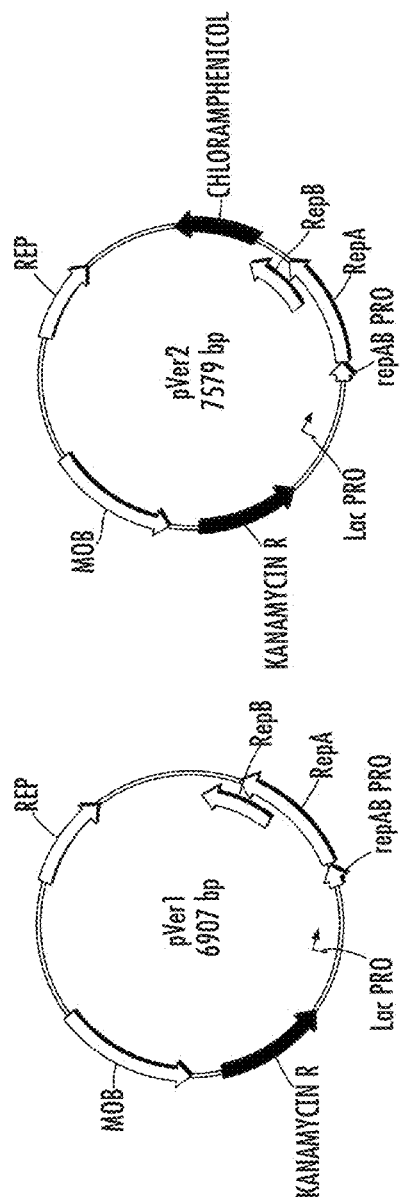
FIG. 11C
FIG. 11D

Fig. 12

| Organism | Plasmid | Transformation method | Kanamycin concentrations | Cultivation time | Number of Colonies |
|---|---|---|---|---|---|
| R. Opacus (44193) | pSeqCo1 | Electroporation[1] | 75 µg/ml | 4 days | 100 |
| R. opacus (44193) | pVer1 | Electroporation[1] | 75 µg/ml | 4 days | 50 |
| R. opacus (44193) | NC | Electroporation[1] | 75 µg/ml | 4 days | 0 |
| R. opacus (43205) | pSeqCo1 | Electroporation[1] | 75 µg/ml | 4 days | 20 |
| R. opacus (43205) | NC | Electroporation[1] | 75 µg/ml | 4 days | 0 |
| Cupriavidus necator (531) | pSeqCO2 | Electroporation[2] | 200 µg/ml | 2 days | 200 |
| Cupriavidus necator (531) | NC | Electroporation[2] | 200 µg/ml | 2 days | 0 |

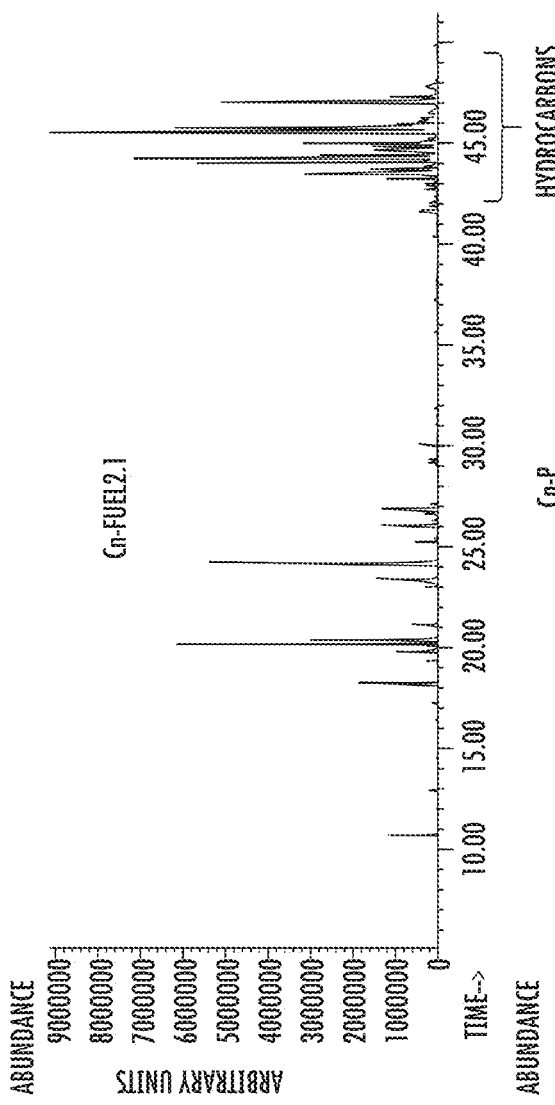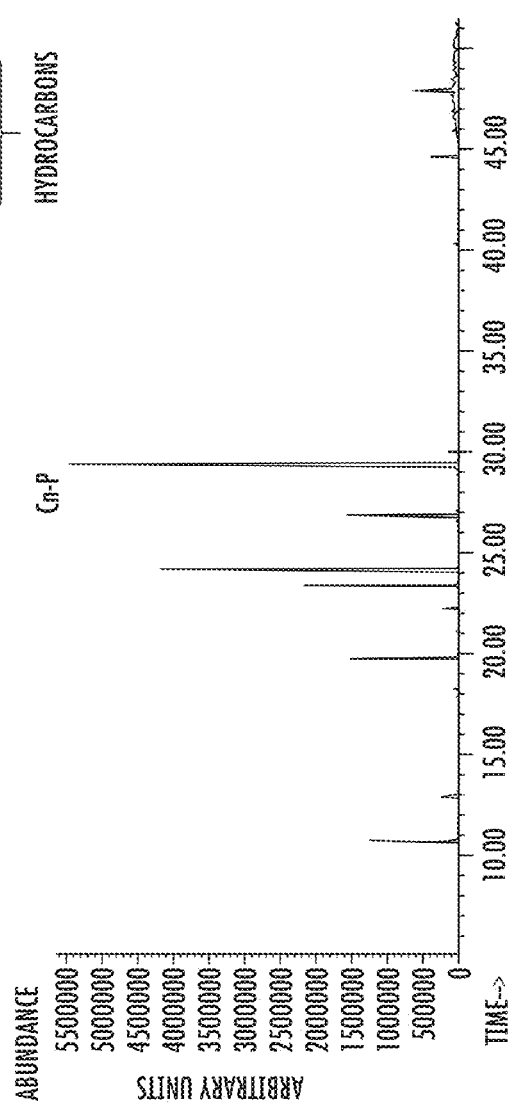
FIG. 21A
FIG. 21B

Fig. 22

| Compound | Cn-FUEL 2.1 | Cn-FUEL 2.2 | Cn-P(1) | Cn-P(2) |
|---|---|---|---|---|
| Spiro[4.5]decane | 2.50% | 0.98% | - | - |
| 11-Hexacosyne | - | 0.41% | - | - |
| 9-Tricosene, (Z)- | 0.70% | 0.23% | - | - |
| Triacontyl acetate | 0.22% | - | - | - |
| 1-Heptacosanol | - | 0.18% | - | - |
| 5-Nonadecen-1-ol | - | 0.40% | - | - |
| Nonadecyl trifluoroacetate | 0.31% | 0.32% | - | - |
| Bicyclo[10.8.0]eicosane, (E)- | 33.09% | 40.34% | - | - |
| cis,cis-1,6-Dimethylspiro[4.5]decane | 3.55% | 3.63% | - | - |
| 1,19-Eicosadiene | 6.63% | 0.24% | - | - |
| Cyclododecene, 1-methyl- | 0.47% | - | - | - |
| Cyclooctacosane | 2.03% | 1.27% | - | - |
| Bicyclo[10.8.0]eicosano, cis- | 3.53% | 3.32% | - | - |
| 1-Pentadecyne | 0.48% | 6.97% | - | - |
| Heptacosyl acetate | 4.12% | 3.48 | - | - |
| Cyclotetracosane | 1.47% | 1.27 | - | - |
| 5-Cyclohexyl-1-pentene | 26.56% | 3.39% | - | - |
| Cyclododecene, 1-methyl- | 0.80% | - | - | - |
| 1-Hexadecyne | 10.41% | 18.95% | - | - |
| 1,21-Docosadiene | 1.64% | 1.78% | - | - |
| Cyclodecacyclotetradecene, -eicosahydro- | - | 10.87% | - | - |
| 17-Pentatriacontene | - | 0.28% | - | - |
| Squalene | - | - | X | X |

Fig. 26

| Definition | GenBank # | Length (amino acids) | Identity to YP_002784058.1 (%) |
|---|---|---|---|
| acyl-CoA thioesterase Rhodococcus opacus B4 | YP_002784058.1 | 590 | 100 |
| acyl-CoA thioesterase II Rhodococcus jostii RHA1 | YP_706811.1 | 563 | 100 |
| acyl-CoA thioesterase Rhodococcus erythropolis PR4 | YP_002766361.1 | 460 | 99 |
| acyl-CoA thioesterase II TesB2 Mycobacterium abscessus ATCC 19977 | YP_001703624.1 | 421 | 100 |
| acyl-CoA thioesterase Rhodococcus equi 103S | YP_004006825.1 | 394 | 95 |
| acyl-CoA thioesterase Nocardia farcinica IFM 10152 | YP_119916.1 | 390 | 95 |
| acyl-CoA thioesterase Gordonia neofelifaecis NRRL B-59395 | ZP_08203815.1 | 379 | 94 |
| acyl-CoA thioesterase II Amycolicicoccus subflavus DQS3-9A1 | YP_004493060.1 | 369 | 96 |
| acyl-CoA thioesterase II Dietzia cinnamea P4 | ZP_08021991.1 | 345 | 94 |
| Choloyl-CoA hydrolase Tsukamurella paurometabola DSM 20162 | YP_003646881.1 | 339 | 94 |
| acyl-coenzyme A thioesterase 8 Corynebacterium amycolatum SK46 | ZP_03394327.1 | 337 | 94 |
| acyl-CoA thioesterase II Mycobacterium smegmatis str. MC2 155 | YP_887257.1 | 333 | 95 |
| acyl-CoA thioesterase II Segniliparus rotundus DSM 44985 | YP_003659169.1 | 304 | 94 |
| acyl-CoA thioesterase II Polymorphum gilvum SL003B-26A1 | YP_004301843.1 | 269 | 95 |
| acyl-coa thioesterase ii protein Stappia aggregata IAM 12614 | ZP_01548795.1 | 264 | 93 |
| acyl-CoA thioesterase II Saccharomonospora viridis DSM 43017 | YP_003134297.1 | 263 | 92 |
| palmitoyl-CoA hydrolase Nocardioides sp. JS614 | YP_924040.1 | 261 | 92 |
| Palmitoyl-CoA hydrolase Catenulispora acidiphila DSM 44928 | YP_003115470.1 | 256 | 94 |
| acyl-CoA thioesterase II Actinosynnema mirum DSM 43827 | YP_003103347.1 | 258 | 92 |
| acyl-CoA thioesterase II Streptomyces bingchenggensis BCW-1 | ADI04815.1 | 249 | 92 |

Figure 32

|  |  | Experimental date | 4/13/11 | 4/26/11 | 5/25/11 | 5/25/11 | 10/14/11 | 2/1/12 |
|---|---|---|---|---|---|---|---|---|
|  |  | Strain | DSM 44193 | DSM 44193 | DSM 43205 | DSM 43205 | C. necator | DSM 43205 |
| C16:0 | stearic acid | 18 octadecanoic acid | 4.08 | 6.18 | 7.55 | 6.95 | 0.91 | 22.03 |
| C18:1n9 | oleic acid | 18 cis-9-octadecanoic acid | 16.79 | 19.28 | 21.94 | 13.06 | 16.28 | 17.14 |
| C18:1n9t | elaidic acid | 18 trans-9-octadecanoic acid | 0.96 |  | 2.29 | 6.8 |  |  |
| C18:2n6 | linoleic acid | 18 all-cis-9,12-octadecadienoic-acid | 2.34 | 1.85 |  |  | 1.33 | 7.6 |
| C18:3n3 | alphaB linolenic | 18 all-cis-9,12,15-octadecatrienoic acid | 0.14 |  |  |  |  | 12.68 |

Figure 33

| GenBank Accession | Protein Name | Organism | Function | Source |
|---|---|---|---|---|
| ABE12594 | Sequence 2 from patent US 6,974,893 | Ricinis communus | omega-6 fatty acid desaturase | Shaklin US 6,974,893 |
| AAF03100.1 GI: 6063030 | oleate 12-hydroxylase | Lactuca sativa | GenBank entrez "oleate 12-hydroxylase" | GenBank entrez "oleate 12 hydroxylases" |
| CAK37451.1 GI:134056016 | Unnamed protein | Aspergillus niger | The Delta12 Fatty Acid Desaturase (Delta12-FADS)-like CD includes the integral-membrane enzymes, delta-12 acyl-lipid desaturases, oleate 12-hydroxylases, omega3 and omega6 fatty acid desaturases, and other related proteins, found in a wide range of...; cd03507 | GenBank entrez "oleate 12 hydroxylases" |
| Q029828.1 CP4AB_HUMAN | Lauric acid omega hydroxylase (Cyt P450 AA11) | Human P450 | Hydroxylates ?? position | GenBank "palmitate hydroxylase" |

Figure 34

| P98188.1<br>C94A2_VICSA | | Vicia sativa | Full P450-<br>dependent FA<br>omega hydroxylase | [Le Bouquin 1999] |
|---|---|---|---|---|
| AAL54885.1<br>AF092914 1 | | Vicia sativa | Cytochrome P45-<br>dependent fatty<br>acid hydroxylase | [via BLAST of P98188.1] |
| ABC59092.1 | | Medicago truncatula | cytochrome P450 monooxygenase CYP94A14 | [via BLAST of P98188.1] |
| AAL54886.1<br>AF092915 1 | | Nicotiana tabacum | cytochrome P450-dependent fatty acid hydroxylase | [via BLAST of P98188.1] |
| AAL54887.1<br>AF092916 1 | | Nicotiana tabacum | cytochrome P450-dependent fatty acid hydroxylase | [via BLAST of P98188.1] |
| CYP86A1<br>NP_200694.1 | | Arabidopsis thaliana | P450 omega-hydroxylates palmitic acid (C16) | [Le Bouquin 1999]<br>[Benveniste 1998] |
| AAL91155.1 | | Arabidopsis thaliana | Cytochrome P450 | [via BLAST NP_200694.1] |
| CAA62082.1 | | Arabidopsis thaliana | Cytochrome P450 | [via BLAST NP_200694.1 |
| XP_002862636.1 | | Arabidopsis lyrata | Cytochrome P450 | [via BLAST NP_200694.1 |
| XP_002883546.1 | | Arabidopsis lyrata | Cytochrome P450 | [via BLAST NP_200694.1 |
| CBI15990.3 | | Vitis vinifera | Cytochrome P450 86A1-like | [via BLAST NP_200694.1 |

Figure 35

| P450 class: Omega-hydroxylation | Specific genes | Organism | Hydroxylation Position | Reference |
|---|---|---|---|---|
| UNKNOWN | | Nicotiana | Hydroxylates 80% of fatty acid pool | Koiwai Matsuzaki 1988 |
| CYP | omega-LAH (sequence not found) | Pisum sativum | omega - hydroxylation of C12 lauric acid only | Benveniste 1982 |
| CYP94 | CYP94A1 GenBank: AAD10204.1 | V. sativa | omega - hydroxylation of 9,10-expoxystearic acid -> 18-hydroxy-9,10-expoxystearic acid | Pinot 1992 |
| CYP94 | CYP94B1 GenBank: AED97750.1, B2 GenBank: AEE73731.1, B3 GenBank: AEE78426.1, C1 (not found) | Arabidopsis thaliana | omega - hydroxylation C12:0, C14:0, C16:0, C18:1 fatty acids (low yields) | Benveniste 2006 |
| CYP94 | CYP94A1 GenBank: AAD10204.1 | Vicia sativa | Unknown substrate? | Tijet 1998 |
| CYP94 | CYP94A5 GenBank: AAL54887.1 | Nicotiana tabacum | | Le Bouquin 2001 |
| CYP78 | CYP78A1 NCBI Reference Sequence: NP_001106069.1 | Zea mays | omega - hydroxylation of C12:0, C14:0, C16:0 | Imaishi 2000 |
| CYP86 | CYP86A1 GenBank: AED97111.1 | Arabidopsis thaliana | omega - hydroxylation of C12-C18 (C18:0, C18:1, C18:2) | Benveniste 1998 |
| CYP86 | CYP86A2 NCBI Reference Sequence: NP_191946.1 | Arabidopsis thaliana | omega - hydroxylation in cutin formation | |
| CYP86 | CYP86A8 GenBank: AEC10625.1 | | omega - hydroxylation of fatty acids with C16:0 and C18:1 best. | |
| CYP92 | CYP92B1 (sequence not found) | Petunia hybrida | omega - hydroxylation of C12:0 | Petkova-Andonova 2002 |

Figure 36

| P450 class (in chain-hydroxylation) | Specific genes | Organism | Hydroxylation Position | Reference |
|---|---|---|---|---|
| CYP81 | CYP81B1 GenBank: CAA04116.1, GenBank: CAA04117.1 | Helianthus tuberosus | omega-1, omega-5 monohydroxylated capric (C10:0), lauric (C12:0), and myristic (C14:0) | Pompon 1996 |
| CYP709 | CYP709C1 GenBank: AAT68297.1 | Triticum aestivum | omega-1, omega-2 positions independent of chain length! | Kandel 2005 |

Figure 37

|  | TKO4-P | TKO4-TE | TKO4-ACoA-BP |
|---|---|---|---|
| C12 | 0 | 3.95 | 1.78 |
| C14 | 1.38 | 6.09 | 4.55 |
| C16 | 59.38 | 55.13 | 65.58 |
| C18 | 36.63 | 15.87 | 23.42 |

Figure 38

|  | 30C | 22C |
|---|---|---|
| C12 | 1.78 | 2.1 |
| C14 | 4.55 | 4.53 |
| C16 | 65.58 | 54.64 |
| C18 | 23.42 | 30.89 |

Figure 43
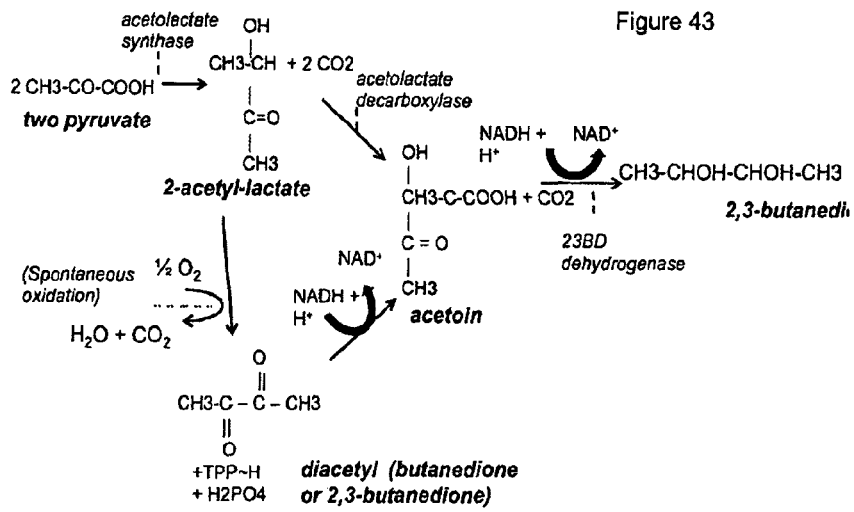
Generating a gas-fermentation process toward 2,3-BDO
Known 3-enzyme biosynthetic pathway
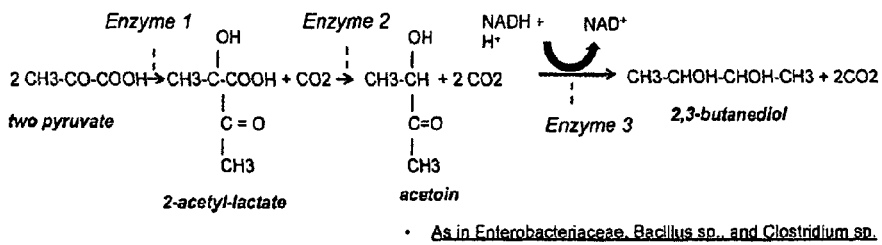
- As in Enterobacteriaceae, Bacillus sp., and Clostridium sp.
Alternate pathway to 2,3-BDO
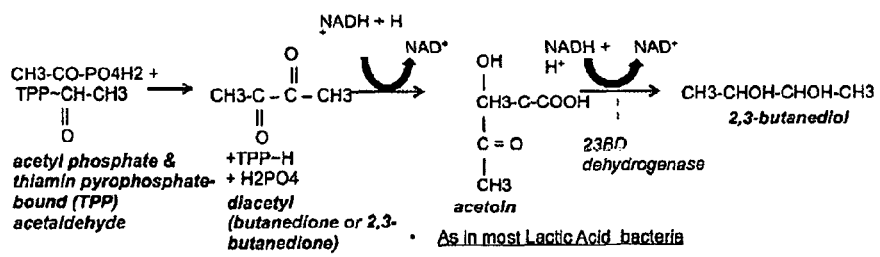
- As in most Lactic Acid bacteria

SEQUENCE LISTING

```
<160> NUMBER OF SEQ ID NOS: 51

<210> SEQ ID NO 1
<211> LENGTH: 10560
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
tcgcgcgttt cggtgatgac ggtgaaaacc tctgacacat gcagctcccg gagacggtca      60
cagcttgtct gtaagcggat gccgggagca gacaagcccg agcgcgcaaa gccactactg     120
ccacttttgg agactgtgta cgtcgagggc ctctgccagt gtcgaacaga cattcgccta     180
cggccctcgt ctgttcgggc tcagggcgcg tcagcgggtg ttggcgggtg tcggggctgg     240
cttaactatg cggcatcaga gcagattgta ctgagagtgc accatatgcg gtgtgaaata     300
```

```
agtcccgcgc agtcgcccac aaccgcccac agccccgacc gaattgatac gccgtagtct   360
cgtctaacat gactctcacg tggtatacgc cacactttat ccgcacagat gcgtaaggag   420
aaaataccgc atcaggcgcc attcgccatt caggctgcgc aactgttggg aagggcgatc   480
ggtgcgggcc tcttcgctat ggcgtgtcta cgcattcctc ttttatggcg tagtccgcgg   540
taagcggtaa gtccgacgcg ttgacaaccc ttcccgctag ccacgcccgg agaagcgata   600
tacgccagct ggcgaaaggg ggatgtgctg caaggcgatt aagttgggta acgcagggt    660
tttcccagtc acgacgttgt aaaacgacgg ccagtgccaa atgcggtcga ccgctttccc   720
cctacacgac gttccgctaa ttcaacccat tgcggtccca aaagggtcag tgctgcaaca   780
ttttgctgcc ggtcacggtt gcttgcatgc ctgcaggtcg acgggcccgg gatccgatgc   840
tcttccgcta agatctgccg cggccgcgtc tcagaagaa ctcgtcaaga aggcgataga    900
cgaacgtacg gacgtccagc tgcccgggcc ctaggctacg agaaggcgat tctagacggc   960
gccggcgcag gagtcttctt gagcagttct tccgctatct aggcgatgcg ctgcgaatcg  1020
ggagcggcga taccgtaaag cacgaggaag cggtcagccc attcgccgcc aagctcttca  1080
gcaatatcac gggtagccaa tccgctacgc gacgcttagc cctcgccgct atggcatttc  1140
gtgctccttc gccagtcggg taagcggcgg ttcgagaagt cgttatagtg cccatcggtt  1200
cgctatgtcc tgatagcggt ccgccacacc cagccggcca cagtcgatga atccagaaaa  1260
gcggccattt tccaccatga tattcggcaa gcaggcatcg gcgatacagg actatcgcca  1320
ggcggtgtgg gtcggccggt gtcagctact taggtctttt cgccggtaaa aggtggtact  1380
ataagccgtt cgtccgtagc ccatgggtca cgacgagatc ctcgccgtcg ggcatgcgcg  1440
ccttgagcct ggcgaacagt tcggctggcg cgagcccctg atgctcttcg tccagatcat  1500
ggtacccagt gctgctctag gagcggcagc ccgtacgcgc ggaactcgga ccgcttgtca  1560
agccgaccgc gctcggggac tacgagaagc aggtctagta cctgatcgac aagaccggct  1620
tccatccgag tacgtgctcg ctcgatgcga tgtttcgctt ggtggtcgaa tgggcaggta  1680
gccggatcaa gcgtatgcag ggactagctg ttctggccga aggtaggctc atgcacgagc  1740
gagctacgct acaaagcgaa ccaccagctt acccgtccat cggcctagtt cgcatacgtc  1800
ccgccgcatt gcatcagcca tgatggatac tttctcggca ggagcaaggt gggatgacag  1860
gagatcctgc cccggcactt cgcccaatag cagccagtcc ggcggcgtaa cgtagtcggt  1920
actacctatg aaagagccgt cctcgttcca ccctactgtc ctctaggacg gggccgtgaa  1980
gcgggttatc gtcggtcagg cttcccgctt cagtgacaac gtcgagcaca gctgcgcaag  2040
gaacgcccgt cgtggccagc cacgatagcc gcgctgcctc gtcctgcagt tcattcaggg  2100
gaagggcgaa gtcactgttg cagctcgtgt cgacgcgttc cttgcgggca gcaccggtcg  2160
gtgctatcgg cgcgacggag caggacgtca agtaagtccc caccggacag gtcggtcttg  2220
acaaaaagaa ccgggcgccc ctgcgctgac agcggaaca cggcggcatc agagcagccg    2280
attgtctgtt gtgcccagtc gtggcctgtc cagccagaac tgttttctt ggcccgcggg    2340
gacgcgactg tcggccttgt gccgccgtag tctcgtcggc taacagacaa cacgggtcag  2400
atagccgaat agcctctcca cccaagcggc cggagaacct gcgtgcaatc catcttgttc  2460
aatcatgata tcccttaatt aaccgttaac actagttcag tatcggctta tcggagaggt  2520
gggttcgccg gcctcttgga cgcacgttag gtagaacaag ttagtactat agggaattaa  2580
ttggcaattg tgatcaagtc tccatctcgc cgtgtatgcg ggcctgacgg atcaacgttc  2640
ccaccgagcc agtcgagatg ttcatctggt cggcgatctg ccggtacttc aaaccttgtt  2700
```

```
aggtagagcg gcacatacgc ccggactgcc tagttgcaag ggtggctcgg tcagctctac    2760
aagtagacca gccgctagac ggccatgaag tttggaacaa tgcgcagttc cacagccttc    2820
ttgcggcgtt cctgcgcacg agcgatgtag tcgcctcggt cttcggcgac gagccgtttg    2880
atggtgcttt tcgagacgcc acgcgtcaag gtgtcggaag aacgccgcaa ggacgcgtgc    2940
tcgctacatc agcggagcca gaagccgctg ctcggcaaac taccacgaaa agctctgcgg    3000
gaacttgtca gccaactcct gcgcggtctg cgtgcgacgc atcacgcgtt ctgcagcacc    3060
catcagtccg tcccctctgc tgctgcgaac agtgccgatc cttgaacagt cggttgagga    3120
cgcgccagac gcacgctgcg tagtgcgcaa gacgtcgtgg gtagtcaggc aggggagacg    3180
acgacgcttg tcacggctag gatcgacctt cttgagcttc ggccgcggcg cggtggcgtt    3240
cttccgtacc gcttccgttt ttgcgctgct gctcactttg ccgcggcgtg cctggatttt    3300
ctagctggaa gaactcgaag ccggcgccgc gccaccgcaa gaaggcatgg cgaaggcaaa    3360
aacgcgacga cgagtgaaac ggcgccgcac ggacctaaaa cgagaactcg gcggcggtga    3420
aggtgcggtg ggtccagtgg gcgactgatt tgccgatctg ctcggcctcg gcccgactca    3480
tggggccgat cccgtcgttg gctcttgagc cgccgccact tccacgccac ccaggtcacc    3540
cgctgactaa acggctagac gagccggagc cgggctgagt accccggcta gggcagcaac    3600
gcgtcgaggg tgaagttggt cagggcggtg aagtcggtga ccatctgccg ccacacagtg    3660
atcgacgggt agttctgttt ccggatctcg cggtaggccc cgcagctccc acttcaacca    3720
gtcccgccac ttcagccact ggtagacggc ggtgtgtcac tagctgccca tcaagacaaa    3780
ggcctagagc gccatccggg attcccgggt gcggtcgaac agttcgacgt tccggcccgt    3840
ttcggtcctg acctgtgtct tgcggccgta gtccggtggg gcggggaaac ggtcaccgag    3900
taagggccca cgccagcttg tcaagctgca aggccgggca aagccaggac tggacacaga    3960
acgccggcat caggccaccc cgcccctttg ccagtggctc cgcttttgcg aggcctttga    4020
gcgagtacgg atccgaggga ccccagaccg tcgtccagtg cgggtggatc gggttctggg    4080
tgagctgctg cgcgtagccc gcgaaaacgc tccggaaact cgctcatgcc taggctccct    4140
ggggtctggc agcaggtcac gcccacctag cccaagaccc actcgacgac gcgcatcggg    4200
tgatcggcgc cgaccaccga ggcgatcagc ccctggttca cccggtcgta gagccgcagc    4260 gggcccgtc gggctgcctg gagggtgtag accgggcttt actagccgcg gctggtggct    4320
ccgctagtcg gggaccaagt gggccagcat ctcggcgtcg cccgggacag cccgacggac    4380
ctcccacatc tggcccgaaa cgagcagcca ccacaggtgc gcgtgctcgg tcgcgggatt    4440
gatcgtcatc acgtcggat cgggcagatc cgcgttacgt gcggcccact gcgcctggtc    4500
gctcgtcggt ggtgtccacg cgcacgagcc agcgccctaa ctagcagtag tgccagccta    4560
gcccgtctag gcgcaatgca cgccgggtga cgcggaccag gtcgtccacg tcgagcacca    4620
agcccaacct gatcgacggg gtgcgggccg caatgtagcg gcgggtgagc gcctccgcgc    4680
gcggctgcgg ccactgcccg cagcaggtgc agctcgtggt tcgggttgga ctagctgccc    4740
cacgcccggc gttacatcgc cgcccactcg cggaggcgcg cgccgacgcc ggtgacgggc    4800
tcccggacgt agtcatccgt cgcgtgcggg tatttgaacc gccagcggtc caaccaggcg    4860
tcaacagcag cggtcatgac cgccaagcta gggccggatc agggcctgca tcagtaggca    4920
gcgcacgccc ataaacttgg cggtcgccag gttggtccgc agttgtcgtc gccagtactg    4980
gcggttcgat cccggcctag tgtaccgatc ggggaggcg cgccgcaaat tatttaagag    5040
```

```
tctcgctagc aaaccatgtc aggtgttgcg gtgggttccg ggtaaacctc cacccgaatt    5100
acatggctag cccctccgc gcggcgttta ataaattctc agagcgatcg tttggtacag    5160
tccacaacgc cacccaaggc ccatttggag gtgggcttaa atttaagagt ctcgctagct    5220
aagccctatc tgatgctgcg cgggggtcc ttcgcactga atctcaaagg tggccggctg    5280
aatttcgtcg cgcgaaaacc taaattctca gagcgatcga ttcgggatag actacgacgc    5340
gcccccagg aagcgtgact tagagtttcc accggccgac ttaaagcagc gcgcttttgg    5400
tccctggaca gttctggaat tcagcaagag gtgtgtctga acttcggtgt ttttttgggg    5460
ggtgactcca gcggggtggg cacaacgcga acagagacct agggacctgt caagaccta    5520
agtcgttctc cacacagact tgaagccaca aaaaaacccc ccactgaggt cgccccaccc    5580
gtgttgcgct tgtctctgga tgtgtgtacg acggcgggag gtaagtcggg tacggctcgg    5640
actgcggtag agcaaccgtc gaatcgattt cgagcagagc gagcagagca agatattcca    5700
acacacatgc tgccgccctc cattcagccc atgccgagcc tgacgccatc tcgttggcag    5760
cttagctaaa gctcgtctcg ctcgtctcgt tctataaggt aaactccggg gttcctcggc    5820
ggcctccccc gtctgtttgc tcaaccgagg gagacctggc ggtcccgcgt ttccggacgc    5880
gcgggaccgc ctaccgctcg tttgaggccc caaggagccg ccggagggg cagacaaacg    5940
agttggctcc ctctggaccg ccagggcgca aaggcctgcg cgccctggcg gatggcgagc    6000
agagcggaag agcatctaga tgcattcgcg aggtaccgag ctcgaattcg taatcatggt    6060
catagctgtt cctgtgtga aattgttatc cgctcacaat tctcgccttc tcgtagatct    6120
acgtaagcgc tccatggctc gagcttaagc attagtacca gtatcgacaa aggacacact    6180
ttaacaatag gcgagtgtta tccacacaac atacgagccg gaagcataaa gtgtaaagcc    6240
tggggtgcct aatgagtgag ctaactcaca ttaattgcgt tgcgctcact gcccgctttc    6300
aggtgtgttg tatgctcggc cttcgtattt cacatttcgg accccacgga ttactcactc    6360
gattgagtgt aattaacgca acgcgagtga cgggcgaaag cagtcgggaa acctgtcgtg    6420
ccagctgcat taatgaatcg gccaacgcgc ggggagaggc ggtttgcgta ttgggcgctc    6480
ttccgcttcc tcgctcactg gtcagccctt tggacagcac ggtcgacgta attacttagc    6540
cggttgcgcg cccctctccg ccaaacgcat aacccgcgag aaggcgaagg agcgagtgac    6600
actcgctgcg ctcggtcgtt cggctgcggc gagcggtatc agctcactca aaggcggtaa    6660
tacggttatc cacagaatca ggggataacg caggaaagaa tgagcgacgc gagccagcaa    6720
gccgacgccg ctcgccatag tcgagtgagt ttccgccatt atgccaatag gtgtcttagt    6780
ccctattgc gtcctttctt catgtgagca aaaggccagc aaaaggccag gaaccgtaaa    6840
aaggccgcgt tgctggcgtt tttccatagg ctccgccccc ctgacgagca tcacaaaaat    6900
gtacactcgt tttccggtcg ttttccggtc cttggcattt ttccggcgca acgaccgcaa    6960
aaaggtatcc gaggcggggg gactgctcgt agtgttttta cgacgctcaa gtcagaggtg    7020
gcgaaacccg acaggactat aaagatacca ggcgtttccc cctggaagct ccctcgtgcg    7080
ctctcctgtt ccgaccctgc gctgcgagtt cagtctccac cgctttgggc tgtcctgata    7140
tttctatggt ccgcaaaggg ggaccttcga gggagcacgc gagaggacaa ggctgggacg    7200
cgcttaccgg atacctgtcc gcctttctcc cttcgggaag cgtggcgctt tctcatagct    7260
cacgctgtag gtatctcagt tcggtgtagg tcgttcgctc gcgaatggcc tatggacagg    7320
cggaaagagg gaagcccttc gcaccgcgaa agagtatcga gtgcgacatc catagagtca    7380
agccacatcc agcaagcgag caagctgggc tgtgtgcacg aaccccccgt tcagcccgac    7440
```

```
cgctgcgcct tatccggtaa ctatcgtctt gagtccaacc cggtaagaca cgacttatcg    7500
gttcgacccg acacacgtgc ttgggggggca agtcgggctg gcgacgcgga ataggccatt    7560
gatagcagaa ctcaggttgg gccattctgt gctgaatagc ccactggcag cagccactgg    7620
taacaggatt agcagagcga ggtatgtagg cggtgctaca gagttcttga agtggtggcc    7680
taactacggc tacactagaa ggtgaccgtc gtcggtgacc attgtcctaa tcgtctcgct    7740
ccatacatcc gccacgatgt ctcaagaact tcaccaccgg attgatgccg atgtgatctt    7800
ggacagtatt tggtatctgc gctctgctga agccagttac cttcggaaaa agagttggta    7860
gctcttgatc cggcaaacaa accaccgctg gtagcgtgg cctgtcataa accatagacg    7920
cgagacgact tcggtcaatg gaagcctttt tctcaaccat cgagaactag gccgtttgtt    7980
tggtggcgac catcgccacc tttttttgtt tgcaagcagc agattacgcg cagaaaaaaa    8040
ggatctcaag aagatccttt gatcttttct acggggtctg acgctcagtg gaacgaaaac    8100
aaaaaaacaa acgttcgtcg tctaatgcgc gtcttttttt cctagagttc ttctaggaaa    8160
ctagaaaaga tgccccagac tgcgagtcac cttgcttttg tcacgttaag ggattttggt    8220
catgagatta tcaaaaagga tcttcaccta gatccttta aattaaaaat gaagttttaa    8280
atcaatctaa agtatatatg agtgcaattc cctaaaacca gtactctaat agttttttcct   8340 agaagtggat ctaggaaaat ttaatttta cttcaaaatt tagttagatt tcatatatac    8400
agtaaacttg gtctgacagt taccaatgct taatcagtga ggcacctatc tcagcgatct    8460
gtctatttcg ttcatccata gttgcctgac tccccgtcgt tcatttgaac cagactgtca    8520
atggttacga attagtcact ccgtggatag agtcgctaga cagataaagc aagtaggtat    8580
caacggactg aggggcagca gtagataact acgatacggg agggcttacc atctggcccc    8640
agtgctgcaa tgataccgcg agacccacgc tcaccggctc cagatttatc agcaataaac    8700
catctattga tgctatgccc tcccgaatgg tagaccgggg tcacgacgtt actatgcgc    8760 tctgggtgcg agtggccgag gtctaaatag tcgttatttg cagccagccg gaagggccga    8820
gcgcagaagt ggtcctgcaa ctttatccgc ctccatccag tctattaatt gttgccggga    8880
agctagagta agtagttcgc gtcggtcggc cttcccggct cgcgtcttca ccaggacgtt    8940
gaaataggcg gaggtaggtc agataattaa caacggccct tcgatctcat tcatcaagcg    9000
cagttaatag tttgcgcaac gttgttgcca ttgctacagg catcgtggtg tcacgctcgt    9060
cgtttggtat ggcttcattc agctccggtt cccaacgatc gtcaattatc aaacgcgttg    9120
caacaacggt aacgatgtcc gtagcaccac agtgcgagca gcaaaccata ccgaagtaag    9180
tcgaggccaa gggttgctag aaggcgagtt acatgatccc ccatgttgtg caaaaaagcg    9240
gttagctcct tcggtcctcc gatcgttgtc agaagtaagt tggccgcagt gttatcactc    9300
ttccgctcaa tgtactaggg ggtacaacac gttttttcgc caatcgagga agccaggagg    9360
ctagcaacag tcttcattca accggcgtca caatagtgag atggttatgg cagcactgca    9420
taattctctt actgtcatgc catccgtaag atgcttttct gtgactggtg agtactcaac    9480
caagtcattc tgagaatagt taccaatacc gtcgtgacgt attaagagaa tgacagtacg    9540
gtaggcattc tacgaaaaga cactgaccac tcatgagttg gttcagtaag actcttatca    9600
gtatgcggcg accgagttgc tcttgcccgg cgtcaatacg ggataatacc gcgccacata    9660
gcagaacttt aaaagtgctc atcattggaa aacgttcttc catacgccgc tggctcaacg    9720
agaacgggcc gcagttatgc cctattatgg cgcggtgtat cgtcttgaaa ttttcacgag    9780
```

```
tagtaacctt ttgcaagaag ggggcgaaaa ctctcaagga tcttaccgct gttgagatcc      9840
agttcgatgt aacccactcg tgcacccaac tgatcttcag catctttttac tttcaccagc     9900 ccccgctttt gagagttcct agaatggcga caactctagg tcaagctaca ttgggtgagc      9960
acgtgggttg actagaagtc gtagaaaatg aaagtggtcg gtttctgggt gagcaaaaac    10020
aggaaggcaa aatgccgcaa aaaagggaat aagggcgaca cggaaatgtt gaatactcat    10080
actcttcctt tttcaatatt caaagaccca ctcgtttttg tccttccgtt ttacggcgtt    10140 ttttcccta ttcccgctgt gcctttacaa cttatgagta tgagaaggaa aaagttataa     10200
attgaagcat ttatcagggt tattgtctca tgagcggata catatttgaa tgtatttaga    10260
aaaataaaca aatagggggt ccgcgcacat ttccccgaaa aacttcgta aatagtccca     10320 ataacagagt actcgcctat gtataaactt acataaatct ttttatttgt ttatccccaa    10380
ggcgcgtgta aaggggcttt agtgccacct gacgtctaag aaaccattat tatcatgaca    10440
ttaacctata aaataggcg tatcacgagg ccctttcgtc tcacggtgga ctgcagattc      10500
tttggtaata atagtactgt aattggatat ttttatccgc atagtgctcc gggaaagcag    10560

<210> SEQ ID NO 2
<211> LENGTH: 10288
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
ggggagccgc gccgaaggcg tgggggaacc ccgcaggggt gcccttcttt gggcaccaaa       60
gaactagata tagggcgaaa tgcgaaagac ttaaaaatca cccctcggcg cggcttccgc      120 accccttgg ggcgtcccca cgggaagaaa cccgtggttt cttgatctat atcccgcttt       180 acgcttctg aatttttagt acaacttaaa aaagggggggt acgcaacagc tcattgcggc     240
accccccgca atagctcatt gcgtaggtta agaaaatct gtaattgact gccacttttta     300 tgttgaattt tttcccccca tgcgttgtcg agtaacgccg tggggggcgt tatcgagtaa     360
cgcatccaat ttcttttaga cattaactga cggtgaaaat cgcaacgcat aattgttgtc     420
gcgctgccga aaagttgcag ctgattgcgc atggtgccgc aaccgtgcgg caccctaccg     480 catgagata agcatggcca gcgttgcgta ttaacaacag cgcgacggct tttcaacgtc       540
gactaacgcg taccacggcg ttggcacgcc gtgggatggc gtacctctat tcgtaccggt     600
cgcagtccag agaaatcggc attcaagcca agaacaagcc cggtcactgg gtgcaaacgg     660
aacgcaaagc gcatgaggcg tgggccgggc ttattgcgag gcgtcaggtc tctttagccg     720
taagttcggt tcttgttcgg gccagtgacc cacgttgcc ttgcgtttcg cgtactccgc      780
acccggcccg aataacgctc gaacccacg gcggcaatgc tgctgcatca cctcgtggcg      840
cagatgggcc accagaacgc cgtggtggtc agccagaaga cactttccaa gctcatcgga     900
ctttgggtgc cgccgttacg acgacgtagt ggagcaccgc gtctaccccgg tggtcttgcg    960 gcaccaccag tcggtcttct gtgaaaggtt cgagtagcct cgttctttgc ggacggtcca    1020
atacgcagtc aaggacttgg tggccgagcg ctggatctcc gtcgtgaagc tcaacggccc    1080
cggcaccgtg tcggcctacg gcaagaaacg cctgccaggt tatgcgtcag ttcctgaacc    1140
accggctcgc gacctagagg cagcacttcg agttgccggg gccgtggcac agccggatgc    1200
tggtcaatga ccgcgtggcg tggggccagc cccgcgacca gttgcgcctg tcggtgttca    1260
```

```
gtgccgccgt ggtggttgat cacgacgacc aggacgaatc accagttact ggcgcaccgc   1320 acccccggtcg gggcgctggt caacgcggac agccacaagt cacggcggca ccaccaacta   1380
gtgctgctgg tcctgcttag gctgttgggg catggcgacc tgcgccgcat cccgacccctg  1440 tatccgggcg agcagcaact accgaccggc cccggcgagg agccgcccag ccagcccggc   1500
cgacaacccc gtaccgctgg acgcggcgta gggctgggac ataggcccgc tcgtcgttga   1560
tggctggccg gggccgctcc tcggcgggtc ggtcggccg attccgggca tggaaccaga    1620
cctgccagcc ttgaccgaaa cggaggaatg ggaacggcgc gggcagcagc gcctgccgat   1680
gcccgatgag ccgtgttttc taaggcccgt accttggtct ggacggtcgg aactggcttt   1740
gcctccttac ccttgccgcg cccgtcgtcg cggacggcta cgggctactc ggcacaaaag   1800
tggacgatgg cgagccgttg gagccgccga cacgggtcac gctgccgcgc cggtagcact   1860
tgggttgcgc agcaacccgt aagtgcgctg ttccagacta acctgctacc gctcggcaac   1920
ctcggcggct gtgcccagtg cgacggcgcg gccatcgtga acccaacgcg tcgttgggca   1980
ttcacgcgac aaggtctgat tcggctgtag ccgcctcgcc gccctatacc ttgtctgcct   2040
ccccgcgttg cgtcgcggtg catggagccg ggccacctcg acctgaatgg aagccggcgg   2100
agccgacatc ggcggagcgg cgggatatgg aacagacgga ggggcgcaac gcagcgccac   2160
gtacctcggc ccggtggagc tggacttacc ttcggccgcc cacctcgcta acggattcac   2220
cgtttttatc aggctctggg aggcagaata aatgatcata tcgtcaatta ttacctccac   2280
ggggagagcc tgagcaaact gtggagcgat tgcctaagtg gcaaaaatag tccgagaccc   2340
tccgtcttat ttactagtat agcagttaat aatgaggtg cccctctcgg actcgtttga    2400
ggcctcaggc atttgagaag cacacggtca cactgcttcc ggtagtcaat aaaccggtaa   2460
accagcaata gacataagcg gctatttaac gaccctgccc ccggagtccg taaactcttc   2520
gtgtgccagt gtgacgaagg ccatcagtta tttggccatt tggtcgttat ctgtattcgc   2580
cgataaattg ctgggacggg tgaaccgacg accgggtcga atttgctttc gaatttctgc   2640
cattcatccg cttattatca cttattcagg cgtagcacca ggcgtttaag ggcaccaata   2700
acttggctgc tggcccagct taaacgaaag cttaaagacg gtaagtaggc gaataatagt   2760
gaataagtcc gcatcgtggt ccgcaaattc ccgtggttat actgccttaa aaaaattacg   2820
ccccgccctg ccactcatcg cagtcggcct attggttaaa aaatgagctg atttaacaaa   2880
aatttaacgc gaattttaac tgacggaatt tttttaatgc ggggcgggac ggtgagtagc   2940
gtcagccgga taaccaattt tttactcgac taaattgttt ttaaattgcg cttaaaattg   3000
aaaatattaa cgcttacaat ttccattcgc cattcaggct gcgcaactgt tgggaagggc   3060
gatcggtgcg ggcctcttcg ctattacgcc agctggcgaa ttttataatt gcgaatgtta   3120
aaggtaagcg gtaagtccga cgcgttgaca accccttcccg ctagccacgc ccggagaagc   3180
gataatgcgg tcgaccgctt aggggggatgt gctgcaaggc gattaagttg ggtaacgcca   3240
gggttttccc agtcacgacg ttgtaaaacg acggccagtg agcgcgcgta atacgactca   3300
tccccctaca cgacgttccg ctaattcaac ccattgcggt cccaaaaggg tcagtgctgc   3360
aacattttgc tgccggtcac tcgcgcgcat tatgctgagt ctataggcg aattggagct     3420 ccaccgcggt ggcggccgct ctagaactag tggatccccc gggctgcagg aattcgatat   3480
caagcttatc gataccgtcg gatatcccgc ttaacctcga ggtggcgcca ccgccgcga    3540 gatcttgatc acctaggggg cccgacgtcc ttaagctata gttcgaatag ctatggcagc   3600
acctcgaggg ggggccccggt acccagcttt tgttcccttt agtgagggtt aattgcgcgc   3660
```

```
ttggcgtaat catggtcata gctgtttcct gtgtgaaatt tggagctccc ccccgggcca    3720
tgggtcgaaa acaagggaaa tcactcccaa ttaacgcgcg aaccgcatta gtaccagtat    3780
cgacaaagga cacactttaa gttatccgct cacaattcca cacaacatac gagccggaag    3840
cataaagtgt aaagcctggg gtgcctaatg agtgagctaa ctcacattaa ttgcgttgcg    3900
caataggcga gtgttaaggt gtgttgtatg ctcggccttc gtatttcaca tttcggaccc    3960
cacggattac tcactcgatt gagtgtaatt aacgcaacgc ctcactgccc gctttccagt    4020
cgggaaacct gtcgtgccag ctgcattaat gaatcggcca acgcgcgggg agaggcggtt    4080
tgcgtattgg gcgcatgcat gagtgacggg cgaaaggtca gcccttttgga cagcacggtc    4140 gacgtaatta cttagccggt tgcgcgcccc tctccgccaa acgcataacc cgcgtacgta    4200
aaaaactgtt gtaattcatt aagcattctg ccgacatgga agccatcaca aacggcatga    4260
tgaacctgaa tcgccagcgg catcagcacc ttgtcgcctt tttttgacaa cattaagtaa    4320
ttcgtaagac ggctgtacct tcggtagtgt ttgccgtact acttggactt agcggtcgcc    4380
gtagtcgtgg aacagcggaa gcgtataata tttgcccatg ggggtgggcg aagaactcca    4440
gcatgagatc cccgcgctgg aggatcatcc agccggcgtc ccggaaaacg attccgaagc    4500
cgcatattat aaacgggtac ccccacccgc ttcttgaggt cgtactctag gggcgcgacc    4560
tcctagtagg tcgccgcag ggccttttgc taaggcttcg ccaacctttc atagaaggcg    4620
gcggtggaat cgaaatctcg tgatggcagg ttgggcgtcg cttggtcggt catttcgaac    4680
cccagagtcc cgctcagaag ggttggaaag tatcttccgc cgccacctta gctttagagc    4740
actaccgtcc aacccgcagc gaaccagcca gtaaagcttg gggtctcagg gcgagtcttc    4800
aactcgtcaa gaaggcgata gaaggcgatg cgctgcgaat cgggagcggc gataccgtaa    4860
agcacgagga agcggtcagc ccattcgccg ccaagctctt tgagcagtt cttccgctat    4920 cttccgctac gcgacgctta gccctcgccg ctatggcatt tcgtgctcct tcgccagtcg    4980
ggtaagcggc ggttcgagaa cagcaatatc acgggtagcc aacgctatgt cctgatagcg    5040
gtccgccaca cccagccggc cacagtcgat gaatccagaa aagcggccat tttccaccat    5100
gtcgttatag tgcccatcgg ttgcgataca ggactatcgc caggcggtgt gggtcggccg    5160
gtgtcagcta cttaggtctt ttcgccggta aaggtggta gatattcggc aagcaggcat    5220
cgccatgggt cacgacgaga tcctcgccgt cgggcatgcg cgccttgagc ctggcgaaca    5280
gttcggctgg cgcgagcccc ctataagccg ttcgtccgta gcggtaccca gtgctgctct    5340
aggagcggca gcccgtacgc gcggaactcg gaccgcttgt caagccgacc gcgctcgggg    5400
tgatgctctt cgtccagatc atcctgatcg acaagaccgg cttccatccg agtacgtgct    5460
cgctcgatgc gatgtttcgc ttggtggtcg aatgggcagg actacgagaa gcaggtctag    5520
taggactagc tgttctggcc gaaggtaggc tcatgcacga gcgagctacg ctacaaagcg    5580
aaccaccagc ttaccgtcc tagccggatc aagcgtatgc agccgccgca ttgcatcagc    5640
catgatggat actttctcgg caggagcaag gtgagatgac aggagatcct gccccggcac    5700
atcggcctag ttcgcatacg tcggcggcgt aacgtagtcg gtactaccta tgaaagagcc    5760
gtcctcgttc cactctactg tcctctagga cggggccgtg ttcgcccaat agcagccagt    5820
cccttcccgc ttcagtgaca acgtcgagca cagctgcgca aggaacgccc gtcgtggcca    5880
gccacgatag ccgcgctgcc aagcgggtta tcgtcggtca gggaagggcg aagtcactgt    5940
tgcagctcgt gtcgacgcgt tccttgcggg cagcaccggt cggtgctatc ggcgcgacgg    6000
```

```
tcgtcctgca gttcattcag ggcaccggac aggtcggtct tgacaaaaag aaccgggcgc    6060
ccctgcgctg acagccggaa cacggcggca tcagagcagc agcaggacgt caagtaagtc    6120
ccgtggcctg tccagccaga actgtttttc ttggcccgcg gggacgcgac tgtcggcctt    6180
gtgccgccgt agtctcgtcg cgattgtctg ttgtgcccag tcatagccga atagcctctc    6240
cacccaagcg gccggagaac ctgcgtgcaa tccatcttgt tcaatcatgc gaaacgatcc    6300
gctaacagac aacacgggtc agtatcggct tatcggagag gtgggttcgc cggcctcttg    6360
gacgcacgtt aggtagaaca agttagtacg ctttgctagg tcatcctgtc tcttgatcag    6420
atcttgatcc cctgcgccat cagatccttg cggcaagaa agccatccag tttactttgc    6480
agggcttccc aaccttacca agtaggacag agaactagtc tagaactagg ggacgcggta    6540
gtctaggaac cgccgttctt tcggtaggtc aaatgaaacg tcccgaaggg ttggaatggt    6600
gagggcgccc cagctggcaa ttccggttcg cttgctgtcc ataaaaccgc ccagtctagc    6660
tatcgccatg taagcccact gcaagctacc tgctttctct ctcccgcggg gtcgaccgtt    6720
aaggccaagc gaacgacagg tattttggcg ggtcagatcg atagcggtac attcgggtga    6780
cgttcgatgg acgaaagaga ttgcgcttgc gttttcccctt gtccagatag cccagtagct    6840
gacattcatc ccaggtggca cttttcgggg aaatgtgcgc gcccgcgttc ctgctggcgc    6900
aacgcgaacg caaaagggaa caggtctatc gggtcatcga ctgtaagtag ggtccaccgt    6960
gaaaagcccc tttacacgcg cggggcgcaag gacgaccgcg tgggcctgtt tctggcgctg    7020
gacttcccgc tgttccgtca gcagttttttc gcccacggcc ttgatgatcg cggcggcctt    7080
ggcctgcata tcccgattca acccggacaa agaccgcgac ctgaagggcg acaaggcagt    7140
cgtcgaaaag cgggtgccgg aactactagc gccgccggaa ccggacgtat agggctaagt    7200
acggccccag ggcgtccaga acgggcttca ggcgctcccg aaggtctcgg gccgtctctt    7260
gggcttgatc ggccttcttg cgcatctcac gcgctcctgc tgccggggtc ccgcaggtct    7320
tgcccgaagt ccgcgagggc ttccagagcc ggcagagaa cccgaactag ccggaagaac    7380
gcgtagagtg cgcgaggacg ggcggcctgt agggcaggct catacccctg ccgaaccgct    7440
tttgtcagcc ggtcggccac ggcttccggc gtctcaacgc gctttgagat tcccagcttt    7500
ccgccggaca tcccgtccga gtatggggac ggcttggcga aaacagtcgg ccagccggtg    7560
ccgaaggccg cagagttgcg cgaaactcta agggtcgaaa tcggccaatc cctgcggtgc    7620
ataggcgcgt ggctcgaccg cttgcgggct gatggtgacg tggcccactg gtggccgctc    7680
cagggcctcg tagaacgcct agccggttag ggacgccacg tatccgcgca ccgagctggc    7740
gaacgcccga ctaccactgc accgggtgac caccggcgag gtcccggagc atcttgcgga    7800
gaatgcgcgt gtgacgtgcc ttgctgccct cgatgcccg ttgcagccct agatcggcca    7860
cagcggccgc aaacgtggtc tggtcgcggg tcatctgcgc cttacgcgca cactgcacgg    7920
aacgacggga gctacggggc aacgtcggga tctagccggt gtcgccggcg tttgcaccag    7980
accagcgccc agtagacgcg tttgttgccg atgaactcct tggccgacag cctgccgtcc    8040
tgcgtcagcg gcaccacgaa cgcggtcatg tgcgggctgg tttcgtcacg gtggatgctg    8100
aaacaacggc tacttgagga accggctgtc ggacggcagg acgcagtcgc cgtggtgctt    8160
gcgccagtac acgcccgacc aaagcagtgc cacctacgac gccgtcacga tgcgatccgc    8220
cccgtacttg tccgcagcc acttgtgcgc cttctcgaag aacgccgcct gctgttcttg    8280
gctggccgac ttccaccatt cggcagtgct acgctaggcg gggcatgaac aggcggtcgg    8340
tgaacacgcg gaagagcttc ttgcggcgga cgacaagaac cgaccggctg aaggtggtaa    8400
```

```
ccgggctggc cgtcatgacg tactcgaccg ccaacacagc gtccttgcgc cgcttctctg   8460
gcagcaactc gcgcagtcgg cccatcgctt catcggtgct ggcccgaccg gcagtactgc   8520
atgagctggc ggttgtgtcg caggaacgcg gcgaagagac cgtcgttgag cgcgtcagcc   8580
gggtagcgaa gtagccacga gctggccgcc cagtgctcgt tctctggcgt cctgctggcg   8640
tcagcgttgg gcgtctcgcg ctcgcggtag gcgtgcttga gactggccgc cacgttgccc   8700
cgaccggcgg gtcacgagca agagaccgca ggacgaccgc agtcgcaacc cgcagagcgc   8760
gagcgccatc cgcacgaact ctgaccggcg gtgcaacggg attttcgcca gcttcttgca   8820
tcgcatgatc gcgtatgccg ccatgcctgc ccctcccttt tggtgtccaa ccggctcgac   8880
gggggcagcg caaggcggtg taaaagcggt cgaagaacgt agcgtactag cgcatacggc   8940
ggtacggacg gggagggaaa accacaggtt ggccgagctg cccccgtcgc gttccgccac   9000
cctccggcgg gccactcaat gcttgagtat actcactaga ctttgcttcg caaagtcgtg   9060
accgcctacg gcggctgcgg cgccctacgg gcttgctctc ggaggccgcc cggtgagtta   9120
cgaactcata tgagtgatct gaaacgaagc gtttcagcac tggcggatgc cgccgacgcc   9180
gcgggatgcc cgaacgagag cgggcttcgc cctgcgcggt cgctgcgctc ccttgccagc   9240
ccgtggatat gtggacgatg gccgcgagcg gccaccggct ggctcgcttc gctcggcccg   9300
gcccgaagcg ggacgcgcca gcgacgcgag ggaacggtcg ggcacctata cacctgctac   9360
cggcgctcgc cggtggccga ccgagcgaag cgagccgggc tggacaaccc tgctggacaa   9420
gctgatggac aggctgcgcc tgcccacgag cttgaccaca gggattgccc accggctacc   9480
cagccttcga ccacataccc acctgttggg acgacctgtt cgactacctg tccgacgcgg   9540
acgggtgctc gaactggtgt ccctaacggg tggccgatgg gtcggaagct ggtgtatggg   9600
accggctcca actgcgcggc ctgcggcctt gccccatcaa ttttttttaat tttctctggg   9660 gaaaagcctc cggcctgcgg cctgcgcgct tcgcttgccg tggccgaggt tgacgcgccg   9720
gacgccggaa cggggtagtt aaaaaaatta aaagagaccc cttttcggag gccggacgcc   9780
ggacgcgcga agcgaacggc gttggacacc aagtggaagg cgggtcaagg ctcgcgcagc   9840
gaccgcgcag cggcttggcc ttgacgcgcc tggaacgacc caagcctatg cgagtggggg   9900
caacctgtgg ttcaccttcc gcccagttcc gagcgcgtcg ctggcgcgtc gccgaaccgg   9960 aactgcgcg accttgctgg gttcggatac gctcacccc cagtcgaagg cgaagcccgc   10020
ccgcctgccc cccgagcctc acggcggcga gtgcgggggt tccaagggg cagcgccacc   10080 ttgggcaagg ccgaaggccg gtcagcttcc gcttcgggcg ggcggacggg gggctcggag   10140
tgccgccgct cacgccccca aggttccccc gtcgcggtgg aacccgttcc ggcttccggc   10200
cgcagtcgat caacaagccc cggaggggcc acttttgcc ggaggcgtca gctagttgtt   10260
cggggcctcc ccggtgaaaa acggcctc                                     10288

<210> SEQ ID NO 3
<211> LENGTH: 12758
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
ggggagccgc gccgaaggcg tgggggaacc ccgcaggggt gcccttcttt gggcaccaaa   60
gaactagata tagggcgaaa tgcgaaagac ttaaaaatca cccctcggcg cggcttccgc   120
```

```
accccttgg ggcgtcccca cgggaagaaa cccgtggttt cttgatctat atcccgcttt    180
acgctttctg aattttagt acaacttaaa aaagggggt acgcaacagc tcattgcggc     240
acccccgca atagctcatt gcgtaggtta agaaaatct gtaattgact gccactttta    300
tgttgaattt tttccccca tgcgttgtcg agtaacgccg tgggggcgt tatcgagtaa    360
cgcatccaat ttcttttaga cattaactga cggtgaaaat cgcaacgcat aattgttgtc   420
gcgctgccga aaagttgcag ctgattgcgc atggtgccgc aaccgtgcgg caccctaccg   480
catggagata agcatggcca gcgttgcgta ttaacaacag cgcgacggct tttcaacgtc   540
gactaacgcg taccacggcg ttggcacgcc gtgggatggc gtacctctat tcgtaccggt   600
cgcagtccag agaaatcggc attcaagcca agaacaagcc cggtcactgg gtgcaaacgg   660
aacgcaaagc gcatgaggcg tgggccgggc ttattgcgag cgtcaggtc tctttagccg    720
taagttcggt tcttgttcgg gccagtgacc cacgtttgcc ttgcgtttcg cgtactccgc   780
acccggcccg aataacgctc gaaacccacg gcggcaatgc tgctgcatca cctcgtggcg   840
cagatgggcc accagaacgc cgtggtggtc agccagaaga cactttccaa gctcatcgga   900
cttgggtgc cgccgttacg acgacgtagt ggagcaccgc gtctaccgg tggtcttgcg     960
gcaccaccag tcggtcttct gtgaaaggtt cgagtagcct cgttctttgc ggacggtcca  1020
atacgcagtc aaggacttgg tggccgagcg ctggatctcc gtcgtgaagc tcaacggccc  1080
cggcaccgtg tcggcctacg gcaagaaacg cctgccaggt tatgcgtcag ttcctgaacc  1140
accggctcgc gacctagagg cagcacttcg agttgccggg gccgtggcac agccggatgc  1200
tggtcaatga ccgcgtggcg tggggccagc cccgcgacca gttgcgcctg tcggtgttca  1260
gtgccgccgt ggtggttgat cacgacgacc aggacgaatc accagttact ggcgcaccgc  1320
accccggtcg gggcgctggt caacgcggac agccacaagt cacggcggca ccaccaacta  1380
gtgctgctgg tcctgcttag gctgttgggg catggcgacc tgcgccgcat cccgaccctg  1440
tatccgggcg agcagcaact accgaccggc cccggcgagg agccgcccag ccagcccggc  1500
cgacaacccc gtaccgctgg acgcggcgta gggctgggac ataggcccgc tcgtcgttga  1560
tggctggccg gggccgctcc tcggcgggtc ggtcgggccg attccgggca tggaaccaga  1620
cctgccagcc ttgaccgaaa cggaggaatg ggaacggcgc gggcagcagc gcctgccgat  1680
gcccgatgag ccgtgttttc taaggcccgt accttggtct ggacggtcgg aactggcttt  1740
gcctccttac ccttgccgcg cccgtcgtcg cggacggcta cgggctactc ggcacaaaag  1800
tggacgatgg cgagccgttg gagccgccga cacgggtcac gctgccgcgc cggtagcact  1860
tgggttgcgc agcaacccgt aagtgcgctg ttccagacta acctgctacc gctcggcaac  1920
ctcggcggct gtgcccagtg cgacggcgcg gccatcgtga acccaacgcg tcgttgggca  1980
ttcacgcgac aaggtctgat tcggctgtag ccgcctcgcc gccctatacc ttgtctgcct  2040
ccccgcgttg cgtcgcggtg catggagccg ggccacctcg acctgaatgg aagccggcgg  2100
agccgacatc ggcggagcgg cgggatatgg aacagacgga ggggcgcaac gcagcgccac  2160
gtacctcggc ccggtggagc tggacttacc ttcggccgcc cacctcgcta acggattcac  2220
cgttttatc aggctctggg aggcagaata aatgatcata tcgtcaatta ttacctccac   2280
ggggagagcc tgagcaaact gtggagcgat tgcctaagtg gcaaaaatag tccgagaccc  2340
tccgtcttat ttactagtat agcagttaat aatgaggtg cccctctcgg actcgtttga   2400
ggcctcaggc atttgagaag cacacggtca cactgcttcc ggtagtcaat aaaccggtaa  2460
```

```
accagcaata gacataagcg gctatttaac gaccctgccc ccggagtccg taaactcttc    2520
gtgtgccagt gtgacgaagg ccatcagtta tttggccatt tggtcgttat ctgtattcgc    2580
cgataaattg ctgggacggg tgaaccgacg accgggtcga atttgctttc gaatttctgc    2640
cattcatccg cttattatca cttattcagg cgtagcacca ggcgtttaag ggcaccaata    2700
acttggctgc tggcccagct taaacgaaag cttaaagacg gtaagtaggc gaataatagt    2760
gaataagtcc gcatcgtggt ccgcaaattc ccgtggttat actgccttaa aaaaattacg    2820
ccccgccctg ccactcatcg cagtcggcct attggttaaa aaatgagctg atttaacaaa    2880
aatttaacgc gaattttaac tgacggaatt ttttaatgc ggggcgggac ggtgagtagc     2940
gtcagccgga taaccaattt tttactcgac taaattgttt ttaaattgcg cttaaaattg    3000
aaaatattaa cgcttacaat ttccattcgc cattcaggct gcgcaactgt tgggaagggc    3060
gatcggtgcg ggcctcttcg ctattacgcc agctggcgaa ttttataatt gcgaatgtta    3120
aaggtaagcg gtaagtccga cgcgttgaca acccttcccg ctagccacgc ccggagaagc    3180
gataatgcgg tcgaccgctt aggggatgt gctgcaaggc gattaagttg ggtaacgcca     3240
gggttttccc agtcacgacg ttgtaaaacg acggccagtg agcgcgcgta atacgactca    3300 tcccctaca cgacgttccg ctaattcaac ccattgcgt cccaaaaggg tcagtgctgc      3360
aacattttgc tgccggtcac tcgcgcgcat tatgctgagt ctatagggcg aattggagct    3420
ccaccgcggt ggcggccgct ctagaactag tggatcccc gggctgcagg aattcgatat     3480
caagcttatc gataccgtcg gatatcccgc ttaacctcga ggtggcgcca ccgccggcga    3540
gatcttgatc acctagggg cccgacgtcc ttaagctata gttcgaatag ctatggcagc     3600
acgggcccgg gatccgatgc tcttccgcta agatctttta ctagttcagt ccatctcgcc    3660
gtgtatgcgg gcctgacgga tcaacgttcc caccgagcca tgcccgggcc ctaggctacg    3720
agaaggcgat tctagaaaat gatcaagtca ggtagagcgg cacatacgcc cggactgcct    3780
agttgcaagg gtggctcggt gtcgagatgt tcatctggtc ggcgatctgc cggtacttca    3840
aaccttgttt gcgcagttcc acagccttct tgcggcgttc ctgcgcacga gcgatgtagt    3900
cagctctaca agtagaccag ccgctagacg gccatgaagt ttggaacaaa cgcgtcaagg    3960
tgtcggaaga acgccgcaag gacgcgtgct cgctacatca cgcctcggtc ttcggcgacg    4020
agccgtttga tggtgctttt cgagacgccg aacttgtcag ccaactcctg cgcggtctgc    4080
gtgcgacgca tcacgcgttc gcggagccag aagccgctgc tcggcaaact accacgaaaa    4140
gctctgcggc ttgaacagtc ggttgaggac gcgccagacg cacgctgcgt agtgcgcaag    4200
tgcagcaccc atcagtccgt cccctctgct gctgcgaaca gtgccgatcg atcgaccttc    4260
ttgagcttcg gccgcggcgc ggtggcgttc ttccgtaccg acgtcgtggg tagtcaggca    4320
ggggagacga cgacgcttgt cacggctagc tagctggaag aactcgaagc cggcgccgcg    4380
ccaccgcaag aaggcatggc cttccgtttt tgcgctgctg ctcactttgc cgcggcgtgc    4440
ctggattttc gagaactcgg cggcggtgaa ggtgcggtgg gtccagtggg cgactgattt    4500
gaaggcaaaa acgcgacgac gagtgaaacg gcgccgcacg gacctaaaag ctcttgagcc    4560
gccgccactt ccacgccacc caggtcaccc gctgactaaa gccgatctgc tcggcctcgg    4620
cccgactcat ggggccgatc ccgtcgttgg cgtcgagggt gaagttggtc agggcggtga    4680
agtcggtgac catctgccgc cggctagacg agcggagcc gggctgagta ccccggctag     4740
ggcagcaacc gcagctccca cttcaaccag tcccgccact tcagccactg gtagacggcg    4800
cacacagtga tcgacgggta gttctgtttc cggatctcgc ggtaggccca ttcccgggtg    4860
```

```
cggtcgaaca gttcgacgtt ccggcccgtt tcggtcctga gtgtgtcact agctgcccat     4920
caagacaaag gcctagagcg ccatccgggt aagggcccac gccagcttgt caagctgcaa     4980
ggccgggcaa agccaggact cctgtgtctt gcggccgtag tccggtgggg cggggaaacg     5040
gtcaccgagc gcttttgcga ggcctttgag cgagtacgga tccagggac cccagaccgt     5100 ggacacagaa cgccggcatc aggccacccc gccccttttgc cagtggctcg cgaaaacgct     5160
ccggaaactc gctcatgcct aggctccctg ggtctggca cgtccagtgc gggtggatcg     5220
ggttctgggt gagctgctgc gcgtagccct gatcggcgcc gaccaccgag gcgatcagcc     5280
cctggttcac ccggtcgtag gcaggtcacg cccacctagc ccaagaccca ctcgacgacg     5340
cgcatcggga ctagccgcgg ctggtggctc cgctagtcgg ggaccaagtg ggccagcatc     5400
agccgcagcg ggccctgtcg ggctgcctgg agggtgtaga ccgggctttc gagcagccac     5460
cacaggtgcg cgtgctcggt cgcgggattg atcgtcatca tcggcgtcgc ccgggacagc     5520
ccgacggacc tcccacatct ggcccgaaag ctcgtcggtg gtgtccacgc gcacgagcca     5580
gcgccctaac tagcagtagt cggtcggatc gggcagatcc gcgttacgtg cggcccactg     5640
cgcctggtcg tcgtccacgt cgagcaccaa gcccaacctg atcgacgggg tgcgggccgc     5700
gccagcctag cccgtctagg cgcaatgcac gccgggtgac gcggaccagc agcaggtgca     5760
gctcgtggtt cgggttggac tagctgcccc acgcccggcg aatgtagcgg cgggtgagcg     5820
cctccgcgcg cggctgcggc cactgcccgt cccggacgta gtcatccgtc gcgtgcgggt     5880
atttgaaccg ccagcggtcc ttacatcgcc gcccactcgc ggaggcgcgc gccgacgccg     5940
gtgacgggca gggcctgcat cagtaggcag cgcacgccca taaacttggc ggtcgccagg     6000
aaccaggcgt caacagcagc ggtcatgacc gccaagctag gccggatct gtaccgatcg     6060 ggggaggcgc gccgcaaatt atttaagagt ctcgctagca ttggtccgca gttgtcgtcg     6120
ccagtactgg cggttcgatc ccggcctaga catggctagc cccctccgcg cggcgtttaa     6180
taaattctca gagcgatcgt aaccatgtca ggtgttgcgg tgggttccgg gtaaacctcc     6240
acccgaatta tttaagagtc tcgctagcta agccctatct gatgctgcgc ggggggtcct     6300
ttggtacagt ccacaacgcc acccaaggcc catttggagg tgggcttaat aaattctcag     6360
agcgatcgat tcgggataga ctacgacgcg cccccccagga tcgcactgaa tctcaaaggt     6420
ggccggctga atttcgtcgc gcgaaaacct ccctggacag ttctggaatt cagcaagagg     6480
tgtgtctgaa cttcggtgtt agcgtgactt agagtttcca ccggccgact taaagcagcg     6540
cgcttttgga gggacctgtc aagaccttaa gtcgttctcc acacagactt gaagccacaa     6600
tttttggggg gtgactccag cggggtgggc acaacgcgaa cagagaccttt gtgtgtacga     6660 cggcgggagg taagtcgggt acggctcgga ctgcggtaga aaaaacccccc cactgaggtc     6720 gccccacccg tgttgcgctt gtctctggaa cacacatgct gccgccctcc attcagccca     6780
tgccgagcct gacgccatct gcaaccgtcg aatcgatttc gagcagagcg agcagagcaa     6840
gatattccaa aactccgggg ttcctcggcg gcctcccccg tctgtttgct caaccgaggg     6900
cgttggcagc ttagctaaag ctcgtctcgc tcgtctcgtt ctataaggtt ttgaggcccc     6960
aaggagccgc cggaggggggc agacaaacga gttggctccc agacctggcg gtcccgcgtt     7020
tccggacgcg cgggaccgcc taccgctcga gagcggaaga gcatctagat gcattcgcga     7080
ggtacccagc ttttgttccc tctgaccgc cagggcgcaa aggcctgcgc gccctggcgg     7140
atggcgagct ctcgccttct cgtagatcta cgtaagcgct ccatgggtcg aaaacaaggg     7200
```

```
tttagtgagg gttaattgcg cgcttggcgt aatcatggtc atagctgttt cctgtgtgaa    7260
attgttatcc gctcacaatt ccacacaaca tacgagccgg aaatcactcc caattaacgc    7320
gcgaaccgca ttagtaccag tatcgacaaa ggacacactt taacaatagg cgagtgttaa    7380
ggtgtgttgt atgctcggcc aagcataaag tgtaaagcct ggggtgccta atgagtgagc    7440
taactcacat taattgcgtt gcgctcactg cccgctttcc agtcgggaaa cctgtcgtgc    7500
ttcgtatttc acatttcgga ccccacggat tactcactcg attgagtgta attaacgcaa    7560
cgcgagtgac gggcgaaagg tcagccctt ggacagcacg cagctgcatt aatgaatcgg    7620
ccaacgcgcg gggagaggcg gtttgcgtat tgggcgcatg cataaaaact gttgtaattc    7680
attaagcatt ctgccgacat gtcgacgtaa ttacttagcc ggttgcgcgc ccctctccgc    7740
caaacgcata acccgcgtac ggaagccatc acaaacggca tgatgaacct gaatcgccag    7800
cggcatcagc accttgtcgc cttgcgtata atatttgccc atggggtgg gcgaagaact    7860 ccttcggtag tgtttgccgt actacttgga cttagcggtc gccgtagtcg tggaacagcg    7920
gaacgcatat tataaacggg tacccccacc cgcttcttga ccagcatgag atccccgcgc    7980
tggaggatca tccagccggc gtcccggaaa acgattccga agcccaacct ttcatagaag    8040
gcggcggtgg aatcgaaatc ggtcgtactc taggggcgcg acctcctagt aggtcggccg    8100
cagggccttt tgctaaggct tcggttgga aagtatcttc cgccgccacc ttagctttag    8160
tcgtgatggc aggttgggcg tcgcttggtc ggtcatttcg aacccagag tcccgctcag    8220 aagaactcgt caagaaggcg atagaaggcg atgcgctgcg agcactaccg tccaacccgc    8280
agcgaaccag ccagtaaagc ttgggggtctc agggcgagtc ttcttgagca gttcttccgc    8340
tatcttccgc tacgcgacgc aatcgggagc ggcgataccg taaagcacga ggaagcggtc    8400
agcccattcg ccgccaagct cttcagcaat atcacgggta gccaacgcta tgtcctgata    8460
ttagccctcg ccgctatggc atttcgtgct ccttcgccag tcgggtaagc ggcggttcga    8520
gaagtcgtta tagtgcccat cggttgcgat acaggactat gcggtccgcc acacccagcc    8580
ggccacagtc gatgaatcca gaaaagcggc cattttccac catgatattc ggcaagcagg    8640
catcgccatg ggtcacgacg cgccaggcgg tgtgggtcgg ccggtgtcag ctacttaggt    8700
cttttcgccg gtaaaggtg gtactataag ccgttcgtcc gtagcggtac ccagtgctgc    8760
agatcctcgc cgtcgggcat gcgcgccttg agcctggcga acagttcggc tggcgcgagc    8820
ccctgatgct cttcgtccag atcatcctga tcgacaagac tctaggagcg gcagcccgta    8880
cgcgcggaac tcggaccgct tgtcaagccg accgcgctcg gggactacga gaagcaggtc    8940
tagtaggact agctgttctg cggcttccat ccgagtacgt gctcgctcga tgcgatgttt    9000
cgcttggtgg tcgaatgggc aggtagccgg atcaagcgta tgcagccgcc gcattgcatc    9060
gccgaaggta ggctcatgca cgagcgagct acgctacaaa gcgaaccacc agcttacccg    9120
tccatcggcc tagttcgcat acgtcggcgg cgtaacgtag agccatgatg gatactttct    9180
cggcaggagc aaggtgagat gacaggagat cctgccccgg cacttcgccc aatagcagcc    9240
agtcccttcc cgcttcagtt cggtactacc tatgaaagag ccgtcctcgt tccactctac    9300
tgtcctctag gacggggccg tgaagcgggt tatcgtcggt cagggaaggg cgaagtcaca    9360
caacgtcgag cacagctgcg caaggaacgc ccgtcgtggc cagccacgat agccgcgctg    9420
cctcgtcctg cagttcattc agggcaccgg acaggtcggt gttgcagctc gtgtcgacgg    9480
gttccttgcg ggcagcaccg gtcggtgcta tcggcgcgac ggagcaggac gtcaagtaag    9540
tcccgtggcc tgtccagcct cttgacaaaa agaaccgggc gcccctgcgc tgacagccgg    9600
```

```
aacacggcgg catcagagca gccgattgtc tgttgtgccc agtcatagcc gaatagccta   9660
gaactgtttt tcttggcccg cggggacgcg actgtcggcc ttgtgccgcc gtagtctcgt   9720
cggctaacag acaacacggg tcagtatcgg cttatcggac tccacccaag cggccggaga   9780
acctgcgtgc aatccatctt gttcaatcat gcgaaacgat cctcatcctg tctcttgatc   9840
agatcttgat cccctgcgcg aggtgggttc gccggcctct tggacgcacg ttaggtagaa   9900
caagttagta cgctttgcta ggagtaggac agagaactag tctagaacta ggggacgcgc   9960
atcagatcct tggcggcaag aaagccatcc agtttacttt gcagggcttc ccaaccttac   10020
cagagggcgc cccagctggc aattccggtt cgcttgctgg tagtctagga accgccgttc   10080
tttcggtagg tcaaatgaaa cgtcccgaag ggttggaatg gtctcccgcg gggtcgaccg   10140
ttaaggccaa gcaacgact ccataaaacc gcccagtcta gctatcgcca tgtaagccca   10200
ctgcaagcta cctgctttct ctttgcgctt gcgttttccc ttgtccagat agcccagtaa   10260
ggtattttgg cgggtcagat cgatagcggt acattcgggt gacgttcgat ggacgaaaga   10320
gaaacgcgaa cgcaaagggg aacaggtcta tcgggtcatg ctgacattca tcccaggtgg   10380
cacttttcgg ggaaatgtgc gcgcccgcgt tcctgctggc gctgggcctg tttctggcgc   10440
tggacttccc gctgttccgc gactgtaagt agggtccacc gtgaaaagcc cctttacacg   10500
cgcgggcgca aggacgaccg cgacccggac aaagaccgcg acctgaaggg cgacaaggct   10560
cagcagcttt tcgcccacgg ccttgatgat cgcggcggcc ttggcctgca tatcccgatt   10620
caacggcccc agggcgtcca gaacgggctt caggcgctca gtcgtcgaaa gcgggtgcc   10680 ggaactacta gcgccgccgg aaccggacgt atagggctaa gttgccgggg tcccgcaggt   10740
cttgcccgaa gtccgcgacc gaaggtctcg ggccgtctct tgggcttgat cggccttctt   10800
gcgcatctca cgcgctcctg cggcggcctg tagggcaggc tcatacccct gccgaaccgg   10860
cttccagagc ccggcagaga acccgaacta gccggaagaa cgcgtagagt gcgcgaggac   10920
gccgccggac atcccgtccg agtatgggga cggcttgggc ttttgtcagc cggtcggcca   10980
cggcttccgg cgtctcaacg cgctttgaga ttcccagctt ttcggccaat ccctgcggtg   11040
cataggcgcg tggctcgacg aaaacagtcg gccagccggt gccgaaggcc gcagagttgc   11100
gcgaaactct aagggtcgaa aagcggtta gggacgccac gtatccgcgc accgagctcc   11160
gcttgcgggc tgatggtgac gtggcccact ggtggccgct ccagggcctc gtagaacgcc   11220
tgaatgcgcg tgtgacgtgc cttgctgccc tcgatgccgg cgaacgcccg actaccactg   11280
caccgggtga ccaccggcga ggtcccggag catcttgcgg acttacgcgc acactgcacg   11340
gaacgacggg agctacggcc gttgcagccc tagatcggcc acagcggccg caaacgtggt   11400
ctggtcgcgg gtcatctgcg ctttgttgcc gatgaactcc ttggccgaca gcctgccggg   11460
caacgtcggg atctagccgg tgtcgccggc gtttgcacca gaccagcgcc cagtagacgc   11520
gaaacaacgg ctacttgagg aaccggctgt cggacggctc ctgcgtcagc ggcaccacga   11580
acgcggtcat gtgcgggctg gtttcgtcac ggtggatgct ggccgtcacg atgcgatccg   11640
ccccgtactt gtccgccaag gacgcagtcg ccgtggtgct tgcgccagta cacgcccgac   11700
caaagcagtg ccacctacga ccggcagtgc tacgctaggc ggggcatgaa caggcggtgc   11760
cacttgtgcg ccttctcgaa gaacgccgcc tgctgttctt ggctggccga cttccaccat   11820
tccgggctgg ccgtcatgac gtactcgacc gccaacaccg tgaacacgc ggaagagctt   11880 cttgcggcgg acgacaagaa ccgaccggct gaaggtggta aggcccgacc ggcagtactg   11940
```

-continued

| | |
|---|---|
| catgagctgg cggttgtgag cgtccttgcg ccgcttctct ggcagcaact cgcgcagtcg | 12000 |
| gcccatcgct tcatcggtgc tgctggccgc ccagtgctcg ttctctggcg tcctgctgtc | 12060 |
| gcaggaacgc ggcgaagaga ccgtcgttga gcgcgtcagc cgggtagcga agtagccacg | 12120 |
| acgaccggcg ggtcacgagc aagagaccgc aggacgacgc gtcagcgttg ggcgtctcgc | 12180 |
| gctcgcggta ggcgtgcttg agactggccg ccacgttgcc cattttcgcc agcttcttgc | 12240 |
| atcgcatgat cgcgtatgcg cagtcgcaac ccgcagagcg cgagcgccat ccgcacgaac | 12300 |
| tctgaccggc ggtgcaacgg gtaaaagcgg tcgaagaacg tagcgtacta gcgcataccc | 12360 |
| gccatgcctg cccctcccct tggtgtcca accggctcga cggggcagc gcaaggcggt | 12420 |
| gcctccggcg ggccactcaa tgcttgagta tactcactgg cggtacggac ggggagggaa | 12480 |
| aaccacaggt tggccgagct gccccgtcg cgttccgcca cggaggccgc ccggtgagtt | 12540 |
| acgaactcat atgagtgaag actttgcttc gcaaagtcgt gaccgcctac ggcggctgcg | 12600 |
| gcgcccacg ggcttgctct ccgggcttcg ccctgcgcgg tcgctgcgct cccttgcctc | 12660 |
| tgaaacgaag cgtttcagca ctggcggatg ccgccgacgc cgcgggatgc ccgaacgaga | 12720 |
| ggcccgaagc gggacgcgcc agcgacgcga gggaacgg | 12758 |

<210> SEQ ID NO 4
<211> LENGTH: 15158
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

| | |
|---|---|
| ggggagccgc gccgaaggcg tgggggaacc ccgcaggggt gcccttcttt gggcaccaaa | 60 |
| gaactagata tagggcgaaa tgcgaaagac ttaaaaatca cccctcggcg cggcttccgc | 120 |
| acccccttgg ggcgtcccca cgggaagaaa cccgtggttt cttgatctat atcccgcttt | 180 |
| acgctttctg aattttagt acaacttaaa aaggggggt acgcaacagc tcattgcggc | 240 |
| accccccgca atagctcatt gcgtaggtta agaaaatct gtaattgact gccactttta | 300 |
| tgttgaattt tttccccca tgcgttgtcg agtaacgccg tgggggcgt tatcgagtaa | 360 |
| cgcatccaat ttcttttaga cattaactga cggtgaaaat cgcaacgcat aattgttgtc | 420 |
| gcgctgccga aaagttgcag ctgattgcgc atggtgccgc aaccgtgcgg caccctaccg | 480 |
| catggagata agcatggcca gcgttgcgta ttaacaacag cgcgacggct tttcaacgtc | 540 |
| gactaacgcg taccacggcg ttggcacgcc gtgggatggc gtacctctat tcgtaccggt | 600 |
| cgcagtccag agaaatcggc attcaagcca agaacaagcc cggtcactgg gtgcaaacgg | 660 |
| aacgcaaagc gcatgaggcg tgggccggc ttattgcgag gcgtcaggtc tctttagccg | 720 |
| taagttcggt tcttgttcgg gccagtgacc cacgtttgcc ttgcgtttcg cgtactccgc | 780 |
| acccggcccg aataacgctc gaaacccacg gcggcaatgc tgctgcatca cctcgtggcg | 840 |
| cagatgggcc accagaacgc cgtggtggtc agccagaaga cactttccaa gctcatcgga | 900 |
| ctttgggtgc cgccgttacg acgacgtagt ggagcaccgc gtctaccgg tggtcttgcg | 960 |
| gcaccaccag tcggtcttct gtgaaaggtt cgagtagcct cgttctttgc ggacggtcca | 1020 |
| atacgcagtc aaggacttgg tggccgagcg ctggatctcc gtcgtgaagc tcaacggccc | 1080 |
| cggcaccgtg tcggcctacg gcaagaaacg cctgccaggt tatgcgtcag ttcctgaacc | 1140 |
| accggctcgc gacctagagg cagcacttcg agttgccggg gccgtggcac agccggatgc | 1200 |

```
tggtcaatga ccgcgtggcg tggggccagc cccgcgacca gttgcgcctg tcggtgttca    1260
gtgccgccgt ggtggttgat cacgacgacc aggacgaatc accagttact ggcgcaccgc    1320
accccggtcg gggcgctggt caacgcggac agccacaagt cacggcggca ccaccaacta    1380
gtgctgctgg tcctgcttag gctgttgggg catggcgacc tgcgccgcat cccgaccctg    1440
tatccgggcg agcagcaact accgaccggc cccggcgagg agccgcccag ccagcccggc    1500 cgacaaccccc gtaccgctgg acgggcgta gggctgggac ataggcccgc tcgtcgttga    1560
tggctggccg gggccgctcc tcggcgggtc ggtcgggccg attccgggca tggaaccaga    1620
cctgccagcc ttgaccgaaa cggaggaatg ggaacggcgc gggcagcagc gcctgccgat    1680
gcccgatgag ccgtgttttc taaggcccgt accttggtct ggacggtcgg aactggcttt    1740
gcctccttac ccttgccgcg cccgtcgtcg cggacggcta cgggctactc ggcacaaaag    1800
tggacgatgg cgagccgttg gagccgccga cacgggtcac gctgccgcgc cggtagcact    1860
tgggttgcgc agcaacccgt aagtgcgctg ttccagacta acctgctacc gctcggcaac    1920
ctcggcggct gtgcccagtg cgacggcgcg gccatcgtga acccaacgcg tcgttgggca    1980
ttcacgcgac aaggtctgat tcggctgtag ccgcctcgcc gccctatacc ttgtctgcct    2040
ccccgcgttg cgtcgcggtg catggagccg gccacctcg acctgaatgg aagccggcgg    2100
agccgacatc ggcggagcgg cgggatatgg aacagacgga ggggcgcaac gcagcgccac    2160
gtacctcggc ccggtggagc tggacttacc ttcggccgcc cacctcgcta acggattcac    2220
cgtttttatc aggctctggg aggcagaata aatgatcata tcgtcaatta ttacctccac    2280
ggggagagcc tgagcaaact gtggagcgat tgcctaagtg gcaaaaatag tccgagaccc    2340
tccgtcttat ttactagtat agcagttaat aatggaggtg ccctctcgg actcgtttga     2400 ggcctcaggc atttgagaag cacacggtca cactgcttcc ggtagtcaat aaaccggtaa    2460
accagcaata gacataagcg gctatttaac gaccctgccc ccggagtccg taaactcttc    2520
gtgtgccagt gtgacgaagg ccatcagtta tttggccatt tggtcgttat ctgtattcgc    2580
cgataaattg ctgggacggg tgaaccgacg accgggtcga atttgctttc gaatttctgc    2640
cattcatccg cttattatca cttattcagg cgtagcacca ggcgtttaag ggcaccaata    2700
acttggctgc tggcccagct taaacgaaag cttaagacg gtaagtaggc gaataatagt     2760
gaataagtcc gcatcgtggt ccgcaaattc ccgtggttat actgccttaa aaaaattacg    2820
ccccgccctg ccactcatcg cagtcggcct attggttaaa aaatgagctg atttaacaaa    2880
aatttaacgc gaattttaac tgacggaatt ttttaatgc ggggcgggac ggtgagtagc     2940
gtcagccgga taaccaattt tttactcgac taaattgttt ttaaattgcg cttaaaattg    3000
aaaatattaa cgcttacaat ttccattcgc cattcaggct gcgcaactgt tgggaagggc    3060
gatcggtgcg ggcctcttcg ctattacgcc agctggcgaa ttttataatt gcgaatgtta    3120
aaggtaagcg gtaagtccga cgcgttgaca acccttcccg ctagccacgc ccggagaagc    3180
gataatgcgg tcgaccgctt agggggatgt gctgcaaggc gattaagttg ggtaacgcca    3240
gggttttccc agtcacgacg ttgtaaaacg acggccagtg agcgcgcgta atacgactca    3300 tcccctaca cgacgttccg ctaattcaac ccattgcggt cccaaaaggg tcagtgctgc     3360
aacattttgc tgccggtcac tcgcgcgcat tatgctgagt ctataggggcg aattggagct    3420 ccaccgcggt ggcggccgct ctagaactag tggatccccc gggctgcagg aattcgatat    3480
caagctttta cgcccgccc gatatcccgc ttaacctcga ggtggcgcca ccgccggcga     3540
gatcttgatc acctaggggg cccgacgtcc ttaagctata gttcgaaaat gcggggcggg    3600
```

```
tgccactcat cgcagtactg ttgtaattca ttaagcattc tgccgacatg aagccatca      3660 caaacggcat gatgaacctg aatcgccagc ggcatcagca acggtgagta gcgtcatgac      3720
aacattaagt aattcgtaag acggctgtac cttcggtagt gtttgccgta ctacttggac      3780
ttagcggtcg ccgtagtcgt ccttgtcgcc ttgcgtataa tatttgccca tggtgaaaac      3840
gggggcgaag aagttgtcca tattggccac gtttaaatca aaactggtga aactcaccca      3900
ggaacagcgg aacgcatatt ataaacgggt accactttg ccccgcttc ttcaacaggt      3960 ataaccggtg caaatttagt tttgaccact ttgagtgggt gggattggct gagacgaaaa      4020
acatattctc aataaaccct ttagggaaat aggccaggtt ttcaccgtaa cacgccacat      4080
cttgcgaata tatgtgtaga ccctaaccga ctctgctttt tgtataagag ttatttggga      4140 aatccctta tccggtccaa aagtggcatt gtgcggtgta aacgcttat atacacatct      4200 aactgccgga aatcgtcgtg gtattcactc cagagcgatg aaaacgtttc agtttgctca      4260
tggaaaacgg tgtaacaagg gtgaacacta tcccatatca ttgacggcct ttagcagcac      4320
cataagtgag gtctcgctac ttttgcaaag tcaaacgagt accttttgcc acattgttcc      4380
cacttgtgat agggtatagt ccagctcacc gtctttcatt gccatacgaa attccggatg      4440
agcattcatc aggcgggcaa gaatgtgaat aaaggccgga taaaacttgt gcttatttt      4500 ggtcgagtgg cagaaagtaa cggtatgctt taaggcctac tcgtaagtag tccgcccgtt      4560
cttacactta ttttccggcct attttgaaca cgaataaaaa ctttacggtc tttaaaaagg      4620
ccgtaatatc cagctgaacg gtctggttat aggtacattg agcaactgac tgaaatgcct      4680
caaaatgttc tttacgatgc gaaatgccag aaatttttcc ggcattatag gtcgacttgc      4740
cagaccaata tccatgtaac tcgttgactg actttacgga gttttacaag aaatgctacg      4800
cattgggata tatcaacggt ggtatatcca gtgatttttt tctccatatg gttaaccta      4860 attaagggt cgacgggccc gggatccgat gctcttccgc gtaacctat atagttgcca      4920 ccatataggt cactaaaaaa agaggtatac caattggaat taattcccca gctgcccggg      4980
ccctaggcta cgagaaggcg taagatcttt tactagttca gtccatctcg ccgtgtatgc      5040
gggcctgacg gatcaacgtt cccaccgagc cagtcgagat gttcatctgg tcggcgatct      5100
attctagaaa atgatcaagt caggtagagc ggcacatacg cccggactgc ctagttgcaa      5160
gggtggctcg gtcagctcta caagtagacc agccgctaga gccggtactt caaaccttgt      5220
ttgcgcagtt ccacagcctt cttgcggcgt tcctgcgcac gagcgatgta gtcgcctcgg      5280
tcttcggcga cgagccgttt cggccatgaa gtttggaaca aacgcgtcaa ggtgtcggaa      5340
gaacgccgca aggacgcgtg ctcgctacat cagcggagcc agaagccgct gctcggcaaa      5400
gatggtgctt ttcgagacgc cgaacttgtc agccaactcc tgcgcggtct gcgtgcgacg      5460
catcacgcgt tctgcagcac ccatcagtcc gtccctctg ctaccacgaa aagctctgcg      5520
gcttgaacag tcggttgagg acgcgccaga cgcacgctgc gtagtgcgca agacgtcgtg      5580
ggtagtcagg caggggagac ctgctgcgaa cagtgccgat cgatcgacct tcttgagctt      5640
cggccgcggc gcggtggcgt tcttccgtac cgcttccgtt tttgcgctgc tgctcacttt      5700
gacgacgctt gtcacggcta gctagctgga agaactcgaa gccggcgccg cgccaccgca      5760
agaaggcatg gcgaaggcaa aaacgcgacg acgagtgaaa gccgcggcgt gcctggattt      5820
tcgagaactc ggcggcggtg aaggtgcggt gggtccagtg ggcgactgat ttgccgatct      5880
gctcggcctc ggcccgactc cggcgccgca cggacctaaa agctcttgag ccgccgccac      5940
```

| | | | | | |
|---|---|---|---|---|---|
| ttccacgcca | cccaggtcac | ccgctgacta | aacggctaga | cgagccggag | ccgggctgag | 6000 |
| atggggccga | tcccgtcgtt | ggcgtcgagg | gtgaagttgg | tcaggggcggt | gaagtcggtg | 6060 |
| accatctgcc | gccacacagt | gatcgacggg | tagttctgtt | taccccggct | agggcagcaa | 6120 |
| ccgcagctcc | cacttcaacc | agtcccgcca | cttcagccac | tggtagacgg | cggtgtgtca | 6180 |
| ctagctgccc | atcaagacaa | tccggatctc | gcggtaggcc | cattcccggg | tgcggtcgaa | 6240 |
| cagttcgacg | ttccggcccg | tttcggtcct | gacctgtgtc | ttgcggccgt | agtccggtgg | 6300 |
| aggcctagag | cgccatccgg | gtaagggccc | acgccagctt | gtcaagctgc | aaggccgggc | 6360 |
| aaagccagga | ctggacacag | aacgccggca | tcaggccacc | ggcggggaaa | cggtcaccga | 6420 |
| gcgcttttgc | gaggcctttg | agcgagtacg | gatccgaggg | accccagacc | gtcgtccagt | 6480 |
| gcgggtggat | cgggttctgg | ccgccccttt | gccagtggct | cgcgaaaacg | ctccggaaac | 6540 |
| tcgctcatgc | ctaggctccc | tggggtctgg | cagcaggtca | cgcccaccta | gcccaagacc | 6600 |
| gtgagctgct | gcgcgtagcc | ctgatcggcg | ccgaccaccg | aggcgatcag | ccctggttc | 6660 |
| acccggtcgt | agagccgcag | cgggccctgt | cgggctgcct | cactcgacga | cgcgcatcgg | 6720 |
| gactagccgc | ggctggtggc | tccgctagtc | ggggaccaag | tgggccagca | tctcggcgtc | 6780 |
| gcccgggaca | gcccgacgga | ggagggtgta | gaccgggctt | tcgagcagcc | accacaggtg | 6840 |
| cgcgtgctcg | gtcgcgggat | tgatcgtcat | cacggtcgga | tcgggcagat | ccgcgttacg | 6900 |
| cctcccacat | ctggcccgaa | agctcgtcgg | tggtgtccac | gcgcacgagc | cagcgcccta | 6960 |
| actagcagta | gtgccagcct | agcccgtcta | ggcgcaatgc | tgcggcccac | tgcgcctggt | 7020 |
| cgtcgtccac | gtcgagcacc | aagcccaacc | tgatcgacgg | ggtgcgggcc | gcaatgtagc | 7080 |
| ggcgggtgag | cgcctccgcg | acgccgggtg | acgcggacca | gcagcaggtg | cagctcgtgg | 7140 |
| ttcgggttgg | actagctgcc | ccacgcccgg | cgttacatcg | ccgcccactc | gcggaggcgc | 7200 |
| cgcggctgcg | gccactgccc | gtcccggacg | tagtcatccg | tcgcgtgcgg | gtatttgaac | 7260 |
| cgccagcggt | ccaaccaggc | gtcaacagca | gcggtcatga | gcgccgacgc | cggtgacggg | 7320 |
| cagggcctgc | atcagtaggc | agcgcacgcc | cataaacttg | gcggtcgcca | ggttggtccg | 7380 |
| cagttgtcgt | cgccagtact | ccgccaagct | agggccggat | ctgtaccgat | cgggggaggc | 7440 |
| gcgccgcaaa | ttatttaaga | gtctcgctag | caaaccatgt | caggtgttgc | ggtgggttcc | 7500 |
| ggcggttcga | tccggccta | gacatggcta | gccccctccg | cgcggcgttt | aataaattct | 7560 |
| cagagcgatc | gtttggtaca | gtccacaacg | ccacccaagg | gggtaaacct | ccaccgaat | 7620 |
| tatttaagag | tctcgctagc | taagcccatt | ctgatgctgc | gcgggggggtc | cttcgcactg | 7680 |
| aatctcaaag | gtggccggct | cccatttgga | ggtgggctta | ataaattctc | agagcgatcg | 7740 |
| attcgggata | gactacgacg | cgcccccag | gaagcgtgac | ttagagtttc | caccggccga | 7800 |
| gaatttcgtc | gcgcgaaaac | ctccctggac | agttctggaa | ttcagcaaga | ggtgtgtctg | 7860 |
| aacttcggtg | tttttttggg | gggtgactcc | agcggggtgg | cttaaagcag | cgcgcttttg | 7920 |
| gagggacctg | tcaagacctt | aagtcgttct | ccacacagac | ttgaagccac | aaaaaaaccc | 7980 |
| cccactgagg | tcgccccacc | gcacaacgcg | aacagagacc | ttgtgtgtac | gacggcggga | 8040 |
| ggtaagtcgg | gtacggctcg | gactgcgtga | gagcaaccgt | cgaatcgatt | tcgagcagag | 8100 |
| cgtgttgcgc | ttgtctctgg | aacacacatg | ctgccgccct | ccattcagcc | catgccgagc | 8160 |
| ctgacgccat | ctcgttggca | gcttagctaa | agctcgtctc | cgagcagagc | aagatattcc | 8220 |
| aaaactccgg | ggttcctcgg | cggcctcccc | cgtctgtttg | ctcaaccgag | ggagacctgg | 8280 |
| cggtcccgcg | tttccggacg | gctcgtctcg | ttctataagg | ttttgaggcc | ccaaggagcc | 8340 |

```
gccggagggg gcagacaaac gagttggctc cctctggacc gccagggcgc aaaggcctgc    8400
cgcgggaccg cctaccgctc gagagcggaa gagcatctag atgcattcgc gaggtaccca    8460
gcttttgttc cctttagtga gggttaattg cgcgcttggc gcgccctggc ggatggcgag    8520
ctctcgcctt ctcgtagatc tacgtaagcg ctccatgggc cgaaaacaag ggaaatcact    8580
cccaattaac gcgcgaaccg gtaatcatgg tcatagctgt ttcctgtgtg aaattgttat    8640
ccgctcacaa ttccacacaa catacgagcc ggaagcataa agtgtaaagc ctggggtgcc    8700
cattagtacc agtatcgaca aaggacacac tttaacaata ggcgagtgtt aaggtgtgtt    8760
gtatgctcgg ccttcgtatt tcacatttcg accccacgg taatgagtga gctaactcac     8820
attaattgcg ttgcgctcac tgcccgcttt ccagtcggga aacctgtcgt gccagctgca    8880
ttaatgaatc ggccaacgcg attactcact cgattgagtg taattaacgc aacgcgagtg    8940
acgggcgaaa ggtcagccct ttggacagca cggtcgacgt aattacttag ccggttgcgc    9000
cggggagagg cggtttgcgt attgggcgca tgcataaaaa ctgttgtaat tcattaagca    9060
ttctgccgac atggaagcca tcacaaacgg catgatgaac gcccctctcc gccaaacgca    9120
taacccgcgt acgtattttt gacaacatta agtaattcgt aagacggctg taccttcggt    9180
agtgtttgcc gtactacttg ctgaatcgcc agcggcatca gcaccttgtc gccttgcgta    9240
taatatttgc ccatggggt gggcgaagaa ctccagcatg agatcccgc gctggaggat      9300 gacttagcgg tcgccgtagt cgtggaacag cggaacgcat attataaacg gtaccccca    9360 cccgcttctt gaggtcgtac tctagggcg cgacctccta catccagccg gcgtcccgga     9420
aaacgattcc gaagcccaac ctttcataga aggcggcggt ggaatcgaaa tctcgtgatg    9480
gcaggttggg cgtcgcttgg gtaggtcggc cgcagggcct tttgctaagg cttcggttg     9540 gaaagtatct tccgccgcca ccttagcttt agagcactac cgtccaaccc gcagcgaacc    9600
tcggtcattt cgaacccag agtcccgctc agaagaactc gtcaagaagg cgatagaagg     9660
cgatgcgctg cgaatcggga gcggcgatac cgtaaagcac agccagtaaa gcttggggtc    9720
tcagggcgag tcttcttgag cagttcttcc gctatcttcc gctacgcgac gcttagccct    9780
cgccgctatg gcatttcgtg gaggaagcgg tcagcccatt cgccgccaag ctcttcagca    9840
atatcacggg tagccaacgc tatgtcctga tagcggtccg ccacacccag ccggccacag    9900
ctccttcgcc agtcgggtaa gcggcggttc gagaagtcgt tatagtgccc atcggttgcg    9960
atacaggact atcgccaggc ggtgtgggtc ggccggtgtc tcgatgaatc cagaaaagcg   10020
gccattttcc accatgatat tcggcaagca ggcatcgcca tgggtcacga cgagatcctc   10080
gccgtcgggc atgcgcgcct agctacttag gtcttttcgc cggtaaaagg tggtactata   10140
agccgttcgt ccgtagcggt acccagtgct gctctaggag cggcagcccg tacgcgcgga   10200
tgagcctggc gaacagttcg gctggcgcga gcccctgatg ctcttcgtcc agatcatcct   10260
gatcgacaag accggcttcc atccgagtac gtgctcgctc actcggaccg cttgtcaagc   10320
cgaccgcgct cggggactac gagaagcagg tctagtagga ctagctgttc tggccgaagg   10380
taggctcatg cacgagcgag gatgcgatgt ttcgcttggt ggtcgaatgg gcaggtagcc   10440
ggatcaagcg tatgcagccg ccgcattgca tcagccatga tggatacttt ctcggcagga   10500
ctacgctaca aagcgaacca ccagcttacc cgtccatcgg cctagttcgc atacgtcggc   10560
ggcgtaacgt agtcggtact acctatgaaa gagccgtcct gcaaggtgag atgacaggag   10620
atcctgcccc ggcacttcgc ccaatagcag ccagtccctt cccgcttcag tgacaacgtc   10680
```

```
gagcacagct gcgcaaggaa cgttccactc tactgtcctc taggacgggg ccgtgaagcg   10740
ggttatcgtc ggtcagggaa gggcgaagtc actgttgcag ctcgtgtcga cgcgttcctt   10800
cgcccgtcgt ggccagccac gatagccgcg ctgcctcgtc ctgcagttca ttcagggcac   10860
cggacaggtc ggtcttgaca aaaagaaccg ggcgccctg gcgggcagca ccggtcggtg    10920
ctatcggcgc gacggagcag gacgtcaagt aagtcccgtg gcctgtccag ccagaactgt   10980 tttttcttggc ccgcgggac cgctgacagc cggaacacgg cggcatcaga gcagccgatt   11040
gtctgttgtg cccagtcata gccgaatagc ctctccaccc aagcggccgg agaacctgcg   11100
gcgactgtcg gccttgtgcc gccgtagtct cgtcggctaa cagacaacac gggtcagtat   11160
cggcttatcg gagaggtggg ttcgccggcc tcttggacgc tgcaatccat cttgttcaat   11220
catgcgaaac gatcctcatc ctgtctcttg atcagatctt gatccctgc gccatcagat    11280 ccttggcggc aagaaagcca acgttaggta gaacaagtta gtacgctttg ctaggagtag   11340
gacagagaac tagtctagaa ctaggggacg cggtagtcta ggaaccgccg ttctttcggt   11400
tccagtttac tttgcagggc ttcccaacct taccagaggg cgcccagct ggcaattccg    11460 gttcgcttgc tgtccataaa accgcccagt ctagctatcg aggtcaaatg aaacgtcccg   11520
aagggttgga atggtctccc gcggggtcga ccgttaaggc caagcgaacg acaggtatt    11580 tggcgggtca gatcgatagc ccatgtaagc ccactgcaag ctacctgctt tctctttgcg   11640
cttgcgtttt cccttgtcca gatagcccag tagctgacat tcatcccagg tggcactttt   11700
ggtacattcg ggtgacgttc gatggacgaa agagaaacgc gaacgcaaaa gggaacaggt   11760
ctatcgggtc atcgactgta agtagggtcc accgtgaaaa cggggaaatg tgcgcgcccg   11820
cgttcctgct ggcgctgggc ctgtttctgg cgctggactt cccgctgttc cgtcagcagc   11880
ttttcgccca cggccttgat gccccttac acgcgcgggc gcaaggacga ccgcgacccg    11940
gacaaagacc gcgacctgaa gggcgacaag gcagtcgtcg aaaagcgggt gccggaacta   12000
gatcgcggcg gccttggcct gcatatcccg attcaacggc cccagggcgt ccagaacggg   12060
cttcaggcgc tcccgaaggt ctcgggccgt ctcttgggct ctagcgccgc cggaaccgga   12120
cgtatagggc taagttgccg gggtcccgca ggtcttgccc gaagtccgcg agggcttcca   12180
gagcccggca gagaacccga tgatcggcct tcttgcgcat ctcacgcgct cctgcggcgg   12240
cctgtagggc aggctcatac ccctgccgaa ccgcttttgt cagccggtcg gccacggctt   12300
actagccgga agaacgcgta gagtgcgcga ggacgccgcc ggacatcccg tccgagtatg   12360
gggacggctt ggcgaaaaca gtcggccagc cggtgccgaa ccggcgtctc aacgcgcttt   12420
gagattccca gcttttcggc caatccctgc ggtgcatagg cgcgtggctc gaccgcttgc   12480
gggctgatgg tgacgtggcc ggccgcagag ttgcgcgaaa ctctaagggt cgaaaagccg   12540
gttagggacg ccacgtatcc gcgcaccgag ctggcgaacg cccgactacc actgcaccgg   12600
cactggtggc cgctccaggg cctcgtagaa cgcctgaatg cgcgtgtgac gtgccttgct   12660
gccctcgatg ccccgttgca gccctagatc ggccacagcg gtgaccaccg gcgaggtccc   12720
ggagcatctt gcggacttac gcgcacactg cacggaacga cgggagctac ggggcaacgt   12780
cgggatctag ccggtgtcgc gccgcaaacg tggtctggtc gcgggtcatc tgcgctttgt   12840
tgccgatgaa ctccttggcc gacagcctgc cgtcctgcgt cagcggcacc acgaacgcgg   12900 cggcgttgc accagaccag cgcccagtag acgcgaaaca acggctactt gaggaaccgg    12960
ctgtcggacg gcaggacgca gtcgccgtgg tgcttgcgcc tcatgtgcgg gctggtttcg   13020
tcacggtgga tgctggccgt cacgatgcga tccgccccgt acttgtccgc cagccacttg   13080
```

-continued

```
tgcgccttct cgaagaacgc agtacacgcc cgaccaaagc agtgccacct acgaccggca   13140
gtgctacgct aggcggggca tgaacaggcg gtcggtgaac acgcggaaga gcttcttgcg   13200
cgcctgctgt tcttggctgg ccgacttcca ccattccggg ctggccgtca tgacgtactc   13260
gaccgccaac acagcgtcct tgcgccgctt ctctggcagc gcggacgaca agaaccgacc   13320
ggctgaaggt ggtaaggccc gaccggcagt actgcatgag ctggcggttg tgtcgcagga   13380
acgcggcgaa gagaccgtcg aactcgcgca gtcggcccat cgcttcatcg gtgctgctgg   13440
ccgcccagtg ctcgttctct ggcgtcctgc tggcgtcagc gttgggcgtc tcgcgctcgc   13500
ttgagcgcgt cagccgggta gcgaagtagc cacgacgacc ggcgggtcac gagcaagaga   13560
ccgcaggacg accgcagtcg caacccgcag agcgcgagcg ggtaggcgtg cttgagactg   13620
gccgccacgt tgcccatttt cgccagcttc ttgcatcgca tgatcgcgta tgccgccatg   13680
cctgcccctc ccttttggtg ccatccgcac gaactctgac cggcggtgca acgggtaaaa   13740
gcggtcgaag aacgtagcgt actagcgcat acggcggtac ggacggggag ggaaaaccac   13800
tccaaccggc tcgacggggg cagcgcaagg cggtgcctcc ggcgggccac tcaatgcttg   13860
agtatactca ctagactttg cttcgcaaag tcgtgaccgc aggttggccg agctgccccc   13920
gtcgcgttcc gccacggagg ccgcccggtg agttacgaac tcatatgagt gatctgaaac   13980
gaagcgtttc agcactggcg ctacggcggc tgcggcgccc tacgggcttg ctctccgggc   14040
ttcgccctgc gcggtcgctg cgctcccttg ccagcccgtg gatatgtgga cgatggccgc   14100
gatgccgccg acgccgcggg atgcccgaac gagaggcccg aagcgggacg cgccagcgac   14160
gcgagggaac ggtcgggcac ctatacacct gctaccggcg gagcggccac cggctggctc   14220
gcttcgctcg gcccgtggac aaccctgctg gacaagctga tggacaggct gcgcctgccc   14280
acgagcttga ccacagggat ctcgccggtg gccgaccgag cgaagcgagc cgggcacctg   14340
ttgggacgac ctgttcgact acctgtccga cgcggacggg tgctcgaact ggtgtcccta   14400
tgcccaccgg ctacccagcc ttcgaccaca tacccaccgg ctccaactgc gcggcctgcg   14460
gccttgcccc atcaattttt ttaattttct ctggggaaaa acgggtggcc gatgggtcgg   14520
aagctggtgt atgggtggcc gaggttgacg cgccggacgc cggaacgggg tagttaaaaa   14580
aattaaaaga gacccctttt gcctccggcc tgcggcctgc gcgcttcgct tgccggttgg   14640
acaccaagtg gaaggcgggt caaggctcgc gcagcgaccg cgcagcggct tggccttgac   14700
cggaggccgg acgccggacg cgcgaagcga acggccaacc tgtggttcac cttccgccca   14760
gttccgagcg cgtcgctggc gcgtcgccga accggaactg gcgcctggaa cgacccaagc   14820
ctatgcgagt gggggcagtc gaaggcgaag cccgcccgcc tgcccccga gcctcacggc   14880 ggcgagtgcg ggggttccaa cgcggacctt gctgggttcg gatacgctca ccccgtcag   14940 cttccgcttc gggcgggcgg acgggggggct cggagtgccg ccgctcacgc ccccaaggtt   15000
gggggcagcg ccaccttggg caaggccgaa ggccgcgcag tcgatcaaca agccccgag   15060 gggccacttt ttgccggagc cccgtcgcg gtggaacccg ttccggcttc cggcgcgtca   15120
gctagttgtt cggggcctcc ccggtgaaaa acggcctc                          15158
```

<210> SEQ ID NO 5
<211> LENGTH: 616
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 5

```
Met Glu Ala Leu Phe Leu Ser Ser Ser Ser Ser Ile Val Ala Ser
1               5                   10                  15

Asn Lys Leu Thr Arg Leu His Asn His Cys Val Trp Ser Thr Val Ile
            20                  25                  30

Arg Asp Lys Lys Arg Phe Gly Pro Thr Trp Cys Arg Val Gly Gly Gly
        35                  40                  45

Gly Asp Gly Gly Arg Asn Ser Asn Ala Glu Arg Pro Ile Arg Val Ser
    50                  55                  60

Ser Leu Leu Lys Asp Arg Gly Gln Val Leu Ile Arg Glu Gln Ser Ser
65                  70                  75                  80

Pro Ala Met Asp Ala Glu Thr Leu Val Leu Ser Pro Asn Gly Asn Gly
                85                  90                  95

Arg Thr Ile Glu Ile Asn Gly Val Lys Thr Leu Met Pro Phe Ser Gly
                100                 105                 110

Ala Ser Met Val Gly Met Lys Glu Gly Leu Gly Ile Ile Ser Phe Leu
            115                 120                 125

Gln Gly Lys Lys Phe Leu Ile Thr Gly Ser Thr Gly Phe Leu Ala Lys
130                 135                 140

Val Leu Ile Glu Lys Val Leu Arg Met Ala Pro Asp Val Ser Lys Ile
145                 150                 155                 160

Tyr Leu Leu Ile Lys Ala Lys Ser Lys Glu Ala Ile Glu Arg Leu
                165                 170                 175

Lys Asn Glu Val Leu Asp Ala Glu Leu Phe Asn Thr Leu Lys Glu Thr
            180                 185                 190

His Gly Ala Ser Tyr Met Ser Phe Met Leu Thr Lys Leu Ile Pro Val
            195                 200                 205

Thr Gly Asn Ile Cys Asp Ser Asn Ile Gly Leu Gln Ala Asp Ser Ala
210                 215                 220

Glu Glu Ile Ala Lys Glu Val Asp Val Ile Asn Ser Ala Ala Asn
225                 230                 235                 240

Thr Thr Phe Asn Glu Arg Tyr Asp Val Ala Leu Asp Ile Asn Thr Arg
                245                 250                 255

Gly Pro Gly Asn Leu Met Gly Phe Ala Lys Lys Cys Lys Lys Leu Lys
            260                 265                 270

Leu Phe Leu Gln Val Ser Thr Ala Tyr Val Asn Gly Gln Arg Gln Gly
            275                 280                 285

Arg Ile Met Glu Lys Pro Phe Ser Met Gly Asp Cys Ile Ala Thr Glu
290                 295                 300

Asn Phe Leu Glu Gly Asn Arg Lys Ala Leu Asp Val Asp Arg Glu Met
305                 310                 315                 320

Lys Leu Ala Leu Glu Ala Ala Arg Lys Gly Thr Gln Asn Gln Asp Glu
                325                 330                 335

Ala Gln Lys Met Lys Asp Leu Gly Leu Glu Arg Ala Arg Ser Tyr Gly
                340                 345                 350

Trp Gln Asp Thr Tyr Val Phe Thr Lys Ala Met Gly Glu Met Met Ile
            355                 360                 365

Asn Ser Thr Arg Gly Asp Val Pro Val Ile Ile Arg Pro Ser Val
            370                 375                 380

Ile Glu Ser Thr Tyr Lys Asp Pro Phe Pro Gly Trp Met Glu Gly Asn
385                 390                 395                 400

Arg Met Met Asp Pro Ile Val Leu Cys Tyr Gly Lys Gly Gln Leu Thr
```

```
                        405                 410                 415
Gly Phe Leu Val Asp Pro Lys Gly Val Leu Asp Val Val Pro Ala Asp
                    420                 425                 430

Met Val Val Asn Ala Thr Leu Ala Ala Ile Ala Lys His Gly Met Ala
                435                 440                 445

Met Ser Asp Pro Glu Pro Glu Ile Asn Val Tyr Gln Ile Ala Ser Ser
450                 455                 460

Ala Ile Asn Pro Leu Val Phe Glu Asp Leu Ala Glu Leu Leu Tyr Asn
465                 470                 475                 480

His Tyr Lys Thr Ser Pro Cys Met Asp Ser Lys Gly Asp Pro Ile Met
                485                 490                 495

Val Arg Leu Met Lys Leu Phe Asn Ser Val Asp Asp Phe Ser Asp His
                500                 505                 510

Leu Trp Arg Asp Ala Gln Glu Arg Ser Gly Leu Met Ser Gly Met Ser
                515                 520                 525

Ser Val Asp Ser Lys Met Met Gln Lys Leu Lys Phe Ile Cys Lys Lys
530                 535                 540

Ser Val Glu Gln Ala Lys His Leu Ala Thr Ile Tyr Glu Pro Tyr Thr
545                 550                 555                 560

Phe Tyr Gly Gly Arg Phe Asp Asn Ser Asn Thr Gln Arg Leu Met Glu
                565                 570                 575

Asn Met Ser Glu Asp Glu Lys Arg Glu Phe Gly Phe Asp Val Gly Ser
                580                 585                 590

Ile Asn Trp Thr Asp Tyr Ile Thr Asn Val His Ile Pro Gly Leu Arg
                595                 600                 605

Arg His Val Leu Lys Gly Arg Ala
610                 615

<210> SEQ ID NO 6
<211> LENGTH: 548
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Ala Thr Thr Asn Val Leu Ala Thr Ser His Ala Phe Lys Leu Asn
1               5                   10                  15

Gly Val Ser Tyr Phe Ser Phe Pro Arg Lys Pro Asn His Tyr Met
                20                  25                  30

Pro Arg Arg Arg Leu Ser His Thr Thr Arg Arg Val Gln Thr Ser Cys
                35                  40                  45

Phe Tyr Gly Glu Thr Ser Phe Glu Ala Val Thr Ser Leu Val Thr Pro
    50                  55                  60

Lys Thr Glu Thr Ser Arg Asn Ser Asp Gly Ile Gly Ile Val Arg Phe
65                  70                  75                  80

Leu Glu Gly Lys Ser Tyr Leu Val Thr Gly Ala Thr Gly Phe Leu Ala
                85                  90                  95

Lys Val Leu Ile Glu Lys Leu Leu Arg Glu Ser Leu Glu Ile Gly Lys
                100                 105                 110

Ile Phe Leu Leu Met Arg Ser Lys Asp Gln Glu Ser Ala Asn Lys Arg
            115                 120                 125

Leu Tyr Asp Glu Ile Ile Ser Ser Asp Leu Phe Lys Leu Leu Lys Gln
            130                 135                 140
```

-continued

Met His Gly Ser Ser Tyr Glu Ala Phe Met Lys Arg Lys Leu Ile Pro
145                 150                 155                 160

Val Ile Gly Asp Ile Glu Asp Asn Leu Gly Ile Lys Ser Glu Ile
            165                 170                 175

Ala Asn Met Ile Ser Glu Glu Ile Asp Val Ile Ile Ser Cys Gly Gly
            180                 185                 190

Arg Thr Thr Phe Asp Asp Arg Tyr Asp Ser Ala Leu Ser Val Asn Ala
            195                 200                 205

Leu Gly Pro Gly Arg Leu Leu Ser Phe Gly Lys Gly Cys Arg Lys Leu
    210                 215                 220

Lys Leu Phe Leu His Phe Ser Thr Ala Tyr Val Thr Gly Lys Arg Glu
225                 230                 235                 240

Gly Thr Val Leu Glu Thr Pro Leu Cys Ile Gly Glu Asn Ile Thr Ser
            245                 250                 255

Asp Leu Asn Ile Lys Ser Glu Leu Lys Leu Ala Ser Glu Ala Val Arg
            260                 265                 270

Lys Phe Arg Gly Arg Glu Glu Ile Lys Lys Leu Lys Glu Leu Gly Phe
    275                 280                 285

Glu Arg Ala Gln His Tyr Gly Trp Glu Asn Ser Tyr Thr Phe Thr Lys
290                 295                 300

Ala Ile Gly Glu Ala Val Ile His Ser Lys Arg Gly Asn Leu Pro Val
305                 310                 315                 320

Val Ile Ile Arg Pro Ser Ile Ile Glu Ser Ser Tyr Asn Glu Pro Phe
            325                 330                 335

Pro Gly Trp Ile Gln Gly Thr Arg Met Ala Asp Pro Ile Ile Leu Ala
            340                 345                 350

Tyr Ala Lys Gly Gln Ile Ser Asp Phe Trp Ala Asp Pro Gln Ser Leu
            355                 360                 365

Met Asp Ile Ile Pro Val Asp Met Val Ala Asn Ala Ile Ala Ala
            370                 375                 380

Met Ala Lys His Gly Cys Gly Val Pro Glu Phe Lys Val Tyr Asn Leu
385                 390                 395                 400

Thr Ser Ser Ser His Val Asn Pro Met Arg Ala Gly Lys Leu Ile Asp
            405                 410                 415

Leu Ser His Gln His Leu Cys Asp Phe Pro Leu Glu Glu Thr Val Ile
            420                 425                 430

Asp Leu Glu His Met Lys Ile His Ser Ser Leu Glu Gly Phe Thr Ser
            435                 440                 445

Ala Leu Ser Asn Thr Ile Ile Lys Gln Glu Arg Val Ile Asp Asn Glu
    450                 455                 460

Gly Gly Gly Leu Ser Thr Lys Gly Lys Arg Lys Leu Asn Tyr Phe Val
465                 470                 475                 480

Ser Leu Ala Lys Thr Tyr Glu Pro Tyr Thr Phe Phe Gln Ala Arg Phe
            485                 490                 495

Asp Asn Thr Asn Thr Thr Ser Leu Ile Gln Glu Met Ser Met Glu Glu
            500                 505                 510

Lys Lys Thr Phe Gly Phe Asp Ile Lys Gly Ile Asp Trp Glu His Tyr
    515                 520                 525

Ile Val Asn Val His Leu Pro Gly Leu Lys Lys Glu Phe Leu Ser Lys
            530                 535                 540

Lys Lys Thr Glu
545

```
<210> SEQ ID NO 7
<211> LENGTH: 491
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Glu Ser Asn Cys Val Gln Phe Leu Gly Asn Lys Thr Ile Leu Ile
1               5                   10                  15

Thr Gly Ala Pro Gly Phe Leu Ala Lys Val Leu Val Glu Lys Ile Leu
            20                  25                  30

Arg Leu Gln Pro Asn Val Lys Lys Ile Tyr Leu Leu Arg Ala Pro
        35                  40                  45

Asp Glu Lys Ser Ala Met Gln Arg Leu Arg Ser Glu Val Met Glu Ile
50                  55                  60

Asp Leu Phe Lys Val Leu Arg Asn Asn Leu Gly Glu Asp Asn Leu Asn
65                  70                  75                  80

Ala Leu Met Arg Glu Lys Ile Val Pro Val Pro Gly Asp Ile Ser Ile
                85                  90                  95

Asp Asn Leu Gly Leu Lys Asp Thr Asp Leu Ile Gln Arg Met Trp Ser
            100                 105                 110

Glu Ile Asp Ile Ile Ile Asn Ile Ala Ala Thr Thr Asn Phe Asp Glu
        115                 120                 125

Arg Tyr Asp Ile Gly Leu Gly Ile Asn Thr Phe Gly Ala Leu Asn Val
130                 135                 140

Leu Asn Phe Ala Lys Lys Cys Val Lys Gly Gln Leu Leu Leu His Val
145                 150                 155                 160

Ser Thr Ala Tyr Ile Ser Gly Glu Gln Pro Gly Leu Leu Leu Glu Lys
                165                 170                 175

Pro Phe Lys Met Gly Glu Thr Leu Ser Gly Asp Arg Glu Leu Asp Ile
            180                 185                 190

Asn Ile Glu His Asp Leu Met Lys Gln Lys Leu Lys Glu Leu Gln Asp
        195                 200                 205

Cys Ser Asp Glu Glu Ile Ser Gln Thr Met Lys Asp Phe Gly Met Ala
210                 215                 220

Arg Ala Lys Leu His Gly Trp Pro Asn Thr Tyr Val Phe Thr Lys Ala
225                 230                 235                 240

Met Gly Glu Met Leu Met Gly Lys Tyr Arg Glu Asn Leu Pro Leu Val
                245                 250                 255

Ile Ile Arg Pro Thr Met Ile Thr Ser Thr Ile Ala Glu Pro Phe Pro
            260                 265                 270

Gly Trp Ile Glu Gly Leu Lys Thr Leu Asp Ser Val Ile Val Ala Tyr
        275                 280                 285

Gly Lys Gly Arg Leu Lys Cys Phe Leu Ala Asp Ser Asn Ser Val Phe
290                 295                 300

Asp Leu Ile Pro Ala Asp Met Val Val Asn Ala Met Val Ala Ala Ala
305                 310                 315                 320

Thr Ala His Ser Gly Asp Thr Gly Ile Gln Ala Ile Tyr His Val Gly
                325                 330                 335

Ser Ser Cys Lys Asn Pro Val Thr Phe Gly Gln Leu His Asp Phe Thr
            340                 345                 350

Ala Arg Tyr Phe Ala Lys Arg Pro Leu Ile Gly Arg Asn Gly Ser Pro
        355                 360                 365
```

```
Ile Ile Val Val Lys Gly Thr Ile Leu Ser Thr Met Ala Gln Phe Ser
    370                 375                 380

Leu Tyr Met Thr Leu Arg Tyr Lys Leu Pro Leu Gln Ile Leu Arg Leu
385                 390                 395                 400

Ile Asn Ile Val Tyr Pro Trp Ser His Gly Asp Asn Tyr Ser Asp Leu
                405                 410                 415

Ser Arg Lys Ile Lys Leu Ala Met Arg Leu Val Glu Leu Tyr Gln Pro
            420                 425                 430

Tyr Leu Leu Phe Lys Gly Ile Phe Asp Asp Leu Asn Thr Glu Arg Leu
                435                 440                 445

Arg Met Lys Arg Lys Glu Asn Ile Lys Glu Leu Asp Gly Ser Phe Glu
    450                 455                 460

Phe Asp Pro Lys Ser Ile Asp Trp Asp Asn Tyr Ile Thr Asn Thr His
465                 470                 475                 480

Ile Pro Gly Leu Ile Thr His Val Leu Lys Gln
                485                 490
```

<210> SEQ ID NO 8
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Met Pro Glu Leu Ala Val Arg Thr Glu Phe Asp Tyr Ser Ser Glu Ile
1               5                   10                  15

Tyr Lys Asp Ala Tyr Ser Arg Ile Asn Ala Ile Val Ile Glu Gly Glu
                20                  25                  30

Gln Glu Ala Tyr Ser Asn Tyr Leu Gln Met Ala Glu Leu Leu Pro Glu
            35                  40                  45

Asp Lys Glu Glu Leu Thr Arg Leu Ala Lys Met Glu Asn Arg His Lys
        50                  55                  60

Lys Gly Phe Gln Ala Cys Gly Asn Asn Leu Gln Val Asn Pro Asp Met
65                  70                  75                  80

Pro Tyr Ala Gln Glu Phe Phe Ala Gly Leu His Gly Asn Phe Gln His
                85                  90                  95

Ala Phe Ser Glu Gly Lys Val Val Thr Cys Leu Leu Ile Gln Ala Leu
                100                 105                 110

Ile Ile Glu Ala Phe Ala Ile Ala Ala Tyr Asn Ile Tyr Ile Pro Val
            115                 120                 125

Ala Asp Asp Phe Ala Arg Lys Ile Thr Glu Gly Val Val Lys Asp Glu
        130                 135                 140

Tyr Thr His Leu Asn Tyr Gly Glu Glu Trp Leu Lys Ala Asn Phe Ala
145                 150                 155                 160

Thr Ala Lys Glu Glu Leu Glu Gln Ala Asn Lys Glu Asn Leu Pro Leu
                165                 170                 175

Val Trp Lys Met Leu Asn Gln Val Gln Gly Asp Ala Lys Val Leu Gly
                180                 185                 190

Met Glu Lys Glu Ala Leu Val Glu Asp Phe Met Ile Ser Tyr Gly Glu
            195                 200                 205

Ala Leu Ser Asn Ile Gly Phe Ser Thr Arg Glu Ile Met Arg Met Ser
        210                 215                 220

Ser Tyr Gly Leu Ala Gly Val
225                 230
```

```
<210> SEQ ID NO 9
<211> LENGTH: 340
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Phe Gly Leu Ile Gly His Leu Thr Ser Leu Glu His Ala Gln Ala
1               5                   10                  15

Val Ala Glu Asp Leu Gly Tyr Pro Glu Tyr Ala Asn Gln Gly Leu Asp
            20                  25                  30

Phe Trp Cys Ser Ala Pro Pro Gln Val Val Asp Asn Phe Gln Val Lys
        35                  40                  45

Ser Val Thr Gly Gln Val Ile Glu Gly Lys Tyr Val Glu Ser Cys Phe
    50                  55                  60

Leu Pro Glu Met Leu Thr Gln Arg Arg Ile Lys Ala Ala Ile Arg Lys
65                  70                  75                  80

Ile Leu Asn Ala Met Ala Leu Ala Gln Lys Val Gly Leu Asp Ile Thr
                85                  90                  95

Ala Leu Gly Gly Phe Ser Ser Ile Val Phe Glu Glu Phe Asn Leu Lys
            100                 105                 110

Gln Asn Asn Gln Val Arg Asn Val Glu Leu Asp Phe Gln Arg Phe Thr
        115                 120                 125

Thr Gly Asn Thr His Thr Ala Tyr Val Ile Cys Arg Gln Val Glu Ser
    130                 135                 140

Gly Ala Lys Gln Leu Gly Ile Asp Leu Ser Gln Ala Thr Val Ala Val
145                 150                 155                 160

Cys Gly Ala Thr Gly Asp Ile Gly Ser Ala Val Cys Arg Trp Leu Asp
                165                 170                 175

Ser Lys His Gln Val Lys Glu Leu Leu Leu Ile Ala Arg Asn Arg Gln
            180                 185                 190

Arg Leu Glu Asn Leu Gln Glu Glu Leu Gly Arg Gly Lys Ile Met Asp
        195                 200                 205

Leu Glu Thr Ala Leu Pro Gln Ala Asp Ile Ile Val Trp Val Ala Ser
    210                 215                 220

Met Pro Lys Gly Val Glu Ile Ala Gly Glu Met Leu Lys Lys Pro Cys
225                 230                 235                 240

Leu Ile Val Asp Gly Gly Tyr Pro Lys Asn Leu Asp Thr Arg Val Lys
                245                 250                 255

Ala Asp Gly Val His Ile Leu Lys Gly Gly Ile Val Glu His Ser Leu
            260                 265                 270

Asp Ile Thr Trp Glu Ile Met Lys Ile Val Glu Met Asp Ile Pro Ser
        275                 280                 285

Arg Gln Met Phe Ala Cys Phe Ala Glu Ala Ile Leu Leu Glu Phe Glu
    290                 295                 300

Gly Trp Arg Thr Asn Phe Ser Trp Gly Arg Asn Gln Ile Ser Val Asn
305                 310                 315                 320

Lys Met Glu Ala Ile Gly Glu Ala Ser Val Lys His Gly Phe Cys Pro
                325                 330                 335

Leu Val Ala Leu
            340
```

-continued

```
<210> SEQ ID NO 10
<211> LENGTH: 410
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
cagtcaatgg agagcattgc cataagtaaa ggcatcccct gcgtgataag attaccttca      60
gaaaacagat agttgctggg ttatcgcaga tttttctcgc gtcagttacc tctcgtaacg     120
gtattcattt ccgtagggga cgcactattc taatggaagt cttttgtcta tcaacgaccc     180
aatagcgtct aaaagagcg aaccaaataa ctgtaaataa taactgtctc tggggcgacg      240 gtaggctta tattgccaaa tttcgcccgt gggagaaagc taggctattc aatgtttatg      300
ttggtttatt gacatttatt attgacagag accccgctgc catccgaaat ataacggttt     360
aaagcgggca ccctctttcg atccgataag ttacaaatac gaggactcct                410

<210> SEQ ID NO 11
<211> LENGTH: 2962
<212> TYPE: DNA
<213> ORGANISM: Rhodococcus opacus
<220> FEATURE:
<221> NAME/KEY: modified_base
<222> LOCATION: (1070)..(1070)
<223> OTHER INFORMATION: a, c, t or g
<220> FEATURE:
<221> NAME/KEY: modified_base
<222> LOCATION: (1170)..(1170)
<223> OTHER INFORMATION: a, c, t or g

<400> SEQUENCE: 11
cctggctcag gacgaacgct ggcggcgtgc ttaacacatg caagtcgagc ggtaaggccc       60
ttcggggtac acgagcggcg aacgggtgag taacacgtgg ggaccgagtc ctgcttgcga     120
ccgccgcacg aattgtgtac gttcagctcg ccattccggg aagccccatg tgctcgccgc     180
ttgcccactc attgtgcacc gtgatctgcc ctgcacttcg ggataagcct gggaaactgg     240
gtctaatacc ggatatgacc ttcggctgca tggctgaggg tggaaaggtt tactggtgca     300
cactagacgg gacgtgaagc cctattcgga ccctttgacc cagattatgg cctatactgg     360
aagccgacgt accgactccc acctttccaa atgaccacgt ggatgggccc gcggcctatc     420
agcttgttgg tggggtaatg gcctaccaag gcgacgacgg tagccgacc tgagagggtg      480 accggccaca ctgggactga cctacccggg cgccggatag tcgaacaacc accccattac     540
cggatggttc cgctgctgcc catcggctgg actctcccac tggccggtgt gaccctgact     600
gacacggccc agactcctac gggaggcagc agtggggaat attgcacaat gggcgaaagc     660
ctgatgcagc gacgccgcgt gagggatgac ggccttcggg ctgtgccggg tctgaggatg     720
ccctccgtcg tcaccccta taacgtgtta cccgctttcg gactacgtcg ctgcggcgca      780
ctccctactg ccggaagccc ttgtaaacct ctttcagcag gacgaagcg aaagtgacgg      840 tacctgcaga agaagcaccg gccaactacg tgccagcagc cgcggtaata cgtagggtgc     900
aacatttgga gaagtcgtc cctgcttcgc tttcactgcc atggacgtct tcttcgtggc      960
cggttgatgc acgtcgtcg cgccattat gcatcccacg aagcgttgtc cggaattact      1020
gggcgtaaag agctcgtagg cggtttgtcg cgtcgtctgt gaaaactcan agctcaacct    1080
cgagcttgca ggcgatacgg ttcgcaacag gccttaatga cccgcatttc tcgagcatcc   1140
gccaaacagc gcagcagaca cttttgagtn tcgagttgga gctcgaacgt ccgctatgcc   1200
```

```
gcagacttga gtactgcagg ggagactgga attcctggtg tagcggtgaa atgcgcagat      1260
atcaggagga acaccggtgg cgaaggcggg tctctgggca cgtctgaact catgacgtcc      1320
cctctgacct taaggaccac atcgccactt tacgcgtcta tagtcctcct tgtggccacc      1380
gcttccgccc agagacccgt gtaactgacg ctgaggagcg aaagcgtggg tagcaaacag      1440
gattagatac cctggtagtc cacgccgtaa acggtgggcg ctaggtgtgg gtttccttcc      1500
cattgactgc gactcctcgc tttcgcaccc atcgtttgtc ctaatctatg ggaccatcag      1560
gtgcggcatt tgccacccgc gatccacacc caaaggaagg acgggatccg tgccgtagtt      1620
aacgcattaa gcgccccgcc tggggagtac ggccgcaagg ttaaaactca aaggaattga      1680
cgggggcccg cacaagcggc tgccctaggc acggcatcaa ttgcgtaatt cgcggggcgg      1740
acccctcatg ccggcgttcc aattttgagt ttccttaact gcccccgggc gtgttcgccg      1800
ggagcatgtg gattaattcg atgcaacgcg aagaaccttac cctgggtttg acatataccg      1860
gaaagccgta gagataccgc ccccttgtg gtcggtatac cctcgtacac ctaattaagc      1920
tacgttgcgc ttcttggaat ggacccaaac tgtatatggc ctttcggcat ctctatggcg      1980
gggggaacac cagccatatg aggtggtgca tggctgtcgt cagctcgtgt cgtgagatgt      2040
tgggttaagt cccgcaacga gcgcaaccct tgtcttatgt tgccagcacg taatggtggg      2100
tccaccacgt accgacagca gtcgagcaca gcactctaca acccaattca gggcgttgct      2160
cgcgttggga acagaataca acggtcgtgc attaccaccc gactcgtaag agactgccgg      2220
ggtcaactcg gaggaaggtg gggacgacgt caagtcatca tgccccttat gtccagggct      2280
tcacacatgc tacaatggcc ctgagcattc tctgacggcc ccagttgagc ctccttccac      2340
ccctgctgca gttcagtagt acggggaata caggtcccga agtgtgtacg atgttaccgg      2400
ggtacagagg gctgcgatac cgtgaggtgg agcgaatccc ttaaagccgg tctcagttcg      2460
gatcggggtc tgcaactcga ccccgtgaag tcggagtcgc ccatgtctcc cgacgctatg      2520
gcactccacc tcgcttaggg aatttcggcc agagtcaagc ctagcccag acgttgagct      2580 ggggcacttc agcctcagcg tagtaatcgc agatcagcaa cgctgcggtg aatacgttcc      2640
cgggccttgt acacaccgcc cgtcacgtca tgaaagtcgg taacacccga agccggtggc      2700
atcattagcg tctagtcgtt gcgacgccac ttatgcaagg gcccggaaca tgtgtggcgg      2760
gcagtgcagt actttcagcc attgtgggct tcggccaccg ctaaccccctt gtgggaggga      2820 gccgtcgaag gtgggatcgg cgattgggac gaagtcgtaa caaggtagcc gtaccggaag      2880
ggattgggga acaccctccc tcggcagctt ccaccctagc cgctaaccct gcttcagcat      2940
tgttccatcg gcatggcctt cc                                               2962
```

<210> SEQ ID NO 12
<211> LENGTH: 3042
<212> TYPE: DNA
<213> ORGANISM: Rhodococcus opacus

<400> SEQUENCE: 12

```
tcaacggaga gtttgatcct ggctcaggac gaacgctggc ggcgtgctta acacatgcaa       60
gtcgagcggt aaggcccttc ggggtacacg agcggcgaac agttgcctct caaactagga      120
ccgagtcctg cttgcgaccg ccgcacgaat tgtgtacgtt cagctcgcca ttccgggaag      180
ccccatgtgc tcgccgcttg gggtgagtaa cacgtgggtg atctgccctg cacttcggga      240
taagcctggg aaactgggtc taataccgga tatgaccttc ggctgcatgg ccgttggtgg      300
```

```
cccactcatt gtgcacccac tagacgggac gtgaagccct attcggaccc tttgacccag    360
attatggcct atactggaag ccgacgtacc ggcaaccacc aaaggtttac tggtgcagga    420
tgggcccgcg gcctatcagc ttgttggtgg ggtaatggcc taccaaggcg acgacgggta    480
gccgacctga gagggtgacc tttccaaatg accacgtcct acccgggcgc cggatagtcg    540
aacaaccacc ccattaccgg atggttccgc tgctgcccat cggctggact ctcccactgg    600
ggccacactg ggactgagac acggcccaga ctcctacggg aggcagcagt ggggaatatt    660
gcacaatggg cgaaagcctg atgcagcgac gccgcgtgag ccggtgtgac cctgactctg    720
tgccgggtct gaggatgccc tccgtcgtca cccctataa cgtgttaccc gctttcggac    780
tacgtcgctg cggcgcactc ggatgacggc cttcgggttg taaacctctt tcagcaggga    840
cgaagcgaaa gtgacggtac ctgcagaaga agcaccggcc aactacgtgc agcagccgc    900 cctactgccg gaagcccaac atttggagaa agtcgtccct gcttcgcttt cactgccatg    960
gacgtcttct tcgtggccgg ttgatgcacg tcgtcggcg ggtaatacgt agggtgcaag   1020
cgttgtccgg aattactggg cgtaaagagc tcgtaggcgg tttgtcgcgt cgtctgtgaa   1080
aactcgaggc tcaacctcga ccattatgca tcccacgttc gcaacaggcc ttaatgaccc   1140
gcatttctcg agcatccgcc aaacagcgca gcagacactt ttgagctccg agttggagct   1200
gcttgcaggc gatacgggca gacttgagta ctgcagggga gactggaatt cctggtgtag   1260
cggtgaaatg cgcagatatc aggaggaaca ccggtggcga cgaacgtccg ctatgcccgt   1320
ctgaactcat gacgtcccct ctgaccttaa ggaccacatc gccactttac gcgtctatag   1380
tcctccttgt ggccaccgct aggcgggtct ctgggcagta actgacgctg aggagcgaaa   1440
gcgtgggtag cgaacaggat tagataccct ggtagtccac gccgtaaacg tgggcgcta   1500 tccgcccaga gacccgtcat tgactgcgac tcctcgcttt cgcacccatc gcttgtccta   1560
atctatggga ccatcaggtg cggcatttgc caccgcgat ggtgtgggtt tccttccacg   1620
ggatccgtgc cgtagctaac gcattaagcg ccccgcctgg ggagtacggc cgcaaggcta   1680
aaactcaaag gaattgacgg ccacacccaa aggaaggtgc cctaggcacg gcatcgattg   1740
cgtaattcgc ggggcggacc cctcatgccg gcgttccgat tttgagtttc cttaactgcc   1800
gggcccgcac aagcggcgga gcatgtggat taattcgatg caacgcgaag aaccttacct   1860
gggtttgaca tataccggaa agctgcagag atgtggcccc ccggggcgtg ttcgccgcct   1920
cgtacaccta attaagctac gttgcgcttc ttggaatgga cccaaactgt atatggcctt   1980
tcgacgtctc tacaccgggg ccttgtggtc ggtatacagg tggtgcatgg ctgtcgtcag   2040
ctcgtgtcgt gagatgttgg gttaagtccc gcaacgagcg caaccccttgt cttatgttgc   2100 ggaacaccag ccatatgtcc accacgtacc gacagcagtc gagcacagca ctctacaacc   2160
caattcaggg cgttgctcgc gttgggaaca gaatacaacg cagcacgtaa tggtggggac   2220
tcgtaagaga ctgccggggt caactcggag aaggtgggg acgacgtcaa gtcatcatgc   2280
cccttatgtc cagggcttca gtcgtgcatt accacccctg agcattctct gacggcccca   2340
gttgagcctc cttccacccc tgctgcagtt cagtagtacg gggaatacag gtcccgaagt   2400
cacatgctac aatggccggt acagagggct gcgataccgt gaggtggagc gaatcccttta   2460 aagccggtct cagttcggat cggggtctgc aactcgaccc gtgtacgatg ttaccggcca   2520
tgtctcccga cgctatggca ctccacctcg cttagggaat tcggccagag tcaagccta   2580 gccccagacg ttgagctggg cgtgaagtcg gagtcgctag taatcgcaga tcagcaacgc   2640
tgcggtgaat acgttcccgg gccttgtaca caccgcccgt cacgtcatga aagtcggtaa   2700
```

```
gcacttcagc ctcagcgatc attagcgtct agtcgttgcg acgccactta tgcaagggcc    2760
cggaacatgt gtggcgggca gtgcagtact ttcagccatt cacccgaagc cggtggccta    2820 accccctcgtg ggagggagcc gtcgaaggtg ggatcggcga ttgggacgaa gtcgtaacaa   2880
ggtagccgta ccggaaggtg gtgggcttcg gccaccggat tggggagcac cctccctcgg    2940
cagcttccac cctagccgct aaccctgctt cagcattgtt ccatcggcat ggccttccac    3000
cggctggatc acctcctttc tgccgaccta gtggaggaaa ga                       3042
```

<210> SEQ ID NO 13
<211> LENGTH: 2924
<212> TYPE: DNA
<213> ORGANISM: Rhodococcus Ralstonia

<400> SEQUENCE: 13

```
acgtggcggc atgccttaca catgcaagtc gaacggcagc gcggacttcg gtctggcggc      60
gagtggcgaa cgggtgagta atacatcgga acgtaccctg tgcaccgccg tacggaatgt    120
gtacgttcag cttgccgtcg cgcctgaagc cagaccgccg ctcaccgctt gcccactcat    180
tatgtagcct tgcatgggac ttgtggggga taactagtcg aaagattagc taataccgca    240
tacgacctga gggtgaaagt gggggaccgc aaggcctcac gcagcaggag cggccgatgt    300 aacacccccct attgatcagc tttctaatcg attatgcgt atgctggact cccactttca    360 cccccctggcg ttccggagtg cgtcgtcctc gccggctaca ctgattagct agttggtggg    420
gtaaaggccc accaaggcga cgatcagtag ctggtctgag aggacgatca gccacactgg    480
gactgagaca cggcccagac gactaatcga tcaaccaccc catttccggg tggttccgct    540
gctagtcatc gaccagactc tcctgctagt cggtgtgacc ctgactctgt gccgggtctg    600
tcctacggga ggcagcagtg gggaattttg dacaatgggg gcaaccctga tccagcaatg    660
ccgcgtgtgt gaagaaggcc ttcgggttgt aaagcacttt aggatgccct ccgtcgtcac    720
cccttaaaac ctgttacccc cgttgggact aggtcgttac ggcgcacaca cttcttccgg    780
aagcccaaca tttcgtgaaa tgtccggaaa gaaatcgcgc tggttaatac ctgcgtgatg    840
acggtaccgg aagaataagc accggctaac tacgtgccag cagccgcggt aatacgtagg    900
acaggccttt ctttagcgcg accaattatg gacgcactac tgccatggcc ttcttattcg    960
tggccgattg atgcacggtc gtcggcgcca ttatgcatcc gtgcgagcgt taatcggaat   1020
tactgggcgt aaagcgtgcg caggcggttt tgtaagacag gcgtgaaatc cccgggctta   1080
acctgggaat tgcgcttgtg cacgctcgca attagcctta tgaccccgca tttcgcacgc   1140
gtccgccaaa acattctgtc cgcactttag gggcccgaat tggacccctta acgcgaacac   1200 actgcaaggc tagagtgcgt cagaggggg tagaattcca cgtgtagcag tgaaatgcgt    1260
agagatgtgg aggaataccg atggcgaagg cgagccccct tgacgttccg atctcacgca    1320 gtctccccccc atcttaaggt gcacatcgtc actttacgca tctctacacc tcctatggc    1380 taccgcttcc gctcggggga ggaccttgac tgacgctcat gcacgaaagc gtggggagca    1440
aacaggatta gataccctgg tagtccacgc cctaaacgat gtcaactagt tgttgggatt    1500
cctggaactg actgcgagta cgtgctttcg caccctcgt tgtcctaat ctatgggacc     1560 atcaggtgcg ggatttgcta cagttgatca acaaccctaa cattttctca gtaacgtagc    1620
taacgcgtga agttgaccgc ctggggagta cggctgcaag attaaaactc aaaggaattg    1680
acggggaccc gcacaagcgg gtaaaagagt cattgcatcg attgcgcact tcaactggcg    1740
```

-continued

```
gaccoctcat gccgacgttc taattttgag tttccttaac tgcccctggg cgtgttcgcc    1800
tggatgatgt ggattaattc gatgcaacgc gaaaaacctt acctaccctt gacatgccct    1860
aacgaagcag agatgcatta gtgcccgcaa agggaaagtg acctactaca cctaattaag    1920
ctacgttgcg cttttggaa tggatgggaa ctgtacggga ttgcttcgtc tctacgtaat     1980
cacgggcgtt tcccttcac ggacacaggt gctgcatggc tgtcgtcagc tcgtgtcgtg     2040
agatgttggg ttaagtcccg caacgagcgc aaccccttgtc tctagttgcc tacgcaagag   2100
cctgtgtcca cgacgtaccg acagcagtcg agcacagcac tctacaaccc aattcagggc    2160
gttgctcgcg ttgggaacag agatcaacgg atgcgttctc cactctagag agactgccgg    2220
tgacaaaccg gaggaaggtg gggatgacgt caagtcctca tggcccttat gggtagggct    2280
tcacacgtca tacaatggtg gtgagatctc tctgacggcc actgtttggc ctccttccac    2340
ccctactgca gttcaggagt accgggaata cccatcccga agtgtgcagt atgttaccac    2400
cgtacagagg gttgccaacc cgcgagggg agctaatccc agaaaacgca tcgtagtccg     2460
gatcgtagtc tgcaactcga ctacgtgaag ctggaatcgc gcatgtctcc caacggttgg    2520
gcgctccccc tcgattaggg tcttttgcgt agcatcaggc ctagcatcag acgttgagct    2580
gatgcacttc gaccttagcg tagtaatcgc ggatcagcat gccgcggtga atacgttccc    2640
gggtcttgta cacaccgccc gtcacaccat gggagtgggt tttgccagaa gtagttagcc    2700
atcattagcg cctagtcgta cggcgccact tatgcaaggg cccagaacat gtgtggcggg    2760
cagtgtggta ccctcaccca aaacggtctt catcaatcgg taaccgcaag gagggcgatt    2820
accacggcag ggttcatgac tggggtgaag tcgtaacaag gtattggcgt tcctcccgct    2880
aatggtgccg tcccaagtac tgaccccact tcagcattgt tcca                    2924
```

<210> SEQ ID NO 14  
<211> LENGTH: 284  
<212> TYPE: PRT  
<213> ORGANISM: Rhodococcus opacus

<400> SEQUENCE: 14

```
Met Ala Ser Ile Glu Asp Ile Leu Glu Leu Glu Ala Leu Glu Lys Asp
1               5                   10                  15

Ile Phe Arg Gly Ala Val His Pro Ser Val Leu Lys Arg Thr Phe Gly
            20                  25                  30

Gly Gln Val Ala Gly Gln Ser Leu Val Ser Ala Val Arg Thr Val Asp
        35                  40                  45

Glu Arg Phe Glu Val His Ser Leu His Gly Tyr Phe Leu Arg Pro Gly
    50                  55                  60

Asn Pro Thr Glu Pro Thr Val Tyr Leu Val Asp Arg Ile Arg Asp Gly
65                  70                  75                  80

Arg Ser Phe Cys Thr Arg Arg Val Thr Gly Ile Gln Asp Gly Lys Ala
                85                  90                  95

Ile Phe Thr Met Ser Ala Ser Phe His Ser Gln Asp Glu Gly Ile Glu
            100                 105                 110

His Gln Asp Thr Met Pro Ser Val Pro Glu Pro Glu Glu Leu Val Asp
        115                 120                 125

Ala Gln Thr Val Glu Glu Met Ala Ala Thr Asp Leu Tyr Arg Glu Trp
    130                 135                 140

Lys Glu Trp Asp Val Arg Ile Val Pro Ala Gly Cys Thr Gly Lys Thr
145                 150                 155                 160

Pro Gly Ile Ala Ala Lys Gln Arg Val Trp Met Arg Tyr Arg Asn Lys
```

```
                     165                 170                 175
Leu Pro Asp Asp Gln Val Phe His Ile Cys Thr Leu Ala Tyr Leu Ser
            180                 185                 190

Asp Met Thr Leu Leu Gly Ala Ser Lys Val Pro His Pro Gly Val Val
            195                 200                 205

Thr Gln Thr Ala Ser Leu Asp His Ala Met Trp Phe Leu Arg Pro Phe
            210                 215                 220

Arg Ala Asp Glu Trp Leu Leu Tyr Asp Gln Thr Ser Pro Ser Ala Gly
225                 230                 235                 240

Phe Gly Arg Ala Leu Thr Gln Gly Arg Met Phe Asp Arg Lys Gly Thr
                245                 250                 255

Met Val Ala Ala Val Val Gln Glu Gly Leu Thr Arg Ile Gln Arg Asp
            260                 265                 270

Gln Asp Gln Arg Asp Ile Glu Thr Gly Asn Met Ala
            275                 280

<210> SEQ ID NO 15
<211> LENGTH: 87
<212> TYPE: PRT
<213> ORGANISM: Bos taurus

<400> SEQUENCE: 15

Met Ser Gln Ala Glu Phe Asp Lys Ala Ala Glu Glu Val Lys His Leu
1               5                   10                  15

Lys Thr Lys Pro Ala Asp Glu Glu Met Leu Phe Ile Tyr Ser His Tyr
            20                  25                  30

Lys Gln Ala Thr Val Gly Asp Ile Asn Thr Glu Arg Pro Gly Met Leu
        35                  40                  45

Asp Phe Lys Gly Lys Ala Lys Trp Asp Ala Trp Asn Glu Leu Lys Gly
    50                  55                  60

Thr Ser Lys Glu Asp Ala Met Lys Ala Tyr Ile Asp Lys Val Glu Glu
65                  70                  75                  80

Leu Lys Lys Lys Tyr Gly Ile
                85

<210> SEQ ID NO 16
<211> LENGTH: 291
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
ggtaccgggc cccccctcga gatgtcccag gccgagttcg acaaggccgc cgaggaagtt    60
aagcacctca agaccaagcc ggcagacgag gagatgctgt tcatctactc ccactacaag   120
caggcaaccg tgggtgacat caacacagaa cggcccggca tgctcgactt caagggcaag   180
gccaagtggg atgcctggaa tgagctgaaa gggacctcca agaagatgc catgaaggcg   240 tacattgaca aggtagaaga actcaagaaa aaatacggca tctaggtcga c            291

<210> SEQ ID NO 17
<211> LENGTH: 533
<212> TYPE: PRT
<213> ORGANISM: Bos taurus

<400> SEQUENCE: 17

Met Phe Gln Phe His Ala Gly Ser Trp Glu Ser Trp Cys Cys Cys Cys
```

```
1               5                   10                  15
Cys Leu Ile Pro Gly Asp Arg Pro Trp Asp Arg Gly Arg Arg Trp Arg
            20                  25                  30

Leu Glu Met Arg His Thr Arg Ser Val His Glu Thr Arg Phe Glu Ala
            35                  40                  45

Ala Val Lys Val Ile Gln Ser Leu Pro Lys Asn Gly Ser Phe Gln Pro
            50                  55                  60

Thr Asn Glu Met Met Leu Lys Phe Tyr Ser Phe Tyr Lys Gln Ala Thr
65                      70                  75                  80

Glu Gly Pro Cys Lys Leu Ser Lys Pro Gly Phe Trp Asp Pro Val Gly
                85                  90                  95

Arg Tyr Lys Trp Asp Ala Trp Ser Ser Leu Gly Asp Met Thr Lys Glu
                100                 105                 110

Glu Ala Met Ile Ala Tyr Val Glu Glu Met Lys Lys Ile Leu Glu Thr
                115                 120                 125

Met Pro Met Thr Glu Lys Val Glu Glu Leu Leu His Val Ile Gly Pro
            130                 135                 140

Phe Tyr Glu Ile Val Glu Asp Lys Lys Ser Gly Arg Ser Ser Asp Leu
145                 150                 155                 160

Thr Ser Val Arg Leu Glu Lys Ile Ser Lys Cys Leu Glu Asp Leu Gly
                165                 170                 175

Asn Val Leu Ala Ser Thr Pro Asn Ala Lys Thr Val Asn Gly Lys Ala
                180                 185                 190

Glu Ser Ser Asp Ser Gly Ala Glu Ser Glu Glu Ala Ala Gln Glu
                195                 200                 205

Asp Pro Lys Arg Pro Glu Pro Arg Asp Ser Lys Lys Met Met Lys
    210                 215                 220

Lys Ser Ala Asp His Lys Asn Leu Glu Ile Ile Val Thr Asn Gly Tyr
225                 230                 235                 240

Asp Lys Asp Ser Phe Val Gln Gly Val Gln Asn Ser Ile His Thr Ser
                245                 250                 255

Pro Ser Leu Asn Gly Arg Cys Thr Glu Glu Val Lys Ser Val Asp Glu
                260                 265                 270

Asn Leu Glu Gln Thr Gly Lys Thr Val Val Phe Val His Gln Asp Val
                275                 280                 285

Asn Ser Asp His Val Glu Asp Ile Ser Gly Ile Gln His Leu Thr Ser
                290                 295                 300

Asp Ser Asp Ser Glu Val Tyr Cys Asp Ser Met Glu Gln Phe Gly Gln
305                 310                 315                 320

Glu Glu Ser Leu Asp Gly Phe Ile Ser Asn Asn Gly Pro Phe Ser Tyr
                325                 330                 335

Tyr Leu Gly Gly Asn Pro Ser Gln Pro Leu Glu Ser Ser Gly Phe Pro
                340                 345                 350

Glu Ala Val Gln Gly Leu Pro Gly Asn Gly Ser Pro Glu Asp Met Gln
                355                 360                 365

Gly Ala Val Val Glu Gly Lys Gly Glu Val Lys Arg Gly Gly Glu Asp
            370                 375                 380

Gly Gly Ser Asn Ser Gly Ala Pro His Arg Glu Lys Arg Ala Gly Glu
385                 390                 395                 400

Ser Glu Glu Phe Ser Asn Ile Arg Arg Gly Arg Gly His Arg Met Gln
                405                 410                 415

His Leu Ser Glu Gly Ser Lys Gly Arg Gln Val Gly Ser Gly Gly Asp
            420                 425                 430
```

```
Gly Glu Arg Trp Gly Ser Asp Arg Gly Ser Arg Gly Ser Leu Asn Glu
        435                 440                 445

Gln Ile Ala Leu Val Leu Met Arg Leu Gln Glu Asp Met Gln Asn Val
    450                 455                 460

Leu Gln Arg Leu His Lys Leu Glu Met Leu Ala Ala Ser Gln Ala Lys
465                 470                 475                 480

Ser Ser Ala Leu Gln Thr Ser Asn Gln Pro Thr Ser Pro Arg Pro Ser
                485                 490                 495

Trp Trp Pro Phe Glu Met Ser Pro Gly Ala Leu Thr Phe Ala Ile Ile
            500                 505                 510

Trp Pro Phe Ile Ala Gln Trp Leu Val His Leu Tyr Tyr Gln Arg Arg
        515                 520                 525

Arg Arg Lys Leu Asn
    530

<210> SEQ ID NO 18
<211> LENGTH: 1750
<212> TYPE: DNA
<213> ORGANISM: Bos taurus

<400> SEQUENCE: 18
gaggagctga ccagctgcgc tttggagtcc tcctcccttc gggaatgttg atccgcggct      60
gcgctccatg tttcagtttc atgcaggctc ctgggaaagc tggtgctgct gctgctgcct     120
gattccaggc gacagacctt gggaccgcgg ccggcgctgg cggctggaga tgcggcacac     180
gagatccgtt cacgaaaccc ggtttgaggc ggctgtgaag gtgatacaga gcttgccgaa     240
aaatggttca ttccagccaa caatgaaat  gatgctcaag ttctatagct tctataagca     300
ggcaactgaa ggaccttgta aactgtcaaa gcctggcttc tgggatcctg ttggaagata     360
caaatgggat gcgtggagtt ctttgggtga tatgaccaaa gaggaagcca tgattgctta     420
tgttgaagaa atgaaaaaga ttcttgaaac tatgccgatg actgaaaaag ttgaagaatt     480
gctacatgtc attggtccat tttatgaaat tgtagaagac aaaaaaagtg gcagaagttc     540
tgatttaacc tcagtccgac tggagaaaat ctctaaatgc ttagaagatc ttggtaatgt     600
tctagcttct actccaaatg ccaaaactgt taatggtaaa gctgaaagca gtgatagtgg     660
agctgaatct gaggaagaag cagcccaaga gacccgaaaa agaccagaac acgtgataag     720
cgataagaaa atgatgaaga atctgcagac catatagaat ttggaaatca ttgtcactaa     780
tggctatgat aaagacagct ttgtgcaggg cgtacagaat agcattcata ccagtccttc     840
cctgaatggc cgatgcactg aggaagtaaa atctgtagat gaaaacttgg agcaaactgg     900
aaaaactgtt gtcttcgttc accaagatgt aaacagtgat catgttgaag atatttcagg     960
aattcagcat ttgacaagtg attcagacag tgaagtttac tgtgattcca tggagcaatt    1020
tgggcaagaa gagtctttag acggctttat atcaaacaat ggaccatttt cctattactt    1080
gggtggtaat cccagtcaac cgttggaaag ttctggtttt cctgaagctg ttcaaggact    1140
tcctgggaac ggcagccctg aggacatgca gggcgcagtg gttgaaggca aggtgaagt     1200
aaagcgtggg ggagaggacg gcgggagtaa cagtggagcc ccgcaccgcg agaaacgggc    1260
tggagaaagt gaggagttct ctaacattag gagagggaga gggcacagga tgcagcattt    1320
gagtgaagga agcaagggtc ggcaagtggg aagtggaggt gatggggaac gctggggttc    1380
ggacagaggc tcaaggggca gcctgaacga gcagatcgcg cttgtgctca tgcgcctgca    1440
ggaggacatg cagaacgtcc tccagagact ccacaaactg gagatgctgg cggcatcaca    1500
```

```
ggcaaaatca tcagcattac agaccagtaa tcagcccact tcaccgagac catcttggtg    1560
gcccttcgag atgtctcctg gtgcattaac cttcgctatc atatggcctt ttattgctca    1620
gtggttggtg catttatatt accaaagaag gagaagaaaa ttgaactaaa gaaaatgaca    1680
ttttgttgaa gaaatctact ggccctggat aacctcggga tgataccaat tgtggagctt    1740
acacgaggga                                                            1750
```

<210> SEQ ID NO 19
<211> LENGTH: 608
<212> TYPE: DNA
<213> ORGANISM: Bos taurus

<400> SEQUENCE: 19

```
gagcaccggt ggagaggcct aaggttgcgc ttctaaaatc gctgccagtt gagtctcttg     60
tgctgctgct accttctctt cgccgcctcc gcgggcttcc tggaatcttt gcaacaccgc    120
cggcatgtct caggctgagt ttgacaaagc tgctgaggaa gttaagcatc ttaagaccaa    180
gccagcagat gaggagatgc tgttcatcta cagccactac aaacaagcaa ctgtgggtga    240
cataaataca gaacgtcctg gaatgttgga cttcaaaggc aaggccaagt gggatgcctg    300
gaatgagctg aaagggactt ctaaagaaga tgccatgaaa gcttacattg acaaagtaga    360
agaactaaag aaaaaatatg gaatataaga gactgagttt ggctgccagc cattcatttc    420
acctaaactg atttaatgcc ttgttttttct aatactgggg atgaagttca taaataacta    480
gctaagccag aagctcaaga cagcccagga tatgactaac agattaggag ctgaaacggt    540
tactaatcct tgctgagtaa tttttatcag tagatgaatt aaaagtatct ttgttacttt    600
acttcgat                                                              608
```

<210> SEQ ID NO 20
<211> LENGTH: 1481
<212> TYPE: DNA
<213> ORGANISM: Rhodococcus opacus
<220> FEATURE:
<221> NAME/KEY: modified_base
<222> LOCATION: (570)..(570)
<223> OTHER INFORMATION: a, c, t or g

<400> SEQUENCE: 20

```
cctggctcag gacgaacgct ggcggcgtgc ttaacacatg caagtcgagc ggtaaggccc     60
ttcggggtac acgagcggcg aacgggtgag taacacgtgg gtgatctgcc ctgcacttcg    120
ggataagcct gggaaactgg gtctaatacc ggatatgacc ttcggctgca tggctgaggg    180
tggaaaggtt tactggtgca ggatgggccc gcggcctatc agcttgttgg tggggtaatg    240
gcctaccaag cgacgacgg gtagccgacc tgagagggtg accggccaca ctgggactga    300
gacacggccc agactcctac gggaggcagc agtggggaat attgcacaat gggcgaaagc    360
ctgatgcagc gacgccgcgt gagggatgac ggccttcggg ttgtaaacct ctttcagcag    420
ggacgaagcg aaagtgacgg tacctgcaga agaagcaccg gccaactacg tgccagcagc    480
cgcggtaata cgtagggtgc aagcgttgtc cggaattact gggcgtaaag agctcgtagg    540
cggtttgtcg cgtcgtctgt gaaaactcan agctcaacct cgagcttgca ggcgatacgg    600
gcagacttga gtactgcagg ggagactgga attcctggtg tagcggtgaa atgcgcagat    660
atcaggagga acaccggtgg cgaaggcggg tctctgggca gtaactgacg ctgaggagcg    720
aaagcgtggg tagcaaacag gattagatac cctggtagtc cacgccgtaa acggtgggcg    780
```

| | |
|---|---|
| ctaggtgtgg gtttccttcc acgggatccg tgccgtagtt aacgcattaa gcgccccgcc | 840 |
| tggggagtac ggccgcaagg ttaaaactca aaggaattga cggggggcccg cacaagcggc | 900 |
| ggagcatgtg gattaattcg atgcaacgcg aagaaccttta cctgggtttg acatataccg | 960 |
| gaaagccgta gagataccgc ccccccttgtg gtcggtatac aggtggtgca tggctgtcgt | 1020 |
| cagctcgtgt cgtgagatgt tgggttaagt cccgcaacga gcgcaaccct tgtcttatgt | 1080 |
| tgccagcacg taatggtggg gactcgtaag agactgccgg ggtcaactcg gaggaaggtg | 1140 |
| gggacgacgt caagtcatca tgccccttat gtccagggct tcacacatgc tacaatggcc | 1200 |
| ggtacagagg gctgcgatac cgtgaggtgg agcgaatccc ttaaagccgg tctcagttcg | 1260 |
| gatcggggtc tgcaactcga ccccgtgaag tcggagtcgc tagtaatcgc agatcagcaa | 1320 |
| cgctgcggtg aatacgttcc cgggccttgt acacaccgcc cgtcacgtca tgaaagtcgg | 1380 |
| taacacccga agccggtggc ctaaccccctt gtgggaggga gccgtcgaag gtgggatcgg | 1440 |
| cgattgggac gaagtcgtaa caaggtagcc gtaccggaag g | 1481 |

<210> SEQ ID NO 21
<211> LENGTH: 1460
<212> TYPE: DNA
<213> ORGANISM: Rhodococcus opacus
<220> FEATURE:
<221> NAME/KEY: modified_base
<222> LOCATION: (799)..(799)
<223> OTHER INFORMATION: a, c, t or g

<400> SEQUENCE: 21

| | |
|---|---|
| ggcggcgtgc ttaacacatg caagtcgagc ggtaaggccc ttcggggtac acgagcggcg | 60 |
| aacgggtgag taacacgtgg gtgatctgcc ctgcacttcg ggataagcct gggaaactgg | 120 |
| gtctaatacc ggatatgacc ttcggctgca tggctgaggg tggaaaggtt tactggtgca | 180 |
| ggatgggccc gcggcctatc agcttgttgg tggggtaatg gcctaccaag cgacgacgg | 240 |
| gtagccgacc tgagagggtg accggccaca ctgggactga cacggccc agactcctac | 300 |
| gggaggcagc agtgggggaat attgcacaat gggcgaaagc ctgatgcagc gacgccgcgt | 360 |
| gagggatgac ggccttcggg ttgtaaacct ctttcagcag ggacgaagcg aaagtgacgg | 420 |
| tacctgcaga agaagcaccg gccaactacg tgccagcagc cgcggtaata cgtagggtgc | 480 |
| aagcgttgtc cggaattact gggcgtaaag agctcgtagg cggtttgtcg cgtcgtctgt | 540 |
| gaaaactcac agctcaacct cgagcttgca ggcgatacgg gcagacttga gtactgcagg | 600 |
| ggagactgga attcctggtg tagcggtgaa atgcgcagat atcaggagga acaccggtgg | 660 |
| cgaaggcggg tctctgggca gtaactgacg ctgaggagcg aaagcgtggg tagcaaacag | 720 |
| gattagatac cctggtagtc cacgccgtaa acgtgggcg ctaggtgtgg gtttccttcc | 780 |
| acgggatccg tgccgtagnt aacgcattaa gcgccccgcc tggggagtac ggccgcaagg | 840 |
| ttaaaactca aaggaattga cggggggcccg cacaagcggc ggagcatgtg gattaattcg | 900 |
| atgcaacgcg aagaaccttta cctgggtttg acatataccg gaaagccgta gagataccgc | 960 |
| cccccttgtg gtcggtatac aggtggtgca tggctgtcgt cagctcgtgt cgtgagatgt | 1020 |
| tgggttaagt cccgcaacga gcgcaaccct tgtcttatgt tgccagcacg taatggtggg | 1080 |
| gactcgtaag agactgccgg ggtcaactcg gaggaaggtg gggacgacgt caagtcatca | 1140 |
| tgccccttat gtccagggct tcacacatgc tacaatggcc ggtacagagg gctgcgatac | 1200 |
| cgtgaggtgg agcgaatccc ttaaagccgg tctcagttcg gatcggggtc tgcaactcga | 1260 |
| ccccgtgaag tcggagtcgc tagtaatcgc agatcagcaa cgctgcggtg aatacgttcc | 1320 |

```
cgggccttgt acacaccgcc cgtcacgtca tgaaagtcgg taacacccga agccggtggc    1380
ctaacccctt gtgggaggga gccgtcgaag gtgggatcgg cgattgggac gaagtcgtaa    1440
caaggtagcc gtaccggaag                                                1460
```

<210> SEQ ID NO 22
<211> LENGTH: 1473
<212> TYPE: DNA
<213> ORGANISM: Rhodococcus opacus
<220> FEATURE:
<221> NAME/KEY: modified_base
<222> LOCATION: (562)..(562)
<223> OTHER INFORMATION: a, c, t or g

<400> SEQUENCE: 22

```
aggacgaacg ctggcggcgt gcttaacaca tgcaagtcga gcggtaaggc ccttcggggt     60
acacgagcgg cgaacgggtg agtaacacgt gggtgatctg ccctgcactt cgggataagc    120
ctgggaaact gggtctaata ccggatatga ccttcggctg catggctgag ggtggaaagg    180
tttactggtg caggatgggc ccgcggccta tcagcttgtt ggtgggtaa tggcctacca     240 agccgacgac gggtagccga cctgagaggg tgaccggcca cactgggact gagacacggc    300
ccagactcct acgggaggca gcagtgggga atattgcaca atgggcgaaa gcctgatgca    360
gcgacgccgc gtgagggatg acggccttcg ggttgtaaac ctctttcagc agggacgaag    420
cgaaagtgac ggtacctgca gaagaagcac cggccaacta cgtgccagca gccgcggtaa    480
tacgtagggt gcaagcgttg tccggaatta ctgggcgtaa agagctcgta ggcggttttgt   540 cgcgtcgtct gtgaaaactc anagctcaac ctcgagcttg caggcgatac gggcagactt    600
gagtactgca ggggagactg gaattcctgg tgtagcggtg aaatgcgcag atatcaggag    660
gaacaccggt ggcgaaggcg ggtctctggg cagtaactga cgctgaggag cgaaagcgtg    720
ggtagcaaac aggattagat accctggtag tccacgccgt aaacggtggg cgctaggtgt    780
gggtttcctt ccacgggatc cgtgccgtag ctaacgcatt aagcgccccg cctggggagt    840
acggccgcaa ggctaaaact caaaggaatt gacgggggcc cgcacaagcg gcggagcatg    900
tggattaatt cgatgcaacg cgaagaacct tacctgggtt tgacatatac cggaaagccg    960
tagagatacg gccccccttg tggtcggtat acaggtggtg catggctgtc gtcagctcgt   1020
gtcgtgagat gttgggttaa gtcccgcaac gagcgcaacc cttgtcttat gttgccagca   1080
cgtaatggtg gggactcgta agagactgcc ggggtcaact cggaggaagg tggggacgac   1140
gtcaagtcat catgccccctt atgtccaggg cttcacacat gctacaatgg ccggtacaga   1200
gggctgcgat accgtgaggt ggagcgaatc ccttaaagcc ggtctcagtt cggatcgggg   1260
tctgcaactc gaccccgtga agtcggagtc gctagtaatc gcagatcagc aacgctgcgg   1320
tgaatacgtt cccgggcctt gtacacaccg cccgtcacgt catgaaagtc ggtaacaccc   1380
gaagccggtg gcctaacccc ttgtgggagg gagccgtcga aggtgggatc ggcgattggg   1440
acgaagtcgt aacaaggtag ccgtaccgga agg                                1473
```

<210> SEQ ID NO 23
<211> LENGTH: 1462
<212> TYPE: DNA
<213> ORGANISM: Cupriavidus necator

<400> SEQUENCE: 23

```
acgtggcggc atgccttaca catgcaagtc gaacggcagc gcggacttcg gtctggcggc     60
```

```
gagtggcgaa cgggtgagta atacatcgga acgtaccctg ttgtggggga taactagtcg      120
aaagattagc taataccgca tacgacctga gggtgaaagt gggggaccgc aaggcctcac      180
gcagcaggag cggccgatgt ctgattagct agttggtggg gtaaaggccc accaaggcga      240
cgatcagtag ctggtctgag aggacgatca gccacactgg gactgagaca cggcccagac      300
tcctacggga ggcagcagtg gggaattttg gacaatgggg caaccctga tccagcaatg       360
ccgcgtgtgt gaagaaggcc ttcggttgt aaagcacttt tgtccggaaa gaaatcgcgc       420
tggttaatac ctgcgtgatg acggtaccgg aagaataagc accggctaac tacgtgccag      480
cagccgcggt aatacgtagg gtgcgagcgt taatcggaat tactgggcgt aaagcgtgcg      540
caggcggttt tgtaagacag gcgtgaaatc cccgggctta acctgggaat tgcgcttgtg      600
actgcaaggc tagagtgcgt cagagggggg tagaattcca cgtgtagcag tgaaatgcgt      660
agagatgtgg aggaataccg atggcgaagg cgagccccct ggaccttgac tgacgctcat      720
gcacgaaagc gtgggagca aacaggatta gataccctgg tagtccacgc cctaaacgat       780
gtcaactagt tgttgggatt catttctca gtaacgtagc taacgcgtga agttgaccgc       840
ctggggagta cggctgcaag attaaaactc aaaggaattg acggggaccc gcacaagcgg      900
tggatgatgt ggattaattc gatgcaacgc gaaaaacctt acctacccctt gacatgccct    960
aacgaagcag agatgcatta gtgcccgcaa agggaaagtg gacacaggt gctgcatggc       1020
tgtcgtcagc tcgtgtcgtg agatgttggg ttaagtcccg caacgagcgc aacccttgtc     1080
tctagttgcc tacgcaagag cactctagag agactgccgg tgacaaaccg gaggaaggtg     1140
gggatgacgt caagtcctca tggcccttat gggtagggct tcacacgtca tacaatggtg     1200
cgtacagagg gttgccaacc cgcgaggggg agctaatccc agaaaacgca tcgtagtccg     1260
gatcgtagtc tgcaactcga ctacgtgaag ctggaatcgc tagtaatcgc ggatcagcat     1320
gccgcggtga atacgttccc gggtcttgta cacaccgccc gtcacaccat gggagtgggt     1380
tttgccagaa gtagttagcc taaccgcaag gagggcgatt accacggcag ggttcatgac     1440
tggggtgaag tcgtaacaag gt                                              1462

<210> SEQ ID NO 24
<211> LENGTH: 1479
<212> TYPE: DNA
<213> ORGANISM: Ralstonia sp.

<400> SEQUENCE: 24
agtttgatcc tggctcagat tgaacgctgg cggcatgcct tacacatgca agtcgaacgg       60
cagcgcggac ttcggtctgg cggcgagtgg cgaacgggtg agtaatacat cggaacgtac      120
cctgttgtgg gggataacta gtcgaaagat tagctaatac cgcatacgac ctgagggtga      180
aagcggggga ccgtaaggcc tcgcgcagca ggagcggccg atgtctgatt agctagttgg      240
tggggtaaag gcccaccaag cgacgatca gtagctggtc tgagaggacg atcagccaca      300
ctgggactga gacacggccc agactcctac gggaggcagc agtggggaat tttgacaat     360
ggggcaacc ctgatccagc aatgccgcgt gtgtgaagaa ggccttcggg ttgtaaagca      420
cttttgtccg gaaagaaaac gctctggtta atacctggag tggatgacgg taccggaaga     480
ataagcaccg gctaactacg tgccagcagc cgcggtaata cgtagggtgc gagcgttaat     540
cggaattact gggcgtaaag cgtgcgcagg cggttttgta agacaggcgt gaaatccccg     600
agctcaactt gggaattgcg cttgtgactg caaggctaga gtatgtcaga ggggggtaga     660
attccacgtg tagcagtgaa atgcgtagag atgtggagga ataccgatgg cgaaggcagc     720
```

-continued

```
cccctgggac gtcactgacg ctcatgcacg aaagcgtggg gagcaaacag gattagatac      780
cctggtagtc cacgccctaa acgatgtcaa ctagttgttg gggattcatt tcttcagtaa      840
cgtagctaac gcgtgaagtt gaccgcctgg ggagtacggt cgcaagatta aaactcaaag      900
gaattgacgg ggacccgcac aagcggtgga tgatgtggat taattcgatg caacgcgaaa      960
aaccttacct acccttgaca tgccactaac gaagcagaga tgcatcaggt gcccgaaagg     1020
gaaagtggac acaggctgtg catggctgtc gtcagctcgt gtcgtgagat gttgggttaa     1080
gtcccgcaac gagcgcaacc cttatcttta gttgctacgc aagggcactc tagagagact     1140
gccggtgaca aaccggagga aggtggggat gacgtcaagt cctcatggcc cttatgggta     1200
gggcttcaca cgtcatacaa tggtgcgtac agagggttgc caacccgcga ggggagcta      1260 atcccagaaa acgcatcgta gtccggatcg cagtctgcaa ctcgactgcg tgaagctgga     1320
atcgctagta atcgcggatc agcatgccgc ggtgaatacg ttcccgggtc ttgtacacac     1380
cgcccgtcac accatgggag tgggttttgc cagaagtagt tagcctaacc gcaaggaggg     1440
cgattaccac ggcagggttc atgactgggg tgaagtcgt                            1479
```

<210> SEQ ID NO 25
<211> LENGTH: 1486
<212> TYPE: DNA
<213> ORGANISM: Gordonia alkanivorans

<400> SEQUENCE: 25

```
gctcaggacg aacgctggcg gcgtgcttaa cacatgcaag tcgaacggaa aggcccagct      60
tgctgggtac tcgagtggcg aacgggtgag taacacgtgg gtgatctgcc ctgaactttg     120
ggataagcct gggaaactgg gtctaatacc ggatatgacc ttggagtgca tgctctgggg     180
tggaaagctt ttgcggttca ggatgggccc gcggcctatc agcttgttgg tggggtaatg     240
gcctaccaag cgacgacgg gtagccgacc tgagagggtg atcggccaca ctgggactga     300
gacacggccc agactcctac gggaggcagc agtggggaat attgcacaat gggcgcaagc     360
ctgatgcagc gacgccgcgt gagggatgac ggccttcggg ttgtaaacct ctttcaccag     420
ggacgaagcg caagtgacgg tacctggaga agaagcaccg gccaactacg tgccagcagc     480
cgcggtaata cgtagggtgc gagcgttgtc cggaattact gggcgtaaag agctcgtagg     540
cggtttgtcg cgtcgtctgt gaaattctgc aactcaattg taggcgtgca ggcgatacgg     600
gcagacttga gtactacagg ggagactgga attcctggtg tagcggtgaa atgcgcagat     660
atcaggagga acaccggtgg cgaaggcggg tctctgggta gtaactgacg ctgaggagcg     720
aaagcgtggg tagcgaacag gattagatac cctggtagtc cacgccgtaa acggtgggta     780
ctaggtgtgg ggctcatttc acgagttccg tgccgtagct aacgcattaa gtaccccgcc     840
tggggagtac ggccgcaagg ctaaaactca aggaattga cggggcccg cacaagcggc      900 ggagcatgtg gattaattcg atgcaacgcg aagaacctta cctgggtttg acatacacca     960
gacgcatgta gagatacatg ttcccttgtg gttggtgtac aggtggtgca tggctgtcgt    1020
cagctcgtgt cgtgagatgt tgggttaagt cccgcaacga gcgcaaccct tgtcctgtat    1080
tgccagcggg ttatgccggg gacttgcagg agactgccgg ggtcaactcg gaggaaggtg    1140
gggatgacgt caagtcatca tgccccttat gtccagggct tcacacatgc tacaatggct    1200
ggtacagagg gctgcgatac cgtgaggtgg agcgaatccc ttaaagccag tctcagttcg    1260
gattggggtc tgcaactcga cccatgaag tcggagtcgc tagtaatcgc agatcagcaa     1320
```

```
cgctgcggtg aatacgttcc cgggccttgt acacaccgcc cgtcacgtca tgaaagtcgg    1380
taacacccga agccggtggc ctaaccccctt gtgggaggga gctgtcgaag gtgggatcgg   1440
cgattgggac gaagtcgtaa caaggtagcc gtaccggaag gtgcgg                   1486
```

<210> SEQ ID NO 26
<211> LENGTH: 1491
<212> TYPE: DNA
<213> ORGANISM: Gordonia sp.

<400> SEQUENCE: 26

```
gatcatggct caggacgaac gctggcggcg tgcttaacac atgcaagtcg aacggaaagg     60
cccgcttgcg ggtactcgag tggcgaacgg gtgagtaaca cgtgggtgat ctgcccctgga   120 ctctgggata agcctgggaa actgggtcta ataccggata tgaccttaca tcgcatggtg   180
tttggtggaa agcttttgcg gttcaggatg ggcccgcggc ctatcagctt gttggtgggg   240
taatggccta ccaaggcgac gacgggtagc cgacctgaga gggtgatcgg ccacactggg   300
actgagacac ggcccagact cctacgggag gcagcagtgg ggaatattgc acaatgggcg   360
caagcctgat gcagcgacgc cgcgtgaggg atgacggcct tcgggttgta aacctctttc   420
accagggacg aagcgcaagt gacggtacct ggagaagaag caccggccaa ctacgtgcca   480
gcagccgcgg taatacgtag ggtgcgagcg ttgtccggaa ttactgggcg taaagagctc   540
gtaggcggtt tgtcgcgtcg tctgtgaaat tctgcaactc aattgtaggc gtgcaggcga   600
tacgggcaga cttgagtact acaggggaga ctggaattcc tggtgtagcg gtgaaatgcg   660
cagatatcag gaggaacacc ggtggcgaag gcgggtctct gggtagtaac tgacgctgag   720
gagcgaaagc gtgggtagcg aacaggatta gataccctgg tagtccacgc cgtaaacggt   780
gggtactagg tgtggggctc atttcacgag ttccgtgccg tagctaacgc attaagtacc   840
ccgcctgggg agtacggccg caaggctaaa actcaaagga attgacgggg gcccgcacaa   900
gcggcggagc atgtggatta attcgatgca acgcgaagaa ccttacctgg gtttgacata   960
caccagaaag ctatagagat atagcccccc ttgtggttgg tgtacaggtg gtgcatggct  1020
gtcgtcagct cgtgtcgtga gatgttgggt taagtcccgc aacgagcgca accctttgtcc 1080 tgtattgcca gcgggttatg ccggggactt gcaggagact gccggggtca actcggagga  1140
aggtggggat gacgtcaagt catcatgccc cttatgtcca gggcttcaca catgctacaa  1200
tggctggtac agagggctgc gataccgtga ggtggagcga atcccttaaa gccagtctca  1260
gttcggattg gggtctgcaa ctcgacccca tgaagtcgga gtcgctagta atcgcagatc  1320
agcaacgctg cggtgaatac gttcccgggc cttgtacaca ccgcccgtca cgtcatgaaa  1380
gtcggtaaca cccgaagccg gtggcctaac cccttgtggg agggagctgt cgaaggtggg  1440
atcggcgatt gggacgaagt cgtaacaagg tagccgtacc ggaaggtgcg g             1491
```

<210> SEQ ID NO 27
<211> LENGTH: 1505
<212> TYPE: DNA
<213> ORGANISM: Mycobacterium fortuitum

<400> SEQUENCE: 27

```
ttgatcctgg ctcaggacga acgctggcgg cgtgcttaac acatgcaagt cgaacggaaa     60
ggcccttcgg ggtactcgag tggcgaacgg gtgagtaaca cgtgggtgat ctgcccctgca   120 cttttgggata agcctgggaa actgggtcta ataccgaata tgaccacgcg cttcatggtg   180
tgtggtggaa agcttttgcg gttgtgggatg ggcccgcggc ctatcagctt gttggtgggg   240
```

```
taatggccta ccaaggcgac gacgggtagc cggcctgaga gggtgaccgg ccacactggg    300
actgagatac ggcccagact cctacgggag gcagcagtgg ggaatattgc acaatgggcg    360
caagcctgat gcagcgacgc cgcgtgaggg atgacggcct tcgggttgta aacctctttc    420
aatagggacg aagcgcaagt gacggtacct atagaagaag gaccggccaa ctacgtgcca    480
gcagccgcgg taatacgtag ggtccgagcg ttgtccggaa ttactgggcg taaagagctc    540
gtaggtggtt tgtcgcgttg ttcgtgaaaa ctcacagctt aactgtgggc gtgcgggcga    600
tacgggcaga ctagagtact gcaggggaga ctggaattcc tggtgtagcg gtggaatgcg    660
cagatatcag gaggaacacc ggtggcgaag gcgggtctct gggcagtaac tgacgctgag    720
gagcgaaagc gtggggagcg aacaggatta gataccctgg tagtccacgc cgtaaacggt    780
gggtactagg tgtgggtttc cttccttggg atccgtgccg tagctaacgc attaagtacc    840
ccgcctgggg agtacggccg caaggctaaa actcaaagga attgacgggg gcccgcacaa    900
gcggcggagc atgtggatta ttcgatgca acgcgaagaa ccttacctgg gtttgacatg    960
cacaggacga ctgcagagat gtggtttccc ttgtggcctg tgtgcaggtg gtgcatggct   1020
gtcgtcagct cgtgtcgtga gatgttgggt taagtcccgc aacgagcgca acccttgtct   1080
catgttgcca gcacgttatg gtggggactc gtgagagact gccgggtca actcggagga   1140 aggtggggat gacgtcaagt catcatgccc cttatgtcca gggcttcaca catgctacaa   1200
tggccggtac aaagggctgc gatgccgtga ggtggagcga atccttcaa agccggtctc   1260 agttcggatc ggggtctgca actcgacccc gtgaagtcgg agtcgctagt aatcgcagat   1320
cagcaacgct gcggtgaata cgttcccggg ccttgtacac accgcccgtc acgtcatgaa   1380
agtcggtaac acccgaagcc ggtggcctaa cccttgtgga gggagccgtc gaaggtggga   1440
tcggcgattg ggacgaagtc gtaacaaggt agccgtaccg gaaggtgcgg ctggatcacc   1500
tcctt                                                              1505

<210> SEQ ID NO 28
<211> LENGTH: 1460
<212> TYPE: DNA
<213> ORGANISM: Mycobacterium parafortuitum

<400> SEQUENCE: 28
cgaacgctgg cggcgtgctt aacacatgca agtcgaacgg aaaggcccctt cggggtactc     60 gagtggcgaa cgggtgagta acacgtgggt gatctgccct gcactttggg ataagcctgg    120
gaaactgggt ctaataccga atatgatcat tggcttcctg gctggtggtg aaagcttttt    180
gcggtgtggg atgggcccgc ggcctatcag cttgttggtg gggtaatggc ctaccaaggc    240
gacgacgggt agccggcctg agagggtgac cggccacact gggactgaga tacggcccag    300
actcctacgg gaggcagcag tggggaatat tgcacaatgg gcgcaagcct gatgcagcga    360
cgccgcgtga gggatgacgg ccttcgggtt gtaaacctct tcgccaggg acgaagcgca    420 agtgacggta cctggagaag aaggaccggc caactacgtg ccagcagccg cggtaatacg    480
tagggtccga gcgttgtccg gaattactgg gcgtaaagag ctcgtaggtg gtttgtcgcg    540
ttgttcgtga aaactcacag cttaactgtg gcgtgcggg cgatacgggc agactagagt    600
actgcagggg agactggaat tcctggtgta gcggtggaat gcgcagatat caggaggaac    660
accggtggcg aaggcgggtc tctggcagt aactgacgct gaggagcgaa agcgtgggga    720
gcgaacagga ttagataccc tggtagtcca cgccgtaaac ggtgggtact aggtgtgggt    780
```

```
ttccttcctt gggatccgtg ccgtagctaa cgcattaagt accccgcctg gggagtacgg      840
ccgcaaggct aaaactcaaa gaaattgacg ggggcccgca caagcggcgg agcatgtgga      900
ttaattcgat gcaacgcgaa gaaccttacc tgggtttgac atgcacagga cgccggcaga      960
gatgtcggtt cccttgtggc ctgtgtgcag gtggtgcatg gctgtcgtca gctcgtgtcg     1020
tgagatgttg ggttaagtcc cgcaacgagc gcaacccttg tctcatgttg ccagcacgta     1080
atggtgggga ctcgtgagag actgccgggg tcaactcgga ggaaggtggg gatgacgtca     1140
agtcatcatg ccccttatgt ccagggcttc acacatgcta caatggccgg tacaaagggc     1200
tgcgatgccg tgaggtggag cgaatccttt caaagccggt ctcagttcgg atcgggtct     1260 gcaactcgac cccgtgaagt cggagtcgct agtaatcgca gatcagcaac gctgcggtga     1320
atacgttccc gggccttgta cacaccgccc gtcacgtcat gaaagtcggt aacacccgaa     1380
gccggtggcc taaccccttg tgggagggag ccgtcgaagg tgggatcggc gattgggacg     1440
aagtcgtaac aaggtagccg                                                 1460

<210> SEQ ID NO 29
<211> LENGTH: 1480
<212> TYPE: DNA
<213> ORGANISM: Mycobacterium sphagni

<400> SEQUENCE: 29
gagtttgatc ctggctcagg acgaacgctg gcggcgtgct taacacatgc aagtcgaacg       60
gaaaggccct tcggggtact cgagtggcga acgggtgagt aacacgtggg tgatctgccc      120
tgcactttgg gataagcctg ggaaactggg tctaataccg aataggaccg catgcttcat      180
ggtgtgtggt ggaaagcttt tgcggtgtgg gatgggcccg cggcctatca gcttgttggt      240
ggggtaatgg cctaccaagg cgacgacggg tagccggcct gagagggtgt ccggccacac      300
tgggactgag atacggccca gactcctacg ggaggcagca gtgggaata ttgcacaatg      360 ggcgcaagcc tgatgcagcg acgccgcgtg agggatgacg ccttcgggt tgtaaacctc       420 tttcagcagg gacgaagcgc aagtgacggt acctgtagaa gaagcaccgg ccaactacgt      480
gccagcagcc gcggtaatac gtagggtgcg agcgttgtcc ggaattactg ggcgtaaaga      540
gctcgtaggt ggtttgtcgc gttgttcgtg aaaactcaca gctcaactgt gggcgtgcgg      600
gcgatacggg cagacttgag tactgcaggg gagactggaa ttcctggtgt agcggtggaa      660
tgcgcagata tcaggaggaa caccggtggc gaaggcgggt ctctgggcag taactgacgc      720
tgaggagcga aagcgtgggg agcgaacagg attagatacc ctggtagtcc acgccgtaaa      780
cggtgggtac taggtgtggg tttccttcct tgggatccgt gccgtagcta acgcattaag      840
taccccgcct ggggagtacg gccgcaaggc taaaactcaa agaaattgac ggggcccgc      900 acaagcggcg gagcatgtgg attaattcga tgcaacgcga gaaccttac ctgggtttga      960 catgcacagg acgccggcag agatgtcggt tcccttgtgg cctgtgtgca ggtggtgcat     1020
ggctgtcgtc agctcgtgtc gtgagatgtt gggttaagtc ccgcaacgag cgcaaccctt     1080
gtctcatgtt gccagcacgt aatggtgggg actcgtgaga actgccggg gtcaactcgg     1140 aggaaggtgg ggatgacgtc aagtcatcat gccccttatg tccagggctt cacacatgct     1200
acaatggccg gtacaaaggg ctgcgatgcc gtgaggtgga gcgaatcctt tcaaagccgg     1260
tctcagttcg gatcgggtc tgcaactcga cccgtgaag tcggagtcgc tagtaatcgc     1320
agatcagcaa cgctgcggtg aatacgttcc cgggccttgt acacaccgcc cgtcacgtca     1380
tgaaagtcgg taacacccga agccggtggc ctaaccccct tgtgggaggga gccgtcgaag     1440
```
gtgggatcgg cgattgggac gaagtcgtaa caaggtagcc            1480

<210> SEQ ID NO 30
<211> LENGTH: 1494
<212> TYPE: DNA
<213> ORGANISM: Nocardia farcinica

<400> SEQUENCE: 30
gacgaacgct ggcggcgtgc ttaacacatg caagtcgagc ggtaaggccc ttcggggtac     60
acgagcggcg aacgggtgag taacacgtgg gtgatctgcc ctgtacttcg ggataagcct    120
gggaaactgg gtctaatacc ggatatgacc ttacatcgca tggtgtttgg tggaaagatt    180
tatcggtaca ggatgggccc gcggcctatc agcttgttgg tggggtaatg gcctaccaag    240
gcgacgacgg gtagccggcc tgagagggcg accggccaca ctgggactga gacacggccc    300
agactcctac gggaggcagc agtggggaat attgcacaat gggcgaaagc ctgatgcagc    360
gacgccgcgt gagggatgac ggccttcggg ttgtaaacct ctttcgacag ggacgaagcg    420
caagtgacgg tacctgtaga agaagcaccg gccaactacg tgccagcagc cgcggtaata    480
cgtagggtgc gagcgttgtc cggaattact gggcgtaaag agcttgtagg cggtttgtcg    540
cgtcgtccgt gaaaacttgg ggctcaaccc caagcttgcg ggcgatacgg gcagacttga    600
gtactgcagg ggagactgga attcctggtg tagcggtgaa atgcgcagat atcaggagga    660
acaccggtgg cgaaggcggg tctctgggca gtaactgacg ctgagaagcg aaagcgtggg    720
tagcgaacag gattagatac cctggtagtc cacgccgtaa acggtgggcg ctaggtgtgg    780
gtttccttcc acgggatccg tgccgtagct aacgcattaa gcgccccgcc tggggagtac    840
ggccgcaagg ctaaaactca aaggaattga cggggcccg cacaagcggc ggagcatgtg    900
gattaattcg atgcaacgcg aagaacctta cctgggtttg acatacaccg gaaacctgca    960
gagatgtagg cccccttgtg gtcggtgtac aggtggtgca tggctgtcgt cagctcgtgt   1020
cgtgagatgt tgggttaagt cccgcaacga gcgcaaccct tgtcctgtgt tgccagcgcg   1080
ttatggcggg gactcgcagg agactgccgg ggtcaactcg aggaaggtg gggacgacgt   1140
caagtcatca tgccccttat gtccagggct tcacacatgc tacaatggcc ggtacagagg   1200
gctgcgatac cgtgaggtgg agcgaatccc ttaaagccgg tctcagttcg gatcggggtc   1260
tgcaactcga ccccgtgaag ttggagtcgc tagtaatcgc agatcagcaa cgctgcggtg   1320
aatacgttcc cgggccttgt acacaccgcc cgtcacgtca tgaaagtcgg taacacccga   1380
agccggtggc ctaacccctt gtgggaggga gccgtcgaag gtgggatcgg cgattgggac   1440
gaagtcgtaa caaggtagcc gtaccggaag gtgcggctgg atcacctcct ttct         1494

<210> SEQ ID NO 31
<211> LENGTH: 1513
<212> TYPE: DNA
<213> ORGANISM: Nocardia sp.

<400> SEQUENCE: 31
gagtttgatc ctggctcagg acgaacgctg gcggcgtgct taacacatgc aagtcgagcg     60
gtaaggccct tcggggtaca cgagcggcga acgggtgagt aacacgtggg tgatctgccc    120
tgtacttcgg gataagcctg ggaaactggg tctaataccg gatatgacct tacatcgcat    180
ggtgtttggt ggaaagattt atcggtacag gatgggcccg cggcctatca gcttgttggt    240
ggggtaatgg cctaccaagg cgacgacggg tagccggcct gagagggcga ccggccacac    300

```
tgggactgag acacggccca gactcctacg ggaggcagca gtggggaata ttgcacaatg      360
ggcgaaagcc tgatgcagcg acgccgcgtg agggatgacg gccttcgggt tgtaaacctc      420
tttcgacagg gacgaagcgc aagtgacggt acctgtagaa gaagcaccgg ccaactacgt      480
gccagcagcc gcggtaatac gtagggtgcg agcgttgtcc ggaattactg ggcgtaaaga      540
gcttgtaggc ggtttgtcgc gtcgtccgtg aaaacttggg gctcaacccc aagcttgcgg      600
gcgatacggg cagacttgag tactgcaggg gagactggaa ttcctggtgt agcggtgaaa      660
tgcgcagata tcaggaggaa caccggtggc gaaggcgggt ctctgggcag taaccgacgc      720
tgagaagcga aagcgtgggt agcgaacagg attagatacc ctggtagtcc acgccgtaaa      780
cggtgggcgc taggtgtggg tttccttcca cgggatccgt gccgtagcta acgcattaag      840
cgccccgcct ggggagtacg gccgcaaggc taaaactcaa aggaattgac ggggccccgc      900
acaagcggcg gagcatgtgg attaattcga tgcaacgcga agaaccttac ctgggtttga      960
catacaccgg aaacctgcag agatgtaggc cccttgtgg tcggtgtaca ggtggtgcat      1020
ggccgtcgtc agctcgtgtc gtgagatgtt gggttaagtc cgcaacgag cgcaacccctt      1080 gtcctgtgtt gccagcgcgt tatgcggggg actcgcagga gactgccggg gtcaactcgg      1140
aggaaggtgg ggacgacgtc aagtcatcat gccccttatg tccagggctt cacacatgct      1200
acaatggccg gtacagaggg ctgcgatacc gtgaggtgga gcgaatccct aaagccggt      1260 ctcagttcgg atcggggtct gcaactcgac cccgtgaagt tggagtcgct agtaatcgca      1320
gatcagcaac gctgcggtga atacgttccc gggccttgta caccgcccc gtcacgtcat      1380 gaaagtcggt aacacccgaa gccggtggcc taacccttg tggagggag ccgtcgaagg      1440 tgggatcggc gattgggacg aagtcgtaac aaggtagccg taccggaagg tgcggctgga      1500
tcacctcctt tct                                                        1513
```

<210> SEQ ID NO 32
<211> LENGTH: 1490
<212> TYPE: DNA
<213> ORGANISM: Rhodococcus rhodochrous

<400> SEQUENCE: 32

```
gagtttgaat ctggctcagg acgaacgctg gcggcgtgct taacacatgc aagtcgaacg       60
atgaagccca gcttgctggg tggattagtg gcgaacgggt gagtaacacg tgggtgatct      120
gccctgcact ctgggataag cctgggaaac tgggtctaat accggatatg acctcttgct      180
gcatggcgag gggtggaaag ttttcggtg caggatgagc ccgcggccta tcagcttgtt      240
ggtggggtaa tggcctacca aggcgacgac gggtagccgg cctgagaggg cgaccggcca      300
cactgggact gagacacggc ccagactcct acgggaggca gcagtgggga atattgcaca      360
atgggcgaaa gcctgatgca gcgacgccgc gtgagggatg acggccttcg ggttgtaaac      420
ctctttcagc agggacgaag cgaaagtgac ggtacctgca gaagaagcac cggccaacta      480
cgtgccagca gccgcggtaa tacgtagggt gcgagcgttg tccggaatta ctgggcgtaa      540
agagctcgta ggcggtttgt cgcgtcgtct gtgaaatccc gcagctcaac tgcgggcttg      600
caggcgatac gggcagactc gagtactgca ggggagactg gaattcctgg tgtagcggtg      660
aaatgcgcag atatcaggag gaacaccggt ggcgaaggcg gtctctggg cagtaactga      720 cgctgaggag cgaaagcgtg gtagcgaac aggattagat accctggtag tccacgccgt      780
aaacggtggg cgctaggtgt gggtttcctt ccacggggatc cgtgccgtag ccaacgcatt      840
aagcgccccg cctggggagt acggccgcaa ggctaaaact caaaggaatt gacggggcc      900
```

-continued

```
cgcacaagcg gcggagcatg tggattaatt cgatgcaacg cgaagaacct tacctgggtt      960
tgacatgtac cggacgactg cagagatgtg gtttcccttg tggccggtag acaggtggtg     1020
catggctgtc gtcagctcgt gtcgtgagat gttgggttaa gtcccgcaac gagcgcaacc     1080
cttgtcctgt gttgccagca cgtaatggtg gggactcgca ggagactgcc ggggtcaact     1140
cggaggaagg tggggacgac gtcaagtcat catgcccctt atgtccaggg cttcacacat     1200
gctacaatgg tcggtacaga gggctgcgat accgtgaggt ggagcgaatc ccttaaagcc     1260
ggtctcagtt cggatcgggg tctgcaactc gaccccgtga agtcggagtc gctagtaatc     1320
gcagatcagc aacgctgcgg tgaatacgtt cccgggcctt gtacacaccg cccgtcacgt     1380
catgaaagtc ggtaacaccc gaagccggtg gcctaacccc ttgtgggagg gagccgtcga     1440
aggtgggatc ggcgattggg acgaagtcgt aacaaggtag ccgtaccgga               1490
```

<210> SEQ ID NO 33
<211> LENGTH: 1481
<212> TYPE: DNA
<213> ORGANISM: Rhodococcus coprophilus

<400> SEQUENCE: 33

```
cctggctcag gacgaacgct ggcggcgtgc ttaacacatg caagtcgaac gatgatgccc       60
agcttgctgg gcggattagt ggcgaacggg tgagtaacac gtgggtgatc tgccctgcac      120
ttcgggataa gcctgggaaa ctgggtctaa taccggatat gaccatggga tgcatgtcct      180
gtggtggaaa ggtttactgg tgcaggatga gcccgcggcc tatcagcttg ttggtggggt      240
aatggcctac caaggcgacg acgggtagcc ggcctgagag ggcgaccggc cacactggga      300
ctgagacacg gcccagactc ctacgggagg cagcagtggg gaatattgca caatgggcga      360
aagcctgatg cagcgacgcc gcgtgaggga tgacggcctt cgggttgtaa acctctttca      420
gcagggacga agcgcaagtg actgtacctg cagaagaagc accggctaac tacgtgccag      480
cagccgcggt aatacgtagg gtgcgagcgt tgtccggaat tactgggcgt aaagagttcg      540
taggcggttt gtcgcgtcgt gtgtgaaatc ccgcagctca actgcgggct tgcaggcgat      600
acgggcagac ttgagtactg caggggagac tggaattcct ggtgtagcgg tgaaatgcgc      660
agatatcagg aggaacaccg gtggcgaagg cgggtctctg gcagtaact gacgctgagg      720 aacgaaagcg tgggtagcga acaggattag ataccctggt agtccacgcc gtaaacggtg      780
ggcgctaggt gtgggtttcc ttccacggga tccgtgccgt agctaacgca ttaagcgccc      840
cgcctgggga gtacggccgc aaggctaaaa ctcaaaggaa ttgacggggg cccgcacaag      900
cggcggagca tgtggattaa ttcgatgcaa cgcgaagaac cttacctggg tttgacatat      960 accgacgac tgcagagatg tggtttccct tgtggtcggt atacaggtgg tgcatggctg     1020
tcgtcagctc gtgtcgtgag atgttgggtt aagtcccgca acgagcgcaa cccttgtctt     1080
atgttgccag cacgtaatgg ggggactcg taagagactg ccggggtcaa ctcggaggaa     1140
ggtggggacg acgtcaagtc atcatgcccc ttatgtccag gcttcacac atgctacaat     1200 ggtcggtaca gagggctgcg ataccgtgag gtggagcgaa tcccttaaag ccggtctcag     1260
ttcggatcgg ggtctgcaac tcgacccgt gaagtcggag tcgctagtaa tcgcagatca     1320
gcaacgctgc ggtgaatacg ttcccgggcc ttgtacacac cgcccgtcac gtcatgaaag     1380
tcggtaacac ccgaagccgg tggcctaacc ccttgtggga gggagccgtc gaaggtggga     1440
tcggcgattg gacgaagtc gtaacaaggt agccgtaccg g                        1481
```

<210> SEQ ID NO 34
<211> LENGTH: 1486
<212> TYPE: DNA
<213> ORGANISM: Rhodococcus triatomae

<400> SEQUENCE: 34

```
ggcggcgtgc ttaacacatg caagtcgagc ggtaaggcct tcggggtac acgagcggcg       60
aacgggtgag taacacgtgg gtgatctgcc ctgcactctg ggataagcct gggaaactgg      120
gtctaatacc ggatatgact accggctgca tggtctggtg gtggaaagat ttatcggtgc      180
aggatgggcc cgcggcctat cagcttgttg gtggggtaat ggcctaccaa ggcgacgacg      240
ggtagccgac ctgagagggt gaccggccac actgggactg agacacggcc cagactccta      300
cgggaggcag cagtggggaa tattgcacaa tgggcgaaag cctgatgcag cgacgccgcg      360
tgagggatga cggccttcgg gttgtaaacc tctttcaaca gggacgaagc gcaagtgacg      420
gtacctgtag aagaagcacc ggccaactac gtgccagcag ccgcggtaat acgtagggtg      480
cgagcgttgt ccggaattac tgggcgtaaa gagctcgtag gcggtttgtc gcgtcgtctg      540
tgaaaaccag cagctcaact gctggcttgc aggcgatacg ggcagacttg agtactgcag      600
gggagactgg aattcctggt gtagcggtga atgcgcagat atcaggagg aacaccggtg      660
gcgaaggcgg gtctctgggc agtaactgac gctgaggagc gaaagcgtgg gtagcgaaca      720
ggattagata ccctggtagt ccacgccgta acggtgggc gctaggtgtg ggttccttc       780
cacgggatcc gtgccgtagc taacgcatta agcgccccgc ctggggagta cggccgcaag      840
gctaaaactc aaaggaattg acggggcccc gcacaagcgg cggagcatgt ggattaattc      900
gatgcaacgc gaagaacctt acctgggttt gacatacacc ggaaagccgt agagatacgg      960
cccccttgt ggtcggtgta caggtggtgc atggctgtcg tcagctcgtg tcgtgagatg     1020
ttgggttaag tcccgcaacg agcgcaaccc ttgtcctgtg ttgccagcac gtaatggtgg     1080
ggactcgcag gagactgccg ggtcaactc ggaggaaggt ggggacgacg tcaagtcatc     1140
atgcccctta tgtccagggc ttcacacatg ctacaatggc cggtacagag gctgcgata     1200
ccgtgaggtg gagcgaatcc cttaaagccg gtctcagttc ggatcggggt ctgcaactcg     1260
accccgtgaa gtcggagtcg ctagtaatcg cagatcagca acgctgcggt gaatacgttc     1320
ccgggccttg tacaccgc ccgtcacgtc atgaaagtcg gtaacacccg aagccggtgg     1380
cctaacccct tgtgggaggg agccgtcgaa ggtgggatcg gcgattggga cgaagtcgta     1440
acaaggtagc cgtaccggaa ggtgcggctg atcacttcc tttcta                    1486
```

<210> SEQ ID NO 35
<211> LENGTH: 1507
<212> TYPE: DNA
<213> ORGANISM: Nocardia coeliaca

<400> SEQUENCE: 35

```
tttgatcctg gctcaggacg aacgctggcg gcgtgcttaa cacatgcaag tcgagcggta       60
aggcctttcg gggtacacga gcggcgaacg ggtgagtaac acgtgggtga tctgccctgc      120
acttcgggat aagcctggga aactgggtct aataccggat atgacctcag ttgcatgac       180
ttggggtgga aagatttatc ggtgcaggat gggcccgcgg cctatcagct tgttggtggg      240
gtaatggcct accaaggcga cgacgggtag ccgacctgag agggtgaccg gccacactgg      300
gactgagaca cggcccagac tcctacggga ggcagcagtg ggaatattg cacaatgggc      360
gaaagcctga tgcagcgacg ccgcgtgagg gatgacggcc ttcggggttgt aaacctcttt      420
```

```
cagcagggac gaagcgcaag tgacggtacc tgcagaagaa gcaccggcta actacgtgcc    480
agcagccgcg gtaatacgta gggtgcaagc gttgtccgga attactgggc gtaaagagtt    540
cgtaggcggt ttgtcgcgtc gtttgtgaaa accagcagct caactgctgg cttgcaggcg    600
atacgggcag acttgagtac tgcaggggag actggaattc ctggtgtagc ggtgaaatgc    660
gcagatatca ggaggaacac cggtggcgaa ggcgggtctc tgggcagtaa ctgacgctga    720
ggaacgaaag cgtgggtagc gaacaggatt agataccctg gtagtccacg ccgtaaacgg    780
tgggcgctag gtgtgggttc cttccacgga atccgtgccg tagctaacgc attaagcgcc    840
ccgcctgggg agtacggccg caaggctaaa actcaaagga attgacgggg cccgcacaa    900 gcggcggagc atgtggatta attcgatgca acgcgaagaa ccttacctgg gtttgacata    960
taccggaaag ctgcagagat gtggcccccc ttgtggtcgg tatacaggtg gtgcatggct   1020
gtcgtcagct cgtgtcgtga gatgttgggt taagtcccgc aacgagcgca accctatct   1080 tatgttgcca gcacgttatg gtggggactc gtaagagact gccggggtca actcggagga   1140
aggtggggac gacgtcaagt catcatgccc cttatgtcca gggcttcaca catgctacaa   1200
tggccagtac agagggctgc gagaccgtga ggtggagcga tcccttaaa gctggtctca   1260 gttcggatcg gggtctgcaa ctcgacccg tgaagtcgga gtcgctagta atcgcagatc   1320
agcaacgctg cggtgaatac gttcccgggc cttgtacaca ccgcccgtca cgtcatgaaa   1380
gtcggtaaca cccgaagccg gtggcttaac cccttgtggg agggagccgt cgaaggtggg   1440
atcggcgatt gggacgaagt cgtaacaagg tagccgtacc ggaaggtgcg gctggatcac   1500
ctccttt                                                              1507

<210> SEQ ID NO 36
<211> LENGTH: 1507
<212> TYPE: DNA
<213> ORGANISM: Nocardia globerula

<400> SEQUENCE: 36
gtttgatcct ggctcaggac gaacgctggc ggcgtgctta acacatgcaa gtcgagcggt     60
aaggcctttc ggggtacacg agcggcgaac gggtgagtaa cacgtgggtg atctgccctg    120
cacttcggga taagcctggg aaactgggtc taataccgga tatgacctcc tatcgcatgg    180
tgggtggtgg aaagatttat cggtgcagga tgggcccgcg gcctatcagc ttgttggtgg    240
ggtaatggcc taccaaggcg acgacgggta gccgacctga gagggtgacc ggccacactg    300
ggactgagac acgcccaga ctcctacggg aggcagcagt ggggaatatt gcacaatggg    360
cgaaagcctg atgcagcgac gccgcgtgag ggacgacggc cttcgggttg taaacctctt    420
tcagcaggga cgaagcgcaa gtgacggtac ctgcagaaga agcaccggct aactacgtgc    480
cagcagccgc ggtaatacgt agggtgcaag cgttgtccgg aattactggg cgtaaagagt    540
tcgtaggcgg tttgtcacgt cgtttgtgaa aactcacagc tcaactgtga gcctgcaggc    600
gatacgggca gacttgagta ctgcagggga gactggaatt cctggtgtag cggtgaaatg    660
cgcagatatc aggaggaaca ccggtggcga aggcgggtct ctgggcagta actgacgctg    720
aggaacgaaa gcgtgggtag cgaacaggat tagataccct ggtagtccac gccgtaaacg    780
gtgggcgcta gtgtgggtt cttccacgg aatccgtgcc gtagctaacg cattaagcgc    840 ccgcctggg gagtacggcc gcaaggctaa aactcaaagg aattgacggg gcccgcaca    900 agcggcggag catgtggatt aattcgatgc aacgcgaaga accttacctg gtttgacat    960
```

```
ataccggaaa gccgtagaga tacggccccc cttgtggtcg gtatacaggt ggtgcatggc    1020
tgtcgtcagc tcgtgtcgtg agatgttggg ttaagtcccg caacgagcgc aacccctatc    1080
ttatgttgcc agcacgttat ggtggggact cgtaagagac tgccggggtc aactcggagg    1140
aaggtgggga cgacgtcaag tcatcatgcc ccttatgtcc agggcttcac acatgctaca    1200
atggccagta cagagggctg cgagaccgtg aggtggagcg aatcccttaa agctggtctc    1260
agttcggatc ggggtctgca actcgacccc gtgaagtcgg agtcgctagt aatcgcagat    1320
cagcaacgct gcggtgaata cgttcccggg ccttgtacac accgcccgtc acgtcatgaa    1380
agtcggtaac acccgaagcc ggtggcttaa cccttgtgg agggagccg tcgaaggtgg    1440 gatcggcgat tgggacgaag tcgtaacaag gtagccgtac cggaaggtgc ggctggatca    1500
cctcctt                                                              1507

<210> SEQ ID NO 37
<211> LENGTH: 1508
<212> TYPE: DNA
<213> ORGANISM: Rhodococcus equi

<400> SEQUENCE: 37
gagtttgatc ctggctcagg acgaacgctg gcggcgtgct taacacatgc aagtcgagcg      60
gtagggccct tcggggtaca cgagcggcga acgggtgagt aacacgtggg tgatctgccc     120
tgcacttcgg gataagcttg ggaaactggg tctaataccg gatatgagcc tctactgcat     180
ggtggaggtt ggaaaggttt actggtgcag gatgggcccg cggcctatca gcttgttggt     240
ggggtaatgg cctaccaagg cgacgacggg tagccggcct gagagggcga ccggccacac     300
tgggactgag acacggccca gactcctacg ggaggcagca gtggggaata ttgcacaatg     360
ggcgaaagcc tgatgcagcg acgccgcgtg agggatgacg ccttcgggt tgtaaacctc     420 tttcagcagg gacgaagcga gagtgacggt acctgcagaa gaagcaccgg ccaactacgt     480
gccagcagcc gcggtaatac gtagggtgcg agcgttgtcc ggaattactg ggcgtaaaga     540
gctcgtaggc ggtttgtcgc gtcgtcggtg aaaaccagca gctcaactgc tggcttgcag     600
gcgatacggg cagacttgag tactgcaggg gagactggaa ttcctggtgt agcggtgaaa     660
tgcgcagata tcaggaggaa caccggtggc gaaggcgggt ctctgggcag taactgacgc     720
tgaggagcga aagcgtgggt agcgaacagg attagatacc ctggtagtcc acgccgtaaa     780
cggtgggcgc taggtgtggg tttccttcca cgggatccgt gccgtagcta acgcattaag     840
cgccccgcct ggggagtacg gccgcaaggc taaaactcaa aggaattgac ggggccccgc     900
acaagcggcg gagcatgtgg attaattcga tgcaacgcga agaaccttac ctgggtttga     960
catataccgg aaagccgtag agatacggcc cccttgtgg tcggtataca ggtggtgcat    1020
ggctgtcgtc agctcgtgtc gtgagatgtt gggttaagtc ccgcaacgag cgcaaccctt    1080
gtcctgtgtt gccagcacgt aatggtgggg actcgcagga ccgccgggg tcaactcgg    1140 aggaaggtgg ggacgacgtc aagtcatcat gccccttatg tccagggctt cacacatgct    1200
acaatggccg gtacagaggg ctgcgatacc gtgaggtgga gcgaatccct aaagccggt    1260 ctcagttcgg atcggggtct gcaactcgac cccgtgaagt cggagtcgct agtaatcgca    1320
gatcagcaac gctgcggtga atacgttccc gggccttgta cacaccgccc gtcacgtcat    1380
gaaagtcggt aacacccgaa gccggtggcc taaccttgt ggagggagcc gtcgaaggtg    1440
ggatcggcga ttgggacgaa gtcgtaacaa ggtagccgta ccggaaggtg cggctggatc    1500
acctcctt                                                            1508
```

<210> SEQ ID NO 38
<211> LENGTH: 1442
<212> TYPE: DNA
<213> ORGANISM: Rhodococcus sp.

<400> SEQUENCE: 38

| | | | | | |
|---|---|---|---|---|---|
| ctggctcagg | acgaacgctg | gcggcgtgct | taacacatgc | aagtcgagcg | gtaaggccct 60 |
| tcggggtaca | cgagcggcga | acgggtgagt | aacacgtggg | tgatctgccc | tgcacttcgg 120 |
| gataagcctg | ggaaactggg | tctaataccg | gatatgacct | tcggctgcat | ggctgagggt 180 |
| ggaaaggttt | actggtgcag | gatgagcccg | cggcctatca | gcttgttggt | ggggtaatgg 240 |
| cctaccaagg | cgacgacggg | tagccgacct | gagagggtga | ccggccacac | tgggactgag 300 |
| acacggccca | gactcctacg | ggaggcagca | gtggggaata | ttgcacaatg | ggcgaaagcc 360 |
| tgatgcagcg | acgccgcgtg | agggatgacg | gccttcgggt | tgtaaacctc | tttcagcagg 420 |
| gacgaagcga | aagtgacggt | acctgcagaa | gaagcaccgg | ctaactacgt | gccagcagcc 480 |
| gcggtaatac | gtagggtgca | agcgttgtcc | ggaattactg | ggcgtaaaga | gttcgtaggc 540 |
| ggtttgtcgc | gtcgtctgtg | aaaactcaca | gctcaactgt | gagcttgcag | gcgatacggg 600 |
| cagacttgag | tactgcaggg | gagactggaa | ttcctggtgt | agcggtgaaa | tgcgcagata 660 |
| tcaggaggaa | caccggtggc | gaaggcgggt | ctctgggcag | taactgacgc | tgaggaacga 720 |
| aagcgtgggt | agcaaacagg | attagatacc | ctggtagtcc | acgccgtaaa | cggtgggcgc 780 |
| taggtgtggg | ttccttccac | gggatctgtg | ccgtagctaa | cgcattaagc | gccccgcctg 840 |
| gggagtacgg | ccgcaaggct | aaaactcaaa | ggaattgacg | ggggcccgca | caagcggcgg 900 |
| agcatgtgga | ttaattcgat | gcaacgcgaa | gaaccttacc | tgggtttgac | atataccgga 960 |
| aagccgtaga | gatacggccc | cccttgtggt | cggtatacag | gtggtgcatg | gctgtcgtca 1020 |
| gctcgtgtcg | tgagatgttg | ggttaagtcc | cgcaacgagc | gcaacccttg | tcttatgttg 1080 |
| ccagcacgta | atggtgggga | ctcgtaagag | actgccgggg | tcaactcgga | ggaaggtggg 1140 |
| gacgacgtca | agtcatcatg | ccccttatgt | ccagggcttc | acacatgcta | caatggccag 1200 |
| tacagagggc | tgcgaaccgt | gaggtggagc | gaatccctta | aagcyggtct | cagttcggat 1260 |
| cggggtctgc | aactcgaccc | cgtgaagtcg | gagtcgctag | taatcgcaga | tcagcaacgc 1320 |
| tgcggtgaat | acgttcccgg | gccttgtaca | caccgcccgt | cacgtcatga | aagtcggtaa 1380 |
| cacccgaagc | cggtggccta | acccttgtg | ggagggagcc | gtcgaaggtg | ggatcggcga 1440 |
| tt | | | | | 1442 |

<210> SEQ ID NO 39
<211> LENGTH: 1474
<212> TYPE: DNA
<213> ORGANISM: Rhodococcus sp.

<400> SEQUENCE: 39

| | | | | | |
|---|---|---|---|---|---|
| agagtttgat | cctggctcag | gacgaacgct | ggcggcgtgc | ttaacacatg | caagtcgagc 60 |
| ggtaaggccc | ttcggggtac | acgagcggcg | aacgggtgag | taacacgtgg | gtgatctgcc 120 |
| ctgcacttcg | ggataagcct | gggaaactgg | gtctaatacc | ggatatgacc | ttcggctgca 180 |
| tggctgaggg | tggaaaggtt | tactggtgca | ggatgggccc | gcggcctatc | agcttgttgg 240 |
| tggggtaatg | gcctaccaag | gcgacgacgg | gtagccgacc | tgagagggtg | accgccaca 300 |
| ctgggactga | gacacggccc | agactcctac | gggaggcagc | agtggggaat | attgcacaat 360 |

```
gggcgaaagc ctgatgcagc gacgccgcgt gagggatgac ggccttcggg ttgtaaacct      420
cttccagcag ggacgaagcg aaagtgacgg tacctgcaga agaagcaccg gctaactacg      480
tgccagcagc cgcggtaata cgtagggtgc aagcgttgtc cggaattact gggcgtaaag      540
agttcgtagg cggtttgtcg cgtcgtttgt gaaaactcam rgctcaactg tgagcttgca      600
ggcgatacgg gcagacttga gtactgcagg ggagactgga attcctggtg tagcggtgaa      660
atgcgcagat atcaggagga acaccggtgg cgaaggcggg tctctgggca gtaactgacg      720
ctgaggaacg aaagcgtggg tagcaaacag gattagatac cctggtagtc cacgccgtaa      780
acggtgggcg ctaggtgtgg gttccttcca cgggatctgt gccgtagcta acgcattaag      840
cgccccgcct ggggagtacg gccgcaaggc taaaactcaa aggaattgac ggggcccgc      900 acaagcggcg gagcatgtgg attaattcga tgcaacgcga agaaccttac ctgggtttga      960
catataccgg aaagccgtag agatacggcc cccttgtgg tcggtataca ggtggtgcat     1020
ggctgtcgtc agctcgtgtc gtgagatgtt gggttaagtc ccgcaacgag cgcaacccct     1080
gtcttatgtt gccagcacgt aatggtgggg actcgtaaga gactgccggg gtcaactcgg     1140
aggaaggtgg ggacgacgtc aagtcatcat gccccttatg tccagggctt cacacatgct     1200
acaatggcca gtacagaggg ctgcgagacc gtgaggtgga cgaatccct taaagctggt      1260 ctcagttcgg atcggggtct gcaactcgac cccgtgaagt cggagtcgct agtaatcgca     1320
gatcagcaac gctgcggtga atacgttccc gggccttgta cacaccgccc gtcacgtcat     1380
gaaagtcggt aacacccgaa gccggtggcc taaccccttg tgggagggag ccgtcgaagg     1440
tgggatcggc gattgggacg aagtcgtaac aagg                                 1474
```

<210> SEQ ID NO 40
<211> LENGTH: 1437
<212> TYPE: DNA
<213> ORGANISM: Rhodococcus jostii

<400> SEQUENCE: 40

```
aggacgaacg ctggcggcgt gcttaacaca tgcaagtcga gcggtaaggc ccttcggggt       60
acacgagcgg cgaacgggtg agtaacacgt gggtgatctg ccctgcactt cgggataagc      120
ctgggaaact gggtctaata ccggatatga ccttcggctg catggctgag ggtggaaagg      180
tttactggtg caggatgggc ccgcggccta tcagcttgtt ggtggggtaa tggcctacca      240
aggcgacgac gggtagccga cctgagaggg tgaccggcca cactgggact gagacacggc      300
ccagactcct acgggaggca gcagtgggga atattgcaca atgggcgaaa gcctgatgca      360
gcgacgccgc gtgagggatg acggccttcg ggttgtaaac ctctttcagc agggacgaag      420
cgaaagtgac ggtacctgca gaagaagcac cggctaacta cgtgccagca gccgcggtaa      480
tacgtagggt gcaagcgttg tccggaatta ctgggcgtaa agagttcgta ggcggtttgt      540
cgcgtcgttt gtgaaaactc acagctcaac tgtgagcctg caggcgatac gggcagactt      600
gagtactgca ggggagactg gaattcctgg tgtagcggtg aaatgcgcag atatcaggag      660
gaacaccggt ggcgaaggcg ggtctctggg cagtaactga cgctgaggaa cgaaagcgtg      720
ggtagcaaac aggattagat accctggtag tccacgccgt aaacggtggg cgctaggtgt      780
gggttccttc cacgggatct gtgccgtagc taacgcatta agcgccccgc ctggggagta      840
cggccgcaag gctaaaactc aaaggaattg acggggcccg cacaagcggc ggagcatgt      900 ggattaattc gatgcaacgc gaagaacctt acctgggttt gacatatacc ggaaagccgt      960
agagatacgg cccccttgt ggtcggtata caggtggtgc atggctgtcg tcagctcgtg     1020
```

```
tcgtgagatg tttgggttaag tcccgcaacg agcgcaaccc ttgtcttatg ttgccagcac    1080
gtaatggtgg ggactcgtaa gagactgccg gggtcaactc ggaggaaggt ggggacgacg    1140
tcaagtcatc atgcccctta tgtccagggc ttcacacatg ctacaatggc cagtacagag    1200
ggctgcgaga ccgtgaggtg gagcgaatcc cttaaagctg gtctcagttc ggatcggggt    1260
ctgcaactcg accccgtgaa gtcggagtcg ctagtaatcg cagatcagca acgctgcggt    1320
gaatacgttc ccgggccttg tacacaccgc ccgtcacgtc atgaaagtcg gtaacacccg    1380
aagccggtgg cctaacccct tgtgggaggg agccgtcgaa ggtgggatcg gcgattg      1437
```

<210> SEQ ID NO 41
<211> LENGTH: 1485
<212> TYPE: DNA
<213> ORGANISM: Rhodococcus opacus
<220> FEATURE:
<221> NAME/KEY: modified_base
<222> LOCATION: (812)..(812)
<223> OTHER INFORMATION: a, c, t or g

<400> SEQUENCE: 41

```
gatcctggct caggacgaac gctggcggcg tgcttaacac atgcaagtcg agcggtaagg      60
cccttcgggg tacacgagcg cgaacgggt gagtaacacg tgggtgatct gccctgcact    120
tcgggataag cctgggaaac tgggtctaat accggatatg accttcggct gcatggctga    180
gggtggaaag gtttactggt gcaggatggg cccgcggcct atcagcttgt tggtggggta    240
atggcctacc aaggcgacga cgggtagccg acctgagagg gtgaccggcc acactgggac    300
tgagacacgg cccagactcc tacgggaggc agcagtgggg aatattgcac aatgggcgaa    360
agcctgatgc agcgacgccg cgtgagggat gacggccttc gggttgtaaa cctctttcag    420
cagggacgaa gcgaaagtga cggtacctgc agaagaagca ccggccaact acgtgccagc    480
agccgcggta atacgtaggg tgcaagcgtt gtccggaatt actgggcgta aagagttcgt    540
aggcggtttg tcgcgtcgtc tgtgaaaact caaagctcaa cctcgagcct gcaggcgata    600
cgggcagact tgagtactgc aggggagact ggaattcctg gtgtagcggt gaaatgcgca    660
gatatcagga ggaacaccgg tggcgaaggc gggtctctgg gcagtaactg acgctgagga    720
acgaaagcgt gggtagcgaa caggattaga taccctggta gtccacgccg taaacggtgg    780
gcgctaggtg tgggtttcct tccacgggat cngtgccgta gctaacgcat aagcgcccc    840 gcctggggag tacggccgca aggctaaaac tcaaaggaat tgacggggc ccgcacaagc    900 ggcggagcat gtggattaat tcgatgcaac gcgaagaacc ttacctgggt ttgacatata    960
ccggaaagcc gtagagatac ggccccctt gtggtcggta tacaggtggt gcatggctgt    1020
cgtcagctcg tgtcgtgaga tgttgggtta agtcccgcaa cgagcgcaac ccttgtctta    1080
tgttgccagc acgtaatggt ggggactcgt aagagactgc cggggtcaac tcggaggaag    1140
gtggggacga cgtcaagtca tcatgcccct tatgtccagg gcttcacaca tgctacaatg    1200
gccggtacag agggctgcga ataccgtgagg tggagcgaat cccttaaagc tggtctcagt    1260
tcggatcggg gtctgcaact cgaccccgtg aagtcggagt cgctagtaat cgcagatcag    1320
caacgctgcg gtgaatacgt tcccgggcct tgtacacacc gcccgtcacg tcatgaaagt    1380
cggtaacacc cgaagccggt ggcctaaccc cttgtgggag gagccgtcg aaggtgggat    1440 cggcgattgg gacgaagtcg taacaaggta gccgtaccgg aaggt                  1485
```

<210> SEQ ID NO 42

```
<211> LENGTH: 1510
<212> TYPE: DNA
<213> ORGANISM: Rhodococcus imtechensis

<400> SEQUENCE: 42
ttgatcctgg ctcaggacga acgctggcgg cgtgcttaac acatgcaagt cgagcggtaa      60
ggcccttcgg ggtacacgag cggcgaacgg gtgagtaaca cgtgggtgat ctgccctgca     120
cttcgggata agcctgggaa actgggtcta ataccggata tgaccttcgg ctgcatggct     180
gagggtggaa aggtttactg gtgcaggatg ggcccgcggc ctatcagctt gttggtgggg     240
taatggccta ccaaggcgac gacgggtagc cgacctgaga gggtgaccgg ccacactggg     300
actgagacac ggcccagact cctacgggag gcagcagtgg ggaatattgc acaatgggcg     360
aaagcctgat gcagcgacgc cgcgtgaggg atgacggcct tcgggttgta aacctctttc     420
agcagggacg aagcgaaagt gacggtacct gcagaagaag caccggccaa ctacgtgcca     480
tcagccgcgg taatacgtag ggtgcaagcg ttgtccggaa ttactgggcg taaagagctc     540
gtaggcggtt tgtcgtgtcg tctgtgaaaa ctcgaggctc aacctcgagc ttgcaggcga     600
tacgggcaga cttgagtact gcaggggaga ctggaattcc tggtgtagcg gtgaaatgcg     660
cagatatcag gaggaacacc ggtggcgaag gcgggtctct gggcagtaac tgacgctgag     720
gagcgaaagc gtggaaaccg aacaggatta gatacctcgg tagtccacgc cgtaaacggt     780
gggcgctagg tgtgggtttc cttccacggg atccgtgccg tagctaacgc attaagcgcc     840
ccgcctgggg agtacggccg caaggctaaa actcaaagga attgacgggg gcccgcacaa     900
gcggcggagc atgtggatta attcgatgca acgcgaagaa ccttacctgg gtttgacata     960
taccggaaag ccgtagagat acggcccccc ttgtggtcgg tatacaggtg gtgcatggct    1020
gtcgtcagct cgtgtcgtaa gatgttgggt taagtcccgc aacgagcgca acccttgtct    1080
tatgttgcca gcacgtaatg gtggggactc gtaagagact gccgggtcaa ctcggagga     1140
aggtggggac gacgtcaagt catcatgccc cttatgtcca gggcttcaca catgctacaa    1200
tggccagtac agagggctgc gagaccgtga ggtggagcga atcccttaaa gctggtctca    1260
gttcggatcg gggtctgcaa ctcgacccccg tgaagtcgga gtcgctagta atcgcagatc    1320
agcaacgctg cggtgaatac gttcccaggc cttgtacaca ccgcccgtca cgtcatgaaa    1380
gtcggtaaca cccgaagccg gtggcctaac cccttgtggg agggagccgt cgaaggtggg    1440
atcggcgatt gggacgaagt cgtaacaagg tagccgtacc ggaaggtgcg gctggaaact    1500
gccgagggg                                                           1510

<210> SEQ ID NO 43
<211> LENGTH: 1473
<212> TYPE: DNA
<213> ORGANISM: Rhodococcus koreensis

<400> SEQUENCE: 43
gacgaacgct ggcggcgtgc ttaacacatg caagtcgagc ggtaaggccc ttcggggtac      60
acgagcggcg aacgggtgag taacacgtgg gtgatctgcc ctgcacttcg ggataagcct     120
gggaaactgg gtctaatacc ggatatgacc aaggactgca tggttttggg tggaaaggtt     180
tactggtgca ggatgggccc gcggcctatc agcttgttgg tggggtaatg gcctaccaag     240
gcgacgacgg gtagccgacc tgagagggtg accggccaca ctgggactga gacacggccc     300
agactcctac gggaggcagc agtggggaat attgcacaat gggcgaaagc ctgatgcagc     360
gacgccgcgt gagggatgac ggccttcggg ttgtaaacct ctttcagcag ggacgaagcg     420
```

```
agagtgacgg tacctgcaga agaagcaccg gccaactacg tgccagcagc cgcggtaata      480
cgtagggtgc aagcgttgtc cggaattact gggcgtaaag agctcgtagg cggtttgtcg      540
cgtcgtctgt gaaaactcga ggctcaacct cgagcttgca ggcgatacgg gcagacttga      600
gtactgcagg ggagactgga attcctggtg tagcggtgaa atgcgcagat atcaggagga      660
acaccggtgg cgaaggcggg tctctgggca gtaactgacg ctgaggagcg aaagcgtggg      720
tagcgaacag gattagatac cctggtagtc cacgccgtaa acgtgggcg ctaggtgtgg       780 gttccttcca cgggatccgt gccgtagcta acgcattaag cgccccgcct ggggagtacg      840
gccgcaaggc taaaactcaa aggaattgac ggggcccgc acaagcggcg gagcatgtgg       900
attaattcga tgcaacgcga agaaccttac ctgggtttga catataccgg aaagccgtag      960
agatacggcc cccttgtggg tcggtataca ggtggtgcat ggctgtcgtc agctcgtgtc     1020
gtgagatgtt gggttaagtc ccgcaacgag cgcaacccct tgtcttatgtt gccagcacgt    1080 aatggtgggg actcgtaaga gactgccggg gtcaactcgg aggaaggtgg ggacgacgtc    1140
aagtcatcat gccccttatg tccagggctt cacacatgct acaatggcca gtacagaggg    1200
ctgcgagacc gtgaggtgga gcgaatccct taaagctggt ctcagttcgg atcgggtct    1260 gcaactcgac cccgtgaagt cggagtcgct agtaatcgca gatcagcaac gctgcggtga    1320
atacgttccc gggccttgta cacaccgccc gtcacgtcat gaaagtcggt aacacccgaa    1380
gccggtggcc taacccttg tgggagggag ccgtcgaagg tgggatcggc gattgggacg     1440
aagtcgtaac aaggtagccg taccggaagg tgc                                 1473
```

<210> SEQ ID NO 44
<211> LENGTH: 1229
<212> TYPE: DNA
<213> ORGANISM: Rhodococcus opacus

<400> SEQUENCE: 44

```
gggtgaccgg ccacactggg actgagacac ggcccagact cctacgggag gcagcagtgg       60
ggaatattgc acaatgggcg aaagcctgat gcagcgacgc cgcgtgaggg atgacggcct      120
tcgggttgta aacctctttc agcagggacg aagcgaaagt gacggtacct gcagaagaag      180
caccggccaa ctacgtgcca gcagccgcgg taatacgtag ggtgcaagcg ttgtccggaa      240
ttactgggcg taaagagctc gtaggcggtt tgtcgcgtcg tctgtgaaaa ctcgaggctc      300
aacctcgagc ttgcaggcga tacgggcaga cttgagtact gcagggagag ctggaattcc      360
tggtgtagcg gtgaaatgcg cagatatcag gaggaacacc ggtggcgaag gcgggtctct      420 ggcagtaac tgacgctgag gagcgaaagc gtgggtagcg aacaggatta gataccctgg      480
tagtccacgc cgtaaacggt gggcgctagg tgtgggtttc cttccacggg atccgtgccg      540
tagctaacgc attaagcgcc ccgcctgggg agtacggccg caaggctaaa actcaaagga      600
attgacgggg cccgcacaa gcggcggagc atgtggatta attcgatgca acgcgaagaa       660
ccttacctgg gtttgacata taccggaaag ctgcagagat gtggcccccc ttgtggtcgg      720
tatacaggtg gtgcatggct gtcgtcagct cgtgtcgtga gatgttgggt taagtcccgc      780
aacgagcgca accttgtct tatgttgcca gcacgtaatg gtgggactc gtaagagact       840 gccggggtca actcggagga aggtgggac gacgtcaagt catcatgccc cttatgtcca       900
gggcttcaca catgctacaa tggccggtac agagggctgc gataccgtga ggtggagcga      960
atcccttaaa gccggtctca gttcggatcg gggtctgcaa ctcgaccccg tgaagtcgga     1020
```

```
gtcgctagta atcgcagatc agcaacgctg cggtgaatac gttcccgggc cttgtacaca    1080
ccgcccgtca cgtcatgaaa gtcggtaaca cccgaagccg gtggcctaac ccctcgtggg    1140
agggagccgt cgaaggtggg atcggcgatt gggacgaagt cgtaacaagg tagccgtacc    1200
ggaaggtgcg gctggatcac ctcctttct                                      1229

<210> SEQ ID NO 45
<211> LENGTH: 1450
<212> TYPE: DNA
<213> ORGANISM: Rhodococcus sp.

<400> SEQUENCE: 45
tcctggctca ggacgaacgc tggcggcgtg cttaacacat gcaagtcgag cggtaaggcc      60
cttcggggta cacgagcggc gaacgggtga gtaacacgtg ggtgatctgc cctgcacttc     120
gggataagcc tgggaaactg ggtctaatac cggatatgac cttcggctgc atggctgttg     180
gtggaaaggt ttactggtgc aggatgggcc cgcggcctat cagcttgttg gtggggtaat     240
ggcctaccaa ggcgacgacg gatagccgac ctgagagggt gaccggccac actgggactg     300
agacacggcc cagactccta cgggaggcag cagtggggaa tattgcacaa tgggcgaaag     360
cctgatgcag cgacgccgcg tgagggatga cggccttcgg gttgtaaacc tctttcagca     420
gggacgaagc gagagtgacg gtacctgcag aagaagcacc ggccaactac gtgccagcag     480
ccgcggtaat acgtagggtg caagcgttgt ccggaattac tgggcgtaaa gagctcgtag     540
gcggtttgtc gcgtcgtctg tgaaaactcg aggctcaacc tcgagcttgc aggcgatacg     600
ggcagacttg agtactgcag gggagactgg aattcctggt gtagcggtga atgcgcaga     660 tatcaggagg aacaccggtg gcgaaggcgg gtctctgggc agtaactgac gctgaggagc     720
gaaagcgtgg gtagcgaaca ggattagata ccctggtagt ccacgccgta acggtgggc     780 gctaggtgtg ggtttccttc cacgggatcc gtgccgtagc taacgcatta agcgccccgc     840
ctggggagta cggccgcaag gctaaaactc aaaggaattg acgggggccc gcacaagcgg     900
cggagcatgt ggattaattc gatgcaacgc gaagaacctt acctgggttt gacatatacc     960
ggaaagccgt agagatacgg ccccccttgt ggtcggtata caggtggtgc atggctgtcg    1020
tcagctcgtg tcgtgagatg ttgggttaag tcccgcaacg agcgcaaccc ttgtcttatg    1080
ttgccagcac gtaatggtgg ggactcgtaa gagactgccg ggtcaactc ggaggaaggt     1140 ggggacgacg tcaagtcatc atgcccctta tgtccagggc ttcacacatg ctacaatggc    1200
cggtacagag ggctgcgata ccgtgaggtg gagcgaatcc cttaaagccg gtctcagttc    1260
ggatcggggt ctgcaactcg acccgtgaa gtcggagtcg ctagtaatcg cagatcagca    1320
acgctgcggt gaatacgttc ccgggccttg tacaccgc ccgtcacgtc atgaaagtcg      1380
gtaacacccg aagccggtgg cctaaccct cgtgggaggg agccgtcgaa ggtgggatcg     1440
gcgattggga                                                          1450

<210> SEQ ID NO 46
<211> LENGTH: 1471
<212> TYPE: DNA
<213> ORGANISM: Rhodococcus opacus

<400> SEQUENCE: 46
gacgaacgct ggcggcgtgc ttaacacatg caagtcgagc ggtaaggccc ttcggggtac      60
acgagcggcg aacgggtgag taacacgtgg gtgatctgcc ctgcacttcg ggataagcct     120
gggaaactgg gtctaatacc ggatatgacc ttcggctgca tggctgaggg tggaaaggtt     180
```

```
tactggtgca ggatgggccc gcggcctatc agcttgttgg tggggtaatg gcctaccaag    240
gcgacgacgg gtagccgacc tgagagggtg accggccaca ctgggactga gacacggccc    300
agactcctac gggaggcagc agtggggaat attgcacaat gggcgaaagc ctgatgcagc    360
gacgccgcgt gagggatgac ggccttcggg ttgtaaacct ctttcagcag ggacgaagcg    420
agagtgacgg tacctgcaga gaagcaccg gccaactacg tgccagcagc cgcggtaata    480
cgtagggtgc aagcgttgtc cggaattact gggcgtaaag agctcgtagg cggtttgtcg    540
cgtcgtctgt gaaaactcga ggctcaacct cgagcttgca ggcgatacgg gcagacttga    600
gtactgcagg ggagactgga attcctggtg tagcggtgaa atgcgcagat atcaggagga    660
acaccggtgg cgaaggcggg tctctgggca gtaactgacg ctgaggagcg aaagcgtggg    720
tagcgaacag gattagatac cctggtagtc cacgccgtaa acggtgggcg ctaggtgtgg    780
gtttccttcc acgggatccg tgccgtagct aacgcattaa gcgccccgcc tggggagtac    840
ggccgcaagg ctaaaactca aaggaattga cggggcccg cacaagcggc ggagcatgtg    900
gattaattcg atgcaacgcg aagaacctta cctgggtttg acatataccg gaaagccgta    960
gagatacggc cccccttgtg gtcggtatac aggtggtgca tggctgtcgt cagctcgtgt    1020
cgtgagatgt tgggttaagt cccgcaacga gcgcaaccct tgtcttatgt tgccagcacg    1080
taatggtggg gactcgtaag agactgccgg ggtcaactcg gaggaaggtg gggacgacgt    1140
caagtcatca tgccccttat gtccagggct tcacacatgc tacaatggcc ggtacagagg    1200
gctgcgatac cgtgaggtgg agcgaatccc ttaaagccgg tctcagttcg gatcggggtc    1260
tgcaactcga ccccgtgaag tcggagtcgc tagtaatcgc agatcagcaa cgctgcggtg    1320
aatacgttcc cgggccttgt acacaccgcc cgtcacgtca tgaaagtcgg taacacccga    1380
agccggtggc ctaaccctc gtgggaggga gccgtcgaag gtgggatcgg cgattgggac    1440
gaagtcgtaa caaggtagcc gtaccggaag g                                    1471

<210> SEQ ID NO 47
<211> LENGTH: 1482
<212> TYPE: DNA
<213> ORGANISM: Rhodococcus sp.

<400> SEQUENCE: 47
gagtttgatc ctggctcagg acgaacgctg gcggcgtgct taacacatgc aagtcgagcg     60
gtaaggccct tcggggtaca cgagcggcga acgggtgagt aacacgtggg tgatctgccc    120
tgcacttcgg gataagcctg ggaaactggg tctaataccg gatatgacct tcggctgcat    180
ggctgagggt ggaaaggttt actggtgcag gatgggcccg cggcctatca gcttgttggt    240
ggggtaatgg cctaccaagg cgacgacggg tagccgacct gagagggtga ccggccacac    300
tgggactgag acacggccca gactcctacg ggaggcagca gtgggaata ttgcacaatg    360 ggcgaaagcc tgatgcagcg acgccgcgtg agggatgaca accttcgggt tgtaaacctc    420
tttcagcagg gacgaagcga aagtgacggt acctgcagaa gaagcaccgg ccaactacgt    480
gccagcagcc gcggtaatac gtagggtgca agcgttgtcc ggaattactg ggcgtaaaga    540
gctcgtaggc ggtttgtcgc gtcgtctgtg aaaactcgag gctcaacctc gagcttgcag    600
gcgatacggg cagacttgag tactgcaggg gagactggaa ttcctggtgt agcggtgaaa    660
tgcgcagata tcaggaggaa caccggtggc gaaggcgggt ctctgggcag taactgacgc    720
tgaggagcga aagcgtgggt agcgaacagg attagatacc ctggtagtcc acgccgtaaa    780
```

| | |
|---|---|
| cggtgggcgc taggtgtggg tttccttcca cgggatccgt gccgtagcta acgcattaag | 840 |
| cgccccgcct ggggagtacg gccgcaaggc taaaactcaa aggaattgac ggggccccgc | 900 |
| acaagcggcg gagcatgtgg attaattcga tgcaacgcga agaaccttac ctgggtttga | 960 |
| catataccgg aaagccgtag agatacggcc cccttgtgg tcggtataca ggtggtgcat | 1020 |
| ggctgtcgtc agctcgtgtc gtgagatgtt gggttaagtc ccgcaacgag cgcaacccctt | 1080 |
| gtcttatgtt gccagcacgt aatggtgggg actcgtaaga gactgccggg gtcaactcgg | 1140 |
| aggaaggtgg ggacgacgtc aagtcatcat gccccttatg tccagggctt cacacatgct | 1200 |
| acaatggccg gtacagaggg ctgcgatacc gtgaggtgga gcgaatccct aaagccggt | 1260 |
| ctcagttcgg atcgggtct gcaactcgac cccgtgaagt cggagtcgct agtaatcgca | 1320 |
| gatcagcaac gctgcggtga atacgttccc gggccttgta cacaccgccc gtcacgtcat | 1380 |
| gaaagtcggt aacacccgaa gccggtggcc taaccccttg tgggagggag ccgtcgaagg | 1440 |
| tgggatcggc gattgggacg aagtcgtaac aaggtagccg ta | 1482 |

<210> SEQ ID NO 48
<211> LENGTH: 1446
<212> TYPE: DNA
<213> ORGANISM: Rhodococcus sp.

<400> SEQUENCE: 48

| | |
|---|---|
| gcggcgtgct taacacatgc aagtcgagcg gtaaggccct tcggggtaca cgagcggcga | 60 |
| acgggtgagt aacacgtggg tgatctgccc tgcacttcgg gataagcctg ggaaactggg | 120 |
| tctaataccg gatatgacct tcggctgcat ggctgagggt ggaaaggttt actggtgcag | 180 |
| gatgggcccg cggcctatca gcttgttggt ggggtaatgg cctaccaagg cgacgacggg | 240 |
| tagccgacct gagagggtga ccggccacac tgggactgag acacgcccca gactcctacg | 300 |
| ggaggcagca gtgggaata ttgcacaatg gcgaaagcc tgatgcagcg acgccgcgtg | 360 |
| agggatgacg gccttcgggt tgtaaacctc tttcagcagg gacgaagcga aagtgacggt | 420 |
| acctgcagaa gaagcaccgg ccaactacgt gccagcagcc gcggtaatac gtagggtgca | 480 |
| agcgttgtcc ggaattactg ggcgtaaaga gctcgtaggc ggtttgtcgc gtcgtctgtg | 540 |
| aaaactcgag gctcaacctc gagcttgcag gcgatacggg cagacttgag tactgcaggg | 600 |
| gagactggaa ttcctggtgt agcggtgaaa tgcgcagata tcaggaggaa caccggtggc | 660 |
| gaaggcgggt ctctgggcag taactgacgc tgaggggcga aagcgtgggt agcgaacagg | 720 |
| attagatacc ctggtagtcc acgccgtaaa cggtgggcgc taggtgtggg tttccttcca | 780 |
| cgggatccgt gccgtagcta acgcattaag cgccccgcct ggggagtacg gccgcaaggc | 840 |
| taaaactcaa aggaattgac ggggccccgc acaagcggcg gagcatgtgg attaattcga | 900 |
| tgcaacgcga agaaccttac ctgggtttga catataccgg aaagccgtag agatacggcc | 960 |
| cccttgtgg tcggtataca ggtggtgcat ggctgtcgtc agctcgtgtc gtgagatgtt | 1020 |
| gggttaagtc ccgcaacgag cgcaacccctt gtcttatgtt gccagcacgt aatggtgggg | 1080 |
| actcgtaaga gactgccggg gtcaactcgg aggaaggtgg ggacgacgtc aagtcatcat | 1140 |
| gccccttatg tccagggctt cacacatgct acaatggccg gtacagaggg ctgcgatacc | 1200 |
| gtgaggtgga gcgaatccct aaagccggt ctcagttcgg atcgggtct gcaactcgac | 1260 |
| cccgtgaagt cggagtcgct agtaatcgca gatcagcaac gctgcggtga atacgttccc | 1320 |
| gggccttgta cacaccgccc gtcacgtcat gaaagtcggt aacacccgaa gccagtggcc | 1380 |
| taaccccttg tgggagggag ccgtcgaagg tgggatcggc gattgggacg aagtcgtaac | 1440 |

<210> SEQ ID NO 49
<211> LENGTH: 1497
<212> TYPE: DNA
<213> ORGANISM: Rhodococcus wratislaviensis

<400> SEQUENCE: 49

```
cctggctcag gacgaacgct ggcggcgtgc ttaacacatg caagtcgagc ggtaaggccc      60
ttcggggtac acgagcggcg aacgggtgag taacacgtgg gtgatctgcc ctgcacttcg     120
ggataagcct gggaaactgg gtctaatacc ggatatgacc ttcggctgca tggctgaggg     180
tggaaaggtt tactggtgca ggatgggccc gcggcctatc agcttgttgg tggggtaatg     240
gcctaccaag cgacgacgg gtagccgacc tgagagggtg accggccaca ctgggactga     300
gacacggccc agactcctac gggaggcagc agtggggaat attgcacaat gggcgaaagc     360
ctgatgcagc gacgccgcgt gagggatgac ggccttcggg ttgtaaacct ctttcagcag     420
ggacgaagcg aaagtgacgg tacctgcaga agaagcaccg gccaactacg tgccagcagc     480
cgcggtaata cgtagggtgc aagcgttgtc ggaattact gggcgtaaag agctcgtagg     540
cggtttgtcg cgtcgtctgt gaaaactcga ggctcaacct cgagcttgca ggcgatacgg     600
gcagacttga gtactgcagg ggagactgga attcctggtg tagcggtgaa atgcgcagat     660
atcaggagga acaccggtgg cgaaggcggg tctctgggca gtaactgacg ctgaggagcg     720
aaagcgtggg tagcgaacag gattagatac cctggtagtc cacgccgtaa acggtgggcg     780
ctaggtgtgg gtttccttcc acgggatccg tgccgtagct aacgcattaa gcgccccgcc     840
tggggagtac ggccgcaagg ctaaaactca aaggaattga cggggcccg cacaagcggc     900
ggagcatgtg gattaattcg atgcaacgcg aagaaccta cctgggtttg acatataccg     960
gaaagccgta gagatacggc cccccttgtg gtcggtatac aggtggtgca tggctgtcgt    1020
cagctcgtgt cgtgagatgt tgggttaagt cccgcaacga gcgcaaccct tgtcttatgt    1080
tgccagcacg taatggtggg gactcgtaag agactgccgg ggtcaactcg gaggaaggtg    1140
gggacgacgt caagtcatca tgcccttat gtccagggct tcacacatgc tacaatggcc    1200
ggtacagagg gctgcgatac cgtgaggtgg agcgaatccc ttaaagccgg tctcagttcg    1260
gatcggggtc tgcaactcga cccgtgaag tcggagtcgc tagtaatcgc agatcagcaa    1320
cgctgcggtg aatacgttcc cgggccttgt acacaccgcc cgtcacgtca tgaaagtcgg    1380
taacacccga agccggtggc ctaaccccctt gtgggaggga gccgtcgaag gtgggatcgg    1440
cgattgggac gaagtcgtaa caaggtagcc gtaccggaag gtgcggctgg atcacct      1497
```

<210> SEQ ID NO 50
<211> LENGTH: 533
<212> TYPE: PRT
<213> ORGANISM: Bos taurus

<400> SEQUENCE: 50

```
Met Phe Gln Phe His Ala Gly Ser Trp Glu Ser Trp Cys Cys Cys Cys
1               5                   10                  15

Cys Leu Ile Pro Gly Asp Arg Pro Trp Asp Arg Gly Arg Arg Trp Arg
                20                  25                  30

Leu Glu Met Arg His Thr Arg Ser Val His Glu Thr Arg Phe Glu Ala
            35                  40                  45

Ala Val Lys Val Ile Gln Ser Leu Pro Lys Asn Gly Ser Phe Gln Pro
```

```
            50                  55                  60
Thr Asn Glu Met Met Leu Lys Phe Tyr Ser Phe Tyr Lys Gln Ala Thr
 65                  70                  75                  80

Glu Gly Pro Cys Lys Leu Ser Lys Pro Gly Phe Trp Asp Pro Val Gly
                 85                  90                  95

Arg Tyr Lys Trp Asp Ala Trp Ser Ser Leu Gly Asp Met Thr Lys Glu
            100                 105                 110

Glu Ala Met Ile Ala Tyr Val Glu Glu Met Lys Lys Ile Leu Glu Thr
        115                 120                 125

Met Pro Met Thr Glu Lys Val Glu Glu Leu Leu His Val Ile Gly Pro
    130                 135                 140

Phe Tyr Glu Ile Val Glu Asp Lys Lys Ser Gly Arg Ser Ser Asp Leu
145                 150                 155                 160

Thr Ser Val Arg Leu Glu Lys Ile Ser Lys Cys Leu Glu Asp Leu Gly
                165                 170                 175

Asn Val Leu Ala Ser Thr Pro Asn Ala Lys Thr Val Asn Gly Lys Ala
            180                 185                 190

Glu Ser Ser Asp Ser Gly Ala Glu Ser Glu Glu Glu Ala Ala Gln Glu
        195                 200                 205

Asp Pro Lys Arg Pro Glu Pro Arg Asp Ser Asp Lys Lys Met Met Lys
    210                 215                 220

Lys Ser Ala Asp His Lys Asn Leu Glu Ile Ile Val Thr Asn Gly Tyr
225                 230                 235                 240

Asp Lys Asp Ser Phe Val Gln Gly Val Gln Asn Ser Ile His Thr Ser
                245                 250                 255

Pro Ser Leu Asn Gly Arg Cys Thr Glu Glu Val Lys Ser Val Asp Glu
            260                 265                 270

Asn Leu Glu Gln Thr Gly Lys Thr Val Val Phe Val His Gln Asp Val
        275                 280                 285

Asn Ser Asp His Val Glu Asp Ile Ser Gly Ile Gln His Leu Thr Ser
    290                 295                 300

Asp Ser Asp Ser Glu Val Tyr Cys Asp Ser Met Glu Gln Phe Gly Gln
305                 310                 315                 320

Glu Glu Ser Leu Asp Gly Phe Ile Ser Asn Asn Gly Pro Phe Ser Tyr
                325                 330                 335

Tyr Leu Gly Gly Asn Pro Ser Gln Pro Leu Glu Ser Ser Gly Phe Pro
            340                 345                 350

Glu Ala Val Gln Gly Leu Pro Gly Asn Gly Ser Pro Glu Asp Met Gln
        355                 360                 365

Gly Ala Val Val Glu Gly Lys Gly Glu Val Lys Arg Gly Gly Glu Asp
    370                 375                 380

Gly Gly Ser Asn Ser Gly Ala Pro His Arg Glu Lys Arg Ala Gly Glu
385                 390                 395                 400

Ser Glu Glu Phe Ser Asn Ile Arg Arg Gly Arg Gly His Arg Met Gln
                405                 410                 415

His Leu Ser Glu Gly Ser Lys Gly Arg Gln Val Gly Ser Gly Gly Asp
            420                 425                 430

Gly Glu Arg Trp Gly Ser Asp Arg Gly Ser Arg Gly Ser Leu Asn Glu
        435                 440                 445
```

Gln Ile Ala Leu Val Leu Met Arg Leu Gln Glu Asp Met Gln Asn Val
    450                 455                 460

Leu Gln Arg Leu His Lys Leu Glu Met Leu Ala Ala Ser Gln Ala Lys
465                 470                 475                 480

Ser Ser Ala Leu Gln Thr Ser Asn Gln Pro Thr Ser Pro Arg Pro Ser
                485                 490                 495

Trp Trp Pro Phe Glu Met Ser Pro Gly Ala Leu Thr Phe Ala Ile Ile
            500                 505                 510

Trp Pro Phe Ile Ala Gln Trp Leu Val His Leu Tyr Tyr Gln Arg Arg
        515                 520                 525

Arg Arg Lys Leu Asn
    530

<210> SEQ ID NO 51
<211> LENGTH: 1750
<212> TYPE: DNA
<213> ORGANISM: Bos taurus

<400> SEQUENCE: 51

| | | | | | | |
|---|---|---|---|---|---|---|
| gaggagctga | ccagctgcgc | tttggagtcc | tcctcccttc | gggaatgttg | atccgcggct | 60 |
| gcgctccatg | tttcagtttc | atgcaggctc | ctgggaaagc | tggtgctgct | gctgctgcct | 120 |
| gattccaggc | gacagacctt | gggaccgcgg | ccggcgctgg | cggctggaga | tgcggcacac | 180 |
| gagatccgtt | cacgaaaccc | ggtttgaggc | ggctgtgaag | gtgatacaga | gcttgccgaa | 240 |
| aaatggttca | ttccagccaa | caaatgaaat | gatgctcaag | ttctatagct | tctataagca | 300 |
| ggcaactgaa | ggaccttgta | aactgtcaaa | gcctggcttc | tgggatcctg | ttggaagata | 360 |
| caaatgggat | gcgtggagtt | ctttgggtga | tatgaccaaa | gaggaagcca | tgattgctta | 420 |
| tgttgaagaa | atgaaaaaga | ttcttgaaac | tatgccgatg | actgaaaaag | ttgaagaatt | 480 |
| gctacatgtc | attggtccat | tttatgaaat | tgtagaagac | aaaaaaagtg | gcagaagttc | 540 |
| tgatttaacc | tcagtccgac | tggagaaaat | ctctaaatgc | ttagaagatc | ttggtaatgt | 600 |
| tctagcttct | actccaaatg | ccaaaactgt | taatggtaaa | gctgaaagca | gtgatagtgg | 660 |
| agctgaatct | gaggaagaag | cagcccaaga | agacccgaaa | agaccagaac | cacgtgatag | 720 |
| cgataagaaa | atgatgaaga | atctgcaga | ccataagaat | ttggaaatca | ttgtcactaa | 780 |
| tggctatgat | aaagacagct | ttgtgcaggg | cgtacagaat | agcattcata | ccagtccttc | 840 |
| cctgaatggc | cgatgcactg | aggaagtaaa | atctgtagat | gaaaacttgg | agcaaactgg | 900 |
| aaaaactgtt | gtcttcgttc | accaagatgt | aaacagtgat | catgttgaag | atatttcagg | 960 |
| aattcagcat | ttgacaagtg | attcagacag | tgaagtttac | tgtgattcca | tggagcaatt | 1020 |
| tgggcaagaa | gagtctttag | acggctttat | atcaaacaat | ggaccatttt | cctattactt | 1080 |
| gggtggtaat | cccagtcaac | cgttggaaag | ttctggtttt | cctgaagctg | ttcaaggact | 1140 |
| tcctgggaac | ggcagccctg | aggacatgca | gggcgcagtg | gttgaaggca | aggtgaagt | 1200 |
| aaagcgtggg | ggagaggacg | gcgggagtaa | cagtggagcc | ccgcaccgcg | agaaacgggc | 1260 |
| tggagaaagt | gaggagttct | ctaacattag | gagagggaga | gggcacagga | tgcagcattt | 1320 |
| gagtgaagga | agcaagggtc | ggcaagtggg | aagtggaggt | gatggggaac | gctgggttc | 1380 |
| ggacagaggc | tcaaggggca | gcctgaacga | gcagatcgcg | cttgtgctca | tgcgcctgca | 1440 |
| ggaggacatg | cagaacgtcc | tccagagact | ccacaaactg | gagatgctgg | cggcatcaca | 1500 |
| ggcaaaatca | tcagcattac | agaccagtaa | tcagcccact | tcaccgagac | catcttggtg | 1560 |

-continued

```
gcccttcgag atgtctcctg gtgcattaac cttcgctatc atatggcctt ttattgctca    1620
gtggttggtg catttatatt accaaagaag gagaagaaaa ttgaactaaa gaaaatgaca    1680
ttttgttgaa gaaatctact ggccctggat aacctcggga tgataccaat tgtggagctt    1740
acacgaggga                                                           1750
```

ENGINEERED CO2-FIXING CHEMOTROPHIC MICROORGANISMS PRODUCING CARBON-BASED PRODUCTS AND METHODS OF USING THE SAME

RELATED APPLICATIONS

This application claims the benefit under 35 U.S.C. § 119(e) of U.S. Provisional Patent Application No. 61/616,560, filed Mar. 28, 2012 and entitled PROCESS FOR GENERATING HYDROXYLATED FATTY ACIDS; U.S. Provisional Patent Application No. 61/635,238, filed Apr. 18, 2012 and entitled PROCESS FOR GENERATING SHORTER FATTY ACIDS WITH AN EXOGENOUS FATTY ACYL-COA BINDING PROTEIN; U.S. Provisional Patent Application No. 61/708,057, filed Oct. 1, 2012 and entitled PROCESS FOR PRODUCING CARBON-BASED CHEMICALS, INCLUDING BUTANEDIOL, USING CHEMOTROPHIC MICROBES. This application is also a continuation-in-part of U.S. patent application Ser. No. 13/623,089, filed Sep. 19, 2012, and entitled "INDUSTRIAL FATTY ACID ENGINEERING GENERAL SYSTEM FOR MODIFYING FATTY ACIDS." Each of these applications is incorporated herein by reference in its entirety for all purposes.

FIELD OF THE INVENTION

This disclosure relates to compositions capable of producing and methods of the producing oils, fuels, and oleochemicals through cultivating bacteria that grow on carbon-containing gas such as syngas, producer gas, $CO_2$, carbon monoxide and mixtures of the same containing hydrogen gas. This disclosure further relates to methods of fixing carbon from gas into useful organic molecules such as diacids, hydroxy acids, fatty acid alcohols, fatty acid aldehydes, fatty acids, unsaturated fatty acids, esters, lipids, alkanes, alkenes, and alkynes. The bacteria of the invention can be genetically engineered for use in the methods or other aspects of the invention described herein. The present invention further describes mechanisms to confer and/or enhance production of carbon-based products to an organism such that it converts carbon dioxide, or other inorganic carbon sources, and inorganic energy, including chemical energy from an inorganic chemical or directly from an electrical source, into carbon-based products of commercial value.

BACKGROUND OF THE INVENTION

Sustainable and renewable sources of liquid fuel to operate machinery, aircraft, and vehicles are necessary to reduce the amount of carbon dioxide emissions in the atmosphere, as well as to reduce global energy consumption based upon coal, oil, and natural gas economies.

Increased demand for energy by the global economy has placed increasing pressure on the cost of hydrocarbons. Aside from energy, many industries, including plastics and chemical manufacturers, rely heavily on the availability of fossil hydrocarbon sources as a feedstock for their manufacturing processes. Cost-effective alternatives to current sources of supply could help mitigate the upward pressure on fossil resource demand and raw material costs.

Biologic systems that fix carbon through natural biochemical metabolic processes are known. Algal systems have been developed to create hydrocarbons through photosynthetic reactions, as well as heterotrophic reactions fed by sugar that indirectly depend upon photosynthesis, but insufficient yields limit the effectiveness, economic feasibility, practicality and commercial adoption. Bacterial cells have been genetically engineered to process sugar feedstocks into useful hydrocarbons in heterotrophic fermentation systems, however, there are significant drawbacks for these systems.

Heterotrophic fermentations are vulnerable to contamination because heterotrophic microorganisms that can grow on fixed carbon nutrients are far more ubiquitous in the surface environment. Heterotrophic technologies also generally suffer limitations in terms of food versus fuel conflict and negative environmental impacts.

Gas-to-liquid (GTL) technologies have the benefit of allowing the utilization of waste carbon sources—including highly lignocellulosic waste through the conversion to synthesis gas (syngas) via gasification, as well as waste $CO_2$ through the provision of reduced hydrogen—in the production of liquid fuels and/or organic chemicals. Syngas is a mix of gases that generally contains $H_2$, CO, and $CO_2$ as major components, which can be generated through steam reforming of methane and/or liquid petroleum gas or through gasification of any organic material, including but not limited to biomass, waste organic matter, various polymers, and coal. Many gasification processes are available for the production of syngas. A number of gasification processes subject the carbonaceous feedstock to partial oxidation at high temperatures (500-1500° C.), with the oxygen supply restricted to prevent complete combustion, producing syngas with varying composition depending on feedstock and reaction conditions such that the ratio of $H_2$:CO can range from 0.5:1 to 3:1. The hydrogen component of syngas can be raised through the reaction of CO with steam in the water gas shift reaction with a concomitant increase in $CO_2$ in the syngas mix.

Some major technologies for syngas conversion to liquid fuels or chemicals include chemical catalytic processes such as the Fischer-Tropsch (F-T) as well as processes for the synthesis of methanol or other mixed alcohols, and biological gas fermentation processes. F-T has been worked on for almost one hundred years and relies on metal-based, inorganic catalysts for the conversion of syngas into longer chain hydrocarbons. Difficulties with F-T include: a wide chain length distribution of products resulting in the need to reprocess short chain length products such as methane and LPG and/or the need to perform additional costly post-processing steps on long chain waxes and tars such as hydrocracking; high catalyst sensitivity to syngas impurities such as sulfur containing compounds, tars, and particulates, generally necessitating multiple costly gas clean up steps; relatively low flexibility in terms of accommodating various ratios of syngas constituents i.e. H2:CO, and low tolerance of $CO_2$, often resulting in additional costly syngas conditioning steps such as water gas shift and $CO_2$ removal; the actual F-T step is relatively high temperature and pressure resulting in costly compression and heating requirements; the wide distribution of products generally necessitates the storage, handling, and transport of a wide array of products which is often uneconomic except for relatively large scale operations; F-T products (e.g. diesel, jet fuel, naphtha, waxes) are relatively low in value at current (2011) prices compared to many different higher value oils, lipids, and oleochemicals that can be produced biologically. The difficulties with F-T generally also apply to other chemical conversion processes such as methanol synthesis.

The gasification of biomass to generate syngas has a long history going back to World War II where biomass gasification was used for running modified automobiles, boats, buses, and trucks. Presently, a number of biomass gasification technologies are at, or near commercialization (able to gasify 10,000 or more tons of biomass per year), and are generally used for the production of heat and/or electricity. The synthesis of chemicals or fuels from syngas generated via biomass gasification is at an earlier stage of development, and is generally pre-commercial.

Using syngas and/or $CO_2$ and/or renewable $H_2$ in gas fermentation enables the utilization of cheaper and more flexible sources of energy and/or carbon for the biological synthesis of sustainable chemicals and fuels than is possible through heterotrophic or phototrophic synthesis. In gas fermentation, syngas acts as both a carbon and energy source for the microbial culture. Some of the advantages of syngas fermentation include: the production of a relatively narrow range of carbon chain length distribution compared to F-T; lower sensitivity to syngas impurities; greater tolerance of varying ratios of H2:CO and the presence of CO2; able to operate at much closer to ambient temperature and pressure; able to produce various higher value oleochemical products.

A fermentation process based upon a gaseous feedstock such as syngas can allow for far lower negative environmental and food production impacts in the biological synthesis of liquid fuels and/or chemicals than the highly land and water intensive heterotrophic or phototrophic-based technologies. However, current biological GTL technologies generally yield relatively short chain alcohols, or other short chain organic compounds, as products, which have relatively low energy density and infrastructure compatibility with current petrochemical and oleochemical processes.

The syngas-growing microorganisms used in current biological GTL technologies are generally inappropriate for the synthesis of high energy density, infrastructure compatible fuels, or other longer carbon chain lipid-based chemicals. Their short chain products are relatively low in value and they generally don't efficiently synthesize drop-in fuels such as diesel or jet fuel, or higher value lipid-based chemicals.

Furthermore the types of microorganisms used in current biological GTL technologies such as Clostridia have a relatively low tolerance for their short carbon chain gas fermentation products such as ethanol, butanol, or acetic acid, which limits titers and complicates product recovery, hurting the overall economics of the GTL process.

There is a need to identify a set of microorganisms that can grow in conventional and scalable contained reaction vessels and that produce commercially viable sets of organic carbon chains of at least eight carbon atoms long in a commercially feasible method. There is a need to identify microorganisms not limited metabolically by typically used carbon and energy inputs such as sugars, and a microorganism that can additionally utilize syngas, producer gas, as well as a wide array of abiotic sources of carbon and energy for the synthesis of drop-in fuels and chemicals, leading to a feedstock flexibility for the present technology that far exceeds comparable heterotrophic systems. There is a need to identify and use microorganisms that can utilize electron donors such as hydrogen, present in syngas, producer gas, as well as readily generated through a wide array of abiotic renewable energy technologies, for growth and carbon fixation.

The targeting of fatty acids produced through fatty acid biosynthesis to relatively shorter fatty acid chain lengths from C8-C14 has been achieved in heterotrophic microorganisms. This has been accomplished through the use of thioesterases to change populations of fatty acids C8-C14 and the over-expression of thioesterases to increase shorter chain length fatty acids. Examples in the prior art include C8-C14 thioesterase expression to produce shorter chain lengths in U.S. Pat. No. 7,883,882 Renewable chemical production from novel fatty acid feedstocks, Franklin et al. Solazyme, p. 58.

However there is a need to target the production of shorter chain length fatty acids in microorganisms that are capable of growing and producing lipids chemotrophically on syngas or $H_2/CO_2$ gas mixes to enable microbial GTL production of lipids with targeted, mid-length carbon chains.

Dicarboxylic acids (Diacids) such as dodecanedoic acid (n=10) are used in production of nylon (nylon-6,12), polyamides, coatings, adhesives, greases, polyesters, dyes, detergents, flame retardants and fragrances. Diacids can be produced by fermentation of long-chain alkanes by *candida tropicalis* (Kroha K, Infom 2004, 15, 568). Traumatic acid, monounsaturated dodecanedoic acid (10E-dodeca-1,12-dicarboxylic acid) has been produced from plant tissues English J et al., Science 1939, 90, 329. *Pyrococcus furiosus* produces an array of dicarboxylic acids (Carballeira, 1997). The total amount of dicarboxylic acids comprises only 3.4% of the total, however, this could be boosted by various literature methods.

There is a need for a biological, non-heterotrophic means of producing diacids from low-cost or sustainable syngas feedstocks.

Nutritionally important n-3 fatty acids include α-linolenic acid (ALA), eicosapentaenoic acid (EPA), and docosahexaenoic acid (DHA), all of which are polyunsaturated. N-3 fatty acids that are important in human physiology are α-linolenic acid (18:3, n-3; ALA), eicosapentaenoic acid (20:5, n-3; EPA), and docosahexaenoic acid (22:6, n-3; DHA). These three polyunsaturates have either 3, 5, or 6 double bonds in a carbon chain of 18, 20, or 22 carbon atoms, respectively. As with most naturally produced fatty acids, all double bonds are in the cis-configuration.

A fatty acid desaturase is an enzyme that removes two hydrogen atoms from a fatty acid, creating a carbon/carbon double bond. These desaturases are classified as delta— indicating that the double bond is created at a fixed position from the carboxyl group of a fatty acid (for example, Δ9 desaturase creates a double bond at the 9th position from the carboxyl end). omega (e.g. ω3desaturase)—indicating the double bond is created between the third and fourth carbon from the methyl end of the fatty acid. In the biosynthesis of essential fatty acids, an elongase alternates with different desaturases (for example, Δ6desaturase) repeatedly inserting an ethyl group, then forming a double bond.

Most polyunsaturated oils come from fish and there is a need for alternate, and particularly microbial sources of polyunsaturated fatty acids, given depleting fish stocks and increasing pollution in the oceans.

SUMMARY OF THE INVENTION

The present invention allows microorganisms to be genetically engineered to convert $CO_2$ gas and/or syngas and/or producer gas to higher value and/or more infrastructure compatible products than current biologically based syngas and/or $CO_2$ conversion technologies. The present technology allows the development of new genetically enhanced strains of microorganisms that can be used for gas fermentation within biological gas-to-liquid (GTL) processes to produce and/or secrete drop-in liquid fuels directly from $CO_2$ or from syngas, as well as various other relatively long chain organic compounds that are drop-in, and are currently only produced in bulk from petroleum or higher plants.

The present invention relates to the engineering of microorganisms, including but not limited to hydrogen oxidizing, carbon monoxide oxidizing, and knallgas microorganisms, with a natural capability to grow and synthesize biomass on gaseous carbon sources such as syngas and/or $CO_2$, such that the engineered microorganisms synthesize targeted products, including chemicals and fuels, under gas fermentation. The microorganisms and methods of the present invention enable low cost synthesis of chemicals and fuels, which can compete on price with petrochemicals and higher-plant derived oleochemicals, and which will generally have a substantially lower price than oleochemicals produced through heterotrophic or phototrophic synthesis.

The invention relates to a composition comprising a microorganism that converts syngas and/or gaseous $CO_2$ and/or a mixture of $CO_2$ gas and $H_2$ gas into one or more lipids. In some embodiments, the composition comprises a microorganism, wherein the microorganism is a carbon monoxide-oxidizing microorganism. In some embodiments, the composition comprises a microorganism, wherein the microorganism is a knallgas microorganism. In some embodiments, the composition comprises a microorganism, wherein the microorganism is chosen from the genera *Rhodococcus* or *Gordonia*. In some embodiments, the composition comprises a microorganism, wherein the microorganism is *Rhodococcus opacus*. In some embodiments, the composition comprises a microorganism, wherein the microorganism is *Rhodococcus opacus* (DSM 43205) or *Rhodococcus* sp (DSM 3346). In some embodiments, the composition comprises a microorganism, wherein the microorganism is chosen from the genera *Ralstonia* or *Cupriavidus*. In some embodiments, the composition comprises a microorganism, wherein the microorganism is *Cupriavidus necator*.

In some embodiments, the composition comprises a microorganism wherein the microorganism can naturally grow on $H_2/CO_2$ and/or syngas, and wherein the microorganism can naturally accumulate lipid to 50% or more of the cell biomass by weight. In some embodiments the microorganisms have a native ability to send a high flux of carbon down the fatty acid biosynthesis pathway. In some embodiments the microorganism exhibiting these traits is *Rhodococcus opacus* (DSM 43205 or DSM 43206).

In some embodiments, the composition comprises a microorganism that can naturally grow on $H_2/CO_2$ and/or syngas, and wherein the microorganism can naturally accumulate polyhydroxybutyrate (PHB) or polyhydroxyalkanoate (PHA) to 50% or more of the cell biomass by weight. In some embodiments the microorganisms have a native ability to direct a high flux of carbon through the acetyl-CoA metabolic intermediate, which can lead into fatty acid biosynthesis, along with a number of other synthetic pathways including PHA and PHB synthesis. A microorganism is considered to direct a high flux of carbon through acetyl-CoA if a product of a synthesis pathway going through the acetyl-CoA metabolic intermediate, including but not limited to polyhydroxybutyrate (PHB) or polyhydroxyalkanoate (PHA), can represent 50% or more of the cell biomass by weight. In some embodiments the microorganism exhibiting these traits is *Cupriavidus necator* (DSM 531 or DSM 541).

In some embodiments, the invention relates to a non-naturally occurring microorganism capable of converting syngas or other gaseous carbon sources into targeted oleochemical and/or monomer products, where the wild-type microorganism is capable of growing on syngas or other gaseous carbon sources, but is either not capable of synthesizing said targeted oleochemical and/or monomer products, or is capable of synthesizing the targeted oleochemicals and/or monomers, but is not capable of synthesizing the targeted biochemical products at the concentration and/or efficiency of the non-natural microorganism. In such microorganisms, one or more proteins or enzymes are expressed in the microorganism, thereby modifying, extending, diverting, enhancing, promoting, or otherwise altering the lipid biosynthesis pathway or its regulation for the synthesis and/or enhanced synthesis of a targeted lipid-based product, oleochemical, monomer, or hydrocarbon.

In some embodiments, the invention relates to a non-naturally occurring microorganism capable of converting syngas or other gaseous carbon sources into targeted oleochemical and monomer products, where the wild-type microorganism is capable of growing on syngas or other gaseous carbon sources and is capable of synthesizing said targeted oleochemical and monomer products, but the non-naturally occurring microorganism is capable of synthesizing the targeted biochemical products at a higher concentration and/or efficiency than the wild-type microorganism due to the overexpression and/or underexpression of one or more proteins or enzymes.

In some embodiments, the invention relates to compositions comprising one or more bacterial cells that consist of one, two, or three exogenous nucleic acid sequences where said bacteria can grow using syngas and/or gaseous $CO_2$ and/or a mixture of $CO_2$ gas and $H_2$ gas as a source of carbon and/or energy.

In some embodiments, the invention relates to compositions comprising one or more bacterial cells of *Rhodococcus opacus* (DSM 43205) that consist of zero, one, two, or three exogenous nucleic acid sequences.

In some embodiments one, two, or three exogenous nucleic acid sequences encode one or more thioesterase proteins.

In some embodiments one, two, or three exogenous nucleic acid sequences encode one or more CYP52A proteins.

In some embodiments one, two, or three exogenous nucleic acid sequences encode a CYP709C1 and/or a CYP81B1 protein.

In some embodiments the source of thioesterase is inherent to the production organisms. In some embodiments the source of thioesterase is *Rhodococcus opacus* B4. In some embodiments the thioesterase is derived from bacteria or plants other than the host microorganism.

In some embodiments, the invention relates to compositions comprising one or more bacterial cells that consist of two exogenous nucleic acid sequences that encode the following proteins: fatty acid acyl-ACP reductase, a fatty acid aldehyde decarbonylase, where said bacteria can grow using syngas and/or gaseous $CO_2$ and/or a mixture of $CO_2$ gas and $H_2$ gas as a source of carbon and/or energy.

In some embodiments, the invention relates to compositions comprising one or more bacterial cells that consist of three exogenous nucleic acid sequences that encode the following proteins: fatty acid acyl-ACP reductase, a fatty acid aldehyde decarbonylase, and a thioesterase, where said bacteria can grow using syngas and/or gaseous $CO_2$ and/or a mixture of $CO_2$ gas and $H_2$ gas as a source of carbon and/or energy.

In some embodiments, the bacterial cell produces and/or secretes one or more lipids in an amount that is greater than the amount of lipids produced and/or secreted by the same cell not comprising the exogenous nucleic acid sequence.

In some embodiments, the bacterial cell produces and/or secretes one or more lipids having a given carbon chain length, where the amount of said lipid produced and/or secreted is greater than the amount produced and/or secreted by the same cell not comprising the exogenous nucleic acid sequence.

In some embodiments, the bacterial cell produces and/or secretes one or more lipid molecules in an amount that is less than the amount of lipids produced and/or secreted by the same cell not comprising the exogenous nucleic acid sequence.

In some embodiments, the bacterial cell produces and/or secretes one or more hydrocarbons in an amount that is greater than the amount of hydrocarbons produced and/or secreted by the same cell not comprising the exogenous nucleic acid sequence.

In some embodiments, the bacterial cell produces and/or secretes one or more lipids or hydrocarbons in a ratio greater than the ratio of lipids or hydrocarbons produced and/or secreted by the same cell not comprising the one or more exogenous nucleic acid sequences. In some embodiments, the bacterial cell produces and/or secretes one or more lipids or hydrocarbons, wherein at least 50% of the one or more lipids or hydrocarbons have 8 to 18 carbon atoms. In some embodiments, the bacterial cell produces and/or secretes one or more lipids or hydrocarbons, wherein at least 60% of the one or more lipids or hydrocarbons have 8 to 18 carbon atoms. In some embodiments, the bacterial cell produces and/or secretes one or more lipids or hydrocarbons, wherein at least 70% of the one or more lipids or hydrocarbons have 8 to 18 carbon atoms. In some embodiments, the bacterial cell produces and/or secretes one or more lipids or hydrocarbons, wherein at least 75% of the one or more lipids or hydrocarbons have 8 to 18 carbon atoms. In some embodiments, the bacterial cell produces and/or secretes one or more lipids or hydrocarbons, wherein at least 80% of the one or more lipids or hydrocarbons have 8 to 18 carbon atoms.

In some embodiments, the bacterial cell or compositions comprising the bacterial cell comprise at least one exogenous nucleic acid sequence that is integrated into the genome of the cell.

In some embodiments, the invention relates to a composition comprising a microorganism that converts syngas and/or gaseous $CO_2$ and/or a mixture of $CO_2$ gas and $H_2$ gas into one or more hydrocarbons including unsaturated hydrocarbons, wherein the microorganism comprises at least a first and a second exogenous nucleic acid sequence, wherein the first exogenous nucleic acid sequence encodes fatty acid acyl-ACP reductase and the second exogenous nucleic acid sequence encodes a fatty acid aldehyde decarbonylase. In some embodiments the microorganism is *Rhodococcus opacus*.

In some embodiments, the invention relates to a composition comprising a microorganism that converts syngas and/or gaseous $CO_2$ and/or a mixture of $CO_2$ gas and $H_2$ gas into one or more hydrocarbons, wherein the microorganism comprises at least a first and a second exogenous nucleic acid sequence, wherein the first exogenous nucleic acid sequence encodes fatty acid acyl-ACP reductase and the second exogenous nucleic acid sequence encodes a fatty acid aldehyde decarbonylase, wherein the one or more hydrocarbons have a carbon chain length of at least 8 carbon atoms. In some embodiments, The invention relates to a composition comprising a microorganism that converts syngas and/or gaseous $CO_2$ and/or a mixture of $CO_2$ gas and $H_2$ gas into one or more hydrocarbons, wherein the microorganism comprises a first and a second exogenous nucleic acid sequence, wherein the first exogenous nucleic acid sequence encodes fatty acid acyl-ACP reductase and the second exogenous nucleic acid sequence encodes a fatty acid aldehyde decarbonylase; wherein the one or more hydrocarbons comprise a mixture of hydrocarbon molecules having a carbon chain length from 8 carbon atoms to 18 carbon atoms. In some embodiments, the invention relates to a composition comprising a microorganism that converts syngas and/or gaseous $CO_2$ and/or a mixture of $CO_2$ gas and $H_2$ gas into one or more lipids, wherein the microorganism comprises at least a first and a second exogenous nucleic acid sequence, wherein the first exogenous nucleic acid sequence encodes fatty acid acyl-ACP reductase and the second exogenous nucleic acid sequence encodes a fatty acid aldehyde decarbonylase; wherein the one or more lipids comprise a quantity of at least one alkane, alkene, alkyne, fatty alcohol, and/or fatty aldehyde at a level higher than the quantity of the alkane, alkene, alkyne, fatty alcohol, and or fatty aldehyde in the same microorganism not comprising the heterologous nucleic acid sequences. In some embodiments, the invention relates to a composition comprising a microorganism that converts syngas and/or gaseous $CO_2$ and/or a mixture of $CO_2$ gas and $H_2$ gas into one or more lipids, wherein the microorganism comprises at least a first and a second exogenous nucleic acid sequence, wherein the first exogenous nucleic acid sequence encodes fatty acid acyl-ACP reductase and the second exogenous nucleic acid sequence encodes a fatty acid aldehyde decarbonylase; wherein the microorganism produces and/or secretes at least 10% of one or more lipids by weight.

In some embodiments, the invention relates to a composition comprising a microorganism that converts syngas and/or gaseous $CO_2$ and/or a mixture of $CO_2$ gas and $H_2$ gas into one or more lipids, wherein the microorganism comprises at least a first and a second exogenous nucleic acid sequence, wherein the first exogenous nucleic acid sequence encodes fatty acid acyl-ACP reductase and the second exogenous nucleic acid sequence encodes a fatty acid aldehyde decarbonylase; wherein the microorganism produces and/or secretes at least 20% of one or more lipids by weight.

In some embodiments, the invention relates to a composition comprising a microorganism that converts syngas and/or gaseous $CO_2$ and/or a mixture of $CO_2$ gas and $H_2$ gas into one or more lipids, wherein the microorganism comprises at least a first and a second exogenous nucleic acid sequence, wherein the first exogenous nucleic acid sequence encodes fatty acid acyl-ACP reductase and the second exogenous nucleic acid sequence encodes a fatty acid aldehyde decarbonylase; wherein the microorganism produces and/or secretes at least 30% of one or more lipids by weight.

In some embodiments, the invention relates to a composition comprising a microorganism that converts syngas and/or gaseous $CO_2$ and/or a mixture of $CO_2$ gas and $H_2$ gas into one or more lipids, wherein the microorganism comprises at least a first and a second exogenous nucleic acid sequence, wherein the first exogenous nucleic acid sequence encodes fatty acid acyl-ACP reductase and the second exogenous nucleic acid sequence encodes a fatty acid aldehyde decarbonylase; wherein the microorganism produces and/or secretes at least 40% of one or more lipids by weight.

In some embodiments, the invention relates to a composition comprising a microorganism that converts syngas and/or gaseous $CO_2$ and/or a mixture of $CO_2$ gas and $H_2$ gas into one or more lipids, wherein the microorganism comprises at least a first and a second exogenous nucleic acid sequence, wherein the first exogenous nucleic acid sequence encodes fatty acid acyl-ACP reductase and the second exogenous nucleic acid sequence encodes a fatty acid aldehyde decarbonylase; wherein the microorganism produces and/or secretes at least 50% of one or more lipids by weight.

In some embodiments, the invention relates to a composition comprising a microorganism that converts syngas and/or gaseous $CO_2$ and/or a mixture of $CO_2$ gas and $H_2$ gas into one or more lipids, wherein the microorganism comprises at least a first and a second exogenous nucleic acid sequence, wherein the first exogenous nucleic acid sequence encodes fatty acid acyl-ACP reductase and the second exogenous nucleic acid sequence encodes a fatty acid aldehyde decarbonylase; wherein the microorganism produces and/or secretes at least 60% of one or more lipids by weight.

In some embodiments, the invention relates to a composition comprising a microorganism that converts syngas and/or gaseous $CO_2$ and/or a mixture of $CO_2$ gas and $H_2$ gas into one or more lipids, wherein the microorganism comprises at least a first and a second exogenous nucleic acid sequence, wherein the first exogenous nucleic acid sequence encodes fatty acid acyl-ACP reductase and the second exogenous nucleic acid sequence encodes a fatty acid aldehyde decarbonylase; wherein the microorganism produces and/or secretes at least 70% of one or more hydrocarbons by weight.

In some embodiments, the invention relates to a composition comprising a microorganism that converts syngas and/or gaseous $CO_2$ and/or a mixture of $CO_2$ gas and $H_2$ gas into one or more lipids, wherein the microorganism comprises at least a first and a second exogenous nucleic acid sequence, wherein the first exogenous nucleic acid sequence encodes fatty acid acyl-ACP reductase and the second exogenous nucleic acid sequence encodes a fatty acid aldehyde decarbonylase; wherein the microorganism produces and/or secretes at least 75% of one or more lipids by weight.

In some embodiments, the invention relates to a composition comprising a microorganism that converts syngas and/or gaseous $CO_2$ and/or a mixture of $CO_2$ gas and $H_2$ gas into one or more lipids, wherein the microorganism comprises at least a first and a second exogenous nucleic acid sequence, wherein the first exogenous nucleic acid sequence encodes fatty acid acyl-ACP reductase and the second exogenous nucleic acid sequence encodes a fatty acid aldehyde decarbonylase; wherein the microorganism produces and/or secretes at least 80% of one or more lipids by weight.

In some embodiments, the invention relates to a composition comprising a microorganism that converts syngas and/or gaseous $CO_2$ and/or a mixture of $CO_2$ gas and $H_2$ gas into one or more lipids, wherein the microorganism comprises at least a first and a second exogenous nucleic acid sequence, wherein the first exogenous nucleic acid sequence encodes fatty acid acyl-ACP reductase and the second exogenous nucleic acid sequence encodes a fatty acid aldehyde decarbonylase; wherein the microorganism produces and/or secretes at least 85% of one or more lipids by weight.

In some embodiments, the invention relates to a composition comprising a microorganism that converts syngas and/or gaseous $CO_2$ and/or a mixture of $CO_2$ gas and $H_2$ gas into one or more hydrocarbons, wherein the microorganism comprises at least a first and a second exogenous nucleic acid sequence, wherein the first exogenous nucleic acid sequence encodes fatty acid acyl-ACP reductase and the second exogenous nucleic acid sequence encodes a fatty acid aldehyde decarbonylase; wherein less than 10% by weight of the hydrocarbons produced is methane. In some embodiments, the invention relates to a composition comprising a microorganism that converts syngas and/or gaseous $CO_2$ and/or a mixture of $CO_2$ gas and $H_2$ gas into one or more organic compounds, wherein the microorganism comprises at least a first and a second exogenous nucleic acid sequence, wherein the first exogenous nucleic acid sequence encodes fatty acid acyl-ACP reductase and the second exogenous nucleic acid sequence encodes a fatty acid aldehyde decarbonylase; wherein less than 10% by weight of the organic compounds produced are organic acids with carbon chain length of four carbons or less.

In some embodiments, the invention relates to a composition comprising a microorganism that converts syngas and/or gaseous $CO_2$ and/or a mixture of $CO_2$ gas and $H_2$ gas into one or more lipids or hydrocarbons, wherein the microorganism comprises at least a first and a second exogenous nucleic acid sequence, wherein the first exogenous nucleic acid sequence encodes fatty acid acyl-ACP reductase and the second exogenous nucleic acid sequence encodes a fatty acid aldehyde decarbonylase; wherein at least one lipid produced is a component or a precursor of a component of jet fuel, diesel fuel, or biodiesel fuel.

In some embodiments, the invention relates to a composition comprising a microorganism that converts syngas and/or gaseous $CO_2$ and/or a mixture of $CO_2$ gas and $H_2$ gas into one or more hydrocarbons, wherein the microorganism comprises at least a first and a second exogenous nucleic acid sequence, wherein the first exogenous nucleic acid sequence encodes fatty acid acyl-ACP reductase and the second exogenous nucleic acid sequence encodes a fatty acid aldehyde decarbonylase; wherein the hydrocarbons produced comprise a mixture of at least two hydrocarbons having a carbon backbone from 8 to 18 carbon atoms.

The present invention also relates to a bacterial cell comprising at least two exogenous nucleic acid sequences, wherein the at least two exogenous nucleic acid sequences encode fatty acid acyl-ACP reductase and fatty acid aldehyde decarbonylase, and wherein the cell converts gaseous $CO_2$ and/or gaseous $H_2$ and/or syngas into lipids. In some embodiments, the invention relates to a bacterial cell comprising at least two exogenous nucleic acid sequences, wherein the at least two exogenous nucleic acid sequences encode fatty acid acyl-ACP reductase and fatty acid aldehyde decarbonylase, and wherein the cell converts gaseous $CO_2$ and/or gaseous $H_2$ and/or syngas into lipid; wherein the cell produces and/or secretes at least 75% of one or more hydrocarbons by weight. In some embodiments, the invention relates to a bacterial cell comprising at least two exogenous nucleic acid sequences, wherein the at least two exogenous nucleic acid sequences encode fatty acid acyl-ACP reductase and fatty acid aldehyde decarbonylase, and wherein the cell converts gaseous $CO_2$ and/or gaseous $H_2$ and/or syngas into lipid; wherein the cell produces and/or secretes at least 75% of one or more hydrocarbons by weight when cultured at least 42 degrees Celsius for at least 1 hour. In some embodiments, the bacterial cell is cultured without exposure to light.

In some embodiments, the invention relates to a bacterial cell comprising at least two exogenous nucleic acid sequences, wherein the at least two exogenous nucleic acid sequences encode fatty acid acyl-ACP reductase and fatty acid aldehyde decarbonylase, and wherein the cell converts gaseous $CO_2$ and/or gaseous $H_2$ and/or syngas into a hydrocarbon or mixture of hydrocarbons, and/or other lipids; wherein the cell is a strain of *Rhodococcus opacus*.

In some embodiments, the invention relates to a bacterial cell comprising at least two exogenous nucleic acid sequences, wherein the at least two exogenous nucleic acid sequences encode fatty acid aldehyde acyl-ACP and fatty acid aldehyde decarbonylase, and wherein the cell converts gaseous $CO_2$ and/or gaseous $H_2$ and/or syngas into a hydrocarbon or mixture of hydrocarbons, and/or other lipids; wherein the cell is a strain of *Cupriavidus necator*.

In some embodiments, the invention relates to a bacterial cell comprising a first, a second, and a third exogenous nucleic acid sequence, wherein the first exogenous nucleic acid sequence encodes fatty acid acyl-ACP reductase, the second exogenous nucleic acid sequence encodes a fatty acid aldehyde decarbonylase, and the third exogenous nucleic acid sequence encodes a thioesterase; and wherein the cell converts gaseous $CO_2$ and/or gaseous $H_2$ and/or syngas into a lipid or mixture of lipids. In some embodiments, the bacterial cell comprises no more than eight exogenous nucleic acids that encode a lipid pathway enzyme. In some embodiments, the bacterial cell comprises no more than seven exogenous nucleic acids that encode a lipid pathway enzyme. In some embodiments, the bacterial cell comprises no more than six exogenous nucleic acids that encode a lipid pathway enzyme. In some embodiments, the bacterial cell comprises no more than five exogenous nucleic acids that encode a lipid pathway enzyme. In some embodiments, the bacterial cell comprises no more than four exogenous nucleic acids that encode a lipid pathway enzyme. In some embodiments, the bacterial cell comprises no more than three exogenous nucleic acids that encode a lipid pathway enzyme. In some embodiments, the bacterial cell comprises no more than two exogenous nucleic acids that encode a lipid pathway enzyme. In some embodiments, the bacterial cell comprises no more than one exogenous nucleic acid that encodes a lipid pathway enzyme. In some embodiments, the bacterial cell comprises no more than eight exogenous nucleic acids that encode a protein. In some embodiments, the bacterial cell comprises no more than seven exogenous nucleic acids that encode a protein. In some embodiments, the bacterial cell comprises no more than six exogenous nucleic acids that encode a protein. In some embodiments, the bacterial cell comprises no more than five exogenous nucleic acids that encode a protein. In some embodiments, the bacterial cell comprises no more than four exogenous nucleic acids that encode a protein. In some embodiments, the bacterial cell comprises no more than three exogenous nucleic acids that encode a protein. In some embodiments, the bacterial cell comprises no more than two exogenous nucleic acids that encode a protein. In some embodiments, the bacterial cell comprises no more than one exogenous nucleic acid that encodes a protein.

In some embodiments the invention relates to a method of producing a lipid or mixture of lipids in a microorganism population comprising the cell or the composition described herein, wherein the method comprises: culturing a population of microorganisms comprising the cell or the composition described herein in a feedstock comprising syngas and/or gaseous $CO_2$ and/or a mixture of $CO_2$ gas and $H_2$ gas.

In some embodiments, the invention relates to a method of producing a lipid or mixture of lipids, wherein the method comprises: culturing a population of bacterial cells comprising the cell or the composition described herein in a feedstock comprising syngas and/or gaseous $CO_2$ and/or a mixture of $CO_2$ gas and $H_2$ gas. In some embodiments, the microorganism population comprises a bacterial strain of *Rhodococcus opacus*. In some embodiments, the microorganism population comprises a bacterial strain of *Rhodococcus opacus* (DSM 43205 or 43206).

In some embodiments, the invention relates to a method of producing a lipid or mixture of lipids, wherein the method comprises: culturing a population of bacterial cells comprising the cell or the composition described herein in a feedstock comprising methanol, a common impurity of syngas, with or without the addition of syngas and/or gaseous $CO_2$ and/or a mixture of $CO_2$ gas and $H_2$ gas. In some embodiments, the microorganism population comprises a bacterial strain of *Rhodococcus opacus*. In some embodiments, the microorganism population comprises a bacterial strain of *Rhodococcus opacus* (DSM 43205).

In some embodiments, the invention relates to a method of producing a lipid or mixture of lipids, wherein the method comprises: culturing a population of bacterial cells comprising the cell or the composition described herein in a feedstock comprising syngas and/or gaseous $CO_2$ and/or a mixture of $CO_2$ gas and $H_2$ gas. In some embodiments, the microorganism population comprises a bacterial strain of *Cupriavidus necator*.

In some embodiments, the molecule produced is one or more alkane, alkene, alkyne, fatty alcohol, and/or fatty aldehyde. In some embodiments, the method produces a lipid or mixture of lipids at a quantity higher than the quantity of lipid or mixture of lipids in the same bacterial cell population not comprising the exogenous nucleic acids described herein. In some embodiments the one or more lipids comprise a quantity of at least one alkane, alkene, alkyne, fatty alcohol, and/or fatty aldehyde at a level higher than the quantity of the alkane, alkene, alkyne, fatty alcohol, and or fatty aldehyde in the same microorganism not comprising the exogenous nucleic acid sequences. In some embodiments, the method comprises a population of microorganisms or bacterial cell described herein that produces and/or secretes lipids of a weight equal to or greater than 10% of the total percentage of cellular dry matter. In some embodiment, the method comprises a population of microorganisms or bacterial cell described herein that produces and/or secretes lipids of a weight equal to or greater than 20% of the total percentage of cellular dry matter. In some embodiment, the method comprises a population of microorganisms or bacterial cell described herein that produces and/or secretes lipids of a weight equal to or greater than 30% of the total percentage of cellular dry matter. In some embodiments, the method comprises a population of microorganisms or bacterial cell described herein that produces and/or secretes lipids of a weight equal to or greater than 40% of the total percentage of cellular dry matter. In some embodiment, the method comprises a population of microorganisms or bacterial cell described herein that produces and/or secretes lipids of a weight equal to or greater than 50% of the total percentage of cellular dry matter. In some embodiments, the method comprises a population of microorganisms or bacterial cells described herein that produces and/or secretes lipids of a weight equal to or greater than 60% of the total percentage of cellular dry matter. In some embodiments, the method comprises a population of microorganisms or bacterial cells described herein that produces and/or secretes lipids of a weight equal to or greater than 70% of the total percentage of cellular dry matter. In some embodiments, the method comprises a population of microorganisms or bacterial cell described herein that produces of secretes lipids of a weight equal to or greater than 75% of the total percentage of cellular dry matter. In some embodiment, the method comprises a population of microorganisms or bacterial cell described herein that produces of secretes lipids of a weight equal to or greater than 80% of the total percentage of cellular dry matter. In some embodiments, the method comprises a population of microorganisms or bacterial cell described herein that produces of secretes lipids of a weight equal to or greater than 85% of the total percentage of cellular dry matter. In some embodiments, the bacterial cell or composition comprising the bacterial cell produces and/or secretes at least 10% of the total percentage of the cellular dry matter or 10% by weight. In some embodiment, the method comprises a population of microorganisms comprising a bacterial cell described herein that produces or secretes lipids, wherein at least 5% of the lipids have carbon backbones from 8 to 18 carbon atoms in length. In some embodiment, the method comprises a population of microorganisms comprising a bacterial cell described herein that produces or secretes lipids, wherein at least 10% of the lipids have carbon backbones from 8 to 18 carbon atoms in length. In some embodiments, the method comprises a population of microorganisms comprising a bacterial cell described herein that produces or secretes lipids, wherein at least 15% of the lipids have carbon backbones from 8 to 18 carbon atoms in length. In some embodiments, the method comprises a population of microorganisms comprising a bacterial cell described herein that produces or secretes lipids, wherein at least 20% of the lipids have carbon backbones from 8 to 18 carbon atoms in length.

In some embodiments, the molecule is chosen from one or more alkene, alkyne, unsaturated fatty acid, hydroxyacid and/or dicarboxylic acid (diacid). In some embodiments the one or more lipids comprise a quantity of at least one alkene, alkyne, unsaturated fatty acid, hydroxyacid and/or diacid at a level higher than the quantity of the alkene, alkyne, unsaturated fatty acid, hydroxyacid and/or diacid in the same microorganism not comprising the exogenous nucleic acid sequences.

In some embodiments of the invention, the invention relates to a method of producing and/or secreting a lipid or mixture of lipids by culturing a population of microorganisms comprising a bacterial cell described herein, wherein the exogenous nucleic acid sequences are operably linked to a promoter that is inducible in response to a first stimulus, and wherein the method further comprises: culturing the population of bacterial cells for a first period of time in the presence of a first stimulus to produce one or more lipids chosen from an alkane, alkene, alkyne, fatty acid, unsaturated fatty acid, diacid, hydroxy acid, alcohol, and/or fatty acid aldehyde.

In some embodiments of the invention, the invention relates to a method of fixing carbon from a gaseous feedstock containing carbonaceous molecules, wherein the method comprises the step of exposing a composition comprising exposing a bacterial cell to syngas and/or gaseous $CO_2$ and/or gaseous $H_2$; wherein the bacterial cell comprises at least one exogenous nucleic acid sequence. In some embodiments the exogenous nucleic acid sequences are fatty acid acyl-ACP reductase or a fatty acid aldehyde decarbonylase. In some embodiments of the method, the bacterial cell comprises at least a first and a second exogenous nucleic acid sequence, wherein the first exogenous nucleic acid sequence encodes a fatty acid acyl-ACP reductase and the second exogenous nucleic acid sequence encodes a fatty acid aldehyde decarbonylase. In some embodiments, the bacterial cell is *Rhodococcus opacus* or the population of microorganisms comprises a *Rhodococcus* cell. In some embodiments, the bacterial cell is *Cupriavidus necator* or the population of microorganisms comprises a *Cupriavidus* cell. In some embodiments, the bacterial cell comprises at least a first, a second, and a third exogenous nucleic acid sequence, wherein the first exogenous nucleic acid sequence encodes a fatty acid acyl-ACP reductase, the second exogenous nucleic acid sequence encodes a fatty acid aldehyde decarbonylase, and the third exogenous nucleic acid sequence encodes a thioesterase. In some embodiments, the bacterial cell comprises at least a first exogenous nucleic acid sequence, wherein the first exogenous nucleic acid sequence encodes a thioesterase. In some embodiments, the bacterial cell comprises no more than five exogenous nucleic acid sequences that encode a lipid pathway enzyme. In some embodiments, the composition comprises a microorganism, wherein the microorganism is *Rhodococcus opacus* (DSM 43205 or 43206) or *Rhodococcus* sp (DSM 3346). In some embodiments, the composition comprises a microorganism, wherein the microorganism is chosen from the genera *Ralstonia* or *Cupriavidus*. In some embodiments, the composition comprises a microorganism, wherein the microorganism is *Cupriavidus necator*. In some embodiments the microorganism is from the suborder corynebacterineae or the family burkholderiaceae. In some embodiments the microorganism through its native machinery produces a complement of fatty acids described in the Fatty Acid Output section below. In some embodiments, the bacterial cell comprises at least a first and a second exogenous nucleic acid sequence but no more than five exogenous nucleic acid sequences, wherein the first exogenous nucleic acid sequence encodes fatty acid acyl-ACP reductase and the second exogenous nucleic acid sequence encodes a fatty acid aldehyde decarbonylase.

In some embodiments, the invention relates to a method of producing one or more hydroxyacid, diacid, or unsaturated fatty acid, alcohols, fatty acid aldehydes, alkanes, alkenes, alkynes, or any combination thereof comprising exposing a bacterial cell to syngas and/or gaseous $CO_2$ or a mixture of gaseous $CO_2$ and gaseous $H_2$; wherein the bacterial cell is capable of fixing gaseous $CO_2$ into one or more fatty acid alcohols, alkanes, alkenes, or alkynes and wherein the microorganism comprises at least a first exogenous nucleic acid and a second exogenous nucleic acid, wherein the first exogenous nucleic acid encodes fatty acid acyl-ACP reductase and the second exogenous nucleic acid encodes fatty acid aldehyde decarbonylase. In some embodiments, the first and second exogenous nucleic acids are heterologous nucleic acid sequences. In some embodiments, the bacterial cell comprises at least a first, a second, and a third exogenous nucleic acid sequence, wherein the first exogenous nucleic acid sequence encodes a fatty acid acyl-ACP reductase, the second exogenous nucleic acid sequence encodes a fatty acid aldehyde decarbonylase, and the third exogenous nucleic acid sequence encodes a thioesterase. In some embodiments, the bacterial cell comprises at least a first exogenous nucleic acid sequence, wherein the first exogenous nucleic acid sequence encodes a thioesterase. In some embodiments, the composition comprises a bacterial cell, wherein the bacteria is *Rhodococcus opacus* (DSM 43205 or 43206) or *Rhodococcus* sp (DSM 3346). In some embodiments, the bacterial cell is chosen from the genera *Ralstonia* or *Cupriavidus*. In some embodiments, the bacterial cell is *Cupriavidus necator*. In some embodiments the bacterial cell is from the suborder corynebacterineae or the family burkholderiaceae. In some embodiments the bacterial cell through its native machinery produces a complement of fatty acids described in the Fatty Acid Output section below.

In some embodiments, the invention relates to a method of producing one or more unsaturated fatty acids, comprising exposing a bacterial cell to syngas and/or gaseous CO2 or a mixture of gaseous $CO_2$ and gaseous $H_2$; wherein the bacterial cell is capable of fixing gaseous $CO_2$ into one or more unsaturated fatty acids and wherein the microorganism comprises at least a first exogenous nucleic acid, wherein the first exogenous nucleic acid encodes a desaturase that introduces double bonds to fatty acids. In some embodiments, the first exogenous nucleic acids is a heterologous nucleic acid sequence. In some embodiments, the bacterial cell comprises at least a first, and a second exogenous nucleic acid sequence, wherein the first exogenous nucleic acid sequence encodes a desaturase, the second exogenous nucleic acid sequence encodes a thioesterase. In some embodiments, the composition the bacterial cell comprises a microorganism, wherein the microorganism is *Rhodococcus opacus* (DSM 43205 or 43206) or *Rhodococcus* sp (DSM 3346). In some embodiments, the composition comprises a microorganism, wherein the microorganism is chosen from the genera *Ralstonia* or *Cupriavidus*. In some embodiments, the composition comprises a microorganism, wherein the microorganism is *Cupriavidus necator*. In some embodiments the microorganism is from the suborder corynebacterineae or the family burkholderiaceae. In some embodiments the microorganism through its native machinery produces a complement of fatty acids described in the Fatty Acid Output section below. In some embodiments, the invention relates to a method of producing one or more hydroxy fatty acids (hydroxy acids), comprising exposing a bacterial cell to syngas and/or gaseous $CO_2$ or a mixture of gaseous $CO_2$ and gaseous $H_2$; wherein the bacterial cell is capable of fixing gaseous $CO_2$ into one or more hydroxy acids and wherein the microorganism comprises at least a first exogenous nucleic acid, wherein the first exogenous nucleic acid encodes a P450-dependent fatty acid hydroxylase that introduces hydroxyl groups at positions along the fatty acid chain. In some embodiments, the first exogenous nucleic acids is a heterologous nucleic acid sequence. In some embodiments, the bacterial cell comprises at least a first, and a second exogenous nucleic acid sequence, wherein the first exogenous nucleic acid sequence encodes a P450-dependent fatty acid hydroxylase, the second exogenous nucleic acid sequence encodes a thioesterase. In some embodiments, the composition comprises a microorganism, wherein the microorganism is *Rhodococcus opacus* (DSM 43205 or 43206) or *Rhodococcus* sp (DSM 3346). In some embodiments, the composition comprises a microorganism, wherein the microorganism is chosen from the genera *Ralstonia* or *Cupriavidus*. In some embodiments, the composition comprises a microorganism, wherein the microorganism is *Cupriavidus necator*. In some embodiments the microorganism is from the suborder corynebacterineae or the family burkholderiaceae. In some embodiments the microorganism through its native machinery produces a complement of fatty acids described in the Fatty Acid Output section below.

In some embodiments, the invention relates to a method of producing one or more hydroxyacid, diacid, or unsaturated fatty acid, alcohols, fatty acid aldehydes, alkanes, alkenes, alkynes, or any combination thereof comprising exposing a bacterial cell to syngas and/or gaseous $CO_2$ or a mixture of gaseous $CO_2$ and gaseous $H_2$; wherein the bacterial cell is capable of fixing gaseous $CO_2$ into one or more lipids; wherein the lipids are recovered from the bioreactor and fed to a second bioreactor wherein the lipids are postprocessed to generate hydroxyacid, diacid, and/or unsaturated fatty acids via a second microorganism such as but not limited to *Candida tropicalis*.

In some embodiments, the invention relates to a method of manufacturing one or more lipids, comprising (a) culturing a cell described herein in a reaction vessel or bioreactor in the presence of syngas and/or gaseous $CO_2$ or a mixture of gaseous $CO_2$ and gaseous $H_2$, wherein the cell produces and/or secretes one or more lipids in an quantity equal to or greater than at least 10% of the cell's total dry cellular mass; and (b) separating the one or more lipids from reaction vessel. In some embodiments, the method further comprises purifying the one or more lipids after separation from the reaction vessel or bioreactor.

In some embodiments, the one or more lipids is a component of or a precursor to a component of jet fuel, diesel fuel, or biodiesel fuel.

In some embodiments, the invention relates to a method of producing a alkene, fatty alcohol, alkyne, or alkane in a bacterial cell comprising at least a first and a second exogenous nucleic acid sequence, wherein the first exogenous nucleic acid sequence encodes a fatty acid acyl-ACP reductase and the second exogenous nucleic acid encodes a fatty acid aldehyde decarbonylase.

In some embodiments, the bacterial cell producing a alkene, fatty alcohol, alkyne, or alkane comprises at least a first, a second, and a third exogenous nucleic acid sequences, wherein the first exogenous nucleic acid sequence encodes a fatty acid acyl-ACP reductase and the second exogenous nucleic acid encodes a fatty acid aldehyde decarbonylase, and the third exogenous nucleic acid encodes a thioesterase.

In some embodiments, the invention relates to a method of producing cycloalkanes in a bacterial cell comprising at least a first exogenous nucleic acid sequence, wherein the first exogenous nucleic acid sequence encodes a fatty acyl-CoA reductase. In some embodiments the cycloalkane is cyclotetradecane. In some embodiments, the bacterial cell is *Cupriavidus necator* or the population of microorganisms comprises a *Cupriavidus* cell. In some embodiments the nucleic acid sequence comprises or consists of SEQ ID NO:5 and/or SEQ ID NO: 6. In some embodiments the nucleic acid sequence has at least 50, 60, 70, 75, 80, 85, 90, 91, 92, 93, 94, 95, 96, 97, 98 or 99% nucleotide homology to one or more of SEQ ID NOs: 5 or 6.

In some embodiments, the invention relates to a bioreactor comprising the composition or bacterial cells described herein.

In some embodiments, the invention relates to a system for the production of one or more lipids or mixture of lipids, comprising a bioreactor, which comprises: (a) a microorganism population comprising a cell described herein; and (b) an inlet connected to a feedstock source allowing delivery of a feedstock comprising syngas and/or gaseous $CO_2$ or a mixture of gaseous $CO_2$ and gaseous $H_2$. In some embodiments, the lipid or mixture of lipids comprise at least one component of or one precursor to a component of jet fuel, diesel fuel, or biodiesel fuel.

In some embodiments, the invention relates to the population of fatty acids being modified to produce molecules of desired carbon chain length by incorporation of one or more thioesterases.

In some embodiments, the invention relates to the population of fatty acids being modified to add additional carboxylic acid (—COOH) groups using exogenous enzymes.

In some embodiments, the invention relates to the population of fatty acids being modified to add hydroxyl groups (—OH) using the exogenous enzymes (hydroxylases).

In some embodiments, the invention relates to the population of fatty acids being modified to add desaturation through the incorporation of one or more double bonds, using the exogenous enzymes (desaturases).

In some embodiments, the invention relates to a method for generating hydroxylated fatty acids in microbes through the transfer of enzymes that are known to hydroxylate fatty acids in plants or microbes into microorganisms where the enzyme is not native.

In some embodiments, the invention relates to a microorganism comprising at least a first exogenous nucleic acid sequence wherein the microorganism converts gaseous CO2 and/or gaseous H2 and/or syngas into one or more hydroxylated fatty acids. In some embodiments, the invention further provides a composition wherein the first exogenous nucleic acid sequence encodes a hydroxylating ezyme. In some embodiments, the invention further comprises a second exogenous nucleic acid sequence encoding a thioesterase enzyme. In some embodiments, the invention further provides a composition wherein the microorganism is the genera *Rhodococcus* or *Gordonia*. In some embodiments, the invention further provides a composition wherein the microorganism is *Rhodococcus opacus*. In some embodiments, the invention further provides a composigion wherein the microorganism is *Rhodococcus opacus* (DSM 43205) or *Rhodococcus opacus* (DSM 43206) or *Rhodococcus opacus* (DSM 44193). In some embodiments, the invention further provides a composition wherein the microorganism is of the family Burkholderiaceae. In some embodiments, the invention further provides a composition wherein the microorganism is *Cupriavidus necator*. In some embodiments, the invention further provides a composition wherein the microorganism is *Cupriavidus metallidurans*. In some embodiments, the invention further provides a composition wherein the microorganism is a knallgas microorganism, also known as an oxyhydrogen microorganism. In some embodiments, the invention further provides a composition wherein the microorganism is a chemoautotrophic microbe. In some embodiments, the invention further provides a composition wherein the wild-type or mutant of the microorganism naturally has a capability for accumulating and/or synthesizing high quantities of triacylglycerol where a high quantity is considered to be 10% or more of the dry cell mass; 20% or more of the dry cell mass; 30% or more of the dry cell mass; 40% or more of the dry cell mass; 50% or more of the dry cell mass; 60% or more of the dry cell mass; 70% or more of the dry cell mass. In some embodiments, the invention further provides a composition wherein the microorganism is a hydrogen-oxidizing chemoautotroph. In some embodiments, the invention further provides a composition wherein the microorganism is capable of growing on syngas as the sole energy and carbon source. In some embodiments, the invention further provides a composition wherein the microorganism is capable of growing on untreated crude glycerol as the sole energy and carbon source.

In some embodiments, the invention relates to a method for producing hydroxylated fatty acids wherein the method comprises culturing an engineered microorganism or a natural strain in a bioreactor or solution with a feedstock comprising syngas and/or gaseous CO2 and/or a mixture of CO2 gas and H2 gas. In some embodiments, the invention further provides a step of up-regulating an endogenous or exogenous thioesterase gene of the microorganism. In some embodiments, the invention further provides a step of down-regulating an endogenous or exogenous thioesterase gene of the microorganism. In some embodiments, the invention further provides a step of down-regulating an endogenous or exogenous acyl carrier protein gene of the microorganism.

In some embodiments, the invention relates to a microorganism comprising at least a first exogenous nucleic acid sequence wherein the microorganism converts gaseous $CO_2$ and/or gaseous $H_2$ and/or syngas into one or more shorter-chain fatty acids. In some embodiments, the invention further provides a composition wherein the first exogenous nucleic acid sequence encodes a fatty acyl-CoA binding protein. In some embodiments, the invention further comprises a second exogenous nucleic acid sequence encoding a thioesterase enzyme. In some embodiments, the invention further provides a composition wherein the microorganism is the genera *Rhodococcus* or *Gordonia*. In some embodiments, the invention further provides a composigion wherein the microorganism is *Rhodococcus opacus*. In some embodiments, the invention further provides a composition wherein the microorganism is *Rhodococcus opacus* (DSM 43205) or *Rhodococcus opacus* (DSM 43206) or *Rhodococcus opacus* (DSM 44193). In some embodiments, the invention further provides a composition wherein the microorganism is of the family Burkholderiaceae. In some embodiments, the invention further provides a composition wherein the microorganism is *Cupriavidus necator*. In some embodiments, the invention further provides a composition wherein the microorganism is *Cupriavidus metallidurans*. In some embodiments, the invention further provides a composition wherein the microorganism is a knallgas microorganism, also known as an oxyhydrogen microorganism. In some embodiments, the invention further provides a composition wherein the microorganism is a chemoautotrophic microbe. In some embodiments, the invention further provides a composition wherein the wild-type or mutant of the microorganism naturally has a capability for accumulating and/or synthesizing high quantities of triacylglycerol where a high quantity is considered to be 10% or more of the dry cell mass; 20% or more of the dry cell mass; 30% or more of the dry cell mass; 40% or more of the dry cell mass; 50% or more of the dry cell mass; 60% or more of the dry cell mass; 70% or more of the dry cell mass. In some embodiments, the invention further provides a composition wherein the microorganism is a hydrogen-oxidizing chemoautotroph. In some embodiments, the invention further provides a composition wherein the microorganism is capable of growing on syngas as the sole energy and carbon source. In some embodiments, the invention further provides a composition wherein the microorganism is capable of growing on untreated crude glycerol as the sole energy and carbon source.

In some embodiments, the invention relates to a method for producing shorter-chain fatty acids wherein the method comprises culturing an engineered microorganism or a natural strain in a bioreactor or solution with a feedstock comprising syngas and/or gaseous $CO_2$ and/or a mixture of $CO_2$ gas and $H_2$ gas. In some embodiments, the invention further provides a step of enhancing expression of enzymes through heat. In some embodiments, the invention further provides a step of up-regulating an endogenous or exogenous thioesterase gene of the microorganism. In some embodiments, the invention further provides a step of down-regulating an endogenous or exogenous thioesterase gene of the microorganism. In some embodiments, the invention further provides a step of down-regulating an endogenous or exogenous acyl carrier protein gene of the microorganism.

In one embodiment, the instant invention provides a method of producing butanediol, or other biochemical precursors to butanediol by microbial fermentation under microaerophilic or anaerobic conditions, including: supplying an inorganic substrate as a primary source of metabolic energy, fermentation in a bioreactor containing a culture of microorganisms utilizing an inorganic substrate as a primary source of metabolic energy and carbon dioxide or other inorganic carbon as the primary source of carbon. In some embodiments, the invention further provides a method wherein the inorganic substrate comprises hydrogen (H2). In some embodiments, the invention further provides a method wherein the butanediol product is 2,3 butanediol, 1,4 butanediol, and/or 1,3 butanediol. In some embodiments, the invention further provides a method wherein the level of hydrogen is supplied at such a level such that butanediol is produced. In some embodiments, the invention further provides a method wherein the level of $CO_2$ is supplied at a level such that butanediol is produced. In some embodiments, the invention further provides a method wherein the culture is propogated in the bioreactor in which oxygen is introduced at a certain flow rate, and the oxygen level is subsequently changed to a lower flow rate, and the oxygen level is subsequently changed to a lower flow rate such that butanediol is produced at enchanced levels. In some embodiments, the invention further provides a method wherein the electron donors include but are not limited to one or more of the following reducing agents: ammonia; ammonium; carbon monoxide; dithionite; elemental sulfur; hydrogen; metabisulfites; nitric oxide; nitrites; sulfates such as thiosulfates including but not limited to sodium thiosulfate ($Na_2S_2O_3$) or calcium thiosulfate ($CaS_2O_3$); sulfides such as hydrogen sulfide; sulfites; thionate; thionite. In some embodiments, the invention further provides a method wherein the primary fermentation microbe is of the genera *Rhodococcus* or *Gordonia*. In some embodiments, the invention further provides a method wherein the primary fermentation microbe is the species *Rhodococcus* sp. DSM 3346 or DSM364. In some embodiments, the invention further provides a method wherein the primary fermentation microbe is a *Rhodococcus opacus*. In some embodiments, the invention further provides a method wherein the primary fermentation microbe is a *Rhodococcus opacus* (DSM 43205) or a *Rhodococcus opacus* (DSM 43206) or a *Rhodococcus opacus* (DSM 44193). In some embodiments, the invention further provides a method wherein the primary fermentation microbe is of the family Burkholderiaceae. In some embodiments, the invention further provides a method wherein the primary fermentation microbe is *Cupriavidus necator*. In some embodiments, the invention further provides a method wherein the primary fermentation microbe is *Cupriavidus metallidurans*. In some embodiments, the invention further provides a method wherein the primary fermentation microbe is a knallgas microorganism, also known as an oxyhydrogen microorganism. In some embodiments, the invention further provides a method wherein the primary fermentation microbe is a chemoautotrophic microbe. In some embodiments, the invention further provides a method wherein the wild-type or mutant of the microorganism naturally has a capability for accumulating and/or synthesizing high quantities of triacylglycerol where a high quantity is considered to be 10% or more of the dry cell mass; 20% or more of the dry cell mass; 30% or more of the dry cell mass; 40% or more of the dry cell mass; 50% or more of the dry cell mass; 60% or more of the dry cell mass; 70% or more of the dry cell mass. In some embodiments, the invention further provides a method wherein the primary fermentation microbe is a hydrogen-oxidizing chemoautotroph. In some embodiments, the invention further provides a composition wherein the primary fermentation microbe is capable of growing on syngas as the sole energy and carbon source. In some embodiments, the invention further provides a composition wherein the primary fermentation microbe is capable of growing on untreated crude glycerol as the sole energy and carbon source. In some embodiments, the invention further provides a step of upregulating an endogenous or exogenous gene regulating the pathway for the production of butanediol. In some embodiments, the invention further provides a step of downregulating an endogenous or exogenous gene regulating the pathway for the production of butanediol.

In one aspect of the invention, a chemotroph capable of $CO_2$ fixation, is engineered to produce a carbon-based product having a desired chemical structure to a level sufficient for commercial production. The product generated may be native to the organism, but produced in non-optimal quantities in the absence of engineering, or completely lacking in the absence of engineering.

In some examples, a host cell is genetically modified with an exogenous nucleic acid sequence encoding a single protein involved in a biosynthetic pathway generating a carbon-based product or intermediate. In other examples, a host cell is genetically modified with an exogenous nuceic acid sequence encoding multiple proteins involved in a biosynthetic pathway generating a carbon-based product or intermediate. In still other examples, a host cell is genetically modified with multiple exogenous nucleic acid sequences encoding multiple proteins involved in a biosynthetic pathway generating a carbon-based product or intermediate, or multiple carbon-based products or intermediates.

In some examples, a host cell is genetically modified with an exogenous nucleic acid sequence encoding a single protein affecting the generation of a carbon-based product or intermediate, but in a manner that does not directly add to or modify the biosynthetic pathway protein sequences. In other examples, a host cell is genetically modified with an exogenous nucleic acid sequence encoding multiple proteins affecting the generation of a carbon-based product or intermediate, but in a manner that does not directly add to or modify the biosynthetic pathway protein sequences.

In one aspect of the invention, a chemotroph capable of $CO_2$ fixation is engineered to produce two or more carbon-based products having desired chemical structures to a level sufficient for commercial production. The products generated may be native to the organism, but produced in non-optimal quantities in the absence of engineering, or completely lacking in the absence of engineering.

In some embodiments, such organisms produce at least 1 mg of carbon-based product of interest per liter of fermentation suspension. In some examples, the product is secreted by the organism into culture medium. In other examples, the product is retained in the organism in the course of fermentation. In some cases, the product may be recovered by lysing the cells and separating the product. In other cases, the product may have commercial value in the intact organism without significant preparation or purification of the product from the organism.

In one embodiment, production of one of more other fermentation byproducts are attenuated or eliminated by downregulation of pathway genes that leads to its production by recombinant DNA methods, including gene knockouts, gene replacement, or partial or complete replacement of gene promoter sequences affecting genes in these pathways. In some examples, these include pathways leading to production of ethanol, acetate, lactate, succinate, butyrate, and butanol.

In one embodiment, production of alcohols (short or long chain, branched or straight-chain, saturated or unsaturated) is optimized by introduction of one or more exogenous nucleic acids encoding proteins in alcohol synthesis pathways. Alcohols can be used as products or used to create products comprised of fatty acid esters, alkyl esters, isoprenyl esters, or other esters.

In one embodiment, such organisms are modified such that they produce or upregulate production of polyhydroxybutyrate (PHB) or other products classified as polyhydroxyalkanoates (PHAs). Organisms that already produce a specific PHA may be modified to produce more of the same or of a different PHA under cultivation conditions appropriate for chemoautotrophic cultivation. Alternatively, organisms that do not produce PHAs may be modified to produce one or multiple types of PHAs. Examples of pathway genes that enable production of PHAs include the following, for production of PHB: a beta-ketothiolase (which converts acetyl-CoA to acetoacetyl-CoA and CoA), Acetoacetyl-CoA reductase (which converts acetoacetyl-CoA and NADPH to 3-hydroxybutyryl-CoA), and PHA synthase (which converts 3-hydroxybutyryl-CoA to PHB and CoA). An example of such a pathway, enabling production of PHB, is encoded by the *Ralstonia eutropha* phaCAB operon. In some embodiments, specific modifications are made by recombinant methods to knockout or attenuate genes that degrade or prevent the accumulation of PHAs. An example of such a gene is poly[(R)-3-hydroxybutanoate] hydrolase.

In one embodiment, such organisms are modified such that they produce detectable levels of hydrocarbons or fatty acids of desired structure from inorganic energy and $CO_2$. For production of specific products of commercial value, desired structures or characteristics includes carbon chain length, branching, and saturation levels. In preferred embodiments, such organisms are modified such that they produce high yields of desired hydrocarbons. In certain embodiments, hydrocarbons produced are secreted by passive transport proteins, active transport proteins or combinations thereof. In certain embodiments, secretion is optimized for maximum yield of secreted hydrocarbons by introducing one or more exogenous nucleic acid sequences encoding transport proteins or gene regulatory sequences (e.g., promoters) that directly modify expression of transport proteins. In certain embodiments, such organisms are optimized for maximum yield of secreted, desired hydrocarbons by introducing one or more exogenous nucleic acid sequences encoding proteins that regulate the expression of transport proteins or gene regulatory sequences (e.g., promoters) that directly modify expression of transport proteins. In certain embodiments, such organisms are optimized for maximum yield of secreted hydrocarbons by introduction of one or more nucleic acid sequences that knock out or attenuate expression of certain endogenous transport proteins or proteins that regulate endogenous transport proteins. In one embodiment, the microorganisms are introduced with one or more exogenous nucleic acid sequences encoding acetyl-CoA carboxylase activity (accBCAD), aldehyde dehydrogenase activity (adhA, adhB), alcohol dehydrogenase activity (ADH I), alkane 1-monooxygenase activity (alkB), 3-hydroxyacyl-ACP dehydratase activity (fabA), 3-ketoacyl-ACP synthase activity (fabB), malonyl-CoA:ACP transacylase activity (fabD), 3-ketoacyl-ACP reductase activity (fabG), acetyl-CoA:ACP transacylase activity (fabH), enoyl-ACP reductase activity (fabI), acyl-ACP hydrolase activity (FAS1), the E1p dehydrogense component of the pyruvate dehydrogenase complex, the E2p dihydrolipoamide acyltransferase component of the 2-oxoglutarate dehydrogenase complex, genes encoding fatty-acyl-coA reductases, fatty alcohol forming acyl-CoA reductases, pyridine nucleotide transhydrogenases, and genes encoding fatty-acyl-coA reductases, acyl-CoA synthetase, alcohol dehydrogenase, alcohol acetyltransferase (EC 2.3.1.84), thioesterase, (EC 3.1.2.14), aceE, aceF, acpP, fadD, cerl, fabA, fabB, fabD, fabG, fabH, fabI, fabZ, lipase, malonyl-CoA decarboxylase, panD, panK, pdh, udhA, and wax synthase (EC 2.3.1.75).

In one embodiment of the invention, such organisms are modified to secrete fatty acid chains by introduction of one or more exogenous nucleic acid sequences encoding an acyl-ACP-thioesterase, wherein the acyl-ACP-thioesterases liberate fatty acid chains from ACP-thioesters. In one example, production of fatty acids of specific lengths, or enriched for specific lengths and structure (including branching and degree of saturation), can be produced by the introduction of one or more nucleic acid sequences encoding specific acyl-ACP-thioesterases showing a bias for producing fatty acid chains of a specific length and structure. In some examples, an organism may be modified by introduction of one or multiple exogenous nucleic acid sequences encoding multiple acyl-ACP-thioesterase proteins into the same organism such that the organism produces fatty acids of multiple specific lengths and structures, or enriched for multiple specific lengths and structures. Several examples of such thioesterases are available in the art, published in the patent literature or in the open literature.

In one embodiment, such organisms are modified by the introduction of one or more nucleic acid sequences to enable or enhance the ability of the organism to utilize inorganic energy, CO2, and water to generate carbon-based products, including amino acids, acrylate, acrylic acid, adipic acid, alcohol, ascorbate, ascorbic acid, aspartate, aspartic acid, 1,3-butadiene, 1,3-butanediol, 2,3-butanediol, 1,4-butanediol, butanol, caprolactam, carotenoid, citrate, citric acid, DHA, diesel, docetaxel, e-caprolactone, erythromycin 7-ADCA/cephalosporin, ethanol, ethyl ester, ethylene, fatty acid ester, fatty alcohols, fuel oxygenates, gamma butyrolactone, gasoline, glucose, fructose, carbohydrate, glutamate, glutamic acid, HPA, hydrocarbons, hydroxybutyrate, 3-hydroxypropionate, isopentenol, isoprene, isoprenoid, isopropanol, itaconate, itaconic acid, JetA, JetA-1, JetB, JP4, JP8, lactate, lactic acid, lanosterol, levulinic acid, limonene, lycopene, lysine, malate, malonic acid, methyl ester, muconic acid, nucleic acids, n-alkanes, alkenes, octane, omega fatty acid, omega-3 DHA, paclitaxel, peptide, PHA, PHB, pharmaceutical products or pharmaceutical intermediates, polyketides, polymers, polyol, propane, 1,3-propanediol, propanol, propylene, pyrrolidones, rubber, serine, sorbitol, statin, steroid, succinate, sucrose, terephthalate, terpene, THF, γ-valerolactone, and wax ester.

In certain embodiments, such organisms provided by the invention comprises a cell line selected from eukaryotic plants, algae, cyanobacteria, green-sulfur bacteria, green non-sulfur bacteria, purple sulfur bacteria, purple non-sulfur bacteria, extremophiles, yeast, fungi, proteobacteria, engineered organisms thereof, and synthetic organisms.

In certain embodiments, such organisms are chemoautotrophic microorganisms that include, but are not limited to, one or more of the following: *Acetoanaerobium* sp., *Acetobacterium* sp., *Acetogenium* sp., *Achromobacter* sp., *Acidianus* sp., *Acinetobacter* sp., *Actinomadura* sp., *Aeromonas* sp., *Alcaligenes* sp., *Alcaligenes* sp., *Arcobacter* sp., *Aureobacterium* sp., *Bacillus* sp., *Beggiatoa* sp., *Butyribacterium* sp., *Carboxydothermus* sp., *Clostridium* sp., *Comamonas* sp., *Dehalobacter* sp., *Dehalococcoide* sp., *Dehalospirillum* sp., *Desulfobacterium* sp., *Desulfomonile* sp., *Desulfotomaculum* sp., *Desulfovibrio* sp., *Desulfurosarcina* sp., *Ectothiorhodospira* sp., *Enterobacter* sp., *Eubacterium* sp., *Ferroplasma* sp., *Halothibacillus* sp., *Hydrogenobacter* sp., *Hydrogenomonas* sp., *Leptospirillum* sp., *Metallosphaera* sp., *Methanobacterium* sp., *Methanobrevibacter* sp., *Methanococcus* sp., *Methanosarcina* sp., *Micrococcus* sp., *Nitrobacter* sp., *Nitrosococcus* sp., *Nitrosolobus* sp., *Nitrosomonas* sp., *Nitrosospira* sp., *Nitrosovibrio* sp., *Nitrospina* sp., *Oleomonas* sp., *Paracoccus* sp., *Peptostreptococcus* sp., *Planctomycetes* sp., *Pseudomonas* sp., *Ralstonia* sp., *Rho-*

*dobacter* sp., *Rhodococcus* sp., *Rhodocyclus* sp., *Rhodomicrobium* sp., *Rhodopseudomonas* sp., *Rhodospirillum* sp., *Shewanella* sp., *Streptomyces* sp., *Sulfobacillus* sp., *Sulfolobus* sp., *Thiobacillus* sp., *Thiomicrospira* sp, *Thioploca* sp., *Thiosphaera* sp., *Thiothrix* sp. Also chemoautotrophic microorganisms that are generally categorized as sulfur-oxidizers, hydrogen-oxidizers, iron-oxidizers, acetogens, and methanogens, as well as a consortiums of microorganisms that include chemoautotrophs.

Such organisms also include but are not limited to extremophiles that can withstand extremes in various environmental parameters such as temperature, radiation, pressure, gravity, vacuum, desiccation, salinity, pH, oxygen tension, and chemicals. They include hyperthermophiles, such as *Pyrolobus fumarii*; thermophiles, such as *Synechococcus lividis*; mesophiles, and psychrophiles, such as *Psychrobacter*. Radiation tolerant organisms include *Deinococcus radiodurans*. Pressure tolerant organisms include piezophiles or barophiles. Dessicant tolerant and anhydrobiotic organisms include xerophiles such as *Artemia salina*; microbes and fungi. Salt tolerant organisms include halophiles, such as Halobacteriacea and *Dunaliella salina*. pH tolerant organisms include alkaliphiles such as Natronobacterium, *Bacillus firmus* OF4, *Spirulina* spp., and acidophiles such as *Cyanidium caldarium*, *Ferroplasma* sp. Gas tolerant organisms, which tolerate pure $CO_2$ include *Cyanidium caldarium* and metal tolerant organisms include metalotolerants such as *Ferroplasma acidarmanus*, *Ralstonia* sp.

Such organisms also include algae and cyanobacteria, which include, but are not limited to the following genera: *Acanthoceras, Acanthococcus, Acaryochloris, Achnanthes, Achnanthidium, Actinastrum, Actinochloris, Actinocyclus, Actinotaenium, Amphichrysis, Amphidinium, Amphikrikos, Amphipleura. Amphiprora, Amphithrix, Amphora, Anabaena. Anabaenopsis, Aneumaatus, Ankistrodesmus, Ankyra, Anomoeoneis, Apatococcus, Aphanizomenon, Aphanocapsa, Aphanochaete, Aphanofhece, Apiocvsis. Apisonema, Arthrodesmus, Artherospira, Ascochloris, Asterionella, Asterococcus, Audouinella, Aulacoseira, Bacillaria, Balbiania, Bambusina, Bangia, Basichlamys, Batrachospermum, Binuclearia, Bitrichia, Blidingia, Botrdiopsis, Botrydium, Botryococcus, Botryosphaerella, Brachiomonas, Brachysira, Brachytrichia, Brebissonia, Bulbochaete, Bumilleria, Bumilleriopsis, Coloneis, Calothrix, Campylodiscus, Copsosiphon, Carteria, Catena, Cavimula, Centritractus, Centronella, Ceratium, Chaetoceros, Chaetochloris, Chaetomorpha, Chaetonella, Chaetonema, Chaetopeltis, Chaetophora, Chaelosphaeridium, Chamaesiphon, Chara, Characiochloris, Characiopsis, Characium, Charales, Chilomonas, Chlainomonas, Chlamydoblepharis, Chlamydocapsa, Chlamydomonas, Chlamydomonopsis, Chlamydomyxa, Chlamydonephris, Chlorangiella, Chlorangiopsis, Chlorella, Chlorobotrys, Chlorobrachis, Chlorochytrium, Chlorococcum, Chlorogloea, Chlorogloeopsis, Chlorogonium, Chlorolobion, Chloromonas, Chlorophysema, Chlorophyta, Chlorosaccus, Chlorosarcina, Choricystis, Chromophyton, Chromulina, Chroococcidiopsis, Chroococcus, Chroodactylon, Chroomonas, Chroothece, Chrysamoeba, Chrysapsis, Chrysidiastrum, Chrysocapsa, Chrysocapsella, Chrysochaete, Chrysochromulina, Chrysococcus, Chrysocrinus, Chrysolepidomonas, Chrysolykos, Chrysonebula, Chrysophyta, Chrysopyxis, Chrysosaccus, Chrysophaerella, Chrysostephanosphaera, Clodophora, Clastidium, Closteriopsis, Closterium, Coccomyxa, Cocconeis, Coelastrella, Coelastrum, Coelosphaerium, Coenochloris, Coenococcus, Coenocystis, Colacium, Coleochaete, Collodictyon, Compsogonopsis, Compsopogon, Conjugatophyta, Conochaete, Coronastrum, Cosmarium, Cosmioneis, Cosmocladium, Crateriportula, Craticula, Crinalium, Crucigenia, Crucigeniella, Cryptoaulax, Cryptomonas, Cryptophyta, Ctenophora, Cyanodictyon, Cyanonephron, Cyanophora, Cyanophyta, Cyanothece, Cyanothomonas, Cyclonexis, Cyclostephanos, Cyclotella, Cylindrocapsa, Cylindrocystis, Cylindrospermum, Cylindrotheca, Cymatopleura, Cymbella, Cymbellanitzschia, Cystodinium Dactylococcopsis, Debarya, Denticula, Dermatochrysis, Dermocarpa, Dermocarpella, Desmatractum, Desmidium, Desmococcus, Desmonema, Desmosiphon, Diacanthos, Diacronema, Diadesmis, Diatoma, Diatomella, Dicellula, Dichothrix, Dichotomococcus, Dicranochaete, Dictyochloris, Dictyococcus, Dictyosphaerium, Didymocystis, Didymogenes, Didymosphenia, Dilabrifilum, Dimorphococcus, Dinobryon, Dinococcus, Diplochloris, Diploneis, Diplostauron, Distrionella, Docidium, Draparnaldia, Dunalielia, Dysmorphococcus, Ecballocystis, Elakatothrix, Ellerbeckia, Encyonema, Enteromorpha, Entocladia, Entomoneis, Entophysalis, Epichrysis, Epipyxis, Epithemia, Eremosphaera, Euastropsis, Euastrum, Eucapsis, Eucocconeis, Eudorina, Euglena, Englenophyta, Eunotia, Eustigmatophyta, Eutreptia, Fallacia, Fischerella, Fragilaria, Fragilariforma, Franceia, Frustulia, Curcilla, Geminella, Genicularia, Glancocystis, Glaucophyta, Glenodiniopsis, Glenodinium, Gloeocapsa, Gloeochaete, Gloeochrysis, Gloeococcus, Glaeocystis, Gloeodendron, Gloeomanas, Gloeoplax, Gloeothece, Gloeotrichia, Gloiodictyon, Golenkinia, Golenkiniopsis, Gomontia, Gomphoxymbella, Gomphonema, Gomphosphaeria, Gonatozygon, Gongrosia, Gongrosira, Goniochloris, Goninm, Gonyostomum, Granulochloris, Gramulocystopsts, Groenbladia, Gymnodinium, Gymnozyga, Gyrosigma, Haematococcus, Hafniomonas, Hallassia, Hammatoidea, Hannaea, Hantzschia, Hapalosiphon, Haplotaenium, Haptophyta, Haslea, Hemidinium, Hemitonia, Heribaudiella, Heteromastix, Heterothrix, Hibberdia, Hildenbrandia, Hillea, Holopedinm, Homoeothrix, Hormanthonema, Hormotila, Hyalobrachion, Hyalocardium, Hyalodiscus, Hyalogonium, Hyalatheca, Hydriamum, Hydrococcus, Hydrocoleum, Hydrocoryne, Hydrodictyon, Hydrosera, Hydrurus, Hyella, Hymenomonas, Isthmochloron, Johannesbaptistia, Juranyiella, Karayevia, Kathablepharis, Katodinium, Kephyrion, Keratococcus, Kirchneriella, Klebsormidium, Kolbesia, Koliella, Komarekia, Korshikoviella, Kraskella, Lagerheimia, Lagynion, Lamprothamnium, Lemanea, Lepocinclis, Leptosira, Lobococcus, Lobocystis, Lobomonas, Luticola, Lyngbya, Malleochloris, Mallomonas, Mantoniella, Marssoniella, Martyana, Mastigocoleus, Gastogloia, Melosira, Merismopedia, Mesostigma, Mesotaenium, Micractinium, Micrasterias, Microchaete, Microcoleaus, Microcystis, Microglena, Micromonas, Microspora, Microthamnion, Mischococcus, Monochrysis, Monodus, Monomastix, Monoraphidium, Monostroma, Mougeotia, Mougeotiopsis, Myochloris, Myromecia, Myxosarcina, Naegeliella, Nannochloris, Nautococcus, Navicula, Neglectella, Neidium, Nephroclamys, Nephrocytium, Nephrodiella, Nephroselmis, Netrium, Nitella, Nitellopsis, Nitzschia, Nodularia, Nostoc, Ochromonas, Oedogonium, Oligochaetophora, Onychonema, Oocardium, Oocystis, Opephora, Ophiocytium, Orthoseira, Oscillaioria, Oxyneis, Pachycladella, Palmella, Palmodictyon, Pnadorina, Pannus, Paralia, Pascherina, Paulschulzia, Pediastrum, Pedinella, Pedinomonas, Pedinopera, Pelagodictyon, Penium, Peranema, Peridiniopsis, Peridinium, Peronia, Petroneis, Phacotus, Phacus, Phaeaster, Phaeodermatium, Phaeophyta, Phaeosphaera, Phaeothamnion, Phormidium, Phycopeltis, Phyllarlochloris, Phyllocardium,*

*Phyllomitas, Pinmularia, Pitophora, Placoneis, Planctonema, Planktosphaeria, Planothidium, Plectonema, Pleodorina, Pleurastrum, Pleurocapsa, Pleurocladia, Pleurodiscus, Pleurosigma, Pleurosira, Pleurotaenium, Pocillomonas, Podohedra, Polyblepharides, Polychaetophora, Polyedriella, Polyedriopsis, Polygoniochloris, Polyepidomonas, Polytaenia, Polytoma, Polytomella, Porphyridium, Posteriochromonas, Prasinochloris, Prasinocladus, Prasinophyta, Prasiola, Prochlorphyta, Prochlorothrix, Protoderma, Protosiphon, Provasoliella, Prymnesium, Psammodictyon, Psammothidium, Pseudanabaena, Pseudenoclonium, Psuedocarteria, Pseudochate, Pseudocharacium, Pseudococcomyxa, Pseudodictyosphaerium, Pseudokephyrion, Pseudoncobyrsa, Pseudoquadrigula, Pseudosphaerocystis, Pseudostaurastrum, Pseudostaurosira, Pseudotetrastrum, Pteromonas, Punctastruata, Pyramichlamys, Pyramimonas, Pyrrophyta, Quadrichloris, Quadricoccus, Quadrigula, Radiococcus, Radiofilum, Raphidiopsis, Raphidocelis, Raphidonema, Raphidophyta, Peimeria, Rhandoderma, Rhabdomonas, Rhizoclonium, Rhodomonas, Rhodophyta, Rhoicosphenia, Rhopalodia, Rivularia, Rosenvingiella, Rossithidium, Roya, Scenedesmus, Scherffelia, Schizochlamydella, Schizochlamys, Schizomeris, Schizothrix, Schroederia, Scolioneis, Scotiella, Scotiellopsis, Scourfieldia, Scytonema, Selenastrum, Selenochloris, Sellaphora, Semiorbis, Siderocelis, Diderocystopsis, Dimonsenia, Siphononema, Sirocladium, Sirogonium, Skeletonema, Sorastrum, Spermatozopsis, Sphaerellocystis, Sphaerellopsis, Sphaerodinium, Sphaeroplea, Sphaerozosma, Spiniferomonas, Spirogyra, Spirotaenia, Spirulina, Spondylomorum, Spondylosium, Sporotetras, Spumella, Staurastrum, Stauerodesmus, Stauroneis, Staurosira, Staurosirella, Stenopterobia, Stephanocostis, Stephanodiscus, Stephanoparos, Stephanosphaera, Stichococcus, Stichogloea, Stigeocionium, Stigonema, Stipitococcus, Stokesiella, Strombomonas, Stylochrysalis, Stylodinium, Stylorxis, Stylosphaeridium, Surirella, Sykidion, Symploca, Synechococcus, Synechocystis, Synedra, Synochromonas, Symura, Tabellaria, Tabularia, Teilingia, Temnogametum, Tetmemorus, Tetrachlorella, Tetracyclus, Tetradesmus, Tetraedriella, Tetraedron, Tetraselmis, Tetraspora, Tetrastrum, Thalassiosira, Thamniochaete, Thorakochloris, Thorea, Tolypella, Tolypothrix, Trachelomonas, Trachydiscus, Trebouxia, Trentepholia, Treubaria, Tribonema, Trichodesmium, Trichodiscus, Trochiscia, Tryblionella, Ulothrix, Uroglena, Uronema Urosoienia, Urospora, Uva, Vacuolaria, Vaucheria, Volvox, Volvulina, Westella, Woloszynskia, Xanthidium, Xanthophyta, Xenococcus, Zygnema, Zygnemopsis,* and *Zygonium.*

Such organisms also include green non-sulfur bacteria, which include but are not limited to the following genera; *Chloroflexus, Chloronema, Oscillochloris, Heliothrix, Herpetosiphon, Roseiflexus,* and *Thermomicrobium.*

Such organisms also include green sulfur bacteria, which include but are not limited to the following genera: *Chlorobium, Clathrochloris,* and *Prosthecochloris.*

Such organisms also include purple sulfur bacteria, which include but are not limited to the following genera: *Allochromatium, Chromatium, Halochromatium, Isochnmatium, Marichromatium, Rhodovulum, Thermochromatium, Thiocapsa, Thiorhodococcus,* and *Thiocystis.*

Such organisms also include purple non-sulfur bacteria, which include but are not limited to the following genera; *Phaeospirillum, Rhodobaca, Rhodobacter, Rhodomicrobium, Rhodopila, Rhodopseudomonas, Rhodothalassium, Rhodospirillum, Rodovibrio,* and *Roseospira.*

Such organisms also include aerobic chemolithotrophic bacteria, which include but are not limited to nitrifying bacteria such as *Nitrobacteraceae* sp., *Nitrobacter* sp., *Nitrospina* sp., *Nitrococcus* sp., *Nitrospira* sp., *Nitrosomonas* sp., *Nitrosococcus* sp., *Nitrosospira* sp., *Nitrosolobus* sp., *Nitrosovibrio* sp.; colorless sulfur bacteria such as, *Thiovulum* sp., *Thiobacillus* sp., *Thiomicrospira* sp., *Thiosphaera* sp., *Thermothrix* sp.; obligately chemolithotrophic hydrogen bacteria such as *Hydrogenobacter* sp., iron and manganese-oxidizing and/or depositing bacteria such as *Siderococcus* sp., and magnetotactic bacteria such as *Aquaspirillum* sp.

Such organisms also include archaeobacteria, which include but are not limited to methanogenic archaeobacteria such as *Methanobacterium* sp., *Methanobrevibacter* sp., *Methanothermus* sp., *Methanococcus* sp., *Methanomicrobium* sp., *Methanospirillum* sp., *Methanogenium* sp., *Methanosarcina*. sp., *Methanolobus* sp., *Methanothrix* sp., *Methanococcoides* sp., *Methanoplanus* sp.; extremely thermophilic sulfur-metabolizers such as *Thermoproteus* sp., *Pyrodictium* sp., *Sulfolobus* sp., *Acidianus* sp.

In some embodiments of the invention a oxyhydrogen microorganism, such as but not limited to *Ralstonia eutropha, Alcaligenes eutrophus* or *Cupriavidus necator*, is grown up to a high cell density in micro aerobic conditions using syngas components as a carbon source and energy, including, but not limited to H2, CO2 and/or CO, and/or using methanol and/or using glycerol, including crude glycerol, which is a by-product of biodiesel or oleochemical manufacturing. Once a high cell density is achieved, feeding oxygen into the bioreactor is stopped and fementation continues under aneaorobic conditions and the microorganisms secrete 1,3 butanediol or 2,3 butanediol and/or other organic compounds, including, but not limited to 2-Oxoglutarate, 2-Oxo-3-methylbutanoate, cis-Aconitate, 3-Hydroxybutanoate, Butanoate, Acetate, Formate, Succinate, 2-methyl propanoate, 2-Methylbutanoate, 3-Methylbutanoate, meso-2,3-Butandiol, Acetoin, DL 2,3-Butandiol. 2-Methylpropan-1-ol, Ethanol, 1-Propanol, and/or Lactate.

Exemplary oxyhydrogen microorganisms that can be used in one or more process steps of certain embodiments of the present invention include but are not limited to one or more of the following: purple non-sulfur photosynthetic bacteria including but not limited to *Rhodopseudomonas palustris, Rhodopseudomonas capsulata, Rhodopseudomonas viridis, Rhodopseudomonas sulfoviridis, Rhodopseudomonas blastica, Rhodopseudomonas spheroides, Rhodopseudomonas acidophila* and other *Rhodopseudomonas* sp., *Rhodospirillum rubrum*, and other *Rhodospirillum* sp.; *Rhodococcus opacus* and other *Rhodococcus* s.p.; *Rhizobium japonicum* and other *Rhizobium* sp.; *Thiocapsa roseopersicina* and other *Thiocapsa* sp.; *Pseudomonas hydrogenovora, Pseudomonas hydrogenothermophila*, and other *Pseudomonas* sp.; *Hydrogenomonas pantotropha, Hydrogenomonas eutropha, Hydrogenomonas facilis*, and other *Hydrogenomonas* sp.; *Hydrogenobacter thermophilus* and other *Hydrogenobacter* sp.; *Hydrogenovibrio marinus* and other *Hydrogenovibrio* sp.; *Helicobacter pylori* and other *Helicobacter* sp.; *Xanthobacter* sp.; *Hydrogenophaga* sp.; *Bradyrhizobium japonicum* and other *Bradyrhizobium* sp.; *Ralstonia eutropha* and other *Ralstonia* sp.; *Alcaligenes eutrophus* and other *Alcaligenes* sp.; *Variovorax paradoxus*, and other *Variovorax* sp.; *Acidovorax facilis*, and other *Acidovorax* sp.; cyanobacteria including but not limited to *Anabaena oscillarioides, Anabaena spiroides, Anabaena cylindrica*, and other *Anabaena* sp.; green algae including but not limited to *Scenedesmus obliquus* and other *Scenedesmus* sp., *Chlamydomonas reinhardii* and other *Chlamy-*

*domonas* sp., *Ankistrodesmus* sp., *Rhaphidium polymorphium* and other *Rhaphidium* sp.; as well as a consortiums of microorganisms that include oxyhydrogen microorganisms.

One feature of certain embodiments of the present invention is the inclusion of one or more process steps within a chemical process for the conversion of C1 carbon sources including but not limited to carbon monoxide, methane, methanol, formate, or formic acid, and/or mixtures containing C1 chemicals including but not limited to various syngas compositions generated from various gasified, pyrolyzed, or steam-reformed fixed carbon feedstocks, that utilize oxyhydrogen microorganisms and/or enzymes from oxyhydrogen microorganisms as a biocatalyst for the conversion of C1 chemicals into longer chain organic chemicals (i.e. C2 or longer and, in some embodiments, C5 or longer carbon chain molecules). In some such embodiments C1 containing syngas, or process gas, or C1 chemicals in a pure liquid form or dissolved in solution is pumped or otherwise added to a vessel or enclosure containing nutrient media and oxyhydrogen microorganisms. In some such cases oxyhydrogen microorganisms perform biochemical synthesis to elongate C1 chemicals into longer carbon chain organic chemicals using the chemical energy stored in the C1 chemical, and/or molecular hydrogen and/or valence or conduction electrons in solid state electrode materials and/or one or more of the following list of electron donors pumped or otherwise provided to the nutrient media including but not limited to: ammonia; ammonium; carbon monoxide; dithionite; elemental sulfur; hydrocarbons; metabisulfites; nitric oxide; nitrites; sulfates such as thiosulfates including but not limited to sodium thiosulfate (Na2S2O3) or calcium thiosulfate (CaS2O3); sulfides such as hydrogen sulfide; sulfites; thionate; thionite; transition metals or their sulfides, oxides, chalcogenides, halides, hydroxides, oxyhydroxides, sulfates, or carbonates, in soluble or solid phases. The electron donors can be oxidized by electron acceptors in a chemosynthetic reaction. Electron acceptors that may be used at this reaction step include oxygen and/or other electron acceptors including but not limited to one or more of the following: carbon dioxide, ferric iron or other transition metal ions, nitrates, nitrites, oxygen, or holes in solid state electrode materials.

The chemosynthetic reaction step or steps of the process whereby carbon dioxide and/or inorganic carbon is fixed into organic carbon in the form of organic compounds and biomass and/or the reaction steps converting C1 chemicals to longer chain organic chemicals whereby a C1 chemical such as but not limited to carbon monoxide, methane, methanol, formate, or formic acid, and/or mixtures containing C1 chemicals including but not limited to various syngas compositions generated from various gasified, pyrolyzed, or steam-reformed fixed carbon feedstocks, are biochemically converted into longer chain organic chemicals (i.e. C2 or longer and, in some embodiments, C5 or longer carbon chain molecules) can be performed in aerobic, microaerobic, anoxic, anaerobic conditions, or facultative conditions. A facultative environment is considered to be one having aerobic upper layers and anaerobic lower layers caused by stratification of the water column.

The present invention relates to the engineering of microorganisms, including but not limited to hydrogen oxidizing and/or carbon monoxide oxidizing knallgas microorganisms, with a natural capability to grow and synthesize biomass on gaseous carbon sources such as syngas and/or $CO_2$, such that the natural or engineered microorganisms synthesize targeted products, including chemicals and fuels, under gas cultivation.

In some embodiments, the composition comprises a microorganism that can naturally grow on H2/CO2 and/or syngas, and wherein the microorganism can naturally accumulate polyhydroxybutyrate (PHB) or polyhydroxyalkanoate (PHA) to 50% or more of the cell biomass by weight. In some embodiments the microorganisms have a native ability to direct a high flux of carbon through the acetyl-CoA metabolic intermediate, which can lead into fatty acid biosynthesis, along with a number of other synthetic pathways including PHA and PHB synthesis. A microorganism is considered to direct a high flux of carbon through acetyl-CoA if a product of a synthesis pathway going through the acetyl-CoA metabolic intermediate, including but not limited to polyhydroxybutyrate (PHB) or polyhydroxyalkanoate (PHA), can represent 50% or more of the cell biomass by weight. In some embodiments the microorganism exhibiting these traits is *Cupriavidus* necator (DSM 531 or DSM 541).

Aspects of the invention relate to a bacterial cell comprising at least a first exogenous nucleic acid sequence wherein the cell converts gaseous $CO_2$ and/or gaseous $H_2$ and/or syngas into one or more lipids or hydrocarbons.

In some embodiments, the first exogenous nucleic acid sequence encodes a protein selected from the group consisting of a fatty acid acyl-ACP reductase and a fatty acid aldehyde decarbonylase. In some embodiments, the first exogenous nucleic acid sequence encodes a CYP52A protein. In certain embodiments, the first exogenous nucleic acid sequence encodes a protein selected from the group consisting of a CYP709C1 and CYP81B1. In some embodiments, the first exogenous nucleic acid sequence encodes a thioesterase protein.

In some embodiments, the cell further comprises a second exogenous nucleic acid sequence. In some embodiments, the first exogenous nucleic acid sequence encodes a fatty acid acyl-ACP reductase and the second exogenous nucleic acid sequence encodes a fatty acid aldehyde decarbonylase. In some embodiments, the cell comprises a first and second exogenous nucleic acid wherein the second exogenous nucleic acid encodes a thioesterase protein or a fatty acyl-CoA ligase. In some embodiments, the cell further comprises a third exogenous nucleic acid sequence that encodes a thioesterase.

In some embodiments, the bacterial cell is of the suborder corynebacterineae. In some embodiments, the bacterial cell is of the family burkholderiaceae. In some embodiments, the cell is of the genera *Rhodococcus* or *Gordonia*. In certain embodiments, the cell is a *Rhodococcus opacus*. In some embodiments, the bacterial cell is an oxyhydrogen microorganisms including oxyhydrogen microorganisms selected from one or more of the following genera: *Rhodopseudomonas* sp.; *Rhodospirillum* sp.; *Rhodococcus* sp.; *Nocardia* sp.; *Mycobacterium* sp.; *Gordonia* sp.; *Tsukamurella* sp.; *Rhodobacter* sp.; *Rhizobium* sp.; *Thiocapsa* sp.; *Pseudomonas* sp.; *Hydrogenomonas* sp.; *Hydrogenobacter* sp.; *Hydrogenovibrio* sp.; *Helicobacter* sp.; *Oleomonas* sp.; *Xanthobacter* sp.; *Hydrogenophaga* sp.; *Bradyrhizobium* sp.; *Ralstonia* sp.; *Alcaligenes* sp.; *Variovorax* sp.; *Acidovorax* sp.; *Anabaena* sp.; *Scenedesmus* sp.; *Chlamydomonas* sp., *Ankistrodesmus* sp., and *Rhaphidium* sp. [all oxyhydrogen] subset of hydrogen oxidizers.

In some embodiments, the bacterial cell produces and/or secretes at least 10% of one or more lipids or hydrocarbons by weight. In some embodiments, the bacterial cell produces and/or secretes one or more lipids or hydrocarbons, wherein at least 50% of the one or more lipids or hydrocarbons have 6 to 30 carbon atoms. In some embodiments, less than 10% by weight of the lipids or hydrocarbons is methane. In some embodiments, less than 10% by weight of the lipids or hydrocarbons is organic acid.

In some embodiments, the one or more lipids or hydrocarbons comprise at least one organic molecule having a carbon chain length of at least 8 carbon atoms and at least one carbon-carbon double bond. In some embodiments, the one or more lipids or hydrocarbons comprise at least one diacid acid molecule having a carbon chain length of at least 6 carbon atoms. In some embodiments, the one or more lipids or hydrocarbons comprise at least one desaturated hydrocarbon molecule having a carbon chain length of at least 6 carbon atoms.

In some embodiments, the one or more lipids or hydrocarbons comprise at least one fatty acid molecule having a carbon chain length of at least 6 carbon atoms. In some embodiments, the one or more lipids or hydrocarbons comprise at least one unsaturated fatty acid molecule having a carbon chain length of at least 6 carbon atoms. In some embodiments, the one or more lipids or hydrocarbons comprise at least one hydroxyl acid molecule having a carbon chain length of at least 6 carbon atoms. In some embodiments, the one or more lipids or hydrocarbons comprise at least one dicarboxylic acid molecule having a carbon chain length of at least 6 carbon atoms.

In some embodiments, the one or more lipids or hydrocarbons comprise at least one alkane, alkene, alkyne, fatty alcohol, and/or fatty aldehyde at a level higher than the quantity of the alkane, alkene, alkyne, fatty alcohol, and or fatty aldehyde in the same microorganism not comprising the exogenous nucleic acid sequences. In some embodiments, the one or more lipids or hydrocarbons comprise at least one component of or one precursor to a component of jet fuel, diesel fuel, or biodiesel fuel.

Further aspects of the invention relate to a method of producing a lipid or a hydrocarbon or a mixture of lipids or hydrocarbons, including culturing a bacterial cell in a feedstock comprising syngas and/or gaseous $CO_2$ and/or a mixture of $CO_2$ gas and $H_2$ gas. In some embodiments, the $H_2$ is generated or recycled using renewable, alternative, or conventional sources of power that are low in greenhouse gas emissions, and wherein said sources of power are selected from at least one of photovoltaics, solar thermal, wind power, hydroelectric, nuclear, geothermal, enhanced geothermal, ocean thermal, ocean wave power, and tidal power. In some embodiments, the syngas is generated from lignocellulosic energy crops, crop residue, bagasse, saw dust, forestry residue, food waste, municipal solid waste, biogas, landfill gas, or stranded natural gas.

In some embodiments, the lipid or hydrocarbon or mixture of lipids or hydrocarbons produced is one or more alkane, alkene, alkyne, fatty alcohol, and/or fatty aldehyde. In some embodiments, at least one exogenous nucleic acid sequences of the bacterial cell is operably linked to a promoter that is inducible in response to a first stimulus, and wherein the method further comprises culturing a population of the bacterial cell of claim 1 for a first period of time in the presence of a first stimulus to produce one or more lipids or hydrocarbons.

Further aspects of the invention relate to culturing of a bacterial cell in a feedstock comprising syngas and/or gaseous $CO_2$ and/or a mixture of $CO_2$ gas and $H_2$ gas in a reaction vessel or a bioreactor wherein the one or more lipids or hydrocarbons are separated from the reaction vessel or bioreactor. In some embodiments, the method further comprises purifying the one or more lipids or hydrocarbons or a mixture of lipids or hydrocarbons after separation from the reaction vessel or bioreactor.

Further aspects of the invention relate to a microorganism comprising at least a first exogenous nucleic acid sequence wherein the microorganism converts gaseous $CO_2$ and/or gaseous $H_2$ and/or syngas into one or more hydroxylated fatty acids. In some embodiments, the first exogenous nucleic acid sequence encodes a hydroxylating ezyme. In some embodiments the cell further comprises a second exogenous nucleic acid sequence encoding a thioesterase enzyme. In some embodiments, the microorganism is the genera *Rhodococcus* or *Gordonia*. In certain embodiments, the microorganism is the species *Rhodococcus* sp. DSM 3346 or DSM 364. In some embodiments, the microorganism is *Rhodococcus opacus*. In certain embodiments, the microorganism is *Rhodococcus opacus* (DSM 43205) or *Rhodococcus opacus* (DSM 43206) or *Rhodococcus opacus* (DSM 44193). In some embodiments, the microorganism is family Burkholderiaceae. In some embodiments, the microorganism is *Cupriavidus* necator. In some embodiments, the microorganism is *Cupriavidus metallidurans*. In some embodiments, the microorganism is a knallgas microorganism, also known as an oxyhydrogen microorganism. In some embodiments, herein the microorganism is a chemoautotrophic microbe.

In some embodiments, the wild-type or mutant of the microorganism naturally has a capability for accumulating and/or synthesizing high quantities of triacylglycerol where a high quantity is considered to be 10% or more of the dry cell mass. In some embodiments, the microorganism is a hydrogen-oxidizing chemoautotroph. In some embodiments, the microorganism is capable of growing on syngas as the sole energy and carbon source. In some embodiments, the microorganism is capable of growing on untreated crude glycerol as the sole energy and carbon source.

Further aspects of the invention relate to a method for producing hydroxylated fatty acids including in a bioreactor or solution, culturing an engineered microorganism or a natural strain in a feedstock comprising syngas and/or gaseous $CO_2$ and/or a mixture of $CO_2$ gas and $H_2$ gas. In some embodiments, the method further comprises the step of up-regulating an endogenous or exogenous thioesterase gene of the microorganism. In some embodiments, the method further comprises the step of down-regulating production of an endogenous or exogenous thioesterase gene of the microorganism. In some embodiments, the method further comprises the step of down regulating an endogenous or exogenous acyl carrier protein gene of the microorganism.

Aspects of the invention relate to a microorganism comprising at least a first exogenous nucleic acid sequence wherein the microorganism converts gaseous $CO_2$ and/or gaseous $H_2$ and/or syngas into one or more shorter-chain fatty acids. In some embodiments, the first exogenous nucleic acid sequence encodes a fatty acyl-CoA binding protein. In some embodiments, the microorganism further comprises a second exogenous nucleic acid sequence encoding a thioesterase enzyme. In some embodiments, the microorganism is of the genera *Rhodococcus* or *Gordonia*. In certain embodiments, the microorganism is the species *Rhodococcus* sp. DSM 3346 or DSM 364. In some embodiments, the microorganism is a *Rhodococcus opacus*. In some embodiments, the microorganism is a *Rhodococcus opacus* (DSM 43205) or a *Rhodococcus opacus* (DSM 43206) or a *Rhodococcus opacus* (DSM 44193). In some embodiments, the microorganism is family burkholderiaceae. In some embodiments, the microorganism is *Cupriavidus* necator. In some embodiments, the microorganism is *Cupriavidus metallidurans*. In some embodiments, the microorganism is a knallgas microorganism, also known as an oxyhydrogen microorganism. In some embodiments, the microorganism is a chemoautotrophic microbe.

In some embodiments, the wild-type or mutant of the microorganism naturally has a capability for accumulating and/or synthesizing high quantities of triacylglycerol where a high quantity is considered to be 10% or more of the dry cell mass. In some embodiments, the microorganism is a hydrogen-oxidizing chemoautotroph. In some embodiments, the microorganism is capable of growing on syngas as the sole energy and carbon source. In some embodiments, the microorganism is capable of growing on untreated crude glycerol as the sole energy and carbon source.

Further aspects of the invention relate to a method for producing shorter-chain fatty acids including in a bioreactor or solution, culturing an engineered microorganism as in claim 55 or a natural strain with a feedstock comprising syngas and/or gaseous $CO_2$ and/or a mixture of $CO_2$ gas and $H_2$ gas. In some embodiments, the method further comprises the step of enhancing expression of enzymes through heat. In some embodiments, the method further comprises the step of up-regulating an endogenous or exogenous thioesterase gene of the microorganism. In some embodiments, the method further comprise the step of down-regulating an endogenous or exogenous thioesterase gene of the microorganism. In some embodiments, the method further comprises the step of down regulating an endogenous or exogenous acyl carrier protein gene of the microorganism.

Further aspects of the invention relate to a method of producing butanediol, or other biochemical precursors to butanediol by microbial fermentation under microaerophilic or anaerobic conditions, including: supplying an inorganic substrate as a primary source of metabolic energy, whereby the substrate consists of one or more electron donors and one or more electron acceptors; and fermentation in a bioreactor containing a culture of microorganisms utilizing an inorganic substrate as a primary source of metabolic energy and carbon dioxide or other inorganic carbon as the primary source of carbon.

In some embodiments, the inorganic substrate comprises hydrogen (H2). In some embodiments, the butanediol product is 2,3-butanediol, 1,4 butanediol or 1,3 butanediol. In some embodiments, the level of hydrogen is supplied at a level such that butanediol is produced. In some embodiments, the level of $CO_2$ is supplied at a level such that butanediol is produced. In some embodiments, the culture is propagated in the bioreactor in which oxygen is introduced at a certain flow rate, and the oxygen level is subsequently changed to a lower flow rate such that butanediol is produced at enhanced levels.

In some embodiments, the electron donors include but are not limited to one or more of the following reducing agents: ammonia; ammonium; carbon monoxide; dithionite; elemental sulfur; hydrogen; metabisulfites; nitric oxide; nitrites; sulfates such as thiosulfates including but not limited to sodium thiosulfate ($Na_2S_2O_3$) or calcium thiosulfate ($CaS_2O_3$); sulfides such as hydrogen sulfide; sulfites; thionate; thionite and said electron acceptors include but are not limited to one or more of the following oxidizing agents: carbon dioxide, ferric iron or other transition metal ions, nitrates, nitrites, oxygen, or holes in solid state electrode materials.

In some embodiments, the primary fermentation microbe is of the genera *Rhodococcus* or *Gordonia*. In some embodiments, the primary fermentation microbe is the species *Rhodococcus* sp. DSM 3346 or DSM 364. In some embodiments, the primary fermentation microbe is a *Rhodococcus opacus*. In some embodiments, the primary fermentation microbe is a *Rhodococcus opacus* (DSM 43205) or a *Rhodococcus opacus* (DSM 43206) or a *Rhodococcus opacus* (DSM 44193). In some embodiments, the primary fermentation microbe is family burkholderiaceae. In some embodiments, the primary fermentation microbe is *Cupriavidus necator*. In some embodiments, the primary fermentation microbe is *Cupriavidus metallidurans*. In some embodiments, the primary fermentation microbe is a knallgas microorganism, also known as an oxyhydrogen microorganism. In some embodiments, the primary fermentation microbe is a chemoautotrophic microbe.

In some embodiments, the wild-type or mutant of the primary fermentation microbe naturally has a capability for accumulating and/or synthesizing high quantities of triacylglycerol where a high quantity is considered to be 10% or more of the dry cell mass. In some embodiments, the primary fermentation microbe is a hydrogen-oxidizing chemoautotroph. In some embodiments, the primary fermentation microbe is capable of growing on syngas as the sole energy and carbon source. In some embodiments, the primary fermentation microbe is capable of growing on untreated crude glycerol as the sole energy and carbon source.

In some embodiments, the method further comprises the step of up-regulating an endogenous or exogenous gene regulating the pathway for the production of butanediol. In some embodiments, the method further comprises the step of down-regulating an endogenous or exogenous gene regulating the pathway for the production of butanediol.

BRIEF DESCRIPTION OF THE DRAWINGS

Non-limiting embodiments of the present invention will be described by way of example with reference to the accompanying figures, which are schematic and are not intended to be drawn to scale. For purposes of clarity, not every component is labeled in every figure, nor is every component of each embodiment of the invention shown where illustration is not necessary to allow those of ordinary skill in the art to understand the invention. In the figures:

FIG. 1 describes the taxonomic names afforded to the chemoautotrophic and oleaginous microorganisms used in selected embodiments of the invention.

FIG. 3 shows the sequence similarity of *Rhodococcus opacus* (DSM 43205) 16S rRNA gene (NR_026186.1) to members of the family gordoniaceae, mycobacteriaceae, nocardiaceae and burkholderiaceae. The Genbank accession numbers, DNA length and % identity of analyzed genes are indicated.

FIG. 4 describes the nucleotide sequence alignment of the 16S rRNA genes SEQ ID NOs: 20-49.

FIG. 5 demonstrates the growth of chemotrophic and oleaginous microorganisms on different carbon sources. Bacterial growth was measured using optical density (OD) detection at 650 nm after the indicated days (in parentheses). Media and growth conditions described in the Examples section below. ND, not done.

FIG. 6 describes the measured lipid content of microorganisms on heterotrophic and chemoautotrophic growth conditions as a percentage of total cellular dry matter (CDM). Cells were grown under conditions described in FIG. 5, harvested after 72 hr (unless otherwise indicated)

and analyzed by gas chromatography. For CDM, total dry weight was determined gravimetrically.

Figure 7:
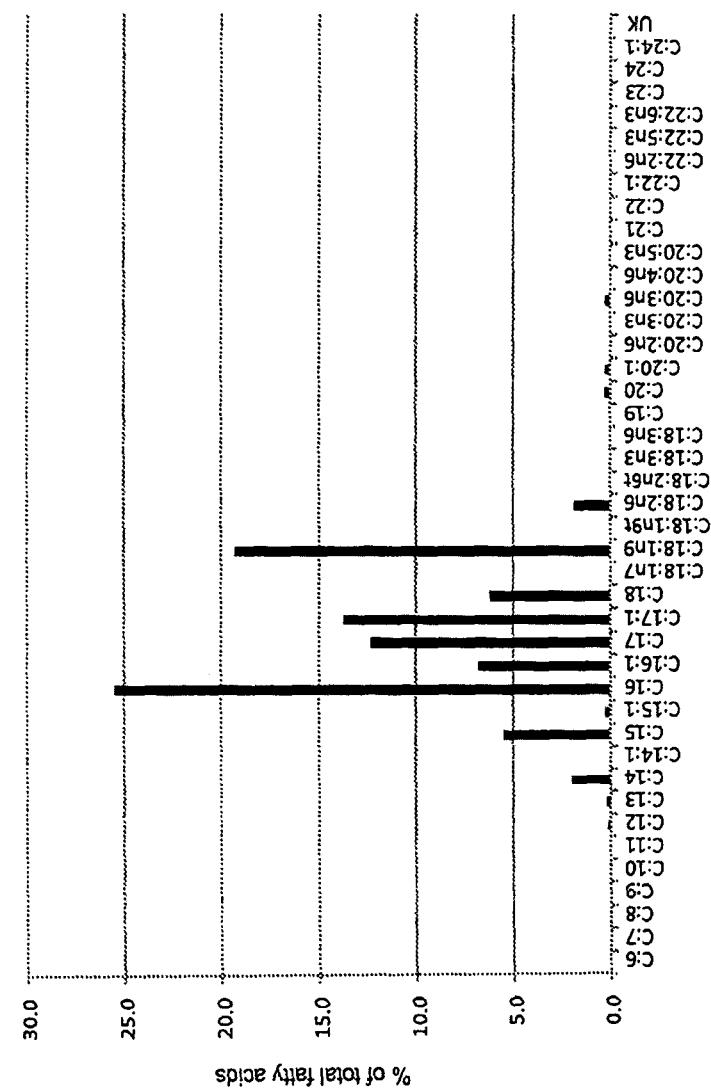

FIG. 7 describes the fatty acid profile of *R. opacus* (DSM 44193) under heterotrophic growth conditions. Cells were harvested after 72 hr and analyzed by gas chromatography.

FIGS. 8A-8B describe the fatty acid profile *R. opacus* (DSM43205) under heterotrophic (FIG. 8A) and chemoautotrophic (FIG. 8B) growth conditions. Cells were harvested after 72 hours of growth and analyzed by gas chromatography.

Figure 9:
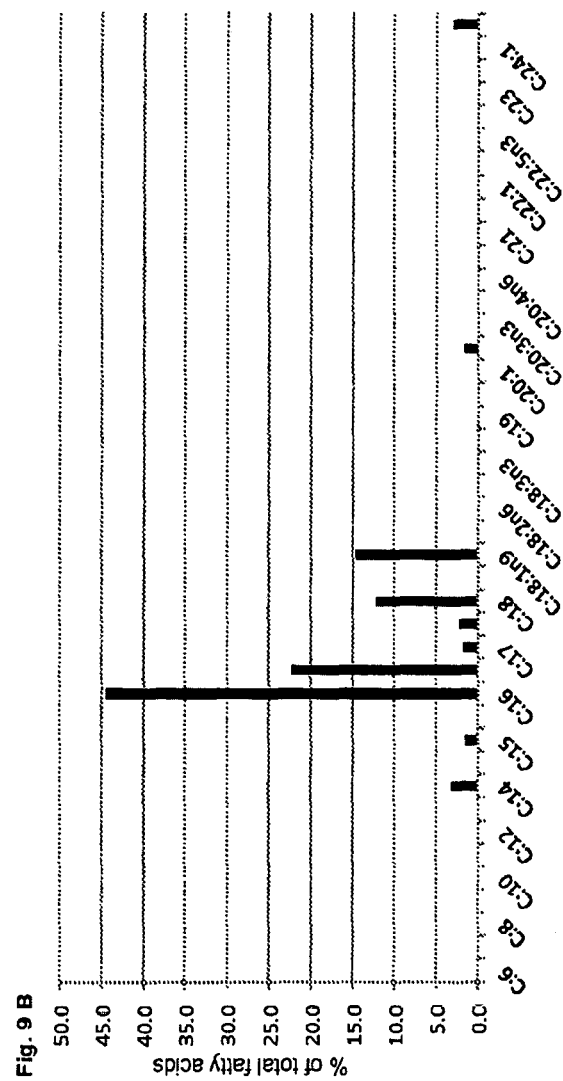

FIGS. 9A-9B describe the fatty acid profile *Rhodococcus* sp. (DSM 3346) under heterotrophic (FIG. 9A) chemoautotrophic (FIG. 9B) growth conditions. Cells were harvested after 72 hr and analyzed by gas chromatography.

FIGS. 10A-10B describe shuttle vectors (FIG. 10A) and genetic elements (FIG. 10B) for transformation and gene expression of in chemoautotrophic and oleaginous microorganisms. MCS: multiple cloning site.

FIGS. 11A-1D describe the map of the plasmids pSeqCO1 (FIG. 11A; SEQ ID: 01), pSeqCO2 (FIG. 11B; SEQ ID: 02), pVer1 (FIG. 11C; SEQ ID: 03) and pVer2 (FIG. 11D; SEQ ID: 04) described in FIGS. 10A-10B. The genetic elements are indicated.

FIG. 12 describes the transformation of chemoautotrophic and oleaginous microorganisms with shuttle vectors described in FIGS. 10A-10B.

Figure 13:
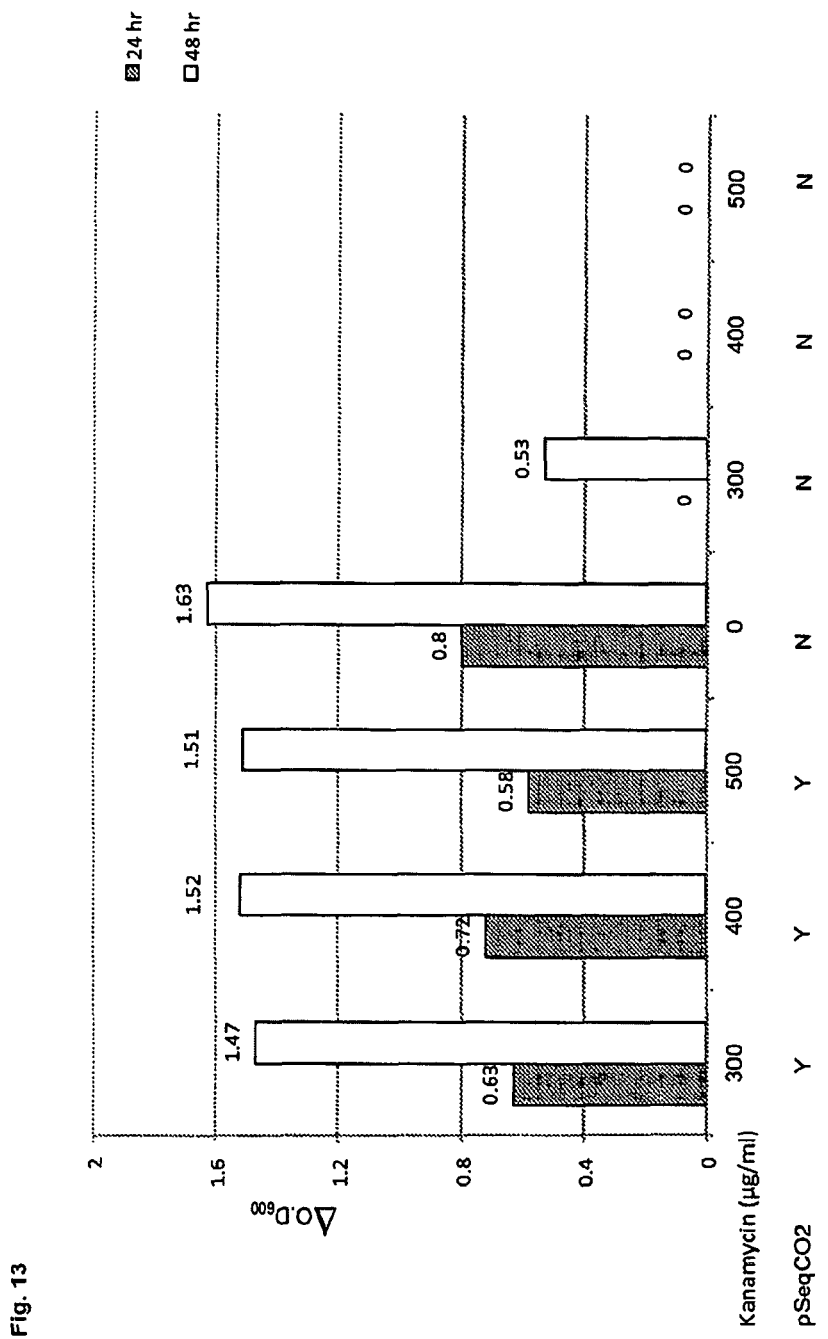

FIG. 13 describes the growth of *Cupriavidus necator* (DSM531) transformed with the plasmid (Y) pSeqCO2 (SEQ ID:2) and untransformed (N) on different kanamycin concentrations. Single colony of transformants and control were grown LB medium (per 1 L: 10 g Bacto-tryptone, 5 g yeast extract, 10 g NaCl pH=7.0) at 30° C. in the indicated kanamycin concentrations. The growth was measured using $O.D_{650}$ after the indicated number of days.

Figure 14:
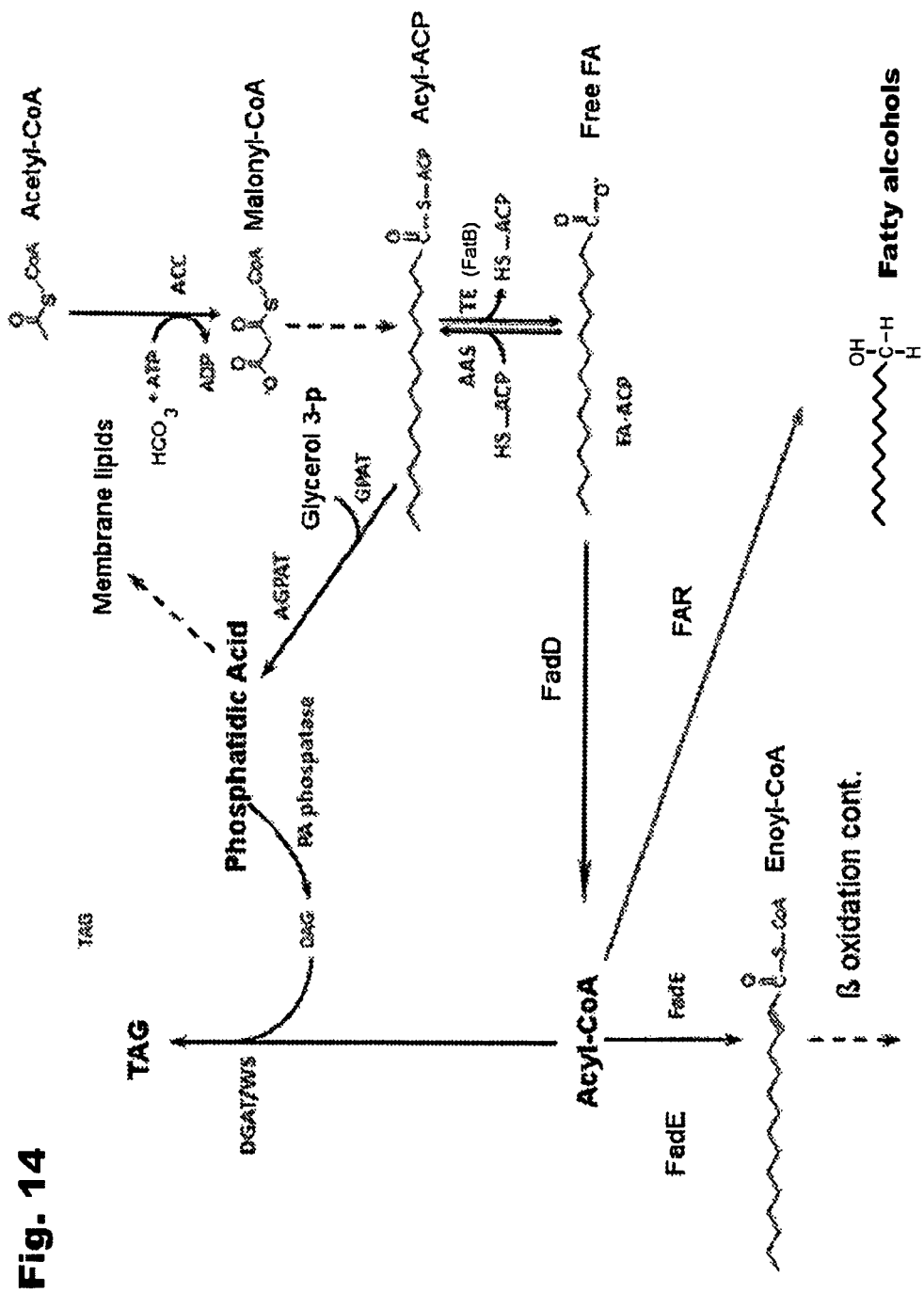

FIG. 14 describes the formation of fatty alcohols in oleaginous bacteria. The role of the fatty acyl-CoA reductases (FAR) gene in the biosynthesis pathway is shown. The *Arabidopsis* genes FAR1 (SEQ ID: 05), FAR2 (SEQ ID: 06) and FAR3 (SEQ ID: 07) were cloned into pSeqCO2 plasmid using the indicated restriction sites to give pSeqCO2::FAR1, pSeqCO2::FAR2, pSeqCO2::FAR3.

Figure 15:
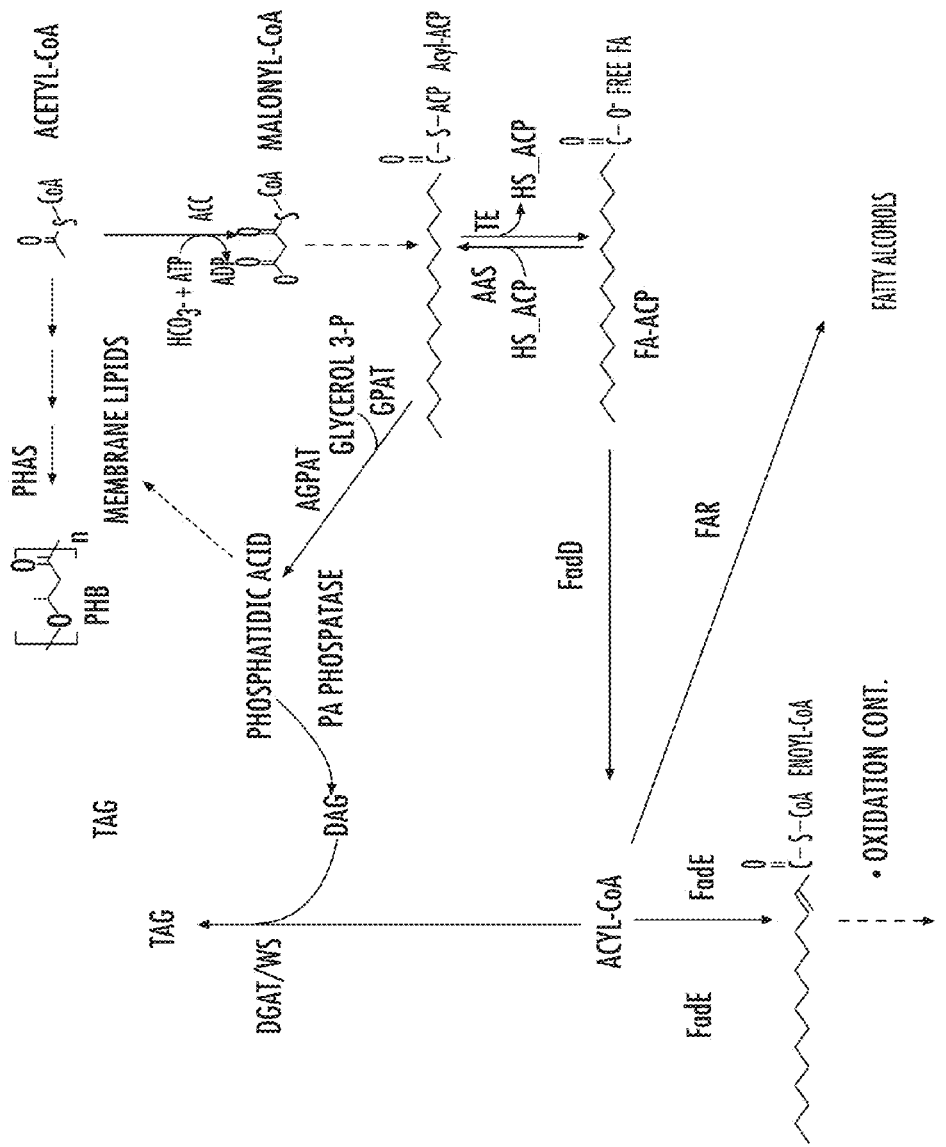

FIG. 15 describes the pathway for formation of fatty alcohols in burkholderiaceae using of the fatty acyl-CoA reductases (FAR) gene.

Figure 16:
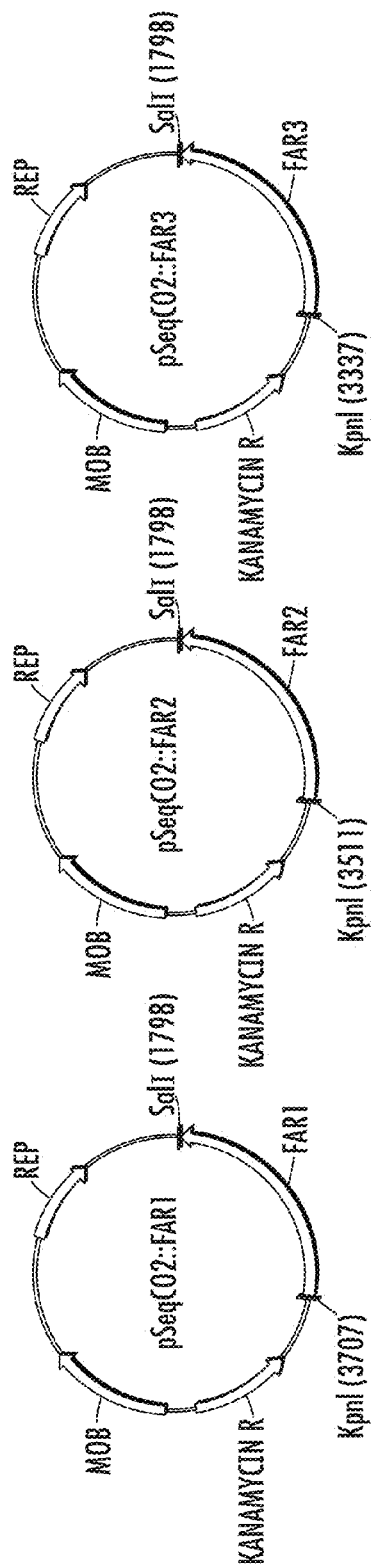

FIG. 16 describes the cloning strategy of FAR gene into pSeqCO2 plasmids. The *Arabidopsis* genes FAR1 (SEQ ID: 05), FAR2 (SEQ ID: 06) and FAR3 (SEQ ID: 07) were cloned into pSeqCO2 plasmid using the indicated restriction sites to give pSeqCO2::FAR1, pSeqCO2::FAR2, pSeqCO2::FAR3.

Figure 17:
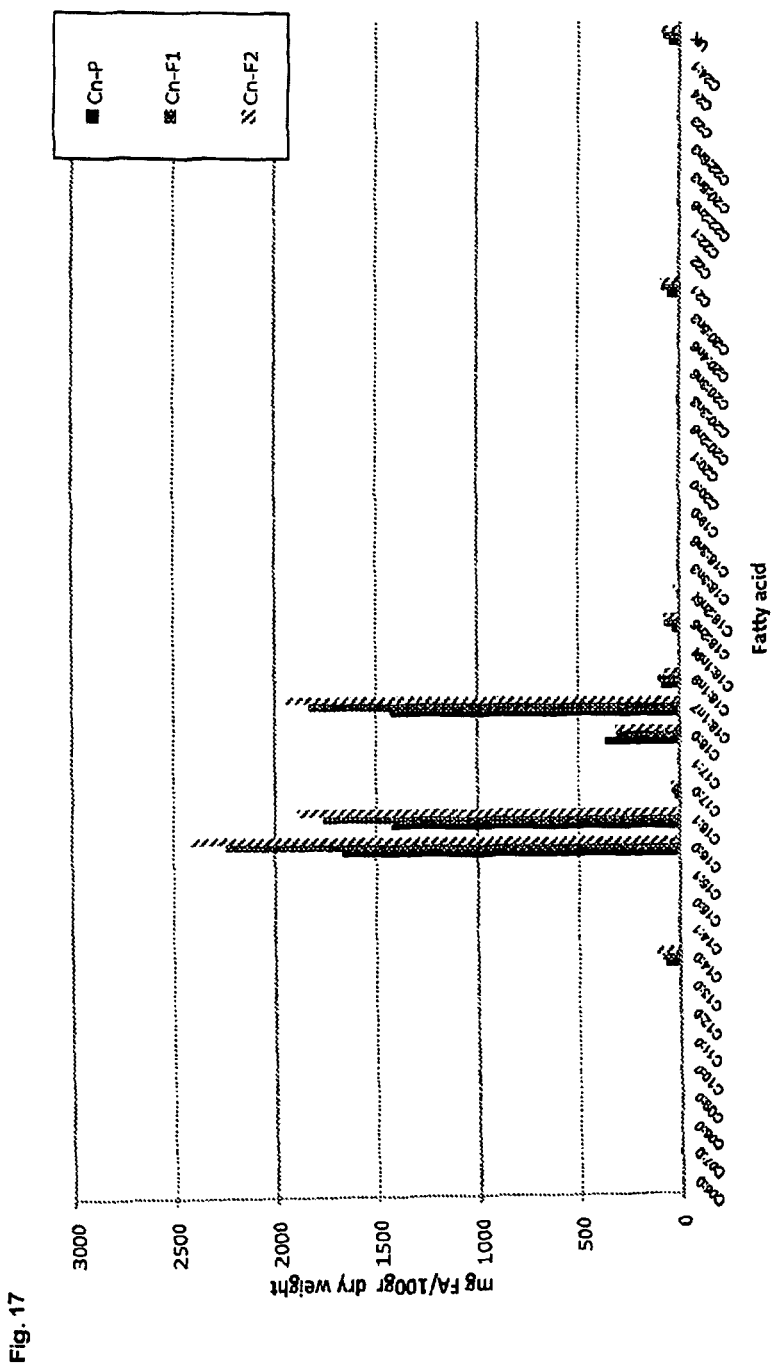

FIG. 17 describes the effect of FAR genes expression on fatty acid synthesis in *Cupriavidus necator*. *C. necator* cells were transformed with pSeqCO2::FAR1 (Cn-F1), pSeqCO2::FAR2 (Cn-F2) and control pSEqCO2 (Cn-P). Cells were harvested (3,000×g for 20 min at 4° C.) and fatty acids were analyzed by gas chromatography.

Figure 18:
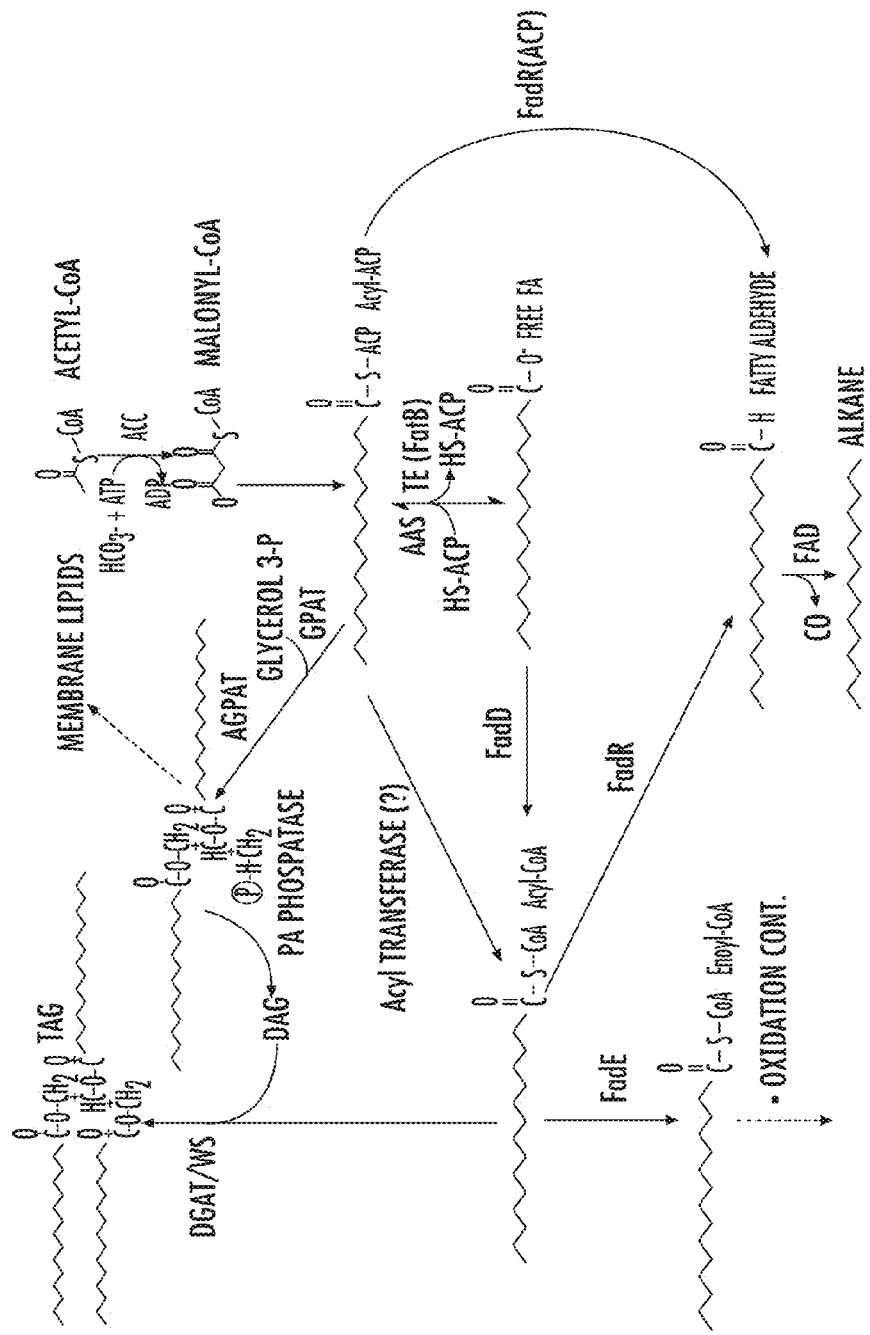

FIG. 18 describes the pathway for formation of hydrocarbons in oleaginous bacteria using the enzymes fatty acid acyl-ACP reductase (FadDR) and fatty acid aldehyde decarbonylase by (FAD) genes. Genes from the cyanobacterium (*Synechocystis* sp. PCC 6803) used in the experiment were FadR (SEQ ID: 08) and FAD (SEQ ID: 09) driven by the *Synechocystis* sp. Rubisco large subunit promoter (SEQ ID: 09) were cloned into pSeqCO2 plasmid using the indicated restriction sites to give pSeqCO2::FUEL.

Figure 19:
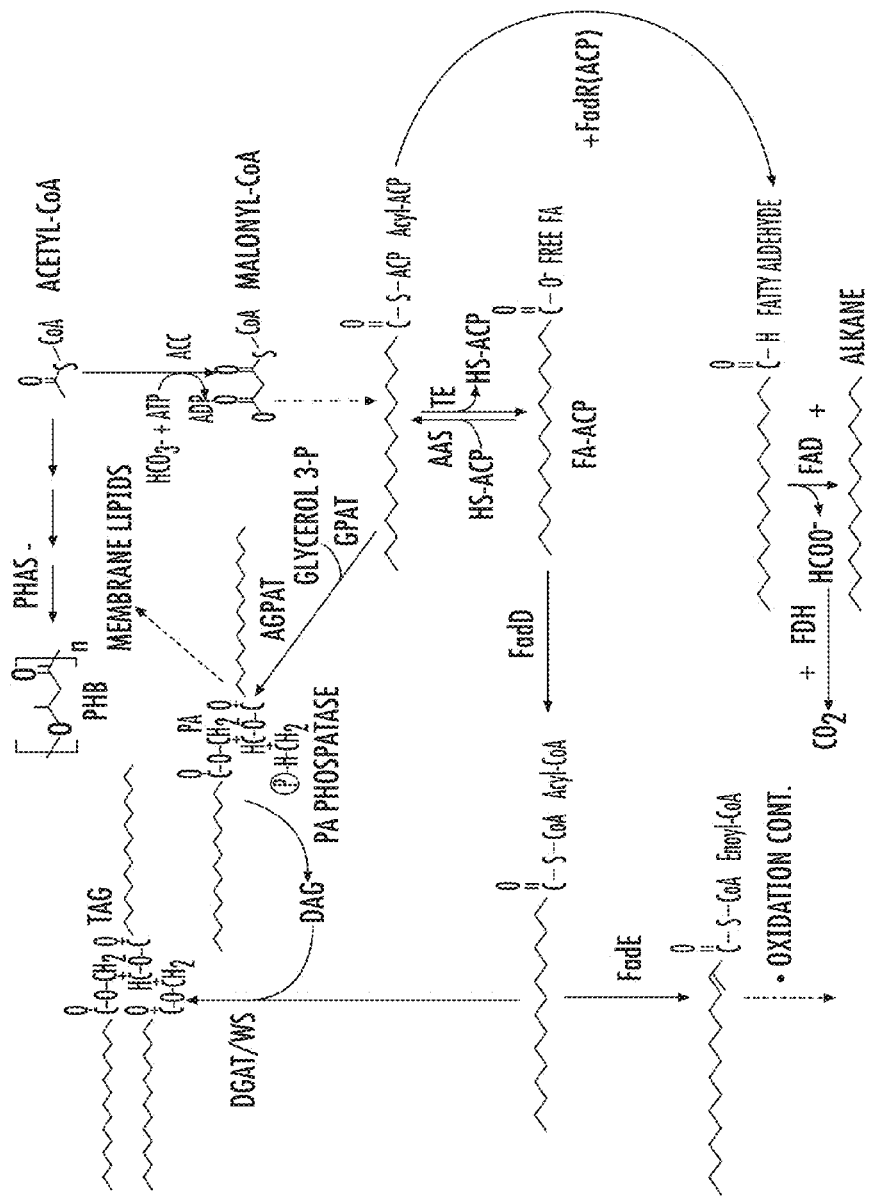
Figure 20:
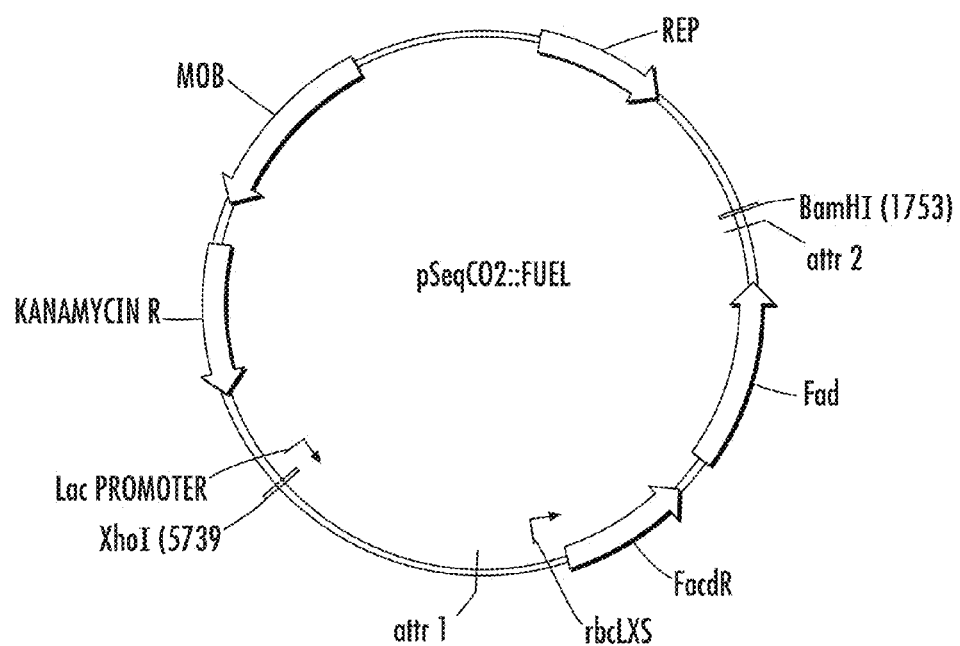

FIG. 19 describes the pathway for formation of hydrocarbons in burkholderiaceae using the enzymes fatty acid acyl-ACP reductase (FadDR) and fatty acid aldehyde decarbonylase by (FAD) genes FIG. 20 describes the restriction map related to the cloning strategy of FadDR and Fad genes into pSeqCO2 plasmid transformed for the experiment. Genes from the cyanobacterium (*Synechocystis* sp. PCC 6803) used in the experiment were FadR (SEQ ID: 08) and FAD (SEQ ID: 09) driven by the *Synechocystis* sp. Rubisco large subunit promoter (SEQ ID: 10) were cloned into pSeqCO2 plasmid using the indicated restriction sites to give pSeqCO2::FUEL.

FIGS. 21A-21B describe the production of Alkanes in *Cupriavidus necator* transformed with pSeqCO2::FUEL (Cn_FUEL2.1) (FIG. 21A) and empty vector (Cn-P) (FIG. 21B). GC chromatogram of hydrocarbon (peaks indicated with label) extracted from transformants grown in 50 ml LB media under previously identified conditions.

FIG. 22 describes the hydrocarbon specific products and distribution (percentage in parentheses) from *Cupriavidus necator* transformed with pSeqCO2::FUEL (Cn_FUEL2.1 and Cn_FUEL2.2) and empty vector (Cn-P).

Figure 23:
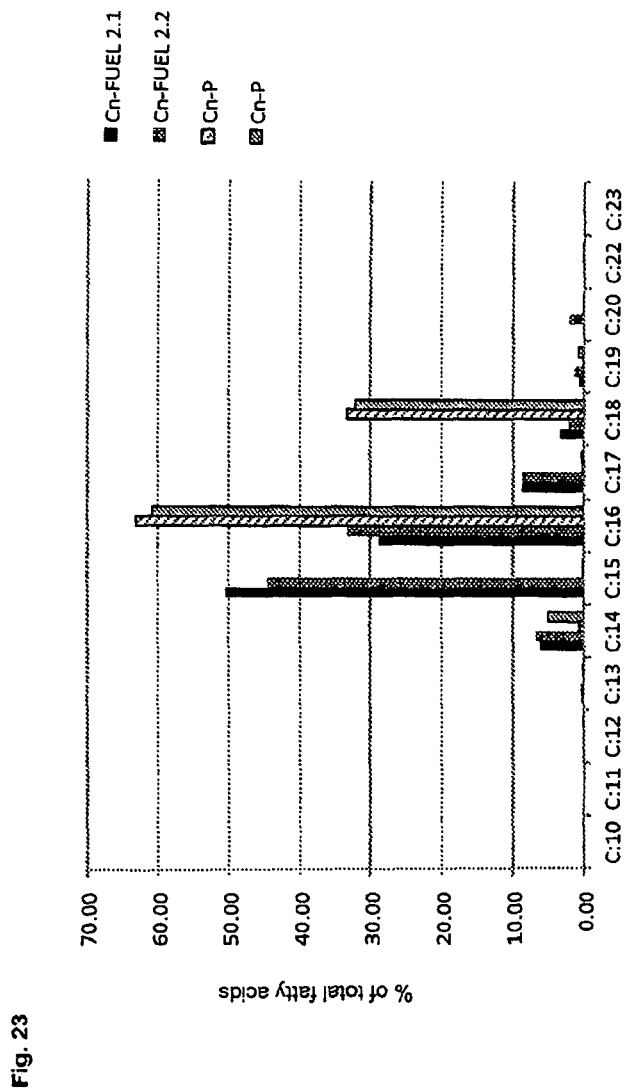

FIG. 23 describes the effect of pSeqCO2::FUEL (Cn_FUEL2.1 and 2.2) and empty vector (Cn-P) on the fatty acids distribution under the experimental conditions described previously.

Figure 24:
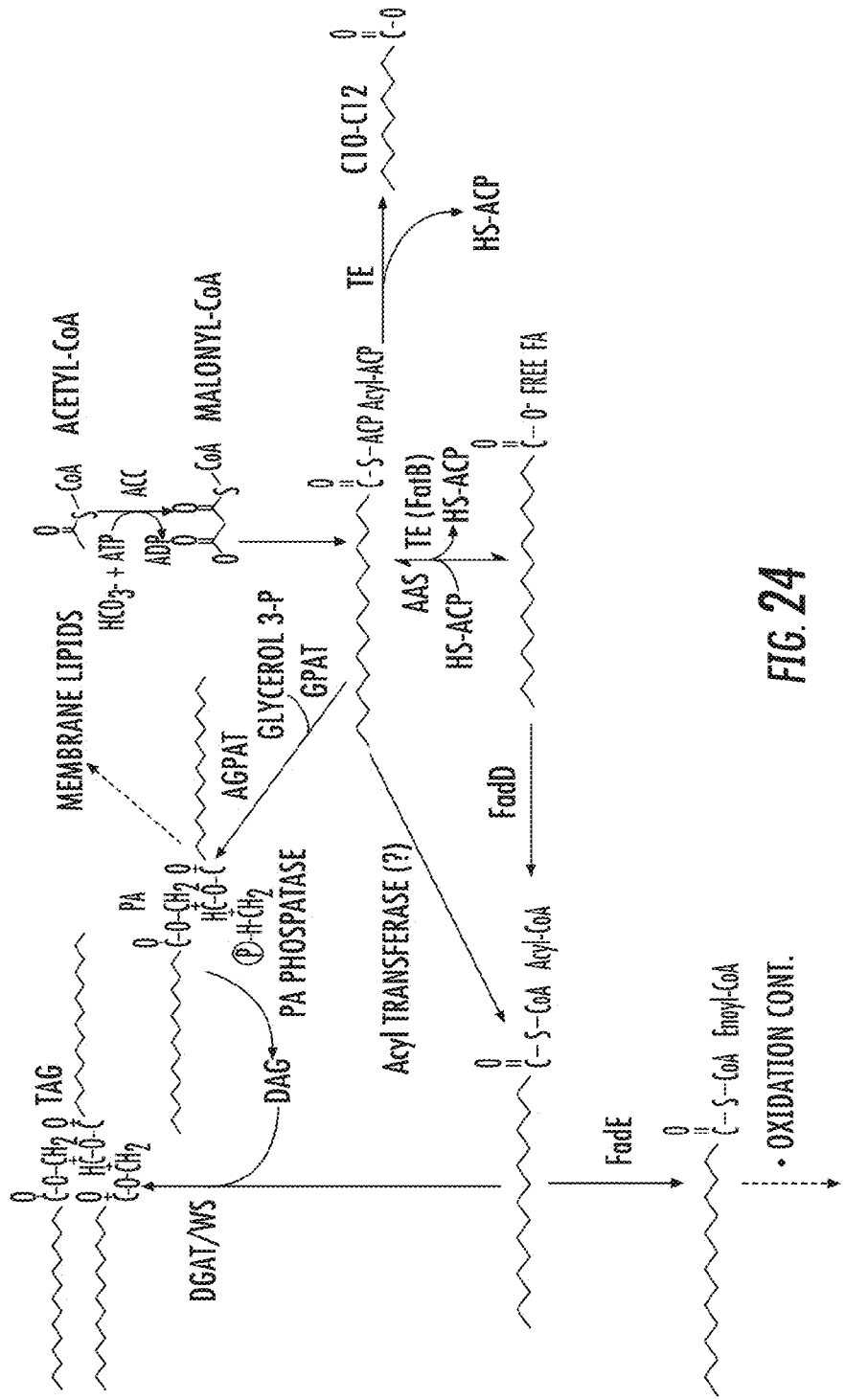

FIG. 24 describes the modification of the fatty acid chain length by the enzymatic action of thioesterase (TE) in oleaginous bacteria.

Figure 25:
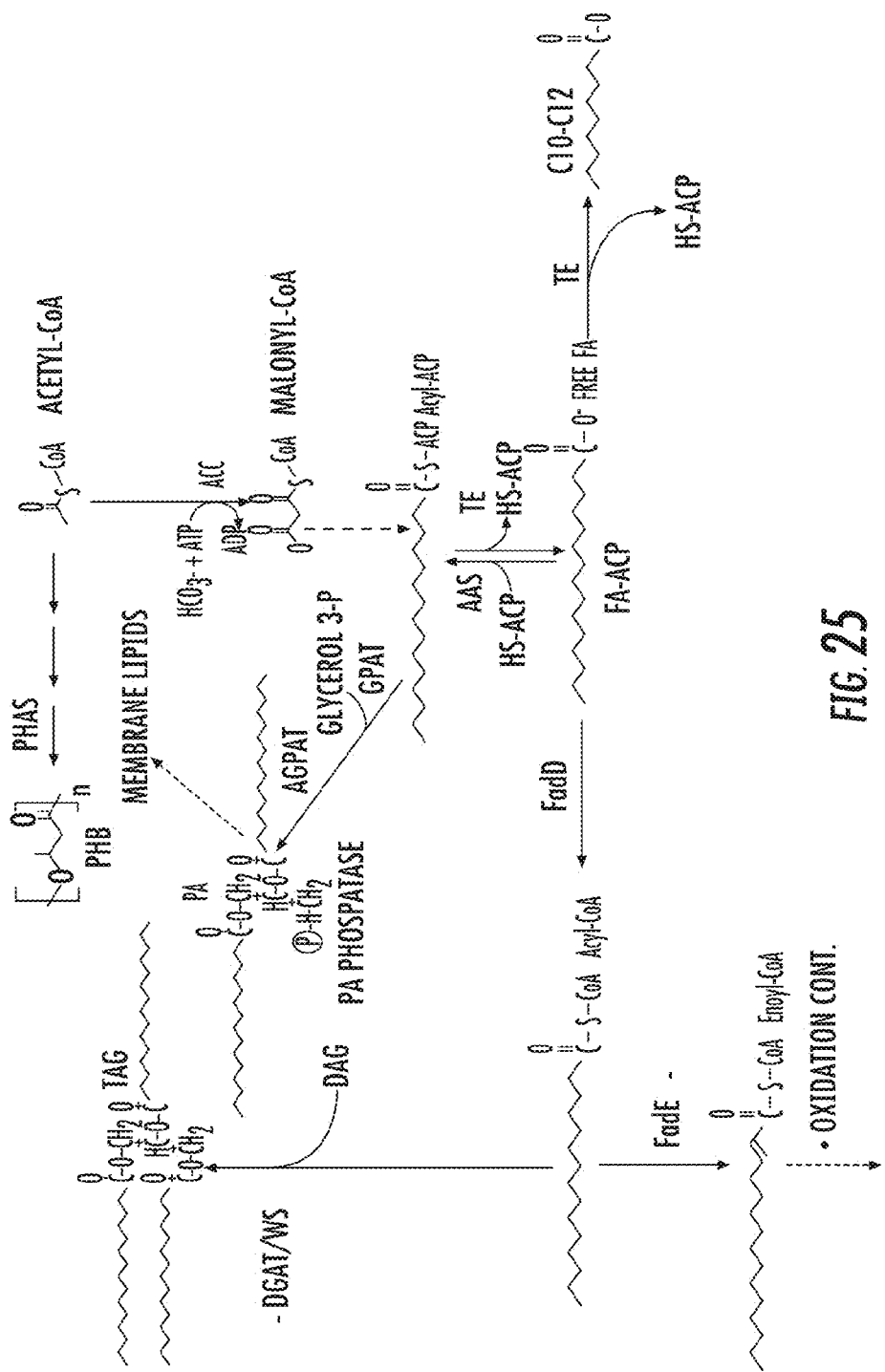

FIG. 25 describes the modification of the fatty acid chain length by the enzymatic action of fatty acyl-ACP thioesterase (TE) in burkholderiaceae.

FIG. 26 describes the similarity of *Rhodococcus opacus* (B4) thioesterases protein sequence (YP_002784058.1) to other organisms. The Genbank accession numbers, amino acid length and % identity of analyzed proteins are indicated.

Figure 27A:
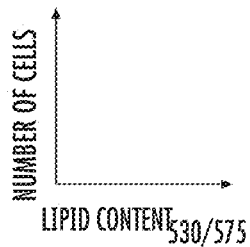
Figure 27B:
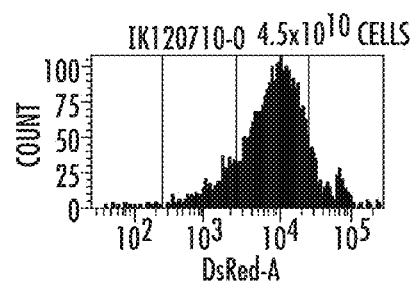
Figure 27C:
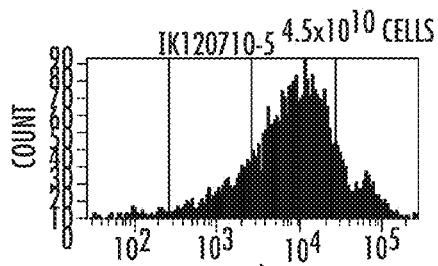

FIGS. 27A-27G describe the fluorescence intensity of *Rhodococcus* Sp exposed to 0, 5, 10, and 20 seconds of (FIG. 27B, FIG. 27C, FIG. 27D and FIG. 27E respectively) of UV light and stained with Nile Red. A legend is shown in FIG. 27A. FACS analysis of untreated cells (negative control; no Nile Red staining and no UV exposure) (FIG. 27F) and mutated population with increased lipid content (FIG. 27G; P3) are shown.

Figure 28:
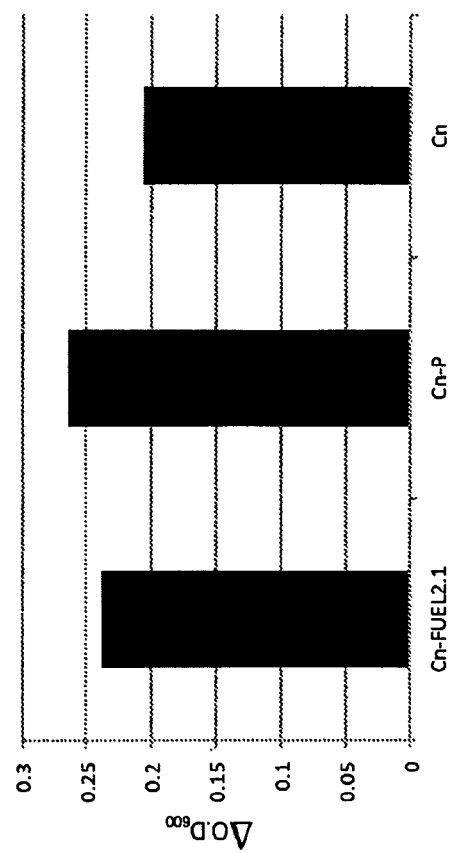

FIG. 28 describes the chemoautotrophic growth of *Cupriavidus necator* transformed with pSeqCO2::FUEL (Cn-FUEL2.1), empty vector (Cn-P) and untransformed (Cn). Bacterial growth was measured at $O.D_{650}$ after 12 days. Media and growth conditions described in FIG. 7.

Figure 29:
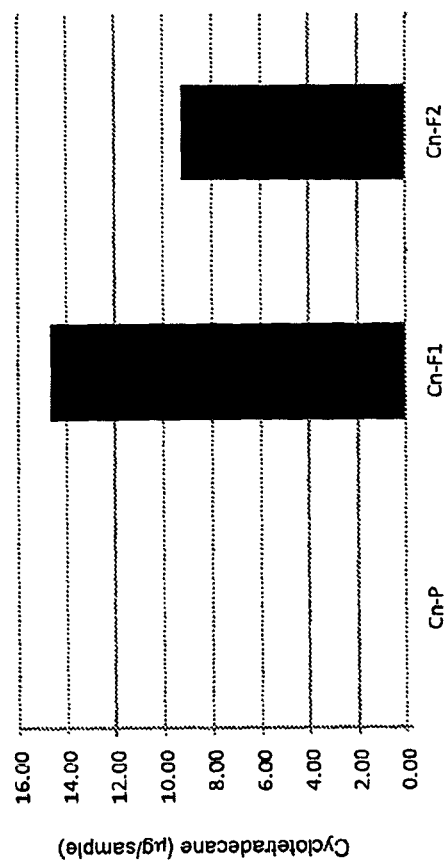
Figure 30:
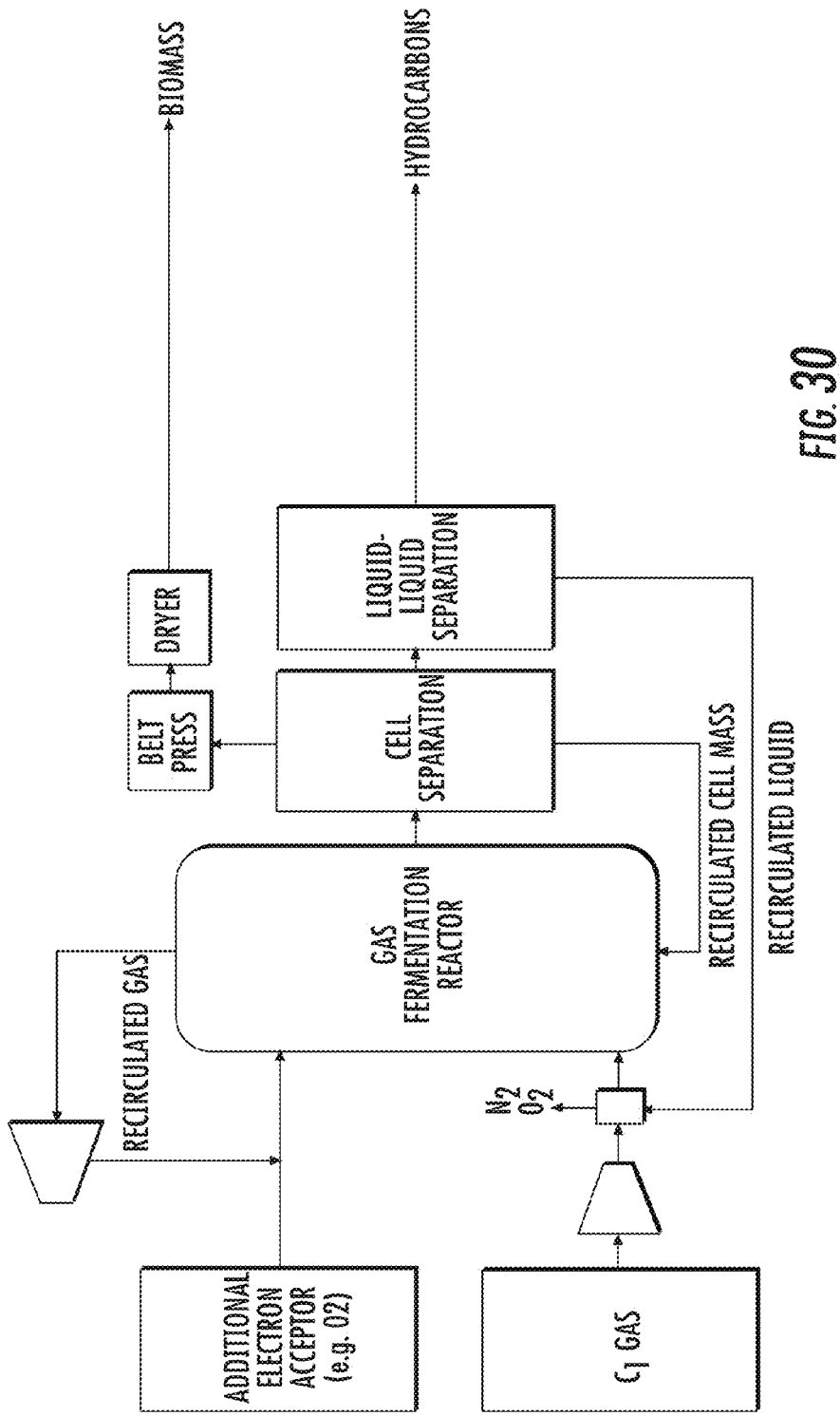

FIG. 29 describes the affect of FAR genes expression on biosynthesis of cyclotetradecane in *Cupriavidus necator*. *C. necator* cells were transformed with pSeqCO2::FAR1 (Cn-F1), pSeqCO2::FAR2 (Cn-F2) and control pSEqCO2 (Cn-P). Cells were harvested (3,000×g for 10 min at 4° C.) and alkanes were analyzed by gas chromatography FIG. 30 shows a schematic block flow diagram of a process for utilizing a gaseous C1 feedstock such as syngas to produce hydrocarbons using the microorganisms of the present invention.

Figure 31:
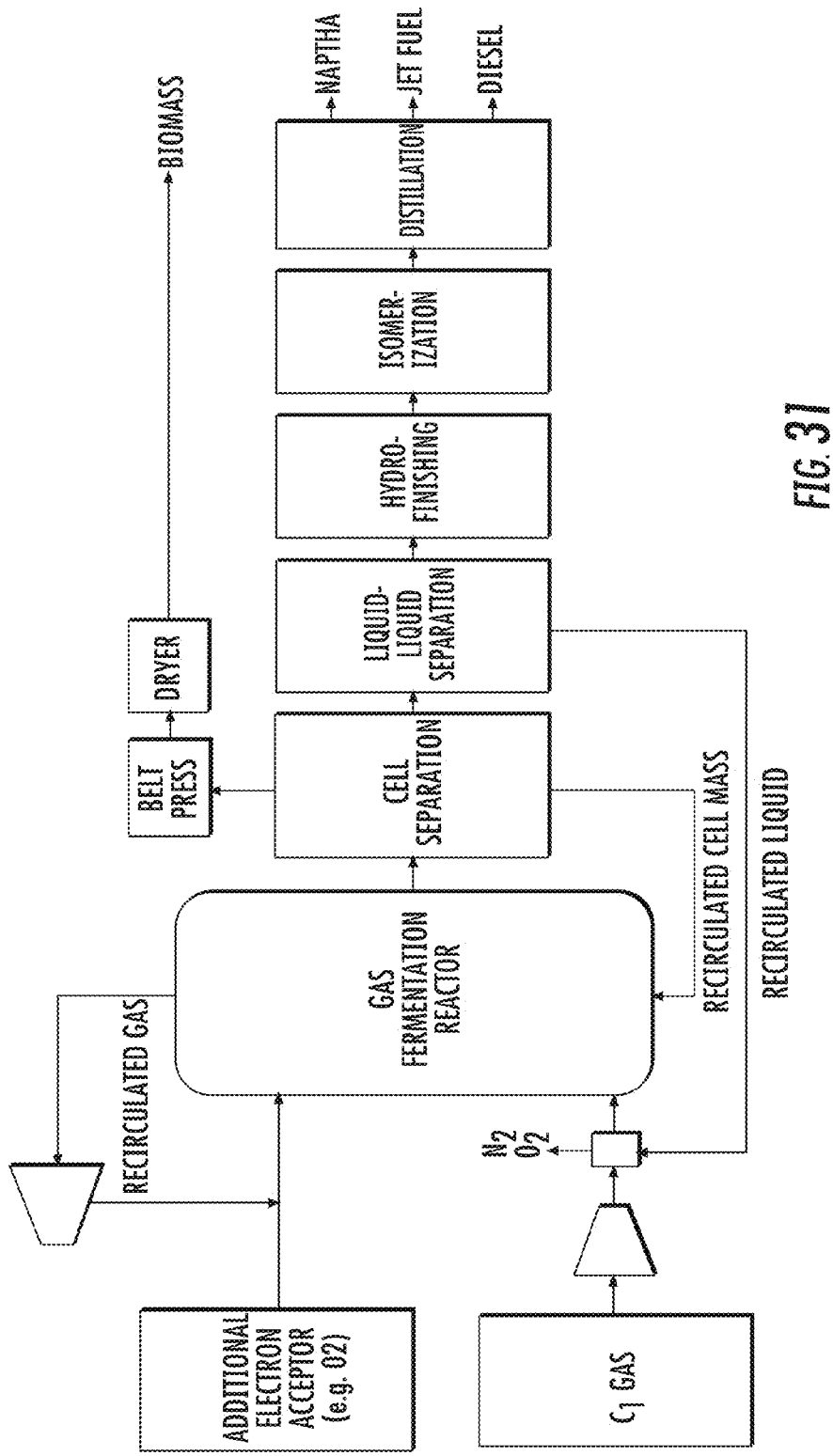

FIG. 31 shows a schematic block flow diagram of a process for utilizing a gaseous C1 feedstock such as syngas to produce lipids using the microorganisms of the present invention with additional post-processing steps converting the lipids to drop-in fuels such as jet fuel and/or diesel.

FIG. 32 shows octadecanoic acid derivatives produced by at least one Kiverdi chemoautotrophic production strain.

Experimental runs for fatty acid percent yields (grams of product/100 grams total fatty acid) from organisms *Rhodococcus opacus* (DSM 44193), *Rhodococcus opacus* (DSM 43205), and *Cupriavidus* necator.

FIG. 33 shows putative 12-hydroxylases culled by word searching Genbank.

FIG. 34 shows genes related to *Vicia sativa* P450 omega hydroxylases.

FIG. 35 shows a list of P450-dependent fatty acid omega hydroxylases.

FIG. 36 shows a list fatty acid hydroxylases.

FIG. 37 shows the percent fatty acid production for plasmid control (TKO4-P), thioesterase expression (TKO4-TE), and fatty acyl-CoA binding protein (TKO4-ACoA-BP).

FIG. 38 shows the percent fatty acid production for fatty acyl-CoA binding protein (TKO4-ACoABP) for T=22C vs. T=30C.

Figure 39A:
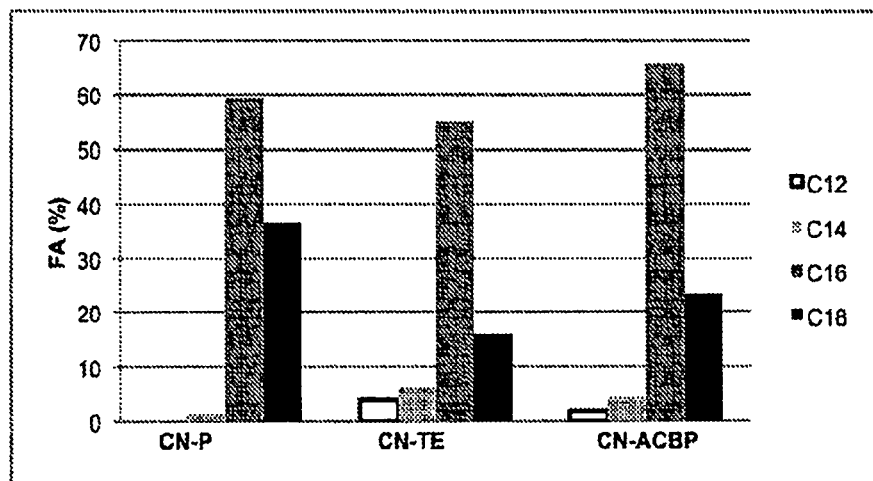
Figure 39B:
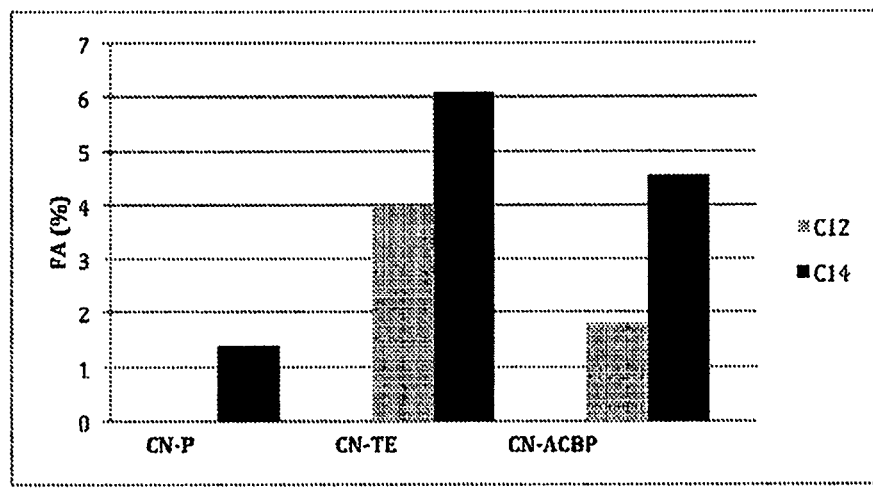

FIGS. 39A-39B show (FIG. 39A) Fatty acid percentages (C12, C14, C16, and C18 chain lengths) for *Cupriavidus necator* (DSM531) organism with control plasmid pSeqCO2 (CN-P), with expression of exogenous thioesterase (CN-TE), and expression of fatty acyl-CoA binding protein (CN-ACBP). (FIG. 39B) Fatty acid percentages (C12 and C14) with expression of exogenous thioesterase (CN-TE), and expression of fatty acyl-CoA binding protein (CN-ACBP) compared with control (CN-P).

Figure 40:
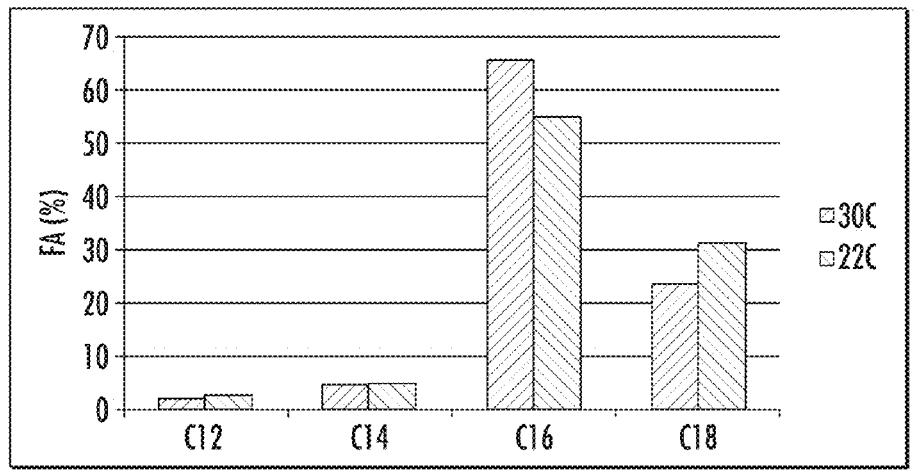

FIG. 40 shows Fatty acid percentages (C12, C14, C16, and C18 chain lengths) for *Cupriavidus* necator expressing ACBP at T=22° C. vs. T=30° C.

Figure 41:
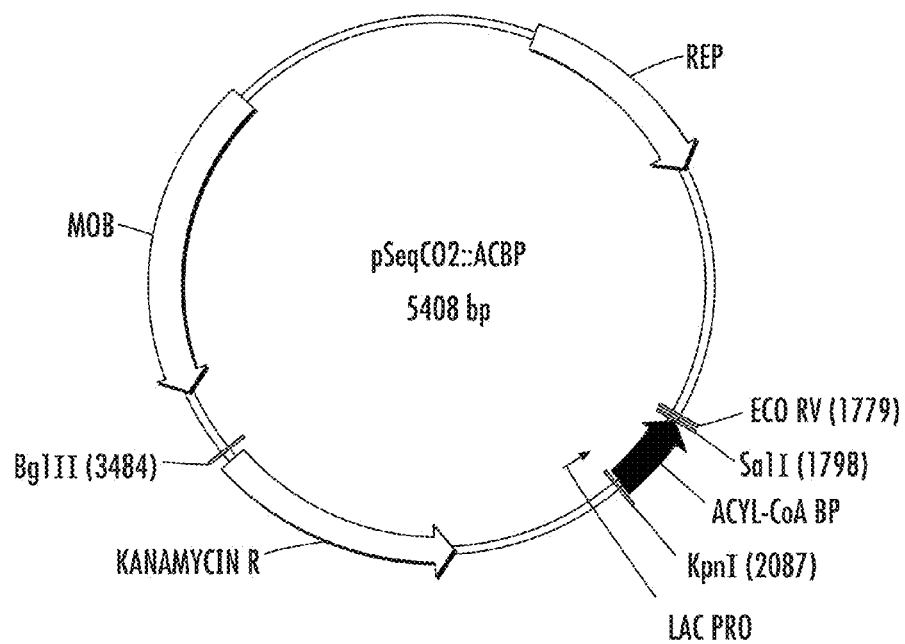

FIG. 41 shows the map of the plasmid pSeqCO2::ACBP. The genetic elements are indicated.

Figure 42:
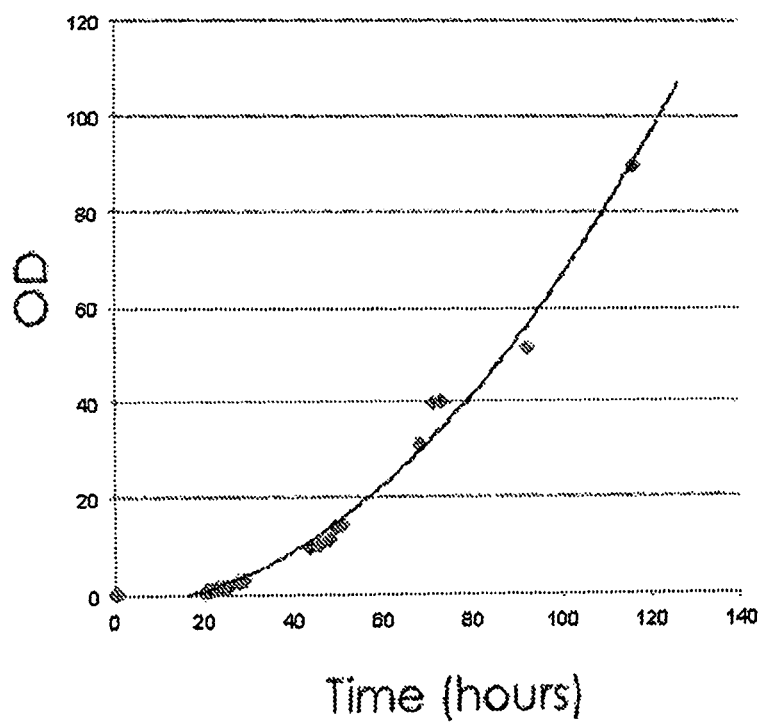

FIG. 42 shows growth (optical density) of *Alcaligenes eutrophus* on H2, CO2 and O2 to a cell density of 35 g/l (dry cell weight). *Alcaligenes eutrophus* was grown microaerobically. Several aspects involve growing *Alcaligenes eutrophus* or other oxyhydrogen microbes, either engineered or not engineered, to a high cell density microaerobically on syngas components (H2, CO2 and/or CO) then switching to anaerobic bioprocessing for the production of 1,3 butandiol and other organic compounds, which are secreted.

FIG. 43 shows 2.3 Butatadiol pathways.

Figure 44:
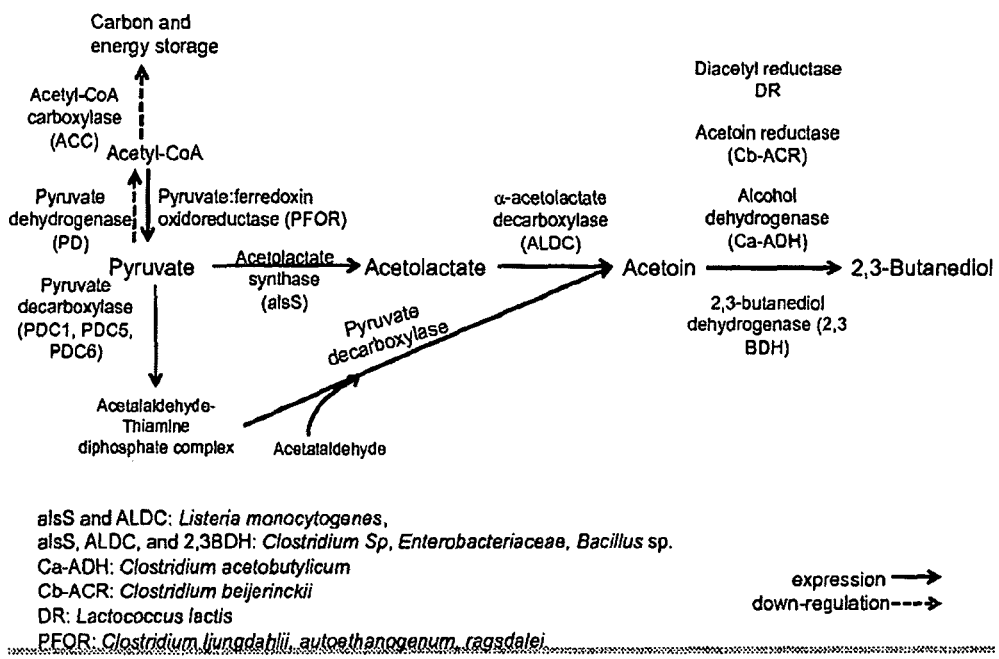

FIG. 44 shows the pathway of introducing BDO metabolic pathway to a organism.

DETAILED DESCRIPTION

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

As used in this specification and the appended claims, the singular forms "a," "an," and "the" include plural referents unless the content clearly dictates otherwise.

The term "about" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The terms "amino acid" refer to a molecule containing both an amine group and a carboxyl group that are bound to a carbon, which is designated the α-carbon. Suitable amino acids include, without limitation, both the D- and L-isomers of the naturally occurring amino acids, as well as non-naturally occurring amino acids prepared by organic synthesis or other metabolic routes. In some embodiments, a single "amino acid" might have multiple sidechain moieties, as available per an extended aliphatic or aromatic backbone scaffold. Unless the context specifically indicates otherwise, the term amino acid, as used herein, is intended to include amino acid analogs.

The term "biodiesel" refers to a biologically produced fatty acid alkyl ester suitable for use as a fuel in a diesel engine.

The term "biomass" refers to a material produced by growth and/or propagation of cells. Biomass may contain cells and/or intracellular contents as well as extracellular material, includes, but is not limited to, compounds secreted by a cell.

The term "bioreactor" or "fermentor" refers to a closed or partially closed vessel in which cells are grown and maintained. The cells may be, but are not necessarily held in liquid suspension. In some embodiments rather than being held in liquid suspension, cells may alternatively be growing and/or maintained in contact with, on, or within another non-liquid substrate including but not limited to a solid growth support material.

The term "catalyst" refers to a chemical actor, such as a molecule or macromolecular structure, which accelerates the speed at which a chemical reaction occurs where a reactant or reactants is converted into a product or products, while the catalyst is not turned into a product itself, or otherwise changed or consumed at the completion of the chemical reaction. After a catalyst participates in one chemical reaction, because it is unchanged, it may participate in further chemical reactions, acting on additional reactants to create additional products. To accelerate a chemical reaction a catalyst decreases the activation energy barrier across the reaction path allowing it to occur at a colder temperature, or faster at a given temperature. In this way a more rapid approach of the system to chemical equilibrium may be achieved. Catalysts subsume enzymes, which are protein catalysts.

The term "cellulosic material" refers to any material with a high amount of cellulose, which is a polysaccharide having the formula $(C_6H_{10}O_5)_n$, that generally consists of a linear chain of hundreds to thousands of β(1→4) linked D-glucose monomers. Sources of cellulosic material include but are not limited to cardboard, cotton, corn stover, paper, lumber chips, sawdust, sugar beet pulp, sugar cane bagasses, and switchgrass.

The term "CoA" or "coenzyme A" refers to an organic cofactor for condensing enzymes involved in fatty acid synthesis and oxidation, pyruvate oxidation, acetyl or other acyl group transfer, and in other acetylation.

The term "cofactor" subsumes all molecules needed by an enzyme to perform its catalytic activity. In some embodiments, the cofactor is any molecule apart from the substrate.

A "conservative amino acid substitution" is one in which the amino acid residue is replaced with an amino acid residue having a similar side chain. Families of amino acid residues having similar side chains have been defined in the art. These families include amino acids with basic side chains (e.g., K, R, H), acidic side chains (e.g., D, E), uncharged polar side chains (e.g., G, N, Q, S, T, Y, C, H), nonpolar side chains (e.g., G, A, V, L, I, P, F, M, W), beta-branched side chains (e.g., T, V, I) and aromatic side chains (e.g., Y, F, W, H). Thus, a predicted nonessential amino acid residue in an amino acid sequence encoded by an exogenous nucleic acid sequence, for example, is replaced with another amino acid residue from the same side chain family. Other examples of acceptable substitutions are substitutions based on isosteric considerations (e.g. norleucine for methionine) or other biochemical properties (e.g. 2-thienylalanine for phenylalanine).

As used herein, "enzyme fragment" is meant to refer to a fragment of an enzyme that includes the sequences sufficient to function substantially similar to the function of the wild-type enzyme upon which the fragment sequence is based. Fragments are generally 10 or more amino acids in length. Some preferred lengths of fatty acid reductase are at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 115, at least 120, at least 125, at least 130, at least 135, at least 140, at least 145, at least 150, at least 155, at least 160, at least 165, at least 170, at least 175, at least 180, at least 185, at least 190, at least 195, at least 200, at least 205, at least 210 at least 215, at least 220, at least 225, least 230 at least 235, at least 240, at least 245, at least 250, at least 255, at least 260, at least 265, at least 270, at least 275, at least 280, at least 285, at least 290, at least 295, at least 300, at least 305, at least 310, at least 315, at least 320, at least 325, at least 330, at least 335, at least 340, at least 345, at least 350, at least 355, at least 360, at least 365, at least 370, at least 375, at least 380, at least 385, at least 390, at least 395, at least 400, at least 405, at least 410, at least 415, at least 420, at least 425, or at least 430 amino acids in length. Some preferred lengths of fatty acid reductase fragments are 15 or fewer, 20 or fewer, 25 or fewer, 30 or fewer, 35 or fewer, 40 or fewer, 45 or fewer, 50 or fewer, 55 or fewer, 60 or fewer, 65 or fewer, 70 or fewer, 75 or fewer, 80 or fewer, 85 or fewer, 90 or fewer, 95 or fewer, 100 or fewer, 105 or fewer, 110 or fewer, 115 or fewer, 120 or fewer, 125 or fewer, 130 or fewer, 135 or fewer, 140 or fewer, 145 or fewer, 150 or fewer, 155 or fewer, 160 or fewer, 165 or fewer, 170 or fewer, 175 or fewer, 180 or fewer, 185 or fewer, 190 or fewer, 195 or fewer, 200 or fewer, 205 or fewer, 210 or fewer, 215 or fewer, 220 or fewer, 225 or fewer, 230 or fewer, 235 or fewer, 240 or fewer, 245 or fewer, 250 or fewer, 255 or fewer, 260 or fewer, 265 or fewer, 270 or fewer, 275 or fewer, 280 or fewer, 285 or fewer, 290 or fewer, 295 or fewer, 300 or fewer, 305 or fewer, 310 or fewer, 315 or fewer, 320 or fewer, 325 or fewer, 330 or fewer, 335 or fewer, 340 or fewer, 345 or fewer, 350 or fewer, 355 or fewer, 360 or fewer, 365 or fewer, 370 or fewer, 375 or fewer, 380 or fewer, 385 or fewer, 390 or fewer, 395 or fewer, 400 or fewer, 415 or fewer, 420 or fewer, 425 or fewer, 430 or fewer, or 435 or fewer. Some preferred lengths of fatty acid decarbonylase are at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 115, at least 120, at least 125, at least 130, at least 135, at least 140, at least 145, at least 150, at least 155, at least 160, at least 165, at least 170, at least 175, at least 180, at least 185, at least 190, at least 195, at least 200, at least 205, at least 210 at least 215, at least 220, at least 225, least 230 at least 235, at least 240, at least 245, at least 250, at least 255, at least 260, at least 265, at least 270, at least 275, at least 280, at least 285, at least 290, at least 295, at least 300, at least 305, at least 310, at least 315, at least 320, at least 325, at least 330, at least 335, at least 340, at least 345, at least 350, at least 355, at least 360, at least 365, at least 370, at least 375, at least 380, at least 385, at least 390, at least 395, at least 400, at least 405, at least 410, at least 415, or at least 420 amino acids long. In some embodiments, the lengths of the fatty acid decarbonylase fragments are 15 or fewer, amino acids, 20 or fewer, 25 or fewer, 30 or fewer, 35 or fewer, 40 or fewer, 45 or fewer, 50 or fewer, 55 or fewer, 60 or fewer, 65 or fewer, 70 or fewer, 75 or fewer, 80 or fewer, 85 or fewer, 90 or fewer, 95 or fewer, 100 or fewer, 105 or fewer, 110 or fewer, 115 or fewer, 120 or fewer, 125 or fewer, 130 or fewer, 135 or fewer, 140 or fewer, 145 or fewer, 150 or fewer, 155 or fewer, 160 or fewer, 165 or fewer, 170 or fewer, 175 or fewer, 180 or fewer, 185 or fewer, 190 or fewer, 195 or fewer, 200 or fewer, 205 or fewer, 210 or fewer, 215 or fewer, 220 or fewer, 225 or fewer, 230 or fewer, 235 or fewer, 240 or fewer, 245 or fewer, 250 or fewer, 255 or fewer, 260 or fewer, 265 or fewer, 270 or fewer, 275 or fewer, 280 or fewer, 285 or fewer, 290 or fewer, 295 or fewer, 300 or fewer, 305 or fewer, 310 or fewer, 315 or fewer, 320 or fewer, 325 or fewer, 330 or fewer, 335 or fewer, 340 or fewer, 345 or fewer, 350 or fewer, 355 or fewer, 360 or fewer, 365 or fewer, 370 or fewer, 375 or fewer, 380 or fewer, 385 or fewer, 390 or fewer, 395 or fewer, 400 or fewer, 415 or fewer, 422 or fewer. Some preferred lengths of thioesterase fragments are at least 10 amino acids, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 115, at least 120, at least 125, at least 130, at least 135, at least 140, at least 145, at least 150, at least 155, at least 160, at least 165, at least 170, at least 175, at least 180, at least 185, at least 190, at least 195, at least 200, at least 205, at least 210 at least 215, at least 220, at least 225, least 230 at least 235, at least 240, at least 245, at least 250 or at least 255. Some preferred lengths of thioesterase fragments are 15 or fewer, 20 or fewer, 25 or fewer, 30 or fewer, 35 or fewer, 40 or fewer, 45 or fewer, 50 or fewer, 55 or fewer, 60 or fewer, 65 or fewer, 70 or fewer, 75 or fewer, 80 or fewer, 85 or fewer, 90 or fewer, 95 or fewer, 100 or fewer, 105 or fewer, 110 or fewer, 115 or fewer, 120 or fewer, 125 or fewer, 130 or fewer, 135 or fewer, 140 or fewer, 145 or fewer, 150 or fewer, 155 or fewer, 160 or fewer, 165 or fewer, 170 or fewer, 175 or fewer, 180 or fewer, 185 or fewer, 190 or fewer, 195 or fewer, 200 or fewer, 205 or fewer, 210 or fewer, 215 or fewer, 220 or fewer, 225 or fewer, 230 or fewer, 235 or fewer, 240 or fewer, 245 or fewer, 250 or fewer, 255 or fewer or 260 or fewer amino acids. As used in the paragraph herein reference to preferred fragment sizes are intended to refer to all permutation of ranges between at least and less than such as ranges may be any number set forth as an "at least" size to any number set forth as an "less than t" size in order to provide a range of sizes such as 20-400, 20-30, 40-100, etc.

The terms "exogenous gene" or "exogenous nucleic acid" means a nucleic acid that has been recombinantly introduced into a cell, which encodes the synthesis of RNA and/or protein. In some embodiments, the exogenous gene is introduced by transformation. In some embodiments, the exogenous gene is introduced into the cell by electroporation. A transformed cell may be referred to as a recombinant cell, into which additional exogenous gene(s) may be introduced. The exogenous gene put into the host species may be taken from a different species (this is called heterologous), or it may naturally occur within the same species (this is homologous as defined below). Therefore, exogenous genes subsume homologous genes that are integrated within or introduced to regions of the genome, episome, or plasmid that differ from the locations where the gene naturally occurs. Multiple copies of the exogenous gene may be introduced into the cell. An exogenous gene may be present in more than one copy within the host cell or transformed cell. In some embodiments, the microorganism comprises between and including 1 and 1,000 copies of the nucleic acid that encodes an exogenous protein. In some embodiments, the microorganism comprises between and including 1 and 10,000 copies of the nucleic acid that encodes an exogenous protein. In some embodiments, the microorganism comprises between and including 1 and 500 copies of the nucleic acid that encodes an exogenous protein. In some embodiments, the exogenous gene is maintained by a cell as an insertion into the genome or as an episomal molecule. In some embodiments, the microorganism comprises no more than 1, 2, 3, 4, 5, 6, 7, 8, 9, 10, 20, 30, 40, 50, 60, 70, 80, 90, 100, or 1000 copies of the one or more nucleic acids that encode one or more exogenous proteins.

As used herein, the term "expressible form" refers to gene constructs that contain the necessary regulatory elements operably linked to a coding sequence that encodes an enzyme or fragment thereof capable of conferring enzymatic activity to a cell, such that when present in the cell, the coding sequence will be expressed. In some embodiments of the invention, the composition comprising the microorganisms or bacterial cells of the present invention comprise no more than ten expressible forms of exogenous nucleic acid sequences. In some embodiments of the invention, the composition comprising the microorganisms or bacterial cells of the present invention comprise no more than nine expressible forms of exogenous nucleic acid sequences. In some embodiments of the invention, the composition comprising the microorganisms or bacterial cells of the present invention comprise no more than eight expressible forms of exogenous nucleic acid sequences. In some embodiments of the invention, the composition comprising the microorganisms or bacterial cells of the present invention comprise no more than seven expressible forms of exogenous nucleic acid sequences. In some embodiments of the invention, the composition comprising the microorganisms or bacterial cells of the present invention comprise no more than six expressible forms of exogenous nucleic acid sequences. In some embodiments of the invention, the composition comprising the microorganisms or bacterial cells of the present invention comprise no more than five expressible forms of exogenous nucleic acid sequences. In some embodiments of the invention, the composition comprising the microorganisms or bacterial cells of the present invention comprise no more than four expressible forms of exogenous nucleic acid sequences. In some embodiments of the invention, the composition comprising the microorganisms or bacterial cells of the present invention comprise no more than three expressible forms of exogenous nucleic acid sequences. In some embodiments of the invention, the composition comprising the microorganisms or bacterial cells of the present invention comprise no more than two expressible forms of exogenous nucleic acid sequences. In some embodiments of the invention, the composition comprising the microorganisms or bacterial cells of the present invention comprise no more than one expressible form of an exogenous nucleic acid sequences. In other embodiments of the invention, the composition comprising the microorganisms or bacterial cells of the present invention comprises more than ten expressible forms of exogenous nucleic acid sequences.

SEQ ID NO: 1 refers to Sequesco plasmid sequence 1.
SEQ ID NO:2 refers to Sequesco plasmid sequence 2.
SEQ ID NO: 3 refers to Sequesco plasmid Ver1 plasmid sequence.
SEQ ID NO:4 refers to Sequesco plasmid Ver2 plasmid sequence.

SEQ ID NO:5 refers to *Arabidopsis* gene FAR1.
SEQ ID NO: 6 refers to *Arabidopsis* gene FAR2.
SEQ ID NO: 7 refers to *Arabidopsis* gene FAR3.
SEQ ID NO:8 refers to cyanobacterium FadR.
SEQ ID NO:9 refers to cyanobacterium FAD.
SEQ ID NO: 10 refers to cyanobacterium Rubisco large subunit promoter
SEQ ID NO: 11, refers to the 16S rRNA sequence from the genus *Rhodococcus opacus* DSM43205
SEQ ID NO: 12 refers to the 16S rRNA sequence from the genus *Rhodococcus opacus* B4.
SEQ ID NO: 13 refers to the 16S rRNA sequence from the genus *Ralstonia*.
SEQ ID NO: 14 refers to *Rhodococcus opacus* TE The terms "fatty acyl-ACP thioesterase" (TE) mean an enzyme that catalyzes the cleavage of a fatty acid from an acyl carrier protein (ACP) during lipid synthesis.

The terms "fatty acyl-CoA reductase" (FAR) refers to an enzyme catalyzing the reaction that produces a fatty alcohol from an acyl-CoA molecule by reduction.

The terms "fatty acyl-ACP/acyl-CoA reductase" (FadR) refers to an enzyme catalyzing the reaction that produces a fatty aldehyde from an acyl-ACP or acyl-CoA molecule by reduction.

The terms "fatty aldehyde decarbonylase" (FAD) refers to an enzyme catalyzing the reaction that produces an alkane from a fatty aldehyde molecule by decarbonylization.

The terms "fatty aldehyde reductase" refers to an enzyme catalyzing the reaction that produces a fatty alcohol from a fatty aldehyde molecule by reduction.

As used herein, the term "functional fragment" is meant to refer to a fragment of any polypeptide or amino acid sequence that is encoded by an exogenous nucleic acid sequence of the present invention which retains its ability to function like the amino acid sequence to which the fragment is homologous. Functional fragments of enzymes are at least about 5 amino acids in length derived from enzyme and may comprise non-wild-type amino acid sequences. One having ordinary skill in the art can readily determine whether a protein or peptide is a functional fragment of a particular amino acid sequence by examining its sequence and testing its ability to function in a fashion similar to that function of the amino acid sequence upon which the fragment is based. Truncated versions of exogenous proteins may be prepared and tested using routine methods and readily available starting material. As used herein, the term "functional fragment" is also meant to refer to peptides, polypeptides, amino acid sequence linked by non-peptidal bonds, or proteins which comprise an amino acid sequence that is identical or substantially homologous to at least a portion of the exogenous amino acid sequence and which are capable of functioning in a similar function to the exogenous amino acid sequence to which the fragment is homologous. The term "substantially homologous" refers to an amino acid sequence that has conservative substitutions. One having ordinary skill in the art can produce functional fragments of the FAR, FadD, FAD, thioesterase, cytochrome P450 enzyme, desaturase, and hydroxylase amino acid sequences following the disclosure provided herein and well known techniques. The functional fragments thus identified may be used and formulated in place of full length FAR, FadD, FAD, thioesterase, cytochrome P450 enzyme, desaturase, and hydroxylase without undue experimentation.

The term "gasification" refers to a generally high temperature (>700° C.) process that converts carbonaceous materials into a mixture of gases including hydrogen, carbon monoxide, and carbon dioxide called syngas or producer gas. The process generally involves partial combustion and/or the application of externally generated heat along with the controlled addition of oxygen and/or steam.

As used herein, "homologous" refers to the sequences homology between two nucleic acid sequences or two amino acid sequences. Two nucleic acid sequences or two amino acid sequences that are sufficiently homologous to retain immunogenic function are "homologues." Sequence homology for nucleotides and amino acids may be determined using FASTA, BLAST and Gapped BLAST (Altschul et al., Nuc. Acids Res., 1997, 25, 3389, which is incorporated herein by reference in its entirety) and PAUP* 4.0b10 software (D. L. Swofford, Sinauer Associates, Massachusetts). "Percentage of similarity" is calculated using PAUP* 4.0b10 software (D. L. Swofford, Sinauer Associates, Massachusetts). The average similarity of the enzymatic sequence or 16S rRNA sequence is calculated compared to all sequences in the phylogenic tree. Briefly, the BLAST algorithm, which stands for Basic Local Alignment Search Tool is suitable for determining sequence similarity (Altschul et al., J. Mol. Biol., 1990, 215, 403410, which is incorporated herein by reference in its entirety). Software for performing BLAST analyses is publicly available though the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighborhood word score threshold (Altschul et al., supra). These initial neighborhood word hits act as seeds for initiating searches to find HSPs containing them. The word hits are extended in both directions along each sequence for as far as the cumulative alignment score can be increased. Extension for the word hits in each direction are halted when: 1) the cumulative alignment score falls off by the quantity X from its maximum achieved value; 2) the cumulative score goes to zero or below, due to the accumulation of one or more negative-scoring residue alignments; or 3) the end of either sequence is reached. The Blast algorithm parameters W, T and X determine the sensitivity and speed of the alignment. The Blast program uses as defaults a word length (W) of 11, the BLOSUM62 scoring matrix (see Henikoff et al., Proc. Natl. Acad. Sci. USA, 1992, 89, 10915-10919, which is incorporated herein by reference in its entirety) alignments (B) of 50, expectation (E) of 10, M=5, N=4, and a comparison of both strands. The BLAST algorithm (Karlin et al., Proc. Natl. Acad. Sci. USA, 1993, 90, 5873-5787, which is incorporated herein by reference in its entirety) and Gapped BLAST perform a statistical analysis of the similarity between two sequences. One measure of similarity provided by the BLAST algorithm is the smallest sum probability (P(N)), which provides an indication of the probability by which a match between two nucleotide sequences would occur by chance. For example, a nucleic acid is considered similar to another if the smallest sum probability in comparison of the test nucleic acid to the other nucleic acid is less than about 1, preferably less than about 0.1, more preferably less than about 0.01, and most preferably less than about 0.001.

The term "hydrocarbon" refers to a molecule composed exclusively of carbon and hydrogen atoms with the carbons bonded covalently in a branched, cyclic, linear, or partially cyclic chain and with hydrogen atoms covalently bonded to the carbons such that the chemical octet rule for the carbons is generally satisfied. In some hydrocarbons there may occur some number of double or triple bonds between adjacent carbon atoms in the chain. Thus, the label hydrocarbon subsumes branched, cyclic, linear, branched, or partially cyclic alkanes (also called paraffins), alkenes (also called olefins), and alkynes. The structure of hydrocarbon molecules range from the smallest, methane ($CH_4$), a primary component of natural gas, to high molecular weight complex molecules including asphaltenes present in bitumens crude oil, and petroleum. Other examples include dodecane (C12), hexadecane (C16), or octadecane (C18) etc. Hydrocarbons of the present invention may be in gaseous, liquid, or solid phases, either as singly or in multiply coexisting phases. In some embodiments, the hydrocarbons are selected from one or more of the following: linear, branched, cyclic, or partially cyclic alkanes, alkenes, alkynes, lipids, and paraffin. In some embodiments the hydrocarbon are selected from one or more of the following: octane, squalene Spiro[4.5]decane, Bicyclo[10.8.0]eicosane, cis,cis-1,6-Dimethylspiro[4.5]decane, 1,19-Eicosadiene, Cyclooctacosane, Bicyclo[10.8.0] eicosane, 1-Pentadecyne, 1-Pentadecyne, Heptacosyl acetate, 5-Cyclohexyl-1-pentene, 1-Hexadecyne and Cyclodecacyclotetradecane, -eicosahydro.

The term "hydrophobic fraction" gives the fraction of matter that has low solubility in water and greater solubility in a hydrophobic phase than in an aqueous phase. In some embodiments, the hydrophobic fraction is non-polar. In some embodiments, the genetically modified bacterial cells described herein increase the hydrophobic fraction in a cell as compared to the same cell that is not genetically modified.

The term "improve lipid yield" refers to an increase in the lipid production of an organism through any means. In some embodiments, the increase is caused by raising the cell dry weight density of a microbial culture and/or raising the fraction of cell mass that is composed of lipid and/or reducing the cell doubling time and/or the biomass doubling time, resulting in an overall increase in the lipid production rate per unit volume.

The terms "jet fuel" means a fuel useful for igniting in the engine of an aircraft comprising a mixture of kerosene (mixture of C9-C16 alkanes of a certain percentage) combined with typical additives. In some embodiments the jet fuel may comprise a mixture of ingredients specified by the Jet A-1, Jet A, Jet B, JP1, JP-2, JP-3, JP-4, JP-5, JP-6, JP-7, JP-8, or other similar compositions. In some embodiments, the jet fuels comprise at least one or more typical additive chosen from antioxidants (including phenolic antioxidants), static inhibitors, corrosion inhibitors, fuel system icing inhibitors, lubrication improvers, biocides, and thermal stability improvers (DOD 1992; IARC 1989; Pearson 1988). These additives are used only in specified amounts, as governed by military specifications (DOD 1992; IARC 1989). Straight-run kerosene, the basic component of the kerosene used for jet fuels, consists of hydrocarbons with carbon numbers mostly in the C9-C16 range. Like all jet fuels, straight-run kerosene consists of a complex mixture of aliphatic and aromatic hydrocarbons (LARC 1989). Aliphatic alkanes (paraffins) and cycloalkanes (naphthenes) are hydrogen saturated, clean burning, and chemically stable and together constitute the major part of kerosene (IARC 1989). In some embodiments, the jet fuel comprises from between about 10%-20% aromatics and less than 1% of olefins. In some embodiments, the boiling range of the jet fuels is well above the boiling point of benzene. In some embodiments, the jet fuel comprises less than or equal to 0.02% of benzene and less than or equal to 0.01% of PAHs.

The term "knallgas" refers to the mixture of molecular hydrogen and oxygen gas. A "knallgas microorganism" is a microbe that can use hydrogen as an electron donor and oxygen as an electron acceptor in the generation of intracellular energy carriers such as Adenosine-5'-triphosphate (ATP). The terms "oxyhydrogen" and "oxyhydrogen microorganism" can be used synonymously with "knallgas" and "knallgas microorganism" respectively.

The term "lignocellulosic material" is any material composed of cellulose, hemicellulose, and lignin where the carbohydrate polymers (cellulose and hemicelluloses) are tightly bound to lignin. Lignocellulosic materials subsume agricultural residues (including corn stover and sugarcane bagasse), most biomass energy crops, wood residues (including sawmill and paper mill discards), and a substantial fraction of municipal waste.

The terms "lipids" refers to category of molecules that can be dissolved in nonpolar solvents (such as chloroform and/or ether) and which also have low or no solubility in water. The hydrophobic character of lipids molecules typically results from the presence of long chain hydrocarbon sections within the molecule. Lipids subsume the following molecule types: hydrocarbons, fatty acids (saturated and unsaturated), fatty alcohols, fatty aldehydes, hydroxy acids, diacids, monoglycerides, diglycerides, triglycerides, phospholipids, sphingolipids, sterols such as cholesterol and steroid hormones, fat-soluble vitamins (such as vitamins A, D, E and K), polyketides, terpenoids, and waxes.

The term "lipid modification enzyme" corresponds to an enzyme that catalyzes a reaction changing a lipid's covalent bonds such as TE, FAR, FadR, FAD, fatty aldehyde reductase, lipase, cytochrome P450 enzyme, desaturase, or hydroxylase. Any enzyme that catalyzes a reaction step or steps in lipid synthesis, catabolism, or modification, including carrier proteins, is called a "lipid pathway enzyme".

The term "lysate" refers to the liquid containing a mixture and/or a solution of cell contents that result from cell lysis. In some embodiments, the methods of the present invention comprise a purification of hydrocarbons or mixture of hydrocarbons in a cellular lysate. In some embodiments, the methods of the present invention comprise a purification of lipids and/or hydrocarbons and/or a mixture of hydrocarbons in a cellular lysate.

The term "lysis" refers to the rupture of the plasma membrane and if present the cell wall of a cell such that a significant amount of intracellular material escapes to the extracellular space. Lysis can be performed using electrochemical, mechanical, osmotic, thermal, or viral means. In some embodiments, the methods of the present invention comprise performing a lysis of cells or microorganisms described herein in order to separate a hydrocarbon or mixture of hydrocarbons from the contents of a bioreactor. In some embodiments, the methods of the present invention comprise performing a lysis of cells or microorganisms described herein in order to separate a lipid or hydrocarbon or mixture of lipids or hydrocarbons or a mixture of lipids and hydrocarbons from the contents of a bioreactor.

The terms "microorganism" and "microbe" mean microscopic single celled life forms.

The term "molecule" means any distinct or distinguishable structural unit of matter comprising one or more atoms, and includes for example hydrocarbons, lipids, polypeptides and polynucleotides.

The term "natural strain" means any wild-type or mutant organism that has not had exogenous genes encoded in it.

The term "oleaginous" refers to something that is rich in oil or produces oil in high quantities.

The term "organic compound" refers to any gaseous, liquid, or solid chemical compounds which contain carbon atoms with the following exceptions that are considered inorganic: carbides, carbonates, simple oxides of carbon, cyanides, and allotropes of pure carbon such as diamond and graphite.

The term "precursor to" or "precursor of" jet fuel, diesel fuel, or biodiesel fuel means a lipid intermediate of one or more of the components of jet, diesel fuel, or biodiesel fuel. For instance, jet fuel is a complex mixture of hydrocarbons that varies depending on crude source and manufacturing process. Consequently, it is impossible to define the exact composition of jet fuel. Specification of jet fuel has therefore evolved primarily as a performance specification rather than a compositional specification and the hydrocarbons typically range between 8 and 17 carbon atoms in hydrocarbon chain length. In some embodiments, a precursor to jet fuel may be composition comprising at least one hydrocarbon having a carbon chain length of 8, 9, 10, 11, 12, 13, 14, 15, 16, 17, 18, or more carbon atoms and having the commonly known specifications for Jet A-1, Jet A, Jet B, JP1, JP-2, JP-3, JP-4, JP-5, JP-6, JP-7, JP-8 fuel when in isolation or mixture with other hydrocarbons. In some embodiments, the precursor to jet fuel is a mixture of different carbon backbone lengths of 8, 9, 10, 11, 12, 13, 14, 15, 16, 17, 18, or more carbon atoms with the commonly known specifications for Jet A-1, Jet A, Jet B, JP1, JP-2, JP-3, JP-4, JP-5, JP-6, JP-7, JP-8 fuel, or other jet fuels. In some embodiments, the precursor to jet fuel may be one or more hydrocarbons that, when exposed to cracking and/or deoxygention and/or isomerization, may be used as a component of Jet A-1, Jet A, Jet B, JP1, JP-2, JP-3, JP-4, JP-5, JP-6, JP-7, JP-8 fuel or other jet fuels.

The term "producing" includes both the production of compounds intracellularly and extracellularly, which is to include the secretion of compounds from the cell.

"Promoter" is a control DNA sequence that regulates transcription. For purposes of the invention, a promoter may includes nucleic acid sequences near the start site of transcription that are required for proper function of the promoter, as for example, a TATA element for a promoter of polymerase II type. Promoters of the present invention can include distal enhancer or repressor elements that may lie in positions up to many thousands of base pairs away from the start site of transcription. The term "inducible promoter" refers to an operable linkage between a promoter and a nucleic acid where the promoter's mediation of nucleic acid transcription is sensitive to a specific stimulus. In some embodiments, the inducible promoter requires a cofactor which can be added to the environment of the composition comprising the nucleic acid sequence that contains the inducible promoter. An "operable linkage" refers to an operative connection between nucleic acid sequences, such as for example between a control sequence (e.g. a promoter) and another sequence that codes for a protein i.e. a coding sequence. If a promoter can regulate transcription of an exogenous gene then it is in operable linkage with the gene.

The term "syngas" (from synthetic gas or synthesis gas) refers to a gas mixture that contains various proportions of hydrogen, carbon monoxide, and carbon dioxide, and which typically also includes a variety of impurities such as methane, hydrogen sulfide, condensable gases, and tars. "Producer gas" is a related term that generally refers to gas mixes similar to syngas except for the presence of a large $N_2$ component that results from using air directly in the gasification process.

Bacterial Species

The invention relates to chemotrophic bacterial strains that comprise one or more exogenous nucleic acid sequences. The present invention results from the discovery that chemotrophic bacteria and particular related microorganisms provide unforeseen advantages in the economic and large scale production of chemicals, oils, fuels, and other hydrocarbon or lipid substances from gaseous and waste carbon feedstocks, and also from the discovery of genetic techniques and systems for modifying these microorganisms for improved performance in these applications. The lipids and other biochemicals synthesized by the microorganisms of the present invention can be applied to uses including but not limited to transportation fuel, petrochemical substitutes, monomers, feedstock for the production of polymers, lubricants, as ingredients in animal feed, food, personal care, and cosmetic products. In some embodiments triglycerides produced in the present invention can be converted by transesterification to long-chain fatty acid esters useful as biodiesel fuel. In some embodiments of the present invention enzymatic and chemical processes can be utilized to produce alkanes, alkenes, alkynes, hydroxy acids, fatty aldehydes, fatty alcohols, fatty acids, diacids, and unsaturated fatty acids. Some embodiments enable the production of renewable jet fuel, diesel, or other hydrocarbons. In addition, the present invention gives methods for culturing and/or modifying chemotrophic bacteria for improved lipid yield and/or lower production costs. In some embodiments the genetically modified bacteria produce more of a certain type or types of lipid molecules as compared to the same bacteria that is not genetically modified.

The present invention relates to compositions comprising and methods of using genetically modified microorganisms to produce and/or secrete carbon-based products from conversion of gaseous carbon feedstocks including but not limited to syngas or producer gas. The present invention relates to methods and mechanisms to confer production and/or secretion of carbon-based products of interest including but not limited to ethylene, chemicals, monomers, polymers, n-alkanes, branched alkanes, cycloalkanes, alkenes, alkynes, hydroxy acids, fatty alcohols, fatty acids, diacids, unsaturated fatty acids, aldehydes, hydrocarbons, isoprenoids, proteins, polysaccharides, nutraceutical or pharmaceutical products or intermediates thereof in obligate or facultative chemotrophic organisms such that these organisms convert carbon dioxide and/or other forms of inorganic carbon and/or syngas and/or other $C_1$ compounds such as methanol and/or the liquid, gaseous, and solid products of pyrolytic reactions such as pyrolysis oil, into carbon-based products of interest, and in particular the use of such organisms for the commercial production of ethylene, chemicals, monomers, polymers, n-alkanes, branched alkanes, cycloalkanes, alkenes, alkynes, hydroxy acids, fatty alcohols, fatty acids, diacids, unsaturated fatty acids, fatty aldehydes, hydrocarbons, isoprenoids, proteins, polysaccharides, nutraceutical or pharmaceutical products or intermediates thereof.

Chemoautotrophs are capable of performing chemosynthetic reactions that fix $CO_2$, and/or other forms of inorganic carbon, to organic compounds, using the potential energy stored in inorganic chemicals to drive the reaction, rather than radiant energy from light as in microorganisms performing photosynthesis [Shively et al, 1998; Smith et al, 1967; Hugler et al, 2005; Hugker et al., 2005; Scott and Cavanaugh, 2007]. Carbon fixing biochemical pathways that occur in chemoautotrophs include the reductive tricarboxylic acid cycle, the Calvin-Benson-Bassham cycle [Jessup Shively, Geertje van Kaulen, Wim Meijer, Annu. Rev. Microbiol., 1998, 191-230], and the Wood-Ljungdahl pathway [Ljungdahl, 1986; Gottschalk, 1989; Lee, 2008; Fischer, 2008].

The invention relates to compositions comprising and methods of using chemoautotrophic metabolism to produce ATP for the support of ATP consuming synthetic reactions and cellular maintenance, without the co-production of methane or short chain organic acids such as acetic or butyric acid, by means of energy conserving reactions for the production of ATP using inorganic electron donors, including but not limited to the oxyhydrogen reaction.

The production of hydrocarbons or other lipids with carbon chain lengths longer than $C_4$ is most commonly and efficiently accomplished biologically through fatty acid biosynthesis [Fischer, Klein-Marcuschamer, Stephanolpoulos, Metabolic Engineering (2008) 10, 295-304]. The initial molecule entering into the fatty acid biosynthesis pathway is acetyl-coenzyme A (acetyl-CoA), a central metabolite from which many high value biochemicals can be derived. In some embodiments, the invention utilizes microorganisms with a naturally occurring pathway for the conversion of CO, $CO_2$ and/or $H_2$ to acetyl-CoA. In some embodiments, the invention utilizes microorganisms that can fix CO and/or $CO_2$ through the reductive tricarboxylic acid cycle, the Calvin-Benson-Bassham cycle, and/or the Wood-Ljungdahl pathway. In some embodiments the invention utilizes microorganisms that fix C1 compounds through a methanotropic pathway. In some embodiments the microorganisms naturally produce enzymes that catalyze the fixation of gaseous inorganic carbon to produce acetyl-CoA, utilizing gaseous electron donors such as are present in syngas as reducing agents, with such enzymatic proteins including but not limited to acetyl-CoA synthase, acetyl-CoA synthase disulfide reductase, cobalamide corrinoid/iron-sulfur protein, carbon monoxide dehydrogenase, hydrogenase, and methyltransferase.

Unlike methanogenic, acetogenic and solventogenic pathways, present in methanogens and acetogens respectively, which can produce short chain organic compounds (C1-C4) with net ATP production or zero net consumption, fatty acid synthesis involves net ATP consumption. For example the following gives the net reaction for synthesis of Palmitic acid (C16) starting from Acetyl-CoA:

$$8\text{Acetyl-CoA}+7\text{ATP}+\text{H}_2\text{O}+14\text{NADPH}+14\text{H}^+ \rightarrow \text{Palmitic acid}+8\text{CoA}+14\text{NADP}^++7\text{ADP}+7P_i$$

A drawback with using an obligate methanogen or acetogen in a GTL process for the production of lipids, is the obligate use of CO2 as an electron acceptor for the production of ATP that is needed for fatty acid synthesis. If $H_2$ is the electron donor, the ATP produced per $H_2$ consumed in an acetogen or methanogen is relatively low: one ATP per $4H_2$ for methane [Thauer, R. K., Kaster, A. K., Seedorf, H., Buckel, W. & Hedderich, R. Methanogenic archaea: ecologically relevant differences in energy conservation. Nat Rev Microbiol 6, 579-591, doi:nrmicro1931 [pii]] or acetic acid production, and one ATP per $10H_2$ for butyric acid production [Papoutsakis, Biotechnology & Bioengineering (1984) 26, 174-187; Heise, Muller, Gottschalk, J. of Bacteriology (1989) 5473-5478; Lee, Park, Jang, Nielsen, Kim, Jung, Biotechnology & Bioengineering (2008) 101, 2, 209-228]. In some embodiments, the invention relates to a microorganism or compositions comprising a microorganism, wherein the microorganism produces ATP from an inorganic electron donor such as but not limited to H2 without synthesis of methane or short chain organic acids.

Hydrogen-oxidizing microorganisms that use more electronegative electron acceptors in energy conserving reactions for ATP production, such as but not limited to hydrogenotrophic oxyhydrogen or knallgas microbes that link the oxyhydrogen reaction, $2H_2+O_2->2H_2O$, to ATP production, can produce more ATP per $H_2$ consumed than acetogens or methanogens. For example knallgas microorganisms can produce up to two ATP per $H_2$ consumed [Bongers, J. Bacteriology, (October 1970) 145-151], which is eight times more ATP produced per $H_2$ consumed than what can be produced in microorganisms undergoing methanogenesis or acetogenesis. For this reason using microorganisms that can utilize more electronegative electron acceptors in the production of ATP, such as but not limited to knallgas microbes, in fatty acid biosynthesis from syngas or $H_2$, can be more efficient for supporting fatty acid biosynthesis than using the acetogens or methanogens that are currently used in biological GTL technologies. In some embodiments, the invention relates to a microorganism or compositions comprising a microorganism, wherein the microorganism is a knallgas microbe and comprises at least one or more exogenous nucleic acid sequences that encodes one or more enzymes to enable fixation of a carbon-containing gas feedstock, including but not limited to syngas or producer gas, into useful carbon-based products of interest including but not limited to ethylene, chemicals, monomers, polymers, n-alkanes, branched alkanes, cycloalkanes, alkenes, alkynes, hydroxy acids, fatty alcohols, fatty acids, diacids, unsaturated fatty acids, fatty aldehydes, hydrocarbons, isoprenoids, polypeptides, polysaccharides, nutraceutical or pharmaceutical products. In some embodiments, the microorganism or composition comprising the microorganism comprises at least one or more exogenous nucleic acid sequences that encodes one or more enzymes that allows the microorganism to convert a carbon-containing gas feedstock, including but not limited to syngas or producer gas, into jet fuel, diesel fuel, biodiesel fuel, or a component or precursor thereof. The invention relates to a genetically modified microorganism and compositions comprising such a microorganism, wherein the microorganism comprises one or more exogenous genes and wherein the microorganism grows on carbon-containing gas or utilizes a gaseous feedstock selected from syngas, $CO_2$, $H_2$, CO, or mixtures of gas comprising one or more gases selected from syngas, $CO_2$, $H_2$, or CO.

The invention relates to a cell and compositions comprising a cell of the class Actinobacteria comprising at least one exogenous gene. The invention also relates to cells and compositions comprising cells of the family of Nocardiaceae comprising at least one exogenous gene. The invention relates to cells and compositions comprising cells of *Corynebacterium, Gordonia, Rhodococcus, Mycobacterium* and *Tsukamurella* comprising at least one exogenous gene. In some embodiments, the invention relate to cells of the family of Nocardiaceae comprising an exogenous gene, wherein the cell is not a cell of the genus *Mycobacterium*. In some embodiments, the invention provides a cell and compositions comprising a cell of the genus *Rhodococcus* comprising an exogenous gene, and in some embodiments the cell is a strain of the species *Rhodococcus* sp., *Rhodococcus opacus, Rhodococcus aurantiacus; Rhodococcus baikonurensis; Rhodococcus boritolerans; Rhodococcus equi; Rhodococcus coprophilus; Rhodococcus corynebacterioides; Nocardia corynebacterioides* (synonym: *Nocardia corynebacterioides*); *Rhodococcus erythropolis; Rhodococcus fascians; Rhodococcus globerulus; Rhodococcus gordoniae; Rhodococcus jostii Rhodococcus koreensis; Rhodococcus kroppenstedtii; Rhodococcus maanshanensis; Rhodococcus marinonascens; Rhodococcus opacus; Rhodococcus percolatus; Rhodococcus phenolicus; Rhodococcus polyvorum; Rhodococcus pyridinivorans; Rhodococcus rhodochrous; Rhodococcus rhodnii;* (synonym: *Nocardia rhodnii*); *Rhodococcus ruber* (synonym: *Streptothrix rubra*); *Rhodococcus* sp. RHA1; *Rhodococcus triatomae; Rhodococcus tukisamuensis; Rhodococcus wratislaviensis* (synonym: *Tsukamurella wratislaviensis*); *Rhodococcus yunnanensis; Rhodococcus zopfii*. In some embodiments the cell comprising one or more exogenous genes is strain *Rhodococcus opacus* DSM number 43205 or 43206. In some embodiments the cell comprising one or more exogenous genes is strain *Rhodococcus* sp. DSM number 3346. In some embodiments, the invention provides cells and compositions comprising a cell of the genus *Rhodococcus* comprising an exogenous gene, wherein the cell or composition comprising a cell of *Rhodococcus* is non-infectious to animals and/or plants. In some embodiments, the invention provides cells and compositions comprising a cell of the genus *Rhodococcus* comprising an exogenous gene, wherein the *Rhodococcus* cell or composition comprising a *Rhodococcus* cell is non-infectious to humans. In some embodiments, the invention provides cells and compositions comprising a cell of the genus *Rhodococcus* comprising an exogenous gene, wherein the *Rhodococcus* cell or composition comprising a *Rhodococcus* cell is non-infectious to plants. In some embodiments, the invention provides cells and compositions comprising cells of the genus *Rhodococcus* comprising an exogenous gene, wherein, if the cell is from *Rhodococcus equi* or *Rhodococcus fascians* species, the species is non-infectious to animals and/or plants. In some embodiments, the invention relates to a *Rhodococcus* cell or composition comprising a *Rhodococcus* cell, wherein the cell is not a species selected from *Rhodococcus equi* or *Rhodococcus fascians*.

In some embodiments, the invention relates to a *Rhodococcus* cell or composition comprising a *Rhodococcus* cell, wherein the cell is incapable of producing any acrylic acid or acrylamide. In some embodiments, the invention relates to a *Rhodococcus* cell or composition comprising a *Rhodococcus* cell, wherein the cell produces less than 10, 9, 8, 7, 6, 5, 4, 3, 2, or 1% of its weight of total dry cellular matter in acrylamide or acrylic/methylacrylic acid. In some embodiments, the invention relates to a *Rhodococcus* cell or composition comprising a *Rhodococcus* cell, wherein the cell is not from the species *Rhodococcus rhodochrous*. In some embodiments, the invention relates to *Rhodococcus* cell or composition comprising a *Rhodococcus* cell, wherein the cell is incapable of producing 10-hydroxy-12-octadecenoic acid. In some embodiments, the invention relates to a *Rhodococcus* cell or composition comprising a *Rhodococcus* cell, wherein the cell is unable to produce more than 10, 9, 8, 7, 6, 5, 4, 3, 2, or 1% of its weight of total dry cellular matter in 10-hydroxy-12-octadecenoic acid. In some embodiments, the invention relates to *Rhodococcus* cell or composition comprising a *Rhodococcus* cell, wherein the cell is incapable of producing optically-active 4-amino-3-hydroxybutyric acid. In some embodiments, the invention relates to a *Rhodococcus* cell or composition comprising a *Rhodococcus* cell, wherein the cell is unable to produce more than 10, 9, 8, 7, 6, 5, 4, 3, 2, or 1% of its weight of total dry cellular matter in optically-active 4-amino-3-hydroxybutyric acid.

In some embodiments, the cell or compositions comprising one of more cells is not *E. coli*. In some embodiments, the cell or compositions comprising one of more cells is from the genus *Rhodococcus* but is not for the species equi. In some embodiments, the cell of the present invention is not pathogenic to animals or plants. In some embodiments, the cell of the present invention is not pathogenic to humans. In some embodiments, the cell or compositions comprising one of more cells is from the genus *Ralstonia*. In some embodiments, the cell or compositions comprising one of more cells is from the species *Ralstonia eutropha*. In some embodiments the cell comprising one or more exogenous genes is strain *Cupriavidus necator* DSM number 531 or 541.

In some embodiments, the cell or compositions comprising the one or more cells have a 16S rRNA sequence with at least 50, 60, 70, 75, 80, 81, 82, 83, 84, 85, 86, 87, 88, 89, 90, 91, 92, 93, 94, 95, 96, 97, 98 or 99% nucleotide homology to one or more of SEQ ID NOs: 11 or 12. In some embodiments, the cell or compositions comprising the one or more cells have a 16S rRNA sequence with at least 70, 75, 80, 81, 82, 83, 84, 85, 86, 87, 88, 89, 90, 91, 92, 93, 94, 95, 96, 97, 98 or 99% nucleotide homology to one or more of SEQ ID NOs: 11. In some embodiments, the cell or compositions comprising the one or more cells have a 16S rRNA sequence with at least 70, 75, 80, 81, 82, 83, 84, 85, 86, 87, 88, 89, 90, 91, 92, 93, 94, 95, 96, 97, 98 or 99% nucleotide homology to one or more of SEQ ID NOs: 12. In some embodiments, the cell or compositions comprising the one or more cells have a 16S rRNA sequence with at least 70, 75, 80, 81, 82, 83, 84, 85, 86, 87, 88, 89, 90, 91, 92, 93, 94, 95, 96, 97, 98 or 99% nucleotide homology to one or more of SEQ ID NOs: 13.

In some embodiments the microorganism of the claimed invention is not dependent upon light to grow and/or metabolize and/or synthesize lipid molecules. In some embodiments, the microorganism of the claimed invention does not require any type of sugar to grow and/or metabolize and/or synthesize lipid molecules. In some embodiments, the microorganism of the claimed invention does not require any type of organic compound to grow and/or metabolize and/or synthesize lipid molecules. In some embodiments, the microorganism of the claimed invention does not require any type of fixed carbon to grow and/or metabolize and/or synthesize lipid molecules. In some embodiments, the microorganism can grow and/or metabolize lipids in a slightly anaerobic or extremely anaerobic environment. In some embodiments, the microorganism of the claimed invention is a facultative microorganism Microbial culturing in the present invention is performed both for the sake of implementing genetic modifications, and for production of organic compounds, and specifically lipids and/or hydrocarbons (e.g., alkenes, alkynes, alkanes, unsaturated fatty acids, fatty acids, fatty alcohols, fatty aldehydes, triacylglycerols, hydroxy acids, diacids). Microbial culturing with the aim of genetic manipulation is generally performed at a small benchtop scale and often under conditions that select for genetically modified traits. Microbial culturing aimed at the commercial production of organic compounds and specifically lipids and/or hydrocarbons is typically performed in bioreactors at much greater scale (e.g., 500 L, 1,000 L 5,000 L, 10,000 L, 50,000 L, 100,000 L, 1,000,000 L bioreactor volumes and higher). In certain embodiments the chemoautotrophs of the present invention are grown in a liquid media inside a bioreactor using the methods of the invention. In some embodiments, the bioreactor containing the microorganisms is constructed of opaque materials that keep the culture in darkness. Bioreactors constructed out of opaque materials such as steel or reinforced concrete can be designed to have extremely big working volumes. In some embodiments of the present invention steel fermenters 50,000 liter and greater in volume are utilized. In some embodiments of the present invention egg-shape or cylindrical digesters 3,000,000 liters and greater in volume are utilized. In some embodiments, the bioreactor comprising the microorganism does not allow light to penetrate its interior.

The bioreactor or fermentor is used to culture cells through the various phases of their physiological cycle. A bioreactor is utilized for the cultivation of cells, which may be maintained at particular phases in their growth curve. The use of bioreactors is advantageous in many ways for cultivating chemoautotrophic growth. For certain embodiments, oleaginous cell mass, which is used to produce fuel, is grown to high densities in liquid suspension. Generally the control of growth conditions including control of dissolved carbon dioxide, oxygen, and other gases such as hydrogen, as well as other dissolved nutrients, trace elements, temperature and pH, is facilitated in a bioreactor.

Nutrient media as well as gases can be added to the bioreactor as either a batch addition, or periodically, or in response to a detected depletion or programmed set point, or continuously over the period the culture is grown and/or maintained. For certain embodiments, the bioreactor at inoculation is filled with a starting batch of nutrient media and/or gases at the beginning of growth, and no additional nutrient media and/or gases are added after inoculation. For certain embodiments, nutrient media and/or gases are added periodically after inoculation. For certain embodiments, nutrient media and/or gas is added after inoculation in response to a detected depletion of nutrient and/or gas. For certain embodiments, nutrient media and/or gas is added continuously after inoculation.

For certain embodiments the bioreactors have mechanisms to enable mixing of the nutrient media that include but are not limited to spinning stir bars, blades, impellers, or turbines, spinning, rocking, or turning vessels, gas lifts and sparging. The culture media may be mixed continuously or intermittently. The ports that are standard in bioreactors may be utilized to deliver, or withdraw, gases, liquids, solids, and/or slurries, into the bioreactor vessel enclosing the microbes of the present invention. Many bioreactors have multiple ports for different purposes (e.g. ports for media addition, gas addition, probes for pH and DO, sampling), and a given port may be used for various purposes during the course of a fermentation run. As an example, a port might be used to add nutrient media to the bioreactor at one point in time and at another time might be used for sampling. Preferably, the multiple use of a sampling port can be performed without introducing contamination or invasive species into the growth environment. A valve or other actuator enabling control of the sample flow or continuous sampling can be provided to a sampling port. For certain embodiments the bioreactors are equipped with at least one port suitable for culture inoculation that can additionally serve other uses including the addition of media or gas. Bioreactors ports enable control of the gas composition and flow rate into the culture environment. For example the ports can be used as gas inlets into the bioreactor through which gases are pumped. For some embodiments gases that may be pumped into a bioreactor include syngas, producer gas, hydrogen gas, CO2, air, air/$CO_2$ mixtures, ammonia, nitrogen, noble gases, such as argon, as well as other gases. In some embodiments that $CO_2$ may come from sources including but are not limited to: $CO_2$ from the gasification of organic matter; $CO_2$ from the calcination of limestone, $CaCO_3$, to produce quicklime, CaO; $CO_2$ from methane steam reforming, such as the $CO_2$ byproduct from ammonia or hydrogen production; combustion; $CO_2$ byproduct of sugar fermentation; $CO_2$ byproduct from sodium phosphate production; geologically or geothermally produced $CO_2$.

Raising the gas flow rate into a bioreactor can enhance mixing of the culture and produce turbulence if the gas inlet is positioned under the surface of the liquid media such that gas bubbles or sparges up through the media. In some embodiments, a bioreactor comprises gas outlet ports for gas escape and pressure release. In some embodiments, gas inlets and outlets are preferably equipped with check valves to prevent gas backflow.

The present invention relates to bioreactors that comprise a cell, which comprises at least one exogenous nucleic acid sequences that encodes a lipid pathway enzyme. The present invention relates to a system of at least one bioreactor that comprise a cell, which comprises at least one exogenous nucleic acid sequences that encodes a lipid pathway enzyme. In some embodiments, the system comprises two or more, three or more, or four or more bioreactors, at least one of which comprise a cell, which comprises at least one exogenous nucleic acid sequences that encodes a lipid pathway enzyme. In some embodiments, the system of bioreactors comprises at least a first and second bioreactor, wherein the first bioreactor comprises a cell, which comprises at least one exogenous nucleic acid sequences that encodes a lipid pathway enzyme; and wherein the second bioreactor comprises a microorganism derived from a different species, wherein the microorganism from a different species comprises at least one exogenous nucleic acid sequence that encodes a lipid pathway enzyme. In some embodiments, the system of bioreactors comprises a first bioreactor that comprises the cell of the present invention and a second bioreactor comprising a microalgal, yeast, or bacterial cell.

In some embodiments, the cells of the present invention are capable of producing desaturated alkanes between 8 and 18 carbon atoms long at greater than 18 grams per liter volume of culture per three day period. In some embodiments, the cells of the present invention are capable of producing desaturated alkanes between 8 and 18 carbon atoms long at greater than or equal to 18 grams per liter volume of culture per three day period, wherein the desaturated alkanes are desatuated at a carbon position other than carbon-9.

Genetic Modifications

The present invention relates to methods of modifying a bacterial cell to express one or more exogenous nucleic acid sequences that encodes one or more enzymes to enable fixation of a carbon-containing gas feedstock into useful carbon-based products of interest in an amount greater than an amount of carbon-based products produced by the same bacterial cell that does not express the exogenous nucleic acid sequences. Methods of selecting and manufacturing nucleic acid sequences for modification of bacterial cells are known and can be performed by transformation, electroporation, phage infection of bacteria, or other techniques for nucleic acid transfer generally known in the art. Standard recombinant DNA and molecular cloning techniques useful for the invention are well known in the art and are described by Sambrook, J., Fritsch, E. F. and Maniatis, T. Molecular Cloning: A Laboratory Manual; Cold Spring Harbor Laboratory Press: Cold Spring Harbor, (1989) (Maniatis) and by T. J. Silhavy, M. L. Bennan, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987), all of which are incorporated by reference in their entireties.

The invention relates to genetic constructs comprising one or more exogenous genes that encode one or more amino acid sequences to enable fixation of a carbon-containing gas feedstock, including but not limited to syngas or producer gas, into useful carbon-based products of interest in an amount greater than an amount of carbon-based products produced by the same bacterial cell that does not express the exogenous nucleic acid sequence or sequences. Another aspect of the present invention relates to compositions that comprise at least one bacterial cell, which comprises at least one nucleic acid sequence that encodes at least one exogenous amino acid sequence that functions as a fatty acid acyl-ACP reductase, a fatty acid aldehyde decarbonylase and/or a thioesterase. In some embodiments, the bacterial cell is transformed with one or more, two or more, three or more, four or more, or five or more exogenous nucleic acid sequences that encode one or more amino acid sequences to enable fixation of a carbon-containing gas feedstock, including but not limited to syngas or producer gas, into useful carbon-based products of interest in an amount greater than an amount of carbon-based products produced by the same bacterial cell that does not express the exogenous nucleic acid sequence or sequences. According to the present invention, genetic material that encodes the enzyme is delivered to a bacterial cell in an expressible form. The genetic material, DNA or RNA, is taken up by the cells of the invention and expressed. The enzyme or enzymes that are thereby produced can biochemically modify lipid molecules to remove or add hydroxyl groups, remove or add carbonyl groups, remove or add carbon-carbon double bonds, remove or add carbon-carbon triple bonds, remove or add aldehyde groups, remove or add hydroxy groups, remove or add carboxylic acid groups, or remove or add ester groups to lipid molecules in lipid.

In some embodiments, the genetic constructs of the present invention comprise DNA, RNA, or combinations of both DNA and RNA. In some embodiments, the genetic construct of the present invention is a plasmid. It will be appreciated that, in some embodiments, the plasmid contains a variety of open reading frames (ORFs) encoding proteins of many diverse functions, including those enzymes that enable hydrocarbon or lipid modification, glutathione-S transferase (GST) activity, origins of replication, multiple cloning sites, promoters, and/or termination sequences. It is contemplated therefore that a host cell transformed with the plasmid will demonstrate the ability to modify a variety of lipids or hydrocarbons as well as maintain its copy number in the cytoplasm of the cell. The glutathione-S transferases (GSTs) represent a large group of detoxification enzymes. GSTs catalyze the conjugation of glutathione, homoglutathione and other glutathione-like analog via sulfhydryl group, to a large range of hydrophobic, electrophilic compounds. The conjugation can result in detoxification of these compounds. GST genes are found in both prokaryotic (e.g., *E. coli*) and eukaryotic organisms (e.g., yeast, plant and human). Although the homologies between the GSTs from prokaryotes and eukaryotes were low, many of the residues assigned to be important for the enzymatic function or structure in the eukaryotes were found to be conserved in prokaryotic GSTs (Nishida et al., *J. Biol Chem* 269:32536-32541 (1994)). It has been suggested that bacterial GST may represent a defense against the effects of antibiotics (Piccolomini et al., J Gen Microbiol 135:3119-3125 (1989)). Accordingly it is contemplated that a host strain transformed with the plasmid will have the ability detoxify harmful compounds via conjugation of those compounds to glutathione.

In some embodiments, the instant plasmid additionally encodes a variety of maintenance proteins, useful for maintaining, stabilizing and replicating the plasmid. It is contemplated that these genes may be used in conjunction with other bacterial plasmids deficient in these functions for the increased stabilization or robust maintenance of the plasmid. In some embodiments, the plasmid comprises maintenance proteins of particular interest including the REP origin of replication (encoded by ORF 38) the TRA proteins (TRAI, TRAJ and TRAK, encoded by ORF's 23, 24 and 25 respectively) and the VAG proteins (VAGD and VAGC, encoded by ORF's 33 and 34 respectively). The tra gene family is known to be involved in plasmid conjugation, a process that promotes DNA transfer from a donor to a recipient cell mediated by physical contact (Firth et al, *Escherichia coli* and *Salmonella*: Cellular and Molecular Biology, ASM press (1996)). Among tra gene products, TraI and TraK proteins are reported to be required for efficient plasmid site-specific recombination (Paterson et al. J. Bacteriol 181:2572-2583 (1999)). Furthermore, TraI is required for conjugal DNA transfer. Fukuda and Ohtsubo (Genes Cells 2:735-751 (1997)) reported that TraI has the activity of site- and strand-specific nicking of the supercoiled plasmid DNA. TraJ, traJ gene product, regulates transcription originating at the tra operon promoter P.sub.traY. (Firth et al., *Escherichia coli* and *Salmonella*: Cellular and Molecular Biology, ASM press (1996)). The stabilization proteins VAGC and VAGD encoded by vagC and vagD are involved in maintaining the plasmid as an autonomous replicating unit. Non-limiting examples of bacterial maintenance proteins of particular interest on the pSeq and pVer plasmids are represented by the following DNA and protein sequences:

```
                                                                        SEQ ID: 01
TCGCGCGTTT CGGTGATGAC GGTGAAAACC TCTGACACAT GCAGCTCCCG GAGACGGTCA CAGCTTGTCT GTAAGCGGAT

GCCGGGAGCA GACAAGCCCG AGCGCGCAAA GCCACTACTG CCACTTTTGG AGACTGTGTA CGTCGAGGGC CTCTGCCAGT

GTCGAACAGA CATTCGCCTA CGGCCCTCGT CTGTTCGGGC TCAGGGCGCG TCAGCGGGTG TTGGCGGGTG TCGGGCTGG

CTTAACTATG CGGCATCAGA GCAGATTGTA CTGAGAGTGC ACCATATGCG GTGTGAAATA AGTCCCGCGC AGTCGCCCAC

AACCGCCCAC AGCCCCGACC GAATTGATAC GCCGTAGTCT CGTCTAACAT GACTCTCACG TGGTATACGC CACACTTTAT

CCGCACAGAT GCGTAAGGAG AAAATACCGC ATCAGGCGCC ATTCGCCATT CAGGCTGCGC AACTGTTGGG AAGGGCGATC

GGTGCGGGCC TCTTCGCTAT GGCGTGTCTA CGCATTCCTC TTTTATGGCG TAGTCCGCGG TAAGCGGTAA GTCCGACGCG

TTGACAACCC TTCCCGCTAG CCACGCCCGG AGAAGCGATA TACGCCAGCT GGCGAAAGGG GGATGTGCTG CAAGGCGATT

AAGTTGGGTA ACGCCAGGGT TTTCCCAGTC ACGACGTTGT AAAACGACGG CCAGTGCCAA ATGCGGTCGA CCGCTTTCCC

CCTACACGAC GTTCCGCTAA TTCAACCCAT GCGGTCCCA AAAGGGTCAG TGCTGCAACA TTTTGCTGCC GGTCACGGTT

GCTTGCATGC CTGCAGGTCG ACGGGCCCGG GATCCGATGC TCTTCCGCTA AGATCTGCCG CGGCCGCGTC CTCAGAAGAA

CTCGTCAAGA AGGCGATAGA CGAACGTACG GACGTCCAGC TGCCCGGGCC CTAGGCTACG AGAAGGCGAT TCTAGACGGC

GCCGGCGCAG GAGTCTTCTT GAGCAGTTCT TCCGCTATCT AGGCGATGCG CTGCGAATCG GGAGCGGCGA TACCGTAAAG

CACGAGGAAG CGGTCAGCCC ATTCGCCGCC AAGCTCTTCA GCAATATCAC GGGTAGCCAA TCCGCTACGC GACGCTTAGC

CCTCGCCGCT ATGGCATTTC GTGCTCCTTC GCCAGTCGGG TAAGCGGCGG TTCGAGAAGT CGTTATAGTG CCCATCGGTT

CGCTATGTCC TGATAGCGGT CCGCCACACC CAGCCGGCCA CAGTCGATGA ATCCAGAAAA GCGGCCATTT TCCACCATGA

TATTCGGCAA GCAGGCATCG GCGATACAGG ACTATCGCCA GGCGGTGTGG GTCGGCCGGT GTCAGCTACT TAGGTCTTTT

CGCCGGTAAA AGGTGGTACT ATAAGCCGTT CGTCCGTAGC CCATGGGTCA CGACGAGATC CTCGCCGTCG GGCATGCGCG

CCTTGAGCCT GGCGAACAGT TCGGCTGGCG CGAGCCCCTG ATGCTCTTCG TCCAGATCAT GGTACCCAGT GCTGCTCTAG

GAGCGGCAGC CCGTACGCGC GGAACTCGGA CCGCTTGTCA AGCCGACCGC GCTCGGGGAC TACGAGAAGC AGGTCTAGTA

CCTGATCGAC AAGACCGGCT TCCATCCGAG TACGTGCTCG CTCGATGCGA TGTTTCGCTT GGTGGTCGAA TGGGCAGGTA

GCCGGATCAA GCGTATGCAG GGACTAGCTG TTCTGGCCGA AGGTAGGCTC ATGCACGAGC GAGCTACGCT ACAAAGCGAA

CCACCAGCTT ACCCGTCCAT CGGCCTAGTT CGCATACGTC CCGCCGCATT GCATCAGCCA TGATGGATAC TTTCTCGGCA

GGAGCAAGGT GGGATGACAG GAGATCCTGC CCCGGCACTT CGCCCAATAG CAGCCAGTCC GGCGGCGTAA CGTAGTCGGT

ACTACCTATG AAAGAGCCGT CCTCGTTCCA CCCTACTGTC CTCTAGGACG GGGCCGTGAA GCGGGTTATC GTCGGTCAGG

CTTCCCGCTT CAGTGACAAC GTCGAGCACA GCTGCGCAAG GAACGCCCGT CGTGGCCAGC CACGATAGCC GCGCTGCCTC

GTCCTGCAGT TCATTCAGGG GAAGGGCGAA GTCACTGTTG CAGCTCGTGT CGACGCGTTC CTTGCGGGCA GCACCGGTCG

GTGCTATCGG CGCGACGGAG CAGGACGTCA AGTAAGTCCC CACCGGACAG GTCGGTCTTG ACAAAAAGAA CCGGGCGCCC

CTGCGCTGAC AGCCGGAACA CGGCGGCATC AGAGCAGCCG ATTGTCTGTT GTGCCCAGTC GTGGCCTGTC CAGCCAGAAC

TGTTTTTCTT GGCCCGCGGG GACGCGACTG TCGGCCTTGT GCCGCCGTAG TCTCGTCGGC TAACAGACAA CACGGGTCAG

ATAGCCGAAT AGCCTCTCCA CCCAAGCGGC CGGAGAACCT GCGTGCAATC CATCTTGTTC AATCATGATA TCCCTTAATT
```

```
AACCGTTAAC ACTAGTTCAG TATCGGCTTA TCGGAGAGGT GGGTTCGCCG GCCTCTTGGA CGCACGTTAG GTAGAACAAG

TTAGTACTAT AGGGAATTAA TTGGCAATTG TGATCAAGTC TCCATCTCGC CGTGTATGCG GGCCTGACGG ATCAACGTTC

CCACCGAGCC AGTCGAGATG TTCATCTGGT CGGCGATCTG CCGGTACTTC AAACCTTGTT AGGTAGAGCG GCACATACGC

CCGGACTGCC TAGTTGCAAG GGTGGCTCGG TCAGCTCTAC AAGTAGACCA GCCGCTAGAC GGCCATGAAG TTTGGAACAA

TGCGCAGTTC CACAGCCTTC TTGCGGCGTT CCTGCGCACG AGCGATGTAG TCGCCTCGGT CTTCGGCGAC GAGCCGTTTG

ATGGTGCTTT TCGAGACGCC ACGCGTCAAG GTGTCGGAAG AACGCCGCAA GGACGCGTGC TCGCTACATC AGCGGAGCCA

GAAGCCGCTG CTCGGCAAAC TACCACGAAA AGCTCTGCGG GAACTTGTCA GCCAACTCCT GCGCGGTCTG CGTGCGACGC

ATCACGCGTT CTGCAGCACC CATCAGTCCG TCCCCTCTGC TGCTGCGAAC AGTGCCGATC CTTGAACAGT CGGTTGAGGA

CGCGCCAGAC GCACGCTGCG TAGTGCGCAA GACGTCGTGG GTAGTCAGGC AGGGGAGACG ACGACGCTTG TCACGGCTAG

GATCGACCTT CTTGAGCTTC GGCCGCGGCG CGGTGGCGTT CTTCCGTACC GCTTCCGTTT TTGCGCTGCT GCTCACTTTG

CCGCGGCGTG CCTGGATTTT CTAGCTGGAA GAACTCGAAG CCGGCGCCGC GCCACCGCAA GAAGGCATGG CGAAGGCAAA

AACGCGACGA CGAGTGAAAC GGCGCCGCAC GGACCTAAAA CGAGAACTCG GCGGCGGTGA AGGTGCGGTG GGTCCAGTGG

GCGACTGATT TGCCGATCTG CTCGGCCTCG GCCCGACTCA TGGGGCCGAT CCCGTCGTTG GCTCTTGAGC CGCCGCCACT

TCCACGCCAC CCAGGTCACC CGCTGACTAA ACGGCTAGAC GAGCCGGAGC CGGGCTGAGT ACCCCGGCTA GGGCAGCAAC

GCGTCGAGGG TGAAGTTGGT CAGGGCGGTG AAGTCGGTGA CCATCTGCCG CCACACAGTG ATCGACGGGT AGTTCTGTTT

CCGGATCTCG CGGTAGGCCC CGCAGCTCCC ACTTCAACCA GTCCCGCCAC TTCAGCCACT GGTAGACGGC GGTGTGTCAC

TAGCTGCCCA TCAAGACAAA GGCCTAGAGC GCCATCCGGG ATTCCCGGGT GCGGTCGAAC AGTTCGACGT TCCGGCCCGT

TTCGGTCCTG ACCTGTGTCT TGCGGCCGTA GTCCGGTGGG GCGGGGAAAC GGTCACCGAG TAAGGGCCCA CGCCAGCTTG

TCAAGCTGCA AGGCCGGGCA AAGCCAGGAC TGGACACAGA ACGCCGGCAT CAGGCCACCC CGCCCCTTTG CCAGTGGCTC

CGCTTTTGCG AGGCCTTTGA GCGAGTACGG ATCCGAGGGA CCCCAGACCG TCGTCCAGTG CGGGTGGATC GGGTTCTGGG

TGAGCTGCTG CGCGTAGCCC GCGAAAACGC TCCGGAAACT CGCTCATGCC TAGGCTCCCT GGGGTCTGGC AGCAGGTCAC

GCCCACCTAG CCCAAGACCC ACTCGACGAC GCGCATCGGG TGATCGGCGC CGACCACCGA GGCGATCAGC CCCTGGTTCA

CCCGGTCGTA GAGCCGCAGC GGGCCCTGTC GGGCTGCCTG GAGGGTGTAG ACCGGGCTTT ACTAGCCGCG GCTGGTGGCT

CCGCTAGTCG GGGACCAAGT GGGCCAGCAT CTCGGCGTCG CCCGGGACAG CCCGACGGAC CTCCCACATC TGGCCCGAAA

CGAGCAGCCA CCACAGGTGC GCGTGCTCGG TCGCGGGATT GATCGTCATC ACGGTCGGAT CGGGCAGATC CGCGTTACGT

GCGGCCCACT GCGCCTGGTC GCTCGTCGGT GGTGTCCACG CGCACGAGCC AGCGCCCTAA CTAGCAGTAG TGCCAGCCTA

GCCCGTCTAG GCGCAATGCA CGCCGGGTGA CGCGGACCAG GTCGTCCACG TCGAGCACCA AGCCCAACCT GATCGACGGG

GTGCGGGCCG CAATGTAGCG GCGGGTGAGC GCCTCCGCGC GCGGCTGCGG CCACTGCCCG CAGCAGGTGC AGCTCGTGGT

TCGGGTTGGA CTAGCTGCCC CACGCCCGGC GTTACATCGC CGCCCACTCG CGGAGGCGCG CGCCGACGCC GGTGACGGGC

TCCCGGACGT AGTCATCCGT CGCGTGCGGG TATTTGAACC GCCAGCGGTC CAACCAGGCG TCAACAGCAG CGGTCATGAC

CGCCAAGCTA GGGCCGGATC AGGGCCTGCA TCAGTAGGCA GCGCACGCCC ATAAACTTGG CGGTCGCCAG GTTGGTCCGC

AGTTGTCGTC GCCAGTACTG GCGGTTCGAT CCCGGCCTAG TGTACCGATC GGGGGAGGCG CGCCGCAAAT TATTTAAGAG

TCTCGCTAGC AAACCATGTC AGGTGTTGCG GTGGGTTCCG GGTAAACCTC CACCCGAATT ACATGGCTAG CCCCCTCCGC

GCGGCGTTTA ATAAATTCTC AGAGCGATCG TTTGGTACAG TCCACAACGC CACCCAAGGC CCATTTGGAG GTGGGCTTAA

ATTTAAGAGT CTCGCTAGCT AAGCCCTATC TGATGCTGCG CGGGGGGTCC TTCGCACTGA ATCTCAAAGG TGGCCGGCTG

AATTTCGTCG CGCGAAAACC TAAATTCTCA GAGCGATCGA TTCGGATAG ACTACGACGC GCCCCCCAGG AAGCGTGACT

TAGAGTTTCC ACCGGCCGAC TTAAAGCAGC GCGCTTTTGG TCCCTGGACA GTTCTGGAAT TCAGCAAGAG GTGTGTCTGA

ACTTCGGTGT TTTTTTGGGG GGTGACTCCA GCGGGGTGGG CACAACGCGA ACAGAGACCT AGGGACCTGT CAAGACCTTA

AGTCGTTCTC CACACAGACT TGAAGCCACA AAAAACCCC CCACTGAGGT CGCCCCACCC GTGTTGCGCT TGTCTCTGGA

TGTGTGTACG ACGGCGGGAG GTAAGTCGGG TACGGCTCGG ACTGCGGTAG AGCAACCGTC GAATCGATTT CGAGCAGAGC

GAGCAGAGCA AGATATTCCA ACACACATGC TGCCGCCCTC CATTCAGCCC ATGCCGAGCC TGACGCCATC TCGTTGGCAG
```

-continued

```
CTTAGCTAAA GCTCGTCTCG CTCGTCTCGT TCTATAAGGT AAACTCCGGG GTTCCTCGGC GGCCTCCCCC GTCTGTTTGC

TCAACCGAGG GAGACCTGGC GGTCCCGCGT TTCCGGACGC GCGGGACCGC CTACCGCTCG TTTGAGGCCC CAAGGAGCCG

CCGGAGGGGG CAGACAAACG AGTTGGCTCC CTCTGGACCG CCAGGGCGCA AAGGCCTGCG CGCCCTGGCG GATGGCGAGC

AGAGCGGAAG AGCATCTAGA TGCATTCGCG AGGTACCGAG CTCGAATTCG TAATCATGGT CATAGCTGTT TCCTGTGTGA

AATTGTTATC CGCTCACAAT TCTCGCCTTC TCGTAGATCT ACGTAAGCGC TCCATGGCTC GAGCTTAAGC ATTAGTACCA

GTATCGACAA AGGACACACT TTAACAATAG GCGAGTGTTA TCCACACAAC ATACGAGCCG AAGCATAAA GTGTAAAGCC

TGGGGTGCCT AATGAGTGAG CTAACTCACA TTAATTGCGT TGCGCTCACT GCCCGCTTTC AGGTGTGTTG TATGCTCGGC

CTTCGTATTT CACATTTCGG ACCCCACGGA TTACTCACTC GATTGAGTGT AATTAACGCA ACGCGAGTGA CGGGCGAAAG

CAGTCGGGAA ACCTGTCGTG CCAGCTGCAT TAATGAATCG GCCAACGCGC GGGGAGAGGC GGTTTGCGTA TTGGGCGCTC

TTCCGCTTCC TCGCTCACTG GTCAGCCCTT TGGACAGCAC GGTCGACGTA ATTACTTAGC CGGTTGCGCG CCCCTCTCCG

CCAAACGCAT AACCCGCGAG AAGGCGAAGG AGCGAGTGAC ACTCGCTGCG CTCGGTCGTT CGGCTGCGGC GAGCGGTATC

AGCTCACTCA AAGGCGGTAA TACGGTTATC CACAGAATCA GGGGATAACG CAGGAAAGAA TGAGCGACGC GAGCCAGCAA

GCCGACGCCG CTCGCCATAG TCGAGTGAGT TTCCGCCATT ATGCCAATAG GTGTCTTAGT CCCCTATTGC GTCCTTTCTT

CATGTGAGCA AAAGGCCAGC AAAAGGCCAG GAACCGTAAA AAGGCCGCGT TGCTGGCGTT TTTCCATAGG CTCCGCCCCC

CTGACGAGCA TCACAAAAAT GTACACTCGT TTTCCGGTCG TTTTCCGGTC CTTGGCATTT TTCCGGCGCA ACGACCGCAA

AAAGGTATCC GAGGCGGGGG GACTGCTCGT AGTGTTTTTA CGACGCTCAA GTCAGAGGTG GCGAAACCCG ACAGGACTAT

AAAGATACCA GGCGTTTCCC CCTGGAAGCT CCCTCGTGCG CTCTCCTGTT CCGACCCTGC GCTGCGAGTT CAGTCTCCAC

CGCTTTGGGC TGTCCTGATA TTTCTATGGT CCGCAAAGGG GGACCTTCGA GGGAGCACGC GAGAGGACAA GGCTGGGACG

CGCTTACCGG ATACCTGTCC GCCTTTCTCC CTTCGGGAAG CGTGGCGCTT TCTCATAGCT CACGCTGTAG GTATCTCAGT

TCGGTGTAGG TCGTTCGCTC GCGAATGGCC TATGGACAGG CGGAAAGAGG GAAGCCCTTC GCACCGCGAA AGAGTATCGA

GTGCGACATC CATAGAGTCA AGCCACATCC AGCAAGCGAG CAAGCTGGGC TGTGTGCACG AACCCCCCGT TCAGCCCGAC

CGCTGCGCCT TATCCGGTAA CTATCGTCTT GAGTCCAACC CGGTAAGACA CGACTTATCG GTTCGACCCG ACACACGTGC

TTGGGGGCA AGTCGGGCTG GCGACGCGGA ATAGGCCATT GATAGCAGAA CTCAGGTTGG GCCATTCTGT GCTGAATAGC

CCACTGGCAG CAGCCACTGG TAACAGGATT AGCAGAGCGA GGTATGTAGG CGGTGCTACA GAGTTCTTGA AGTGGTGGCC

TAACTACGGC TACACTAGAA GGTGACCGTC GTCGGTGACC ATTGTCCTAA TCGTCTCGCT CCATACATCC GCCACGATGT

CTCAAGAACT TCACCACCGG ATTGATGCCG ATGTGATCTT GGACAGTATT TGGTATCTGC GCTCTGCTGA AGCCAGTTAC

CTTCGGAAAA AGAGTTGGTA GCTCTTGATC CGGCAAACAA ACCACCGCTG GTAGCGGTGG CCTGTCATAA ACCATAGACG

CGAGACGACT TCGGTCAATG GAAGCCTTTT TCTCAACCAT CGAGAACTAG GCCGTTTGTT TGGTGGCGAC CATCGCCACC

TTTTTTTGTT TGCAAGCAGC AGATTACGCG CAGAAAAAAA GGATCTCAAG AAGATCCTTT GATCTTTTCT ACGGGGTCTG

ACGCTCAGTG GAACGAAAAC AAAAAAACAA ACGTTCGTCG TCTAATGCGC GTCTTTTTTT CCTAGAGTTC TTCTAGGAAA

CTAGAAAAGA TGCCCCAGAC TGCGAGTCAC CTTGCTTTTG TCACGTTAAG GGATTTTGGT CATGAGATTA TCAAAAGGA

TCTTCACCTA GATCCTTTTA AATTAAAAAT GAAGTTTTAA ATCAATCTAA AGTATATATG AGTGCAATTC CCTAAAACCA

GTACTCTAAT AGTTTTTCCT AGAAGTGGAT CTAGGAAAAT TTAATTTTTA CTTCAAAATT TAGTTAGATT TCATATATAC

AGTAAACTTG GTCTGACAGT TACCAATGCT TAATCAGTGA GGCACCTATC TCAGCGATCT GTCTATTTCG TTCATCCATA

GTTGCCTGAC TCCCCGTCGT TCATTTGAAC CAGACTGTCA ATGGTTACGA ATTAGTCACT CCGTGGATAG AGTCGCTAGA

CAGATAAAGC AAGTAGGTAT CAACGGACTG AGGGGCAGCA GTAGATAACT ACGATACGGG AGGGCTTACC ATCTGGCCCC

AGTGCTGCAA TGATACCGCG AGACCCACGC TCACCGGCTC CAGATTTATC AGCAATAAAC CATCTATTGA TGCTATGCCC

TCCCGAATGG TAGACCGGGG TCACGACGTT ACTATGGCGC TCTGGGTGCG AGTGGCCGAG GTCTAAATAG TCGTTATTTG

CAGCCAGCCG GAAGGGCCGA GCGCAGAAGT GGTCCTGCAA CTTTATCCGC CTCCATCCAG TCTATTAATT GTTGCCGGGA

AGCTAGAGTA AGTAGTTCGC GTCGGTCGGC CTTCCCGGCT CGCGTCTTCA CCAGGACGTT GAAATAGGCG GAGGTAGGTC
```

-continued

```
AGATAATTAA CAACGGCCCT TCGATCTCAT TCATCAAGCG CAGTTAATAG TTTGCGCAAC GTTGTTGCCA TTGCTACAGG
CATCGTGGTG TCACGCTCGT CGTTTGGTAT GGCTTCATTC AGCTCCGGTT CCCAACGATC GTCAATTATC AAACGCGTTG
CAACAACGGT AACGATGTCC GTAGCACCAC AGTGCGAGCA GCAAACCATA CCGAAGTAAG TCGAGGCCAA GGGTTGCTAG
AAGGCGAGTT ACATGATCCC CCATGTTGTG CAAAAAAGCG GTTAGCTCCT TCGGTCCTCC GATCGTTGTC AGAAGTAAGT
TGGCCGCAGT GTTATCACTC TTCCGCTCAA TGTACTAGGG GGTACAACAC GTTTTTTCGC CAATCGAGGA AGCCAGGAGG
CTAGCAACAG TCTTCATTCA ACCGGCGTCA CAATAGTGAG ATGGTTATGG CAGCACTGCA TAATTCTCTT ACTGTCATGC
CATCCGTAAG ATGCTTTTCT GTGACTGGTG AGTACTCAAC CAAGTCATTC TGAGAATAGT TACCAATACC GTCGTGACGT
ATTAAGAGAA TGACAGTACG GTAGGCATTC TACGAAAAGA CACTGACCAC TCATGAGTTG GTTCAGTAAG ACTCTTATCA
GTATGCGGCG ACCGAGTTGC TCTTGCCCGG CGTCAATACG GGATAATACC GCGCCACATA GCAGAACTTT AAAAGTGCTC
ATCATTGGAA AACGTTCTTC CATACGCCGC TGGCTCAACG AGAACGGGCC GCAGTTATGC CCTATTATGG CGCGGTGTAT
CGTCTTGAAA TTTTCACGAG TAGTAACCTT TTGCAAGAAG GGGGCGAAAA CTCTCAAGGA TCTTACCGCT GTTGAGATCC
AGTTCGATGT AACCCACTCG TGCACCCAAC TGATCTTCAG CATCTTTTAC TTTCACCAGC CCCCGCTTTT GAGAGTTCCT
AGAATGGCGA CAACTCTAGG TCAAGCTACA TTGGGTGAGC ACGTGGGTTG ACTAGAAGTC GTAGAAAATG AAAGTGGTCG
GTTTCTGGGT GAGCAAAAAC AGGAAGGCAA AATGCCGCAA AAAAGGGAAT AAGGGCGACA CGGAAATGTT GAATACTCAT
ACTCTTCCTT TTTCAATATT CAAAGACCCA CTCGTTTTTG TCCTTCCGTT TTACGGCGTT TTTTCCCTTA TTCCCGCTGT
GCCTTTACAA CTTATGAGTA TGAGAAGGAA AAAGTTATAA ATTGAAGCAT TTATCAGGGT TATTGTCTCA TGAGCGGATA
CATATTTGAA TGTATTTAGA AAAATAAACA AATAGGGGTT CCGCGCACAT TTCCCCGAAA TAACTTCGTA AATAGTCCCA
ATAACAGAGT ACTCGCCTAT GTATAAACTT ACATAAATCT TTTTATTTGT TTATCCCCAA GGCGCGTGTA AAGGGGCTTT
AGTGCCACCT GACGTCTAAG AAACCATTAT TATCATGACA TTAACCTATA AAATAGGCG TATCACGAGG CCCTTTCGTC
TCACGGTGGA CTGCAGATTC TTTGGTAATA ATAGTACTGT AATTGGATAT TTTTATCCGC ATAGTGCTCC GGGAAAGCAG
                                                                            SEQ ID: 02
GGGGAGCCGC GCCGAAGGCG TGGGGGAACC CCGCAGGGGT GCCCTTCTTT GGGCACCAAA GAACTAGATA TAGGGCGAAA
TGCGAAAGAC TTAAAAATCA CCCCTCGGCG CGGCTTCCGC ACCCCCTTGG GGCGTCCCCA CGGGAAGAAA CCCGTGGTTT
CTTGATCTAT ATCCCGCTTT ACGCTTTCTG AATTTTTAGT ACAACTTAAA AAGGGGGGT ACGCAACAGC TCATTGCGGC
ACCCCCCGCA ATAGCTCATT GCGTAGGTTA AGAAAATCT GTAATTGACT GCCACTTTTA TGTTGAATTT TTTCCCCCCA
TGCGTTGTCG AGTAACGCCG TGGGGGGCGT TATCGAGTAA CGCATCCAAT TTCTTTTAGA CATTAACTGA CGGTGAAAAT
CGCAACGCAT AATTGTTGTC GCGCTGCCGA AAAGTTGCAG CTGATTGCGC ATGGTGCCGC AACCGTGCGG CACCCTACCG
CATGGAGATA AGCATGGCCA GCGTTGCGTA TTAACAACAG CGCGACGGCT TTTCAACGTC GACTAACGCG TACCACGGCG
TTGGCACGCC GTGGGATGGC GTACCTCTAT TCGTACCGGT CGCAGTCCAG AGAAATCGGC ATTCAAGCCA AGAACAAGCC
CGGTCACTGG GTGCAAACGG AACGCAAAGC GCATGAGGCG TGGGCCGGGC TTATTGCGAG GCGTCAGGTC TCTTTAGCCG
TAAGTTCGGT TCTTGTTCGG GCCAGTGACC CACGTTTGCC TTGCGTTTCG CGTACTCCGC ACCCGGCCCG AATAACGCTC
GAAACCCACG GCGGCAATGC TGCTGCATCA CCTCGTGGCG CAGATGGGCC ACCAGAACGC CGTGGTGGTC AGCCAGAAGA
CACTTTCCAA GCTCATCGGA CTTTGGGTGC CGCCGTTACG ACGACGTAGT GGAGCACCGC GTCTACCCGG TGGTCTTGCG
GCACCACCAG TCGGTCTTCT GTGAAAGGTT CGAGTAGCCT CGTTCTTTGC GGACGGTCCA ATACGCAGTC AAGGACTTGG
TGGCCGAGCG CTGGATCTCC GTCGTGAAGC TCAACGGCCC CGGCACCGTG TCGGCCTACG GCAAGAAACG CCTGCCAGGT
TATGCGTCAG TTCCTGAACC ACCGGCTCGC GACCTAGAGG CAGCACTTCG AGTTGCCGGG GCCGTGGCAC AGCCGGATGC
TGGTCAATGA CCGCGTGGCG TGGGGCCAGC CCCGCGACCA GTTGCGCCTG TCGGTGTTCA GTGCCGCCGT GGTGGTTGAT
CACGACGACC AGGACGAATC ACCAGTTACT GGCGCACCGC ACCCCGGTCG GGGCGCTGGT CAACGCGGAC AGCCACAAGT
CACGGCGGCA CCACCAACTA GTGCTGCTGG TCCTGCTTAG GCTGTTGGGG CATGGCGACC TGCGCCGCAT CCCGACCCTG
TATCCGGGCG AGCAGCAACT ACCGACCGGC CCCGGCGAGG AGCCGCCCAG CCAGCCCGGC CGACACCCCC GTACCGCTGG
ACGCGGCGTA GGGCTGGGAC ATAGGCCCGC TCGTCGTTGA TGGCTGGCCG GGGCCGCTCC TCGGCGGGTC GGTCGGGCCG
```

```
ATTCCGGGCA TGGAACCAGA CCTGCCAGCC TTGACCGAAA CGGAGGAATG GGAACGGCGC GGGCAGCAGC GCCTGCCGAT

GCCCGATGAG CCGTGTTTTC TAAGGCCCGT ACCTTGGTCT GGACGGTCGG AACTGGCTTT GCCTCCTTAC CCTTGCCGCG

CCCGTCGTCG CGGACGGCTA CGGGCTACTC GGCACAAAAG TGGACGATGG CGAGCCGTTG GAGCCGCCGA CACGGGTCAC

GCTGCCGCGC CGGTAGCACT TGGGTTGCGC AGCAACCCGT AAGTGCGCTG TTCCAGACTA ACCTGCTACC GCTCGGCAAC

CTCGGCGGCT GTGCCCAGTG CGACGGCGCG GCCATCGTGA ACCCAACGCG TCGTTGGGCA TTCACGCGAC AAGGTCTGAT

TCGGCTGTAG CCGCCTCGCC GCCCTATACC TTGTCTGCCT CCCCGCGTTG CGTCGCGGTG CATGGAGCCG GGCCACCTCG

ACCTGAATGG AAGCCGGCGG AGCCGACATC GGCGGAGCGG CGGGATATGG AACAGACGGA GGGGCGCAAC GCAGCGCCAC

GTACCTCGGC CCGGTGGAGC TGGACTTACC TTCGGCCGCC CACCTCGCTA ACGGATTCAC CGTTTTTATC AGGCTCTGGG

AGGCAGAATA AATGATCATA TCGTCAATTA TTACCTCCAC GGGGAGAGCC TGAGCAAACT GTGGAGCGAT TGCCTAAGTG

GCAAAAATAG TCCGAGACCC TCCGTCTTAT TTACTAGTAT AGCAGTTAAT AATGGAGGTG CCCCTCTCGG ACTCGTTTGA

GGCCTCAGGC ATTTGAGAAG CACACGGTCA CACTGCTTCC GGTAGTCAAT AAACCGGTAA ACCAGCAATA GACATAAGCG

GCTATTTAAC GACCCTGCCC CCGGAGTCCG TAAACTCTTC GTGTGCCAGT GTGACGAAGG CCATCAGTTA TTTGGCCATT

TGGTCGTTAT CTGTATTCGC CGATAAATTG CTGGGACGGG TGAACCGACG ACCGGGTCGA ATTTGCTTTC GAATTTCTGC

CATTCATCCG CTTATTATCA CTTATTCAGG CGTAGCACCA GGCGTTTAAG GCACCAATA ACTTGGCTGC TGGCCCAGCT

TAAACGAAAG CTTAAAGACG GTAAGTAGGC GAATAATAGT GAATAAGTCC GCATCGTGGT CCGCAAATTC CCGTGGTTAT

ACTGCCTTAA AAAATTACG CCCCGCCCTG CCACTCATCG CAGTCGGCCT ATTGGTTAAA AAATGAGCTG ATTTAACAAA

AATTTAACGC GAATTTTAAC TGACGGAATT TTTTTAATGC GGGGCGGGAC GGTGAGTAGC GTCAGCCGGA TAACCAATTT

TTTACTCGAC TAAATTGTTT TTAAATTGCG CTTAAAATTG AAAATATTAA CGCTTACAAT TTCCATTCGC CATTCAGGCT

GCGCAACTGT TGGGAAGGGC GATCGGTGCG GGCCTCTTCG CTATTACGCC AGCTGGCGAA TTTTATAATT GCGAATGTTA

AAGGTAAGCG GTAAGTCCGA CGCGTTGACA ACCCTTCCCG CTAGCCACGC CCGGAGAAGC GATAATGCGG TCGACCGCTT

AGGGGGATGT GCTGCAAGGC GATTAAGTTG GGTAACGCCA GGGTTTTCCC AGTCACGACG TTGTAAAACG ACGGCCAGTG

AGCGCGCGTA ATACGACTCA TCCCCCTACA CGACGTTCCG CTAATTCAAC CCATTGCGGT CCCAAAAGGG TCAGTGCTGC

AACATTTTGC TGCCGGTCAC TCGCGCGCAT TATGCTGAGT CTATAGGGCG AATTGGAGCT CCACCGCGGT GGCGGCCGCT

CTAGAACTAG TGGATCCCCC GGGCTGCAGG AATTCGATAT CAAGCTTATC GATACCGTCG GATATCCCGC TTAACCTCGA

GGTGGCGCCA CCGCCGGCGA GATCTTGATC ACCTAGGGGG CCCGACGTCC TTAAGCTATA GTTCGAATAG CTATGGCAGC

ACCTCGAGGG GGGGCCCGGT ACCCAGCTTT TGTTCCCTTT AGTGAGGGTT AATTGCGCGC TTGGCGTAAT CATGGTCATA

GCTGTTTCCT GTGTGAAATT TGGAGCTCCC CCCCGGGCCA TGGGTCGAAA CAAGGGAAA TCACTCCCAA TTAACGCGCG

AACCGCATTA GTACCAGTAT CGACAAAGGA CACACTTTAA GTTATCCGCT CACAATTCCA CACAACATAC GAGCCGGAAG

CATAAAGTGT AAAGCCTGGG GTGCCTAATG AGTGAGCTAA CTCACATTAA TTGCGTTGCG CAATAGGCGA GTGTTAAGGT

GTGTTGTATG CTCGGCCTTC GTATTTCACA TTTCGGACCC CACGGATTAC TCACTCGATT GAGTGTAATT AACGCAACGC

CTCACTGCCC GCTTTCCAGT CGGGAAACCT GTCGTGCCAG CTGCATTAAT GAATCGGCCA ACGCGCGGGG AGAGGCGGTT

TGCGTATTGG GCGCATGCAT GAGTGACGGG CGAAAGGTCA GCCCTTTGGA CAGCACGGTC GACGTAATTA CTTAGCCGGT

TGCGCGCCCC TCTCCGCCAA ACGCATAACC CGCGTACGTA AAAAACTGTT GTAATTCATT AAGCATTCTG CCGACATGGA

AGCCATCACA AACGGCATGA TGAACCTGAA TCGCCAGCGG CATCAGCACC TTGTCGCCTT TTTTTGACAA CATTAAGTAA

TTCGTAAGAC GGCTGTACCT TCGGTAGTGT TTGCCGTACT ACTTGGACTT AGCGGTCGCC GTAGTCGTGG AACAGCGGAA

GCGTATAATA TTTGCCCATG GGGGTGGGCG AAGAACTCCA GCATGAGATC CCCGCGCTGG AGGATCATCC AGCCGGCGTC

CCGGAAAACG ATTCCGAAGC CGCATATTAT AAACGGGTAC CCCCACCCGC TTCTTGAGGT CGTACTCTAG GGGCGCGACC

TCCTAGTAGG TCGGCCGCAG GGCCTTTTGC TAAGGCTTCG CCAACCTTTC ATAGAAGGCG GCGGTGGAAT CGAAATCTCG

TGATGGCAGG TTGGGCGTCG CTTGGTCGGT CATTTCGAAC CCCAGAGTCC CGCTCAGAAG GGTTGGAAAG TATCTTCCGC

CGCCACCTTA GCTTTAGAGC ACTACCGTCC AACCCGCAGC GAACCAGCCA GTAAAGCTTG GGGTCTCAGG GCGAGTCTTC

AACTCGTCAA GAAGGCGATA GAAGGCGATG CGCTGCGAAT CGGGAGCGGC GATACCGTAA AGCACGAGGA AGCGGTCAGC
```

-continued

```
CCATTCGCCG CCAAGCTCTT TTGAGCAGTT CTTCCGCTAT CTTCCGCTAC GCGACGCTTA GCCCTCGCCG CTATGGCATT

TCGTGCTCCT TCGCCAGTCG GGTAAGCGGC GGTTCGAGAA CAGCAATATC ACGGGTAGCC AACGCTATGT CCTGATAGCG

GTCCGCCACA CCCAGCCGGC CACAGTCGAT GAATCCAGAA AAGCGGCCAT TTTCCACCAT GTCGTTATAG TGCCCATCGG

TTGCGATACA GGACTATCGC CAGGCGGTGT GGGTCGGCCG GTGTCAGCTA CTTAGGTCTT TTCGCCGGTA AAAGGTGGTA

GATATTCGGC AAGCAGGCAT CGCCATGGGT CACGACGAGA TCCTCGCCGT CGGGCATGCG CGCCTTGAGC CTGGCGAACA

GTTCGGCTGG CGCGAGCCCC CTATAAGCCG TTCGTCCGTA GCGGTACCCA GTGCTGCTCT AGGAGCGGCA GCCCGTACGC

GCGGAACTCG GACCGCTTGT CAAGCCGACC GCGCTCGGGG TGATGCTCTT CGTCCAGATC ATCCTGATCG ACAAGACCGG

CTTCCATCCG AGTACGTGCT CGCTCGATGC GATGTTTCGC TTGGTGGTCG AATGGGCAGG ACTACGAGAA GCAGGTCTAG

TAGGACTAGC TGTTCTGGCC GAAGGTAGGC TCATGCACGA GCGAGCTACG CTACAAAGCG AACCACCAGC TTACCCGTCC

TAGCCGGATC AAGCGTATGC AGCCGCCGCA TTGCATCAGC CATGATGGAT ACTTTCTCGG CAGGAGCAAG GTGAGATGAC

AGGAGATCCT GCCCCGGCAC ATCGGCCTAG TTCGCATACG TCGGCGGCGT AACGTAGTCG GTACTACCTA TGAAAGAGCC

GTCCTCGTTC CACTCTACTG TCCTCTAGGA CGGGGCCGTG TTCGCCCAAT AGCAGCCAGT CCCTTCCCGC TTCAGTGACA

ACGTCGAGCA CAGCTGCGCA AGGAACGCCC GTCGTGGCCA GCCACGATAG CCGCGCTGCC AAGCGGGTTA TCGTCGGTCA

GGGAAGGGCG AAGTCACTGT TGCAGCTCGT GTCGACGCGT TCCTTGCGGG CAGCACCGGT CGGTGCTATC GGCGCGACGG

TCGTCCTGCA GTTCATTCAG GGCACCGGAC AGGTCGGTCT TGACAAAAAG AACCGGGCGC CCCTGCGCTG ACAGCCGGAA

CACGGCGGCA TCAGAGCAGC AGCAGGACGT CAAGTAAGTC CCGTGGCCTG TCCAGCCAGA ACTGTTTTTC TTGGCCCGCG

GGGACGCGAC TGTCGGCCTT GTGCCGCCGT AGTCTCGTCG CGATTGTCTG TTGTGCCCAG TCATAGCCGA ATAGCCTCTC

CACCCAAGCG GCCGGAGAAC CTGCGTGCAA TCCATCTTGT TCAATCATGC GAAACGATCC GCTAACAGAC AACACGGGTC

AGTATCGGCT TATCGGAGAG GTGGGTTCGC CGGCCTCTTG GACGCACGTT AGGTAGAACA AGTTAGTACG CTTTGCTAGG

TCATCCTGTC TCTTGATCAG ATCTTGATCC CCTGCGCCAT CAGATCCTTG GCGGCAAGAA AGCCATCCAG TTTACTTTGC

AGGGCTTCCC AACCTTACCA AGTAGGACAG AGAACTAGTC TAGAACTAGG GGACGCGGTA GTCTAGGAAC CGCCGTTCTT

TCGGTAGGTC AAATGAAACG TCCCGAAGGG TTGGAATGGT GAGGGCGCCC CAGCTGGCAA TTCCGGTTCG CTTGCTGTCC

ATAAAACCGC CCAGTCTAGC TATCGCCATG TAAGCCCACT GCAAGCTACC TGCTTTCTCT CTCCCGCGGG GTCGACCGTT

AAGGCCAAGC GAACGACAGG TATTTTGGCG GGTCAGATCG ATAGCGGTAC ATTCGGGTGA CGTTCGATGG ACGAAAGAGA

TTGCGCTTGC GTTTTCCCTT GTCCAGATAG CCCAGTAGCT GACATTCATC CCAGGTGGCA CTTTTCGGGG AAATGTGCGC

GCCCGCGTTC CTGCTGGCGC AACGCGAACG CAAAAGGGAA CAGGTCTATC GGGTCATCGA CTGTAAGTAG GGTCCACCGT

GAAAAGCCCC TTTACACGCG CGGGCGCAAG GACGACCGCG TGGGCCTGTT TCTGGCGCTG GACTTCCCGC TGTTCCGTCA

GCAGCTTTTC GCCCACGGCC TTGATGATCG CGGCGGCCTT GGCCTGCATA TCCCGATTCA ACCCGGACAA AGACCGCGAC

CTGAAGGGCG ACAAGGCAGT CGTCGAAAAG CGGGTGCCGG AACTACTAGC GCCGCCGGAA CCGGACGTAT AGGGCTAAGT

ACGGCCCCAG GGCGTCCAGA ACGGGCTTCA GGCGCTCCCG AAGGTCTCGG CCGTCTCTT GGGCTTGATC GGCCTTCTTG

CGCATCTCAC GCGCTCCTGC TGCCGGGGTC CCGCAGGTCT TGCCCGAAGT CCGCGAGGGC TTCCAGAGCC CGGCAGAGAA

CCCGAACTAG CCGGAAGAAC GCGTAGAGTG CGCGAGGACG GGCGGCCTGT AGGGCAGGCT CATACCCCTG CCGAACCGCT

TTTGTCAGCC GGTCGGCCAC GGCTTCCGGC GTCTCAACGC GCTTTGAGAT TCCCAGCTTT CCGCCGGACA TCCCGTCCGA

GTATGGGGAC GGCTTGGCGA AAACAGTCGG CCAGCCGGTG CCGAAGGCCG CAGAGTTGCG CGAAACTCTA AGGGTCGAAA

TCGGCCAATC CCTGCGGTGC ATAGGCGCGT GGCTCGACCG CTTGCGGGCT GATGGTGACG TGGCCCACTG GTGGCCGCTC

CAGGGCCTCG TAGAACGCCT AGCCGGTTAG GGACGCCACG TATCCGCGCA CCGAGCTGGC GAACGCCCGA CTACCACTGC

ACCGGGTGAC CACCGGCGAG GTCCCGGAGC ATCTTGCGGA GAATGCGCGT GTGACGTGCC TTGCTGCCCT CGATGCCCCG

TTGCAGCCCT AGATCGGCCA CAGCGGCCGC AAACGTGGTC TGGTCGCGGG TCATCTGCGC CTTACGCGCA CACTGCACGG

AACGACGGGA GCTACGGGGC AACGTCGGGA TCTAGCCGGT GTCGCCGGCG TTTGCACCAG ACCAGCGCCC AGTAGACGCG

TTTGTTGCCG ATGAACTCCT TGGCCGACAG CCTGCCGTCC TGCGTCAGCG GCACCACGAA CGCGGTCATG TGCGGGCTGG
```

-continued

```
TTTCGTCACG GTGGATGCTG AAACAACGGC TACTTGAGGA ACCGGCTGTC GGACGGCAGG ACGCAGTCGC CGTGGTGCTT

GCGCCAGTAC ACGCCCGACC AAAGCAGTGC CACCTACGAC GCCGTCACGA TGCGATCCGC CCCGTACTTG TCCGCCAGCC

ACTTGTGCGC CTTCTCGAAG AACGCCGCCT GCTGTTCTTG GCTGGCCGAC TTCCACCATT CGGCAGTGCT ACGCTAGGCG

GGGCATGAAC AGGCGGTCGG TGAACACGCG AAGAGCTTC TTGCGGCGGA CGACAAGAAC CGACCGGCTG AAGGTGGTAA

CCGGGCTGGC CGTCATGACG TACTCGACCG CCAACACAGC GTCCTTGCGC CGCTTCTCTG GCAGCAACTC GCGCAGTCGG

CCCATCGCTT CATCGGTGCT GGCCCGACCG GCAGTACTGC ATGAGCTGGC GGTTGTGTCG CAGGAACGCG GCGAAGAGAC

CGTCGTTGAG CGCGTCAGCC GGGTAGCGAA GTAGCCACGA GCTGGCCGCC CAGTGCTCGT TCTCTGGCGT CCTGCTGGCG

TCAGCGTTGG GCGTCTCGCG CTCGCGGTAG GCGTGCTTGA GACTGGCCGC CACGTTGCCC CGACCGGCGG GTCACGAGCA

AGAGACCGCA GGACGACCGC AGTCGCAACC CGCAGAGCGC GAGCGCCATC CGCACGAACT CTGACCGGCG GTGCAACGGG

ATTTTCGCCA GCTTCTTGCA TCGCATGATC GCGTATGCCG CCATGCCTGC CCCTCCCTTT TGGTGTCCAA CCGGCTCGAC

GGGGGCAGCG CAAGGCGGTG TAAAAGCGGT CGAAGAACGT AGCGTACTAG CGCATACGGC GGTACGGACG GGGAGGGAAA

ACCACAGGTT GGCCGAGCTG CCCCCGTCGC GTTCCGCCAC CCTCCGGCGG GCCACTCAAT GCTTGAGTAT ACTCACTAGA

CTTTGCTTCG CAAAGTCGTG ACCGCCTACG GCGGCTGCGG CGCCCTACGG GCTTGCTCTC GGAGGCCGCC CGGTGAGTTA

CGAACTCATA TGAGTGATCT GAAACGAAGC GTTTCAGCAC TGGCGGATGC CGCCGACGCC GCGGGATGCC CGAACGAGAG

CGGGCTTCGC CCTGCGCGGT CGCTGCGCTC CCTTGCCAGC CCGTGGATAT GTGGACGATG GCCGCGAGCG GCCACCGGCT

GGCTCGCTTC GCTCGGCCCG GCCCGAAGCG GGACGCGCCA GCGACGCGAG GAACGGTCG GCACCTATA CACCTGCTAC

CGGCGCTCGC CGGTGGCCGA CCGAGCGAAG CGAGCCGGGC TGGACAACCC TGCTGGACAA GCTGATGGAC AGGCTGCGCC

TGCCCACGAG CTTGACCACA GGGATTGCCC ACCGGCTACC CAGCCTTCGA CCACATACCC ACCTGTTGGG ACGACCTGTT

CGACTACCTG TCCGACGCGG ACGGGTGCTC GAACTGGTGT CCCTAACGGG TGGCCGATGG GTCGGAAGCT GGTGTATGGG

ACCGGCTCCA ACTGCGCGGC CTGCGGCCTT GCCCCATCAA TTTTTTTAAT TTTCTCTGGG GAAAAGCCTC CGGCCTGCGG

CCTGCGCGCT TCGCTTGCCG TGGCCGAGGT TGACGCGCCG GACGCCGGAA CGGGGTAGTT AAAAAAATTA AAAGAGACCC

CTTTTCGGAG GCCGGACGCC GGACGCGCGA AGCGAACGGC GTTGGACACC AAGTGGAAGG CGGGTCAAGG CTCGCGCAGC

GACCGCGCAG CGGCTTGGCC TTGACGCGCC TGGAACGACC CAAGCCTATG CGAGTGGGGG CAACCTGTGG TTCACCTTCC

GCCCAGTTCC GAGCGCGTCG CTGGCGCGTC GCCGAACCGG AACTGCGCGG ACCTTGCTGG GTTCGGATAC GCTCACCCCC

CAGTCGAAGG CGAAGCCCGC CCGCCTGCCC CCCGAGCCTC ACGGCGGCGA GTGCGGGGGT TCCAAGGGGG CAGCGCCACC

TTGGGCAAGG CCGAAGGCCG GTCAGCTTCC GCTTCGGGCG GGCGGACGGG GGGCTCGGAG TGCCGCCGCT CACGCCCCCA

AGGTTCCCCC GTCGCGGTGG AACCCGTTCC GGCTTCCGGC CGCAGTCGAT CAACAAGCCC CGGAGGGGCC ACTTTTTGCC

GGAGGCGTCA GCTAGTTGTT CGGGGCCTCC CCGGTGAAAA ACGGCCTC
```

SEQ ID: 03
```
GGGGAGCCGC GCCGAAGGCG TGGGGGAACC CCGCAGGGGT GCCCTTCTTT GGGCACCAAA GAACTAGATA TAGGGCGAAA

TGCGAAAGAC TTAAAAATCA CCCCTCGGCG CGGCTTCCGC ACCCCCTTGG GGCGTCCCCA CGGGAAGAAA CCCGTGGTTT

CTTGATCTAT ATCCCGCTTT ACGCTTTCTG AATTTTTAGT ACAACTTAAA AAAGGGGGT ACGCAACAGC TCATTGCGGC

ACCCCCCGCA ATAGCTCATT GCGTAGGTTA AGAAAATCT GTAATTGACT GCCACTTTTA TGTTGAATTT TTTCCCCCCA

TGCGTTGTCG AGTAACGCCG TGGGGGGCGT TATCGAGTAA CGCATCCAAT TTCTTTTAGA CATTAACTGA CGGTGAAAAT

CGCAACGCAT AATTGTTGTC GCGCTGCCGA AAAGTTGCAG CTGATTGCGC ATGGTGCCGC AACCGTGCGG CACCCTACCG

CATGGAGATA AGCATGGCCA GCGTTGCGTA TTAACAACAG CGCGACGGCT TTTCAACGTC GACTAACGCG TACCACGGCG

TTGGCACGCC GTGGGATGGC GTACCTCTAT TCGTACCGGT CGCAGTCCAG AGAAATCGGC ATTCAAGCCA AGAACAAGCC

CGGTCACTGG GTGCAAACGG AACGCAAAGC GCATGAGGCG TGGGCCGGGC TTATTGCGAG GCGTCAGGTC TCTTTAGCCG

TAAGTTCGGT TCTTGTTCGG GCCAGTGACC CACGTTTGCC TTGCGTTTCG CGTACTCCGC ACCCGGCCCG AATAACGCTC

GAAACCCACG GCGGCAATGC TGCTGCATCA CCTCGTGGCG CAGATGGGCC ACCAGAACGC GTGGTGGTC AGCCAGAAGA

CACTTTCCAA GCTCATCGGA CTTTGGGTGC CGCCGTTACG ACGACGTAGT GGAGCACCGC GTCTACCCGG TGGTCTTGCG
```

-continued

```
GCACCACCAG TCGGTCTTCT GTGAAAGGTT CGAGTAGCCT CGTTCTTTGC GGACGGTCCA ATACGCAGTC AAGGACTTGG

TGGCCGAGCG CTGGATCTCC GTCGTGAAGC TCAACGGCCC CGGCACCGTG TCGGCCTACG GCAAGAAACG CCTGCCAGGT

TATGCGTCAG TTCCTGAACC ACCGGCTCGC GACCTAGAGG CAGCACTTCG AGTTGCCGGG GCCGTGGCAC AGCCGGATGC

TGGTCAATGA CCGCGTGGCG TGGGGCCAGC CCCGCGACCA GTTGCGCCTG TCGGTGTTCA GTGCCGCCGT GGTGGTTGAT

CACGACGACC AGGACGAATC ACCAGTTACT GGCGCACCGC ACCCCGGTCG GGGCGCTGGT CAACGCGGAC AGCCACAAGT

CACGGCGGCA CCACCAACTA GTGCTGCTGG TCCTGCTTAG GCTGTTGGGG CATGGCGACC TGCGCCGCAT CCCGACCCTG

TATCCGGGCG AGCAGCAACT ACCGACCGGC CCCGGCGAGG AGCCGCCCAG CCAGCCCGGC CGACAACCCC GTACCGCTGG

ACGCGGCGTA GGGCTGGGAC ATAGGCCCGC TCGTCGTTGA TGGCTGGCCG GGGCCGCTCC TCGGCGGGTC GGTCGGGCCG

ATTCCGGGCA TGGAACCAGA CCTGCCAGCC TTGACCGAAA CGGAGGAATG GGAACGGCGC GGGCAGCAGC GCCTGCCGAT

GCCCGATGAG CCGTGTTTTC TAAGGCCCGT ACCTTGGTCT GGACGGTCGG AACTGGCTTT GCCTCCTTAC CCTTGCCGCG

CCCGTCGTCG CGGACGGCTA CGGGCTACTC GGCACAAAAG TGGACGATGG CGAGCCGTTG GAGCCGCCGA CACGGGTCAC

GCTGCCGCGC CGGTAGCACT TGGGTTGCGC AGCAACCCGT AAGTGCGCTG TTCCAGACTA ACCTGCTACC GCTCGGCAAC

CTCGGCGGCT GTGCCCAGTG CGACGGCGCG GCCATCGTGA ACCCAACGCG TCGTTGGGCA TTCACGCGAC AAGGTCTGAT

TCGGCTGTAG CCGCCTCGCC GCCCTATACC TTGTCTGCCT CCCCGCGTTG CGTCGCGGTG CATGGAGCCG GGCCACCTCG

ACCTGAATGG AAGCCGGCGG AGCCGACATC GGCGGAGCGG CGGGATATGG AACAGACGGA GGGGCGCAAC GCAGCGCCAC

GTACCTCGGC CCGGTGGAGC TGGACTTACC TTCGGCCGCC CACCTCGCTA ACGGATTCAC CGTTTTTATC AGGCTCTGGG

AGGCAGAATA AATGATCATA TCGTCAATTA TTACCTCCAC GGGGAGAGCC TGAGCAAACT GTGGAGCGAT TGCCTAAGTG

GCAAAAATAG TCCGAGACCC TCCGTCTTAT TTACTAGTAT AGCAGTTAAT AATGGAGGTG CCCCTCTCGG ACTCGTTTGA

GGCCTCAGGC ATTTGAGAAG CACACGTCA CACTGCTTCC GGTAGTCAAT AAACCGGTAA ACCAGCAATA GACATAAGCG

GCTATTTAAC GACCCTGCCC CCGGAGTCCG TAAACTCTTC GTGTGCCAGT GTGACGAAGG CCATCAGTTA TTTGGCCATT

TGGTCGTTAT CTGTATTCGC CGATAAATTG CTGGGACGGG TGAACCGACG ACCGGGTCGA ATTTGCTTTC GAATTTCTGC

CATTCATCCG CTTATTATCA CTTATTCAGG CGTAGCACCA GGCGTTTAAG GGCACCAATA ACTTGGCTGC TGGCCCAGCT

TAAACGAAAG CTTAAAGACG GTAAGTAGGC GAATAATAGT GAATAAGTCC GCATCGTGGT CCGCAAATTC CCGTGGTTAT

ACTGCCTTAA AAAAATTACG CCCCGCCCTG CCACTCATCG CAGTCGGCCT ATTGGTTAAA AAATGAGCTG ATTTAACAAA

AATTTAACGC GAATTTTAAC TGACGGAATT TTTTTAATGC GGGGCGGGAC GGTGAGTAGC GTCAGCCGGA TAACCAATTT

TTTACTCGAC TAAATTGTTT TTAAATTGCG CTTAAAATTG AAAATATTAA CGCTTACAAT TTCCATTCGC CATTCAGGCT

GCGCAACTGT TGGGAAGGGC GATCGGTGCG GGCCTCTTCG CTATTACGCC AGCTGGCGAA TTTTATAATT GCGAATGTTA

AAGGTAAGCG GTAAGTCCGA CGCGTTGACA ACCCTTCCCG CTAGCCACGC CCGGAGAAGC GATAATGCGG TCGACCGCTT

AGGGGGATGT GCTGCAAGGC GATTAAGTTG GGTAACGCCA GGGTTTTCCC AGTCACGACG TTGTAAAACG ACGGCCAGTG

AGCGCGCGTA ATACGACTCA TCCCCCTACA CGACGTTCCG CTAATTCAAC CCATTGCGGT CCCAAAAGGG TCAGTGCTGC

AACATTTTGC TGCCGGTCAC TCGCGCGCAT TATGCTGAGT CTATAGGGCG AATTGGAGCT CCACCGCGGT GGCGGCCGCT

CTAGAACTAG TGGATCCCCC GGGCTGCAGG AATTCGATAT CAAGCTTATC GATACCGTCG GATATCCCGC TTAACCTCGA

GGTGGCGCCA CCGCCGGCGA GATCTTGATC ACCTAGGGGG CCCGACGTCC TTAAGCTATA GTTCGAATAG CTATGGCAGC

ACGGGCCCGG GATCCGATGC TCTTCCGCTA AGATCTTTTA CTAGTTCAGT CCATCTCGCC GTGTATGCGG GCCTGACGGA

TCAACGTTCC CACCGAGCCA TGCCCGGGCC CTAGGCTACG AGAAGGCGAT TCTAGAAAAT GATCAAGTCA GGTAGAGCGG

CACATACGCC CGGACTGCCT AGTTGCAAGG GTGGCTCGGT GTCGAGATGT TCATCTGGTC GGCGATCTGC CGGTACTTCA

AACCTTGTTT GCGCAGTTCC ACAGCCTTCT TGCGGCGTTC CTGCGCACGA GCGATGTAGT CAGCTCTACA AGTAGACCAG

CCGCTAGACG GCCATGAAGT TTGGAACAAA CGCGTCAAGG TGTCGGAAGA ACGCCGCAAG GACGCGTGCT CGCTACATCA

CGCCTCGGTC TTCGGCGACG AGCCGTTTGA TGGTGCTTTT CGAGACGCCG AACTTGTCAG CCAACTCCTG CGCGGTCTGC

GTGCGACGCA TCACGCGTTC GCGGAGCCAG AAGCCGCTGC TCGGCAAACT ACCACGAAAA GCTCTGCGGC TTGAACAGTC

GGTTGAGGAC GCGCCAGACG CACGCTGCGT AGTGCGCAAG TGCAGCACCC ATCAGTCCGT CCCCTCTGCT GCTGCGAACA
```

-continued

```
GTGCCGATCG ATCGACCTTC TTGAGCTTCG GCCGCGGCGC GGTGGCGTTC TTCCGTACCG ACGTCGTGGG TAGTCAGGCA
GGGGAGACGA CGACGCTTGT CACGGCTAGC TAGCTGGAAG AACTCGAAGC CGGCGCCGCG CCACCGCAAG AAGGCATGGC
CTTCCGTTTT TGCGCTGCTG CTCACTTTGC CGCGGCGTGC CTGGATTTTC GAGAACTCGG CGGCGGTGAA GGTGCGGTGG
GTCCAGTGGG CGACTGATTT GAAGGCAAAA ACGCGACGAC GAGTGAAACG CGCCGCACG  GACCTAAAAG CTCTTGAGCC
GCCGCCACTT CCACGCCACC CAGGTCACCC GCTGACTAAA GCCGATCTGC TCGGCCTCGG CCCGACTCAT GGGGCCGATC
CCGTCGTTGG CGTCGAGGGT GAAGTTGGTC AGGGCGGTGA AGTCGGTGAC CATCTGCCGC CGGCTAGACG AGCCGGAGCC
GGGCTGAGTA CCCCGGCTAG GGCAGCAACC GCAGCTCCCA CTTCAACCAG TCCCGCCACT TCAGCCACTG GTAGACGGCG
CACACAGTGA TCGACGGGTA GTTCTGTTTC CGGATCTCGC GGTAGGCCCA TTCCGGGTG  CGGTCGAACA GTTCGACGTT
CCGGCCCGTT TCGGTCCTGA GTGTGTCACT AGCTGCCCAT CAAGACAAAG GCCTAGAGCG CCATCCGGGT AAGGGCCCAC
GCCAGCTTGT CAAGCTGCAA GGCCGGGCAA AGCCAGGACT CCTGTGTCTT GCGGCCGTAG TCCGGTGGGG CGGGGAAACG
GTCACCGAGC GCTTTTGCGA GGCCTTTGAG CGAGTACGGA TCCGAGGGAC CCCAGACCGT GGACACAGAA CGCCGGCATC
AGGCCACCCC GCCCCTTTGC CAGTGGCTCG CGAAAACGCT CCGGAAACTC GCTCATGCCT AGGCTCCCTG GGGTCTGGCA
CGTCCAGTGC GGGTGGATCG GGTTCTGGGT GAGCTGCTGC GCGTAGCCCT GATCGGCGCC GACCACCGAG GCGATCAGCC
CCTGGTTCAC CCGGTCGTAG GCAGGTCACG CCCACCTAGC CCAAGACCCA CTCGACGACG CGCATCGGGA CTAGCCGCGG
CTGGTGGCTC CGCTAGTCGG GGACCAAGTG GGCCAGCATC AGCCGCAGCG GGCCCTGTCG GGCTGCCTGG AGGGTGTAGA
CCGGGCTTTC GAGCAGCCAC CACAGGTGCG CGTGCTCGGT CGCGGGATTG ATCGTCATCA TCGGCGTCGC CCGGGACAGC
CCGACGGACC TCCCACATCT GGCCCGAAAG CTCGTCGGTG GTGTCCACGC GCACGAGCCA GCGCCCTAAC TAGCAGTAGT
CGGTCGGATC GGGCAGATCC GCGTTACGTG CGGCCCACTG CGCCTGGTCG TCGTCCACGT CGAGCACCAA GCCCAACCTG
ATCGACGGGG TGCGGCCGC  GCCAGCCTAG CCCGTCTAGG CGCAATGCAC GCCGGGTGAC GCGGACCAGC AGCAGGTGCA
GCTCGTGGTT CGGGTTGGAC TAGCTGCCCC ACGCCCGGCG AATGTAGCGG CGGGTGAGCG CCTCCGCGCG CGGCTGCGGC
CACTGCCCGT CCCGGACGTA GTCATCCGTC GCGTGCGGGT ATTTGAACCG CCAGCGGTCC TTACATCGCC GCCCACTCGC
GGAGGCGCGC GCCGACGCCG GTGACGGGCA GGGCCTGCAT CAGTAGGCAG CGCACGCCCA TAAACTTGGC GGTCGCCAGG
AACCAGGCGT CAACAGCAGC GGTCATGACC GCCAAGCTAG GGCCGGATCT GTACCGATCG GGGGAGGCGC GCCGCAAATT
ATTTAAGAGT CTCGCTAGCA TTGGTCCGCA GTTGTCGTCG CCAGTACTGG CGGTTCGATC CCGGCCTAGA CATGGCTAGC
CCCCTCCGCG CGGCGTTTAA TAAATTCTCA GAGCGATCGT AACCATGTCA GGTGTTGCGG TGGGTTCCGG GTAAACCTCC
ACCCGAATTA TTTAAGAGTC TCGCTAGCTA AGCCCTATCT GATGCTGCGC GGGGGGTCCT TTGGTACAGT CCACAACGCC
ACCCAAGGCC CATTTGGAGG TGGGCTTAAT AAATTCTCAG AGCGATCGAT TCGGGATAGA CTACGACGCG CCCCCCAGGA
TCGCACTGAA TCTCAAAGGT GGCCGGCTGA ATTTCGTCGC GCGAAAACCT CCCTGGACAG TTCTGGAATT CAGCAAGAGG
TGTGTCTGAA CTTCGGTGTT AGCGTGACTT AGAGTTTCCA CCGGCCGACT TAAAGCAGCG CGCTTTTGGA GGGACCTGTC
AAGACCTTAA GTCGTTCTCC ACACAGACTT GAAGCCACAA TTTTTGGGGG GTGACTCCAG CGGGGTGGGC ACAACGCGAA
CAGAGACCTT GTGTGTACGA CGGCGGGAGG TAAGTCGGGT ACGGCTCGGA CTGCGGTAGA AAAAACCCCC CACTGAGGTC
GCCCCACCCG TGTTGCGCTT GTCTCTGGAA CACACATGCT GCCGCCCTCC ATTCAGCCCA TGCCGAGCCT GACGCCATCT
GCAACCGTCG AATCGATTTC GAGCAGAGCG AGCAGAGCAA GATATTCCAA AACTCCGGGG TTCCTCGGCG GCCTCCCCCG
TCTGTTTGCT CAACCGAGGG CGTTGGCAGC TTAGCTAAAG CTCGTCTCGC TCGTCTCGTT CTATAAGGTT TGAGGCCCC
AAGGAGCCGC CGGAGGGGGC AGACAAACGA GTTGGCTCCC AGACCTGGCG GTCCCGCGTT TCCGGACGCG CGGGACCGCC
TACCGCTCGA GAGCGGAAGA GCATCTAGAT GCATTCGCGA GGTACCCAGC TTTTGTTCCC TCTGGACCGC CAGGGCGCAA
AGGCCTGCGC GCCCTGGCGG ATGGCGAGCT CTCGCCTTCT CGTAGATCTA CGTAAGCGCT CCATGGGTCG AAAACAAGGG
TTTAGTGAGG GTTAATTGCG CGCTTGGCGT AATCATGGTC ATAGCTGTTT CCTGTGTGAA ATTGTTATCC GCTCACAATT
CCACACAACA TACGAGCCGG AAATCACTCC CAATTAACGC GCGAACCGCA TTAGTACCAG TATCGACAAA GGACACACTT
TAACAATAGG CGAGTGTTAA GGTGTGTTGT ATGCTCGGCC AAGCATAAAG TGTAAAGCCT GGGGTGCCTA ATGAGTGAGC
```

-continued

```
TAACTCACAT TAATTGCGTT GCGCTCACTG CCCGCTTTCC AGTCGGGAAA CCTGTCGTGC TTCGTATTTC ACATTTCGGA

CCCCACGGAT TACTCACTCG ATTGAGTGTA ATTAACGCAA CGCGAGTGAC GGGCGAAAGG TCAGCCCTTT GGACAGCACG

CAGCTGCATT AATGAATCGG CCAACGCGCG GGGAGAGGCG GTTTGCGTAT TGGGCGCATG CATAAAAACT GTTGTAATTC

ATTAAGCATT CTGCCGACAT GTCGACGTAA TTACTTAGCC GGTTGCGCGC CCCTCTCCGC CAAACGCATA ACCCGCGTAC

GGAAGCCATC ACAAACGGCA TGATGAACCT GAATCGCCAG CGGCATCAGC ACCTTGTCGC CTTGCGTATA ATATTTGCCC

ATGGGGTGG GCGAAGAACT CCTTCGGTAG TGTTTGCCGT ACTACTTGGA CTTAGCGGTC GCCGTAGTCG TGGAACAGCG

GAACGCATAT TATAAACGGG TACCCCCACC CGCTTCTTGA CCAGCATGAG ATCCCCGCGC TGGAGGATCA TCCAGCCGGC

GTCCCGGAAA ACGATTCCGA AGCCCAACCT TTCATAGAAG GCGGCGGTGG AATCGAAATC GGTCGTACTC TAGGGGCGCG

ACCTCCTAGT AGGTCGGCCG CAGGGCCTTT TGCTAAGGCT TCGGGTTGGA AAGTATCTTC CGCCGCCACC TTAGCTTTAG

TCGTGATGGC AGGTTGGGCG TCGCTTGGTC GGTCATTTCG AACCCCAGAG TCCCGCTCAG AAGAACTCGT CAAGAAGGCG

ATAGAAGGCG ATGCGCTGCG AGCACTACCG TCCAACCCGC AGCGAACCAG CCAGTAAAGC TTGGGGTCTC AGGGCGAGTC

TTCTTGAGCA GTTCTTCCGC TATCTTCCGC TACGCGACGC AATCGGGAGC GGCGATACCG TAAAGCACGA GGAAGCGGTC

AGCCCATTCG CCGCCAAGCT CTTCAGCAAT ATCACGGGTA GCCAACGCTA TGTCCTGATA TTAGCCCTCG CCGCTATGGC

ATTTCGTGCT CCTTCGCCAG TCGGGTAAGC GGCGGTTCGA GAAGTCGTTA TAGTGCCCAT CGGTTGCGAT ACAGGACTAT

GCGGTCCGCC ACACCCAGCC GGCCACAGTC GATGAATCCA GAAAAGCGGC CATTTTCCAC CATGATATTC GGCAAGCAGG

CATCGCCATG GGTCACGACG CGCCAGGCGG TGTGGGTCGG CCGGTGTCAG CTACTTAGGT CTTTTCGCCG GTAAAGGTG

GTACTATAAG CCGTTCGTCC GTAGCGGTAC CCAGTGCTGC AGATCCTCGC CGTCGGGCAT GCGCGCCTTG AGCCTGGCGA

ACAGTTCGGC TGGCGCGAGC CCCTGATGCT CTTCGTCCAG ATCATCCTGA TCGACAAGAC TCTAGGAGCG GCAGCCCGTA

CGCGCGAAC TCGGACCGCT TGTCAAGCCG ACCGCGCTCG GGGACTACGA GAAGCAGGTC TAGTAGGACT AGCTGTTCTG

CGGCTTCCAT CCGAGTACGT GCTCGCTCGA TGCGATGTTT CGCTTGGTGG TCGAATGGGC AGGTAGCCGG ATCAAGCGTA

TGCAGCCGCC GCATTGCATC GCCGAAGGTA GGCTCATGCA CGAGCGAGCT ACGCTACAAA GCGAACCACC AGCTTACCCG

TCCATCGGCC TAGTTCGCAT ACGTCGGCGG CGTAACGTAG AGCCATGATG GATACTTTCT CGGCAGGAGC AAGGTGAGAT

GACAGGAGAT CCTGCCCCGG CACTTCGCCC AATAGCAGCC AGTCCCTTCC CGCTTCAGT  TCGGTACTAC CTATGAAAGA

GCCGTCCTCG TTCCACTCTA CTGTCCTCTA GGACGGGGCC GTGAAGCGGG TTATCGTCGG TCAGGGAAGG GCGAAGTCAC

ACAACGTCGA GCACAGCTGC GCAAGGAACG CCCGTCGTGG CCAGCCACGA TAGCCGCGCT GCCTCGTCCT GCAGTTCATT

CAGGGCACCG GACAGGTCGG TGTTGCAGCT CGTGTCGACG CGTTCCTTGC GGGCAGCACC GGTCGGTGCT ATCGGCGCGA

CGGAGCAGGA CGTCAAGTAA GTCCCGTGGC CTGTCCAGCC TCTTGACAAA AGAACCGGG CGCCCCTGCG CTGACAGCCG

GAACACGGCG GCATCAGAGC AGCCGATTGT CTGTTGTGCC CAGTCATAGC CGAATAGCCT AGAACTGTTT TTCTTGGCCC

GCGGGGACGC GACTGTCGGC CTTGTGCCGC CGTAGTCTCG TCGGCTAACA GACAACACGG GTCAGTATCG GCTTATCGGA

CTCCACCCAA GCGGCCGGAG AACCTGCGTG CAATCCATCT TGTTCAATCA TGCGAAACGA TCCTCATCCT GTCTCTTGAT

CAGATCTTGA TCCCCTGCGC GAGGTGGGTT CGCCGGCCTC TTGGACGCAC GTTAGGTAGA ACAAGTTAGT ACGCTTTGCT

AGGAGTAGGA CAGAGAACTA GTCTAGAACT AGGGGACGCG CATCAGATCC TTGGCGGCAA GAAAGCCATC CAGTTTACTT

TGCAGGGCTT CCCAACCTTA CCAGAGGGCG CCCCAGCTGG CAATTCCGGT TCGCTTGCTG GTAGTCTAGG AACCGCCGTT

CTTTCGGTAG GTCAAATGAA ACGTCCCGAA GGGTTGGAAT GGTCTCCCGC GGGGTCGACC GTTAAGGCCA AGCGAACGAC

TCCATAAAAC CGCCCAGTCT AGCTATCGCC ATGTAAGCCC ACTGCAAGCT ACCTGCTTTC TCTTTGCGCT TGCGTTTTCC

CTTGTCCAGA TAGCCCAGTA AGGTATTTTG GCGGGTCAGA TCGATAGCGG TACATTCGGG TGACGTTCGA TGGACGAAAG

AGAAACGCGA ACGCAAAAGG GAACAGGTCT ATCGGGTCAT GCTGACATTC ATCCCAGGTG GCACTTTTCG GGGAAATGTG

CGCGCCCGCG TTCCTGCTGG CGCTGGGCCT GTTTCTGGCG CTGGACTTCC CGCTGTTCCG CGACTGTAAG TAGGGTCCAC

CGTGAAAAGC CCCTTTACAC GCGCGGGCGC AAGGACGACC GCGACCCGGA CAAAGACCGC GACCTGAAGG GCGACAAGGC

TCAGCAGCTT TTCGCCCACG GCCTTGATGA TCGCGGCGGC CTTGGCCTGC ATATCCCGAT TCAACGGCCC CAGGGCGTCC

AGAACGGGCT TCAGGCGCTC AGTCGTCGAA AAGCGGGTGC CGGAACTACT AGCGCCGCCG GAACCGGACG TATAGGGCTA
```

-continued

```
AGTTGCCGGG GTCCCGCAGG TCTTGCCCGA AGTCCGCGA  CCGAAGGTCT CGGGCCGTCT CTTGGGCTTG ATCGGCCTTC
TTGCGCATCT CACGCGCTCC TGCGGCGGCC TGTAGGGCAG GCTCATACCC CTGCCGAACC GGCTTCCAGA GCCCGGCAGA
GAACCCGAAC TAGCCGGAAG AACGCGTAGA GTGCGCGAGG ACGCCGCCGG ACATCCCGTC CGAGTATGGG ACGGCTTGG
GCTTTTGTCA GCCGGTCGGC CACGGCTTCC GGCGTCTCAA CGCGCTTTGA GATTCCCAGC TTTTCGGCCA ATCCCTGCGG
TGCATAGGCG CGTGGCTCGA CGAAAACAGT CGGCCAGCCG GTGCCGAAGG CCGCAGAGTT GCGCGAAACT CTAAGGGTCG
AAAAGCCGGT TAGGGACGCC ACGTATCCGC GCACCGAGCT CCGCTTGCGG GCTGATGGTG ACGTGGCCCA CTGGTGGCCG
CTCCAGGGCC TCGTAGAACG CCTGAATGCG CGTGTGACGT GCCTTGCTGC CCTCGATGCC GGCGAACGCC CGACTACCAC
TGCACCGGGT GACCACCGGC GAGGTCCCGG AGCATCTTGC GGACTTACGC GCACACTGCA CGGAACGACG GGAGCTACGG
CCGTTGCAGC CCTAGATCGG CCACAGCGGC CGCAAACGTG GTCTGGTCGC GGGTCATCTG CGCTTTGTTG CCGATGAACT
CCTTGGCCGA CAGCCTGCCG GGCAACGTCG GGATCTAGCC GGTGTCGCCG GCGTTTGCAC CAGACCAGCG CCCAGTAGAC
GCGAAACAAC GGCTACTTGA GGAACCGGCT GTCGGACGGC TCCTGCGTCA GCGGCACCAC GAACGCGGTC ATGTGCGGGC
TGGTTTCGTC ACGGTGGATG CTGGCCGTCA CGATGCGATC CGCCCCGTAC TTGTCCGCCA AGGACGCAGT CGCCGTGGTG
CTTGCGCCAG TACACGCCCG ACCAAAGCAG TGCCACCTAC GACCGGCAGT GCTACGCTAG GCGGGGCATG AACAGGCGGT
GCCACTTGTG CGCCTTCTCG AAGAACGCCG CCTGCTGTTC TTGGCTGGCC GACTTCCACC ATTCCGGGCT GGCCGTCATG
ACGTACTCGA CCGCCAACAC CGGTGAACAC GCGGAAGAGC TTCTTGCGGC GGACGACAAG AACCGACCGG CTGAAGGTGG
TAAGGCCCGA CCGGCAGTAC TGCATGAGCT GGCGGTTGTG AGCGTCCTTG CGCCGCTTCT CTGGCAGCAA CTCGCGCAGT
CGGCCCATCG CTTCATCGGT GCTGCTGGCC GCCCAGTGCT CGTTCTCTGG CGTCCTGCTG TCGCAGGAAC GCGGCGAAGA
GACCGTCGTT GAGCGCGTCA GCCGGGTAGC GAAGTAGCCA CGACGACCGG CGGGTCACGA GCAAGAGACC GCAGGACGAC
GCGTCAGCGT TGGGCGTCTC GCGCTCGCGG TAGGCGTGCT TGAGACTGGC CGCCACGTTG CCCATTTTCG CCAGCTTCTT
GCATCGCATG ATCGCGTATG CGCAGTCGCA ACCCGCAGAG CGCGAGCGCC ATCCGCACGA ACTCTGACCG GCGGTGCAAC
GGGTAAAAGC GGTCGAAGAA CGTAGCGTAC TAGCGCATAC CCGCCATGCC TGCCCCTCCC TTTTGGTGTC CAACCGGCTC
GACGGGGGCA GCGCAAGGCG GTGCCTCCGG CGGGCCACTC AATGCTTGAG TATACTCACT GGCGGTACGG ACGGGGAGGG
AAAACCACAG GTTGGCCGAG CTGCCCCCGT CGCGTTCCGC CACGGAGGCC GCCCGGTGAG TTACGAACTC ATATGAGTGA
AGACTTTGCT TCGCAAAGTC GTGACCGCCT ACGGCGGCTG CGGCGCCCTA CGGGCTTGCT CTCCGGGCTT CGCCCTGCGC
GGTCGCTGCG CTCCCTTGCC TCTGAAACGA AGCGTTTCAG CACTGGCGGA TGCCGCCGAC GCCGCGGGAT GCCCGAACGA
GAGGCCCGAA GCGGGACGCG CCAGCGACGC GAGGGAACGG
```
SEQ ID: 04
```
GGGGAGCCGC GCCGAAGGCG TGGGGGAACC CCGCAGGGGT GCCCTTCTTT GGGCACCAAA GAACTAGATA TAGGGCGAAA
TGCGAAAGAC TTAAAAATCA CCCCTCGGCC CGGCTTCCGC ACCCCCTTGG GGCGTCCCCA CGGGAAGAAA CCCGTGGTTT
CTTGATCTAT ATCCCGCTTT ACGCTTTCTG AATTTTTAGT ACAACTTAAA AAAGGGGGGT ACGCAACAGC TCATTGCGGC
ACCCCCCGCA ATAGCTCATT GCGTAGGTTA AAGAAAATCT GTAATTGACT GCCACTTTTA TGTTGAATTT TTTCCCCCCA
TGCGTTGTCG AGTAACGCCG TGGGGGGCGT TATCGAGTAA CGCATCCAAT TTCTTTTAGA CATTAACTGA CGGTGAAAAT
CGCAACGCAT AATTGTTGTC GCGCTGCCGA AAAGTTGCAG CTGATTGCGC ATGGTGCCGC AACCGTGCGG CACCCTACCG
CATGGAGATA AGCATGGCCA GCGTTGCGTA TTAACAACAG CGCGACGGCT TTTCAACGTC GACTAACGCG TACCACGGCG
TTGGCACGCC GTGGGATGGC GTACCTCTAT TCGTACCGGT CGCAGTCCAG AGAAATCGGC ATTCAAGCCA GAACAAGCC
CGGTCACTGG GTGCAAACGG AACGCAAAGC GCATGAGGCG TGGGCGGGC TTATTGCGAG GCGTCAGGTC TCTTTAGCCG
TAAGTTCGGT TCTTGTTCGG GCCAGTGACC CACGTTTGCC TTGCGTTTCG CGTACTCCGC ACCCGGCCCG AATAACGCTC
GAAACCCACG GCGGCAATGC TGCTGCATCA CCTCGTGGCG CAGATGGGCC ACCAGAACGC CGTGGTGGTC AGCCAGAAGA
CACTTTCCAA GCTCATCGGA CTTTGGGTGC CGCCGTTACG ACGACGTAGT GGAGCACCGC GTCTACCCGG TGGTCTTGCG
GCACCACCAG TCGGTCTTCT GTGAAAGGTT CGAGTAGCCT CGTTCTTTGC GGACGGTCCA ATACGCAGTC AAGGACTTGG
TGGCCGAGCG CTGGATCTCC GTCGTGAAGC TCAACGGCCC CGGCACCGTG TCGGCCTACG GCAAGAAACG CCTGCCAGGT
```

-continued

```
TATGCGTCAG TTCCTGAACC ACCGGCTCGC GACCTAGAGG CAGCACTTCG AGTTGCCGGG GCCGTGGCAC AGCCGGATGC
TGGTCAATGA CCGCGTGGCG TGGGGCCAGC CCCGCGACCA GTTGCGCCTG TCGGTGTTCA GTGCCGCCGT GGTGGTTGAT
CACGACGACC AGGACGAATC ACCAGTTACT GGCGCACCGC ACCCCGGTCG GGGCGCTGGT CAACGCGGAC AGCCACAAGT
CACGGCGGCA CCACCAACTA GTGCTGCTGG TCCTGCTTAG GCTGTTGGGG CATGGCGACC TGCGCCGCAT CCCGACCCTG
TATCCGGGCG AGCAGCAACT ACCGACCGGC CCCGGCGAGG AGCCGCCCAG CCAGCCCGGC CGACAACCCC GTACCGCTGG
ACGCGGCGTA GGGCTGGGAC ATAGGCCCGC TCGTCGTTGA TGGCTGGCCG GGGCCGCTCC TCGGCGGGTC GGTCGGGCCG
ATTCCGGGCA TGGAACCAGA CCTGCCAGCC TTGACCGAAA CGGAGGAATG GGAACGGCGC GGGCAGCAGC GCCTGCCGAT
GCCCGATGAG CCGTGTTTTC TAAGGCCCGT ACCTTGGTCT GGACGGTCGG AACTGGCTTT GCCTCCTTAC CCTTGCCGCG
CCCGTCGTCG CGGACGGCTA CGGGCTACTC GGCACAAAAG TGGACGATGG CGAGCCGTTG GAGCCGCCGA CACGGGTCAC
GCTGCCGCGC CGGTAGCACT TGGGTTGCGC AGCAACCCGT AAGTGCGCTG TTCCAGACTA ACCTGCTACC GCTCGGCAAC
CTCGGCGGCT GTGCCCAGTG CGACGGCGCG GCCATCGTGA ACCCAACGCG TCGTTGGGCA TTCACGCGAC AAGGTCTGAT
TCGGCTGTAG CCGCCTCGCC GCCCTATACC TTGTCTGCCT CCCCGCGTTG CGTCGCGGTG CATGGAGCCG GGCCACCTCG
ACCTGAATGG AAGCCGGCGG AGCCGACATC GGCGGAGCGG CGGGATATGG AACAGACGGA GGGGCGCAAC GCAGCGCCAC
GTACCTCGGC CCGGTGGAGC TGGACTTACC TTCGGCCGCC CACCTCGCTA ACGGATTCAC CGTTTTTATC AGGCTCTGGG
AGGCAGAATA AATGATCATA TCGTCAATTA TTACCTCCAC GGGGAGAGCC TGAGCAAACT GTGGAGCGAT GCCTAAGTG
GCAAAAATAG TCCGAGACCC TCCGTCTTAT TTACTAGTAT AGCAGTTAAT AATGGAGGTG CCCCTCTCGG ACTCGTTTGA
GGCCTCAGGC ATTTGAGAAG CACACGGTCA CACTGCTTCC GGTAGTCAAT AAACCGGTAA ACCAGCAATA GACATAAGCG
GCTATTTAAC GACCCTGCCC CCGGAGTCCG TAAACTCTTC GTGTGCCAGT GTGACGAAGG CCATCAGTTA TTTGGCCATT
TGGTCGTTAT CTGTATTCGC CGATAAATTG CTGGGACGGG TGAACCGACG ACCGGGTCGA ATTTGCTTTC GAATTTCTGC
CATTCATCCG CTTATTATCA CTTATTCAGG CGTAGCACCA GGCGTTTAAG GGCACCAATA ACTTGGCTGC TGGCCCAGCT
TAAACGAAAG CTTAAAGACG GTAAGTAGGC GAATAATAGT GAATAAGTCC GCATCGTGGT CCGCAAATTC CCGTGGTTAT
ACTGCCTTAA AAAAATTACG CCCCGCCCTG CCACTCATCG CAGTCGGCCT ATTGGTTAAA AAATGAGCTG ATTTAACAAA
AATTTAACGC GAATTTTAAC TGACGGAATT TTTTTAATGC GGGGCGGGAC GGTGAGTAGC GTCAGCCGGA TAACCAATTT
TTTACTCGAC TAAATTGTTT TTAAATTGCG CTTAAAATTG AAAATATTAA CGCTTACAAT TTCCATTCGC CATTCAGGCT
GCGCAACTGT TGGGAAGGGC GATCGGTGCG GGCCTCTTCG CTATTACGCC AGCTGGCGAA TTTTATAATT GCGAATGTTA
AAGGTAAGCG GTAAGTCCGA CGCGTTGACA ACCCTTCCCG CTAGCCACGC CCGGAGAAGC GATAATGCGG TCGACCGCTT
AGGGGGATGT GCTGCAAGGC GATTAAGTTG GGTAACGCCA GGGTTTTCCC AGTCACGACG TTGTAAAACG ACGGCCAGTG
AGCGCGCGTA ATACGACTCA TCCCCCTACA CGACGTTCCG CTAATTCAAC CCATTGCGGT CCCAAAAGGG TCAGTGCTGC
AACATTTTGC TGCCGGTCAC TCGCGCGCAT TATGCTGAGT CTATAGGGCG AATTGGAGCT CCACCGCGGT GGCGGCCGCT
CTAGAACTAG TGGATCCCCC GGGCTGCAGG AATTCGATAT CAAGCTTTTA CGCCCCGCCC GATATCCCGC TTAACCTCGA
GGTGGCGCCA CCGCCGGCGA GATCTTGATC ACCTAGGGGG CCCGACGTCC TTAAGCTATA GTTCGAAAAT GCGGGCGGG
TGCCACTCAT CGCAGTACTG TTGTAATTCA TTAAGCATTC TGCCGACATG GAAGCCATCA CAAACGGCAT GATGAACCTG
AATCGCCAGC GGCATCAGCA ACGGTGAGTA GCGTCATGAC AACATTAAGT AATTCGTAAG ACGGCTGTAC CTTCGGTAGT
GTTTGCCGTA CTACTTGGAC TTAGCGGTCG CCGTAGTCGT CCTTGTCGCC TTGCGTATAA TATTTGCCCA TGGTGAAAAC
GGGGGCGAAG AAGTTGTCCA TATTGGCCAC GTTTAAATCA AAACTGGTGA AACTCACCCA GGAACAGCGG AACGCATATT
ATAAACGGGT ACCACTTTTG CCCCCGCTTC TTCAACAGGT ATAACCGGTG CAAATTTAGT TTTGACCACT TTGAGTGGGT
GGGATTGGCT GAGACGAAAA ACATATTCTC AATAAACCCT TTAGGGAAAT AGGCCAGGTT TTCACCGTAA CACGCCACAT
CTTGCGAATA TATGTGTAGA CCCTAACCGA CTCTGCTTTT TGTATAAGAG TTATTTGGGA ATCCCTTTA TCCGGTCCAA
AAGTGGCATT GTGCGGTGTA GAACGCTTAT ATACACATCT AACTGCCGGA AATCGTCGTG GTATTCACTC CAGAGCGATG
AAAACGTTTC AGTTTGCTCA TGGAAAACGG TGTAACAAGG GTGAACACTA TCCCATATCA TTGACGGCCT TTAGCAGCAC
```

-continued

```
CATAAGTGAG GTCTCGCTAC TTTTGCAAAG TCAAACGAGT ACCTTTTGCC ACATTGTTCC CACTTGTGAT AGGGTATAGT

CCAGCTCACC GTCTTTCATT GCCATACGAA ATTCCGGATG AGCATTCATC AGGCGGGCAA GAATGTGAAT AAAGGCCGGA

TAAAACTTGT GCTTATTTTT GGTCGAGTGG CAGAAAGTAA CGGTATGCTT TAAGGCCTAC TCGTAAGTAG TCCGCCCGTT

CTTACACTTA TTTCCGGCCT ATTTTGAACA CGAATAAAAA CTTTACGTC TTTAAAAAGG CCGTAATATC CAGCTGAACG

GTCTGGTTAT AGGTACATTG AGCAACTGAC TGAAATGCCT CAAAATGTTC TTTACGATGC GAAATGCCAG AAATTTTTCC

GGCATTATAG GTCGACTTGC CAGACCAATA TCCATGTAAC TCGTTGACTG ACTTTACGGA GTTTTACAAG AAATGCTACG

CATTGGGATA TATCAACGGT GGTATATCCA GTGATTTTTT TCTCCATATG GTTAACCTTA ATTAAGGGGT CGACGGGCCC

GGGATCCGAT GCTCTTCCGC GTAACCCTAT ATAGTTGCCA CCATATAGGT CACTAAAAAA AGAGGTATAC CAATTGGAAT

TAATTCCCCA GCTGCCCGGG CCCTAGGCTA CGAGAAGGCG TAAGATCTTT TACTAGTTCA GTCCATCTCG CCGTGTATGC

GGGCCTGACG GATCAACGTT CCCACCGAGC CAGTCGAGAT GTTCATCTGG TCGGCGATCT ATTCTAGAAA ATGATCAAGT

CAGGTAGAGC GGCACATACG CCCGGACTGC CTAGTTGCAA GGGTGGCTCG GTCAGCTCTA CAAGTAGACC AGCCGCTAGA

GCCGGTACTT CAAACCTTGT TTGCGCAGTT CCACAGCCTT CTTGCGGCGT TCCTGCGCAC GAGCGATGTA GTCGCCTCGG

TCTTCGGCGA CGAGCCGTTT CGGCCATGAA GTTTGGAACA AACGCGTCAA GGTGTCGGAA GAACGCCGCA AGGACGCGTG

CTCGCTACAT CAGCGGAGCC AGAAGCCGCT GCTCGGCAAA GATGGTGCTT TTCGAGACGC CGAACTTGTC AGCCAACTCC

TGCGCGGTCT GCGTGCGACG CATCACGCGT TCTGCAGCAC CCATCAGTCC GTCCCCTCTG CTACCACGAA AAGCTCTGCG

GCTTGAACAG TCGGTTGAGG ACGCGCCAGA CGCACGCTGC GTAGTGCGCA AGACGTCGTG GGTAGTCAGG CAGGGGAGAC

CTGCTGCGAA CAGTGCCGAT CGATCGACCT TCTTGAGCTT CGGCCGCGGC GCGGTGGCGT TCTTCCGTAC CGCTTCCGTT

TTTGCGCTGC TGCTCACTTT GACGACGCTT GTCACGGCTA GCTAGCTGGA AGAACTCGAA GCCGGCGCCG CGCCACCGCA

AGAAGGCATG GCGAAGGCAA AAACGCGACG ACGAGTGAAA GCCGCGGCGT GCCTGGATTT TCGAGAACTC GGCGGCGGTG

AAGGTGCGGT GGGTCCAGTG GGCGACTGAT TTGCCGATCT GCTCGGCCTC GGCCCGACTC CGGCGCCGCA CGGACCTAAA

AGCTCTTGAG CCGCCGCCAC TTCCACGCCA CCCAGGTCAC CCGCTGACTA AACGGCTAGA CGAGCCGGAG CCGGGCTGAG

ATGGGGCCGA TCCCGTCGTT GGCGTCGAGG GTGAAGTTGG TCAGGGCGGT GAAGTCGGTG ACCATCTGCC GCCACACAGT

GATCGACGGG TAGTTCTGTT TACCCCGGCT AGGGCAGCAA CCGCAGCTCC CACTTCAACC AGTCCCGCCA CTTCAGCCAC

TGGTAGACGG CGGTGTGTCA CTAGCTGCCC ATCAAGACAA TCCGGATCTC GCGGTAGGCC CATTCCCGGG TGCGGTCGAA

CAGTTCGACG TTCCGGCCCG TTTCGGTCCT GACCTGTGTC TTGCGGCCGT AGTCCGGTGG AGGCCTAGAG CGCCATCCGG

GTAAGGGCCC ACGCCAGCTT GTCAAGCTGC AAGGCCGGGC AAAGCCAGGA CTGGACACAG AACGCCGGCA TCAGGCCACC

GGCGGGGAAA CGGTCACCGA GCGCTTTTGC GAGGCCTTTG AGCGAGTACG ATCCGAGGG ACCCCAGACC GTCGTCCAGT

GCGGGTGGAT CGGGTTCTGG CCGCCCCTTT GCCAGTGGCT CGCGAAAACG CTCCGGAAAC TCGCTCATGC CTAGGCTCCC

TGGGGTCTGG CAGCAGGTCA CGCCCACCTA GCCCAAGACC GTGAGCTGCT GCGCGTAGCC CTGATCGGCG CCGACCACCG

AGGCGATCAG CCCCTGGTTC ACCCGGTCGT AGAGCCGCAG CGGGCCCTGT CGGGCTGCCT CACTCGACGA CGCGCATCGG

GACTAGCCGC GGCTGGTGGC TCCGCTAGTC GGGGACCAAG TGGGCCAGCA TCTCGGCGTC GCCCGGGACA GCCCGACGGA

GGAGGGTGTA GACCGGGCTT TCGAGCAGCC ACCACAGGTG CGCGTGCTCG GTCGCGGGAT TGATCGTCAT CACGGTCGGA

TCGGGCAGAT CCGCGTTACG CCTCCCACAT CTGGCCCGAA AGCTCGTCGG TGGTGTCCAC GCGCACGAGC CAGCGCCCTA

ACTAGCAGTA GTGCCAGCCT AGCCCGTCTA GGCGCAATGC TGCGGCCCAC TGCGCCTGGT CGTCGTCCAC GTCGAGCACC

AAGCCCAACC TGATCGACGG GGTGCGGGCC GCAATGTAGC GGCGGGTGAG CGCCTCCGCG ACGCCGGGTG ACGCGGACCA

GCAGCAGGTG CAGCTCGTGG TTCGGGTTGG ACTAGCTGCC CCACGCCCGG CGTTACATCG CCGCCCACTC GCGGAGGCGC

CGCGGCTGCG GCCACTGCCC GTCCCGGACG TAGTCATCCG TCGCGTGCGG GTATTTGAAC CGCCAGCGGT CCAACCAGGC

GTCAACAGCA GCGGTCATGA GCGCCGACGC CGGTGACGGG CAGGGCCTGC ATCAGTAGGC AGCGCACGCC CATAAACTTG

GCGGTCGCCA GGTTGGTCCG CAGTTGTCGT CGCCAGTACT CCGCCAAGCT AGGGCCGGAT CTGTACCGAT CGGGGGAGGC

GCGCCGCAAA TTATTTAAGA GTCTCGCTAG CAAACCATGT CAGGTGTTGC GGTGGGTTCC GGCGGTTCGA TCCCGGCCTA

GACATGGCTA GCCCCCTCCG CGCGGCGTTT AATAAATTCT CAGAGCGATC GTTTGGTACA GTCCACAACG CCACCCAAGG
```

-continued

```
GGGTAAACCT CCACCCGAAT TATTTAAGAG TCTCGCTAGC TAAGCCCTAT CTGATGCTGC GCGGGGGGTC CTTCGCACTG

AATCTCAAAG GTGGCCGGCT CCCATTTGGA GGTGGGCTTA ATAAATTCTC AGAGCGATCG ATTCGGGATA GACTACGACG

CGCCCCCCAG GAAGCGTGAC TTAGAGTTTC CACCGGCCGA GAATTTCGTC GCGCGAAAAC CTCCCTGGAC AGTTCTGGAA

TTCAGCAAGA GGTGTGTCTG AACTTCGGTG TTTTTTTGGG GGGTGACTCC AGCGGGGTGG CTTAAAGCAG CGCGCTTTTG

GAGGGACCTG TCAAGACCTT AAGTCGTTCT CCACACAGAC TTGAAGCCAC AAAAAAACCC CCCACTGAGG TCGCCCCACC

GCACAACGCG AACAGAGACC TTGTGTGTAC GACGGCGGGA GGTAAGTCGG GTACGGCTCG GACTGCGGTA GAGCAACCGT

CGAATCGATT TCGAGCAGAG CGTGTTGCGC TTGTCTCTGG AACACACATG CTGCCGCCCT CCATTCAGCC CATGCCGAGC

CTGACGCCAT CTCGTTGGCA GCTTAGCTAA AGCTCGTCTC CGAGCAGAGC AAGATATTCC AAAACTCCGG GGTTCCTCGG

CGGCCTCCCC CGTCTGTTTG CTCAACCGAG GGAGACCTGG CGGTCCCGCG TTTCCGGACG GCTCGTCTCG TTCTATAAGG

TTTTGAGGCC CCAAGGAGCC GCCGGAGGGG GCAGACAAAC GAGTTGGCTC CCTCTGGACC GCCAGGGCGC AAAGGCCTGC

CGCGGGACCG CCTACCGCTC GAGAGCGGAA GAGCATCTAG ATGCATTCGC GAGGTACCCA GCTTTTGTTC CCTTTAGTGA

GGGTTAATTG CGCGCTTGGC GCGCCCTGGC GGATGGCGAG CTCTCGCCTT CTCGTAGATC TACGTAAGCG CTCCATGGGT

CGAAAACAAG GGAAATCACT CCCAATTAAC GCGCGAACCG GTAATCATGG TCATAGCTGT TTCCTGTGTG AAATTGTTAT

CCGCTCACAA TTCCACACAA CATACGAGCC GGAAGCATAA AGTGTAAAGC CTGGGGTGCC CATTAGTACC AGTATCGACA

AAGGACACAC TTTAACAATA GGCGAGTGTT AAGGTGTGTT GTATGCTCGG CCTTCGTATT TCACATTTCG GACCCCACGG

TAATGAGTGA GCTAACTCAC ATTAATTGCG TTGCGCTCAC TGCCCGCTTT CCAGTCGGGA AACCTGTCGT GCCAGCTGCA

TTAATGAATC GGCCAACGCG ATTACTCACT CGATTGAGTG TAATTAACGC AACGCGAGTG ACGGGCGAAA GGTCAGCCCT

TTGGACAGCA CGGTCGACGT AATTACTTAG CCGGTTGCGC CGGGGAGAGG CGGTTTGCGT ATTGGGCGCA TGCATAAAAA

CTGTTGTAAT TCATTAAGCA TTCTGCCGAC ATGGAAGCCA TCACAAACGG CATGATGAAC GCCCCTCTCC GCCAAACGCA

TAACCCGCGT ACGTATTTTT GACAACATTA AGTAATTCGT AAGACGGCTG TACCTTCGGT AGTGTTTGCC GTACTACTTG

CTGAATCGCC AGCGGCATCA GCACCTTGTC GCCTTGCGTA TAATATTTGC CCATGGGGGT GGGCGAAGAA CTCCAGCATG

AGATCCCCGC GCTGGAGGAT GACTTAGCGG TCGCCGTAGT CGTGGAACAG CGGAACGCAT ATTATAAACG GGTACCCCCA

CCCGCTTCTT GAGGTCGTAC TCTAGGGGCG CGACCTCCTA CATCCAGCCG GCGTCCCGGA AAACGATTCC GAAGCCCAAC

CTTTCATAGA AGGCGGCGGT GGAATCGAAA TCTCGTGATG GCAGGTTGGG CGTCGCTTGG GTAGGTCGGC CGCAGGGCCT

TTTGCTAAGG CTTCGGGTTG GAAAGTATCT TCCGCCGCCA CCTTAGCTTT AGAGCACTAC CGTCCAACCC GCAGCGAACC

TCGGTCATTT CGAACCCCAG AGTCCCGCTC AGAAGAACTC GTCAAGAAGG CGATAGAAGG CGATGCGCTG CGAATCGGGA

GCGGCGATAC CGTAAAGCAC AGCCAGTAAA GCTTGGGGTC TCAGGGCGAG TCTTCTTGAG CAGTTCTTCC GCTATCTTCC

GCTACGCGAC GCTTAGCCCT CGCCGCTATG GCATTTCGTG GAGGAAGCGG TCAGCCCATT CGCCGCCAAG CTCTTCAGCA

ATATCACGGG TAGCCAACGC TATGTCCTGA TAGCGGTCCG CCACACCCAG CCGGCCACAG CTCCTTCGCC AGTCGGGTAA

GCGGCGGTTC GAGAAGTCGT TATAGTGCCC ATCGGTTGCG ATACAGGACT ATCGCCAGGC GGTGTGGGTC GGCCGGTGTC

TCGATGAATC CAGAAAAGCG GCCATTTTCC ACCATGATAT TCGGCAAGCA GGCATCGCCA TGGGTCACGA CGAGATCCTC

GCCGTCGGGC ATGCGCGCCT AGCTACTTAG GTCTTTTCGC CGGTAAAAGG TGGTACTATA AGCCGTTCGT CCGTAGCGGT

ACCCAGTGCT GCTCTAGGAG CGGCAGCCCG TACGCGCGGA TGAGCCTGGC GAACAGTTCG GCTGGCGCGA GCCCCTGATG

CTCTTCGTCC AGATCATCCT GATCGACAAG ACCGGCTTCC ATCCGAGTAC GTGCTCGCTC ACTCGGACCG CTTGTCAAGC

CGACCGCGCT CGGGGACTAC GAGAAGCAGG TCTAGTAGGA CTAGCTGTTC TGGCCGAAGG TAGGCTCATG CACGAGCGAG

GATGCGATGT TTCGCTTGGT GGTCGAATGG GCAGGTAGCC GGATCAAGCG TATGCAGCCG CCGCATTGCA TCAGCCATGA

TGGATACTTT CTCGGCAGGA CTACGCTACA AAGCGAACCA CCAGCTTACC CGTCCATCGG CCTAGTTCGC ATACGTCGGC

GGCGTAACGT AGTCGGTACT ACCTATGAAA GAGCCGTCCT GCAAGGTGAG ATGACAGGAG ATCCTGCCCC GGCACTTCGC

CCAATAGCAG CCAGTCCCTT CCCGCTTCAG TGACAACGTC GAGCACAGCT GCGCAAGGAA CGTTCCACTC TACTGTCCTC

TAGGACGGGG CCGTGAAGCG GGTTATCGTC GGTCAGGGAA GGGCGAAGTC ACTGTTGCAG CTCGTGTCGA CGCGTTCCTT
```

```
CGCCCGTCGT GGCCAGCCAC GATAGCCGCG CTGCCTCGTC CTGCAGTTCA TTCAGGGCAC CGGACAGGTC GGTCTTGACA
AAAAGAACCG GGCGCCCCTG GCGGGCAGCA CCGGTCGGTG CTATCGGCGC GACGGAGCAG GACGTCAAGT AAGTCCCGTG
GCCTGTCCAG CCAGAACTGT TTTTCTTGGC CCGCGGGGAC CGCTGACAGC CGGAACACGG CGGCATCAGA GCAGCCGATT
GTCTGTTGTG CCCAGTCATA GCCGAATAGC CTCTCCACCC AAGCGGCCGG AGAACCTGCG GCGACTGTCG GCCTTGTGCC
GCCGTAGTCT CGTCGGCTAA CAGACAACAC GGGTCAGTAT CGGCTTATCG GAGAGGTGGG TTCGCCGGCC TCTTGGACGC
TGCAATCCAT CTTGTTCAAT CATGCGAAAC GATCCTCATC CTGTCTCTTG ATCAGATCTT GATCCCCTGC GCCATCAGAT
CCTTGGCGGC AAGAAAGCCA ACGTTAGGTA GAACAAGTTA GTACGCTTTG CTAGGAGTAG GACAGAGAAC TAGTCTAGAA
CTAGGGGACG CGGTAGTCTA GGAACCGCCG TTCTTTCGGT TCCAGTTTAC TTTGCAGGGC TTCCCAACCT TACCAGAGGG
CGCCCCAGCT GGCAATTCCG GTTCGCTTGC TGTCCATAAA ACCGCCCAGT CTAGCTATCG AGGTCAAATG AAACGTCCCG
AAGGGTTGGA ATGGTCTCCC GCGGGGTCGA CCGTTAAGGC CAAGCGAACG ACAGGTATTT GGCGGGTCA GATCGATAGC
CCATGTAAGC CCACTGCAAG CTACCTGCTT TCTCTTTGCG CTTGCGTTTT CCCTTGTCCA GATAGCCCAG TAGCTGACAT
TCATCCCAGG TGGCACTTTT GGTACATTCG GGTGACGTTC GATGGACGAA AGAGAAACGC GAACGCAAAA GGGAACAGGT
CTATCGGGTC ATCGACTGTA AGTAGGGTCC ACCGTGAAAA CGGGGAAATG TGCGCGCCCG CGTTCCTGCT GGCGCTGGGC
CTGTTTCTGG CGCTGGACTT CCCGCTGTTC CGTCAGCAGC TTTTCGCCCA CGGCCTTGAT GCCCCTTTAC ACGCGCGGGC
GCAAGGACGA CCGCGACCCG GACAAAGACC GCGACCTGAA GGGCGACAAG GCAGTCGTCG AAAAGCGGGT GCCGGAACTA
GATCGCGGCG GCCTTGGCCT GCATATCCCG ATTCAACGGC CCCAGGGCGT CCAGAACGGG CTTCAGGCGC TCCCGAAGGT
CTCGGGCCGT CTCTTGGGCT CTAGCGCCGC CGGAACCGGA CGTATAGGGC TAAGTTGCCG GGGTCCCGCA GGTCTTGCCC
GAAGTCCGCG AGGGCTTCCA GAGCCCGGCA GAGAACCCGA TGATCGGCCT TCTTGCGCAT CTCACGCGCT CCTGCGGCGG
CCTGTAGGGC AGGCTCATAC CCCTGCCGAA CCGCTTTTGT CAGCCGGTCG GCCACGCGCTT ACTAGCCGGA AGAACGCGTA
GAGTGCGCGA GGACGCCGCC GGACATCCCG TCCGAGTATG GGGACGGCTT GGCGAAAACA GTCGGCCAGC CGGTGCCGAA
CCGGCGTCTC AACGCGCTTT GAGATTCCCA GCTTTTCGGC CAATCCCTGC GGTGCATAGG CGCGTGGCTC GACCGCTTGC
GGGCTGATGG TGACGTGGCC GGCCGCAGAG TTGCGCGAAA CTCTAAGGGT CGAAAAGCCG GTTAGGGACG CCACGTATCC
GCGCACCGAG CTGGCGAACG CCCGACTACC ACTGCACCGG CACTGGTGGC CGCTCCAGGG CCTCGTAGAA CGCCTGAATG
CGCGTGTGAC GTGCCTTGCT GCCCTCGATG CCCCGTTGCA GCCCTAGATC GGCCACAGCG GTGACCACCG GCGAGGTCCC
GGAGCATCTT GCGGACTTAC GCGCACACTG CACGGAACGA CGGGAGCTAC GGGGCAACGT CGGGATCTAG CCGGTGTCGC
GCCGCAAACG TGGTCTGGTC GCGGGTCATC TGCGCTTTGT TGCCGATGAA CTCCTTGGCC GACAGCCTGC CGTCCTGCGT
CAGCGGCACC ACGAACGCGG CGGCGTTTGC ACCAGACCAG CGCCCAGTAG ACGCGAAACA ACGGCTACTT GAGGAACCGG
CTGTCGGACG GCAGGACGCA GTCGCCGTGG TGCTTGCGCC TCATGTGCGG GCTGGTTTCG TCACGGTGGA TGCTGGCCGT
CACGATGCGA TCCGCCCCGT ACTTGTCCGC CAGCCACTTG TGCGCCTTCT CGAAGAACGC AGTACACGCC CGACCAAAGC
AGTGCCACCT ACGACCGGCA GTGCTACGCT AGGCGGGGCA TGAACAGGCG GTCGGTGAAC ACGCGGAAGA GCTTCTTGCG
CGCCTGCTGT TCTTGGCTGG CCGACTTCCA CCATTCCGGG CTGGCCGTCA TGACGTACTC GACCGCCAAC ACAGCGTCCT
TGCGCCGCTT CTCTGGCAGC GCGGACGACA AGAACCGACC GGCTGAAGGT GGTAAGGCCC GACCGGCAGT ACTGCATGAG
CTGGCGGTTG TGTCGCAGGA ACGCGGCGAA GAGACCGTCG AACTCGCGCA GTCGGCCCAT CGCTTCATCG GTGCTGCTGG
CCGCCCAGTG CTCGTTCTCT GGCGTCCTGC TGGCGTCAGC GTTGGGCGTC TCGCGCTCGC TTGAGCGCGT CAGCCGGGTA
GCGAAGTAGC CACGACGACC GGCGGGTCAC GAGCAAGAGA CCGCAGGACG ACCGCAGTCG CAACCCGCAG AGCGCGAGCG
GGTAGGCGTG CTTGAGACTG GCCGCCACGT TGCCCATTTT CGCCAGCTTC TTGCATCGCA TGATCGCGTA TGCCGCCATG
CCTGCCCCTC CCTTTTGGTG CCATCCGCAC GAACTCTGAC CGGCGGTGCA ACGGGTAAAA GCGGTCGAAG AACGTAGCGT
ACTAGCGCAT ACGGCGGTAC GGACGGGGAG GGAAAACCAC TCCAACCGGC TCGACGGGGG CAGCGCAAGG CGGTGCCTCC
GGCGGGCCAC TCAATGCTTG AGTATACTCA CTAGACTTTG CTTCGCAAAG TCGTGACCGC AGGTTGGCCG AGCTGCCCCC
GTCGCGTTCC GCCACGGAGG CCGCCCGGTG AGTTACGAAC TCATATGAGT GATCTGAAAC GAAGCGTTTC AGCACTGGCG
CTACGGCGGC TGCGGCGCCC TACGGGCTTG CTCTCCGGGC TTCGCCCTGC GCGGTCGCTG CGCTCCCTTG CCAGCCCGTG
```

```
GATATGTGGA CGATGGCCGC GATGCCGCCG ACGCCGCGGG ATGCCCGAAC GAGAGGCCCG AAGCGGGACG CGCCAGCGAC
GCGAGGGAAC GGTCGGGCAC CTATACACCT GCTACCGGCG GAGCGGCCAC CGGCTGGCTC GCTTCGCTCG GCCCGTGGAC
AACCCTGCTG GACAAGCTGA TGGACAGGCT GCGCCTGCCC ACGAGCTTGA CCACAGGGAT CTCGCCGGTG GCCGACCGAG
CGAAGCGAGC CGGGCACCTG TTGGGACGAC CTGTTCGACT ACCTGTCCGA CGCGGACGGG TGCTCGAACT GGTGTCCCTA
TGCCCACCGG CTACCCAGCC TTCGACCACA TACCCACCGG CTCCAACTGC GCGGCCTGCG GCCTTGCCCC ATCAATTTTT
TTAATTTTCT CTGGGGAAAA ACGGGTGGCC GATGGGTCGG AAGCTGGTGT ATGGGTGGCC GAGGTTGACG CGCCGGACGC
CGGAACGGGG TAGTTAAAAA AATTAAAAGA GACCCCTTTT GCCTCCGGCC TGCGGCCTGC GCGCTTCGCT TGCCGGTTGG
ACACCAAGTG GAAGGCGGGT CAAGGCTCGC GCAGCGACCG CGCAGCGGCT TGGCCTTGAC CGGAGGCCGG ACGCCGGACG
CGCGAAGCGA ACGGCCAACC TGTGGTTCAC CTTCCGCCCA GTTCCGAGCG CGTCGCTGGC GCGTCGCCGA ACCGGAACTG
GCGCCTGGAA CGACCCAAGC CTATGCGAGT GGGGGCAGTC GAAGGCGAAG CCCGCCCGCC TGCCCCCCGA GCCTCACGGC
GGCGAGTGCG GGGGTTCCAA CGCGGACCTT GCTGGGTTCG GATACGCTCA CCCCCGTCAG CTTCCGCTTC GGGCGGGCGG
ACGGGGGGCT CGGAGTGCCG CCGCTCACGC CCCCAAGGTT GGGGGCAGCG CCACCTTGGG CAAGGCCGAA GGCCGCGCAG
TCGATCAACA AGCCCCGGAG GGGCCACTTT TTGCCGGAG  CCCCCGTCGC GGTGGAACCC GTTCCGGCTT CCGGCGCGTC
AGCTAGTTGT TCGGGGCCTC CCCGGTGAAA AACGGCCTC
```

SEQ ID: 05
MEALFLSSSS SSIVASNKLT RLHNHCVWST VIRDKKRFGP TWCRVGGGGD GGRNSNAERP IRVSSLLKDR GQVLIREQSS
PAMDAETLVL SPNGNGRTIE INGVKTLMPF SGASMVGMKE GLGIISFLQG KKFLITGSTG FLAKVLIEKV LRMAPDVSKI
YLLIKAKSKE AAIERLKNEV LDAELFNTLK ETHGASYMSF MLTKLIPVTG NICDSNIGLQ ADSAEEIAKE VDVIINSAAN
TTFNERYDVA LDINTRGPGN LMGFAKKCKK LKLFLQVSTA YVNGQRQGRI MEKPFSMGDC IATENFLEGN RKALDVDREM
KLALEAARKG TQNQDEAQKM KDLGLERARS YGWQDTYVFT KAMGEMMINS TRGDVPVVII RPSVIESTYK DPFPGWMEGN
RMMDPIVLCY GKGQLTGFLV DPKGVLDVVP ADMVVNATLA AIAKHGMAMS DPEPEINVYQ IASSAINPLV FEDLAELLYN
HYKTSPCMDS KGDPIMVRLM KLFNSVDDFS DHLWRDAQER SGLMSGMSSV DSKMMQKLKF ICKKSVEQAK HLATIYEPYT
FYGGRFDNSN TQRLMENMSE DEKREFGFDV GSINWTDYIT NVHIPGLRRH VLKGRA

SEQ ID: 06
MATTNVLATS HAFKLNGVSY FSSFPRKPNH YMPRRRLSHT TRRVQTSCFY GETSFEAVTS LVTPKTETSR NSDGIGIVRF
LEGKSYLVTG ATGFLAKVLI EKLLRESLEI GKIFLLMRSK DQESANKRLY DEIISSDLFK LLKQMHGSSY EAFMKRKLIP
VIGDIEEDNL GIKSEIANMI SEEIDVIISC GGRTTFDDRY DSALSVNALG PGRLLSEGKG CRKLKLFLHF STAYVTGKRE
GTVLETPLCI GENITSDLNI KSELKLASEA VAKFRGREEI KKLKELGFER AQHYGWENSY TFTKAIGEAV IHSKRGNLPV
VIIRPSIIES SYNEPFPGWI QGTRMADPII LAYAKGQISD FWADPQSLMD IIPVDMVANA AIAAMAKHGC GVPEFKVYNL
TSSSHVNPMR AGKLIDLSHQ HLCDFPLEET VIDLEHMKIH SSLEGFTSAL SNTIIKQERV IDNEGGGLST KGKRKLNYFV
SLAKTYEPYT FFQARFDNTN TTSLIQEMSM EEKKTFGFDI KGIDWEHYIV NVHLPGLKKE FLSKKKTE

SEQ ID: 07
MESNCVQFLG NKTILITGAP GFLAKVLVEK ILRLQPNVKK TYLLLRAPDE KSAMQRLRSE VMEIDLFKVL RNNLGEDNLN
ALMREKIVPV PGDISIDNLG LKDTDLIQRM WSEIDIIINI AATTNFDERY DIGLGINTFG ALNVLNFAKK CVKGQLLLHV
STAYISGEQP GLLLEKPFKM GETLSGDREL DINIEHDLMK QKLKELQDCS DEEISQTMKD FGMARAKLHG WPNTYVFTKA
MGEMLMGKYR ENLPLVIIRP TMITSTIAEP FPGWIEGLKT LDSVIVAYGK GRLKCFLADS NSVFDLIPAD MVVNAMVAAA
TAHSGDTGIQ AIYHVGSSCK NPVTFGQLHD FTARYFAKRP LIGRNGSPII VVKGTILSTM AQFSLYMTLR YKLPLQILRL
INIVYPWSHG DNYSDLSRKI KLAMRLVELY QPYLLFKGIF DDLNTERLRM KRKENIKELD GSFEFDPKSI DWDNYITNTH
IPGLITHVLK Q

SEQ ID: 08
MPELAVRTEF DYSSEIYKDA YSRINAIVIE GEQEAYSNYL QMAELLPEDK EELTRLAKME NRHKKGFQAC GNNLQVNPDM
PYAQEFFAGL HGNFQHAFSE GKVVTCLLIQ ALIIEAFAIA AYNIYIPVAD DFARKITEGV VKDEYTHLNY GEEWLKANFA
TAKEELEQAN KENLPLVWKM LNQVQGDAKV LGMEKEALVE DFMISYGEAL SNIGFSTREI MAMSSYGLAG V

SEQ ID: 09
MFGLIGHLTS LEHAQAVAED LGYPEYANQG LDFWCSAPPQ VVDNFQVKSV TGQVIEGKYV ESCFLPEMLT QRRIKAAIRK
ILNAMALAQK VGLDITALGG FSSIVFEEFN LKQNNQVRNV ELDFQRFTTG NTHTAYVICR QVESGAKQLG IDLSQATVAV
CGATGDIGSA VCRWLDSKHQ VKELLLIARN RQRLENLQEE LGRGKIMDLE TALPQADIIV WVASMPKGVE IAGEMLKKPC
LIVDGGYPKN LDTRVKADGV HILKGGIVEH SLDITWEIMK IVEMDIPSRQ MFACFAEAIL LEFEGWRTNF SWGRNQISVN
KMEAIGEASV KHGFCPLVAL

SEQ ID: 10
CAGTCAATGG AGAGCATTGC CATAAGTAAA GGCATCCCCT GCGTGATAAG ATTACCTTCA GAAAACAGAT AGTTGCTGGG
TTATCGCAGA TTTTTCTCGC GTCAGTTACC TCTCGTAACG GTATTCATTT CCGTAGGGGA CGCACTATTC TAATGGAAGT
CTTTTGTCTA TCAACGACCC AATAGCGTCT AAAAAGAGCG AACCAAATAA CTGTAAATAA TAACTGTCTC TGGGGCGACG
GTAGGCTTTA TATTGCCAAA TTTCGCCCGT GGGAGAAAGC TAGGCTATTC AATGTTTATG TTGGTTTATT GACATTTATT
ATTGACAGAG ACCCCGCTGC CATCCGAAAT ATAACGGTTT AAAGCGGGCA CCCTCTTTCG ATCCGATAAG TTACAAATAC
GAGGACT CCT

SEQ ID: 11
CCTGGCTCAG GACGAACGCT GGCGGCGTGC TTAACACATG CAAGTCGAGC GGTAAGGCCC TTCGGGGTAC ACGAGCGGCG
AACGGGTGAG TAACACGTGG GGACCGAGTC CTGCTTGCGA CCGCCGCACG AATTGTGTAC GTTCAGCTCG CCATTCCGGG
AAGCCCCATG TGCTCGCCGC TTGCCCACTC ATTGTGCACC GTGATCTGCC CTGCACTTCG GGATAAGCCT GGGAAACTGG
GTCTAATACC GGATATGACC TTCGGCTGCA TGGCTGAGGG TGGAAAGGTT TACTGGTGCA CACTAGACGG GACGTGAAGC
CCTATTCGGA CCCTTTGACC CAGATTATGG CCTATACTGG AAGCCGACGT ACCGACTCCC ACCTTTCCAA ATGACCACGT
GGATGGGCCC GCGGCCTATC AGCTTGTTGG TGGGGTAATG GCCTACCAAG CGACGACGG GTAGCCGACC TGAGAGGGTG
ACCGGCCACA CTGGGACTGA CCTACCCGGG CGCCGGATAG TCGAACAACC ACCCCATTAC CGGATGGTTC CGCTGCTGCC
CATCGGCTGG ACTCTCCCAC TGGCCGGTGT GACCCTGACT GACACGGCCC AGACTCCTAC GGGAGGCAGC AGTGGGGAAT
ATTGCACAAT GGGCGAAAGC CTGATGCAGC GACGCCGCGT GAGGGATGAC GGCCTTCGGG CTGTGCCGGG TCTGAGGATG
CCCTCCGTCG TCACCCCTTA TAACGTGTTA CCCGCTTTCG GACTACGTCG CTGCGGCGCA CTCCCTACTG CCGGAAGCCC
TTGTAAACCT CTTTCAGCAG GGACGAAGCG AAAGTGACGG TACCTGCAGA AGAAGCACCG GCCAACTACG TGCCAGCAGC
CGCGGTAATA CGTAGGGTGC AACATTTGGA GAAAGTCGTC CCTGCTTCGC TTTCACTGCC ATGGACGTCT TCTTCGTGGC
CGGTTGATGC ACGGTCGTCG GCGCCATTAT GCATCCCACG AAGCGTTGTC CGGAATTACT GGGCGTAAAG AGCTCGTAGG
CGGTTTGTCG CGTCGTCTGT GAAAACTCAN AGCTCAACCT CGAGCTTGCA GGCGATACGG TTCGCAACAG GCCTTAATGA
CCCGCATTTC TCGAGCATCC GCCAAACAGC GCAGCAGACA CTTTTGAGTN TCGAGTTGGA GCTCGAACGT CCGCTATGCC
GCAGACTTGA GTACTGCAGG GGAGACTGGA ATTCCTGGTG TAGCGGTGAA ATGCGCAGAT ATCAGGAGGA ACACCGGTGG
CGAAGGCGGG TCTCTGGGCA CGTCTGAACT CATGACGTCC CCTCTGACCT AAGGACCAC ATCGCCACTT TACGCGTCTA
TAGTCCTCCT TGTGGCCACC GCTTCCGCCC AGAGACCCGT GTAACTGACG CTGAGGAGCG AAAGCGTGGG TAGCAAACAG
GATTAGATAC CCTGGTAGTC CACGCCGTAA ACGGTGGGCG CTAGGTGTGG GTTTCCTTCC CATTGACTGC GACTCCTCGC
TTTCGCACCC ATCGTTTGTC CTAATCTATG GACCATCAG GTGCGGCATT TGCCACCCGC GATCCACACC CAAAGGAAGG
ACGGGATCCG TGCCGTAGTT AACGCATTAA GCGCCCCGCC TGGGGAGTAC GGCCGCAAGG TTAAAACTCA AAGGAATTGA
CGGGGGCCCG CACAAGCGGC TGCCCTAGGC ACGGCATCAA TTGCGTAATT CGCGGGCGG ACCCCTCATG CCGGCGTTCC
AATTTTGAGT TCCTTAACT GCCCCCGGGC GTGTTCGCCG GGAGCATGTG GATTAATTC ATGCAACGCG AAGAACCTTA
CCTGGGTTTG ACATATACCG GAAAGCCGTA GAGATACCGC CCCCCTTGTG GTCGGTATAC CCTCGTACAC CTAATTAAGC

-continued

```
TACGTTGCGC TTCTTGGAAT GGACCCAAAC TGTATATGGC CTTTCGGCAT CTCTATGGCG GGGGGAACAC CAGCCATATG

AGGTGGTGCA TGGCTGTCGT CAGCTCGTGT CGTGAGATGT TGGGTTAAGT CCCGCAACGA GCGCAACCCT TGTCTTATGT

TGCCAGCACG TAATGGTGGG TCCACCACGT ACCGACAGCA GTCGAGCACA GCACTCTACA ACCCAATTCA GGGCGTTGCT

CGCGTTGGGA ACAGAATACA ACGGTCGTGC ATTACCACCC GACTCGTAAG AGACTGCCGG GGTCAACTCG GAGGAAGGTG

GGGACGACGT CAAGTCATCA TGCCCCTTAT GTCCAGGGCT TCACACATGC TACAATGGCC CTGAGCATTC TCTGACGGCC

CCAGTTGAGC CTCCTTCCAC CCCTGCTGCA GTTCAGTAGT ACGGGAATA CAGGTCCCGA AGTGTGTACG ATGTTACCGG

GGTACAGAGG GCTGCGATAC CGTGAGGTGG AGCGAATCCC TTAAAGCCGG TCTCAGTTCG GATCGGGGTC TGCAACTCGA

CCCCGTGAAG TCGGAGTCGC CCATGTCTCC CGACGCTATG GCACTCCACC TCGCTTAGGG AATTTCGGCC AGAGTCAAGC

CTAGCCCCAG ACGTTGAGCT GGGGCACTTC AGCCTCAGCG TAGTAATCGC AGATCAGCAA CGCTGCGGTG AATACGTTCC

CGGGCCTTGT ACACACCGCC CGTCACGTCA TGAAAGTCGG TAACACCCGA AGCCGGTGGC ATCATTAGCG TCTAGTCGTT

GCGACGCCAC TTATGCAAGG GCCCGGAACA TGTGTGGCGG GCAGTGCAGT ACTTTCAGCC ATTGTGGGCT TCGGCCACCG

CTAACCCCTT GTGGGAGGGA GCCGTCGAAG GTGGGATCGG CGATTGGGAC GAAGTCGTAA CAAGGTAGCC GTACCGGAAG

GGATTGGGGA ACACCCTCCC TCGGCAGCTT CCACCCTAGC CGCTAACCCT GCTTCAGCAT TGTTCCATCG GCATGGCCTT

CC

SEQ ID: 12
TCAACGGAGA GTTTGATCCT GGCTCAGGAC GAACGCTGGC GGCGTGCTTA ACACATGCAA GTCGAGCGG AAGGCCCTTC

GGGGTACACG AGCGGCGAAC AGTTGCCTCT CAAACTAGGA CCGAGTCCTG CTTGCGACCG CCGCACGAAT TGTGTACGTT

CAGCTCGCCA TTCCGGGAAG CCCCATGTGC TCGCCGCTTG GGGTGAGTAA CACGTGGGTG ATCTGCCCTG CACTTCGGGA

TAAGCCTGGG AAACTGGGTC TAATACCGGA TATGACCTTC GGCTGCATGG CCGTTGGTGG CCCACTCATT GTGCACCCAC

TAGACGGGAC GTGAAGCCCT ATTCGGACCC TTTGACCCAG ATTATGGCCT ATACTGGAAG CCGACGTACC GGCAACCACC

AAAGGTTTAC TGGTGCAGGA TGGGCCCGCG GCCTATCAGC TTGTTGGTGG GGTAATGGCC TACCAAGGCG ACGACGGGTA

GCCGACCTGA GAGGGTGACC TTTCCAAATG ACCACGTCCT ACCCGGGCGC CGGATAGTCG AACAACCACC CCATTACCGG

ATGGTTCCGC TGCTGCCCAT CGGCTGGACT CTCCCACTGG GGCCACACTG GGACTGAGAC ACGGCCCAGA CTCCTACGGG

AGGCAGCAGT GGGGAATATT GCACAATGGG CGAAAGCCTG ATGCAGCGAC GCCGCGTGAG CCGGTGTGAC CCTGACTCTG

TGCCGGGTCT GAGGATGCCC TCCGTCGTCA CCCCTTATAA CGTGTTACCC GCTTTCGGAC TACGTCGCTG CGGCGCACTC

GGATGACGGC CTTCGGGTTG TAAACCTCTT TCAGCAGGGA CGAAGCGAAA GTGACGGTAC CTGCAGAAGA AGCACCGGCC

AACTACGTGC CAGCAGCCGC CCTACTGCCG GAAGCCCAAC ATTTGGAGAA AGTCGTCCCT GCTTCGCTTT CACTGCCATG

GACGTCTTCT TCGTGGCCGG TTGATGCACG GTCGTCGGCG GGTAATACGT AGGGTGCAAG CGTTGTCCGG AATTACTGGG

CGTAAAGAGC TCGTAGGCGG TTTGTCGCGT CGTCTGTGAA AACTCGAGGC TCAACCTCGA CCATTATGCA TCCCACGTTC

GCAACAGGCC TTAATGACCC GCATTTCTCG AGCATCCGCC AAACAGCGCA GCAGACACTT TGAGCTCCG AGTTGGAGCT

GCTTGCAGGC GATACGGGCA GACTTGAGTA CTGCAGGGGA GACTGGAATT CCTGGTGTAG CGGTGAAATG CGCAGATATC

AGGAGGAACA CCGGTGGCGA CGAACGTCCG CTATGCCCGT CTGAACTCAT GACGTCCCCT CTGACCTTAA GGACCACATC

GCCACTTTAC GCGTCTATAG TCCTCCTTGT GGCCACCGCT AGGCGGGTCT CTGGGCAGTA ACTGACGCTG AGGAGCGAAA

GCGTGGGTAG CGAACAGGAT TAGATACCCT GGTAGTCCAC GCCGTAAACG GTGGGCGCTA TCCGCCCAGA GACCCGTCAT

TGACTGCGAC TCCTCGCTTT CGCACCCATC GCTTGTCCTA ATCTATGGGA CCATCAGGTG CGGCATTTGC CACCCGCGAT

GGTGTGGGTT TCCTTCCACG GGATCCGTGC CGTAGCTAAC GCATTAAGCG CCCCGCCTGG GGAGTACGGC CGCAAGGCTA

AAACTCAAAG GAATTGACGG CCACACCCAA AGGAAGGTGC CTAGGCACG GCATCGATTG CGTAATTCGC GGGGCGGACC

CCTCATGCCG GCGTTCCGAT TTGAGTTTC CTTAACTGCC GGGCCCGCAC AAGCGGCGGA GCATGTGGAT TAATTCGATG

CAACGCGAAG AACCTTACCT GGGTTTGACA TATACCGGAA AGCTGCAGAG ATGTGGCCCC CCCGGGCGTG TTCGCCGCCT

CGTACACCTA ATTAAGCTAC GTTGCGCTTC TTGGAATGGA CCCAAACTGT ATATGGCCTT TCGACGTCTC TACACCGGGG

CCTTGTGGTC GGTATACAGG TGGTGCATGG CTGTCGTCAG CTCGTGTCGT GAGATGTTGG GTTAAGTCCC GCAACGAGCG
```

-continued

CAACCCTTGT CTTATGTTGC GGAACACCAG CCATATGTCC ACCACGTACC GACAGCAGTC GAGCACAGCA CTCTACAACC

CAATTCAGGG CGTTGCTCGC GTTGGGAACA GAATACAACG CAGCACGTAA TGGTGGGGAC TCGTAAGAGA CTGCCGGGGT

CAACTCGGAG GAAGGTGGGG ACGACGTCAA GTCATCATGC CCCTTATGTC CAGGGCTTCA GTCGTGCATT ACCACCCCTG

AGCATTCTCT GACGGCCCCA GTTGAGCCTC CTTCCACCCC TGCTGCAGTT CAGTAGTACG GGGAATACAG GTCCCGAAGT

CACATGCTAC AATGGCCGGT ACAGAGGGCT GCGATACCGT GAGGTGGAGC GAATCCCTTA AGCCGGTCT CAGTTCGGAT

CGGGGTCTGC AACTCGACCC GTGTACGATG TTACCGGCCA TGTCTCCCGA CGCTATGGCA CTCCACCTCG CTTAGGGAAT

TTCGGCCAGA GTCAAGCCTA GCCCCAGACG TTGAGCTGGG CGTGAAGTCG GAGTCGCTAG TAATCGCAGA TCAGCAACGC

TGCGGTGAAT ACGTTCCCGG GCCTTGTACA CACCGCCCGT CACGTCATGA AGTCGGTAA GCACTTCAGC CTCAGCGATC

ATTAGCGTCT AGTCGTTGCG ACGCCACTTA TGCAAGGGCC CGGAACATGT GTGGCGGGCA GTGCAGTACT TTCAGCCATT

CACCCGAAGC CGGTGGCCTA ACCCCTCGTG GGAGGGAGCC GTCGAAGGTG GGATCGGCGA TTGGGACGAA GTCGTAACAA

GGTAGCCGTA CCGGAAGGTG GTGGGCTTCG GCCACCGGAT TGGGGAGCAC CCTCCCTCGG CAGCTTCCAC CCTAGCCGCT

AACCCTGCTT CAGCATTGTT CCATCGGCAT GGCCTTCCAC CGGCTGGATC ACCTCCTTTC TGCCGACCTA GTGGAGGAAA

GA

SEQ ID: 13
ACGTGGCGGC ATGCCTTACA CATGCAAGTC GAACGGCAGC GCGGACTTCG GTCTGGCGGC GAGTGGCGAA CGGGTGAGTA

ATACATCGGA ACGTACCCTG TGCACCGCCG TACGGAATGT GTACGTTCAG CTTGCCGTCG CGCCTGAAGC CAGACCGCCG

CTCACCGCTT GCCCACTCAT TATGTAGCCT TGCATGGGAC TTGTGGGGGA TAACTAGTCA AAAGATTAGC TAATACCGCA

TACGACCTGA GGGTGAAAGT GGGGGACCGC AAGGCCTCAC GCAGCAGGAG CGGCCGATGT AACACCCCCT ATTGATCAGC

TTTCTAATCG ATTATGGCGT ATGCTGGACT CCCACTTTCA CCCCCTGGCG TTCCGGAGTG CGTCGTCCTC GCCGGCTACA

CTGATTAGCT AGTTGGTGGG GTAAAGGCCC ACCAAGGCGA CGATCAGTAG CTGGTCTGAG AGGACGATCA GCCACACTGG

GACTGAGACA CGGCCCAGAC GACTAATCGA TCAACCACCC CATTTCCGGG TGGTTCCGCT GCTAGTCATC GACCAGACTC

TCCTGCTAGT CGGTGTGACC CTGACTCTGT GCCGGGTCTG TCCTACGGGA GGCAGCAGTG GGGAATTTTG GACAATGGGG

GCAACCCTGA TCCAGCAATG CCGCGTGTGT GAAGAAGGCC TTCGGGTTGT AAAGCACTTT AGGATGCCCT CCGTCGTCAC

CCCTTAAAAC CTGTTACCCC CGTTGGGACT AGGTCGTTAC GGCGCACACA CTTCTTCCGG AAGCCCAACA TTTCGTGAAA

TGTCCGGAAA GAAATCGCGC TGGTTAATAC CTGCGTGATG ACGGTACCGG AAGAATAAGC ACCGGCTAAC TACGTGCCAG

CAGCCGCGGT AATACGTAGG ACAGGCCTTT CTTTAGCGCG ACCAATTATG GACGCACTAC TGCCATGGCC TTCTTATTCG

TGGCCGATTG ATGCACGGTC GTCGGCGCCA TTATGCATCC GTGCGAGCGT TAATCGGAAT TACTGGGCGT AAAGCGTGCG

CAGGCGGTTT TGTAAGACAG GCGTGAAATC CCCGGGCTTA ACCTGGGAAT TGCGCTTGTG CACGCTCGCA ATTAGCCTTA

ATGACCCGCA TTTCGCACGC GTCCGCCAAA ACATTCTGTC CGCACTTTAG GGGCCCGAAT TGGACCCTTA ACGCGAACAC

ACTGCAAGGC TAGAGTGCGT CAGAGGGGGG TAGAATTCCA CGTGTAGCAG TGAAATGCGT AGAGATGTGG AGGAATACCG

ATGGCGAAGG CGAGCCCCCT TGACGTTCCG ATCTCACGCA GTCTCCCCCC ATCTTAAGGT GCACATCGTC ACTTTACGCA

TCTCTACACC TCCTTATGGC TACCGCTTCC GCTCGGGGGA GGACCTTGAC TGACGCTCAT GCACGAAAGC GTGGGGAGCA

AACAGGATTA GATACCCTGG TAGTCCACGC CCTAAACGAT GTCAACTAGT TGTTGGGATT CCTGGAACTG ACTGCGAGTA

CGTGCTTTCG CACCCCTCGT TTGTCCTAAT CTATGGGACC ATCAGGTGCG GGATTTGCTA CAGTTGATCA ACAACCCTAA

CATTTTCTCA GTAACGTAGC TAACGCGTGA AGTTGACCGC CTGGGAGTA CGGCTGCAAG ATTAAAACTC AAAGGAATTG

ACGGGGACCC GCACAAGCGG GTAAAAGAGT CATTGCATCG ATTGCGCACT TCAACTGGCG GACCCCTCAT GCCGACGTTC

TAATTTTGAG TTTCCTTAAC TGCCCCTGGG CGTGTTCGCC TGGATGATGT GGATTAATTC GATGCAACGC GAAAAACCTT

ACCTACCCTT GACATGCCCT AACGAAGCAG AGATGCATTA GTGCCCGCAA AGGGAAAGTG ACCTACTACA CCTAATTAAG

CTACGTTGCG CTTTTTGGAA TGGATGGGAA CTGTACGGGA TTGCTTCGTC TCTACGTAAT CACGGGCGTT TCCCTTTCAC

GGACACAGGT GCTGCATGGC TGTCGTCAGC TCGTGTCGTG AGATGTTGGG TTAAGTCCCG CAACGAGCGC AACCCTTGTC

TCTAGTTGCC TACGCAAGAG CCTGTGTCCA CGACGTACCG ACAGCAGTCG AGCACAGCAC TCTACAACCC AATTCAGGGC

```
                                                          -continued
GTTGCTCGCG TTGGGAACAG AGATCAACGG ATGCGTTCTC CACTCTAGAG AGACTGCCGG TGACAAACCG GAGGAAGGTG GGGATGACGT CAAGTCCTCA TGGCCCTTAT GGGTAGGGCT TCACACGTCA TACAATGGTG GTGAGATCTC TCTGACGGCC ACTGTTTGGC CTCCTTCCAC CCCTACTGCA GTTCAGGAGT ACCGGGAATA CCCATCCCGA AGTGTGCAGT ATGTTACCAC CGTACAGAGG GTTGCCAACC CGCGAGGGGG AGCTAATCCC AGAAAACGCA TCGTAGTCCG GATCGTAGTC TGCAACTCGA CTACGTGAAG CTGGAATCGC GCATGTCTCC CAACGGTTGG GCGCTCCCCC TCGATTAGGG TCTTTTGCGT AGCATCAGGC CTAGCATCAG ACGTTGAGCT GATGCACTTC GACCTTAGCG TAGTAATCGC GGATCAGCAT GCCGCGGTGA ATACGTTCCC GGGTCTTGTA CACACCGCCC GTCACACCAT GGGAGTGGGT TTTGCCAGAA GTAGTTAGCC ATCATTAGCG CCTAGTCGTA CGGCGCCACT TATGCAAGGG CCCAGAACAT GTGTGGCGGG CAGTGTGGTA CCCTCACCCA AAACGGTCTT CATCAATCGG TAACCGCAAG GAGGGCGATT ACCACGGCAG GGTTCATGAC TGGGGTGAAG TCGTAACAAG GTATTGGCGT TCCTCCCGCT

AATGGTGCCG TCCCAAGTAC TGACCCCACT TCAGCATTGT TCCA

SEQ ID 14
MASIEDILEL EALEKDIFRG AVHPSVLKRT FGGQVAGQSL VSAVRTVDER FEVHSLHGYF LRPGNPTEPT VYLVDRIRDG

RSFCTRRVTG IQDGKAIFTM SASFHSQDEG IEHQDTMPSV PEPEELVDAQ TVEEMAATDL YREWKEWDVR IVPAGCTGKT

PGIAAKQRVW MRYRNKLPDD QVFHICTLAY LSDMTLLGAS KVPHPGVVTQ TASLDHAMWF LRPFRADEWL LYDQTSPSAG

FGRALTQGRM FDRKGTMVAA VVQEGLTRIQ RDQDQRDIET GNMA
```

In some embodiments, the cell comprises a plasmid that contains one or more exogenous nucleic acid sequences encoding enzymes or proteins that include but are not limited to one or more of the following: an acyl carrier protein, a TE, a FAR, a FadR, a FAD, a fatty aldehyde reductase, a cytochrome P450 enzyme, a NADH or NADPH cytochrome 55 P450 reductase, a desaturase, a hydroxylase, and an antibiotic resistance enabling protein; wherein the plasmid is at least 20, 30, 40, 50, 60, 70, 80, 81, 82, 83, 84, 85, 86, 87, 88, 89, 90, 91, 92, 93, 94, 95, 96, 97, 98, or 99% homologous to SEQ ID NO: 1, SEQ ID NO:2, SEQ ID NO:3, or SEQ ID NO:4. In some embodiments, the exogenous nucleic acid sequence is incorporated into the genome of the cell. In some embodiments, the cell or composition comprising a cell comprises at least one exogenous nucleic acid that encodes a FAR or a functional fragment of a FAR derived from one of the following organisms: *Arabidopsis thaliana, Arabidopsis lyrata, Vitis vinifera, Populus trichocarpa, Artermisia annua, Ricinus communis, Simmondsia chineis, Oryza sativa japonica, Hevea brasiliensis, Hordeum vulgare, Triticum aestivum, Sorghum bicolor, Zea mays*, and *Selaginella moelllendorf*.

In one embodiment, the exogenous gene encodes a FAR. In some cases, the FAR encoded by the exogenous gene catalyzes the reduction of a 20 to 30-carbon fatty acyl-CoA to a corresponding primary alcohol. In some cases, the FAR encoded by the exogenous gene catalyzes the reduction of an 8 to 18-carbon fatty acyl-CoA to a corresponding primary alcohol. In some cases, the FAR encoded by the exogenous gene catalyzes the reduction of a 10 to 14-carbon fatty acyl-CoA to a corresponding primary alcohol. In one embodiment, the FAR encoded by the exogenous gene catalyzes the reduction of a 12-carbon fatty acyl-CoA to dodecanol.

In one embodiment, the exogenous gene encodes a FadR. In some cases, the reductase encoded by the exogenous gene catalyzes the reduction of an 8 to 18-carbon fatty acyl-CoA to a corresponding aldehyde. In one embodiment, the reductase encoded by the exogenous gene catalyzes the reduction of a 12-carbon fatty acyl-CoA to dodecanal.

In some embodiments, the invention relates to a bacterial cell or a compositions comprising at least one bacterial cell that comprises at least a first and a second exogenous nucleic acid sequence, wherein the first nucleic acid sequence encodes a FadR or a functional fragment of a FadR and the second exogenous nucleic acid sequence encodes a fatty acyl-CoA ligase or a functional fragment thereof. In some embodiments, the functional fragments of the enzymes encoded by the one or more exogenous nucleic acid sequences are at least 40, 45, 50, 55, 60, 65, 70, 75, 80, 81, 82, 83, 84, 85, 86, 87, 88, 89, 90, 91, 92, 93, 94, 95, 96, 97, 98, or 99% homologous to the nucleic acid sequences that encode the full-length amino acid sequence upon which the functional fragment is based. Any enzyme disclosed in this application and part of the invention may be replaced with a functional fragment or variant. Any composition or cell disclosed in the application may be used in any disclosed method of this application.

In some embodiments, the genetic constructs contain sequences directing transcription and translation of the relevant exogenous (either heterologous or homologous) gene, a selectable marker, and/or sequences allowing autonomous replication or chromosomal integration. In some embodiments, suitable vectors comprise a region 5' of the gene or DNA fragment which harbors transcriptional initiation controls and a region 3' of the gene or DNA fragment which controls transcriptional termination. It is most preferred when both control regions are derived from genes homologous to the transformed host cell, although it is to be understood that such control regions need not be derived from the genes native to the specific species chosen as a production host. In some cells the exogenous gene is coding sequence and is in operable linkage with a promoter, and in some embodiments the promoter is derived from a gene endogenous to a species of the genus *Rhodococcus* or *Ralstonia*. Initiation control regions or promoters, which are useful to drive expression of the instant ORFs in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO; and lac, ara, tet, trp, $IP_L$, $IP_R$, T7, tac, and trc as well as the amy, apr, npr promoters and various phage promoters useful for expression in the lipid-producing bacteria of the present invention. In other embodiments the promoter is upregulated in response to reduction or elimination of a cofactor in the culture media of the cell, such as at least a 3-fold upregulation as determined by transcript abundance in a cell when the cell is exposed to extracellular environment changes from containing at least 10 mM or 5 mM cofactor to containing no cofactor.

Termination control regions may also be derived from various genes native to the preferred hosts. Optionally, the genetic constructs of the present invention do not comprise a termination control region.

In some embodiments, the bacterial cell or the composition comprising the bacterial cell comprises at least one genetic construct, which comprises one or more coding sequences. In some embodiments, the invention relates to the bacterial cell or the composition comprising at least one bacterial cell wherein the at least one cell comprises two or more genetic constructs, three or more genetic constructs, or four or more genetic constructs, each comprising one or more coding sequences. In some embodiments, the coding sequences of the claimed invention encode at least one protein that modifies or accelerates lipid production in the host cell. In some embodiments the coding sequence encodes at least one protein that alters the levels of individual lipids or hydrocarbons produced by the cell as compared to the same cell not modified by an exogenous nucleic acid sequence. In some embodiments, the coding sequence may encode at least one protein that alters the amount of one specific lipid or hydrocarbon molecule of the cell as compared to the same cell not modified by the nucleic acid. For example, in one embodiment, the one or more exogenous nucleic acid sequence encodes at least one lipid pathway enzyme that causes an increase in the ratio of C14:C16:C18 lipids or hydrocarbons produced or secreted by the cell as compared to the C14:C16:C18 lipids or hydrocarbons produced or secreted by the same cell not transformed with the nucleic acid sequence that encodes the lipid pathway enzyme. In one embodiment, the one or more exogenous nucleic acid sequence encodes at least one lipid pathway enzyme that causes a decrease in the ratio of C14:C16:C18 lipids or hydrocarbons produced or secreted by the cell as compared to the C14:C16:C18 lipids or hydrocarbons produced or secreted by the same cell not transformed with the nucleic acid sequence that encodes the lipid pathway enzyme. In some embodiments, the one or more cells comprising one or more exogenous nucleic acid sequences produces at least 5% more C8 hydrocarbon as compared to the same one or more cells not transformed or modified with the one or more exogenous nucleic acid sequences. In some embodiments, the one or more cells comprising one or more exogenous nucleic acid sequences produces at least 5% more C8 hydrocarbon as compared to the same one or more cells not transformed or modified with the one or more exogenous nucleic acid sequences.

In some embodiments, the bacterial cell produces and/or secretes one or more unsaturated lipids or hydrocarbons in a ratio greater than the ratio of unsaturated lipids or hydrocarbons produced and/or secreted by the same cell not cells comprising one or more exogenous nucleic acid sequences.

In some embodiments, the bacterial cell produces and/or secretes at least 6% more C8 hydrocarbon as compared to the same one or more cells not transformed or modified with the one or more exogenous nucleic acid sequences.

In some embodiments, the one or more cells comprising one or more exogenous nucleic acid sequences produces at least 7% more C8 hydrocarbon as compared to the same one or more cells not transformed or modified with the one or more exogenous nucleic acid sequences.

In some embodiments, the one or more cells comprising one or more exogenous nucleic acid sequences produces at least 8% more C8 hydrocarbon as compared to the same one or more cells not transformed or modified with the one or more exogenous nucleic acid sequences.

In some embodiments, the one or more cells comprising one or more exogenous nucleic acid sequences produces at least 9% more C8 hydrocarbon as compared to the same one or more cells not transformed or modified with the one or more exogenous nucleic acid sequences.

In some embodiments, the one or more cells comprising one or more exogenous nucleic acid sequences produces at least 10% more C8 hydrocarbon as compared to the same one or more cells not transformed or modified with the one or more exogenous nucleic acid sequences.

In some embodiments, the one or more cells comprising one or more exogenous nucleic acid sequences produces at least 15% more C8 hydrocarbon as compared to the same one or more cells not transformed or modified with the one or more exogenous nucleic acid sequences.

In some embodiments, the one or more cells comprising one or more exogenous nucleic acid sequences produces at least 20% more C8 hydrocarbon as compared to the same one or more cells not transformed or modified with the one or more exogenous nucleic acid sequences.

In some embodiments, the one or more cells comprising one or more exogenous nucleic acid sequences produces at least 25% more C8 hydrocarbon as compared to the same one or more cells not transformed or modified with the one or more exogenous nucleic acid sequences.

In some embodiments, the one or more cells comprising one or more exogenous nucleic acid sequences produces at least 30% more C8 hydrocarbon as compared to the same one or more cells not transformed or modified with the one or more exogenous nucleic acid sequences.

In some embodiments, the one or more cells comprising one or more exogenous nucleic acid sequences produces at least 35% more C8 hydrocarbon as compared to the same one or more cells not transformed or modified with the one or more exogenous nucleic acid sequences.

In some embodiments, the one or more cells comprising one or more exogenous nucleic acid sequences produces at least 40% more C8 hydrocarbon as compared to the same one or more cells not transformed or modified with the one or more exogenous nucleic acid sequences.

In some embodiments, the one or more cells comprising one or more exogenous nucleic acid sequences produces at least 45% more C8 hydrocarbon as compared to the same one or more cells not transformed or modified with the one or more exogenous nucleic acid sequences.

In some embodiments, the one or more cells comprising one or more exogenous nucleic acid sequences produces at least 50% more C8 hydrocarbon as compared to the same one or more cells not transformed or modified with the one or more exogenous nucleic acid sequences.

In some embodiments, the one or more cells comprising one or more exogenous nucleic acid sequences produces at least 5% more C9 hydrocarbon as compared to the same one or more cells not transformed or modified with the one or more exogenous nucleic acid sequences. In some embodiments, the one or more cells comprising one or more exogenous nucleic acid sequences produces at least 6% more C9 hydrocarbon as compared to the same one or more cells not transformed or modified with the one or more exogenous nucleic acid sequences. In some embodiments, the one or more cells comprising one or more exogenous nucleic acid sequences produces at least 7% more C9 hydrocarbon as compared to the same one or more cells not transformed or modified with the one or more exogenous nucleic acid sequences. In some embodiments, the one or more cells comprising one or more exogenous nucleic acid sequences produces at least 8% more C9 hydrocarbon as compared to the same one or more cells not transformed or modified with the one or more exogenous nucleic acid sequences. In some embodiments, the one or more cells comprising one or more exogenous nucleic acid sequences produces at least 9% more C9 hydrocarbon as compared to the same one or more cells not transformed or modified with the one or more exogenous nucleic acid sequences. In some embodiments, the one or more cells comprising one or more exogenous nucleic acid sequences produces at least 10% more C9 hydrocarbon as compared to the same one or more cells not transformed or modified with the one or more exogenous nucleic acid sequences. In some embodiments, the one or more cells comprising one or more exogenous nucleic acid sequences produces at least 15% more C9 hydrocarbon as compared to the same one or more cells not transformed or modified with the one or more exogenous nucleic acid sequences. In some embodiments, the one or more cells comprising one or more exogenous nucleic acid sequences produces at least 20% more C9 hydrocarbon as compared to the same one or more cells not transformed or modified with the one or more exogenous nucleic acid sequences. In some embodiments, the one or more cells comprising one or more exogenous nucleic acid sequences produces at least 25% more C9 hydrocarbon as compared to the same one or more cells not transformed or modified with the one or more exogenous nucleic acid sequences. In some embodiments, the one or more cells comprising one or more exogenous nucleic acid sequences produces at least 30% more C9 hydrocarbon as compared to the same one or more cells not transformed or modified with the one or more exogenous nucleic acid sequences. In some embodiments, the one or more cells comprising one or more exogenous nucleic acid sequences produces at least 35% more C9 hydrocarbon as compared to the same one or more cells not transformed or modified with the one or more exogenous nucleic acid sequences. In some embodiments, the one or more cells comprising one or more exogenous nucleic acid sequences produces at least 40% more C9 hydrocarbon as compared to the same one or more cells not transformed or modified with the one or more exogenous nucleic acid sequences. In some embodiments, the one or more cells comprising one or more exogenous nucleic acid sequences produces at least 45% more C9 hydrocarbon as compared to the same one or more cells not transformed or modified with the one or more exogenous nucleic acid sequences. In some embodiments, the one or more cells comprising one or more exogenous nucleic acid sequences produces at least 50% more C9 hydrocarbon as compared to the same one or more cells not transformed or modified with the one or more exogenous nucleic acid sequences.

In some embodiments, the one or more cells comprising one or more exogenous nucleic acid sequences produces at least 5% more C10 hydrocarbon as compared to the same one or more cells not transformed or modified with the one or more exogenous nucleic acid sequences.

In some embodiments, the one or more cells comprising one or more exogenous nucleic acid sequences produces at least 6% more C10 hydrocarbon as compared to the same one or more cells not transformed or modified with the one or more exogenous nucleic acid sequences.

In some embodiments, the one or more cells comprising one or more exogenous nucleic acid sequences produces at least 7% more C10 hydrocarbon as compared to the same one or more cells not transformed or modified with the one or more exogenous nucleic acid sequences.

In some embodiments, the one or more cells comprising one or more exogenous nucleic acid sequences produces at least 8% more C10 hydrocarbon as compared to the same one or more cells not transformed or modified with the one or more exogenous nucleic acid sequences.

In some embodiments, the one or more cells comprising one or more exogenous nucleic acid sequences produces at least 9% more C10 hydrocarbon as compared to the same one or more cells not transformed or modified with the one or more exogenous nucleic acid sequences.

In some embodiments, the one or more cells comprising one or more exogenous nucleic acid sequences produces at least 10% more C10 hydrocarbon as compared to the same one or more cells not transformed or modified with the one or more exogenous nucleic acid sequences.

In some embodiments, the one or more cells comprising one or more exogenous nucleic acid sequences produces at least 15% more C10 hydrocarbon as compared to the same one or more cells not transformed or modified with the one or more exogenous nucleic acid sequences.

In some embodiments, the one or more cells comprising one or more exogenous nucleic acid sequences produces at least 20% more C10 hydrocarbon as compared to the same one or more cells not transformed or modified with the one or more exogenous nucleic acid sequences.

In some embodiments, the one or more cells comprising one or more exogenous nucleic acid sequences produces at least 25% more C10 hydrocarbon as compared to the same one or more cells not transformed or modified with the one or more exogenous nucleic acid sequences.

In some embodiments, the one or more cells comprising one or more exogenous nucleic acid sequences produces at least 30% more C10 hydrocarbon as compared to the same one or more cells not transformed or modified with the one or more exogenous nucleic acid sequences.

In some embodiments, the one or more cells comprising one or more exogenous nucleic acid sequences produces at least 35% more C10 hydrocarbon as compared to the same one or more cells not transformed or modified with the one or more exogenous nucleic acid sequences.

In some embodiments, the one or more cells comprising one or more exogenous nucleic acid sequences produces at least 40% more C10 hydrocarbon as compared to the same one or more cells not transformed or modified with the one or more exogenous nucleic acid sequences.

In some embodiments, the one or more cells comprising one or more exogenous nucleic acid sequences produces at least 45% more C10 hydrocarbon as compared to the same one or more cells not transformed or modified with the one or more exogenous nucleic acid sequences.

In some embodiments, the one or more cells comprising one or more exogenous nucleic acid sequences produces at least 50% more C10 hydrocarbon as compared to the same one or more cells not transformed or modified with the one or more exogenous nucleic acid sequences.

In some embodiments, the one or more cells comprising one or more exogenous nucleic acid sequences produces at least 5% more C11 hydrocarbon as compared to the same one or more cells not transformed or modified with the one or more exogenous nucleic acid sequences.

In some embodiments, the one or more cells comprising one or more exogenous nucleic acid sequences produces at least 6% more C11 hydrocarbon as compared to the same one or more cells not transformed or modified with the one or more exogenous nucleic acid sequences.

In some embodiments, the one or more cells comprising one or more exogenous nucleic acid sequences produces at least 7% more C11 hydrocarbon as compared to the same one or more cells not transformed or modified with the one or more exogenous nucleic acid sequences.

In some embodiments, the one or more cells comprising one or more exogenous nucleic acid sequences produces at least 8% more C11 hydrocarbon as compared to the same one or more cells not transformed or modified with the one or more exogenous nucleic acid sequences.

In some embodiments, the one or more cells comprising one or more exogenous nucleic acid sequences produces at least 9% more C11 hydrocarbon as compared to the same one or more cells not transformed or modified with the one or more exogenous nucleic acid sequences.

In some embodiments, the one or more cells comprising one or more exogenous nucleic acid sequences produces at least 10% more C11 hydrocarbon as compared to the same one or more cells not transformed or modified with the one or more exogenous nucleic acid sequences.

In some embodiments, the one or more cells comprising one or more exogenous nucleic acid sequences produces at least 15% more C11 hydrocarbon as compared to the same one or more cells not transformed or modified with the one or more exogenous nucleic acid sequences.

In some embodiments, the one or more cells comprising one or more exogenous nucleic acid sequences produces at least 20% more C11 hydrocarbon as compared to the same one or more cells not transformed or modified with the one or more exogenous nucleic acid sequences.

In some embodiments, the one or more cells comprising one or more exogenous nucleic acid sequences produces at least 25% more C11 hydrocarbon as compared to the same one or more cells not transformed or modified with the one or more exogenous nucleic acid sequences.

In some embodiments, the one or more cells comprising one or more exogenous nucleic acid sequences produces at least 30% more C11 hydrocarbon as compared to the same one or more cells not transformed or modified with the one or more exogenous nucleic acid sequences.

In some embodiments, the one or more cells comprising one or more exogenous nucleic acid sequences produces at least 35% more C11 hydrocarbon as compared to the same one or more cells not transformed or modified with the one or more exogenous nucleic acid sequences.

In some embodiments, the one or more cells comprising one or more exogenous nucleic acid sequences produces at least 40% more C11 hydrocarbon as compared to the same one or more cells not transformed or modified with the one or more exogenous nucleic acid sequences.

In some embodiments, the one or more cells comprising one or more exogenous nucleic acid sequences produces at least 45% more C11 hydrocarbon as compared to the same one or more cells not transformed or modified with the one or more exogenous nucleic acid sequences.

In some embodiments, the one or more cells comprising one or more exogenous nucleic acid sequences produces at least 50% more C11 hydrocarbon as compared to the same one or more cells not transformed or modified with the one or more exogenous nucleic acid sequences.

In some embodiments, the one or more cells comprising one or more exogenous nucleic acid sequences produces at least 5% more C12 hydrocarbon as compared to the same one or more cells not transformed or modified with the one or more exogenous nucleic acid sequences.

In some embodiments, the one or more cells comprising one or more exogenous nucleic acid sequences produces at least 6% more C12 hydrocarbon as compared to the same one or more cells not transformed or modified with the one or more exogenous nucleic acid sequences.

In some embodiments, the one or more cells comprising one or more exogenous nucleic acid sequences produces at least 7% more C12 hydrocarbon as compared to the same one or more cells not transformed or modified with the one or more exogenous nucleic acid sequences.

In some embodiments, the one or more cells comprising one or more exogenous nucleic acid sequences produces at least 8% more C12 hydrocarbon as compared to the same one or more cells not transformed or modified with the one or more exogenous nucleic acid sequences.

In some embodiments, the one or more cells comprising one or more exogenous nucleic acid sequences produces at least 9% more C12 hydrocarbon as compared to the same one or more cells not transformed or modified with the one or more exogenous nucleic acid sequences.

In some embodiments, the one or more cells comprising one or more exogenous nucleic acid sequences produces at least 10% more C12 hydrocarbon as compared to the same one or more cells not transformed or modified with the one or more exogenous nucleic acid sequences.

In some embodiments, the one or more cells comprising one or more exogenous nucleic acid sequences produces at least 15% more C12 hydrocarbon as compared to the same one or more cells not transformed or modified with the one or more exogenous nucleic acid sequences.

In some embodiments, the one or more cells comprising one or more exogenous nucleic acid sequences produces at least 20% more C12 hydrocarbon as compared to the same one or more cells not transformed or modified with the one or more exogenous nucleic acid sequences.

In some embodiments, the one or more cells comprising one or more exogenous nucleic acid sequences produces at least 25% more C12 hydrocarbon as compared to the same one or more cells not transformed or modified with the one or more exogenous nucleic acid sequences.

In some embodiments, the one or more cells comprising one or more exogenous nucleic acid sequences produces at least 30% more C12 hydrocarbon as compared to the same one or more cells not transformed or modified with the one or more exogenous nucleic acid sequences.

In some embodiments, the one or more cells comprising one or more exogenous nucleic acid sequences produces at least 35% more C12 hydrocarbon as compared to the same one or more cells not transformed or modified with the one or more exogenous nucleic acid sequences.

In some embodiments, the one or more cells comprising one or more exogenous nucleic acid sequences produces at least 40% more C12 hydrocarbon as compared to the same one or more cells not transformed or modified with the one or more exogenous nucleic acid sequences.

In some embodiments, the one or more cells comprising one or more exogenous nucleic acid sequences produces at least 45% more C12 hydrocarbon as compared to the same one or more cells not transformed or modified with the one or more exogenous nucleic acid sequences.

In some embodiments, the one or more cells comprising one or more exogenous nucleic acid sequences produces at least 50% more C12 hydrocarbon as compared to the same one or more cells not transformed or modified with the one or more exogenous nucleic acid sequences.

In some embodiments, the one or more cells comprising one or more exogenous nucleic acid sequences produces at least 5% more C13 hydrocarbon as compared to the same one or more cells not transformed or modified with the one or more exogenous nucleic acid sequences.

In some embodiments, the one or more cells comprising one or more exogenous nucleic acid sequences produces at least 6% more C13 hydrocarbon as compared to the same one or more cells not transformed or modified with the one or more exogenous nucleic acid sequences.

In some embodiments, the one or more cells comprising one or more exogenous nucleic acid sequences produces at least 7% more C13 hydrocarbon as compared to the same one or more cells not transformed or modified with the one or more exogenous nucleic acid sequences.

In some embodiments, the one or more cells comprising one or more exogenous nucleic acid sequences produces at least 8% more C13 hydrocarbon as compared to the same one or more cells not transformed or modified with the one or more exogenous nucleic acid sequences.

In some embodiments, the one or more cells comprising one or more exogenous nucleic acid sequences produces at least 9% more C13 hydrocarbon as compared to the same one or more cells not transformed or modified with the one or more exogenous nucleic acid sequences.

In some embodiments, the one or more cells comprising one or more exogenous nucleic acid sequences produces at least 10% more C13 hydrocarbon as compared to the same one or more cells not transformed or modified with the one or more exogenous nucleic acid sequences.

In some embodiments, the one or more cells comprising one or more exogenous nucleic acid sequences produces at least 15% more C13 hydrocarbon as compared to the same one or more cells not transformed or modified with the one or more exogenous nucleic acid sequences.

In some embodiments, the one or more cells comprising one or more exogenous nucleic acid sequences produces at least 20% more C13 hydrocarbon as compared to the same one or more cells not transformed or modified with the one or more exogenous nucleic acid sequences.

In some embodiments, the one or more cells comprising one or more exogenous nucleic acid sequences produces at least 25% more C13 hydrocarbon as compared to the same one or more cells not transformed or modified with the one or more exogenous nucleic acid sequences.

In some embodiments, the one or more cells comprising one or more exogenous nucleic acid sequences produces at least 30% more C13 hydrocarbon as compared to the same one or more cells not transformed or modified with the one or more exogenous nucleic acid sequences.

In some embodiments, the one or more cells comprising one or more exogenous nucleic acid sequences produces at least 35% more C13 hydrocarbon as compared to the same one or more cells not transformed or modified with the one or more exogenous nucleic acid sequences.

In some embodiments, the one or more cells comprising one or more exogenous nucleic acid sequences produces at least 40% more C13 hydrocarbon as compared to the same one or more cells not transformed or modified with the one or more exogenous nucleic acid sequences.

In some embodiments, the one or more cells comprising one or more exogenous nucleic acid sequences produces at least 45% more C13 hydrocarbon as compared to the same one or more cells not transformed or modified with the one or more exogenous nucleic acid sequences.

In some embodiments, the one or more cells comprising one or more exogenous nucleic acid sequences produces at least 50% more C13 hydrocarbon as compared to the same one or more cells not transformed or modified with the one or more exogenous nucleic acid sequences.

In some embodiments, the one or more cells comprising one or more exogenous nucleic acid sequences produces at least 5% more C14 hydrocarbon as compared to the same one or more cells not transformed or modified with the one or more exogenous nucleic acid sequences.

In some embodiments, the one or more cells comprising one or more exogenous nucleic acid sequences produces at least 6% more C14 hydrocarbon as compared to the same one or more cells not transformed or modified with the one or more exogenous nucleic acid sequences.

In some embodiments, the one or more cells comprising one or more exogenous nucleic acid sequences produces at least 7% more C14 hydrocarbon as compared to the same one or more cells not transformed or modified with the one or more exogenous nucleic acid sequences.

In some embodiments, the one or more cells comprising one or more exogenous nucleic acid sequences produces at least 8% more C14 hydrocarbon as compared to the same one or more cells not transformed or modified with the one or more exogenous nucleic acid sequences.

In some embodiments, the one or more cells comprising one or more exogenous nucleic acid sequences produces at least 9% more C14 hydrocarbon as compared to the same one or more cells not transformed or modified with the one or more exogenous nucleic acid sequences.

In some embodiments, the one or more cells comprising one or more exogenous nucleic acid sequences produces at least 10% more C14 hydrocarbon as compared to the same one or more cells not transformed or modified with the one or more exogenous nucleic acid sequences.

In some embodiments, the one or more cells comprising one or more exogenous nucleic acid sequences produces at least 15% more C14 hydrocarbon as compared to the same one or more cells not transformed or modified with the one or more exogenous nucleic acid sequences.

In some embodiments, the one or more cells comprising one or more exogenous nucleic acid sequences produces at least 20% more C14 hydrocarbon as compared to the same one or more cells not transformed or modified with the one or more exogenous nucleic acid sequences.

In some embodiments, the one or more cells comprising one or more exogenous nucleic acid sequences produces at least 25% more C14 hydrocarbon as compared to the same one or more cells not transformed or modified with the one or more exogenous nucleic acid sequences.

In some embodiments, the one or more cells comprising one or more exogenous nucleic acid sequences produces at least 30% more C14 hydrocarbon as compared to the same one or more cells not transformed or modified with the one or more exogenous nucleic acid sequences.

In some embodiments, the one or more cells comprising one or more exogenous nucleic acid sequences produces at least 35% more C14 hydrocarbon as compared to the same one or more cells not transformed or modified with the one or more exogenous nucleic acid sequences.

In some embodiments, the one or more cells comprising one or more exogenous nucleic acid sequences produces at least 40% more C14 hydrocarbon as compared to the same one or more cells not transformed or modified with the one or more exogenous nucleic acid sequences.

In some embodiments, the one or more cells comprising one or more exogenous nucleic acid sequences produces at least 45% more C14 hydrocarbon as compared to the same one or more cells not transformed or modified with the one or more exogenous nucleic acid sequences.

In some embodiments, the one or more cells comprising one or more exogenous nucleic acid sequences produces at least 50% more C14 hydrocarbon as compared to the same one or more cells not transformed or modified with the one or more exogenous nucleic acid sequences.

In some embodiments, the one or more cells comprising one or more exogenous nucleic acid sequences produces at least 5% more C15 hydrocarbon as compared to the same one or more cells not transformed or modified with the one or more exogenous nucleic acid sequences.

In some embodiments, the one or more cells comprising one or more exogenous nucleic acid sequences produces at least 6% more C15 hydrocarbon as compared to the same one or more cells not transformed or modified with the one or more exogenous nucleic acid sequences.

In some embodiments, the one or more cells comprising one or more exogenous nucleic acid sequences produces at least 7% more C15 hydrocarbon as compared to the same one or more cells not transformed or modified with the one or more exogenous nucleic acid sequences.

In some embodiments, the one or more cells comprising one or more exogenous nucleic acid sequences produces at least 8% more C15 hydrocarbon as compared to the same one or more cells not transformed or modified with the one or more exogenous nucleic acid sequences.

In some embodiments, the one or more cells comprising one or more exogenous nucleic acid sequences produces at least 9% more C15 hydrocarbon as compared to the same one or more cells not transformed or modified with the one or more exogenous nucleic acid sequences.

In some embodiments, the one or more cells comprising one or more exogenous nucleic acid sequences produces at least 10% more C15 hydrocarbon as compared to the same one or more cells not transformed or modified with the one or more exogenous nucleic acid sequences.

In some embodiments, the one or more cells comprising one or more exogenous nucleic acid sequences produces at least 15% more C15 hydrocarbon as compared to the same one or more cells not transformed or modified with the one or more exogenous nucleic acid sequences.

In some embodiments, the one or more cells comprising one or more exogenous nucleic acid sequences produces at least 20% more C15 hydrocarbon as compared to the same one or more cells not transformed or modified with the one or more exogenous nucleic acid sequences.

In some embodiments, the one or more cells comprising one or more exogenous nucleic acid sequences produces at least 25% more C15 hydrocarbon as compared to the same one or more cells not transformed or modified with the one or more exogenous nucleic acid sequences.

In some embodiments, the one or more cells comprising one or more exogenous nucleic acid sequences produces at least 30% more C15 hydrocarbon as compared to the same one or more cells not transformed or modified with the one or more exogenous nucleic acid sequences.

In some embodiments, the one or more cells comprising one or more exogenous nucleic acid sequences produces at least 35% more C15 hydrocarbon as compared to the same one or more cells not transformed or modified with the one or more exogenous nucleic acid sequences.

In some embodiments, the one or more cells comprising one or more exogenous nucleic acid sequences produces at least 40% more C15 hydrocarbon as compared to the same one or more cells not transformed or modified with the one or more exogenous nucleic acid sequences.

In some embodiments, the one or more cells comprising one or more exogenous nucleic acid sequences produces at least 45% more C15 hydrocarbon as compared to the same one or more cells not transformed or modified with the one or more exogenous nucleic acid sequences.

In some embodiments, the one or more cells comprising one or more exogenous nucleic acid sequences produces at least 50% more C15 hydrocarbon as compared to the same one or more cells not transformed or modified with the one or more exogenous nucleic acid sequences.

In some embodiments, the one or more cells comprising one or more exogenous nucleic acid sequences produces at least 5% more C16 hydrocarbon as compared to the same one or more cells not transformed or modified with the one or more exogenous nucleic acid sequences.

In some embodiments, the one or more cells comprising one or more exogenous nucleic acid sequences produces at least 6% more C16 hydrocarbon as compared to the same one or more cells not transformed or modified with the one or more exogenous nucleic acid sequences.

In some embodiments, the one or more cells comprising one or more exogenous nucleic acid sequences produces at least 7% more C16 hydrocarbon as compared to the same one or more cells not transformed or modified with the one or more exogenous nucleic acid sequences.

In some embodiments, the one or more cells comprising one or more exogenous nucleic acid sequences produces at least 8% more C16 hydrocarbon as compared to the same one or more cells not transformed or modified with the one or more exogenous nucleic acid sequences.

In some embodiments, the one or more cells comprising one or more exogenous nucleic acid sequences produces at least 9% more C16 hydrocarbon as compared to the same one or more cells not transformed or modified with the one or more exogenous nucleic acid sequences.

In some embodiments, the one or more cells comprising one or more exogenous nucleic acid sequences produces at least 10% more C16 hydrocarbon as compared to the same one or more cells not transformed or modified with the one or more exogenous nucleic acid sequences.

In some embodiments, the one or more cells comprising one or more exogenous nucleic acid sequences produces at least 15% more C16 hydrocarbon as compared to the same one or more cells not transformed or modified with the one or more exogenous nucleic acid sequences.

In some embodiments, the one or more cells comprising one or more exogenous nucleic acid sequences produces at least 20% more C16 hydrocarbon as compared to the same one or more cells not transformed or modified with the one or more exogenous nucleic acid sequences.

In some embodiments, the one or more cells comprising one or more exogenous nucleic acid sequences produces at least 25% more C16 hydrocarbon as compared to the same one or more cells not transformed or modified with the one or more exogenous nucleic acid sequences.

In some embodiments, the one or more cells comprising one or more exogenous nucleic acid sequences produces at least 30% more C16 hydrocarbon as compared to the same one or more cells not transformed or modified with the one or more exogenous nucleic acid sequences.

In some embodiments, the one or more cells comprising one or more exogenous nucleic acid sequences produces at least 35% more C16 hydrocarbon as compared to the same one or more cells not transformed or modified with the one or more exogenous nucleic acid sequences.

In some embodiments, the one or more cells comprising one or more exogenous nucleic acid sequences produces at least 40% more C16 hydrocarbon as compared to the same one or more cells not transformed or modified with the one or more exogenous nucleic acid sequences.

In some embodiments, the one or more cells comprising one or more exogenous nucleic acid sequences produces at least 45% more C16 hydrocarbon as compared to the same one or more cells not transformed or modified with the one or more exogenous nucleic acid sequences.

In some embodiments, the one or more cells comprising one or more exogenous nucleic acid sequences produces at least 50% more C16 hydrocarbon as compared to the same one or more cells not transformed or modified with the one or more exogenous nucleic acid sequences.

In some embodiments, the one or more cells comprising one or more exogenous nucleic acid sequences produces at least 5% more C17 hydrocarbon as compared to the same one or more cells not transformed or modified with the one or more exogenous nucleic acid sequences.

In some embodiments, the one or more cells comprising one or more exogenous nucleic acid sequences produces at least 6% more C17 hydrocarbon as compared to the same one or more cells not transformed or modified with the one or more exogenous nucleic acid sequences.

In some embodiments, the one or more cells comprising one or more exogenous nucleic acid sequences produces at least 7% more C17 hydrocarbon as compared to the same one or more cells not transformed or modified with the one or more exogenous nucleic acid sequences.

In some embodiments, the one or more cells comprising one or more exogenous nucleic acid sequences produces at least 8% more C17 hydrocarbon as compared to the same one or more cells not transformed or modified with the one or more exogenous nucleic acid sequences.

In some embodiments, the one or more cells comprising one or more exogenous nucleic acid sequences produces at least 9% more C17 hydrocarbon as compared to the same one or more cells not transformed or modified with the one or more exogenous nucleic acid sequences.

In some embodiments, the one or more cells comprising one or more exogenous nucleic acid sequences produces at least 10% more C17 hydrocarbon as compared to the same one or more cells not transformed or modified with the one or more exogenous nucleic acid sequences.

In some embodiments, the one or more cells comprising one or more exogenous nucleic acid sequences produces at least 15% more C17 hydrocarbon as compared to the same one or more cells not transformed or modified with the one or more exogenous nucleic acid sequences.

In some embodiments, the one or more cells comprising one or more exogenous nucleic acid sequences produces at least 20% more C17 hydrocarbon as compared to the same one or more cells not transformed or modified with the one or more exogenous nucleic acid sequences.

In some embodiments, the one or more cells comprising one or more exogenous nucleic acid sequences produces at least 25% more C17 hydrocarbon as compared to the same one or more cells not transformed or modified with the one or more exogenous nucleic acid sequences.

In some embodiments, the one or more cells comprising one or more exogenous nucleic acid sequences produces at least 30% more C17 hydrocarbon as compared to the same one or more cells not transformed or modified with the one or more exogenous nucleic acid sequences.

In some embodiments, the one or more cells comprising one or more exogenous nucleic acid sequences produces at least 35% more C17 hydrocarbon as compared to the same one or more cells not transformed or modified with the one or more exogenous nucleic acid sequences.

In some embodiments, the one or more cells comprising one or more exogenous nucleic acid sequences produces at least 40% more C17 hydrocarbon as compared to the same one or more cells not transformed or modified with the one or more exogenous nucleic acid sequences.

In some embodiments, the one or more cells comprising one or more exogenous nucleic acid sequences produces at least 45% more C17 hydrocarbon as compared to the same one or more cells not transformed or modified with the one or more exogenous nucleic acid sequences.

In some embodiments, the one or more cells comprising one or more exogenous nucleic acid sequences produces at least 50% more C17 hydrocarbon as compared to the same one or more cells not transformed or modified with the one or more exogenous nucleic acid sequences.

In some embodiments, the one or more cells comprising one or more exogenous nucleic acid sequences produces at least 5% more C18 hydrocarbon as compared to the same one or more cells not transformed or modified with the one or more exogenous nucleic acid sequences.

In some embodiments, the one or more cells comprising one or more exogenous nucleic acid sequences produces at least 6% more C18 hydrocarbon as compared to the same one or more cells not transformed or modified with the one or more exogenous nucleic acid sequences.

In some embodiments, the one or more cells comprising one or more exogenous nucleic acid sequences produces at least 7% more C18 hydrocarbon as compared to the same one or more cells not transformed or modified with the one or more exogenous nucleic acid sequences.

In some embodiments, the one or more cells comprising one or more exogenous nucleic acid sequences produces at least 8% more C18 hydrocarbon as compared to the same one or more cells not transformed or modified with the one or more exogenous nucleic acid sequences.

In some embodiments, the one or more cells comprising one or more exogenous nucleic acid sequences produces at least 9% more C18 hydrocarbon as compared to the same one or more cells not transformed or modified with the one or more exogenous nucleic acid sequences.

In some embodiments, the one or more cells comprising one or more exogenous nucleic acid sequences produces at least 10% more C18 hydrocarbon as compared to the same one or more cells not transformed or modified with the one or more exogenous nucleic acid sequences.

In some embodiments, the one or more cells comprising one or more exogenous nucleic acid sequences produces at least 15% more C18 hydrocarbon as compared to the same one or more cells not transformed or modified with the one or more exogenous nucleic acid sequences.

In some embodiments, the one or more cells comprising one or more exogenous nucleic acid sequences produces at least 20% more C18 hydrocarbon as compared to the same one or more cells not transformed or modified with the one or more exogenous nucleic acid sequences.

In some embodiments, the one or more cells comprising one or more exogenous nucleic acid sequences produces at least 25% more C18 hydrocarbon as compared to the same one or more cells not transformed or modified with the one or more exogenous nucleic acid sequences.

In some embodiments, the one or more cells comprising one or more exogenous nucleic acid sequences produces at least 30% more C18 hydrocarbon as compared to the same one or more cells not transformed or modified with the one or more exogenous nucleic acid sequences.

In some embodiments, the one or more cells comprising one or more exogenous nucleic acid sequences produces at least 35% more C18 hydrocarbon as compared to the same one or more cells not transformed or modified with the one or more exogenous nucleic acid sequences.

In some embodiments, the one or more cells comprising one or more exogenous nucleic acid sequences produces at least 40% more C18 hydrocarbon as compared to the same one or more cells not transformed or modified with the one or more exogenous nucleic acid sequences.

In some embodiments, the one or more cells comprising one or more exogenous nucleic acid sequences produces at least 45% more C18 hydrocarbon as compared to the same one or more cells not transformed or modified with the one or more exogenous nucleic acid sequences.

In some embodiments, the one or more cells comprising one or more exogenous nucleic acid sequences produces at least 50% more C18 hydrocarbon as compared to the same one or more cells not transformed or modified with the one or more exogenous nucleic acid sequences.

In some embodiments, the one or more exogenous nucleic acid sequence encodes at least one lipid pathway enzyme that causes an increase in the ratio of C12:C14:C16 lipids or hydrocarbons produced or secreted by the cell as compared to the C12:C14:C16 lipids or hydrocarbons produced or secreted by the same cell not transformed with the nucleic acid sequence that encodes the lipid pathway enzyme. In one embodiment, the one or more exogenous nucleic acid sequence encodes at least one lipid pathway enzyme that causes a decrease in the ratio of C12:C14:C16 lipids or hydrocarbons produced or secreted by the cell as compared to the C12:C14:C16 lipids or hydrocarbons produced or secreted by the same cell not transformed with the nucleic acid sequence that encodes the lipid pathway enzyme. In some embodiments, the one or more exogenous nucleic acid sequence encodes at least one lipid pathway enzyme that causes an increase in the ratio of C13:C15:C17 lipids or hydrocarbons produced or secreted by the cell as compared to the C13:C15:C17 lipids or hydrocarbons produced or secreted by the same cell not transformed with the nucleic acid sequence that encodes the lipid pathway enzyme. In one embodiment, the one or more exogenous nucleic acid sequence encodes at least one lipid pathway enzyme that causes a decrease in the ratio of C13:C15:C17 lipids or hydrocarbons produced or secreted by the cell as compared to the C13:C15:C17 lipids or hydrocarbons produced or secreted by the same cell not transformed with the nucleic acid sequence that encodes the lipid pathway enzyme. In some embodiments, the one or more exogenous nucleic acid sequence encodes at least one lipid pathway enzyme that causes an increase in the ratio of odd-numbered lipids or hydrocarbons produced or secreted by the cell as compared to the odd-numbered lipids or hydrocarbons produced or secreted by the same cell not transformed with the nucleic acid sequence that encodes the lipid pathway enzyme. In some embodiments, the one or more exogenous nucleic acid sequence encodes at least one lipid pathway enzyme that causes a decrease in the ratio of odd-numbered lipids or hydrocarbons produced or secreted by the cell as compared to the odd-numbered lipids or hydrocarbons produced or secreted by the same cell not transformed with the nucleic acid sequence that encodes the lipid pathway enzyme. In one embodiment, the one or more exogenous nucleic acid sequence encodes at least one lipid pathway enzyme that causes a decrease in the ratio of even:odd carbon numbered lipids or hydrocarbons produced or secreted by the cell as compared to the ratio of even:odd carbon numbered lipids or hydrocarbons produced or secreted by the same cell not transformed with the nucleic acid sequence that encodes the one or more lipid pathway enzymes. In one embodiment, the one or more exogenous nucleic acid sequence encodes at least one lipid pathway enzyme that causes a increase in the ratio of even:odd carbon numbered lipids or hydrocarbons produced or secreted by the cell as compared to the ratio of even:odd carbon numbered lipids or hydrocarbons produced or secreted by the same cell not transformed with the nucleic acid sequence that encodes the one or more lipid pathway enzymes.

In some embodiments, the one or more exogenous nucleic acid sequence encodes at least one lipid pathway enzyme that causes at least a 5% increase in the ratio of C12:C14:C16 lipids or hydrocarbons produced or secreted by the cell as compared to the C12:C14:C16 lipids or hydrocarbons produced or secreted by the same cell not transformed or modified with the nucleic acid sequence that encodes the lipid pathway enzyme. In some embodiments, the one or more exogenous nucleic acid sequence encodes at least one lipid pathway enzyme that causes at least a 5% increase in the ratio of C12:C14:C16 lipids or hydrocarbons produced or secreted by the cell as compared to the C12:C14:C16 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 6% increase in the ratio of C12:C14:C16 lipids or hydrocarbons produced or secreted by the cell as compared to the C12:C14:C16 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 7% increase in the ratio of C12:C14:C16 lipids or hydrocarbons produced or secreted by the cell as compared to the C12:C14:C16 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 8% increase in the ratio of C12:C14:C16 lipids or hydrocarbons produced or secreted by the cell as compared to the C12:C14:C16 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 9% increase in the ratio of C12:C14:C16 lipids or hydrocarbons produced or secreted by the cell as compared to the C12:C14:C16 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 10% increase in the ratio of C12:C14:C16 lipids or hydrocarbons produced or secreted by the cell as compared to the C12:C14:C16 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 11% increase in the ratio of C12:C14:C16 lipids or hydrocarbons produced or secreted by the cell as compared to the C12:C14:C16 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 12% increase in the ratio of C12:C14:C16 lipids or hydrocarbons produced or secreted by the cell as compared to the C12:C14:C16 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 13% increase in the ratio of C12:C14:C16 lipids or hydrocarbons produced or secreted by the cell as compared to the C12:C14:C16 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 14% increase in the ratio of C12:C14:C16 lipids or hydrocarbons produced or secreted by the cell as compared to the C12:C14:C16 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 15% increase in the ratio of C12:C14:C16 lipids or hydrocarbons produced or secreted by the cell as compared to the C12:C14:C16 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 20% increase in the ratio of C12:C14:C16 lipids or hydrocarbons produced or secreted by the cell as compared to the C12:C14:C16 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 25% increase in the ratio of C12:C14:C16 lipids or hydrocarbons produced or secreted by the cell as compared to the C12:C14:C16 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 30% increase in the ratio of C12:C14:C16 lipids or hydrocarbons produced or secreted by the cell as compared to the C12:C14:C16 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 35% increase in the ratio of C12:C14:C16 lipids or hydrocarbons produced or secreted by the cell as compared to the C12:C14:C16 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 40% increase in the ratio of C12:C14:C16 lipids or hydrocarbons produced or secreted by the cell as compared to the C12:C14:C16 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 45% increase in the ratio of C12:C14:C16 lipids or hydrocarbons produced or secreted by the cell as compared to the C12:C14:C16 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 50% increase in the ratio of C12:C14:C16 lipids or hydrocarbons produced or secreted by the cell as compared to the C12:C14:C16 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 55% increase in the ratio of C12:C14:C16 lipids or hydrocarbons produced or secreted by the cell as compared to the C12:C14:C16 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 60% increase in the ratio of C12:C14:C16 lipids or hydrocarbons produced or secreted by the cell as compared to the C12:C14:C16 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 65% increase in the ratio of C12:C14:C16 lipids or hydrocarbons produced or secreted by the cell as compared to the C12:C14:C16 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 70% increase in the ratio of C12:C14:C16 lipids or hydrocarbons produced or secreted by the cell as compared to the C12:C14:C16 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 75% increase in the ratio of C12:C14:C16 lipids or hydrocarbons produced or secreted by the cell as compared to the C12:C14:C16 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 80% increase in the ratio of C12:C14:C16 lipids or hydrocarbons produced or secreted by the cell as compared to the C12:C14:C16 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 85% increase in the ratio of C12:C14:C16 lipids or hydrocarbons produced or secreted by the cell as compared to the C12:C14:C16 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 5% increase in the ratio of C13:C15:C17 lipids or hydrocarbons produced or secreted by the cell as compared to the C13:C15:C17 lipids or hydrocarbons produced or secreted by the same cell not transformed or modified with the nucleic acid sequence that encodes the lipid pathway enzyme. In some embodiments, the one or more exogenous nucleic acid sequence encodes at least one lipid pathway enzyme that causes at least a 5% increase in the ratio of C13:C15:C17 lipids or hydrocarbons produced or secreted by the cell as compared to the C13:C15:C17 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 6% increase in the ratio of C13:C15:C17 lipids or hydrocarbons produced or secreted by the cell as compared to the C13:C15:C17 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 7% increase in the ratio of C13:C15:C17 lipids or hydrocarbons produced or secreted by the cell as compared to the C13:C15:C17 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 8% increase in the ratio of C13:C15:C17 lipids or hydrocarbons produced or secreted by the cell as compared to the C13:C15:C17 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 9% increase in the ratio of C13:C15:C17 lipids or hydrocarbons produced or secreted by the cell as compared to the C13:C15:C17 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 10% increase in the ratio of C13:C15:C17 lipids or hydrocarbons produced or secreted by the cell as compared to the C13:C15:C17 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 11% increase in the ratio of C13:C15:C17 lipids or hydrocarbons produced or secreted by the cell as compared to the C13:C15:C17 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 12% increase in the ratio of C13:C15:C17 lipids or hydrocarbons produced or secreted by the cell as compared to the C13:C15:C17 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 13% increase in the ratio of C13:C15:C17 lipids or hydrocarbons produced or secreted by the cell as compared to the C13:C15:C17 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 14% increase in the ratio of C13:C15:C17 lipids or hydrocarbons produced or secreted by the cell as compared to the C13:C15:C17 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 15% increase in the ratio of C13:C15:C17 lipids or hydrocarbons produced or secreted by the cell as compared to the C13:C15:C17 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 20% increase in the ratio of C13:C15:C17 lipids or hydrocarbons produced or secreted by the cell as compared to the C13:C15:C17 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 25% increase in the ratio of C13:C15:C17 lipids or hydrocarbons produced or secreted by the cell as compared to the C13:C15:C17 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 30% increase in the ratio of C13:C15:

C17 lipids or hydrocarbons produced or secreted by the cell as compared to the C13:C15:C17 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 35% increase in the ratio of C13:C15:C17 lipids or hydrocarbons produced or secreted by the cell as compared to the C13:C15:C17 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 40% increase in the ratio of C13:C15:C17 lipids or hydrocarbons produced or secreted by the cell as compared to the C13:C15:C17 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 45% increase in the ratio of C13:C15:C17 lipids or hydrocarbons produced or secreted by the cell as compared to the C13:C15:C17 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 50% increase in the ratio of C13:C15:C17 lipids or hydrocarbons produced or secreted by the cell as compared to the C13:C15:C17 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 55% increase in the ratio of C13:C15:C17 lipids or hydrocarbons produced or secreted by the cell as compared to the C13:C15:C17 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 60% increase in the ratio of C13:C15:C17 lipids or hydrocarbons produced or secreted by the cell as compared to the C13:C15:C17 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 65% increase in the ratio of C13:C15:C17 lipids or hydrocarbons produced or secreted by the cell as compared to the C13:C15:C17 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 70% increase in the ratio of C13:C15:C17 lipids or hydrocarbons produced or secreted by the cell as compared to the C13:C15:C17 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 75% increase in the ratio of C13:C15:C17 lipids or hydrocarbons produced or secreted by the cell as compared to the C13:C15:C17 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 80% increase in the ratio of C13:C15:C17 lipids or hydrocarbons produced or secreted by the cell as compared to the C13:C15:C17 lipids or hydrocarbons produced or secreted by the same cell not transformed or modified with the nucleic acid sequence that encodes the lipid pathway enzyme.

In some embodiments, the one or more exogenous nucleic acid sequence encodes at least one lipid pathway enzyme that causes at least a 85% increase in the ratio of C13:C15:C17 lipids or hydrocarbons produced or secreted by the cell as compared to the C13:C15:C17 lipids or hydrocarbons produced or secreted by the same cell not transformed or modified with the nucleic acid sequence that encodes the lipid pathway enzyme.

In some embodiments the exogenous gene or genes codes for enzymes or proteins including but not limited to one or more of the following: an acyl carrier protein, a TE, a FAR, a FadR, a FAD, a fatty aldehyde reductase, a cytochrome P450 enzyme, a NADH or NADPH cytochrome P450 reductase, a desaturase, a hydroxylase, and an antibiotic resistance enabling protein or a fragment or variant thereof. In some embodiments, the coding sequence comprises an exogenous nucleic acid sequence that encodes a TE that catalyzes hydrolysis of one or more fatty acyl-ACP substrates with chain lengths ranging over C8, C9, C10, C11, C12, C13, C14, C15, C16, C17, or C18. In some embodiments, the cell comprises a plasmid that contains one or more exogenous nucleic acid sequences that encode an amino acid sequence for an enzyme or protein such as but not limited to one or more of the following: an acyl carrier protein, a TE, a FAR, a FadR, a FAD, a fatty aldehyde reductase, a cytochrome P450 enzyme, a NADH or NADPH cytochrome P450 reductase, a desaturase, a hydroxylase, and an antibiotic resistance enabling protein or a fragment or variant thereof. In some embodiments, the one or more exogenous nucleic acid sequences comprise SEQ ID NO:5 or a functional fragment or variant thereof that is at least 70%, 75%, 80%, 81%, 82%, 83%, 84%, 85%, 86%, 87%, 88%, 89%, 90%, 91%, 92%, 93%, 94%, 95%, 96%, 97%, 98%, or 99% homologous to SEQ ID NO:5. In some embodiments, the one or more exogenous nucleic acid sequences comprise SEQ ID NO:6 or a functional fragment thereof that is at least 70%, 75%, 80%, 81%, 82%, 83%, 84%, 85%, 86%, 87%, 88%, 89%, 90%, 91%, 92%, 93%, 94%, 95%, 96%, 97%, 98%, or 99% homologous to SEQ ID NO:6. In some embodiments, the one or more exogenous nucleic acid sequences comprise SEQ ID NO:7 or a functional fragment thereof that is at least 70%, 75%, 80%, 81%, 82%, 83%, 84%, 85%, 86%, 87%, 88%, 89%, 90%, 91%, 92%, 93%, 94%, 95%, 96%, 97%, 98%, or 99% homologous to SEQ ID NO:7. In some embodiments, the one or more exogenous nucleic acid sequences comprise SEQ ID NO:8 or a functional fragment thereof that is at least 70%, 75%, 80%, 81%, 82%, 83%, 84%, 85%, 86%, 87%, 88%, 89%, 90%, 91%, 92%, 93%, 94%, 95%, 96%, 97%, 98%, or 99% homologous to SEQ ID NO:8. In some embodiments, the one or more exogenous nucleic acid sequences comprise SEQ ID NO:9 or a functional fragment thereof that is at least 70%, 75%, 80%, 81%, 82%, 83%, 84%, 85%, 86%, 87%, 88%, 89%, 90%, 91%, 92%, 93%, 94%, 95%, 96%, 97%, 98%, or 99% homologous to SEQ ID NO:9.

In further embodiments, at least one coding sequence of the at least one exogenous nucleic acid sequence encodes a lipid pathway enzyme or a functional fragment or variant therof. In some embodiments, the at least one coding sequence of the at least one exogenous nucleic acid sequence encodes a lipid modification enzyme or a functional fragment or variant therof. In some embodiments, the composition or cell comprises a nucleic acid that encodes at least one fatty acid decarbonylase, at least one fatty acid reductase, a thioesterase, or any combination of any one more full-length lipid pathway enzymes or functional fragments or variants thereof. In some embodiments the one or more exogenous nucleic acid sequences are integrated into the genome of the cell. In some embodiments, the one or more exogenous nucleic acid sequences are on an episomal plasmid within the transformed host cell.

Methods of Isolation and Purification

Following the methods of the present invention microorganisms are grown and maintained for the production of lipids in a medium containing a gaseous carbon source, such as but not limited to syngas or producer gas, in the absence of light; such growth is known as chemotrophic growth. In some embodiments, the invention relates to methods of cultivating oleaginous cells for the large scale production of oil and/or fuel. In some embodiments, the invention relates to methods of cultivating oleaginous cells in bioreactors 50,000 liters or greater in volume, which are conventionally constructed out of low cost, sturdy, and opaque materials such as steel or reinforced concrete or earthworks. The size, depth, and construction of such bioreactors dictate that the cells will be grown in near or total darkness. In some embodiments, the oleaginous microorganisms are cultured for the synthesis of lipids in accordance with the methods of the present invention in a medium containing gaseous inorganic carbon, such as but not limited to syngas or producer gas, as the primary or sole carbon source, and without any exposure to light. This type of growth is known as chemoautotrophic growth.

To give an illustration, a bioreactor containing nutrient medium is inoculated with of oleaginous bacterial cells; generally there will follow a lag phase prior to the cells beginning to double. After the lag phase, the cell doubling time decreases and the culture goes into the logarithmic phase. The logarithmic phase is eventually followed by an increase of the doubling time that, while not intending to be limited by theory, is thought to result from either a depletion of nutrients including nitrogen sources, or a rise in the concentration of inhibitory chemicals, or quorum sensing by the microbes. The growth slows down and then ceases when the culture goes into the stationary phase. In order to harvest cell mass with high lipid content, the culture is generally harvested late in the logarithmic phase or in the stationary phase. In some embodiments, the cells are harvested in logarithmic phase. In some embodiments, the cells are harvested in stationary phase. The accumulation of lipid can generally be triggered by the depletion of the nitrogen source or another key nutrient excepting the carbon or the energy source (e.g. hydrogen). This signals the cells to store lipids produced from the excess carbon and energy sources. Optimization of lipid production and the targeting of specific lipid distributions can be achieved by control of bioreactor conditions and/or nutrient levels and/or through genetic modifications of the cells. In some embodiments the lipid production and distribution of lipid molecules produced is optimized through one or more of the following: control of bioreactor conditions, control of nutrient levels, genetic modifications of the cells.

The synthesis of lipids by the microbes disclosed in the present invention can happen during the logarithmic phase and afterwards during the stationary phase when cell doubling has stopped provided there is an ample supply of carbon and energy sources, In some embodiments, microorganisms grown using conditions described herein and known in the art comprise at least 20% lipid content by weight, but under chemotrophic conditions, comprise at least 10% lipid content by weight. In some embodiments, under chemotrophic conditions, the microorganisms of the present invention comprise at least about 10, 15, 20, 25, 30, 35, or 40% by weight of lipids, at least about 50% by weight, or at least about 60% by weight of lipids. Improved lipid yield and/or lower production costs can be achieved by controlling process parameters. In certain embodiments, a bacterium is grown in a nutrient media and/or gas mix having a nitrogen, oxygen, phosphorous, or sulfur limitation, while a gaseous carbon and energy source such as syngas is provided in excess. Lipid yield is generally higher in microbial cultures grown with a nitrogen limitation versus microbial cultures grown without nitrogen limitation. In certain embodiments, lipid yield rises by at least: 10%, 50%, 100%, 200%, 500%, or 1000%. The microbial growth can occur with nutrient limitation for a part or for all of the fermentation run. Feeding an excess of energy and carbon source to a population of oleaginous microbes, but little or no nitrogen, can produce a rise in cellular lipid content. In some embodiments, microbial growth occurs on limited amounts of nitrogen or in the complete absence of nitrogen.

Genes are well known in the art that code for cofactors useful in the present invention, or that are involved in synthesizing such cofactors.

In another embodiment, genes that code for cofactors useful in the present invention, or that are involved in synthesizing such cofactors, are put in oleaginous bacteria, using the constructs and methods such as described above. Lipid yield is improved in another embodiment by growing an oleaginous bacteria with one or more lipid pathway enzyme cofactor(s) added to the culture environment. The lipid yield is generally improved in the presence of a certain concentration of the cofactor(s) compared to lipid yield without supplemental cofactor(s). In some embodiments, the cofactor(s) are delivered to the culture by having a microbe (e.g., bacteria) present in the culture that contains an exogenous gene coding for the cofactor(s) at a concentration sufficient to increase lipid yield as compared to the lipid yield of the microbe in the absence of the cofactor. Cofactor(s) may also be delivered to a culture by having a microbe (e.g., bacteria) present in the culture that contains an exogenous gene that coding for a protein involved in the cofactor synthesis. In some embodiments, any vitamin needed for the proper function of a lipid pathway enzyme including biotin and/or pantothenate is included in the culture environment.

The specific examples of bioreactors, culture conditions, heterotrophic and chemotrophic growth, maintenance, and lipid production methods described herein can be combined in any suitable manner to improve efficiencies of microbial growth and lipid and/or protein production.

In another aspect of the invention, the invention relates to a method of producing a molecule or mixture of molecules in a microorganism population comprising the cell or the composition described herein, wherein the method comprises: culturing a population of microorganisms comprising the cell or the composition described herein in a feedstock comprising syngas and/or gaseous $CO_2$ and/or a mixture of $CO_2$ gas and $H_2$ gas.

In another aspect of the invention, the invention relates to a method of producing a hydrocarbon or mixture of hydrocarbons in a microorganism population comprising the cell or the composition described herein, wherein the method comprises: culturing a population of microorganisms comprising the cell or the composition described herein in a feedstock comprising syngas and/or gaseous $CO_2$ and/or a mixture of $CO_2$ gas and $H_2$ gas.

In another aspect of the invention, the invention relates to a method of producing a lipid or mixture of lipids in a microorganism population comprising the cell or the composition described herein, wherein the method comprises: culturing a population of microorganisms comprising the cell or the composition described herein in a feedstock comprising syngas and/or gaseous $CO_2$ and/or a mixture of $CO_2$ gas and $H_2$ gas.

In another aspect of the invention, the invention relates to a method of producing an alkane or mixture of alkanes in a microorganism population comprising the cell or the composition described herein, wherein the method comprises: culturing a population of microorganisms comprising the cell or the composition described herein in a feedstock comprising syngas and/or gaseous $CO_2$ and/or a mixture of $CO_2$ gas and $H_2$ gas.

In another aspect of the invention, the invention relates to a method of producing an alkene or mixture of alkenes in a microorganism population comprising the cell or the composition described herein, wherein the method comprises: culturing a population of microorganisms comprising the cell or the composition described herein in a feedstock comprising syngas and/or gaseous $CO_2$ and/or a mixture of $CO_2$ gas and $H_2$ gas.

In another aspect of the invention, the invention relates to a method of producing an alkyne or mixture of alkynes in a microorganism population comprising the cell or the composition described herein, wherein the method comprises: culturing a population of microorganisms comprising the cell or the composition described herein in a feedstock comprising syngas and/or gaseous $CO_2$ and/or a mixture of $CO_2$ gas and $H_2$ gas.

In some embodiments, the methods of the claimed invention do not rely on desulfonation to produce and/or secrete one or more hydrocarbons. In some embodiments, an exogenous nucleic acid is introduced into the cells of the claimed invention to silence or disrupt transcription of endogenous genes of the cell that encode enzymes capable of desulfonation of commercial surfactants under conditions and for a time period sufficient for growth of the cell with a gaseous feedstock comprising a gas comprising carbon.

In another aspect of the invention, the invention relates to a method of producing a primary alcohol in a microorganism population comprising the cell or the composition described herein, wherein the method comprises: culturing a population of microorganisms comprising the cell or the composition described herein in a feedstock comprising syngas and/or gaseous $CO_2$ and/or a mixture of $CO_2$ gas and $H_2$ gas. In some embodiments, the bacterial cell comprises a first and second exogenous nucleic acid sequence, wherein the first nucleic acid sequence encodes a FAR or functional fragment thereof and the second exogenous nucleic acid encodes a fatty-acyl-CoA ligase or functional fragment thereof.

In some embodiments, the feedstock does not include linoleic acid.

In addition to providing the new genes for post-production fatty acid hydroxylation, in order to boost yields of the desired hydroxylated products, one can increase the production of the C18 fatty acid precursors. Several ways have been identified to accomplish this: (1) up-regulate the thioesterase gene responsible for production of C18 fatty acids; (2) down-regulate production of endogenous thioesterases for other fatty acid chain lengths; and/or (3) down regulation of endogenous acyl carrier proteins.

Aspects of this invention involve the expression of fatty acyl-CoA binding protein in chemoautotrophic microbes for modification of the fatty acid profile. The fatty acyl-CoA binding protein exhibit broad specificity and sequester fatty acyl-CoA esters from the synthesizing machinery resulting in the production of shorter chain fatty acids.

Mikkelsen et al. identified a fatty acyl-CoA-binding protein (ACBP) with an apparent Mr of 7000 (Mogensen et al., 1987). This protein could bind and thereby induce medium-chain fatty acyl-CoA synthesis by goat mammary-gland fatty acid synthetase in vitro. "(Mikkelsen 1987)

In some embodiments, the production strain is in the genera *Rhodococcus* or *Gordonia* or *Nocardia*. In some embodiments, the production strain is *Rhodococcus opacus*.In some embodiments, the composition comprises a microorganism, wherein the microorganism is *Rhodococcus opacus* (DSM 43205) or *Rhodococcus opacus* (DSM 43206) or *Rhodococcus opacus* (DSM 44193). In some embodiments the production strain is *Cupriavidus* necator. In some embodiments the production strain is a knallgas microorganism, also known as an oxyhydrogen microorganism. In some embodiments the wild-type of the production strain naturally has a capability for accumulating and/or synthesizing high quantities of triacylglycerol where a high quantity is considered to be 10% or more of the dry cell mass; 20% or more of the dry cell mass; 30% or more of the dry cell mass; 40% or more of the dry cell mass; 50% or more of the dry cell mass; 60% or more of the dry cell mass; 70% or more of the dry cell mass. In some embodiments the production strain is a hydrogen-oxidizing chemoautotroph. In some embodiments the production strain is capable of growing on syngas as the sole energy and carbon source. In some embodiments the production strain is capable of growing on untreated crude glycerol as the sole energy and carbon source. In some embodiments the production strain is capable of growing on methanol as the sole energy and carbon source. In some embodiments the production strain is capable of growing on acetate as the sole energy and carbon sources. In some embodiments process conditions are used to enhance the effect on fatty acid chains lengths of the expressed enzymes. In some embodiments the process condition used to enhance the effect of the expressed enzymes is temperature.

The following documents are incorporated herein by reference in their entirety for all purposes:

U.S. Provisional Patent Application No. 61/616,560, filed Oct. 1, 2012 and entitled "PROCESS FOR GENERATING HYDROXYLATED FATTY ACIDS"; U.S. Provisional Patent Application No. 61/635,238, filed Apr. 18, 2012 and entitled "PROCESS FOR GENERATING SHORTER FATTY ACIDS WITH AN EXOGENOUS FATTY ACYL-COA BINDING PROTEIN"; U.S. Provisional Patent Application No. 61/708,057, filed Oct. 1, 2012 and entitled "PROCESS FOR PRODUCING CAR- BON-BASED CHEMICALS, INCLUDING BUTANE-DIOL, USING CHEMOTROPHIC MICROBES"; U.S. Provisional Patent Application No. 61/542,823, filed Sep. 19, 2011 and entitled "Engineered CO2-Fixing Chemotrophic Microorganisms Producing Carbon-Based Products And Methods Of Using The Same"; International Patent Application Serial No. PCT/US2011/34218, filed May 27, 2011, entitled "Use Of Oxyhydrogen Microorganisms For Non-Photosynthetic Carbon Capture And Conversion Of Inorganic And/Or C1 Carbon Sources Into Useful Organic Compounds"; U.S. Provisional Patent Application No. 61/328,184, filed Apr. 27, 2010 and entitled "USE OF OXYHYDROGEN MICROORGANISMS FOR NON-PHOTOSYNTHETIC CARBON CAPTURE AND CONVERSION OF INORGANIC CARBON SOURCES INTO USEFUL ORGANIC COMPOUNDS"; International Patent Application Serial No. PCT/US2010/001402, filed May 12, 2010, entitled "BIOLOGICAL AND CHEMICAL PROCESS UTILIZING CHEMOAUTOTROPHIC MICROORGNISMS FOR THE CHEMOSYTHETIC FIXATION OF CARBON DIOXIDE AND/OR OTHER INORGANIC CARBON SOURCES INTO ORGANIC COMPOUNDS, AND THE GENERATION OF ADDITIONAL USEFUL PRODUCTS"; and U.S. Patent Application Publication No. 2010/0120104, filed Nov. 6, 2009, entitled "BIOLOGICAL AND CHEMICAL PROCESS UTILIZING CHEMOAUTOTROPHIC MICROORGNISMS FOR THE CHEMOSYTHETIC FIXATION OF CARBON DIOXIDE AND/OR OTHER INORGANIC CARBON SOURCES INTO ORGANIC COMPOUNDS, AND THE GENERATION OF ADDITIONAL USEFUL PRODUCTS.

Doan T T P, Carlsson A S, Hamberg M, Bulow L, Stymne S, Olsson P, Functional expression of five *Arabidopsis* fatty acyl-CoA reductase genes in *Escherichia coli*, J Plant Phys 166(2008):787-96.

Kavanagh K L, Jornvall H, Persson B, Oppermann U, The SDR superfamily: functional and structural diversity within a family of metabolic and regulatory enzymes, Cell Mol Life Sci 65 (2008) 3895-3906.

Labesse G, Vidal-Cros A, Chomilier J, Gaudry M, Mornon J-P, Structural comparisons lead to the definition of a new superfamily of NAD(PXH)-accepting oxidoreductases: the single-domain reductases/epimerases/dehydrogenases (the 'RED' family), Biochem J (1994) 304:95-99.

Benveniste I, Tijet N, Adas F, Phillips G, Salaun J P, Durst F. 1998 Biochem. Biophys. Res. Commun. 243: 688-693.

Cellini F, Cifarelli R A, Carriero F, *Ricinus communis*-origin gene encoding novel protein interacting with oleate 12-hydroxylase, Patent JP 2002543842-A4 24 Dec. 2002.

Cellini F, Cifarelli R A, Carriero F, *Ricinus communis*-origin gene encoding novel protein interacting with oleate 12-hydroxylase, Patent WO 0070052-A4 23 Nov. 2000.

Dauk M, Lam P, Kunst L, Smith M A. A FAD2 homologue from *Lewquerella lindheimeri* has predominantly fatty acid hydroxylase activity, 2007 J Plant Sci 173(1):43-49.

McKeon T A, Chen G Q, He X, Ahn Y-J, Lin J-T, The enzymology of Castor Oil biosynthesis, Eds. Janick J, Whipkey A, "Issues in new crops and new uses, ASHS Press, Alexandria, Va. (2007) 101-104.

Meesapyodsuk D, Qiu X. An oleate hydroxylase from the fungus *Claviceps purpurea*: cloning, functional analysis, and expression in *Arabidopsis*. Plant Physiol. 2008 147 (3):1325-1333.

Meesapyodsuk D, Qiu X. Fatty acid desaturases and uses thereof. U.S. Pat. No. 8,003,853, Aug. 23, 2011.

Meesapyodsuk D, Qiu X. Fatty acid hydroxylases and uses thereof. U.S. Pat. No. 7,923,598, Apr. 12, 2011.

van de Loo F J, Broun P, Turner S, Somerville C. An oleate 12-hydroxylase from *Ricinus communis* L. is a fatty acyl desaturase homolog. Proc Natl Acad Sci USA. 1995 Jul. 18; 92(15):6743-7.

The following examples are provided to describe the invention in greater detail. They are intended to illustrate, not to limit, the invention. Various publications, including patents, published applications, technical articles and scholarly articles are cited throughout the specification. Each of these cited publications is incorporated by reference herein, in its entirety.

EXAMPLES

Example 1

Characterization of Organisms Sharing High 16SrRNA Sequence Similarity

Figure 2:
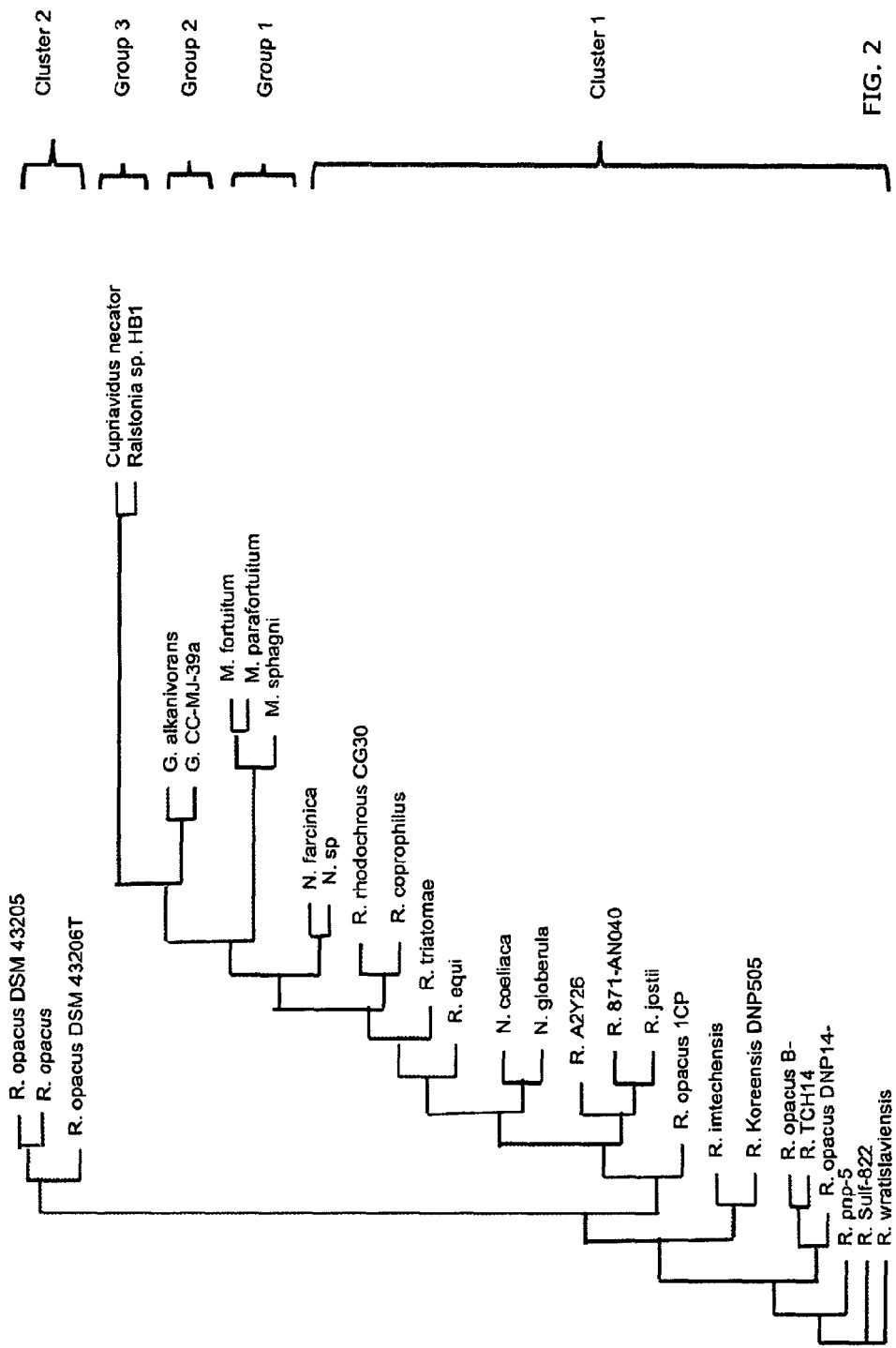
FIG. 2 shows the 16S rRNA gene based-rooted phylogenetic tree of gordoniaceae, mycobacteriaceae, nocardiaceae and burkholderiaceae.
Bar, 0.01% estimated sequence divergence.

To identify organisms closely related to *R. opacus* strain (DSM43205), a basic local alignment search (BLAST$^R$) with the BLASTN programs search of nucleotide databases using the 16S rRNA (NR_026186.1) was carried out. The phylogenetic relationships, based on the 16S rRNA gene sequence homology, between the tested strain and the reference strains of the suborder corynebacterineae (*corynebacterium*, gordoniaceae, mycobacteriaceae and nocardiaceae) and the family burkholderiaceae (genus *cupriavidus* and *ralstonia*) are shown in FIG. 2. The nocardiaceae are related and form two clusters of organisms: clusturel that contains 20 organisms from the genus *nocardia* and *rhodococcus* and cluster 2 that contains 3 *R. opacus* strains (DSM43205, GM14 and DSM43206). The gordoniaceae, mycobacteriaceae and burkholderiaceae form 3 separated groups (1, 2 and 3). The gram positive chemoautotroph lipid accumulating strain *R. opacus* (DSM43205; NR_026186.1) exhibits high sequence similarity to cluster 1 (94.3-99.1%) and to the gram positive groups 1 and 2 (92.7-93.5% and 93.3-93.6% respectively) (FIGS. 3 and 4). The sequence similarity to the gram negative chemoautotroph poly(3-hydroxybutyrate) (PHB) accumulating strains in group 3 is 73.7%.

Plasmid Design and Construction

To generate an *E. coli* Rhodococci shuttle vector suitable for electroporation, the plasmid pSeqCO1 (SEQ ID: 01) was constructed with the genetic elements described in FIG. 10A. pSeqCO1 consists of the replication gene operon, ampicillin and kanamycin resistance genes, LacZ operon and the multiple cloning site as described in FIG. 10B and FIG. 11A. For replication in *Rhodococci*, the DNA fragment of the repAB operon (1744 bp downsteam from the XhoI restriction site in the native pKNR01 plasmid of the bacteria *Rhodococcus opacus* B4; Na et al. 2005, J Biosci Bioeng. 99: 408-414) was synthesized with the restriction sites KpnI and SalI and cloned into PUC18 digested with KpnI and SalI. The resultant vector was digested with SpeI and BglII and ligated with the PCR product of the Kanamycin resistance gene from pBBR1MCS-2 (Kovach et al. 1995 Gene 166: 175-176) digested with the engineered restriction sites SpeI and BglI to give pSeqCO1.

To generate an *E. coli-cupriavidus* shuttle vector suitable for electroporation and bacterial conjugation, the plasmid pSeqCO2 (SEQ ID: 02) was used with the genetic elements described in FIG. 10A. pSeqCO2 (SEQ ID: 02; FIGS. 10 and 11B) is the plasmid pBBR1MCS-2 described in Kovach et al. (1995 Gene 166: 175-176) that contains the IncQ like replication gene, Mob gene that mobilized when the RK2 transfer functions are provided in trans, kanamycin resistance gene, LacZ operon and the multiple cloning site as described in FIG. 10B and FIG. 11B.

Pver1 (SEQ ID: 03; FIGS. 10 and 11C) is an *E. coli-cupriavidus-Rhodococci* shuttle vector suitable for electroporation and bacterial conjugation. The plasmid was generated by cloning the repAB operon (described in pSeqCO1) into pSeqCO2 using the KpnI and SalI restriction sites.

Pver2 (SEQ ID: 04; FIGS. 10 and 11D) is an *E. coli-cupriavidus-Rhodococci* shuttle vector suitable for electroporation and bacterial conjugation. The plasmid was generated by cloning the synthesized chloramphenicol gene (Alton and Vapnek Nature 1979 282: 864-869) with the engineered restriction sites SalI and HindIII into Pver1.

The *arabidopsis* genes FAR1 (SEQ ID: 05), FAR2 (SEQ ID: 06) and FAR3 (SEQ ID: 07): were synthesized and cloned into the plasmid pUC57. FAR1, FAR2 and FAR3 were rescued from PUC57 using the restriction enzymes KpnI and SalI and cloned into pSeqCO2 digested with KpnI and SalI to give pSeqCO2::FAR1, pSeqCO2::FAR2 and pSeqCO2::FAR3 respectively (FIG. 16). The genes FadDR (SEQ ID: 08) and Fad (SEQ ID: 09) and the rbcLXS promoter (SEQ ID: 10) were PCR amplified from the cyanobacterium *Synechocystis* sp. PCC 6803 genome and cloned into gateway plasmid to give pFUEL. A 4 kBp XhoI BamHI fragment that contains FadDR, Fad and rbcLXS was rescued from pFUEL and cloned into pSeqCO2 digested XhoI BamHI with to give pSeqCO2::FUEL (FIG. 20).

Microorganism Mutagenesis and Screening for High Lipid Content

*Rhodococcus* sp. (DSM3346) was incubated for 2 days in LB medium (per 1 L: 10 g Bacto-tryptone, 5 g yeast extract, 10 g NaCl pH=7.0) at 30° C., 200 rpm, and approximately $7.2 \times 10^6$ CFU (20 µl from O.D=1.2) were spread onto fresh LB plates. Two plates were immediately exposed to shortwave (254-nm) UV light for 0 (control), 5, 10 and 20 sec at a distance of 3.5 cm. Plates were then incubated at 30° C. for 48 h. Colonies from plates were collected in 1.5 ml eppendorf tubes by adding 1 ml LB into the plate and gentle scraping. The mutated colonies were spun down (10,000 rpm, 5 min at room temperature) and washed twice in PBS. Six µl of dilute Nile red DMSO stock solution (0.5 mg/ml) was added to final concentration of 0.75 µg/ml and incubated for 30 min at 4° C. Colonies were washed twice (10,000 rpm, 5 min at RT) with PBS (137 mM NaCl, 2.7 mM KCl, 4.3 mM $Na_2HPO_4$, 1.47 mM $KH_2PO_4$; pH of 7.4) and the final concentration was detected by $O.D._{660}$. The Final colonies concentration for FACS analysis was set to approximately $1 \times 10^8$ CFU/ml. For negative control (no NR), colonies from 0 sec treatment (control) were washed twice in PBS, incubated for 30 min at 4° C. and washed twice again. Analysis was carried out immediately after the staining by Fluorescence-activated cell sorting (FACS) (BD FACSAria™ II cell sorter). Fluorescence was detected with an excitation wavelength of 530 nm and an emission wavelength of 575 nm.

Figure 27D:
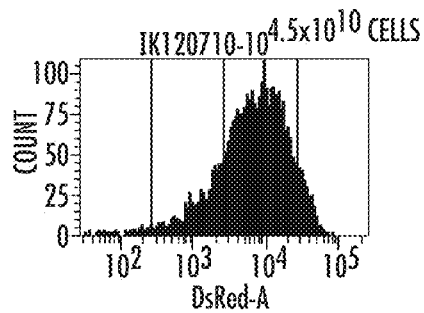
Figure 27E:
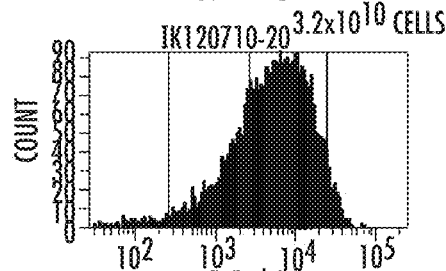
Figure 27F:
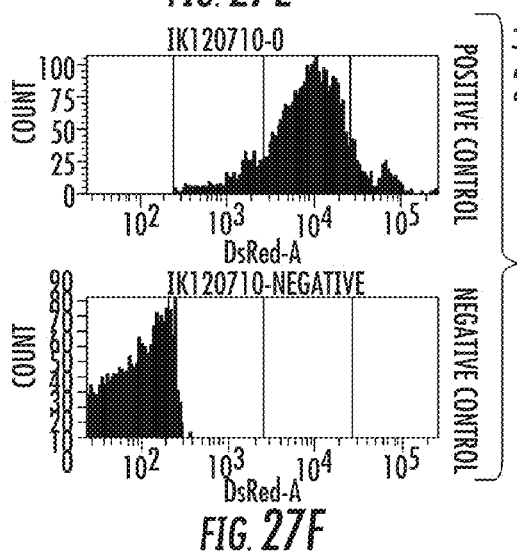

FIGS. 27A-27FG show the fluorescence intensity of *Rhodococcus* Sp exposed to 0, 5, 10, and 20 sec of UV light (FIG. 27B, FIG. 27C, FIG. 27D and FIG. 27E respectively). A legend is shown in FIG. 27A. Exposure for 5 sec (FIG. 27C) increased the population that contains high lipid compared to the control (FIG. 27B) while exposure for 10 and 20 second negatively affected the lipid content (FIG. 27D and FIG. 27E respectively). FACS analysis of untreated cells (negative control; no Nile Red staining and no UV exposure) (FIG. 27F) indicated that *Rhodococcus* Sp autofluorescence does not overlap with Nile Red staining.

Figure 27G:
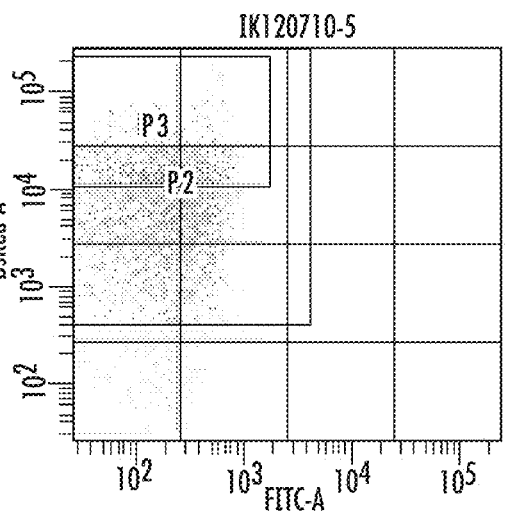

As shown in FIG. 27G, 100,000 mutants of *Rhodococcus* Sp with increased lipid content (100% to 115%) from 5 sec UV mutagenesis treatment (P3; purple) were selected by comparison to the untreated population (P2; orange). Negative control (no Nile Red staining and no UV exposure) is indicated in green.

Microorganism Transformation

Transformation of *Rhodococci* was carried out using the plasmids pSeqCO1 and pVer1 (FIG. 12) as described below.

*Rhodococci* competent cells were prepared by incubating a single colony 2 ml NB medium (5 g/L peptone, 1 g/L meat extract, 2 g/L yeast extract, 5 g/L NaCl; pH=7.0±0.2) at 30° C. overnight. One ml was inoculated to 50 ml NB medium supplemented with 0.85% (w/v) glycine and 1% (w/v) sucrose in a 250 ml baffled Erlenmeyer Flask and incubated to a cell density of $O.D._{600}$=0.5. Cells were collected by centrifugation at 3,000×g for 10 min at 4° C. and washed 3 times with 50 ml (each) of sterile ice-cold double distilled water ($ddH_2O$). Cells were concentrated 20-fold by re-suspending the collected cells in 2.5 ml of $ddH_2O$ and 400 µl aliquots stored in 1.5 ml tube at −70° C. Electroporation was carried out by thawing the competent cells on ice and mixing with the plasmid DNA (final concentration 0.1-0.25 µg/ml). The competent cells and plasmid DNA mixture was incubated at 40° C. for 5 min, transferred into 0.2 cm width and electroporated using a single-pulse electroporation (10 kV/cm, 600Ω, 25 µF and 3-5 ms pulse time). The pulsed cells were regenerated at 30° C. for 4 h (DSM 44193) and 6 h (DSM 43205) in the presence of 600 µl NB. Transformants were selected after cultivation for 3-4 days at 30° C. on NB-agar plate containing kanamycin (75 µg/ml). As shown in FIG. 12, the plasmids pSeqCO1 and pVer1 confer resistance to kanamycin (75 µg/ml) in transformed *R. opacus* strains (44193 and 43205). Untransformed *R. opacus* strains (44193 and 43205) (NC) were sensitive to the concentration described above.

Transformation of genus *cupriavidus* was carried out using the plasmids pSeqCO2 (FIG. 12) as described below.

*Cupriavidus necator* (DSM531) competent cells were prepared by incubating a single colony in 5 ml NR medium (10 g/l polypeptone, 10 g/l yeast extract, 5 g/l beef extract and 5 g/l ammonium sulfate; pH 7.0) at 30° C. overnight. The pre-culture was inoculated into 100 ml of fresh NR medium and incubated to a cell density of $O.D._{600}$=0.8. Cells were collected by centrifugation at 3,000×g for 10 min at 4° C. and washed 3 times with 50 ml (each) of sterile ice-cold $ddH_2O$. The collected cells were re-suspended in 400 µl of 10% (v/v) sterile glycerol in sterile ice-cold $ddH_2O$ and stored in 50 µl aliquots at −70° C.

For electroporation, the competent cells were thawed on ice, transferred into 0.2 cm width of ice cold cuvette and gently mixed with 1 µg of plasmid DNA. Cells were electroporated using a single-pulse electroporation (11.5 kV/cm, 25 µF and 5 ms pulse time). The pulsed cells were transferred into 1 ml of fresh NR medium and culture for 2 h at 30° C. Transformants were selected after cultivation for 48 h at 30° C. on NR-agar plate containing kanamycin (200 µg/ml). As shown in FIG. 12, the plasmid pSeqCO2 confers resistance to kanamycin (200 µg/ml) in transformed *Cupriavidus necator* (DSM531). Untransformed *Cupriavidus neca-* tor (DSM531) cells (NC) were sensitive to the concentration described above.

Inoculation and Growth Conditions

Organisms from the genus *Rhodococcus* and from the genus *Cupriavidus* were tested for their ability to grow on different carbon sources (FIG. 5). Colonies from strains grown on LB agar plates at 30° C. were transferred into flasks containing 10% (v/v) of the indicated media for 3-20 days at 30° C. and 250 rpm. *R. opacus* strain DSM 44193 exhibited growth only under heterotrophic growth conditions as measured by optical density (OD) at 650 nm on MSM medium (1 L Medium A:9 g $Na_2HPO_412H_2O$, 1.5 g $H_2PO_4$, 1.0 g $NH_4Cl$ and 0.2 g $MgSO_4.7H_2O$ per 1 L; 10 ml Medium B:50 mg Ferric ammonium citrate and 100 mg $CaCl_2$ per 100 ml; 10 ml Medium C:5 g $NaHCO_3$ per 100 ml; and 1 ml Trace Mineral Solution:100 mg $ZnSO_4.7H_2O$, 30 mg $MnCl_2$. $4H_2O$, 300 mg $H_3BO_3$, 200 mg $COCL_2.6H_2O$, 10 mg $CuCl_2.2H_2O$, 20 mg $NiCl_2.6H_2O$ and 30 mg $Na_2MoO_4.2H_2O$ per 1 L) supplemented with 40 g/L glucose. *R. opacus* strain DSM 43205 showed identical growth rates under heterotrophic conditions reaching O.D=9.0. Strain DSM 43205 was also able to grow on chemoautotrophic conditions (MSM medium supplemented with 66.7% $H_2$, 9.5% $CO_2$, 5% $O_2$ and 18.8% $N_2$) and heterotrophically on a single carbon compound as the solely carbon source (MSM medium supplemented with 25 g/l methanol). *Rhodococcus* sp. (DSM 3346) exhibited growth under heterotrophic conditions and chemoautotrophic conditions (DSMZ Medium 81:1 L of Mineral Medium for chemolithotrophic growth: 2.9 g $Na_2HPO_4.2H_2O$, 2.3 g $KH_2PO_4$, 1.0 g $NH_4Cl$, 0.5 g $MgSO_4.7H_2O$, 0.5 g $NaHCO_3$, 0.01 g $CaCl.2H_2O$ and 0.05 g $Fe(NH_4)$ citrate per 1 L; and 5 ml Trace Mineral Solution, supplemented with 80% $H_2$, 10% $CO_2$ and 10% $O_2$). *Cupriavidus necator* (DSM 531) was able to grow under heterotrophic and chemoautotrophic conditions (media described for Strain DSM 43205) (FIG. 5 and FIG. 28). *Cupriavidus necator* (DSM 531) transformed with pSeqCO2 was able to grow on LB media supplemented with 300 400 and 500 μg/ml kanamycin exhibiting $O.D_{600}$ of 1.47, 1.52 and 1.51 respectively (FIG. 13). Untransformed cells exhibited growth on control (LB only) and some growth on 300 μg/ml kanamycin while no growth was detected on 400 and 500 μg/ml kanamycin.

Example 2

Lipid Profiles, Production of Fatty Acid

Under heterotrophic growth conditions strains DSM 44193, DSM 43205, DSM 3346 and DSM 531 produce lipid (FIG. 6). Lipid content determined by gas chromatography analysis of cells harvested after 72 hr (unless otherwise indicated) showed over 19% of cellular dry matter (CDM) determined gravimetrically for strains DSM 44193, DSM 43205 and DSM 3346. The lipid content of DSM 43205 was higher than 10% of under chemoautotrophic conditions. Under heterotrophic growth conditions DSM 44193 produces 32%, 26% and 21% of 16, 17 and 18-carbon fatty acid respectively (FIG. 7). DSM43205 produces similar amounts of 16, 17 and 18-carbon fatty acid (30%, 24% and 32% respectively) (FIG. 8A). Chemoautotrophic growth condition significantly reduces the 17-carbon fatty acid abundance (6%) and maintains similar levels of 16 and 18-carbon fatty acid (36% and 27% respectively) (FIG. 8B). DSM3346 exhibits similar fatty acid distribution of 16, 17 and 18-carbon fatty acid (39%, 24% and 25% respectively) (FIG. 9A) under heterotrophic growth. Chemoautotrophic growth condition significantly increases the 16-carbon fatty acid levels (66%) and reduces the 17 and 18-carbon fatty acid levels (4%, 14%) (FIG. 9B).

Example 3

Production of Alkanes

To redirect carbon flux from fatty acid toward alkanes biosynthesis, the genes Fatty acyl-CoA/Fatty acyl-ACP reductase (FadR) and Fatty aldehyde decarbonylase (FAD) from the decarbonylation pathway of cyanobacteria (indicated in red) were expressed in *Cupriavidus necator* (DSM 531) (FIG. 19).

The plasmid pSeqCO2::FUEL (FIG. 20) described in the text was introduced into *Cupriavidus necator* (DSM 531) as described above and 2 independent transformants (Cn-FUEL2.1 and Cn-FUEL2.2) were selected. One hundred ml of Cn-FUEL2.1, Cn-FUEL2.2 and control cells (empty plasmid: Cn-P) were incubated on LB medium with 400 μg/ml kanamycin for 30 hr. Cells were harvested at 3,000×g for 10 min at 4° C. and pellet was analyzed by GC/MS. Cn-FUEL2.1 (FIG. 21A) and Cn-FUEL2.2 showed a specific peak at 45.00 min compared to control Cn-P (FIG. 21B) indicating the presence of hydrocarbons in the engineered strains. Cn-FUEL2.1, Cn-FUEL2.2 produced high levels (over 2%) of unique molecules such as: Spiro[4.5]decane, Bicyclo[10.8.0]eicosane, cis,cis-1,6-Dimethylspiro[4.5]decane, 1,19-Eicosadiene, Cyclooctacosane, Bicyclo[10.8.0] eicosane, 1-Pentadecyne, 1-Pentadecyne, Heptacosyl acetate, 5-Cyclohexyl-1-pentene, 1-Hexadecyne and Cyclodecacyclotetradecene, -eicosahydro (FIG. 22).

The effect of the production of alkanes on fatty acid distribution is shown in FIG. 23. The fatty acids profile of 2 independent control experiments (Cn-P) shows predominantly 16-carbon (63% and 61%) and 18-carbon (33% and 32%) fatty acids. In contrast, Cn-FUEL2.1 and Cn-FUEL2.2 exhibit significantly lower levels of 16-carbon (29%, 33% respectively) and 18-carbon (3% and 2% respectively) fatty acids. Cn-FUEL2.1 and Cn-FUEL2.2 show a significant increase in the 15-carbon fatty acid (50% and 45% respectively) compared to 0.08% and 0.09% in the control strains Cn-P.

The formation of alkanes in *Cupriavidus necator* was demonstrated by the expression of fatty acyl-CoA reductases (FAR) genes. The *Arabidopsis* genes FAR1 (SEQ ID: 05), FAR2 (SEQ ID: 06) and FAR3 (SEQ ID: 07) were cloned into pSeqCO2 plasmid using the indicated restriction sites to give pSeqCO2::FAR1 and pSeqCO2::FAR2 respectively (FIG. 16). pSeqCO2::FAR1 and pSeqCO2::FAR2 and control (pSeqCO2, empty plasmid) were introduced into *Cupriavidus necator* (DSM 531) as described in the text. One hundred ml of transformants of pSeqCO2::FAR1 (Cn-F1), pSeqCO2::FAR2 (Cn-F2) and control cells (empty plasmid: Cn-P) were incubated on LB medium with 400 g/ml kanamycin for 30 hr. Cells were harvested at 3,000×g for 10 min at 4° C. and pellet was analyzed by GC. Cn-F1 and Cn-F2 produced cyclotetradecane compared to control Cn-P (FIG. 29) indicating the presence of alkanes in the engineered strains. It is believed, without the present invention being limited to any particular theory, that cyclotetradecane is produced within *Cupriavidus necator* from a C14 fatty alcohol intermediate, that results from the introduction and expression of the FAR gene in *Cupriavidus necator*. The absence of cyclotetradecane in Cn-P is thought to be due to the lack of FAR gene and hence lack of C14 fatty alcohol intermediate in *Cupriavidus necator*, without the present invention being limited to any particular theory.

Example 4

Purification of Alkanes

To produce alkanes in bacteria, genes from the decarbonylation pathway of cyanobacteria, including but not limited to, the FadR (SEQ ID: 08) and FAD (SEQ ID: 09) genes are cloned into pVer2 (SEQ ID: 04) to give pVer2::FUEL. Bacteria, including but not limited to, *R. opacus* strain (DSM43205) are transformed with the plasmid pVer2::FUEL by electroporation and grown in 100 ml LB medium supplemented with 75 µg/ml kanamycin for hr. The cells (2×50 ml) are harvested at 3,000×g for 10 min at 4° C. and the pellet and the supernatant are further analyzed. Analysis of alkanes from the cell pellet is carried out in 25 mm×150 mm glass tube in the presence of 50 µL of Eicosane standard (approx 200 µg/ml) and 50 µl lipid standard (~200 µg/ml). The pellet is extracted with 5 mL chloroform, 10 ml methanol, 4 ml phosphate buffer (phosphate buffer reagent: 50 mM, pH 7.4, 8.7 g $K_2HPO_4$ in 1 L water, and about 2.5 ml 6N HCl to adjust pH=7.4, and 50 ml chloroform per 1 L buffer). The mixture is vortexed for 30 sec, sonicated for 2 min and incubated in dark for at least 3 hr. Phases are separated in the presence of 5 mL chloroform and 5 ml $ddH_2O$, vortexed and spun down 2000 rpm for 1 min. The bottom layer is transferred with a glass Pasteur pipette to clean 16 mm×125 mm glass tube with Teflon-lined screw top and dried under N2. The dried extract is re-suspended in hexane and analyzed by Gas Chromatography for the presence of hydrocarbons, including but not limited to 1-Hexadecyne.

Example 5

Purification of Fatty Alcohols

To produce fatty alcohols in bacteria, the fatty acyl-CoA reductases (FARs) that catalyze the formation of a fatty alcohol from an acyl-CoA, including but not limited to the FAR1 gene (SEQ ID: 05) are cloned into pVer2 (SEQ ID: 04) to give pVer2::FAR1. Bacteria including but not limited to *R. opacus* strain (DSM43205) are transformed with the plasmid pVer2::FAR1 by electroporation, grown in 100 ml LB medium supplemented with 75 µg/ml kanamycin for 30 hr. The cells (2×50 ml) are harvested at 3,000×g for 10 min at 4° C. and the pellet and the supernatant are further analyzed. Analysis of fatty alcohols from the cell pellet is carried out in 1.5 ml eppendorf tube in the presence of 50 µl pure HCl and 500 µl ethyl acetate (EtAc). The mixture is vortexed for 10 sec and spun down at max speed for 1 min. The EtAc (top) layer is recovered and transferred to a glass GC vial. The sample is derivatized by adding 100 µl of MeOH:HCl (9:1) to the EtAc extract and mixing. About 50-100 µl of TMS-diazomethane (2M in hexanes) is mixed and incubated for 10-15 min. Aliquots of 50µ are analyzed by Gas Chromatography-Flame Ionization Detector (GC-FID) for the presence of alkanes, including but not limited to 1-tetradecanol.

Example 6

Purification of Fatty Acids

To modify the fatty acid distribution in bacteria, thioesterases that regulate the fatty acid chain length, including but not limited to the YP_002784058.1 gene are cloned into pVer2 (SEQ ID: 04) to give pVer2::TE. Bacteria, including but not limited to, *R. opacus* strain (DSM43205) are transformed with the plasmid pVer2::TE by electroporation and grown in 100 ml LB medium supplemented with 75 µg/ml kanamycin for 30 hr. The cells (2×50 ml) are harvested at 3,000×g for 10 min at 4° C. and the pellet and the supernatant are further analyzed. Analysis of fatty acids from the cell pellet is carried out in 25 mm×150 mm glass tube in the presence of 50 µL of Eicosane standard (approx 200 µg/mL) and 50 µL lipid standard (~200 ug/ml). The pellet is extracted with 5 ml chloroform, 10 ml methanol, 4 ml phosphate buffer (phosphate buffer reagent: 50 mM, pH 7.4, 8.7 g $K_2HPO_4$ in 1 L water, and about 2.5 mL 6N HCl to adjust pH=7.4, and 50 ml chloroform per 1 L buffer). The mixture is vortexed for 30 sec, sonicated for 2 min and incubated in dark for at least 3 hr. Phases are separated in the presence of 5 ml chloroform and 5 ml $ddH_2O$, vortexed and spun down 2000 rpm for 1 min. The bottom layer is transferred with a glass Pasteur pipette to clean 16 mm×125 mm glass tube with Teflon-lined screw top and dried under N2. The dried extract is re-suspended 1.5 ml of a 10:1:1 mixture of Methanol:CHCl3:concentrated HCl, vortexed and incubated in 60° C. for 14-16 hr (overnight). The extracts are cooled and 2 ml of $ddH_2O$ and 2 ml of hexane are added, vortexed and centrifuged for 5 min at 2000 rpm for phase separation. The top hexane layer is transferred to clean 16 mm tube. Additional two hexane extraction (vortex, centrifugation and phase separation) is carried out in the extract tube. The hexane extracts are dried in a GC vial and analyzed by Gas Chromatography for the presence of fatty acids, including but not limited to dodecanoic acid.

Dicarboxylic Acids with Targeted Chain Length.

Bacteria from the suborder corynebacterineae or the family burkholderiaceae are genetically engineered to express thioesterases which yield different length fatty acids. For example, non-limiting embodiments include the YP_002784058.1 gene discussed above or:

| UniProt Entry | Protein name | Organism | C length |
|---|---|---|---|
| FATB_GOSHI | Myristoyl-acyl carrier protein thioesterase | *Gossypium hirsutum* | 16:0 |
| FATB_UMBCA | Lauroyl-acyl carrier protein thioesterase | *Umbelliularia californica* | 12:0 |
| FATB_CINCA | Myristoyl-acyl carrier protein thioesterase | *Cinnamomum camphora* | 14:0 |
| FATA_CORSA | Oleoyl-acyl carrier protein thioesterase | *Coriandrum sativum* | 18:0 |
| FATB_CUPHO | Myristyl-acyl carrier protein thioesterase | *Cyphea hookeriana* | 16:0 |

Thioesterases generating shorter chain fatty acids (e.g., C10:0 or C12:0) are identified and incorporated into the bacteria from the suborder corynebacterineae and the family burkholderiaceae.

The resulting lipids are extracted and provided as the sole source of carbon to a culture of *Candida tropicalis* ATCC 20336, which contains the relevant enzymatic pathways to produce the alpha, omega-dicarboxylic acids. Dicarboxylic acid end products are identified and purified from the second culture.

Also, the cytochrome P450 pathway from *Candida tropicalis* is engineered into a host strain, including the CYP52A genes with NADPH cytochrome P450 reductase to generate dicarboxylic acid from the fatty acids. Craft et al. have identified genes for generation of alpha, omega-dicarboxylic acids in *Candida tropicalis*: CYP52A13, CYP52A14, CYP52A17, CYP52A18, and CYP52A12 along with the corresponding reductase (Craft 2003).

A single culture is performed, which generates appropriate length fatty acids, then modified to attach a second carboxylic acid.

Dicarboxylic Acids.

The hyperthermophilic archaeon *Pyrococcus furiosus* is cultured in order to generate the dicarboxylic acids described in Carballeira et al. (Carballeira 1997). Genetic machinery for generating these dicarboxylic acids is determined, and the *P furiosus* genome is compared with bacteria from the suborder corynebacterineae and the family burkholderiaceae genomes. The relevant genetic modules are moved from *P furiosus* into bacteria from the suborder corynebacterineae and the family burkholderiaceae in order to post-process lipids into dicarboxylic acids. This can be combined with genes which produce shorter fatty acids through the appropriate thioesterases.

Hydroxy-Acids

For generating omega-hydroxylated fatty acids, *vicia sativa* P450-dependent fatty acid omega hydroxylase is incorporated into bacteria from the suborder corynebacterineae and the family burkholderiaceae cell line. This enzyme hydroxylates myristic acid (C14), lauric acid (C12), pamitic acid (C16), but not oleic acid (C18).

For generating in-chain hydroxylated fatty acids, CYP81B1 (*H tuberosus*) or CYP709C1 (unknown) fatty acid hydroxylases are incorporated into bacteria from the suborder corynebacterineae and the family burkholderiaceae cell line. The CYP81B1 enzyme omega-1 and omega-5 mono-hydroxylates capric (C10:0), lauric (C12:0), and myristic (C14:0) (Pompon 1996). The CYP709C1 gene hydroxylates the omega-1 and omega-2 positions independent of chain length (Kandel 2005).

Example 7

Hydroxylation of Octadecanoic Acid to Produce 12-Hydroxy Octadecanoic Acid, Also Known as 12-Hydroxy Stearic Acid or 12-HSA The *Physaria lindheimeri* oleate 12-hydroxylase ABQ01458.1 GI: 146141441 can convert 9,12-octadecadienoic acid or the cis-9-cotadecenoic acid or trans-9 octadecanoic acid or octadecanoic acid (made by production strains) to 12-HSA, which is fully saturated and a hydroxyl group at the C12 position.

Octadecanoic acid is one modification away from 12-HSA. With a specialized enzyme, which adds a hydroxyl group to position 12, one can produce the 12-HSA product. *Physaria lindheimeri*, produces an oleate 12-hydroxylase ABQ01458.1 GI: 146141441 (Dauk 2007) that is known to hydroxylate the 12-position.

A Basic Local Alignment Search Tool (BLAST) of protein sequence against the NCBI nr database (All non-redundant GenBank CDS translations+PDB+SwissProt+PIR+PRF excluding environmental samples from WGS projects) yielded multiple hits against the 12-hydroxylase sequence itself (ABQ01458.1), and some bifunctional 12-hydroxylase/desaturases from *Physaria* of 91% identity. The closest related sequences beyond that are in the 80% range against *Capsellsa rubells, lepidium campestre*, and *Arabidopsis lyurata*.

The 12-hydroxylase gene from *Physaria lindheimeri* is synthesized, transfected and expressed in chemoautotrophic production strains described herein and the presence of 12-HSA is investigated.

Example 8

Hydroxylation of Octadecanoic Acid, Cis-6-Octadecanoic Acid, or Cis-6, Cis-9-Octadecanoic Acid to Produce Ricinoleic Acid or (9Z,12R)-12-Hydroxyoctadec-9-Enoic Acid or R12-Hydroxy-9-Cis-Octadecenoic Acid The *Ricinus communis* oleate 12-hydroxylase can convert 9,12-octadecadienoic acid or the cis-9-cotadecenoic acid or trans-9 octadecanoic acid or octadecanoic acid (made by production strains) to ricinoleic acid, which has a double bond at C9 and a hydroxyl group at the C12 position.

"In castor (*Ricinus communis*), where ricinoleic acid can account for up to 90% of the total fatty acids in seeds, biosynthesis of this fatty acid involves a membrane bound fatty acid hydroxylase-catalyzing hydroxylation at position 12 of oleic acid esterified to the sn-2 position of phosphatidylcholine, using cytochrome b5 and NADH as cofactors." (Meesapyodsuk 2008).

Van de Loo et al. (van de Loo 1995) isolated oleate 12-hydroxylase genes from *Ricinus communis*. A search of Genbank for other genes annotated as such yield:

gi|722350|gb|U22378.1|RCU22378 *Ricinus communis* oleate 12-hydroxylase mRNA, complete cds gi|187940238|gb|EU523112.1| *Ricinus communis* oleate 12-hydroxylase (FAH12) mRNA, gi|255574427|ref|XM_002528081.1| *Ricinus communis* oleate 12-hydroxylase, mRNA Also found is an adjunct protein, which putatively binds the 12-hydroxylase enzymes (Cellini JP 2002543842-A 2002) (Cellini WO 0070052-A4 2000).

gi|33080346|dbj|BD270578.1| *Ricinus communis*-origin gene encoding novel protein interacting with oleate 12-hydroxylase]

gi|33080345|dbj|BD270577.1| *Ricinus communis*-origin gene encoding novel protein interacting with oleate 12-hydroxylase gi|33080344|dbj|BD270576.1| *Ricinus communis*-origin gene encoding novel protein interacting with oleate 12-hydroxylase Example 9

Hydroxylation of Oleic Acid with Oleate Hydroxylase from Fungus, *Claviceps purpurea*

The fatty acid hydroxylase gene GenBank: ACF37070.1 from *Claviceps purpurea* (Meesapyodsuk 2008) (Meesapyodsuk U.S. Pat. No. 8,003,853 2011) (Meesapyodsuk U.S. Pat. No. 7,923,598) contains both an oleate 12-hydroxylase and an omega-6 fatty acid desaturase. According to Meesapyodsuk and Qiu, biosynthesis of this fatty acid in *C. purpurea* involves a hydration process with linoleic acid as the substrate. Furthermore, their data indicate the biosynthesis of ricinoleic acid in *C. purpurea* is catalyzed by the fungal desaturase-like hydroxylase.

Example 10

Production of 12-HSA Using Other Plant Hydroxylases

More limited plants families (e.g., *Ricinus communis*) produce ricinoleic acid (D-12-hydroxyoctadec-cis-8-enoic acid) via oleoyl-12-hydroxylase (McKeon 2007) (an oleate hydroxylase) close in sequence homology to oleate desaturases. These hydroxylases do not appear in the ThYme database. They act on free C18 fatty acids, not TAGs.

Other Fatty Acid 12-Hydroxylases

An array of relevant P450 genes is expressed in order to determine hydroxylation in production strains. (FIG. 33.)

Example 11

Hydroxy-Acids (Omega Hydroxylation with P450-Dependent Fatty Acid Hydroxylases

For generating omega-hydroxylated fatty acids, *Vicia sativa* P450-dependent fatty acid omega hydroxylase is incorporated into bacteria from the suborder corynebacterineae and the family burkholderiaceae cell line. This enzyme hydroxylates myristic acid (C14), lauric acid (C12), palmitic acid (C16), but not oleic acid (C18). Genes related to *Vicia* saliva P450 omega hydroxylases can also be incorporated; see FIG. 34 from BLAST runs below.

*Vicia sativa* contains a documented full P450-dependent fatty acid omega hydroxylase (Le Bouquin, 1999).

According to Le Bouquin et al., the hydroxylase in *S. cerevisiae:* a. Hydroxylates myristic acid (C14)
b. Hydroxylates lauric acid (C12)
c. Hydroxylates palmitic acid (C16)
d. No hydroxylation of oleic acid (C18)

" . . . only cytochrome P450 enzymes have been demonstrated to catalyze hydroxylation at the end of the aliphatic chain, i.e. at the omega-, (omega-1) and (omega-2) positions of saturated and unsaturated FAs of various chain lengths. There is no cross talk of C94A1_VICSA with hydroxylation of non-FA substrates.

Comparison of *Vicia sativa* P450 to other sequences:

a. BLASTP P98188.1→>100 hits with 4e-123; hits *Ricinus communis*: NCBI "Blast/sp|P98188.1|(513 letters).pdf"
b. Refining BLAST to only *Ricinus* →~50 hits with <43-7×. All appear to be putative P450 genes.

Hydroxy-Acids (Omega Hydroxylation with P450-Dependent Fatty Acid Hydroxylases).

For generating omega-hydroxylated fatty acids, one of the P450-dependent fatty acid omega hydroxylase described herein (see FIG. 35) is incorporated into bacteria from the suborder corynebacterineae and the family burkholderiaceae cell line.

Kandel et al. review hydroxylation reactions/enzymes, providing cytochrome P450-dependent fatty acid hydroxylases in plants (Kandel_2006).

Hydroxy-Acids (in-Chain Hydroxylation).

For generating in-chain hydroxylated fatty acids, CYP81B1 (*H tuberosus*) or CYP709C1 (unknown) fatty acid hydroxylases are incorporated into bacteria from the suborder corynebacterineae and the family burkholderiaceae cell line. The CYP81B1 enzyme omega-1 and omega-5 mono-hydroxylates capric (C10:0), lauric (C12:0), and myristic (C14:0) (Pompon 1996). The CYP709C1 gene hydroxylates the omega-1 and omega-2 positions independent of chain length (Kandel 2005). See FIG. 36.

Example 12

Expression of ACBP in *Cupriavidus necator*

*Bos Taurus* (cow) ACBP (SEQ ID: 01) was codon optimized for expression in *Cupriavidus* and *Rhodococci* and synthesized with the restriction sites KpnI and SalI (SEQ ID: 02). The resultant gene was cloned into pSeqCO2 (pBBR1MCS-2; Kovach et al. 1995) digested with KpnI and SalI to give pSeqCO2::ACBP (FIG. 41). *Cupriavidus necator* competent cells were prepared by incubating a single colony in 5 ml NR medium (O1 g/1 polypeptone, 10 g/l yeast extract, 5 g/1 beef extract and 5 g/l ammonium sulfate; pH 7.0) at 30° C. overnight. The pre-culture was inoculated into 100 ml of fresh NR medium and incubated to a cell density of $O.D_{600}$=0.8. Cells were collected by centrifugation at 3,000×G for 10 min at 4° C. and washed 3 times with 50 ml (each) of sterile ice-cold $ddH_2O$. The collected cells were re-suspended in 400 μl of 10% (v/v) sterile glycerol in sterile ice-cold $ddH_2O$ and stored in 50 μl aliquots at −80° C.

For electroporation, the competent cells were thawed on ice, transferred into 0.2 cm width of ice-cold cuvette and gently mixed with 1 g of plasmid DNA. Cells were electroporated using a single-pulse electroporation (11.5 kV/cm, 25 μF and 5 ms pulse time). The pulsed cells were transferred into 1 ml of fresh NR medium and culture for 2 h at 30° C. Transformants were selected after cultivation for 48 h at 30° C. on NR-agar plate containing kanamycin (200 μg/ml).

For fatty acid analysis, transformants were grown in 100 ml LB media supplemented with 400 μg/ml kanamycin at 30° C., harvested after 48 hr and analyzed by gas chromatography.

Shifting of Fatty Acid Profile to Shorter Chain Lengths Through Expression of Fatty Acyl-CoA Binding Protein from Bovine Exogenous Gene (NP_001106792).

It is hypothesized that expression of the *Bos Taurus* (cow) gene for the fatty acyl-CoA binding protein will result in a shorter chain fatty acid profile.

As shown in FIG. 39A, the expression of a thioesterase (TKO4-TE) reduces production of C18 and C16, resulting in increased production of C12 (from 0% to 3.95%) and C14 (from 1.38% to 6.09%), compared to plasmid control (TKO4-P). As shown in FIG. 39B, expression of the fatty acyl-CoA carrier protein results in reduced production of C18 and increase production of C12 (from 0% to 1.78%) and C14 (from 1.38% to 4.55%) compared to control.

Sample Sequences from GenBank.

Some organisms have multiple forms of these ACBP proteins. *Bos Taurus* appears to have a single short-chain form.

```
gi|164518978|ref|NP_001106792.1| acyl-CoA-binding protein [Bos
taurus]                                                                    SEQID: 15
MSQAEFDKAAEEVKHLKTKPADEEMLFIYSHYKQATVGDINTERPGMLDFKGKAKWDAWNEL KGTSKEDA MKAYIDKVEELKKKYGI
                                                                           SEQ 19
[BRnote]
gi|164518977|ref|NM_001113321.1| Bos taurus diazepam binding
inhibitor (GABA receptor modulator, acyl-CoA binding protein)
(DBI), mRNA
GAGCACCGGTGGAGAGGCCTAAGGTTGCGCTTCTAAAATCGCTGCCAGTTGAGTCTCTTGTG

CTGCTGCTACCTTCTCTTCGCCGCCTCCGCGGGCTTCCTGGAATCTTTGCAACACCGCCGGC

ATGTCTCAGGCTGAGT

TTGACAAAGCTGCTGAGGAAGTTAAGCATCTTAAGACCAAGCCAGCAGATGAGGAGATGCTG

TTCATCTA

CAGCCACTACAAACAAGCAACTGTGGGTGACATAAATACAGAACGTCCTGGAATGTTGGACT

TCAAAGGC

AAGGCCAAGTGGGATGCCTGGAATGAGCTGAAAGGGACTTCTAAAGAAGATGCCATGAAAGC

TTACATTG

ACAAAGTAGAAGAACTAAAGAAAAAATATGGAATATAAGAGACTGAGTTTGGCTGCCAGCCA

TTCATTTC

ACCTAAACTGATTTAATGCCTTGTTTTTCTAATACTGGGGATGAAGTTCATAAATAACTAGC

TAAGCCAGAAGCTCAAGACAGCCCAGGATATGACTAACAGATTAGGAGCTGAAACGGTTACT

AATCCTTGCTGAGTAA

TTTTTATCAGTAGATGAATTAAAAGTATCTTTGTTACTTTACTTCGAT

SEQID: 15: gi|164518978|ref|NP_001106792.1|acyl-CoA-binding protein [Bos taurus]
                                                                           SEQ ID: 15
MSQAEFDKAAEEVKHLKTKPADEEMLFIYSHYKQATVGDINTERPGMLDFKGKAK WDAWNELKGTSKEDAMKAYIDKVEELKKKYGI
                                                                           SEQ ID: 16
GGTACCGGGCCCCCCCTCGAGATGTCCCAGGCCGAGTTCGACAAGGCCGCCGAG

GAAGTTAAGCACCTCAAGACCAAGCCGGCAGACGAGGAGATGCTGTTCATCTAC

TCCCACTACAAGCAGGCAACCGTGGGTGACATCAACACAGAACGGCCCGGCATG

CTCGACTTCAAGGGCAAGGCCAAGTGGGATGCCTGGAATGAGCTGAAAGGGACC

TCCAAAGAAGATGCCATGAAGGCGTACATTGACAAGGTAGAAGAACTCAAGAA

AAAATACGGCATCTAGGTCGAC

The long-form ACBP:
gi|30794364|ref|NP_851381.1|acyl-CoA-binding domain-containing protein 5 [Bos taurus]
MFQFHAGSWESWCCCCLIPGDRPWDRGRRWRLEMRHTRSVHETRFEAAVKVIQS

LPKNGSFQPTNEMML

KFYSFYKQATEGPCKLSKPGFWDPVGRYKWDAWSSLGDMTKEEAMIAYVEEMKKI

LETMPMTEKVEELLH

VIGPFYEIVEDKKSGRSSDLTSVRLEKISKCLEDLGNVLASTPNAKTVNGKAESSDSG

AESEEEAAQEDP

KRPEPRDSDKKMMKKSADHKNLEIIVTNGYDKDSFVQGVQNSIHTSPSLNGRCTEEV

KSVDENLEQTGKT

VVFVHQDVNSDHVEDISGIQHLTSDSDSEVYCDSMEQFGQEESLDGFISNNGPFSYYL
```

GGNPSQPLESSG

FPEAVQGLPGNGSPEDMQGAVVEGKGEVKRGGEDGGSNSGAPHREKRAGESEEFSN

IRRGRGHRMQHLSE

GSKGRQVGSGGDGERWGSDRGSRGSLNEQIALVLMRLQEDMQNVLQRLHKLEMLA

ASQAKSSALQTSNQP

TSPRPSWWPFEMSPGALTFAIIWPFIAQWLVHLYYQRRRRKLN gi|31341043|ref|NM_181038.2|*Bos taurus* acyl-CoA binding domain containing 5 (ACBD5), mRNA

GAGGAGCTGACCAGCTGCGCTTTGGAGTCCTCCTCCCTTCGGGAATGTTGATCCG

CGGCTGCGCTCCATG

TTTCAGTTTCATGCAGGCTCCTGGGAAAGCTGGTGCTGCTGCTGCTGCCTGATTC

CAGGCGACAGACCTT

GGGACCGCGGCCGGCGCTGGCGGCTGGAGATGCGGCACACGAGATCCGTTCACG

AAACCCGGTTTGAGGC

GGCTGTGAAGGTGATACAGAGCTTGCCGAAAAATGGTTCATTCCAGCCAACAAA

TGAAATGATGCTCAAG

TTCTATAGCTTCTATAAGCAGGCAACTGAAGGACCTTGTAAACTGTCAAAGCCTG

GCTTCTGGGATCCTG

TTGGAAGATACAAATGGGATGCGTGGAGTTCTTTGGGTGATATGACCAAAGAGG

AAGCCATGATTGCTTA

TGTTGAAGAAATGAAAAAGATTCTTGAAACTATGCCGATGACTGAAAAAGTTGA

AGAATTGCTACATGTC

ATTGGTCCATTTTATGAAATTGTAGAAGACAAAAAAAGTGGCAGAAGTTCTGATT

TAACCTCAGTCCGAC

TGGAGAAAATCTCTAAATGCTTAGAAGATCTTGGTAATGTTCTAGCTTCTACTCC

AAATGCCAAAACTGT

TAATGGTAAAGCTGAAAGCAGTGATAGTGGAGCTGAATCTGAGGAAGAAGCAGC

CCAAGAAGACCCGAAA

AGACCAGAACCACGTGATAGCGATAAGAAAATGATGAAGAAATCTGCAGACCAT

AAGAATTTGGAAATCA

TTGTCACTAATGGCTATGATAAAGACAGCTTTGTGCAGGGCGTACAGAATAGCAT

TCATACCAGTCCTTC

CCTGAATGGCCGATGCACTGAGGAAGTAAAATCTGTAGATGAAAACTTGGAGCA

AACTGGAAAAACTGTT

GTCTTCGTTCACCAAGATGTAAACAGTGATCATGTTGAAGATATTTCAGGAATTC

AGCATTTGACAAGTG

ATTCAGACAGTGAAGTTTACTGTGATTCCATGGAGCAATTTGGGCAAGAAGAGTC

TTTAGACGGCTTTAT

ATCAAACAATGGACCATTTTCCTATTACTTGGGTGGTAATCCCAGTCAACCGTTG

GAAAGTTCTGGTTTT

CCTGAAGCTGTTCAAGGACTTCCTGGGAACGGCAGCCCTGAGGACATGCAGGGC

GCAGTGGTTGAAGGCA

-continued

AAGGTGAAGTAAAGCGTGGGGGAGAGGACGGCGGGAGTAACAGTGGAGCCCCG

CACCGCGAGAAACGGGC

TGGAGAAAGTGAGGAGTTCTCTAACATTAGGAGAGGGAGAGGGCACAGGATGC

AGCATTTGAGTGAAGGA

AGCAAGGGTCGGCAAGTGGGAAGTGGAGGTGATGGGGAACGCTGGGGTTCGGA

CAGAGGCTCAAGGGGCA

GCCTGAACGAGCAGATCGCGCTTGTGCTCATGCGCCTGCAGGAGGACATGCAGA

ACGTCCTCCAGAGACT

CCACAAACTGGAGATGCTGGCGGCATCACAGGCAAAATCATCAGCATTACAGAC

CAGTAATCAGCCCACT

TCACCGAGACCATCTTGGTGGCCCTTCGAGATGTCTCCTGGTGCATTAACCTTCG

CTATCATATGGCCTT

TTATTGCTCAGTGGTTGGTGCATTTATATTACCAAAGAAGGAGAAGAAAATTGAA

CTAAAGAAAATGACA

TTTTGTTGAAGAAATCTACTGGCCCTGGATAACCTCGGGATGATACCAATTGTGG

AGCTTACACGAGGGA

SEQ ID: 17

The long-form ACBP: gi|30794364|ref|NP_851381.1|acyl-CoA-binding domain-
containing protein 5 [Bos taurus]

SEQ ID: 17

MFQFHAGSWESWCCCCCLIPGDRPWDRGRRWRLEMRHTRSVHETRFEAAVKVIQS

LPKNGSFQPTNEMML

KFYSFYKQATEGPCKLSKPGFWDPVGRYKWDAWSSLGDMTKEEAMIAYVEEMKKI

LETMPMTEKVEELLH

VIGPFYEIVEDKKSGRSSDLTSVRLEKISKCLEDLGNVLASTPNAKTVNGKAESSDSG

AESEEEAAQEDP

KRPEPRDSDKKMMKKSADHKNLEIIVTNGYDKDSFVQGVQNSIHTSPSLNGRCTEEV

KSVDENLEQTGKT

VVFVHQDVNSDHVEDISGIQHLTSDSDSEVYCDSMEQFGQEESLDGFISNNGPFSYYL

GGNPSQPLESSG

FPEAVQGLPGNGSPEDMQGAVVEGKGEVKRGGEDGGSNSGAPHREKRAGESEEFSN

IRRGRGHRMQHLSE

GSKGRQVGSGGDGERWGSDRGSRGSLNEQIALVLMRLQEDMQNVLQRLHKLEMLA

ASQAKSSALQTSNQP

TSPRPSWWPFEMSPGALTFAIIWPFIAQWLVHLYYQRRRRKLN

SEQ ID: 18 gi|31341043|ref|NM_181038.2|Bos taurus acyl-CoA binding domain containing 5 (ACBD5), mRNA

SEQ ID: 18

GAGGAGCTGACCAGCTGCGCTTTGGAGTCCTCCTCCCTTCGGGAATGTTGATCCG

CGGCTGCGCTCCATG

TTTCAGTTTCATGCAGGCTCCTGGGAAAGCTGGTGCTGCTGCTGCTGCCTGATTC

CAGGCGACAGACCTT

GGGACCGCGGCCGGCGCTGGCGGCTGGAGATGCGGCACACGAGATCCGTTCACG

AAACCCGGTTTGAGGC

```
GGCTGTGAAGGTGATACAGAGCTTGCCGAAAAATGGTTCATTCCAGCCAACAAA

TGAAATGATGCTCAAG

TTCTATAGCTTCTATAAGCAGGCAACTGAAGGACCTTGTAAACTGTCAAAGCCTG

GCTTCTGGGATCCTG

TTGGAAGATACAAATGGGATGCGTGGAGTTCTTTGGGTGATATGACCAAAGAGG

AAGCCATGATTGCTTA

TGTTGAAGAAATGAAAAAGATTCTTGAAACTATGCCGATGACTGAAAAAGTTGA

AGAATTGCTACATGTC

ATTGGTCCATTTTATGAAATTGTAGAAGACAAAAAAAGTGGCAGAAGTTCTGATT

TAACCTCAGTCCGAC

TGGAGAAAATCTCTAAATGCTTAGAAGATCTTGGTAATGTTCTAGCTTCTACTCC

AAATGCCAAAACTGT

TAATGGTAAAGCTGAAAGCAGTGATAGTGGAGCTGAATCTGAGGAAGAAGCAGC

CCAAGAAGACCCGAAA

AGACCAGAACCACGTGATAGCGATAAGAAAATGATGAAGAAATCTGCAGACCAT

AAGAATTTGGAAATCA

TTGTCACTAATGGCTATGATAAAGACAGCTTTGTGCAGGGCGTACAGAATAGCAT

TCATACCAGTCCTTC

CCTGAATGGCCGATGCACTGAGGAAGTAAAATCTGTAGATGAAAACTTGGAGCA

AACTGGAAAAACTGTT

GTCTTCGTTCACCAAGATGTAAACAGTGATCATGTTGAAGATATTTCAGGAATTC

AGCATTTGACAAGTG

ATTCAGACAGTGAAGTTTACTGTGATTCCATGGAGCAATTTGGGCAAGAAGAGTC

TTTAGACGGCTTTAT

ATCAAACAATGGACCATTTTCCTATTACTTGGGTGGTAATCCCAGTCAACCGTTG

GAAAGTTCTGGTTTT

CCTGAAGCTGTTCAAGGACTTCCTGGGAACGGCAGCCCTGAGGACATGCAGGGC

GCAGTGGTTGAAGGCA

AAGGTGAAGTAAAGCGTGGGGGAGAGGACGGCGGGAGTAACAGTGGAGCCCCG

CACCGCGAGAAACGGGC

TGGAGAAAGTGAGGAGTTCTCTAACATTAGGAGAGGGAGAGGGCACAGGATGC

AGCATTTGAGTGAAGGA

AGCAAGGGTCGGCAAGTGGGAAGTGGAGGTGATGGGAACGCTGGGGTTCGGA

CAGAGGCTCAAGGGGCA

GCCTGAACGAGCAGATCGCGCTTGTGCTCATGCGCCTGCAGGAGGACATGCAGA

ACGTCCTCCAGAGACT

CCACAAACTGGAGATGCTGGCGGCATCACAGGCAAAATCATCAGCATTACAGAC

CAGTAATCAGCCCACT

TCACCGAGACCATCTTGGTGGCCCTTCGAGATGTCTCCTGGTGCATTAACCTTCG

CTATCATATGGCCTT
```

-continued

```
TTATTGCTCAGTGGTTGGTGCATTTATATTACCAAAGAAGGAGAAGAAAATTGAA

CTAAAGAAAATGACA

TTTTGTTGAAGAAATCTACTGGCCCTGGATAACCTCGGGATGATACCAATTGTGG

AGCTTACACGAGGGA
```

Specific preferred embodiments of the present invention have been described here in sufficient detail to enable those skilled in the art to practice the full scope of invention. However it is to be understood that many possible variations of the present invention, which have not been specifically described, still fall within the scope of the present invention and the appended claims. Hence these descriptions given herein are added only by way of example and are not intended to limit, in any way, the scope of this invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively.

What is claimed is:

1. A microorganism comprising at least a first exogenous nucleic acid sequence that encodes a polypeptide selected from a thioesterase, an acyl carrier protein, a fatty acyl-CoA binding protein, a fatty acyl-CoA reductase, and a fatty acid desaturase, wherein the microorganism cell converts gaseous $CO_2$ and/or gaseous $H_2$ and/or syngas into one or more lipids or hydrocarbons,
   wherein the microorganism is *Rhodococcus* sp. DSM 3346 or DSM 364, or *Rhodococcus opacus* DSM 43205 or DSM 43206, and
   wherein the microorganism produces and/or secretes lipids in a quantity that is 10% or more of the dry cell mass.

2. The microorganism of claim 1, wherein the microorganism is the species *Rhodococcus* sp. DSM 3346 or DSM 364.

3. The microorganism of claim 1, wherein the microorganism is *Rhodococcus opacus* (DSM 43205) or *Rhodococcus opacus* (DSM 43206).

4. The microorganism of claim 1, wherein the microorganism is a knallgas microorganism, also known as an oxyhydrogen microorganism.

5. The microorganism of claim 1, wherein the microorganism produces and/or secretes lipids in a quantity that is 20% or more of the dry cell mass.

6. The microorganism of claim 1, wherein the microorganism is a hydrogen-oxidizing chemoautotroph.

7. The microorganism of claim 1, wherein the microorganism is capable of growing on syngas as the sole energy and carbon source.

8. A method for producing lipids or hydrocarbons, wherein the method comprises: in a bioreactor or solution, culturing a microorganism according to claim 1 with a feedstock comprising syngas and/or gaseous $CO_2$ and/or a mixture of $CO_2$ gas and $H_2$ gas, wherein said microorganism converts said feedstock into one or more lipids or hydrocarbons, wherein the microorganism produces and/or secretes lipids in a quantity that is 10% or more of the dry cell mass.

9. The method of claim 8 further comprising the step of up-regulating an endogenous or exogenous thioesterase gene of the microorganism.

10. The method of claim 8 further comprising the step of down-regulating an endogenous or exogenous thioesterase gene of the microorganism.

11. The method of claim 8 further comprising the step of down regulating an endogenous or exogenous acyl carrier protein gene of the microorganism.

12. The method of claim 8, wherein the microorganism produces and/or secretes lipids in a quantity that is 20% or more of the dry cell mass.

13. The method of claim 8, wherein the microorganism is capable of growing on syngas as the sole energy and carbon source.

14. The microorganism of claim 1, wherein the first exogenous nucleic acid sequence encodes a codon optimized Bos Taurus fatty acyl-CoA binding protein.

15. The microorganism of claim 14, further comprising a second exogenous nucleic acid sequence encoding a thioesterase enzyme.

16. The microorganism of claim 1, further comprising a second exogenous nucleic acid sequence that encodes a CYP52A protein selected from CYP52A13, CYP52A14, CYP52A17, CYP52A18, and CYP52A12, a CYP709C1 protein, or a CYP81B1 protein.

17. The microorganism of claim 1, further comprising a second exogenous nucleic acid sequence that encodes a fatty acid aldehyde acyl-ACP reductase and/or a fatty acid aldehyde decarbonylase.

* * * * *